(12) United States Patent
Rilatt et al.

(10) Patent No.: US 10,912,841 B2
(45) Date of Patent: Feb. 9, 2021

(54) ANTIBODY-DRUG-CONJUGATE AND ITS USE FOR THE TREATMENT OF CANCER

(71) Applicant: PIERRE FABRE MEDICAMENT, Boulogne-Billancourt (FR)

(72) Inventors: Ian Rilatt, Castres (FR); Michel Perez, Castres (FR); Marie Lamothe, Montredon Labessonnie (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 15/885,220

(22) Filed: Jan. 31, 2018

(65) Prior Publication Data

US 2018/0228915 A1 Aug. 16, 2018

Related U.S. Application Data

(63) Continuation of application No. 15/306,404, filed as application No. PCT/EP2015/059052 on Apr. 27, 2015, now Pat. No. 10,314,921.

(30) Foreign Application Priority Data

Apr. 25, 2014 (EP) .................................. 14305621

(51) Int. Cl.
*A61K 47/68* (2017.01)

(52) U.S. Cl.
CPC ...... *A61K 47/6803* (2017.08); *A61K 47/6855* (2017.08); *A61K 47/6857* (2017.08); *A61K 47/6859* (2017.08); *A61K 47/6863* (2017.08); *A61K 47/6865* (2017.08); *A61K 47/6867* (2017.08); *A61K 47/6869* (2017.08)

(58) Field of Classification Search
CPC ............ A61K 47/6803; A61K 47/6855; A61K 47/6857; A61K 47/6859; A61K 47/6863; A61K 47/6865; A61K 47/6867; A61K 47/6869

See application file for complete search history.

(56) References Cited

U.S. PATENT DOCUMENTS

| | | |
|---|---|---|
| 5,530,101 A | 6/1996 | Queen et al. |
| 5,585,089 A | 12/1996 | Queen et al. |
| 5,639,641 A | 6/1997 | Pedersen et al. |
| 5,693,761 A | 12/1997 | Queen et al. |
| 5,877,293 A | 3/1999 | Adair et al. |
| 5,886,152 A | 3/1999 | Nakatani et al. |
| 6,054,297 A | 4/2000 | Carter et al. |
| 6,180,370 B1 | 1/2001 | Queen et al. |
| 7,241,444 B2 | 7/2007 | Goetsch et al. |
| 7,521,541 B2 | 4/2009 | Eigenbrot et al. |
| 7,723,485 B2 | 5/2010 | Junutula et al. |
| 2008/0279868 A1 | 11/2008 | Boyd et al. |
| 2009/0035258 A1 | 2/2009 | Haskova et al. |
| 2009/0098115 A1 | 4/2009 | Crocker et al. |
| 2013/0101546 A1 | 4/2013 | Yurkovetskiy et al. |
| 2013/0157960 A1 | 6/2013 | Lerchen et al. |
| 2013/0261064 A1 | 10/2013 | Lerchen et al. |
| 2014/0080763 A1 | 3/2014 | Lerchen et al. |

FOREIGN PATENT DOCUMENTS

| | | | |
|---|---|---|---|
| EP | 0731106 A1 | 9/1996 | |
| EP | 0 682 040 B1 | 8/1999 | |
| EP | 0 566 647 B1 | 10/2003 | |
| EP | 0 451 216 B9 | 6/2012 | |
| EP | 2 589 609 A1 | 5/2013 | |
| EP | 0 939 127 B1 | 9/2014 | |
| FR | 3005051 A1 * | 10/2014 | ........... A61K 31/475 |
| WO | WO 2008/079849 A3 | 7/2008 | |
| WO | WO 2009/052249 A1 | 4/2009 | |
| WO | WO 2009/126934 A2 | 10/2009 | |
| WO | WO 2009/126934 A3 | 10/2009 | |
| WO | WO 2010/111018 A1 | 9/2010 | |
| WO | WO 2010/146059 A2 | 12/2010 | |
| WO | WO 2011/117330 A1 | 9/2011 | |
| WO | WO 2011/130598 A1 | 10/2011 | |
| WO | WO 2011/154359 A1 | 12/2011 | |
| WO | WO 2012/041805 A1 | 4/2012 | |
| WO | WO 2012/059882 A2 | 5/2012 | |
| WO | WO 2012/123423 A1 | 9/2012 | |
| WO | WO 2012/142164 A1 | 10/2012 | |
| WO | WO 2012/166559 A1 | 12/2012 | |
| WO | WO 2012/166560 A1 | 12/2012 | |
| WO | WO 2013/185115 A1 | 12/2013 | |
| WO | WO 2013/185117 A1 | 12/2013 | |

(Continued)

OTHER PUBLICATIONS

Machine translation of FR 3005051 A1, pp. 1-64, accessed Feb. 27, 2019.*
F. Dosio et al., "Immunotoxins and Anticancer Drug Conjugate Assemblies: The Role of the Linkage between Components", *Toxins*, vol. 3, pp. 848-883 (2011).
Alley, S.C. et al., "Contribution of Linker Stability to the Activities of Anticancer Immunoconjugates," *Bioconjugate Chem.*, 19:759-765, (2008).
Axup, J. Y. et al., "Synthesis of site-specific antibody-drug conjugates using unnatural amino acids", Proceedings of the National Academy Sciences, 109(40), 16101-16106 (2012).
Barok, M. et al., "Trastuzumab-DM1 causes tumour growth inhibition by mitotic catastrophe in trastuzumabresistant breast cancer cells in vivo", *Breast Cancer Research*, 13: R46 (2011).

(Continued)

*Primary Examiner* — Li N Komatsu
(74) *Attorney, Agent, or Firm* — Finnegan, Henderson, Farabow, Garrett & Dunner, L.L.P.

(57) ABSTRACT

The present invention relates to an antibody-drug-conjugate. From one aspect, the invention relates to an anti-body-drug-conjugate comprising an antibody capable of binding to a Target, said antibody being conjugated to at least one drug selected from derivatives of dolastatin 10 and auristatins. The invention also comprises method of treatment and the use of said anti-body-drug-conjugate for the treatment of cancer.

17 Claims, 28 Drawing Sheets

Figures 1A, 1B, 1C:
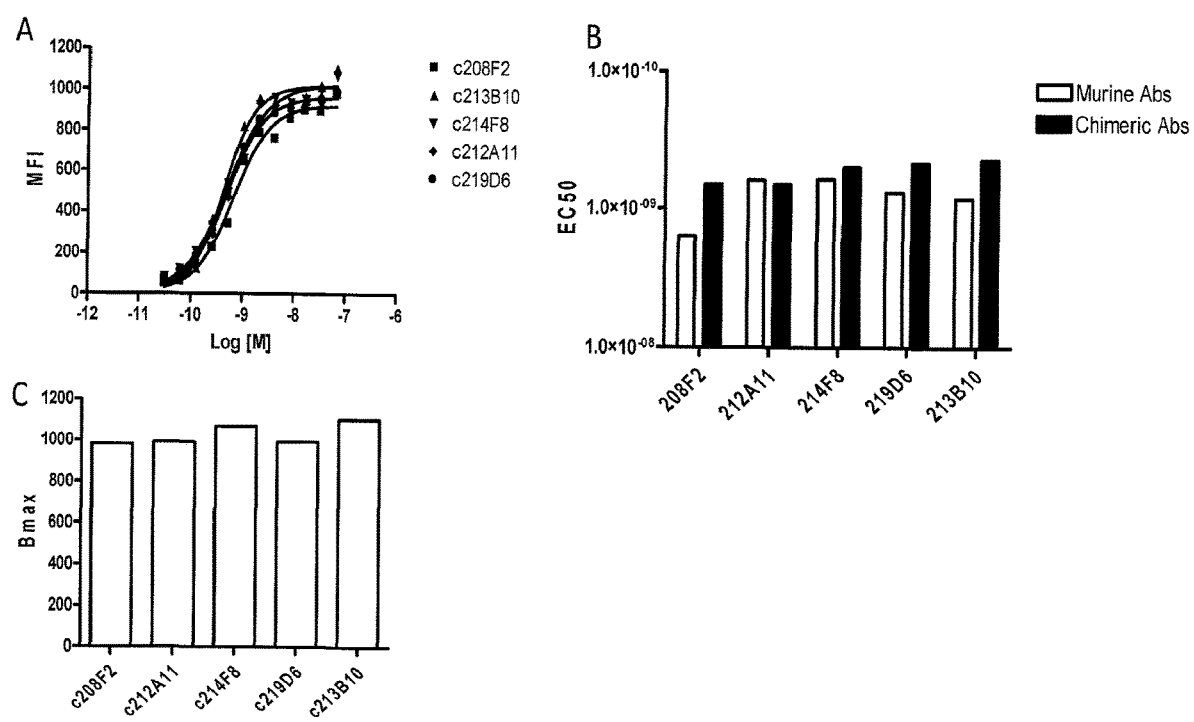

Specification includes a Sequence Listing.

(56) References Cited

FOREIGN PATENT DOCUMENTS

| WO | WO 2013/192360 A1 | 12/2013 |
|---|---|---|
| WO | WO 2014/008375 A1 | 1/2014 |
| WO | WO 2014/026286 A1 | 2/2014 |
| WO | WO 2014/096551 A1 | 6/2014 |
| WO | WO 2015/162293 A1 | 10/2015 |

OTHER PUBLICATIONS

Bitelman, C. et al., "IGF1R-Directed Targeted Therapy Enhances the Cytotoxic Effect of Chemotherapy in Endometrial Cancer," *Can. Let.*, 335:153-159 (2013).
Boulianne, G.L. et al., "Production of Functional Chimaeric Mouse/Human Antibody," *Nature*, 312:643-646, (1984).
Cretella, D. et al., "Trastuzumab Emtansine is Active on HER-2 Overexpressing NSCLC Cell Lines and Overcomes Gefitnib Resistance," *Mol. Can.*, 13:142, (2014).
Dornan, D. et al., "Dissecting Cancer Heterogeneity," *Nature Biotech.*, 29:1095-1096, (2011).
Dornan, D. et al., "Therapeutic Potential of an Anti-CD79b Antibody-Drug Conjugate, Anti-CD79n-vc-MMAE, for the Treatment of Non-Hodgkin Lymphoma," *Blood*, 114:2721-2729, (2009).
Doronina, S. et al., "Development of Potent Monoclonal Antibody Auristatin Conjugates for Cancer Therapy," *Nature Biotech.*, 21:778-784, (2003).
Francisco, J.A. et al., "cAC10-vcMMAE, An anti-CD30-Monomethyl Auristatin E Conjugate With Potent and Selective Antitumor Activity," *Blood*, 102:1458-1465, (2003).
Gerber, H. et al., "Potent Antitumor Activity of the anti-CD19 Auristatin Antibody Drug Conjugate hBu12-vcMMAE Against Rituximab-Sensitive and Resistant Lymphomas," *Blood*, 113:4352-4361, (2008).
International Search Report for PCT Application No. PCT/EP2014/058422 dated Aug. 21, 2014.
International Search Report for PCT Application No. PCT/EP2015/059050 dated Sep. 2, 2015.
Junutula, J. et al., "Site-Specific Conjugation of a Cytotoxic Drug to an Antibody Improves the Therapeutic Index," *Nature Biotech.*, 26:925-932, (2008).
Kaas, Q. et al., "IMGAT/3Dstructure-DB and IMGT/StructuralQuery, a Database and a Tool for Immunoglobulin, T Cell Receptor and MHC Structural Data," *Nucleic Acids Res.*, 32:D208-D210, (2004).
Kaas, Q. et al., "IMGT Colliers de Perles: Standardized Sequence-Structure Representations of the IgSF and MhcSF Superfamily Domains," *Curr. Bioinform.*, 2:21-30, (2007).
Kohler, G. et al., "Continuous Cultures of Fused Cells Secreting Antibody of Predefined Specificity," *Nature*, 256:495-497, (1975).
Law, C.L. et al., "Efficient Elimination of B-Lineage Lymphomas by anti-CD20-Auristatin Conjugates," *Clin. Can. Res.*, 10:7842-7851, (2004).
LeFranc, M.P. et al., "IMGT Unique Numbering for Immunoglobulin and T Cell Receptor Variable Domains and Ig Superfamily V-Like Domains," *Devl. & Comp. Immuno.*, 27:55-77, (2003).
LeFranc, M.P. et al., "The IMGT Unique Numbering for Immunoglobulins, T-Cell Receptors, and Ig-Like Domains," *The Immuno.*, 7:132-136, (1999).
LeFranc, M.P. et al., "Unique Database Numbering System for Immunogenetic Analysis," *Immuno. Today*, 18, (1997).
Li, D. et al., "DCDT2980S, An Anti-CD22-Monomethyl Auristatin E Antibody-Drug Conjugate, Is a Potential Treatment for Non-Hodgkin Lymphoma," *Mol. Can. Ther.*, 12:1255-1265 (2013).
Liu, H. et al., "Disulfide Bond Structures of IgG Molecules," mAbs, 4:17-23, (2012).
Miyasaki, K. et al., "Synthesis and Antitumor Activity of Novel Dolastatin 10 Analogs",*Chem. Pharm. Bull.*, 43, 1706-1718 (1995).
Miyasaki, K. et al., "Synthesis of dolastatin 10 analogs", *Peptide Chemistry*, 31, 85-88 (1993).
Needleman, S.B. et al., "A General Method Applicable to the search for Similarities in the Amino Acid Sequence of Two Proteins," *J. Mol. Biol.*, 48:443-453, (1970).
Ohtani, M. et al., "Mechanisms of Antibody-Mediated Insulin-Like Growth Factor I Receptor (IGF-IR) Down-Regulation in MCF-7 Breast Cancer Cells," *BioScience Trends*, 3:131-138, (2009).
Pearson, W.R. et al., "Improved Tools for Biological Sequence Comparison," *Proc. Natl. Acad. Sci.*, 85:2444-2449, (1988).
Pelicano, H. et al., "Glycolysis inhibition for anticancer treatment," Oncogene, 25, pp. 4633-4646 (2006).
Pettit, G.R. et al., "Chiral Modifications of Dolastatin 10: The Potent Cytostatic Peptide (19aR)-Isodolastatin $10^1$", *J. Med. Chem.*, 33, 3132-3133 (1990).
Pettit, G.R. et al., "Isolation and Structure of the Cell Growth Inhibitory Depsipeptides Dolastatins 11 and $12.^{1a,b}$" *Heterocycles*, 28, 553-558 (1989).
Pettit, G.R. et al., "Isolation and Structure of the Cytostatic Depsipeptide Dolastatin 13 from the Sea Hare *Dolabella auricularia*$^1$", *J. Am. Chem. Soc.*, 111, 5015-5017 (1989).
Pettit, G.R. et al., "The Isolation and Structure of a Remarkable Marine Animal Antineoplastic Constituent: Dolastatin $10^{1a}$", *J. Am. Chem. Soc.*, 109, 6883-6885 (1987).
Pettit, G.R. et al., "The Structure and Synthesis of Dolastatin $3^{1a}$", *J. Am. Chem. Soc.*, 109, 7581-7582 (1987).
Pettit, G.R., "Antineoplastic agents 365. Dolastatin 10 SAR probes", *Anti-cancer Drug Design*, 13, 243-277 (1998).
Pettit, G.R., "Antineoplastic Agents. 220. Synthesis of Natural (--)—Dolastatin $15^1$", *J. Am. Chern. Soc.*, 113, 6692-6693 (1991).
Pettit, R.K. et al., "Specific Activities of Dolastatin 10 and Peptide Derivatives against *Cryptococcus neoformans*"*Antimicrobial Agents and Chemotherapy*, 42:11, 2961-2965 (1998).
Polson, A.G. et al., "Antibody-Drug Conjugates Targeted to CD79 for the Treatment of Non-Hodgkin Lymphoma," *Blood*, 110:616-623 (2007).
Polson, A.G., et al., "Antibody-Drug Conjugates Targeted to CD79 for the Treatment of Non-Hodgkin Lymphoma," *Blood*, 110:1458-1465, (2007).
Reichmann, L. et al., "Reshaping Human Antibodies for Therapy," *Nature*, 332:323-327, (1988).
Ruiz, M. et al., "IMGT Gene Identificatoin and Colliers de Perles of Human Immunoglobulins with Known 3D Structures," *Immunogen.*, 53:857-883, (2002).
Smith, M.S. et al, "Comparison of Biosequences," Advan. App. Math., 2:482-489, (1981).
Tatsuova, T.A. et al., "BLAST 2 Sequences, a New Tool for Comparing Protein and Nucleotide Sequences," *FEMS Microbiol. Ltrs.*, 174:247-250, (1999).
Teicher, B.A. et al., "Antibody-Drug Conjugate Targets," *Curr. Can. Drug, Targ.*, 9:982-1004, (2009).
Zhu et al. "Design of next generation antibody drug conjugates," Acta Pharmaceutica Sinica 2013, 48(7), 1053-1070, Abstract only.

* cited by examiner

ANTIBODY-DRUG-CONJUGATE AND ITS USE FOR THE TREATMENT OF CANCER

CROSS-REFERENCE TO RELATED APPLICATIONS

This application is a continuation of application Ser. No. 15/306,404, filed on Oct. 24, 2016, which is a U.S. national phase entry of International Application No. PCT/EP2015/059052, filed on Apr. 27, 2015, which claims priority of European Patent Application No. 14305621.6, filed on Apr. 25, 2014.

SEQUENCE LISTING

The instant application contains a Sequence Listing which has been submitted electronically in ASCII format and is hereby incorporated by reference in its entirety. Said ASCII copy, submitted on May 7, 2018, is named 03715_0212_01000_SL.txt and is 164,281 bytes in size.

FIELD

The present invention relates to an antibody-drug-conjugate. From one aspect, the invention relates to an antibody-drug-conjugate comprising an antibody capable of binding to a target, said antibody being conjugated to at least one drug selected from derivatives of dolastatin 10 and auristatins. The invention also comprises method of treatment and the use of said antibody-drug-conjugate for the treatment of cancer.

BACKGROUND OF THE INVENTION

The invention relates to an antibody-drug-conjugate (ADC) or conjugate and its use for the treatment of cancer.

ADCs combine the binding specificity of an antibody with the potency of drugs such as, for example, cytotoxic agents. The technology associated with the development of monoclonal antibodies, the use of more effective drugs and the design of chemical linkers to covalently bind these components, has progressed rapidly in recent years.

The use of ADCs allows the local delivery of drugs which, if administered as unconjugated drugs, may result in unacceptable levels of toxicity to normal cells.

In other words, maximal efficacy with minimal toxicity is sought thereby. Efforts to design and refine ADC have focused on the selectivity of antibody as well as drug mechanism of action, drug-linking, drug/antibody ratio (loading or DAR), and drug-releasing properties. Drug moieties may impart their cytotoxic and cytostatic effects by mechanisms including tubulin binding, DNA binding, proteasome, impairment of ribosome function, protein synthesis and/or topoisomerase inhibition. Some cytotoxic drugs tend to be inactive or less active when conjugated to large antibody.

Each antibody must be characterized separately, an appropriate linker designed, and a suitable cytotoxic agent identified that retains its potency upon delivery to tumor cells. One must consider the antigen density on the cancer target and whether normal tissues express the target antigen. Other considerations include whether the entire ADC is internalized upon binding the target; whether a cytostatic or cytotoxic drug is preferable when considering possible normal tissue exposure and/or the type and stage of the cancer being treated; and, whether the linker connecting the antibody to the drug payload is a cleavable or a non-cleavable linkage.

Furthermore, the antibody to drug moiety conjugation ratio must be sufficient without compromising the binding activity of the antibody and/or the potency of the drug and without modifying physicochemical properties of the ADC resulting on aggregation or deleterious properties regarding to the future development process of the compound.

An ADC is a complex biological molecule and the challenges to develop an effective ADC remain a significant issue.

SUMMARY OF THE INVENTION

In a first aspect, the present invention is directed to an antibody-drug-conjugate of the following formula (I):

or a pharmaceutically acceptable salt thereof,
wherein
Ab is a [Target] antibody or an antigen antibody, or a [Target] binding fragment thereof or an antigen binding fragment thereof;
L is a linker;
D is a drug moiety of the following formula (II):

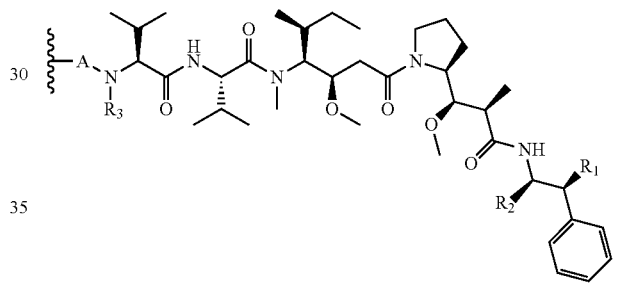

wherein:
$R_1$ is H or OH;
$R_2$ is a group: $(C_1-C_6)$alkyl, COOH, COO—$((C_1-C_6)$alkyl) or thiazolyl;
$R_3$ is H or a $(C_1-C_6)$alkyl group;
A is:
a group of formula -Het-Alk- wherein Alk is a $(C_1-C_8)$ alkanediyl group and is linked to $NR_3$, and Het is a heterocycle optionally substituted by a $(C_1-C_6)$alkyl group and containing at least one nitrogen atom, said nitrogen atom being linked to L, or
a group of formula -$A_a$-$A_b$- wherein $A_a$ is linked to L and is O or $NR_9$ with $R_9$ being H or $(C_1-C_6)$alkyl and $A_b$ is linked to $NR_3$ and is:
a $(C_1-C_8)$alkanediyl group,
a —$(CH_2CH_2X_1)_{a1}(CH_2CH_2X_2)_{a2}(CH_2CH_2X_3)_{a3}$ $(CH_2CH_2X_4)_{a4}CH_2CH_2$— group with $X_1$, $X_2$, $X_3$ and $X_4$ each independently of one another representing O or $NR_8$; a1, a2, a3 and a4 each independently of one another representing 0 or 1; and $R_8$ representing H or a $(C_1-C_6)$alkyl group,
an aryl-$(C_1-C_8)$alkanediyl or heterocycle-$(C_1-C_8)$alkanediyl group, said group being optionally substituted by a $(C_1-C_6)$alkyl group, the aryl or heterocycle moiety being linked to $A_a$ and the $(C_1-C_8)$alkanediyl moiety being linked to $NR_3$;
the wavy line indicates the point of attachment to L; and
n is 1 to 12.

In an embodiment, the present invention relates to an antibody-drug-conjugate according to the invention, wherein the [Target] or antigen of said [Target] antibody or antigen antibody according to the invention, or a [Target] or an antigen binding fragment thereof, is selected from CD19, CD20, CD22, CD25, CD30, CD33, CD40, CD56, CD64, CD70, CD74, CD79, CD105, CD138, CD174, CD205, CD227, CD326, CD340, MUC16, GPNMB, PSMA, Cripto, ED-B, TMEFF2, EphB2, EphA2, FAP, av integrin, Mesothelin, EGFR, TAG-72, GD2, CAIX, 5T4, HER1, HER3, HER2, IGF-1R, Axl and their extra cellular membrane (ECD) fragment.

In an embodiment, the present invention relates to an antibody-drug-conjugate according to the invention, wherein the [Target] or antigen of said [Target] antibody or antigen antibody according to the invention, or a [Target] or an antigen binding fragment thereof, is selected from the HER2, the IGF-1R and the protein Axl, preferably the human HER2, human IGF-1R and the human protein Axl, and their extra cellular membrane (ECD) fragment.

In an embodiment, the present invention relates to an antibody-drug-conjugate according to the invention, wherein said Ab is an antibody, or an antigen binding fragment thereof, capable of binding to the human IGF-1R selected from:
i) the antibodies 208F2, 212A11, 214F8, 219D6 and 213B10;
ii) the antibodies which compete for binding to IGF-1R with the antibodies of i); and
iii) the antibodies which bind to the same epitope of IGF-1R as the antibodies of i).

In an embodiment, the present invention relates to an antibody-drug-conjugate according to the invention, wherein said Ab is an antibody, or an antigen binding fragment thereof, capable of binding to the human IGF-1R selected from:
i) an antibody which comprises the three heavy chain CDRs of sequence SEQ ID NO: 1, 2 and 3 and the three light chain CDRs of sequence SEQ ID NO: 4, 5 and 6;
ii) an antibody which competes for binding to IGF-1R with the antibody of i); and
iii) an antibody which binds to the same epitope of IGF-1R as the antibody of i).

In an embodiment, the present invention relates to an antibody-drug-conjugate according to the invention, wherein said Ab is an antibody which comprises:
a) a heavy chain variable domain (VH) of sequence SEQ ID NO: 33 wherein said sequence SEQ ID NO: 33 comprises at least 1 back-mutation selected from the residues 20, 34, 35, 38, 48, 50, 59, 61, 62, 70, 72, 74, 76, 77, 79, 82 or 95; and
b) a light chain variable domain (VL) of sequence SEQ ID NO: 35, wherein said sequence SEQ ID NO: 35 comprises at least 1 back-mutation selected from the residues 22, 53, 55, 65, 71, 72, 77 or 87.

In an embodiment, the present invention relates to an antibody-drug-conjugate according to the invention, wherein said Ab is an antibody, or an antigen binding fragment thereof, capable of binding to the human protein Axl selected from:
i) an antibody which comprises the three heavy chain CDRs of sequence SEQ ID NO: 59, 60 and 61 and the three light chain CDRs of sequence SEQ ID NO: 56, 57 and 58;
ii) an antibody which competes for binding to Axl with the antibody of i); and
iii) an antibody which binds to the same epitope of Axl as the antibody of i).

In an embodiment, the present invention relates to an antibody-drug-conjugate according to the invention, wherein said Ab is an antibody, or an antigen binding fragment thereof, capable of binding to the human HER2, preferably consisting of Trastuzumab.

In an embodiment, the present invention relates to an antibody-drug-conjugate according to the invention, wherein L is a linker of the following formula (III):

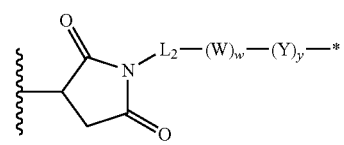

(III)

wherein
$L_2$ is $(C_4-C_{10})$cycloalkyl-carbonyl, $(C_2-C_6)$alkyl, $(C_2-C_6)$alkyl-carbonyl,
W is an amino acid unit; w is an integer comprised between 0 and 5;
Y is PAB-carbonyl with PAB being

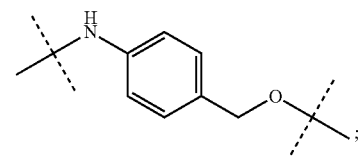

;

y is 0 or 1;
the asterisk indicates the point of attachment to D; and
the wavy line indicates the point of attachment to Ab.

In an embodiment, the present invention relates to an antibody-drug-conjugate according to the invention, wherein $L_2$ is of the following formula:

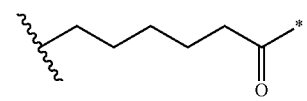 [SMILES: *CCCCCC(*)=O]

wherein
the asterisk indicates the point of attachment to $(W)_w$; and
the wavy line indicates the point of attachment to the nitrogen atom of the maleimide moiety.

In an embodiment, the present invention relates to an antibody-drug-conjugate according to the invention, wherein w=0, or w=2 and then $(W)_w$ is selected from:

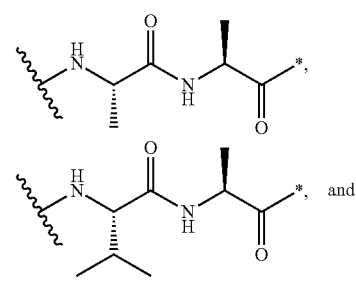

-continued

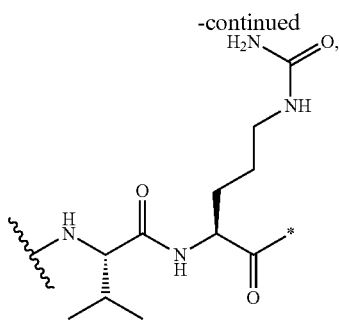

wherein
the asterisk indicates the point of attachment to $(Y)_y$; and
the wavy line indicates the point of attachment to $L_2$.

In an embodiment, the present invention relates to an antibody-drug-conjugate according to the invention, wherein L is selected from:

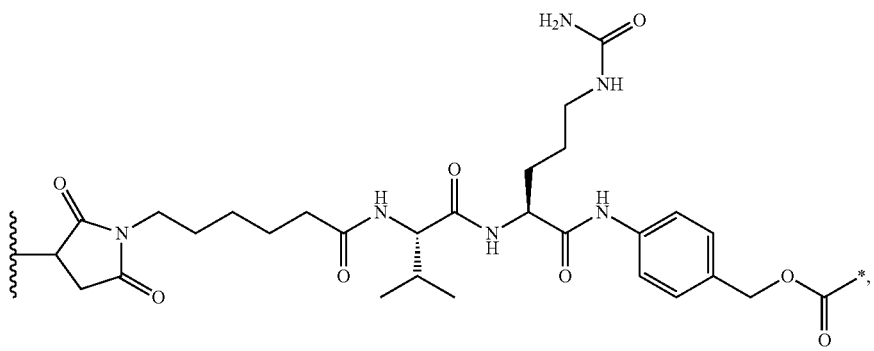

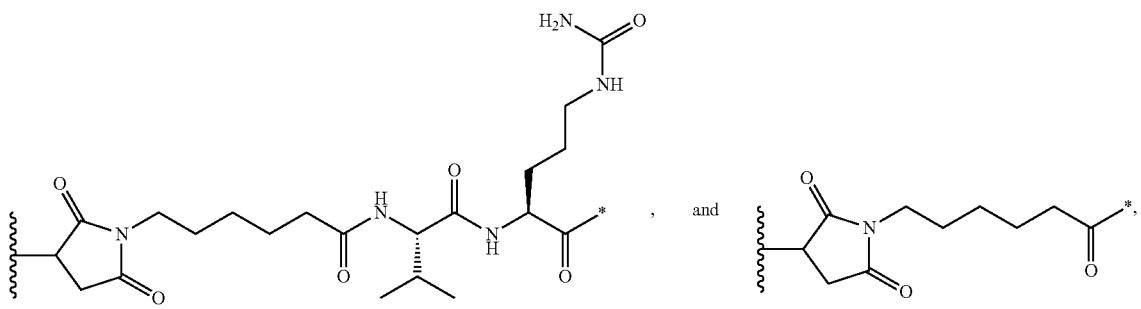

wherein the asterisk indicates the point of attachment to D, and the wavy line indicates the point of attachment to Ab.

In an embodiment, the present invention relates to an antibody-drug-conjugate according to the invention, wherein A is a group of formula $-A_a-A_b-$ in which $A_a$ is as defined in claim 1 and $A_b$ is a group:
phenyl-$(C_1-C_2)$alkanediyl, or
heterocycle-$(C_1-C_2)$alkanediyl optionally substituted by a $(C_1-C_6)$alkyl group (notably unsubstituted), the heterocycle being a saturated, unsaturated or aromatic ring with 5 or 6 members comprising 1 or 2 nitrogen atoms, chosen in particular from among pyridine, piperidine and imidazole, and being preferably a pyridine.

In an embodiment, the present invention relates to an antibody-drug-conjugate according to the invention, wherein A is a group of the following formula:

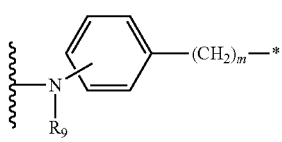

wherein:
$R_9$ is as defined in claim 1 and m is an integer comprised between 1 and 8, and preferably wherein $R_9$=H or Me and m=1 or 2,
the wavy line indicates the point of attachment to L, and
the asterisk indicates the point of attachment to $NR_3$.

In an embodiment, the present invention relates to an antibody-drug-conjugate according to the invention, wherein (L-D) is selected from:

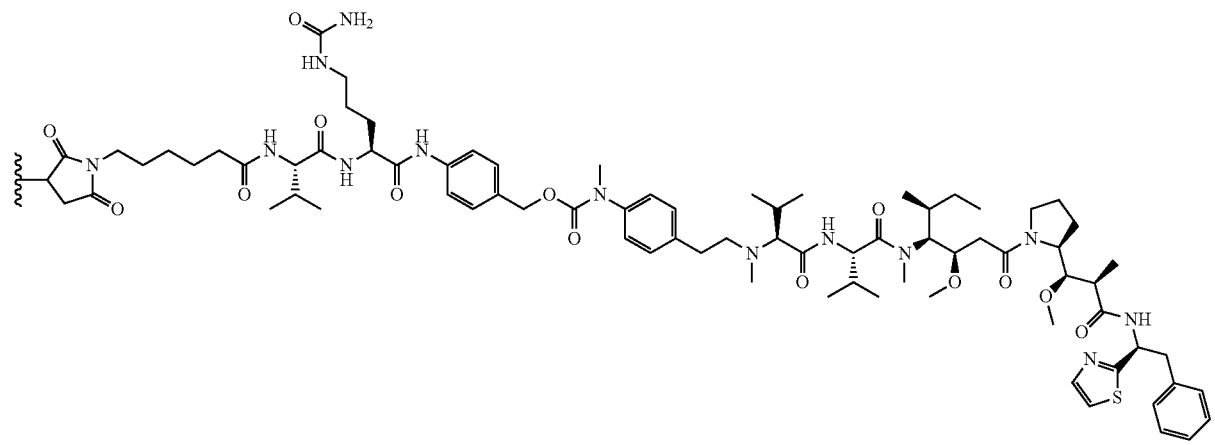
(E-11)
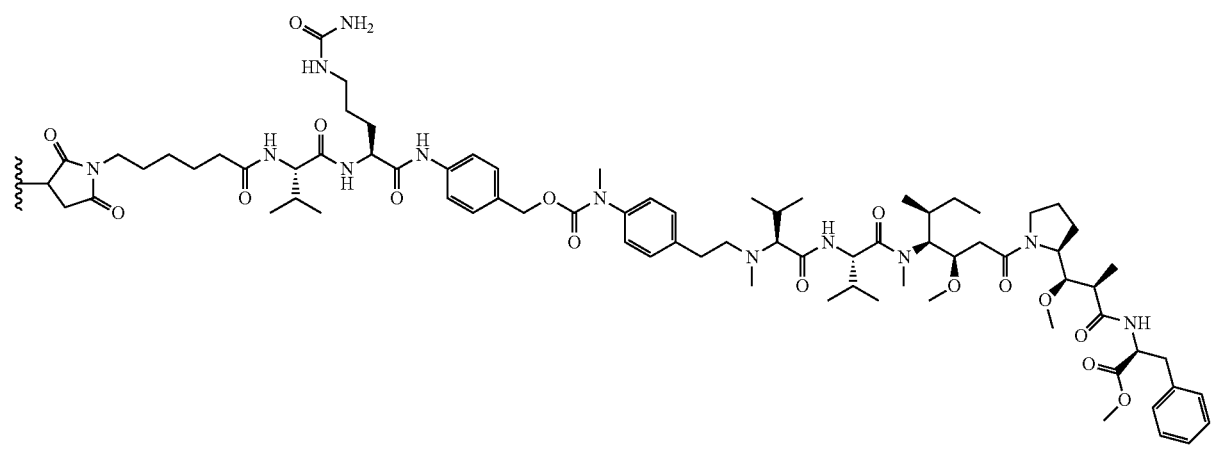
(E-12)
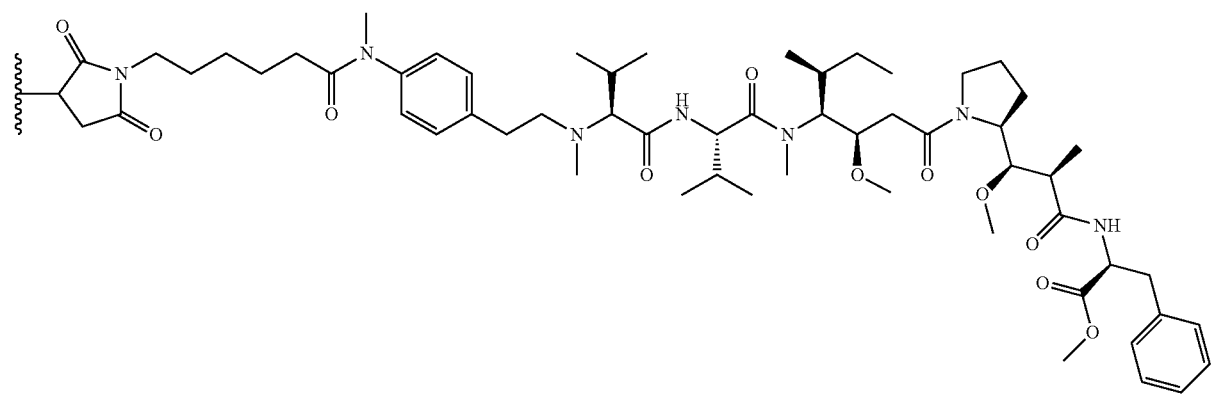
(G-12)

(E-13)
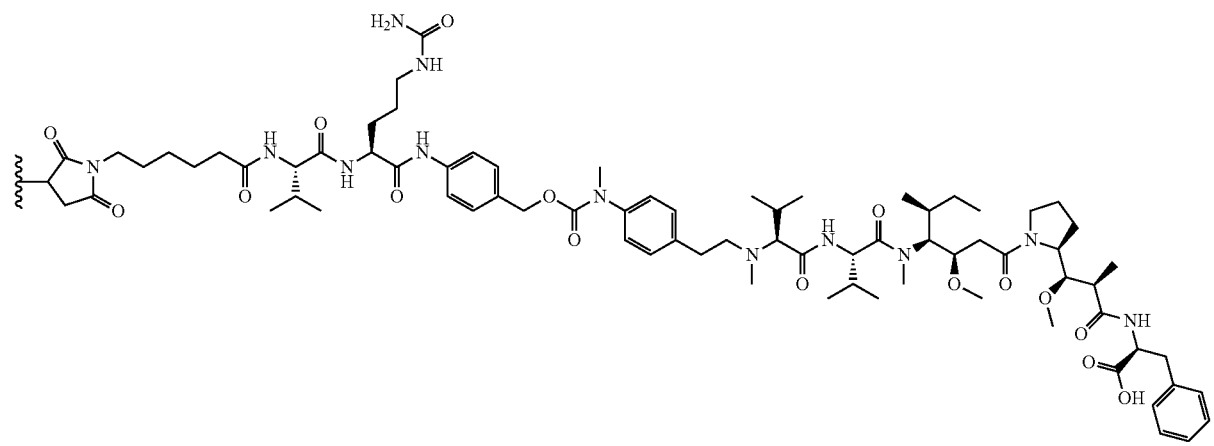
(F-13)
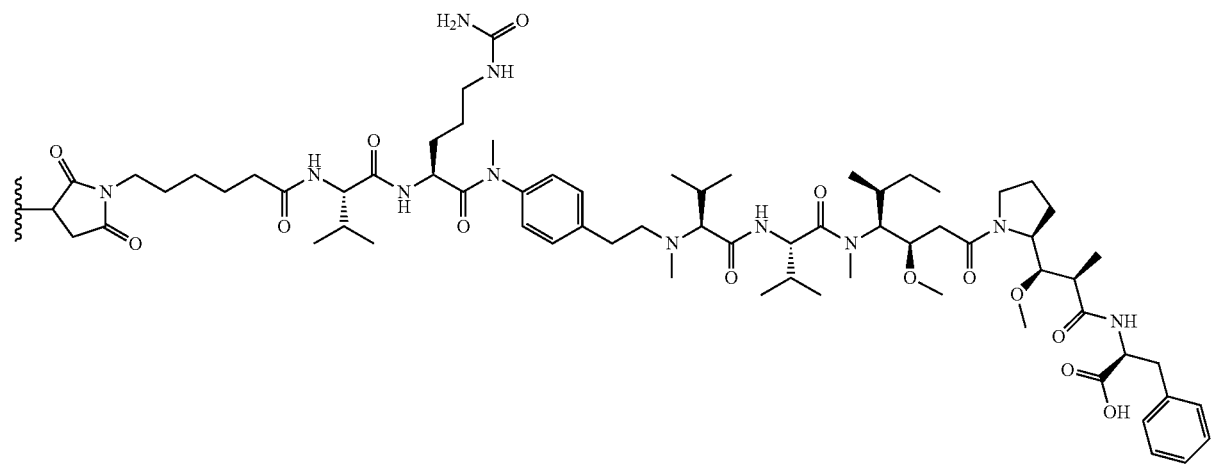
(G-13)
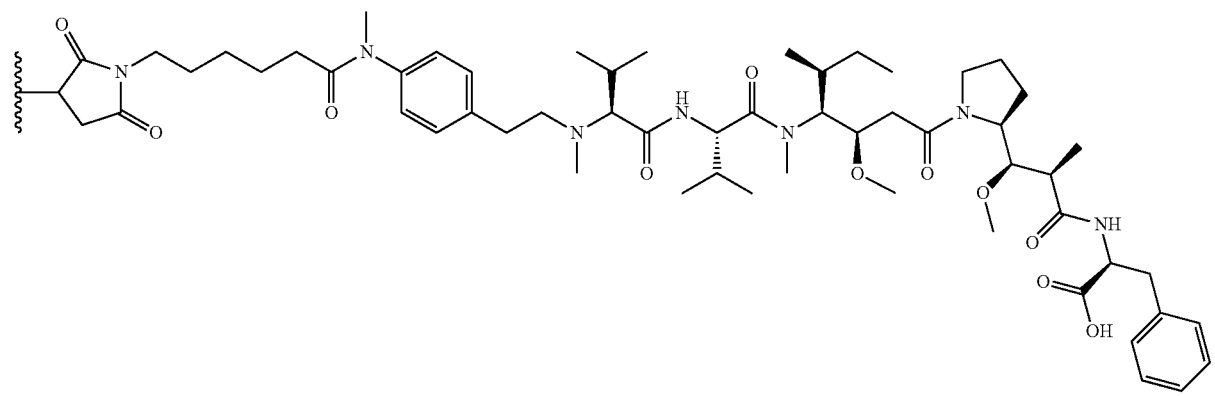

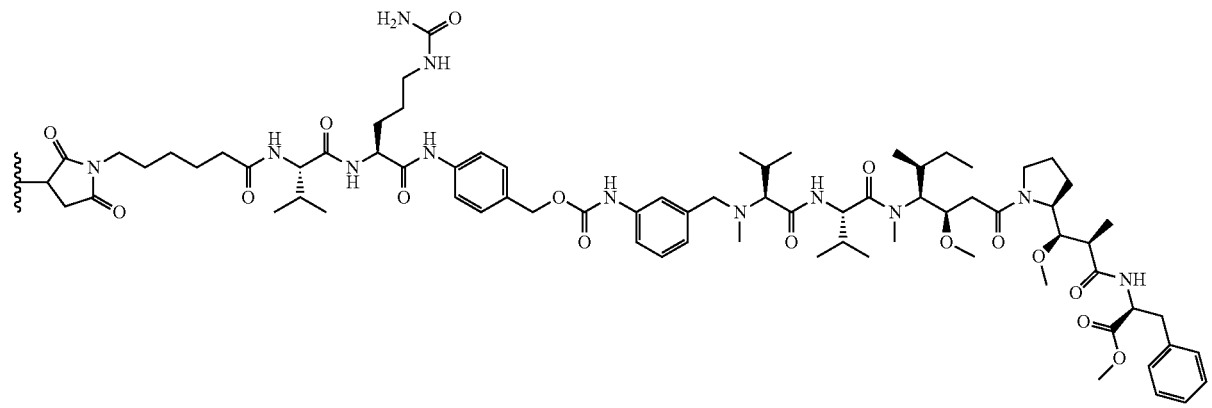
(E-15)
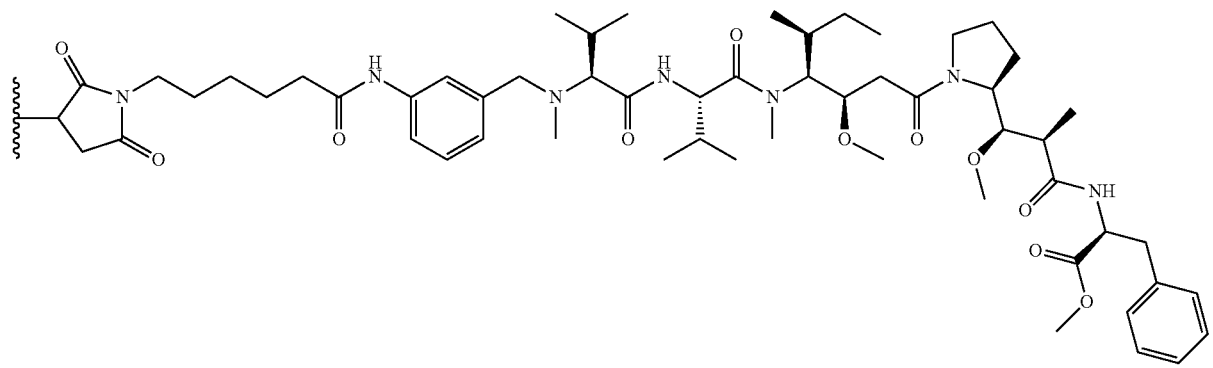
(G-15)
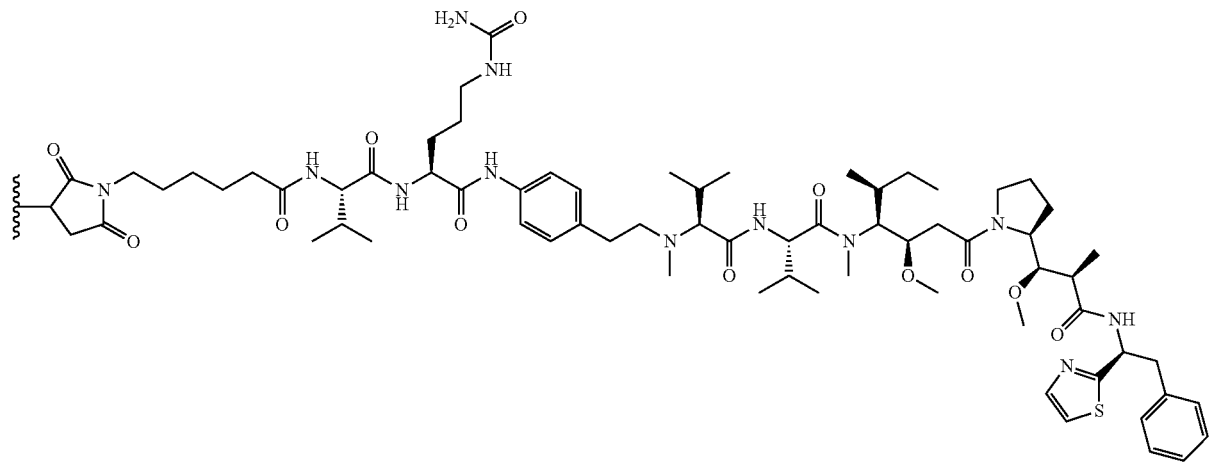
(F-61)

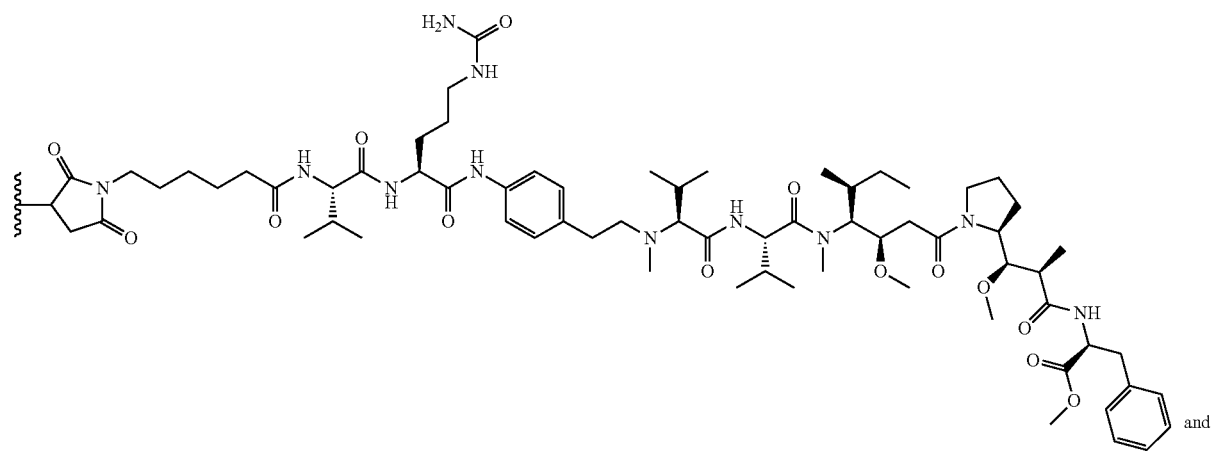
(F-62)
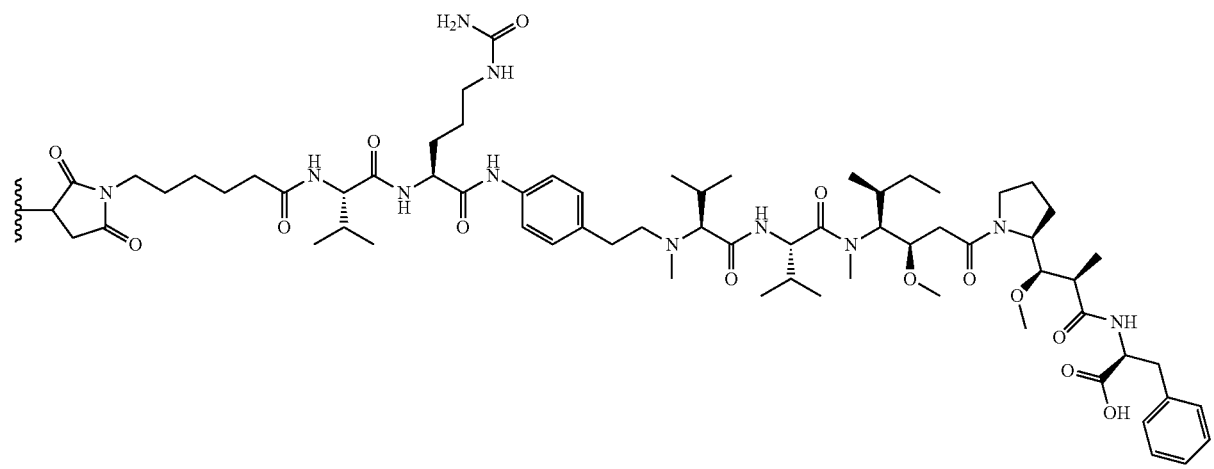
and
(F-63)
wherein the wavy line indicates the point of attachment to Ab.
In another embodiment, the present invention relates to an antibody-drug-conjugate according to the invention, having the formula selected from:
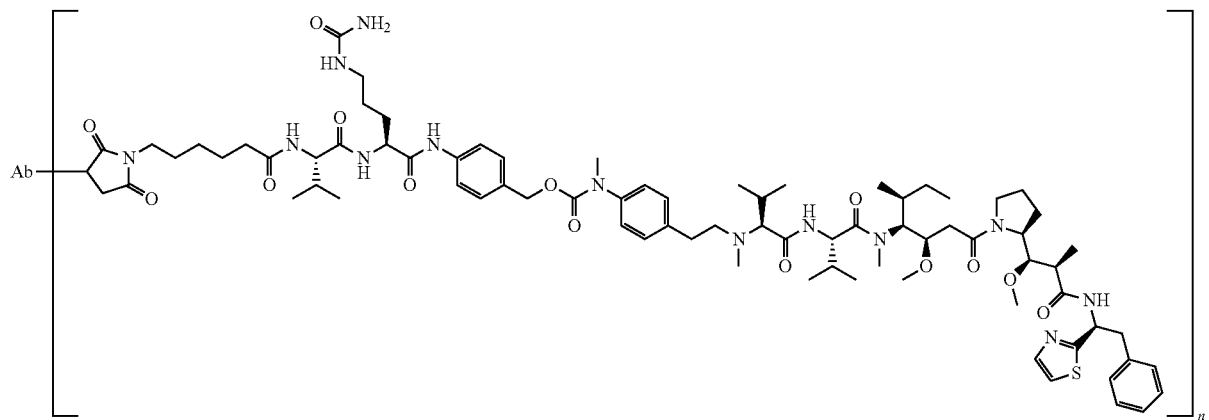
(Ab-E-11)

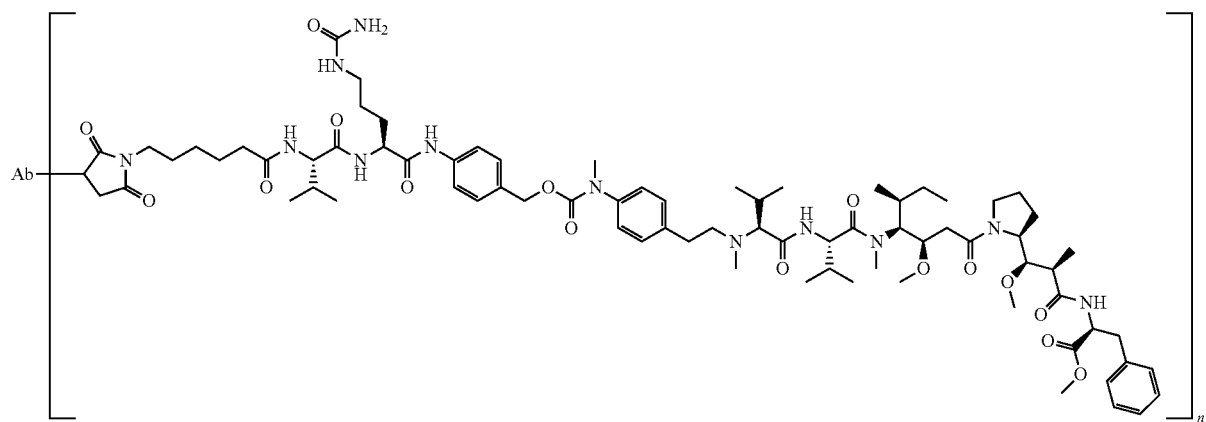
(Ab-E-12)
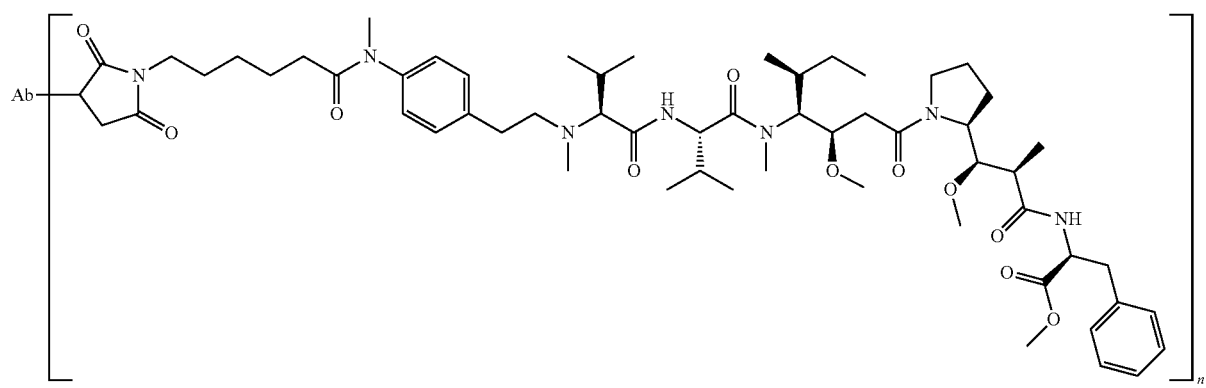
(Ab-G-12)
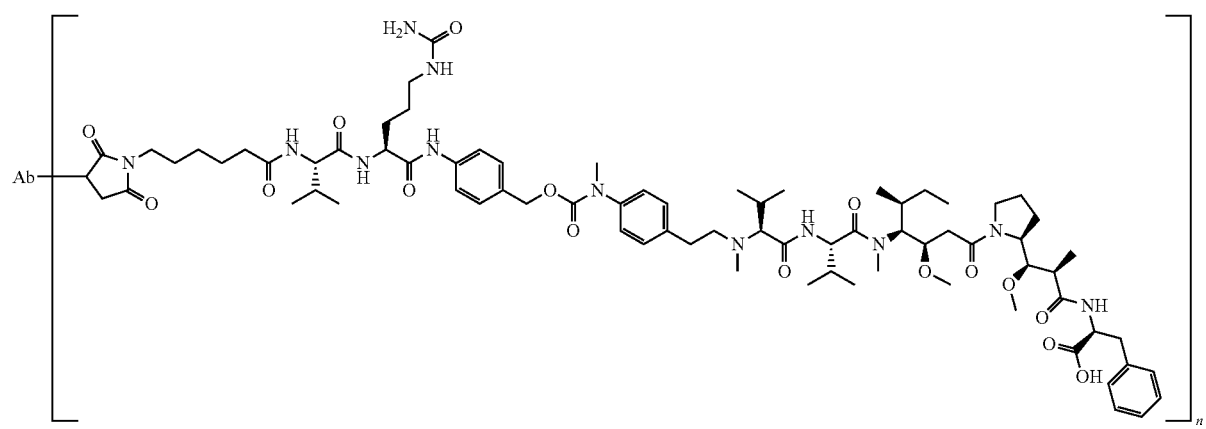
(Ab-E-13)

-continued
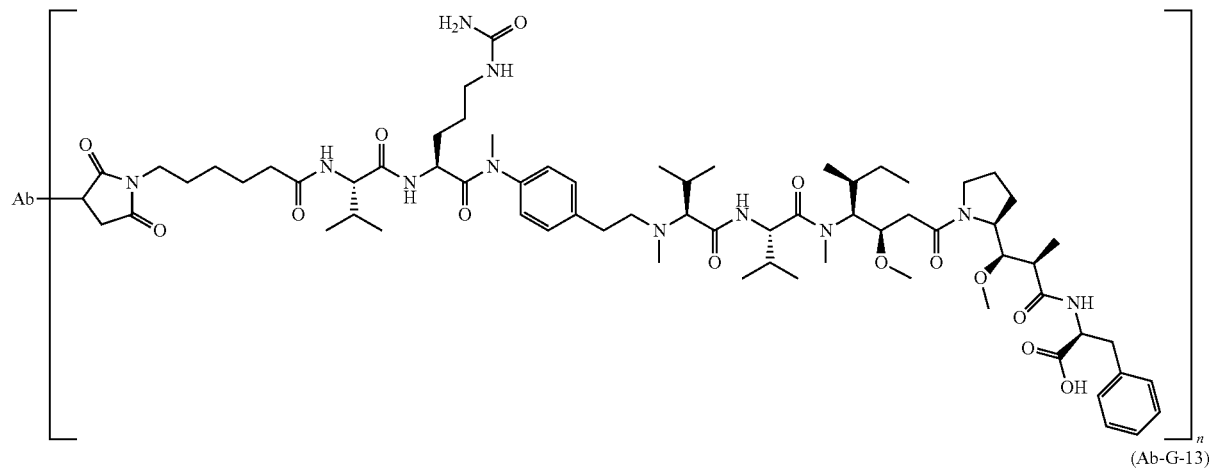
(Ab-F-13)
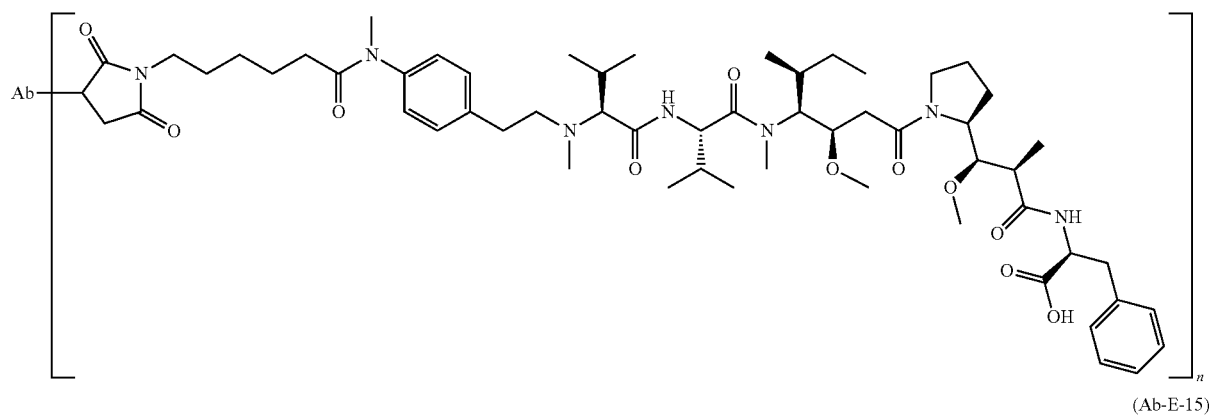
(Ab-G-13)
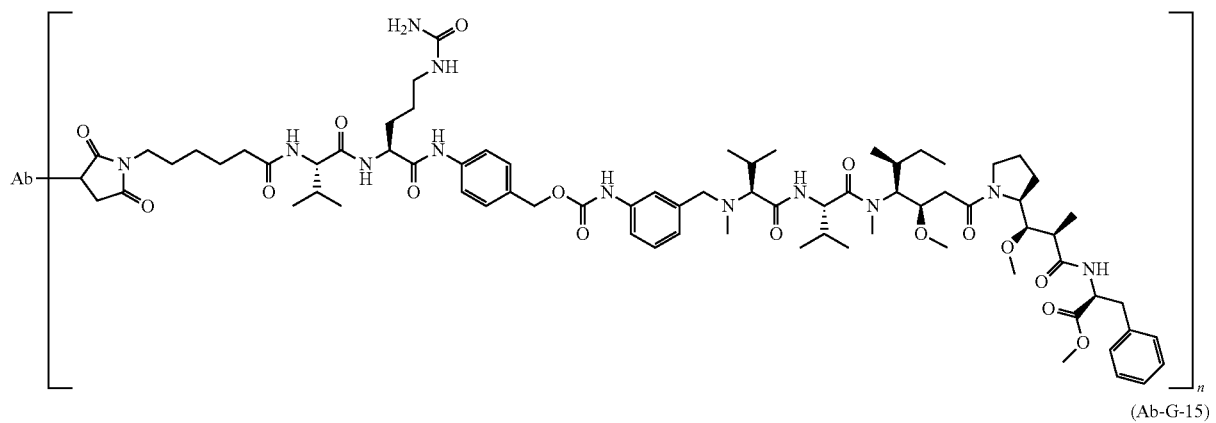
(Ab-E-15)
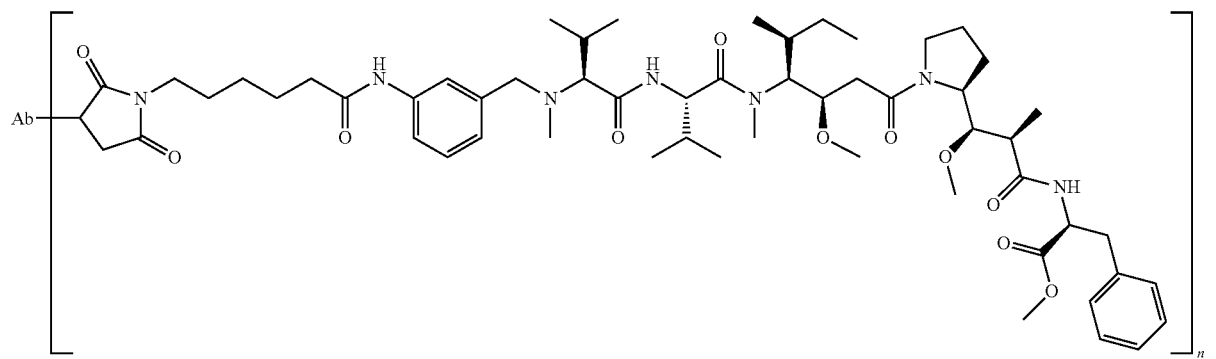
(Ab-G-15)

-continued

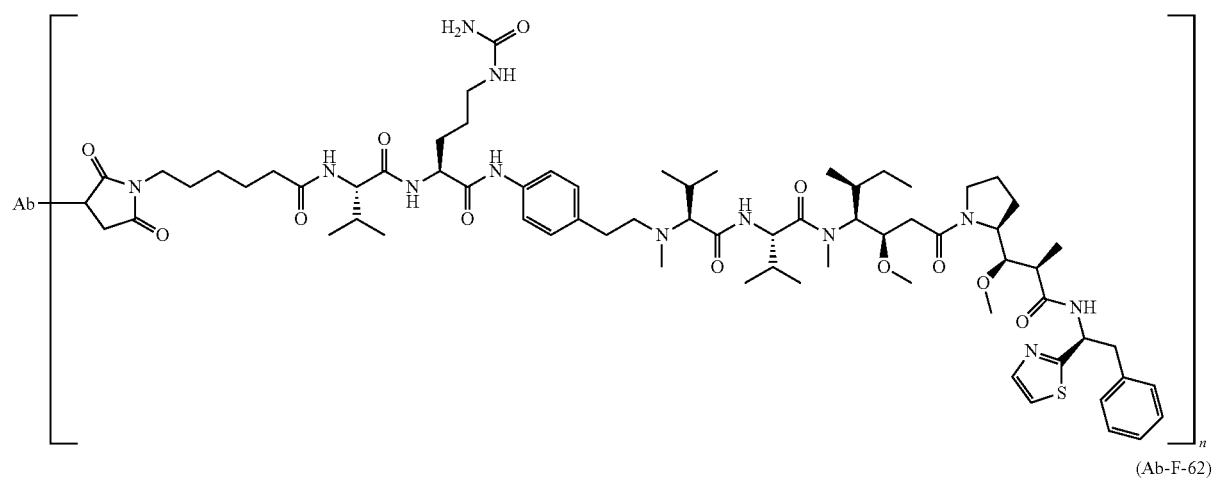
(Ab-F-61)

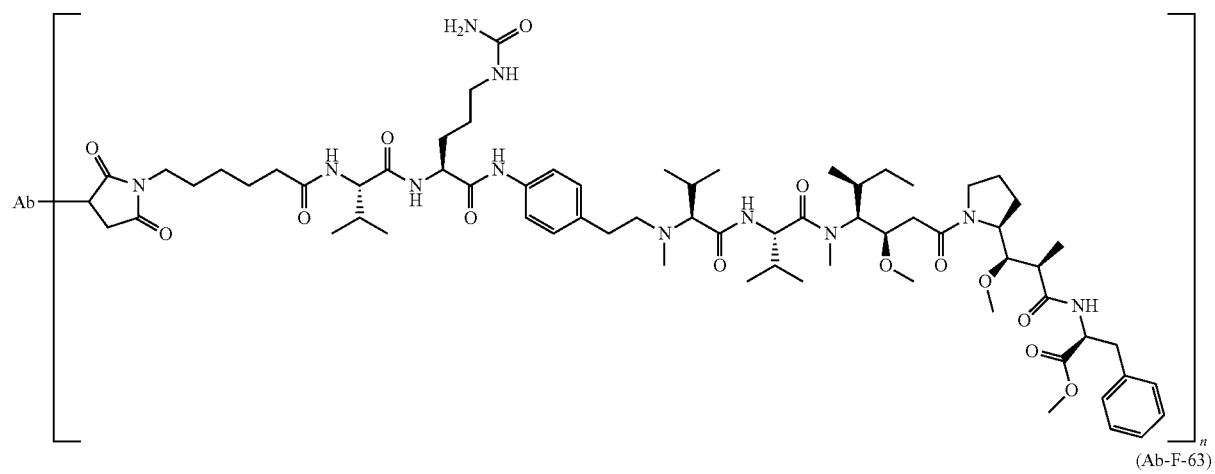
(Ab-F-62)

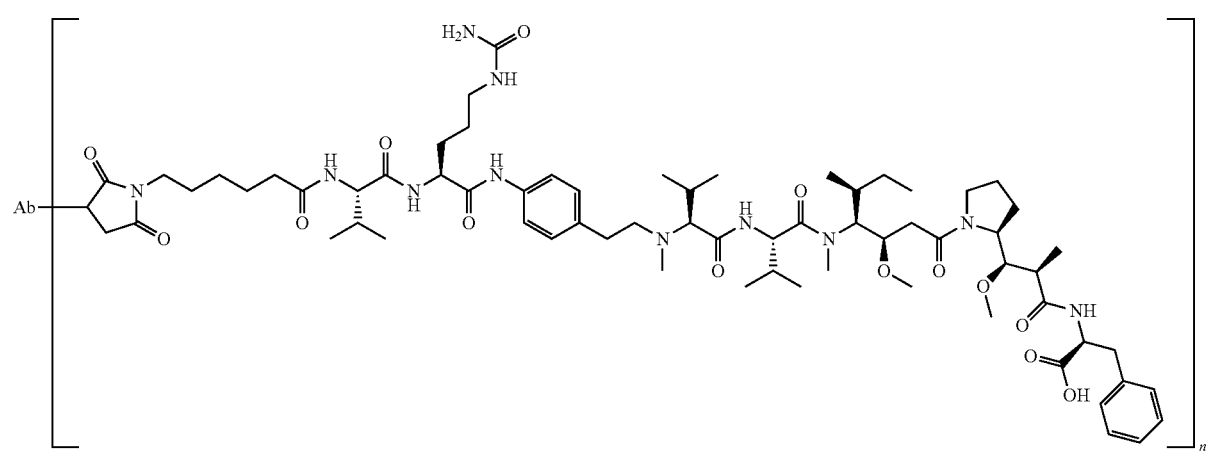
(Ab-F-63)

and the pharmaceutically acceptable salts thereof, wherein Ab is a [Target] antibody or an antigen antibody, or a [Target] binding fragment thereof or an antigen binding fragment thereof.

In an embodiment, and according to the invention, said Ab is a [Target] antibody or an antigen antibody, or a [Target] binding fragment thereof or an antigen binding fragment thereof wherein said [Target] or antigen is selected from CD19, CD20, CD22, CD25, CD30, CD33, CD40, CD56, CD64, CD70, CD74, CD79, CD105, CD138, CD174, CD205, CD227, CD326, CD340, MUC16, GPNMB, PSMA, Cripto, ED-B, TMEFF2, EphB2, EphA2, FAP, av integrin, Mesothelin, EGFR, TAG-72, GD2, CAIX, 5T4, HER1, HER3, HER2, IGF-1R, Axl and their extra cellular membrane (ECD) fragment.

In an embodiment, and according to the invention, said Ab is a [Target] antibody or antigen antibody, or a [Target] or an antigen binding fragment thereof, wherein said [Target] or antigen is selected from the HER2, the IGF-1R and the protein Axl, preferably the human HER2, the human IGF-1R and the human protein Axl, and their extra cellular membrane (ECD) fragment.

In an embodiment, and according to the invention, said Ab is an antibody, or an antigen binding fragment thereof, and is selected from:

a) an Ab, or an antigen binding fragment thereof, capable of binding to the human IGF-1R selected from:
  i) the antibodies 208F2, 212A11, 214F8, 219D6 and 213B10;
  ii) the antibodies which compete for binding to IGF-1R with the antibodies of i); and
  iii) the antibodies which bind to the same epitope of IGF-1R as the antibodies of i), b) an Ab, or an antigen binding fragment thereof, capable of binding to the human IGF-1R selected from:
  i) an antibody which comprises the three heavy chain CDRs of sequence SEQ ID NO: 1, 2 and 3 and the three light chain CDRs of sequence SEQ ID NO: 4, 5 and 6;
  ii) an antibody which competes for binding to IGF-1R with the antibody of i); and
  iii) an antibody which binds to the same epitope of IGF-1R as the antibody of i), c) an Ab which comprises:
  i) a heavy chain variable domain (VH) of sequence SEQ ID NO: 33 wherein said sequence SEQ ID NO: 33 comprises at least 1 back-mutation selected from the residues 20, 34, 35, 38, 48, 50, 59, 61, 62, 70, 72, 74, 76, 77, 79, 82 or 95; and
  ii) a light chain variable domain (VL) of sequence SEQ ID NO: 35, wherein said sequence SEQ ID NO: 35 comprises at least 1 back-mutation selected from the residues 22, 53, 55, 65, 71, 72, 77 or 87, d) an Ab, or an antigen binding fragment thereof, capable of binding to the human protein Axl selected from:
  i) an antibody which comprises the three heavy chain CDRs of sequence SEQ ID NO: 59, 60 and 61 and the three light chain CDRs of sequence SEQ ID NO: 56, 57 and 58;
  ii) an antibody which competes for binding to Axl with the antibody of i); and
  iii) an antibody which binds to the same epitope of Axl as the antibody of i), and e) an Ab, or an antigen binding fragment thereof, capable of binding to the human HER2, preferably consisting of Trastuzumab or Pertuzumab.

In an embodiment, and according to the invention, n is 2 or n is 4.

In another embodiment, the present invention is directed to an antibody-drug-conjugate according to the present invention for use as a medicament.

In another embodiment, the present is directed to a composition comprising at least one antibody-drug-conjugate according to the present invention.

In an embodiment, the composition according to the present invention further comprises a pharmaceutically acceptable vehicle.

In another embodiment, the present invention is directed to a composition according to the present invention for use in the treatment of a [Target]- or an antigen-expressing cancer, said Target]- or an antigen being preferably selected from CD19, CD20, CD22, CD25, CD30, CD33, CD40, CD56, CD64, CD70, CD74, CD79, CD105, CD138, CD174, CD205, CD227, CD326, CD340, MUC16, GPNMB, PSMA, Cripto, ED-B, TMEFF2, EphB2, EphA2, FAP, av integrin, Mesothelin, EGFR, TAG-72, GD2, CAIX, 5T4, HER1, HER3, HER2, IGF-1R, Axl and their extra cellular membrane (ECD) fragment, more preferably from the HER2, the IGF-1R and the protein Axl, also more preferably the human HER2, the human IGF-1R and the human protein Axl, and their extra cellular membrane (ECD) fragment.

In an embodiment, said [Target]- or antigen-expressing cancer is a cancer chosen from breast, colon, esophageal carcinoma, hepatocellular, gastric, glioma, lung, melanoma, osteosarcoma, ovarian, prostate, rhabdomyosarcoma, renal, thyroid, uterine endometrial cancer, mesothelioma, oral squamous carcinoma, Kaposi sarcoma, acute leukemia, colorectal carcinoma, melanoma, pancreatic ductal adenocarcinoma and any drug resistant cancer.

In an embodiment, the present invention relates to a method for the treatment of a [Target]- or antigen-expressing cancer in a subject in need thereof, comprising administering to the subject an effective amount of at least one antibody-drug-conjugate according to the present invention or of a composition according to the present invention.

DETAILED DESCRIPTION OF THE INVENTION

I—The Antibody (Ab)

The terms "antibody", "antibodies" "ab", "MAb" or "immunoglobulin" are used interchangeably in the broadest sense and include monoclonal antibodies, preferably isolated, engineered or recombinant antibodies (e.g., full length or intact monoclonal antibodies), polyclonal antibodies, multivalent antibodies or multispecific antibodies (e.g., bispecific antibodies) and also antibody fragment thereof, so long as they exhibit the desired biological activity.

In an embodiment, the antibody of the invention consists of a recombinant antibody. The term "recombinant antibody" refers to an antibody that results from the expression of recombinant DNA within living cells. A recombinant antibody of the invention is obtained by using laboratory methods of genetic recombination, well known by a person skilled in the art, creating DNA sequences that would not be found in biological organisms.

In another embodiment, the antibody of the invention consists of a chemically synthesized antibody.

More particularly, such a molecule consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (C1q) of the classical complement system.

By "antigen binding fragment" or "target binding fragment" of an antibody according to the invention, it is intended to indicate any peptide, polypeptide, or protein retaining the ability to bind to the target (also generally referred as antigen) of the antibody. and comprising an amino acid sequence of at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of the antibody.

In an embodiment, such "antigen binding fragments" are selected in the group consisting of Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PE-Gylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of the antibody according to the invention. Preferably, said "antigen binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to ¹⁄₁₀₀, in a more preferred manner to at least ¹⁄₁₀, of the affinity of the antibody from which it is descended, with respect to the target.

By "binding", "binds", or the like, it is intended that antibody, or any antigen binding fragment thereof, forms a complex with an antigen that is relatively stable under physiologic conditions. Specific binding can be characterized by an equilibrium dissociation constant of at least about $1.10^{-6}$ M. Methods for determining whether two molecules bind are well known in the art and include, for example, equilibrium dialysis, surface plasmon resonance, radiolabelled assays and the like. For the avoidance of doubt, it does not mean that the said antibody could not bind or interfere, at a low level, to another antigen. Nevertheless, as a preferred embodiment, the said antibody binds only to the said antigen.

As used in the present specification, the expression "[Target] antibody" should be interpreted as similar to "anti-[Target] antibody" and means an antibody capable of binding to the [Target].

The expression "Target" or [Target] shall be interpreted as any molecule present at the surface of cells, preferably tumoral cells, more preferably mammals and human cells, and which can be used for drug delivery. Preferably, the Target is specifically express or overexpress on the surface of tumoral cells in comparison with normal cells.

More particularly, the Target can be selected from CD19, CD20, CD22, CD25, CD30, CD33, CD40, CD56, CD64, CD70, CD74, CD79, CD105, CD138, CD174, CD205, CD227, CD326, CD340, MUC16, GPNMB, PSMA, Cripto, ED-B, TMEFF2, EphB2, EphA2, FAP, av integrin, Mesothelin, EGFR, TAG-72, GD2, CAIX, 5T4, HER1, HER3, HER2, IGF-1R or Axl (B. A. Teicher, Current Cancer Drug Targets, 2009, 9, 982-1004).

As preferred Target, it can be mentioned HER2, IGF-1R and Axl, preferably human HER2, IGF-1R and Axl.

As non limitative example, the expression "HER2 antibody", "IGF-1R antibody" or "Axl antibody" should be interpreted as similar to "anti-HER2 antibody", "anti-IGF-1R antibody" or "anti-Axl antibody" and means an antibody capable of binding to HER2, IGF-1R or Axl, respectively.

In the present application, the epitope of the antibody is preferentially localized into the extracellular domain of the Target.

In a particular embodiment, the antibody, or any antigen binding fragment thereof, is capable of binding to the Target with an $EC_{50}$ comprised between $10 \cdot 10^{-10}$ to $1 \times 10^{-10}$, and more preferentially between $8 \times 10^{-10}$ to $2 \times 10^{-10}$.

The term half maximal effective concentration ($EC_{50}$) corresponds to the concentration of a drug, antibody or toxicant which induces a response halfway between the baseline and maximum after some specified exposure time. It is commonly used as a measure of drug's potency. The $EC_{50}$ of a graded dose response curve therefore represents the concentration of a compound where 50% of its maximal effect is observed. The $EC_{50}$ of a quantal dose response curve represents the concentration of a compound where 50% of the population exhibits a response, after specified exposure duration. Concentration measures typically follow a sigmoidal curve, increasing rapidly over a relatively small change in concentration. This can be determined mathematically by derivation of the best-fit line.

As a preferred embodiment, the $EC_{50}$, determined in the present invention, characterizes the potency of antibody to bind on the Target ECD exposed on human tumor cells. The $EC_{50}$ parameter is determined using FACS analysis. The $EC_{50}$ parameter reflects the antibody concentration for which 50% of the maximal binding on the human Target expressed on tumor cells is obtained. Each $EC_{50}$ value was calculated as the midpoint of the dose response curve using a four-parameter regression curve fitting program (PRISM® Software). This parameter has been selected as to be representative of physiological/pathological conditions.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The competition for binding to the Target can be determined by any methods or techniques known by the person skilled in the art such as, without limitation, radioactivity, BIACORE®, ELISA, Flow cytometry, etc. As "which competes for binding to the Target" it is meant a competition of at least 20%, preferentially at least 50% and more preferentially at least 70%.

The determination of the binding to the same epitope can be determined by any methods or techniques known by the person skilled in the art such as, without limitation in the examples, radioactivity, BIACORE®, ELISA, Flow cytometry. As "which bind to the same epitope of the Target", it is meant a competition of at least 20%, preferentially at least 50% and more preferentially at least 70%.

As above mentioned, and contrary to the general knowledge, the present invention focuses on specific antibodies presenting a high ability to be internalized following their binding to the Target. As used herein, an antibody that "is internalized" or that "internalized" (the two expressions being similar) is one that is taken up by (meaning it "enters") the cell upon binding to the Target on a mammalian cell. Such an antibody is interesting as part of the ADC, so it addresses the linked cytotoxic into the targeted cancer cells. Once internalized the cytotoxic triggers cancer cell death.

Important keys to success with ADC therapy are thought to be the target antigen specificity and the internalization of the antigen-antibody complexes into the cancer cells. Obviously non-internalizing antigens are less effective than internalizing antigens to delivers cytotoxic agents. Internalization processes are variable across antigens and depend on multiple parameters that can be influenced by antibodies.

In the ADC, the cytotoxic confers the cytotoxic activity and the used antibody is responsible for the specificity against cancer cells, as well as a vector for entering within the cells to correctly address the cytotoxic. Thus to improve the ADC, the antibody must exhibit high ability to internalize into the targeted cancer cells. The efficiency of the antibody mediated internalisation differs significantly depending on the epitope targeted. Selection of potent internalizing antibodies requires various experimental data studying not only the Target downregulation but also following the antibody penetration into the cells.

In a preferred embodiment, the internalization of the antibody according to the invention can be evaluated by immunofluorescence or FACS (Flow Cytometry) (as exemplified hereinafter in the present application) or any method or process known by the person skilled in the art specific for the internalization mechanism. In a preferred embodiment, the antibody according to the invention can induce internalization after binding to the Target of at least 30%, preferentially 50% and more preferentially 80%.

The complex Target/antibody is internalized after binding of the antibody to the ECD of said Target, and a reduction in the quantity of Target at the surface of the cells is induced. This reduction can be quantified by any method known by the person skilled in the art (western-blot, FACS, immunofluorescence, etc).

In one embodiment, this reduction, thus reflecting the internalization, can be preferably measured by FACS and expressed as the difference or delta between the Mean Fluorescence Intensity (MFI) measured at 4° C. with the MFI measured at 37° C. after 4 hours incubation with the antibody.

As non limitative example, this delta is determined based on MFIs obtained with untreated cells and cells treated with the antibody using i) cancer cells, such as for example MCF,7 after a 4 hour incubation period with the antibody herein described and ii) a secondary antibody labelled with ALEXA FLUOR® 488. This parameter is defined as calculated with the following formula: $\Delta(MFI_{4°\ C.} - MFI_{37°\ C.})$. Other embodiments will be detailed in the following examples.

This difference between MFIs reflects the Target downregulation as MFIs are proportional to Target expressed on the cell-surface.

In an advantageous aspect, the antibodies consist of antibodies triggering, as an example, a $\Delta(MFI_{4°\ C.} - MFI_{37°\ C.})$ on cancer cell, such as MCF-7, of at least 280, preferably of at least 400.

In more details, the above mentioned delta can be measured according to the following process, which must be considered as an illustrative and non limitative example:

a) Treating and incubating tumor cells of interest with the antibody of the invention in either cold (4° C.) or warm (37° C.) complete culture medium;

b) Treating the treated cells of step a) and, in parallel, untreated cells with a secondary antibody;

c) Measuring the MFI (representative of the quantity of IGF-1R present at the surface) for the treated and the non treated cells with a secondary labeled antibody capable of binding to the antibody of the invention; and d) Calculating the delta as the subtraction of the MFI obtained with the treated cells from the MFI obtained with the non treated cells.

From this delta MFI, an internalization percentage can be determined as:

$$100 \times (MFI_{4°\ C.} - MFI_{37°\ C.}) / MFI_{4°\ C.}$$

The antibodies, according to the invention, present, preferably, an internalization percentage comprised between 50% and 99%, 70% and 90%, preferentially between 75% and 87%.

A particular advantage of the antibodies herein described relies on their rate of internalization.

It is generally known that, for an ADC, it is desirable that the used antibodies exhibit a rapid rate of internalization, preferably within 24 hours from administration of the antibody and, more preferably within 12 hours and, even more preferably within 6 hours.

In the present invention, the internalization rate, also referred as cell surface bound antibody decrease or cell surface antibody decay, is expressed as t½ (half life) and corresponds as the time necessary to obtain a decrease of 50% of the ΔMFI (this aspect will be clearly understood regarding the following examples).

A particular advantage is that the antibodies of the invention have a t½ comprised between 5 and 25 minutes, and preferentially between 10 and 20 minutes.

In the following specificiation, two preferred Target will be exemplified.

For these two preferred Target, by "antibody according to the invention" or "antibody of the invention" it must be understood: "antibody of the ADC according to the invention" or "antibody of the ADC of the invention" respectively.

I.1: IGF-1R antibodies

A particular embodiment of the invention relates to an ADC wherein the antibody Ab comprises three heavy chain CDRs with CDR-H2 of sequence SEQ ID NO: 2 and CDR-H3 of sequence SEQ ID NO: 3, and three light chain CDRs with CDR-L2 of sequence SEQ ID NO: 5.

A particular embodiment of the invention relates to an ADC wherein the antibody Ab comprises the three heavy chain CDRs of sequences SEQ ID Nos. 1, 2 and 3 and the three light chain CDRs of sequences SEQ ID Nos. 4, 5 and 6.

An embodiment of the ADC comprises an antibody comprising the three heavy chain CDRs comprising the sequences SEQ ID Nos. 1, 2 and 3, or any sequence exhibiting at least 80%, preferably 85%, 90%, 95% and 98% identity with SEQ ID Nos. 1, 2 and 3; and the three light chain CDRs comprising the sequences SEQ ID Nos. 4, 5 and 6, or any sequence exhibiting at least 80%, preferably 85%, 90%, 95% and 98% identity with SEQ ID Nos. 4, 5 and 6.

In another embodiment, the antibody, or any antigen binding fragment thereof, comprises the three light chain CDRs comprising the sequences SEQ ID Nos. 1, 2 and 3; and the three heavy chain CDRs comprising the sequences SEQ ID Nos. 4, 5 and 6.

The IMGT® (International ImMunoGeneTics Information System) unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommie, C., Ruiz, M., Giudicelli, V., Foulquier, E., Truong, L., Thouvenin-Contet, V. and Lefranc, Dev. Comp. Immunol., 27, 55-77 (2003)]. In the IMGT® unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT® unique numbering provides a standardized delimitation of the framework regions (FR1-IMGT®: positions 1 to 26, FR2-IMGT®: 39 to 55, FR3-IMGT®: 66 to 104 and FR4-IMGT®: 118 to 128) and of the complementarity determining regions: CDR1-IMGT®: 27 to 38, CDR2-IMGT®: 56 to 65 and CDR3-IMGT®: 105 to 117. As gaps represent unoccupied positions, the CDR-IMGT® lengths (shown between brackets and separated by dots, e.g. [8.8.13]) become crucial information. The IMGT® unique numbering is used in 2D graphical representations, designated as IMGT® Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT®/3Dstructure-DB [Kaas, Q., Ruiz, M. and Lefranc, M.-P., T cell receptor and MHC structural data. Nucl. Acids. Res., 32, D208-D210 (2004)].

It must be understood that, without contradictory specification in the present specification, complementarity-determining regions or CDRs, mean the hypervariable regions of the heavy and light chains of immunoglobulins as defined according to the IMGT® numbering system.

Nevertheless, CDRs can also be defined according to the Kabat numbering system (Kabat et al., Sequences of proteins of immunological interest, 5$^{th}$ Ed., U.S. Department of Health and Human Services, NIH, 1991, and later editions). There are three heavy chain CDRs and three light chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes. In order to simplify the reading of the present application, the CDRs according to Kabat are not defined. Nevertheless, it would be obvious for the person skilled in the art, using the definition of the CDRs according to IMGT®, to define the CDRs according to Kabat.

In the sense of the present invention, the "identity" or "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to by comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST® (Basic Local Alignment Search Tool) NR or BLAST® P).

Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST® program, "BLAST® 2 sequences" (Tatusova et al., "BLAST® 2 sequences—a new tool for comparing protein and nucleotide sequences", FEMS Microbiol., 1999, Lett. 174:247-250) available on the site <http://www.ncbi.nlm.nih.gov/gorf/bl2.html>, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

As a non-limiting example, table 1 below summarizes the possible substitutions likely to be carried out without resulting in a significant modification of the biological activity of the corresponding modified antibody; inverse substitutions are naturally possible under the same conditions.

TABLE 1

| Original residue | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |

TABLE 1-continued

| Original residue | Substitution(s) |
|---|---|
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

A particular aspect of the invention is that the antibody, does not bind to the Insulin receptor (IR). This aspect is of interest as the antibody herein described will not have any negative impact on the IR, meaning the Insulin metabolism.

Still another advantageous aspect of the antibody of the ADC of the invention is that it is capable of binding not only to the human IGF-1R but also to the monkey IGF-1R, and more particularly to the cynomolgus IGF-1R. This aspect is also of interest as it will facilitate the toxicity assessement required for clinical trials.

In still another embodiment, the antibody of the ADC of the invention consists of a monoclonal antibody.

The term "monoclonal antibody" or "Mab" as used herein refers to an antibody obtained from a population of substantially homogeneous antibodies, i.e. the individual antibodies of the population are identical except for possible naturally occurring mutations that may be present in minor amounts. Monoclonal antibodies are highly specific, being directed against a single epitope. Such monoclonal antibody may be produced by a single clone of B cells or hybridoma. Monoclonal antibodies may also be recombinant, i.e. produced by protein engineering or chemical synthesis. Monoclonal antibodies may also be isolated from phage antibody libraries. In addition, in contrast with preparations of polyclonal antibodies which typically include various antibodies directed against various determinants, or epitopes, each monoclonal antibody is directed against a single epitope of the antigen.

The monoclonal antibody herein includes murine, chimeric and humanized antibody, such as described after.

The antibody is preferably derived from an hybridoma of murine origin filed within the French collection for microorganism cultures (CNCM, Pasteur Institute, 25 Rue du Docteur Roux, 75724 Paris Cedex 15, France), said hybridoma being obtained by the fusion of Balb/C immunized mice splenocytes/lymphocytes and cells of the myeloma Sp 2/O-Ag 14 cell line.

In an embodiment, the IGF-1R antibody of the ADC of the invention consists of a murine antibody, then referred as m[name of the antibody].

In an embodiment, the IGF-1R antibody consists of a chimeric antibody, then referred as c[name of the antibody].

In an embodiment, the IGF-1R antibody consists of a humanized antibody, then referred as hz[name of the antibody].

For the avoidance of doubt, in the following specification, the expressions "IGF-1R antibody" and "[name of the antibody]" are similar and include (without contrary specification) the murine, the chimeric and the humanized versions of the said IGF-1R antibody or of the said "[name of the antibody]". When necessary, the prefix m- (murine), c-(chimeric) or hz- (humanized) is used.

For more clarity, the following table 2 illustrates the CDR sequences, defined according to IMGT®, for the preferred antibodies.

TABLE 2

| | Heavy chain | Light chain | SEQ ID No. |
|---|---|---|---|
| Consensus | CDR-H1 | | 1 |
| | CDR-H2 | | 2 |
| | CDR-H3 | | 3 |
| | | CDR-L1 | 4 |
| | | CDR-L2 | 5 |
| | | CDR-L3 | 6 |
| 208F2 | CDR-H1 | | 7 |
| | CDR-H2 | | 2 |
| | CDR-H3 | | 3 |
| | | CDR-L1 | 9 |
| | | CDR-L2 | 5 |
| | | CDR-L3 | 11 |
| 212A11 | CDR-H1 | | 7 |
| | CDR-H2 | | 2 |
| | CDR-H3 | | 3 |
| | | CDR-L1 | 10 |
| | | CDR-L2 | 5 |
| | | CDR-L3 | 11 |
| 214F8 & 213B10 | CDR-H1 | | 7 |
| | CDR-H2 | | 2 |
| | CDR-H3 | | 3 |
| | | CDR-L1 | 9 |
| | | CDR-L2 | 5 |
| | | CDR-L3 | 12 |
| 219D6 | CDR-H1 | | 8 |
| | CDR-H2 | | 2 |
| | CDR-H3 | | 3 |
| | | CDR-L1 | 9 |
| | | CDR-L2 | 5 |
| | | CDR-L3 | 11 |

It will be obvious for the man skilled in the art that any combination of 6 CDRs as above described should be considered as part of the present invention.

As can be observed from this table 2, all the antibodies herein described have the same sequences for the CDR-H2, CDR-H3 and CDR-L2, this property being of particular interest as above described.

A specific aspect relates to a murine antibody characterized in that said antibody also comprises light chain and heavy chain constant regions derived from an antibody of a species heterologous with the mouse, notably man.

Another specific aspect relates to a chimeric (c) antibody characterized in that said antibody also comprises light chain and heavy chain constant regions derived from an antibody of a species heterologous with the mouse, notably human.

A chimeric antibody is one containing a natural variable region (light chain and heavy chain) derived from an antibody of a given species in combination with constant regions of the light chain and the heavy chain of an antibody of a species heterologous to said given species.

The chimeric antibodies can be prepared by using the techniques of recombinant genetics. For example, the chimeric antibody could be produced by cloning recombinant DNA containing a promoter and a sequence coding for the variable region of a nonhuman monoclonal antibody of the ADC of the invention, notably murine, and a sequence coding for heterologous species antibody constant region, preferably human. A chimeric antibody the ADC according to the invention coded by one such recombinant gene could be, for example, a mouse-human chimera, the specificity of this antibody being determined by the variable region derived from the murine DNA and its isotype determined by the constant region derived from human DNA.

In a preferred, but not limitative, embodiment, the antibody of the ADC of the invention is selected from:

a) an antibody comprising a heavy chain variable domain of sequence SEQ ID NO: 13 or any sequence exhibiting at least 80% identity with SEQ ID NO: 13 and the three light chain CDRs of sequences SEQ ID Nos. 9, 5 and 11;
  b) an antibody comprising a heavy chain variable domain of sequence SEQ ID NO: 14 or any sequence exhibiting at least 80% identity with SEQ ID NO: 14 and the three light chain CDRs of sequences SEQ ID Nos. 10, 5 and 11;
  c) an antibody comprising a heavy chain variable domain of sequence SEQ ID NO: 15 or any sequence exhibiting at least 80% identity with SEQ ID NO: 15 and the three light chain CDRs of sequences SEQ ID Nos. 9, 5 and 12;
  d) an antibody comprising a heavy chain variable domain of sequence SEQ ID NO: 16 or any sequence exhibiting at least 80% identity with SEQ ID NO: 16 and the three light chain CDRs of sequences SEQ ID Nos. 9, 5 and 11; and
  e) an antibody comprising a heavy chain variable domain of sequence SEQ ID NO: 17 or any sequence exhibiting at least 80% identity with SEQ ID NO: 17 and the three light chain CDRs of sequences SEQ ID Nos. 9, 5 and 12.

By "any sequence exhibiting at least 80%, preferably 85%, 90%, 95% and 98% identity with SEQ ID NO: 13 to 17", its is intended to designate the sequences exhibiting the three heavy chain CDRs SEQ ID Nos. 1, 2 and 3 and, in addition, exhibiting at least 80%, preferably 85%, 90%, 95% and 98%, identity with the full sequence SEQ ID NO: 13 to 17 outside the sequences corresponding to the CDRs (i.e. SEQ ID NO: 1, 2 and 3).

In another preferred, but not limitative, embodiment, the antibody of the ADC of the invention is selected from:
  a) an antibody comprising a light chain variable domain of sequence SEQ ID NO: 18 or any sequence exhibiting at least 80% identity with SEQ ID NO: 18 and the three heavy chain CDRs of sequences SEQ ID Nos. 7, 2 and 3;
  b) an antibody comprising a light chain variable domain of sequence SEQ ID NO: 19 or any sequence exhibiting at least 80% identity with SEQ ID NO: 19 and the three heavy chain CDRs of sequences SEQ ID Nos. 7, 2 and 3;
  c) an antibody comprising a light chain variable domain of sequence SEQ ID NO: 20 or any sequence exhibiting at least 80% identity with SEQ ID NO: 20 and the three heavy chain CDRs of sequences SEQ ID Nos. 7, 2 and 3;
  d) an antibody comprising a light chain variable domain of sequence SEQ ID NO: 21 or any sequence exhibiting at least 80% identity with SEQ ID NO: 21 and the three heavy chain CDRs of sequences SEQ ID Nos. 8, 2 and 3; and
  e) an antibody comprising a light chain variable domain of sequence SEQ ID NO: 22 or any sequence exhibiting at least 80% identity with SEQ ID NO: 22 and the three heavy chain CDRs of sequences SEQ ID Nos. 7, 2 and 3.

By "any sequence exhibiting at least 80%, preferably 85%, 90%, 95% and 98% identity with SEQ ID NO: 18 to 22", its is intended to designate the sequences exhibiting the three light chain CDRs SEQ ID Nos. 4, 5 and 6 and, in addition, exhibiting at least 80%, preferably 85%, 90%, 95% and 98%, identity with the full sequence SEQ ID NO: 18 to 22 outside the sequences corresponding to the CDRs (i.e. SEQ ID NO: 4, 5 and 6).

An embodiment of the invention relates to an ADC wherein Ab is an antibody selected from:
  a) an antibody comprising a heavy chain variable domain of sequence SEQ ID NO: 13 or any sequence exhibiting at least 80% identity with SEQ ID NO: 13 and a light chain variable domain of sequence SEQ ID NO: 18 or any sequence exhibiting at least 80% identity with SEQ ID NO: 18;
  b) an antibody comprising a heavy chain variable domain of sequence SEQ ID NO: 14 or any sequence exhibiting at least 80% identity with SEQ ID NO: 14 and a light chain variable domain of sequence SEQ ID NO: 19 or any sequence exhibiting at least 80% identity with SEQ ID NO: 19;
  c) an antibody comprising a heavy chain variable domain of sequence SEQ ID NO: 15 or any sequence exhibiting at least 80% identity with SEQ ID NO: 15 and a light chain variable domain of sequence SEQ ID NO: 20 or any sequence exhibiting at least 80% identity with SEQ ID NO: 20;
  d) an antibody comprising a heavy chain variable domain of sequence SEQ ID NO: 16 or any sequence exhibiting at least 80% identity with SEQ ID NO: 16 and a light chain variable domain of sequence SEQ ID NO: 21 or any sequence exhibiting at least 80% identity with SEQ ID NO: 21; and
  e) an antibody comprising a heavy chain variable domain of sequence SEQ ID NO: 17 or any sequence exhibiting at least 80% identity with SEQ ID NO: 17 and a light chain variable domain of sequence SEQ ID NO: 22 or any sequence exhibiting at least 80% identity with SEQ ID NO: 22.

Chimeric antibodies herein described can be also characterized by the constant domain and, more particularly, said chimeric antibodies can be selected or designed such as, without limitation, IgG1, IgG2, IgG3, IgM, IgA, IgD or IgE. More preferably, in the context of the present invention, said chimeric antibodies are IgG1 or IgG4.

An embodiment of the invention relates to an ADC wherein Ab is a chimeric antibody comprising variable domains VH and VL as above described in the format IgG1. More preferably, said chimeric antibody comprises a constant domain for the VH of sequence SEQ ID NO: 43 and a Kappa domain for the VL of sequence SEQ ID NO: 45.

An embodiment of the invention relates to an ADC wherein Ab is a chimeric antibody comprising variable domains VH and VL as above described in the format IgG4. More preferably, said chimeric antibody comprises a constant domain for the VH of sequence SEQ ID NO: 44 and a Kappa domain for the VL of sequence SEQ ID NO: 45.

In another preferred, but not limitative, embodiment, the antibody of the ADC of the invention is selected from:
  a) an antibody comprising or consisting of a heavy chain of sequence SEQ ID NO: 23 or any sequence exhibiting at least 80% identity with SEQ ID NO: 23 and a light chain of sequence SEQ ID NO: 28 or any sequence exhibiting at least 80% identity with SEQ ID NO: 28;
  b) an antibody comprising or consisting of a heavy chain of sequence SEQ ID NO: 24 or any sequence exhibiting at least 80% identity with SEQ ID NO: 24 and a light chain of sequence SEQ ID NO: 29 or any sequence exhibiting at least 80% identity with SEQ ID NO: 29;
  c) an antibody comprising or consisting of a heavy chain of sequence SEQ ID NO: 25 or any sequence exhibiting at least 80% identity with SEQ ID NO: 25 and a light chain of sequence SEQ ID NO: 30 or any sequence exhibiting at least 80% identity with SEQ ID NO: 30;
  d) an antibody comprising or consisting of a heavy chain of sequence SEQ ID NO: 26 or any sequence exhibiting at least 80% identity with SEQ ID NO: 26 and a light chain of sequence SEQ ID NO: 31 or any sequence exhibiting at least 80% identity with SEQ ID NO: 31; and
  e) an antibody comprising or consisting of a heavy chain of sequence SEQ ID NO: 27 or any sequence exhibiting at least 80% identity with SEQ ID NO: 27 and a light chain of sequence SEQ ID NO: 32 or any sequence exhibiting at least 80% identity with SEQ ID NO: 32.

For more clarity, the following table 3 illustrates the sequences of the VH and VL, respectively, for the preferred chimeric antibodies.

TABLE 3

|  | Heavy Chain | Light chain | SEQ ID No. |
|---|---|---|---|
| c208F2 | Variable domain (VH) |  | 13 |
|  |  | Variable domain (VL) | 18 |
|  | Full length |  | 23 |
|  |  | Full length | 28 |
| c212A11 | Variable domain (VH) |  | 14 |
|  |  | Variable domain (VL) | 19 |
|  | Full length |  | 24 |
|  |  | Full length | 29 |
| c214F8 | Variable domain (VH) |  | 15 |
|  |  | Variable domain (VL) | 20 |
|  | Full length |  | 25 |
|  |  | Full length | 30 |
| c219D6 | Variable domain (VH) |  | 16 |
|  |  | Variable domain (VL) | 21 |
|  | Full length |  | 26 |
|  |  | Full length | 31 |
| c213B10 | Variable domain (VH) |  | 17 |
|  |  | Variable domain (VL) | 22 |
|  | Full length |  | 27 |
|  |  | Full length | 32 |

Yet another specific aspect of the present invention relates to an ADC wherein Ab is a humanized antibody characterized in that the constant regions of the light chain and the heavy chain derived from human antibody are, respectively, the lambda or kappa region and the gamma-1, gamma-2 or gamma-4 region.

"Humanized antibodies" means an antibody that contains CDR regions derived from an antibody of nonhuman origin, the other parts of the antibody molecule being derived from one (or several) human antibodies. In addition, some of the skeleton segment residues (called FR) can be modified to preserve binding affinity.

The humanized antibodies or fragments of same can be prepared by techniques known to a person skilled in the art. Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 216, EP 0 682 040, EP 0 939 127, EP 0 566 647 or U.S. Pat. Nos. 5,530,101, 6,180,370, 5,585,089 and 5,693,761. U.S. Pat. No. 5,639,641 or 6,054,297, 5,886,152 and 5,877,293 can also be cited.

As a particular embodiment of the invention, and as it will be explicated in more details in the examples after, it is herein described an antibody consisting of the hz208F2. Such humanization can also be applied to the other antibodies part of the present invention.

In a preferred embodiment, the antibody of the ADC according to the present invention comprises a heavy chain variable domain (VH) having:

i) the CDR-H1, CDR-H2 and CDR-H3 of sequences SEQ ID Nos. 7, 2 and 3, respectively, and ii) the FR1, FR2 and FR3 derived from the human germline IGHV1-46*01 (SEQ ID NO: 46), and iii) the FR4 derived from the human germline IGHJ4*01 (SEQ ID NO: 48).

In a preferred embodiment, the antibody of the ADC according to the present invention comprises a light chain variable domain (VL) having:

i) the CDR-L1, CDR-$L_2$ and CDR-L3 of sequences SEQ ID Nos. 9, 5 and 11, respectively, and ii) the FR1, FR2 and FR3 derived from the human germline IGKV1-39*01 (SEQ ID NO: 47), and iii) the FR4 derived from the human germline IGKJ4*01 (SEQ ID NO: 49).

In a preferred, but not limitative, embodiment of the invention, the antibody of the ADC comprises:

a) a heavy chain having CDR-H1, CDR-H2 and CDR-H3 of sequences SEQ ID Nos. 7, 2 and 3, respectively, and FR1, FR2 and FR3 derived from the human germline IGHV1-46*01 (SEQ ID NO: 46), and the FR4 derived from the human germline IGHJ4*01 (SEQ ID NO: 48); and b) a light chain having CDR-L1, CDR-$L_2$ and CDR-L3 of sequences SEQ ID Nos. 9, 5 and 11, respectively, and FR1, FR2 and FR3 derived from the human germline IGKV1-39*01 (SEQ ID NO: 47), and the FR4 derived from the human germline IGKJ4*01 (SEQ ID NO: 49).

In an embodiment, the antibody of the ADC according to the invention comprises a heavy chain variable domain (VH) of sequence SEQ ID NO: 33 and a light chain variable domain (VL) of sequence SEQ ID NO: 35. Said humanized antibody will be called thereinafter hz208F2 ("Variant 1" or "Var. 1").

In another embodiment, the antibody of the ADC according to the present invention comprises a heavy chain variable domain (VH) of sequence SEQ ID NO: 33 wherein said sequence SEQ ID NO: 33 comprises at least 1 back-mutation selected from the residues 20, 34, 35, 38, 48, 50, 59, 61, 62, 70, 72, 74, 76, 77, 79, 82 or 95.

By the expressions "back-mutation" or "back mutation" it is meant a mutation or replacement of the human residue present in the germline by the corresponding residue initially present in the murine sequence.

In another embodiment, the antibody of the ADC according to the present invention comprises a heavy chain variable domain (VH) of sequence SEQ ID NO: 33 wherein said sequence SEQ ID NO: 33 comprises 2, 3, 4, 5, 6, 7, 8, 9, 10, 11, 12, 13, 14, 15, 16 or 17 back-mutations selected from the residues 20, 34, 35, 38, 48, 50, 59, 61, 62, 70, 72, 74, 76, 77, 79, 82 or 95.

For more clarity, the following table 4 illustrates the preferred back-mutations.

TABLE 4

| | No résidu | | | | | | | |
|---|---|---|---|---|---|---|---|---|
| | 20 | 34 | 35 | 38 | 48 | 50 | 59 | 61 |
| Murin | M | I | Y | K | L | W | K | N |
| humain | V | M | H | R | M | I | S | A |

| | No résidu | | | | | | | |
|---|---|---|---|---|---|---|---|---|
| | 62 | 70 | 72 | 74 | 76 | 77 | 79 | 82 | 95 |
| Murin | E | L | A | K | S | N | A | F | F |
| humain | Q | M | R | T | T | S | V | E | Y |

In an embodiment, the antibody of the ADC according to the present invention comprises a light chain variable domain (VL) of sequence SEQ ID NO: 35, wherein said sequence SEQ ID NO: 35 comprises at least 1 back-mutation selected from the residues 22, 53, 55, 65, 71, 72, 77 or 87.

In an embodiment, the antibody of the ADC according to the present invention comprises a light chain variable domain (VL) of sequence SEQ ID NO: 35, wherein said sequence SEQ ID NO: 35 comprises 2, 3, 4, 5, 6, 7 or 8 back-mutations selected from the residues 22, 53, 55, 65, 71, 72, 77 or 87.

In another embodiment, the antibody of the ADC according to the present invention comprises:

a) a heavy chain variable domain (VH) of sequence SEQ ID NO: 33 wherein said sequence SEQ ID NO: 33 comprises at least 1 back-mutation selected from the residues 20, 34, 35, 38, 48, 50, 59, 61, 62, 70, 72, 74, 76, 77, 79, 82 or 95; and
b) a light chain variable domain (VL) of sequence SEQ ID NO: 35, wherein said sequence SEQ ID NO: 35 comprises at least 1 back-mutation selected from the residues 22, 53, 55, 65, 71, 72, 77 or 87.

For more clarity, the following table 5 illustrates the preferred back-mutations.

TABLE 5

| | No résidu | | | | | | |
|---|---|---|---|---|---|---|---|
| | 22 | 53 | 55 | 65 | 71 | 72 | 77 | 87 |
| Murin | S | R | H | R | Y | S | N | F |
| humain | T | S | Q | S | F | T | S | Y |

In such an embodiment, the antibody of the ADC according to the invention comprises all the back-mutations above mentioned and corresponds to an antibody comprising a heavy chain variable domain (VH) of sequence SEQ ID NO: 34 and a light chain variable domain (VL) of sequence SEQ ID NO: 36. Said humanized antibody will be called thereinafter hz208F2 ("Variant 3" or "Var. 3").

In another embodiment, all the humanized forms comprised between the Variant 1 and the Variant 3 are also encompassed by the present invention. In other words, the antibody of the ADC according to the invention corresponds to an antibody comprising a heavy chain variable domain (VH) of "consensus" sequence SEQ ID NO: 41 and a light chain variable domain (VL) of "consensus" sequence SEQ ID NO: 42. Said humanized antibody, as a whole, will be called thereinafter hz208F2 ("Variant2" or "Var.2").

In a preferred, but not limitative, embodiment, the antibody of the ADC of the invention is selected from:

a) an antibody comprising a heavy chain variable domain of sequence SEQ ID NO: 33 or any sequence exhibiting at least 80% identity with SEQ ID NO: 33 and the three light chain CDRs of sequences SEQ ID Nos. 9, 5 and 11; or
b) an antibody comprising a heavy chain variable domain of sequence SEQ ID NO: 34 or any sequence exhibiting at least 80% identity with SEQ ID NO: 34 and the three light chain CDRs of sequences SEQ ID Nos. 9, 5 and 11.

By "any sequence exhibiting at least 80%, preferably 85%, 90%, 95% and 98% identity with SEQ ID NO: 33 or 34", its is intended to designate the sequences exhibiting the three heavy chain CDRs SEQ ID Nos. 1, 2 and 3 and, in addition, exhibiting at least 80%, preferably 85%, 90%, 95% and 98%, identity with the full sequence SEQ ID NO: 33 or 34 outside the sequences corresponding to the CDRs (i.e. SEQ ID Nos. 1, 2 and 3).

In a preferred, but not limitative, embodiment, the antibody of the ADC of the invention is selected from:

a) an antibody comprising a light chain variable domain of sequence SEQ ID NO: 35 or any sequence exhibiting at least 80% identity with SEQ ID NO: 35 and the three heavy chain CDRs of sequences SEQ ID Nos. 7, 2 and 3; and
b) an antibody comprising a heavy chain variable domain of sequence SEQ ID NO: 36 or any sequence exhibiting at least 80% identity with SEQ ID NO: 36 and the three heavy chain CDRs of sequences SEQ ID Nos. 7, 2 and 3.

By "any sequence exhibiting at least 80%, preferably 85%, 90%, 95% and 98% identity with SEQ ID NO: 35 or 36", its is intended to designate the sequences exhibiting the three light chain CDRs SEQ ID Nos. 4, 5 and 6 and, in addition, exhibiting at least 80%, preferably 85%, 90%, 95% and 98%, identity with the full sequence SEQ ID NO: 35 or 36 outside the sequences corresponding to the CDRs (i.e. SEQ ID Nos. 4, 5 and 6).

Humanized antibodies herein described can be also characterized by the constant domain and, more particularly, said humanized antibodies can be selected or designed such as, without limitation, IgG1, IgG2, IgG3, IgM, IgA, IgD or IgE. More preferably, in the context of the present invention, said humanized antibodies are IgG1 or IgG4.

An embodiment of the invention relates to an ADC wherein Ab is a humanized antibody comprising variable domains VH and VL as above described in the format IgG1. More preferably, said humanized antibody comprises a constant domain for the VH of sequence SEQ ID NO: 43 and a Kappa domain for the VL of sequence SEQ ID NO: 45.

An embodiment of the invention relates to an ADC wherein Ab is a humanized antibody comprising variable domains VH and VL as above described in the format IgG4. More preferably, said humanized antibody comprises a constant domain for the VH of sequence SEQ ID NO: 44 and a Kappa domain for the VL of sequence SEQ ID NO: 45.

Still another embodiment of the invention relates to an ADC wherein Ab is an antibody selected from:

a) an antibody comprising a heavy chain of sequence SEQ ID NO: 37 or any sequence exhibiting at least 80% identity with SEQ ID NO: 37 and a light chain of sequence SEQ ID NO: 39 or any sequence exhibiting at least 80% identity with SEQ ID NO: 39; and
b) an antibody comprising a heavy chain of sequence SEQ ID NO: 38 or any sequence exhibiting at least 80% identity with SEQ ID NO: 38 and a light chain of sequence SEQ ID NO: 40 or any sequence exhibiting at least 80% identity with SEQ ID NO: 40.

For more clarity, the following table 6 illustrates non limitative examples of sequences of the VH and VL for the variant 1 (Var. 1) and the variant 3 (Var. 3) of the humanized antibody hz208F2. It also comprises the consensus sequence for the variant 2 (Var. 2).

TABLE 6

| | Heavy Chain | Light chain | SEQ ID No. |
|---|---|---|---|
| hz208F2 (var. 1) | Variable domain (VH) | | 33 |
| | | Variable domain (VL) | 35 |
| | Full length | | 37 |
| | | Full length | 39 |
| hz208F2 (Var. 3) | Variable domain (VH) | | 34 |
| | | Variable domain (VL) | 36 |
| | Full length | | 38 |
| | | Full length | 40 |
| hz208F2 (Var. 2) | Variable domain (VH) | | 41 |
| | | Variable domain (VL) | 42 |

Another aspect of the present invention is an ADC wherein Ab is an antibody selected from i) an antibody produced by the hybridoma I-4757, I-4773, I-4775, I-4736 or I-4774 deposited at the CNCM, Institut Pasteur France on the 30 May 2013, 26 Jun. 2013, 26 Jun. 2013, 24 Apr. 2013 and 26 Jun. 2013, respectively, ii) an antibody which competes for binding to IGF-1R with the antibody of i); or iii) an antibody which binds to the same epitope of IGF-1R as does the antibody of i).

It is described herein a murine hybridoma selected from the hybridoma I-4757, I-4773, I-4775, I-4736 and I-4774 deposited at the CNCM, Institut Pasteur France on the 30 May 2013, 26 Jun. 2013, 26 Jun. 2013, 24 Apr. 2013 and 26 Jun. 2013, respectively.

It is also described an isolated nucleic acid coding for an antibody, or for an antigen binding fragment thereof, according to the invention.

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

The nucleic sequences of the antibodies of the ADC of present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

It is also described a vector comprising a nucleic acid coding for an antibody of the ADC of the invention, or for an antigen binding fragment thereof, according to the invention.

It is disclosed notably targets cloning and/or expression vectors that contain such a nucleotide sequence.

The vectors preferably contain elements which allow the expression and/or the secretion of nucleotide sequences in a given host cell. The vector thus may contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the chosen host or be integrative vectors of the chosen host.

The vectors are, for example, vectors of plasmid or viral origin. They are used to transform host cells in order to clone or express the nucleotide sequences of the invention.

Such vectors are prepared by methods typically used by a person skilled in the art and the resulting clones can be introduced into a suitable host by standard methods such as lipofection, electroporation, conjugation, heat shock or chemical methods.

It is disclosed also isolated host cells transformed by or comprising a vector as above described.

The host cell can be selected among prokaryotic or eukaryotic systems such as bacterial cells, for example, but also yeast cells or animal cells, notably mammal cells (with the exception of human). Insect or plant cells can also be used.

It is also disclosed a method for the production of an antibody according to the invention, or an antigen binding fragment thereof, characterized in that said method comprises the following steps:

a) the culture in a medium with the suitable culture conditions for a host cellas disclosed above; and b) the recovery of the antibody thus produced from the culture medium or from said cultured cells.

The transformed cells are of use in methods for the preparation of recombinant antibodies. Methods for the preparation of antibodies in recombinant form using a vector and/or a cell transformed by a vector, are also comprised in the present specification.

Preferably, a cell transformed by a vector as above described is cultured under conditions that allow the expression of the aforesaid antibody and recovery of said antibody.

As already mentioned, the host cell can be selected among prokaryotic or eukaryotic systems. In particular, it is possible to identify the nucleotide sequences that facilitate secretion in such a prokaryotic or eukaryotic system. A vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The antibody of the ADC of the invention can also be prepared by chemical synthesis. One such method of preparation is also an object of the invention. A person skilled in the art knows methods for chemical synthesis, such as solid-phase techniques or partial solid-phase techniques, by condensation of fragments or by conventional synthesis in solution. Polypeptides obtained by chemical synthesis and capable of containing corresponding unnatural amino acids are also comprised in the invention.

The ADC comprising antibody likely to be obtained by the method above described are also comprised in the present invention.

According to a particular aspect, the invention concerns an ADC wherein Ab is an antibody, or an antigen binding fragment thereof, as above described for use as an addressing vehicle for delivering a cytotoxic agent at a host target site, said host target site consisting of an epitope localized into IGF-1R, preferably the IGF-1R extracellular domain, more preferably the human IGF-1R (SEQ ID NO: 50) and still more preferably the human IGF-1R extracellular domain (SEQ ID NO: 51), and still more preferably to the N-terminal of the human IGF-1R extracellular domain (SEQ ID NO: 52), or any natural variant sequence thereof.

In a preferred embodiment, said host target site is a target site of a mammalian cell, more preferably of a human cell, more preferably cells which naturally or by way of genetic recombination, express IGF-1R.

I.2: Axl Antibodies

Without any contradictory indication, the definition or expression used and defined in the paragraph "I.1, IGF-1R antibodies" are the same in the present paragraph and can be applied to all the ADC of the present invention.

The Axl antibody is capable of binding to the human protein Axl. More particularly, the said target is an epitope located into the extracellular domain of Axl (referred as the Axl ECD for "Axl Extra Cellular Domain").

The Axl ECD is a 451 amino acids fragment, corresponding to amino acids 1-451 of the sequence SEQ ID NO: 103, which sequence is represented in the sequence listing as SEQ ID NO: 105. Amino acids 1-25 corresponding to the signal peptide, the ECD of the human protein Axl without the signal peptide corresponds to the amino acids 26-451 of the sequence SEQ ID NO:104, represented by the sequence SEQ ID NO: 106.

The Axl antibody of the ADC of the invention comprises the three light chain CDRs comprising the sequences SEQ ID Nos. 56, 57 and 58, or any sequence exhibiting at least 90%, preferably 95% and 98% identity with SEQ ID Nos. 56, 57 and 58; and the three heavy chain CDRs comprising the sequences SEQ ID Nos. 59, 60 and 61, or any sequence exhibiting at least 90%, preferably 95% and 98% identity with SEQ ID Nos. 59, 60 and 61.

In an embodiment, the Axl antibody comprises the three light chain CDRs comprising respectively the sequences SEQ ID Nos. 56, 57 and 58; and the three heavy chain CDRs comprising respectively the sequences SEQ ID Nos. 59, 60 and 61.

In an embodiment, the Axl antibody consists of the m1613F12 comprising i) a light chain variable domain of sequence SEQ ID NO: 62, or any sequence exhibiting at least 80%, preferably 85%, 90%, 95% and 98% identity with SEQ ID NO: 62; and/or ii) a heavy chain variable domain of sequence SEQ ID NO: 63, or any sequence exhibiting at least 80%, preferably 85%, 90%, 95% and 98% identity with SEQ ID NO: 63.

For more clarity, table 7a below summarizes the various amino acid sequences corresponding to the Axl antibody.

TABLE 7a

| | CDR numbering | Heavy chain | Light chain | SEQ ID NO. |
|---|---|---|---|---|
| 1613F12 | IMGT ® | | CDR-L1 | 56 |
| | | | CDR-L2 | 57 |
| | | | CDR-L3 | 58 |
| | | CDR-H1 | | 59 |
| | | CDR-H2 | | 60 |
| | | CDR-H3 | | 61 |
| | | | variable domain | 62 |
| | | variable domain | | 63 |

In an embodiment, the Axl antibody consists of the c1613F12 comprising the three light chain CDRs comprising the sequences SEQ ID NO: 56, 57 and 58, or any sequence exhibiting at least 80%, preferably 85%, 90%, 95% and 98% identity with SEQ ID NO: 56, 57 and 58; and the three heavy chain CDRs comprising the sequences SEQ ID NO: 59, 60 and 61, or any sequence exhibiting at least 80%, preferably 85%, 90%, 95% and 98% identity with SEQ ID NO: 59, 60 and 61.

In an embodiment, c1613F12 comprises the three light chain CDRs comprising respectively the sequences SEQ ID Nos. 56, 57 and 58; and the three heavy chain CDRs comprising respectively the sequences SEQ ID Nos. 59, 60 and 61.

In an embodiment, the Axl antibody consists of the c1613F12 comprising i) a light chain variable domain of sequence SEQ ID NO: 62, or any sequence exhibiting at least 80%, preferably 85%, 90%, 95% and 98% identity with SEQ ID NO: 62; and/or ii) a heavy chain variable domain of sequence SEQ ID NO: 63, or any sequence exhibiting at least 80%, preferably 85%, 90%, 95% and 98% identity with SEQ ID NO: 63.

In an embodiment, the Axl antibody consists of the hz1613F12 comprising the three light chain CDRs comprising the sequences SEQ ID NO: 56, 57 and 58, or any sequence exhibiting at least 80%, preferably 85%, 90%, 95% and 98% identity with SEQ ID NO: 56, 57 and 58; and the three heavy chain CDRs comprising the sequences SEQ ID NO: 59, 60 and 61, or any sequence exhibiting at least 80%, preferably 85%, 90%, 95% and 98% identity with SEQ ID NO: 59, 60 and 61.

In an embodiment, hz1613F12 comprises the three light chain CDRs comprising respectively the sequences SEQ ID Nos. 56, 57 and 58; and the three heavy chain CDRs comprising respectively the sequences SEQ ID Nos. 59, 60 and 61.

In an embodiment, hz1613F12 comprises a light chain variable domain consisting of the sequence SEQ ID NO: 70, or any sequence exhibiting at least 80%, preferably 85%, 90%, 95% and 98% identity with SEQ ID NO: 70; and the three heavy chain CDRs consisting of sequences SEQ ID NO: 59, 60 and 61.

In another embodiment of the invention, hz1613F12 comprises a light chain variable domain of sequence selected in the group consisting of SEQ ID NO: 71 to 81 or any sequence exhibiting at least 80%, preferably 85%, 90%, 95% and 98% identity with SEQ ID NO: 71 to 81; and the three heavy chain CDRs consisting of SEQ ID NO: 59, 60 and 61.

In order to illustrate the identity percentage as defined before, by "any sequence exhibiting at least 80%, preferably 85%, 90%, 95% and 98% identity with SEQ ID NO: 70 to 81", its is intended to designate the sequences exhibiting the three light chain CDRs SEQ ID NO: 56, 57 and 58 and, in addition, exhibiting at least 80%, preferably 85%, 90%, 95% and 98%, identity with the full sequence SEQ ID NO: 70 to 81 outside the sequences corresponding to the CDRs (i.e. SEQ ID NO: 56, 57 and 58).

For more clarity, table 7b below summarizes the various amino acid sequences corresponding to the humanized Axl antibody light chain (VL) of the ADC of the invention (with hz.=humanized)

TABLE 7b

| | Version | SEQ ID NO. |
|---|---|---|
| hz1613F12 VL | consensus | 70 |
| | VL1 | 71 |
| | VL1 I2V | 72 |
| | VL1 M4I | 73 |
| | VL2.1 | 74 |
| | VL2.1 V49T | 75 |
| | VL2.1 P50N | 76 |
| | VL2.2 | 77 |
| | VL2.2 V49T | 78 |
| | VL2.2 P50N | 79 |
| | VL2.3 | 80 |
| | VL3 | 81 |

In an embodiment, hz1613F12 comprises a heavy chain variable domain consisting of the sequence SEQ ID NO: 82, or any sequence exhibiting at least 80%, preferably 85%, 90%, 95% and 98% identity with SEQ ID NO: 82; and the three light chain CDRs consisting of sequences SEQ ID NO: 56, 57 and 58.

In another embodiment, hz1613F12 comprises a heavy chain variable domain of sequence selected in the group consisting of SEQ ID NO: 83 to 102, or any sequence exhibiting at least 80%, preferably 85%, 90%, 95% and 98% identity with SEQ ID NO: 83 to 102; and the three light chain CDRs consisting of SEQ ID NO: 56, 57 and 58.

In order to illustrate the identity percentage as defined before, by "any sequence exhibiting at least 80%, preferably 85%, 90%, 95% and 98% identity with SEQ ID NO: 82 to 102", its is intended to designate the sequences exhibiting the three heavy chain CDRs SEQ ID NO: 59, 60 and 61 and, in addition, exhibiting at least 80%, preferably 85%, 90%, 95% and 98%, identity with the full sequence SEQ ID NO: 82 to 102 outside the sequences corresponding to the CDRs (i.e. SEQ ID NO: 59, 60 and 61).

For more clarity, table 7c below summarizes the various amino acid sequences corresponding to the humanized antigen binding protein heavy chain (VH) of the invention (with hz.=humanized)

TABLE 7c

| | Version | SEQ ID NO. |
|---|---|---|
| hz1613F12 VH | consensus | 82 |
| | VH1 | 83 |
| | VH1 M39I | 84 |
| | VH1 W55R N66K | 85 |
| | VH1 I84S | 86 |
| | VH1 S85N | 87 |
| | VH1 I84N S85N | 88 |
| | VH2.1 | 89 |
| | VH2.1 Q3H | 90 |
| | VH2.1 W55R | 91 |
| | VH2.1 N66K | 92 |
| | VH2.1 W55 RN66K | 93 |
| | VH2.1 R80S | 94 |
| | VH2.1 N66K R80S | 95 |
| | VH2.2 | 96 |
| | VH2.2 M89L | 97 |
| | VH2.3 | 98 |
| | VH2.3 W55R | 99 |
| | VH2.3 Q3H W55R | 100 |
| | VH2.4 | 101 |
| | VH3 | 102 |

In an embodiment, hz1613F12 comprises a light chain variable domain of sequence selected in the group consisting of SEQ ID NO: 70 and any sequence exhibiting at least 80%, preferably 85%, 90%, 95% and 98% identity with SEQ ID NO: 70; and a heavy chain variable domain of sequence selected in the group consisting of SEQ ID NO: 82 and any sequence exhibiting at least 80%, preferably 85%, 90%, 95% and 98% identity with SEQ ID NO: 82.

In an embodiment, hz1613F12 comprises a light chain variable domain of sequence selected in the group consisting of SEQ ID NO: 71 to 81, or any sequence exhibiting at least 80%, preferably 85%, 90%, 95% and 98% identity with SEQ ID NO: 71 to 81; and a heavy chain variable domain of sequence selected in the group consisting of SEQ ID NO: 83 to 102, or any sequence exhibiting at least 80%, preferably 85%, 90%, 95% and 98% identity with SEQ ID NO: 83 to 102.

Another aspect of the present invention is an ADC wherein Ab is an antibody selected from i) an antibody produced by the hybridoma 1-4505, deposited at the CNCM, Institut Pasteur France on the 28 Jul. 2011, ii) an antibody which competes for binding to Axl with the antibody of i); or iii) an antibody which binds to the same epitope of Axl as does the antibody of i).

According to another aspect, It is disclosed a murine hybridoma selected from the hybridoma 1-4505.

Table 8 below summarizes the nucleotide sequences concerning CDRs of the 1613F12.

TABLE 8

| Antibody | CDR numbering | Heavy chain | Light chain | SEQ ID NO. |
|---|---|---|---|---|
| 1613F12 | IMGT | | CDR-L1 | 64 |
| | | | CDR-L2 | 65 |
| | | | CDR-L3 | 66 |
| | | CDR-H1 | | 67 |
| | | CDR-H2 | | 68 |
| | | CDR-H3 | | 69 |

In an embodiment, nucleic acid sequences of the CDRs can be selected from the sequences SEQ ID Nos. 64 to 69.

A non limitative embodiment it is disclosed an isolated nucleic acid or a combination thereof coding for an antibody characterized in that said nucleic acid or its combination comprises the 6 CDRs sequences SEQ ID Nos. 64 to 69.

I.3: HER2 Antibodies

The HER2 antibodies can consist of any antibody capable of binding to HER2 such as, without limitation, TRASGEX® (Glycotope), Trastuzumab, Pertuzumab or any biosimilar thereof.

In a preferred embodiment, the HER2 antibody is the Trastuzumab (HERCEPTIN®; 4D5; Genentech, San Francisco, Calif.).

II—The Drug (D)

The drug moiety according to the invention has the following formula (II)

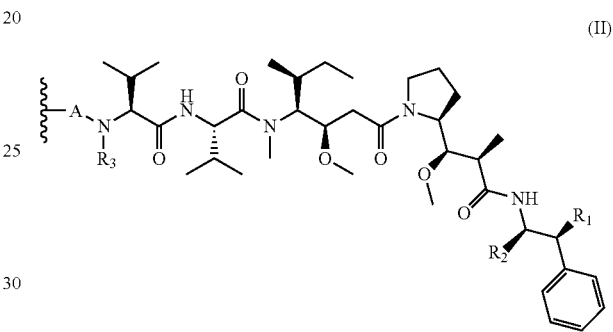

(II)

wherein:

R$_1$ is H or OH;

R$_2$ is a group: (C$_1$-C$_6$)alkyl (e.g. methyl), COOH, COO—((C$_1$-C$_6$)alkyl) (such as COOMe) or thiazolyl (such as thiazol-2-yl);

R$_3$ is H or a (C$_1$-C$_6$)alkyl group (such as methyl), in particular a (C$_1$-C$_6$)alkyl group, A is:

a group of formula -Het-Alk- wherein Alk is a (C$_1$-C$_8$) alkanediyl group and is linked to NR$_3$, and Het is a heterocycle optionally substituted by a (C$_1$-C$_6$)alkyl group and containing at least one nitrogen atom, said nitrogen atom being linked to L, or a group of formula -A$_a$-A$_b$- wherein A$_a$ is linked to L and is O or NR$_9$ with R$_9$ being H or (C$_1$-C$_6$)alkyl (such as methyl) and A$_b$ is linked to NR$_3$ and is:

a (C$_1$-C$_8$)alkanediyl group (such as —(CH$_2$)$_m$— with m comprised between 1 and 8), a —(CH$_2$CH$_2$X$_1$)$_{a1}$(CH$_2$CH$_2$X$_2$)$_{a2}$(CH$_2$CH$_2$X$_3$)$_{a3}$ (CH$_2$CH$_2$X$_4$)$_{a4}$CH$_2$CH$_2$— group with X$_1$, X$_2$, X$_3$ and X$_4$ each independently of one another representing O or NR$_8$; a1, a2, a3 and a4 each independently of one another representing 0 or 1 (in particular with a1+a2+a3+a4=1 or 2, in particular 1); and R$_8$ representing H or a (C$_1$-C$_6$)alkyl group (such as methyl), an aryl-(C$_1$-C$_8$)alkanediyl or heterocycle-(C$_1$-C$_8$)alkanediyl group, said group being optionally substituted by a (C$_1$-C$_6$)alkyl group, the aryl or heterocycle moiety being linked to A$_a$ and the (C$_1$-C$_8$)alkanediyl moiety being linked to NR$_3$;

the wavy line indicates the point of attachment to L.

The radicals R$_2$, R$_3$ and A may be chiral groups and may be in the form of their different stereoisomers and optionally in the form of a mixture of stereoisomers.

By «stereoisomer», in the meaning of the present invention is meant a geometric isomer or an optical isomer.

Geometrical isomers result from the different position of the substituents on a double bond which may therefore have a Z or E configuration.

Optical isomers result in particular from the different position in space of the substituents on a carbon atom comprising 4 different substituents. This carbon atom then forms a chiral or asymmetric centre. Optical isomers comprise diastereoisomers and enantiomers. Optical isomers which are images of one another in a mirror but which cannot be superimposed are called «enantiomers». Optical isomers which are not superimposable images of one another in a mirror are called «diastereoisomers».

A mixture containing equal quantities of two individual enantiomer forms of opposite chirality is called a «racemic mixture».

By «alkyl» in the present invention is meant a monovalent linear or branched, saturated hydrocarbon chain. For example, mention can be made of methyl, ethyl, propyl, isopropyl, butyl, isobutyl, sec-butyl, tert-butyl, pentyl or hexyl groups.

By «$(C_x-C_y)$alkyl» in the meaning of the present invention is meant an alkyl chain such as defined above comprising x to y carbon atoms. Therefore, a $(C_1-C_6)$alkyl group is an alkyl chain having 1 to 6 carbon atoms. The $(C_1-C_6)$alkyl is advantageously a $(C_1-C_4)$alkyl, preferably a $(C_1-C_2)$alkyl.

By «alkanediyl» in the present invention is meant a divalent linear or branched, saturated hydrocarbon chain. For example, mention can be made of methanediyl, ethanediyl, propanediyl, butanediyl, pentanediyl, hexanediyle, and the like.

By «$(C_x-C_y)$alkanediyl» in the meaning of the present invention is meant an alkanediyl chain such as defined above comprising x to y carbon atoms. Therefore, a $(C_1-C_8)$alkanediyl group is an alkanediyl chain having 1 to 8 carbon atoms.

By «aryl» in the meaning of present invention is meant an aromatic hydrocarbon group preferably having 6 to 10 carbon atoms and able to comprise one or two fused rings. For example a phenyl or a naphthyl can be cited. Advantageously it is a phenyl.

By «heterocycle» in the meaning of present invention is meant a saturated, unsaturated or aromatic hydrocarbon group having 1 or 2 fused rings and in which one or more, advantageously 1 to 4, more advantageously 1 or 2 of the carbon atoms are each replaced by a heteroatom chosen from among oxygen, nitrogen and sulfur. Advantageously the heterocycle comprises 5 to 10 carbon atoms and heteroatoms. For example, mention can be made of furan, pyrrole, thiophene, thiazole, isothiazole, oxadiazole, imidazole, oxazole, isoxazole, pyridine, pyrimidine, piperazine, piperidine, quinazoline, quinoline, quinoxaline, benzofuran, benzothiophene, indoline, indolizine, benzothiazole, benzothiophene, benzopyran, benzoxazole, benzo[1,3]dioxole, benzoisoxazole, benzimidazole, chromane, chromene, dihydrobenzofuran, dihydrobenzothiophene, dihydroisoxazole, isoquinoline, dihydrobenzo[1,4]dioxin, imidazo[1,2a]pyridine, furo[2,3c]pyridine, 2,3-dihydro-1H indene, [1,3]dioxolo[4,5c]pyridine, pyrrolo[1,2c]pyrimidine, pyrrolo[1,2a]pyrimidine, tetrahydronaphthalene and benzo[b][1,4]oxazin.

In the present invention, the heterocycle is more particularly a saturated, unsaturated or aromatic ring with 5 to 6 members comprising 1 or 2 nitrogen atoms. For example, mention can be made of pyrrole, imidazole, pyridine, pyrimidine, piperazine and piperidine rings. Preferably it is a pyridine, a piperidine, or an imidazole.

Among the drug moieties of the invention, one particularly appreciated class of drug moieties corresponds to the formula (II) drug moieties in which $R_1$ is OH and $R_2$ represents a $(C_1-C_6)$alkyl group, such as methyl.

Another particularly appreciated class of drug moieties corresponds to the formula (II) drug moieties in which $R_1$ is a hydrogen and $R_2$ is a thiazolyl (in particular a thiazol-2-yl group).

Another class of particularly appreciated drug moieties corresponds to the formula (II) drug moieties in which $R_1$ is a hydrogen and $R_2$ is a COO—($(C_1-C_6)$alkyl) group such as COOMe.

Another class of particularly appreciated compounds corresponds to the formula (II) drug moieties in which $R_1$ is a hydrogen and $R_2$ is a COOH group.

According to one particular embodiment of the present invention, $R_2$ is a methyl, COOH, COOMe or thiazol-2-yl group.

Therefore the drug moieties of the invention are advantageously formula (II) drug moieties in which:
$R_1$=OH and $R_2$=Me (methyl), or
$R_1$=H and $R_2$=COOH, COOMe or thiazol-2-yl.

According to a preferred embodiment, $R_1$=H and $R_2$=COOH, COOMe or thiazol-2 yl, preferably $R_2$=COOH or COOMe, and more preferably $R_2$=COOH.

$R_3$ particularly represents H or a methyl group, advantageously a methyl group.

In a preferred embodiment, $R_1$ is H, $R_2$ is COOH and $R_3$ is a methyl group.

In the definition of A:
the $(C_1-C_8)$alkanediyl group is advantageously a $(C_1-C_6)$ alkanediyl group, preferably a $(C_1-C_4)$alkanediyl group and more preferably a $(C_1-C_2)$alkanediyl group, and in particular it is a straight chain having the formula —$(CH_2)_m$— wherein m is an integer comprised between 1 and 8, advantageously between 1 and 6, preferably between 1 and 4, more preferably m is 1 or 2, the aryl group is advantageously a phenyl group, and the heterocycle is advantageously a saturated, unsaturated or aromatic ring with 5 or 6 members having 1 or 2 nitrogen atoms; for example, a pyrrole, imidazole, pyridine, pyrimidine, piperazine, or piperidine ring; preferably a pyridine, piperidine or imidazole; more preferably a pyridine.

When A is a group of formula -Het-Alk-, Het is more particularly a heterocycle chosen among a piperidine and an imidazole.

When A is a group of formula -$A_a$-$A_b$- wherein $A_b$ is a heterocycle-$(C_1-C_8)$alkanediyl group optionally substituted by a $(C_1-C_6)$alkyl group, the heterocycle is more particularly a pyridine.

According to a preferred embodiment, A is a group of formula -$A_a$-$A_b$- as defined above.

$A_a$ is O or $NR_9$, and preferably $NR_9$, with $R_9$ as defined above, and preferably with $R_9$ =H or Me.

According to a particular embodiment of the invention, $A_b$ represents a group:
$(C_1-C_6)$alkanediyl, in particular $(C_2-C_6)$alkanediyl (such as —$(CH_2)_m$— with m comprised between 1 and 6, preferably between 2 and 6),
—$(CH_2CH_2X_1)_{a1}(CH_2CH_2X_2)_{a2}CH_2CH_2$— with a1+a2 advantageously representing 1 or 2, in particular 1, aryl-$(C_1-C_6)$alkanediyl, or heterocycle-$(C_1-C_6)$alkanediyl optionally substituted by a $(C_1-C_6)$alkyl group (notably unsubstituted).

According to another particular embodiment of the invention, $A_b$ represents a group:

$(C_1-C_4)$alkanediyl, in particular $(C_2-C_4)$alkanediyl (such as —$(CH_2)_m$— with m comprised between 1 and 4 and preferably being 2, 3 or 4), —$(CH_2CH_2X_1)CH_2CH_2$—  or  —$(CH_2CH_2X_1)(CH_2CH_2X_2)CH_2CH_2$—, aryl-$(C_1-C_4)$alkanediyl, or heterocycle-$(C_1-C_4)$alkanediyl optionally substituted by a $(C_1-C_6)$alkyl group (notably unsubstituted).

According to another particular embodiment of the invention, $A_b$ represents a group:

$(C_1-C_4)$alkanediyl, in particular $(C_2-C_4)$alkanediyl (such as —$(CH_2)_m$— with m comprised between 1 and 4 and preferably being 2, 3 or 4),

—$(CH_2CH_2X_1)CH_2CH_2$—, aryl-$(C_1-C_2)$alkanediyl, or heterocycle-$(C_1-C_2)$alkanediyl optionally substituted by a $(C_1-C_6)$alkyl group (notably unsubstituted).

According to another particular embodiment, $A_b$ represents:

an aryl-$(C_1-C_8)$alkanediyl group; or a heterocycle-$(C_1-C_8)$alkanediyl group optionally substituted by a $(C_1-C_6)$alkyl group (notably unsubstituted);

notably an aryl-$(C_1-C_6)$alkanediyl group; or a heterocycle-$(C_1-C_6)$alkanediyl group optionally substituted by a $(C_1-C_6)$alkyl group (notably unsubstituted);

advantageously an aryl-$(C_1-C_4)$alkanediyl group; or a heterocycle-$(C_1-C_4)$alkanediyl group optionally substituted by a $(C_1-C_6)$alkyl group (notably unsubstituted);

and preferably an aryl-$(C_1-C_2)$alkanediyl group; or a heterocycle-$(C_1-C_2)$alkanediyl group optionally substituted by a $(C_1-C_6)$alkyl group (notably unsubstituted).

According to yet another particular embodiment, $A_b$ is an aryl-$(C_1-C_8)$alkanediyl group; notably an aryl-$(C_1-C_6)$alkanediyl group; advantageously an aryl-$(C_1-C_4)$alkanediyl group; and preferably an aryl-$(C_1-C_2)$alkanediyl group.

In the above particular embodiments for $A_b$, the aryl group is advantageously a phenyl group.

In the above particular embodiments for $A_b$, the heterocycle is advantageously a saturated, unsaturated or aromatic ring with 5 or 6 members having 1 or 2 nitrogen atoms. For example, mention can be made of pyrrole, imidazole, pyridine, pyrimidine, piperazine, or piperidine rings. Preferably it is a pyridine, piperidine or imidazole, and more preferably, it is a pyridine.

Advantageously, $A_b$ represents a group:

phenyl-$(C_1-C_2)$alkanediyl, or heterocycle-$(C_1-C_2)$alkanediyl optionally substituted by a $(C_1-C_6)$alkyl group (notably unsubstituted), the heterocycle being a saturated, unsaturated or aromatic ring with 5 or 6 members comprising 1 or 2 nitrogen atoms, chosen in particular from among pyridine, piperidine and imidazole, and being preferably a pyridine.

In a preferred embodiment, $A_b$ is a phenyl-$(C_1-C_2)$alkanediyl group.

According to a preferred embodiment, A has the following formula:

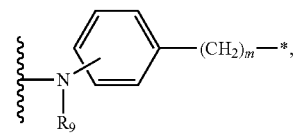

and preferably the following formula:

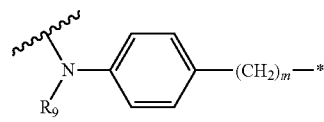

wherein:

$R_9$ and m are as defined previously, and preferably with $R_9$=H or Me and m=1 or 2, the wavy line indicates the point of attachment to L, and the asterisk indicates the point of attachment to $NR_3$.

Advantageously, the drug moiety is chosen from among the following moieties:

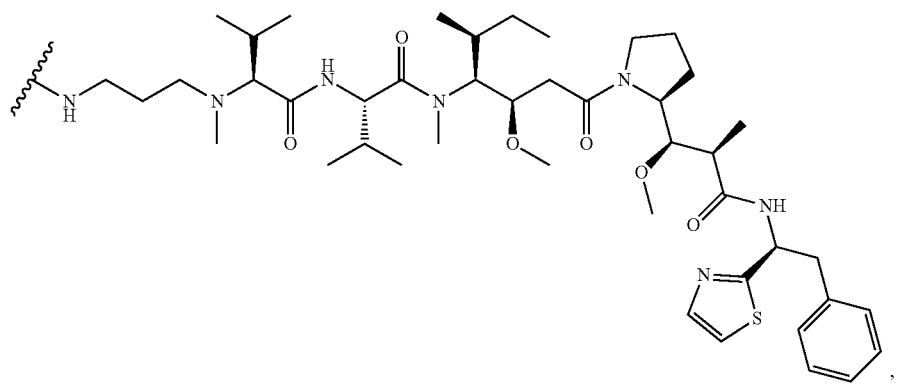

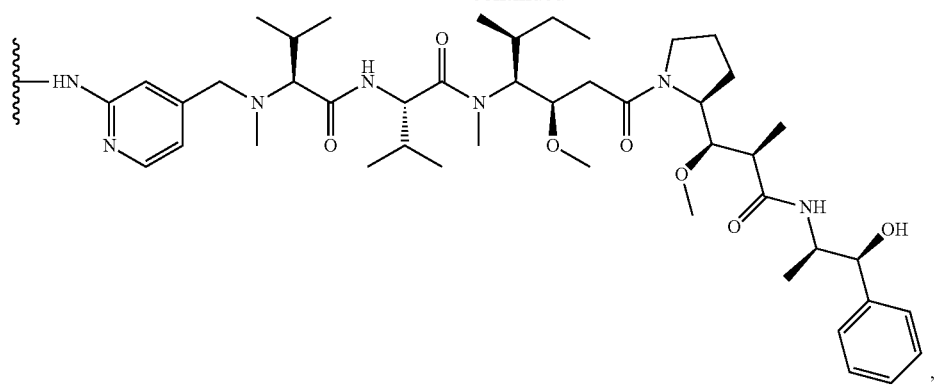
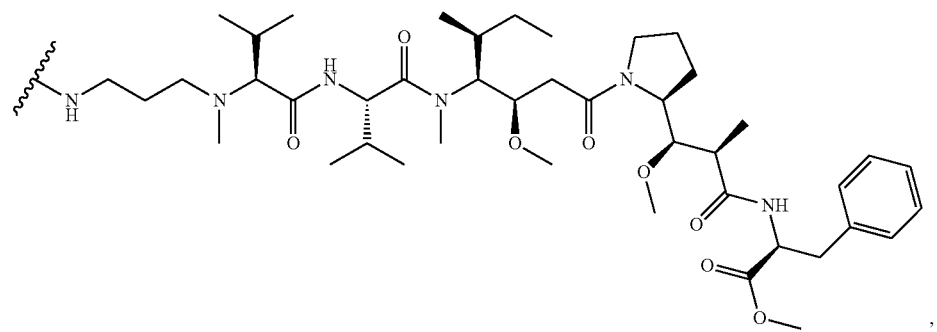
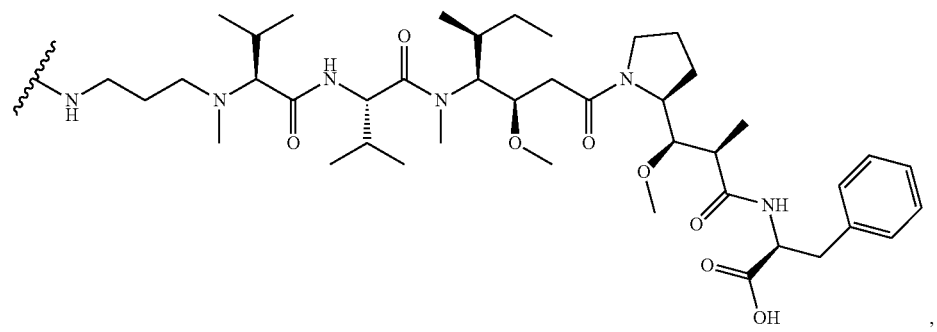
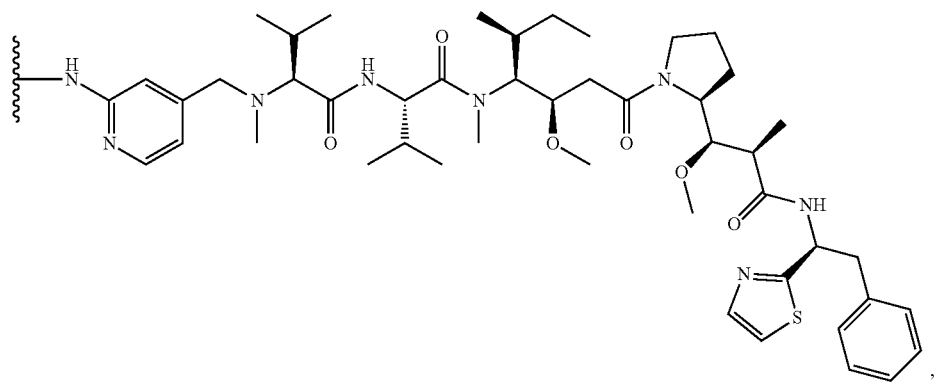

-continued
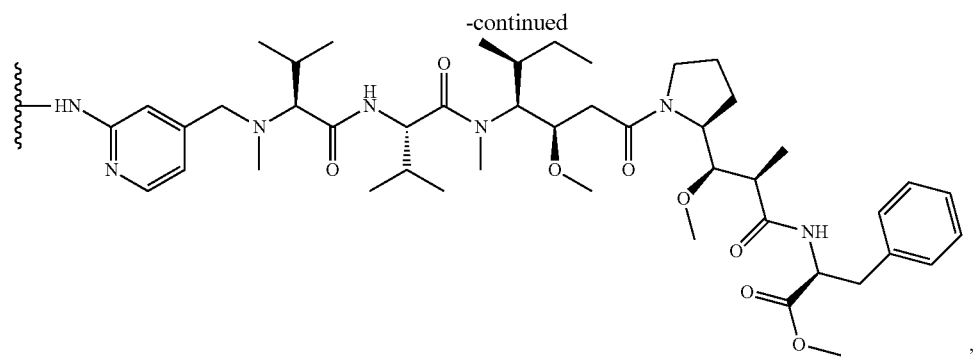
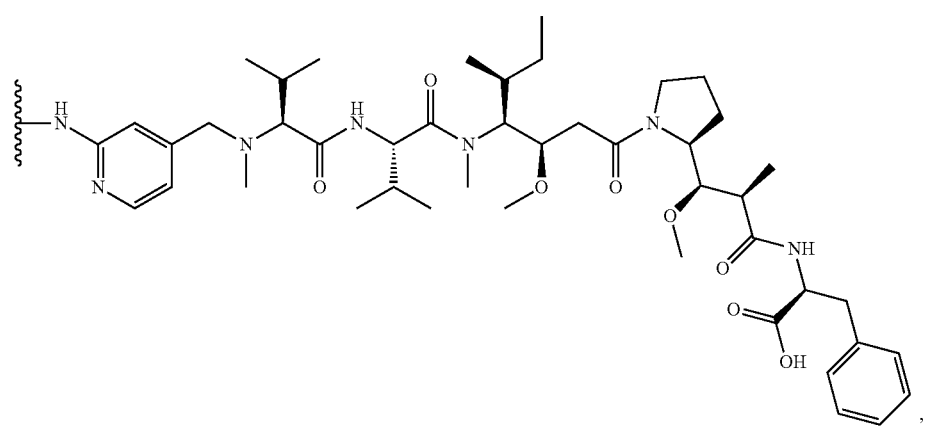
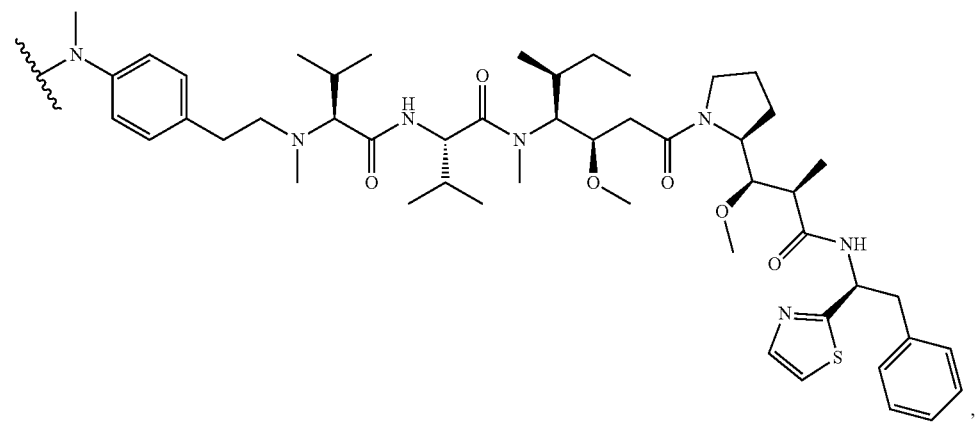
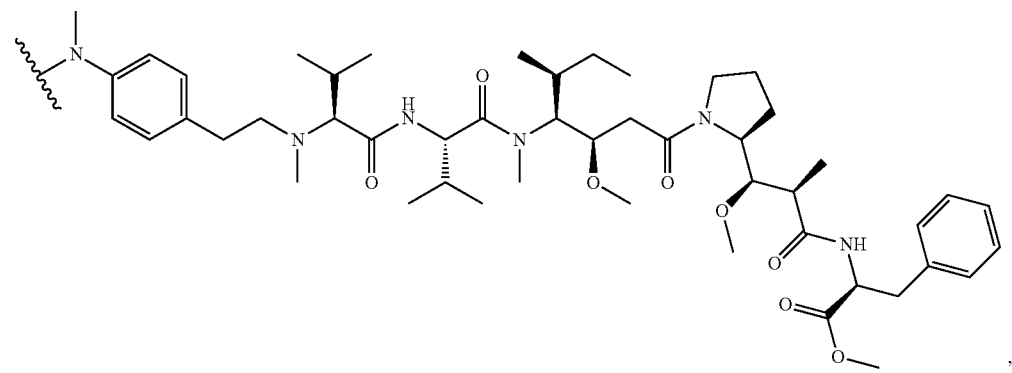

-continued
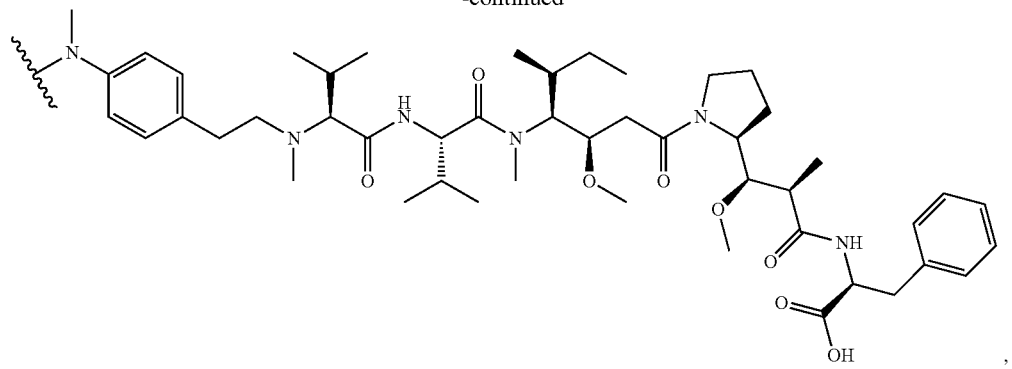
,
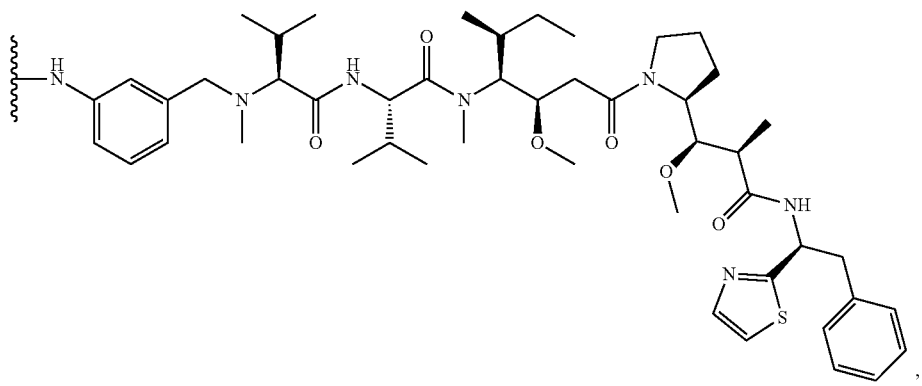
,
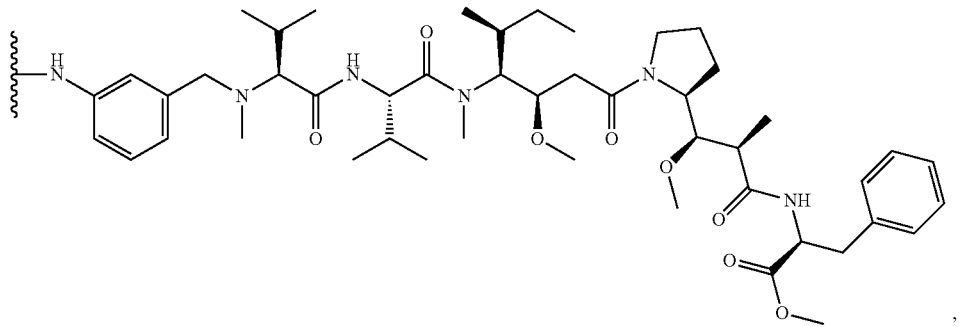
,
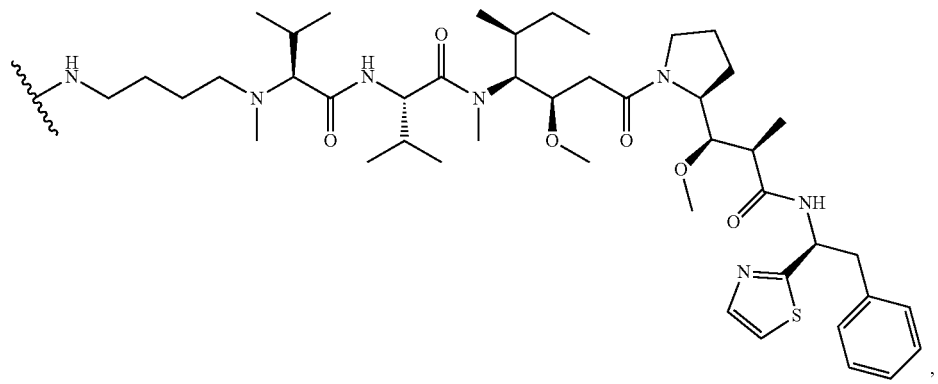
,

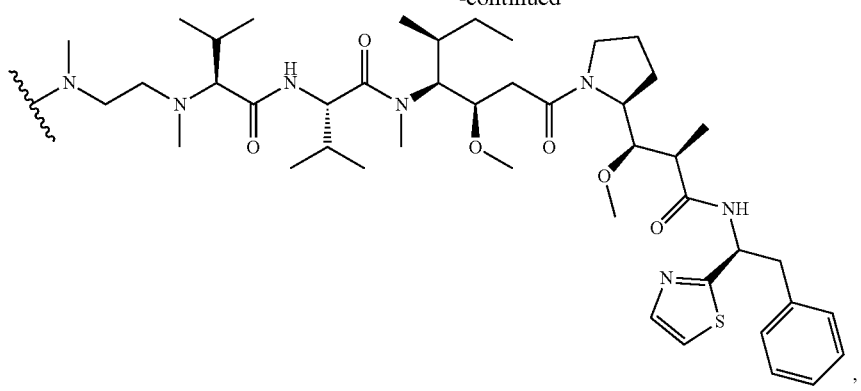
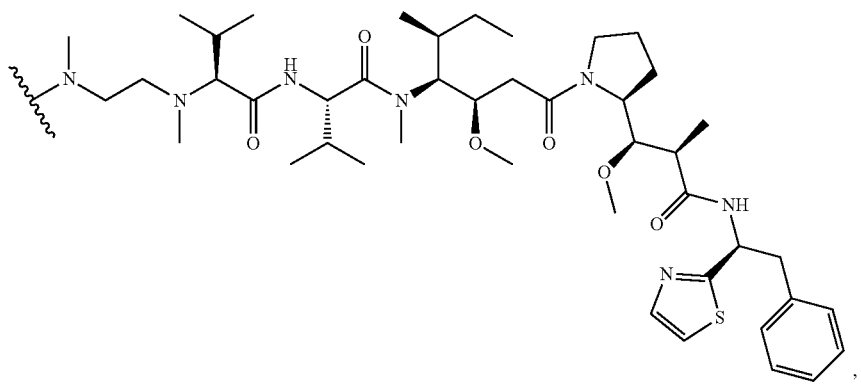
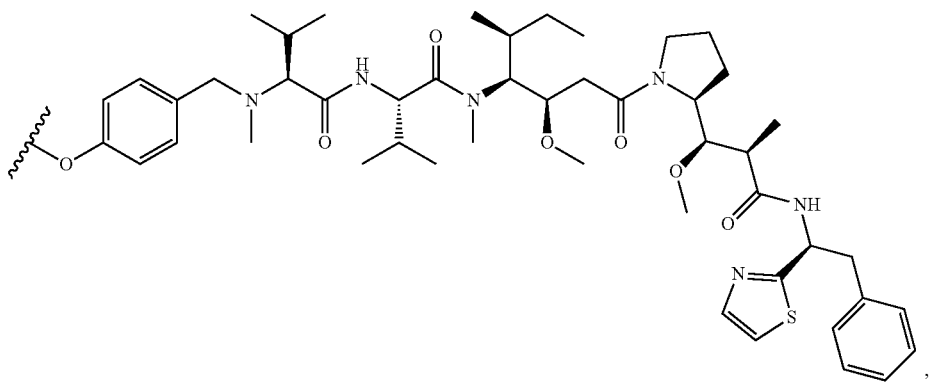
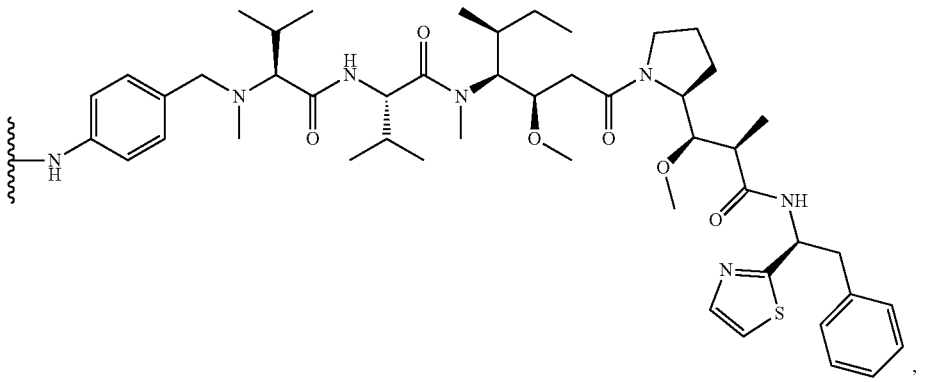

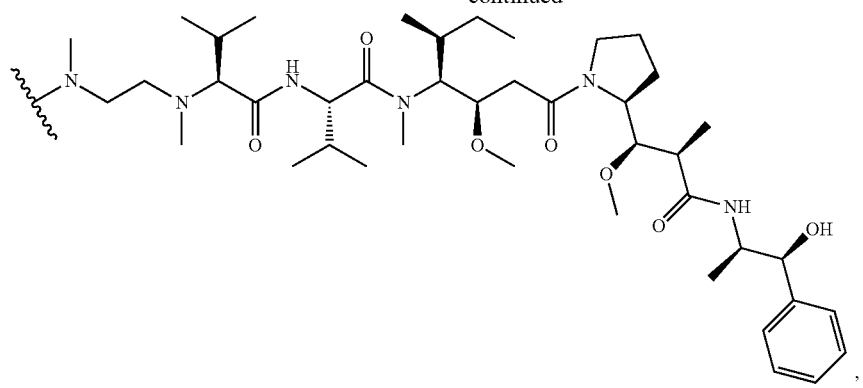
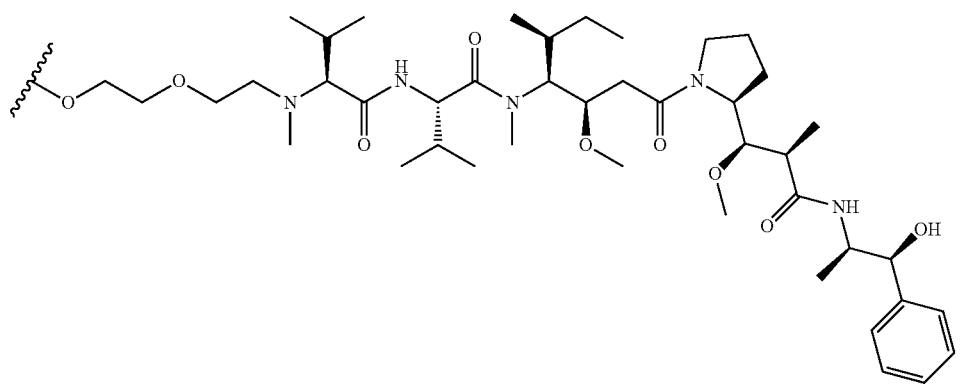
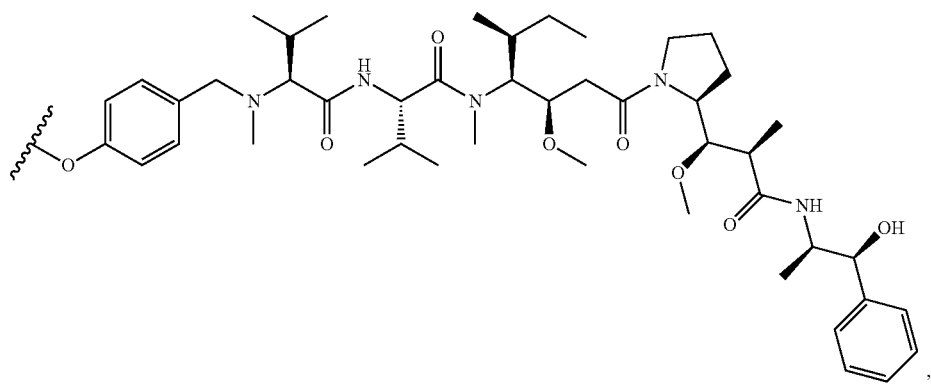
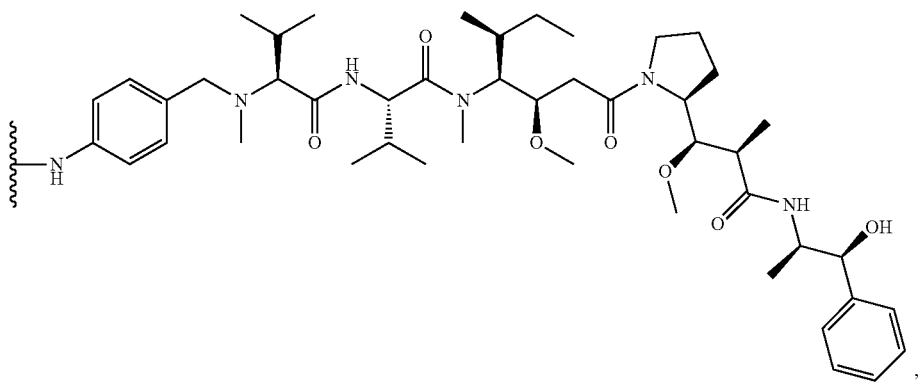

-continued
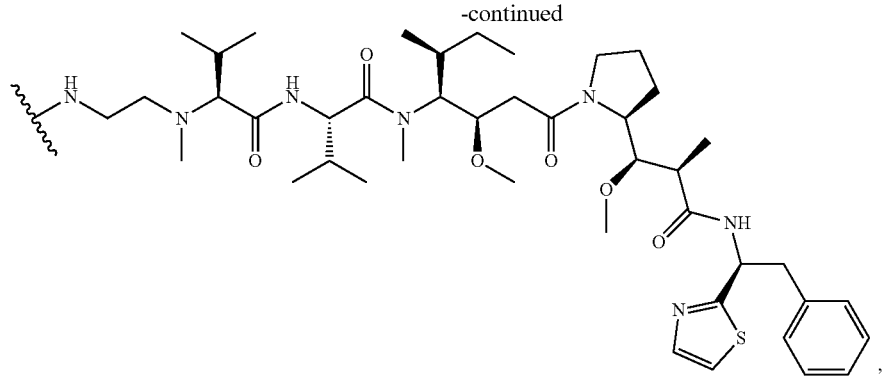
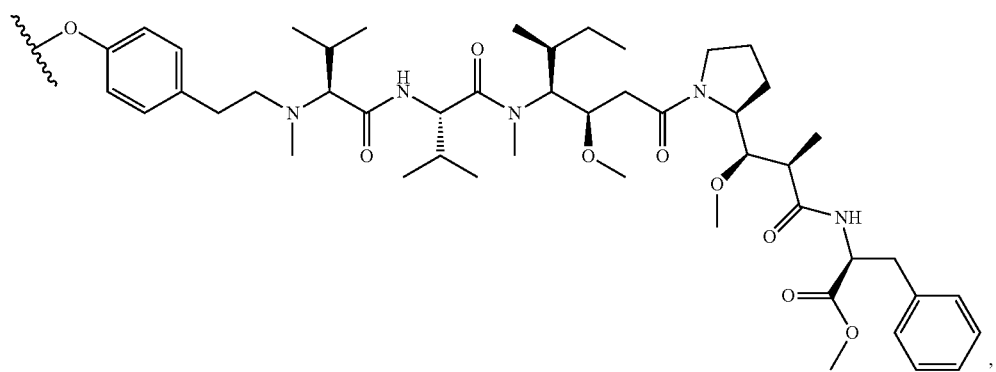
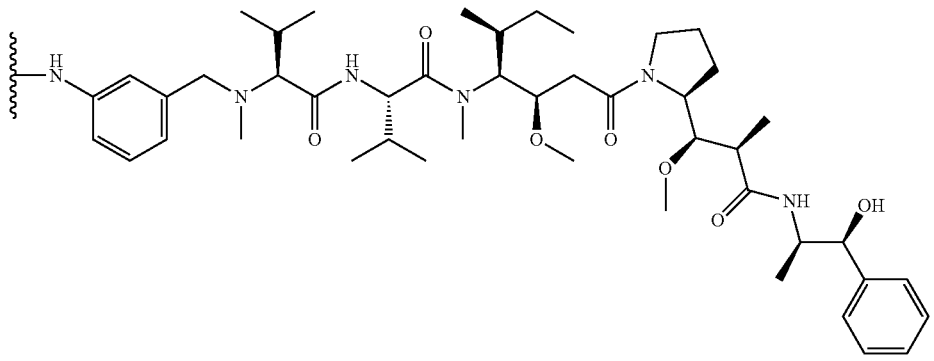
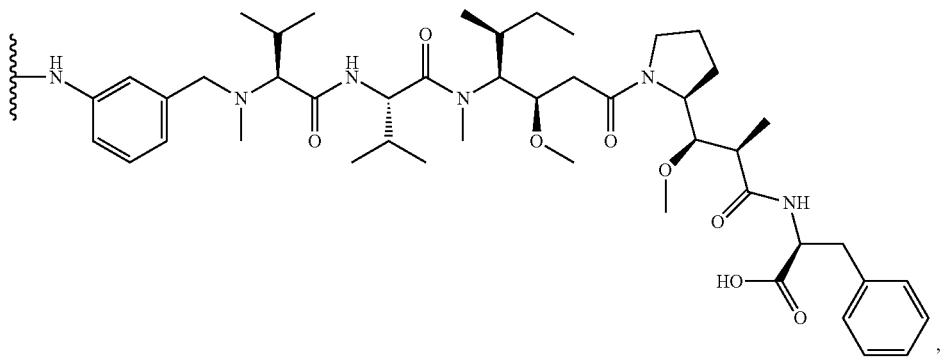

-continued
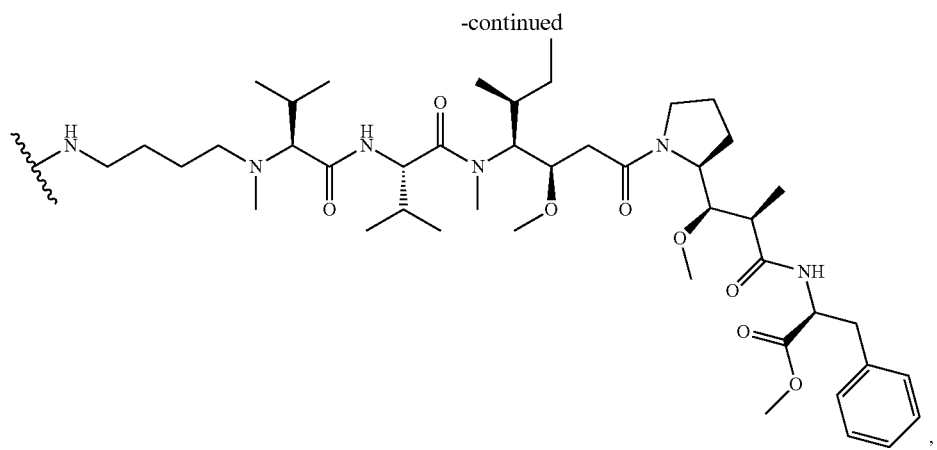
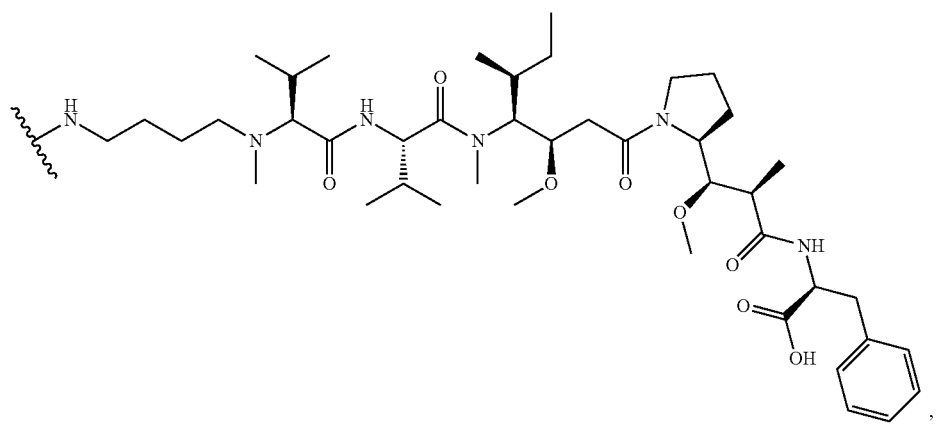
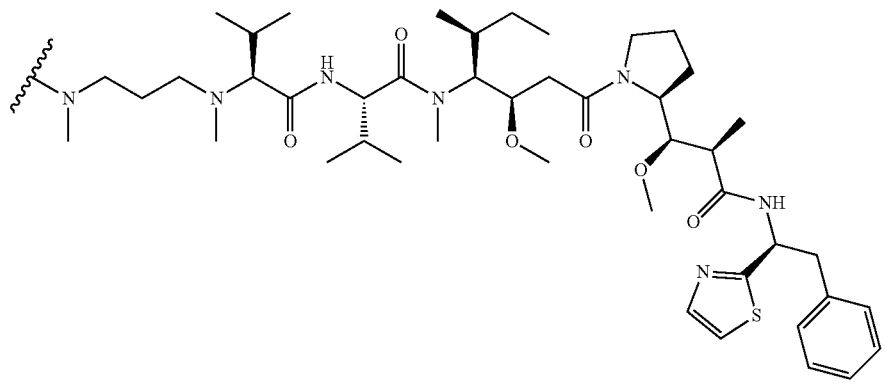
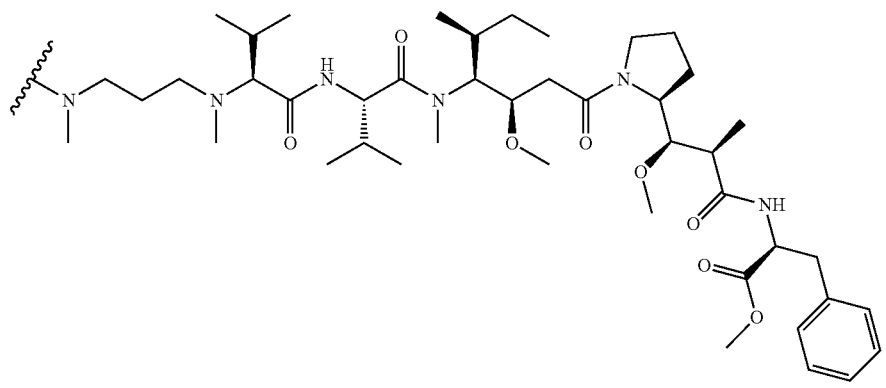

-continued
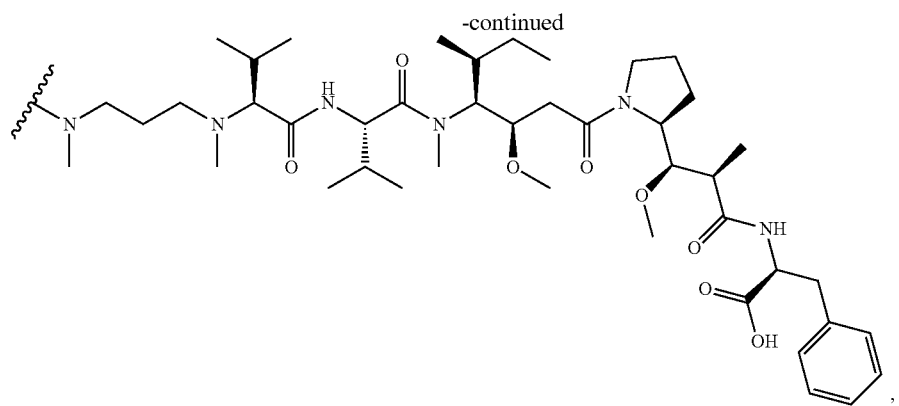
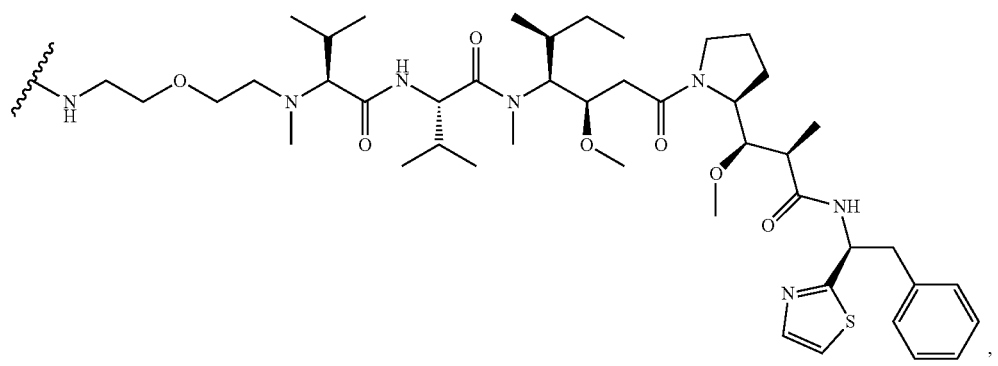
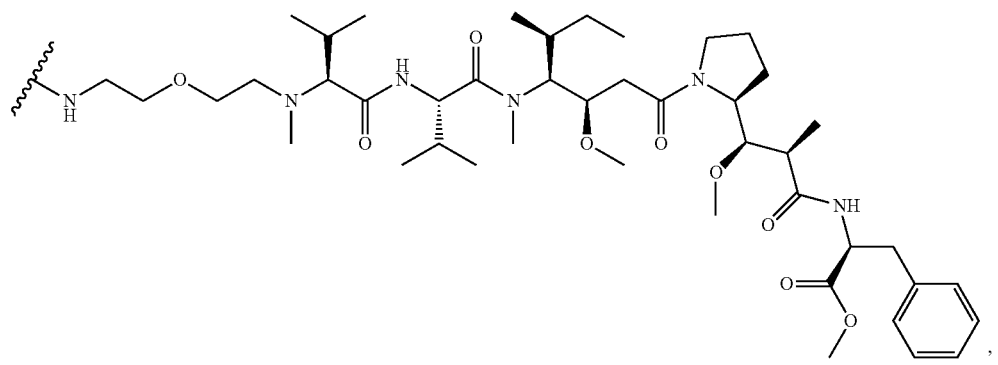
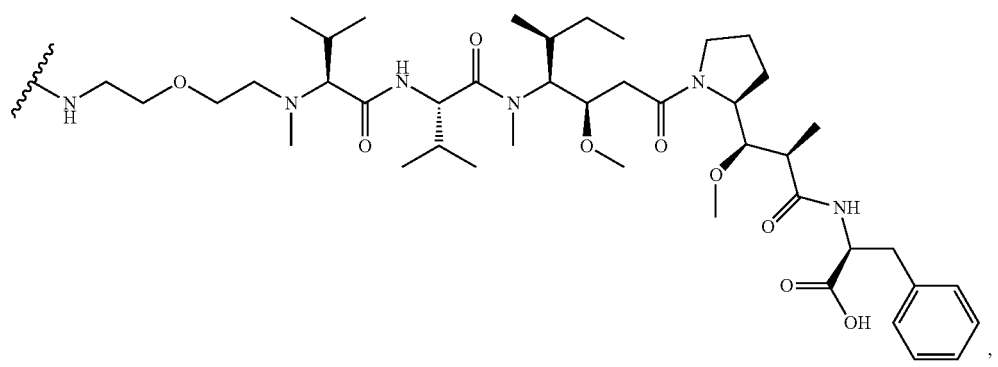

-continued
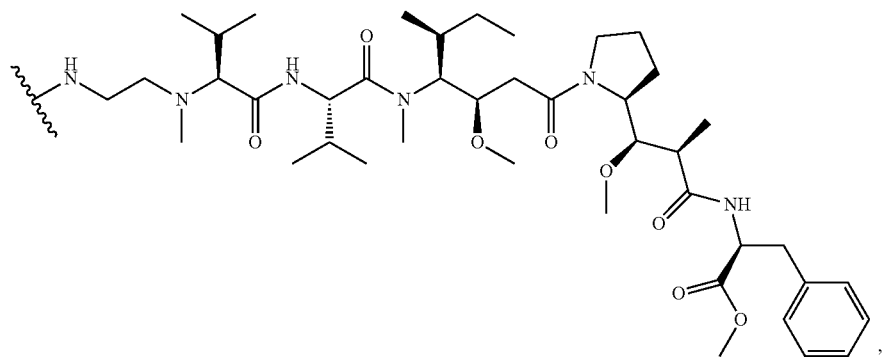
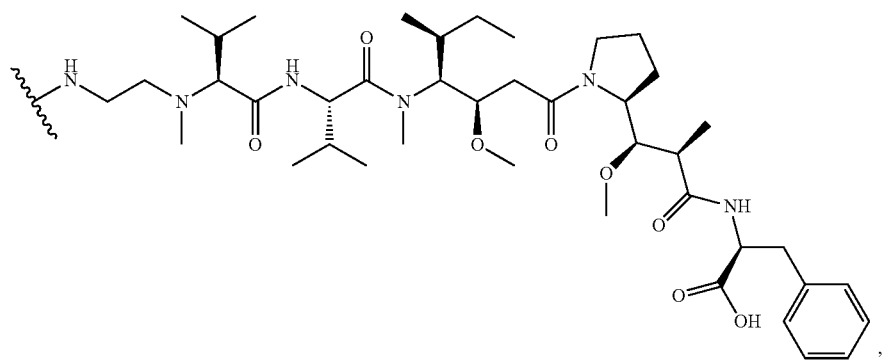
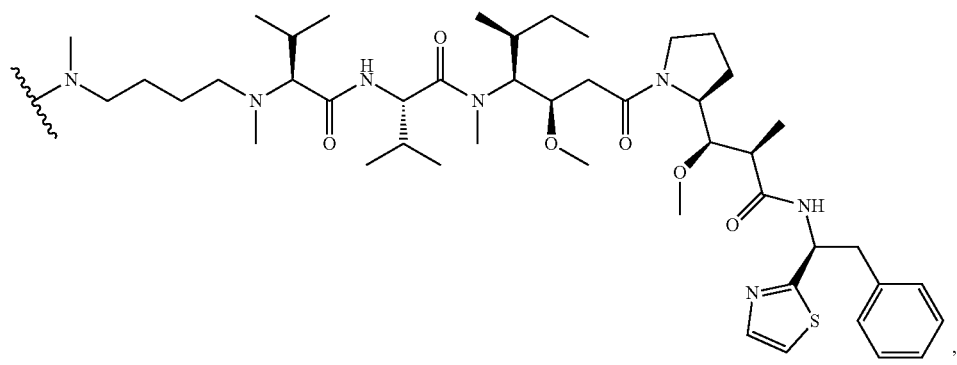
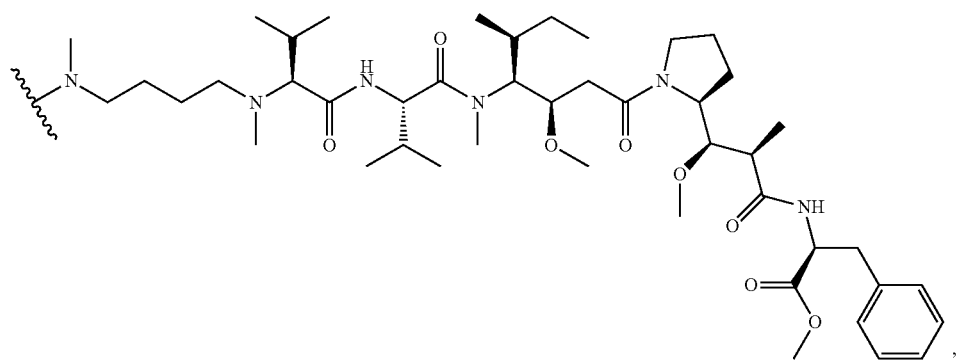

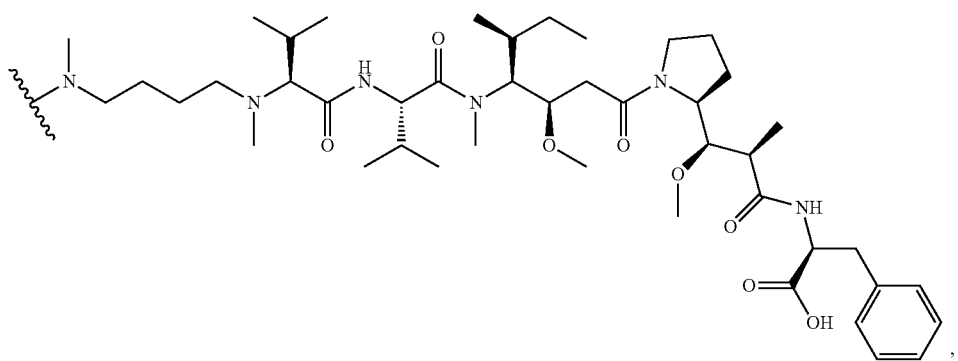
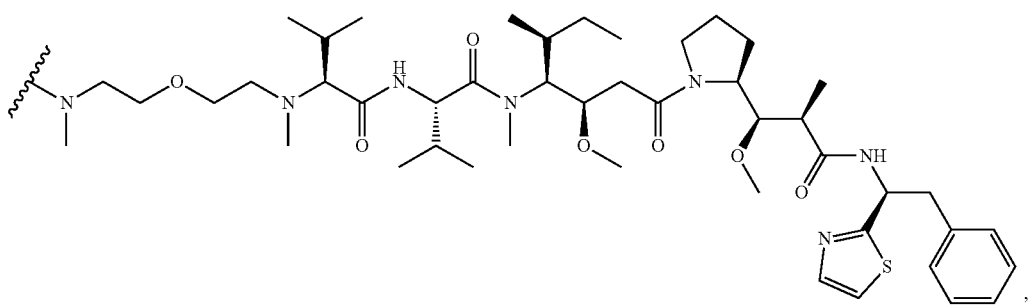
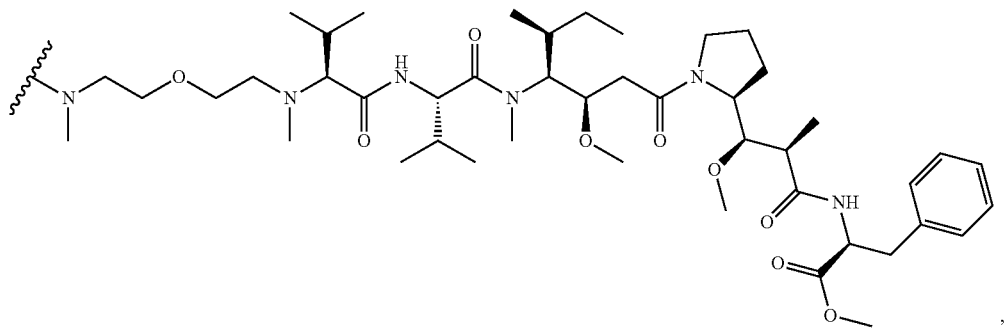
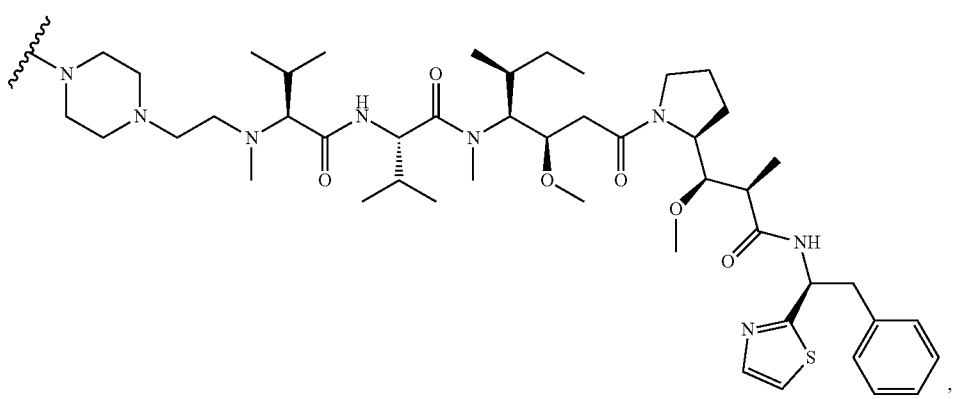

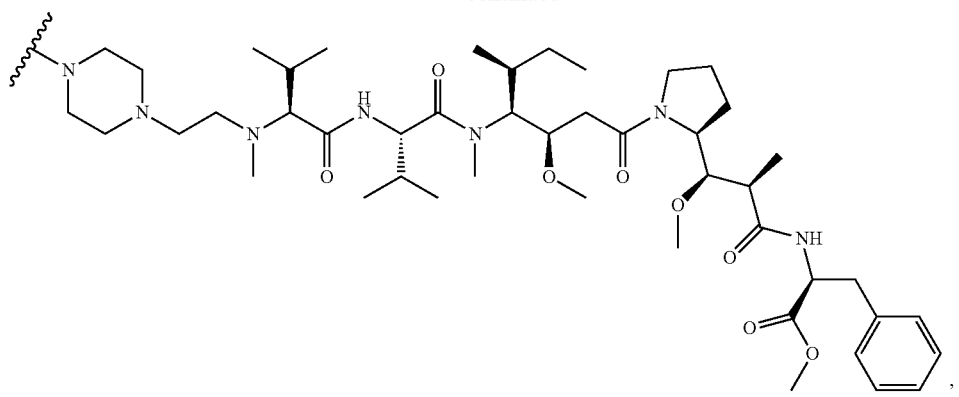
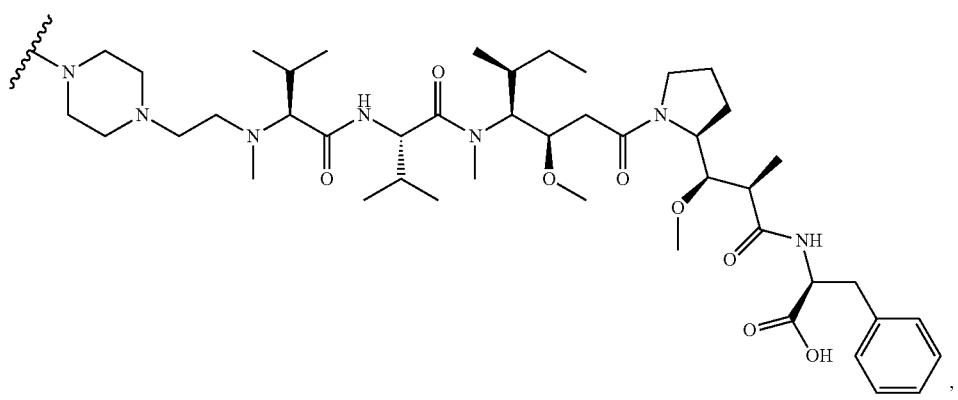
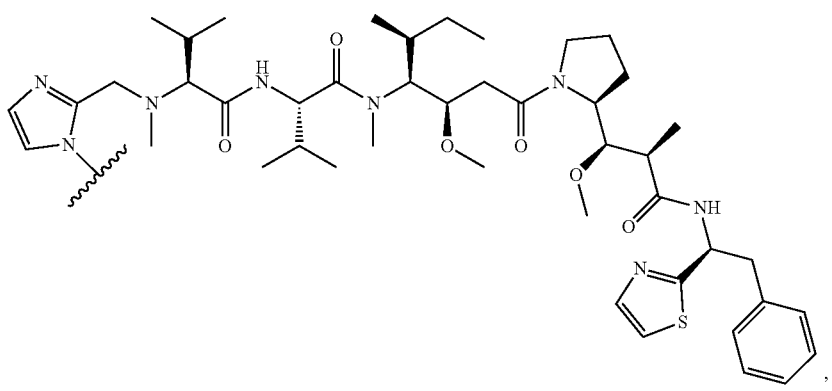
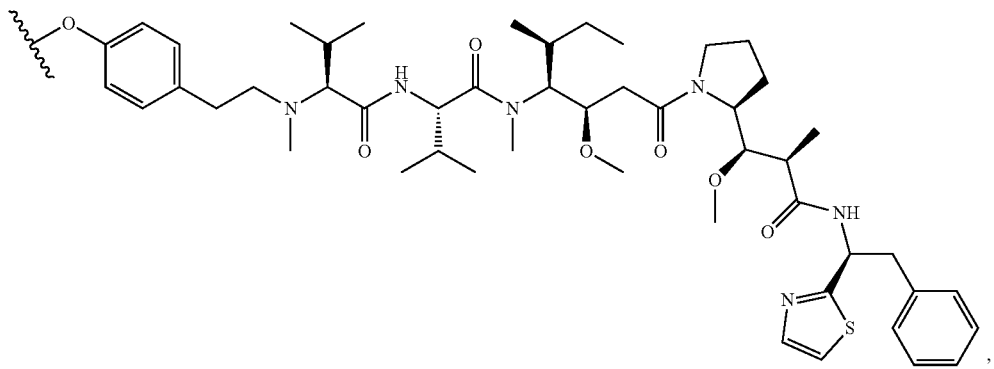

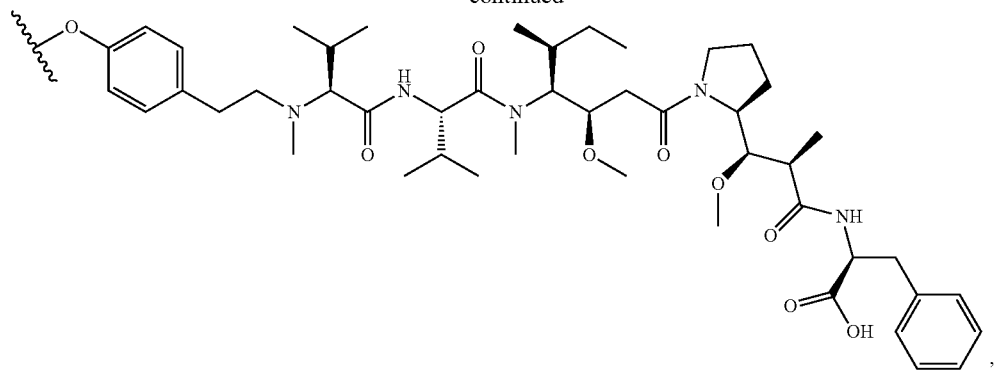
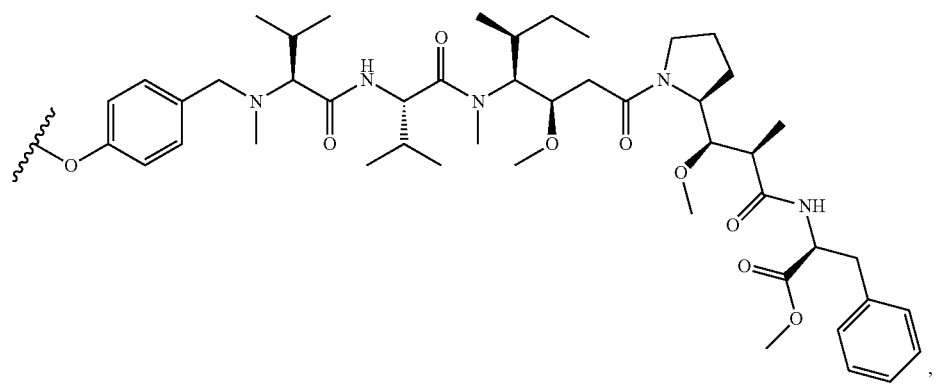
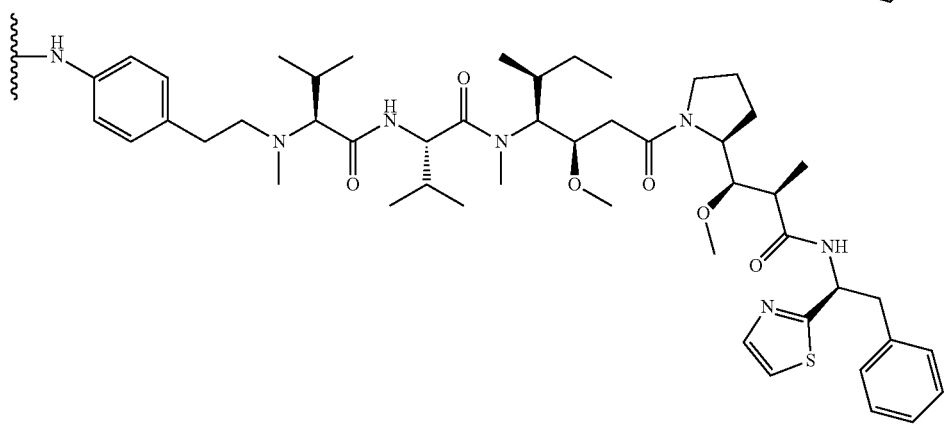
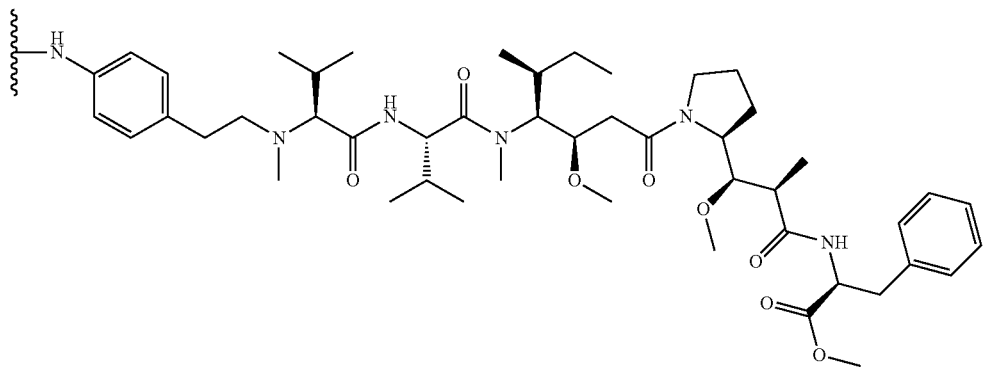

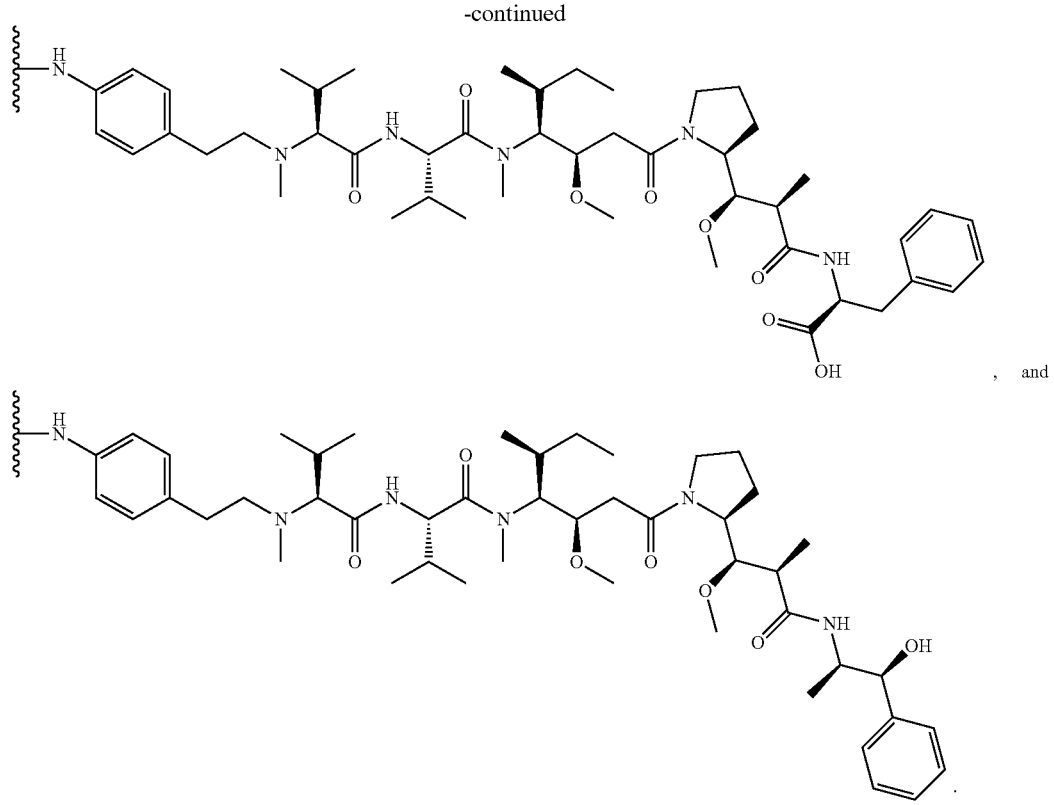
, and
Preparation of the Drug (of Formula DH):
The drug can be prepared using the general methods described in the following synthesis schemes, optionally supplemented by any standard operation when needed that is described in the literature or well known to persons skilled in the art, or described in the examples in the experimental part hereof.
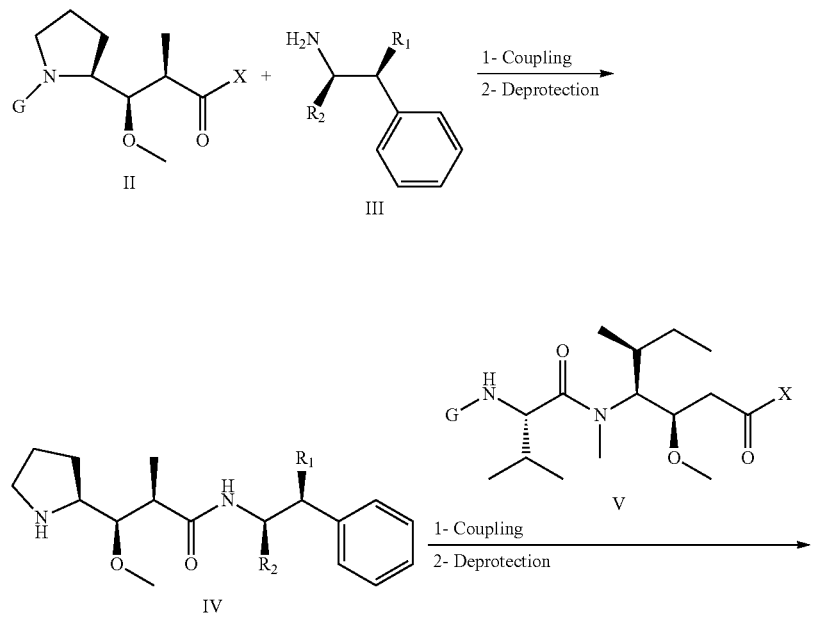

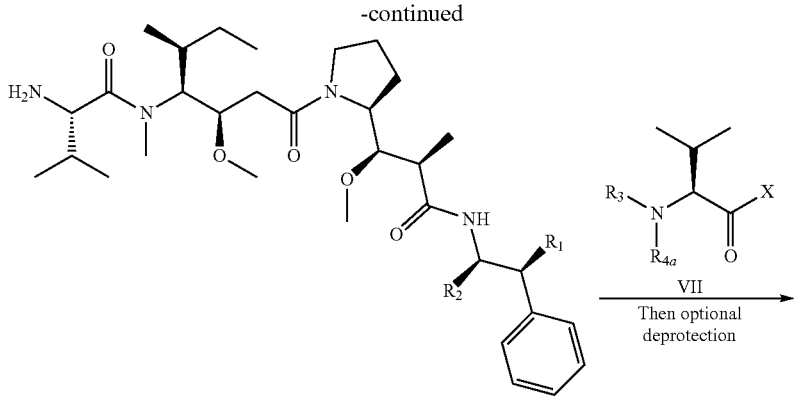

VI

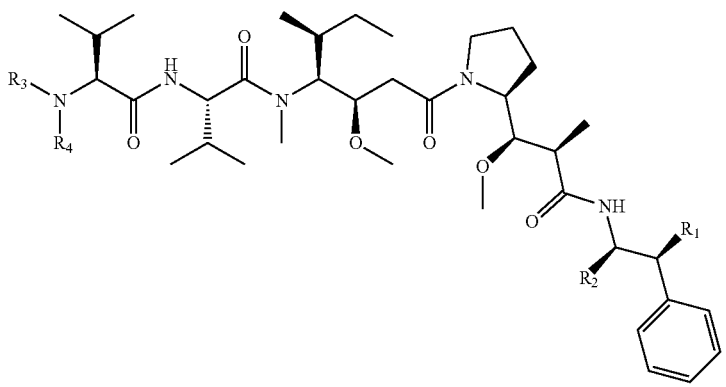

I

Scheme 1 illustrates the first general method which can be used to prepare the drug. In the above general formulas, $R_1$, $R_2$ and $R_3$ are such as previously defined, $R_4$ represents -AH, and $R_{4a}$ represents a $R_4$ group such as previously defined optionally in protected form and G is a protective group.

The first step consists of the condensing of compound (II), protected on its amine function by a protective group G, with compound (III). X may represent a leaving group such as a chlorine. In this case the first step consists of the reaction between an acid chloride and an amine. This reaction can be conducted using methods and techniques well known to those skilled in the art. In one particularly appreciated method, the two entities are caused to react in the presence of an organic or inorganic base e.g. $Et_3N$, $iPr_2NEt$, pyridine, NaH, $Cs_2CO_3$, $K_2CO_3$ in a solvent such as THF, dichloromethane, DMF, DMSO, at a temperature notably between −20° C. and 100° C. X may also be a hydroxyl (OH). In this case, the first step is a condensation reaction between the carboxylic acid (II) and the amine (III). This reaction can be performed following methods and techniques well known to skilled persons. In one particularly appreciated method, these two entities are caused to react in the presence of a coupling agent such as 1-(3-dimethylaminopropyl)-3-ethyl-carbodiimide (EDC), 3-hydroxy-1,2,3-benzotriazin-4(3H)-one, a tertiary amine such as diisopropylethylamine, in a polar aprotic solvent such as dichloromethane or DMF, at a temperature notably between −15° C. and 40° C. In another particularly appreciated method, these two entities are caused to react in the presence of diethyl phosphorocyanidate (DEPC), a tertiary amine such as triethylamine, in a polar aprotic solvent such as dichloromethane or DMF, at a temperature of between −15° C. and 40° C. Another particularly appreciated method consists of causing these two entities to react in the presence of O-(7-azabenzotriazol-1-yl)-1,1,3,3-tetramethyl-uroniumhexafluorophosphate (HATU), a tertiary amine such as diisopropylethylamine, in a polar aprotic solvent such as dichloromethane or DMF, at a temperature of between −15° C. and 100° C.

After deprotection of the intermediate using techniques well known to those skilled in the art («Protective Groups in Organic Synthesis», T.W. Greene, John Wiley & Sons, 2006 and «Protecting Groups», P. J. Kocienski, Thieme Verlag, 1994), compound (IV) can be condensed with compound (V) following the methods and techniques described above to lead to compound (VI) after a deprotection step. This compound can then, after condensation with the intermediate (VII) and optional deprotection, lead to the formation of the drug. Compound (VI) can also be coupled with a compound (VII') in which $R'_3$ is a precursor of $R_3$, in particular an $R_3$ group protected by a protective group. Coupling followed by deprotection of group $R'_3$ to lead to $R_3$ can be carried out following the same procedures as described previously.

Scheme 2

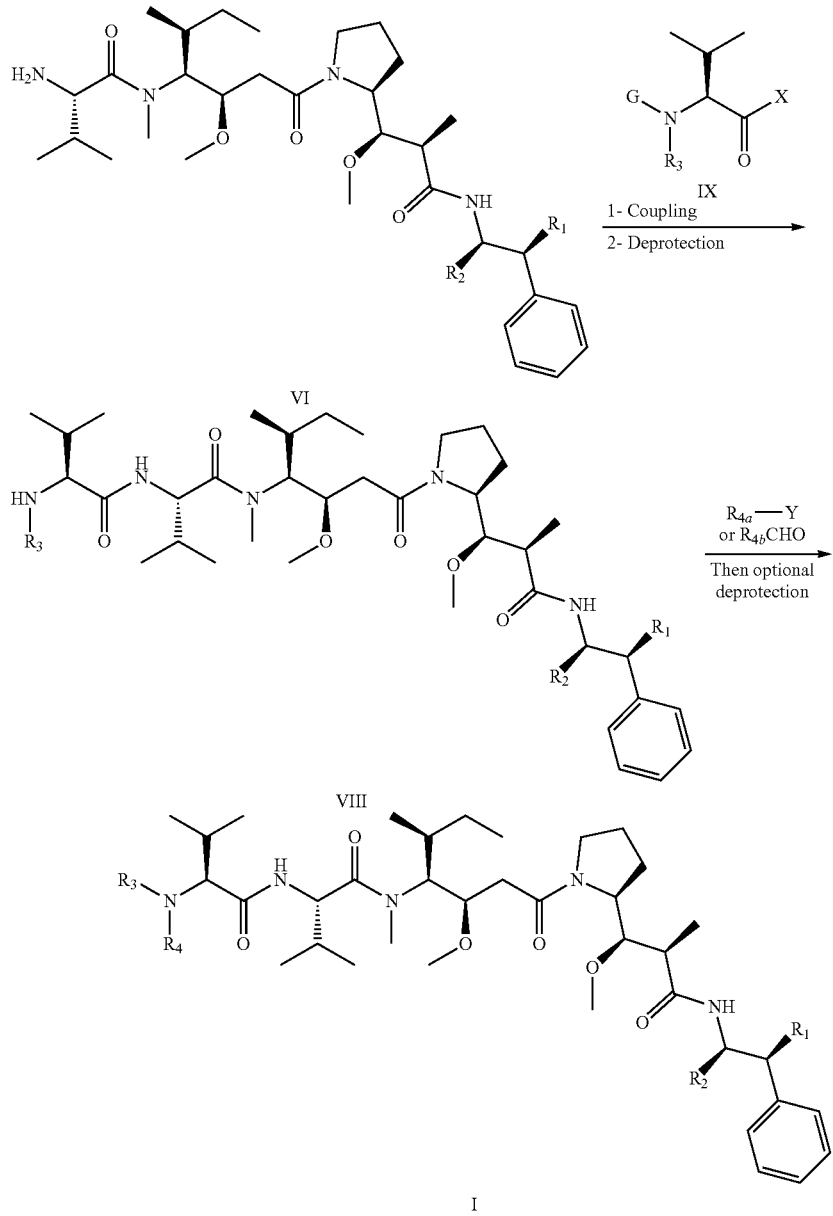

Scheme 2 illustrates the second general method which can be used to prepare the drug. In the above general formulas, G is a protective group, $R_1$, $R_2$, $R_3$ and $R_{4a}$ are such as previously defined, and $R_{4b}$ represents -$A_c$-$A_a$H with $A_a$ as defined previously and $A_c$ representing:

a ($C_1$-$C_7$)alkanediyl group, a —($CH_2CH_2X_1$)$_{a1}$($CH_2CH_2X_2$)$_{a2}$($CH_2CH_2X_3$)$_{a3}$ ($CH_2CH_2X_4$)$_{a4}$$CH_2$*— group wherein the $CH_2$ group marked with an asterisk is linked to the CHO group of $R_{4b}$CHO, an aryl or heterocycle group, an aryl-($C_1$-$C_7$)alkanediyl or heterocycle-($C_1$-$C_7$)alkanediyl group, said group being optionally substituted by a ($C_1$-$C_6$)alkyl group, the ($C_1$-$C_7$)alkanediyl moiety being linked to the CHO group of $R_{4b}$CHO.

At the first step, compound (IX) protected on its amine function by a protective group G is condensed with compound (VI). X may represent a leaving group e.g. a chlorine. In this case, the first step consists of the reaction between an acid chloride and an amine. This reaction can be performed using methods and techniques well known to persons skilled in the art. In one particularly appreciated method the two entities are caused to react in the presence of an organic or inorganic base such as $Et_3N$, $iPr_2NEt$, pyridine, NaH, $Cs_2CO_3$, $K_2CO_3$ in a solvent such as THF, dichloromethane, DMF, DMSO at a temperature notably between −20° and 100° C. X may also represent a hydroxyl. In this case, the first step is a condensation reaction between the carboxylic acid (IX) and the amine (VI). This reaction can be conducted following methods and techniques well known to skilled persons. In one particularly appreciated method, the two entities are caused to react in the presence of 1-(3-dimethylaminopropyl)-3-ethyl-carbodiimide (EDC), 3-hydroxy-1, 2,3-benzotriazin-4(3H)-one, a tertiary amine such as diisopropylethylamine, in a polar aprotic solvent such as dichloromethane or DMF, at a temperature notably between −15° C. and 40° C. In another particularly appreciated method, these two entities are caused to react in the presence of diethyl phosphorocyanidate (DEPC), a tertiary amine such as triethylamine, in a polar aprotic solvent such as dichloromethane or DMF, at a temperature notably between −15° C. and 40° C.

After deprotection of the intermediate, using techniques well known to skilled persons, the obtained compound (VIII) can lead to the drug after reaction with $R_4Y$. In this case, Y is a leaving group such as Cl, Br, I, $OSO_2CH_3$, $OSO_2CF_3$ or O-Tosyl. The reaction is conducted in the presence of an organic or inorganic base such as $Et_3N$, $iPr_2NEt$, NaH, $Cs_2CO_3$, $K_2CO_3$, in a polar anhydrous solvent such as dichloromethane, THF, DMF, DMSO at a temperature notably between −20° and 100° C. In another particularly appreciated method, compound (VIII) is caused to react with an aldehyde of formula $R_{4b}$—CHO where $R_{4b}$ corresponds to a precursor of $R_4$. In this case, the reaction is a reductive amination in the presence of a reducing agent such as $NaBH_4$, $NaBH_3CN$, $NaBH(OAc)_3$, in a polar solvent such as 1,2-dichloroethane, dichloromethane, THF, DMF, MeOH, in the optional presence of titanium isopropoxide (IV), at a pH which can be controlled by the addition of an acid such as acetic acid at a temperature notably between −20° C. and 100° C.

In the foregoing synthesis schemes, a drug may lead to another drug after an additional reaction step such as saponification for example using methods well known to skilled persons whereby an $R_2$ group representing an ester (COOMe), is changed to an $R_2$ group representing a carboxylic acid (COOH).

If it is desired to isolate a drug containing at least one base function in the state of an acid addition salt, this is possible by treating the free base of the drug (containing at least one base function) with a suitable acid, preferably in equivalent quantity. The suitable acid may in particular be trifluoroacetic acid.

III—The Linker (L)

"Linker", "Linker Unit", "L" or "link" means, in the present invention, a chemical moiety comprising a covalent bond or a chain of atoms that covalently attaches an antibody to at least one drug.

Linkers may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of cyctotoxic agents to the addressing system. Other cross-linker reagents may be BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from PIERCE® Biotechnology, Inc., Rockford, Ill., U.S.A).

The linker may be a "non cleavable" or "cleavable".

In a preferred embodiment, it consists in a "cleavable linker" facilitating release of the drug in the cell. For example, an acid-labile linker, peptidase-sensitive linker, photolabile linker, dimethyl linker or disulfide-containing linker may be used. The linker is, in a preferred embodiment, cleavable under intracellular conditions, such that cleavage of the linker releases the drug from the antibody in the intracellular environment.

For example, in some embodiments, the linker is cleavable by a cleaving agent that is present in the intracellular environment (e.g., within a lysosome or endosome or caveolea). The linker can be, for example, a peptidyl linker that is cleaved by an intracellular peptidase or protease enzyme, including, but not limited to, a lysosomal or endosomal protease. Typically, the peptidyl linker comprises at least two successive amino acids or at least three successive amino acids or is at least two amino acids long or at least three amino acids long. Cleaving agents can include cathepsins B and D and plasmin, all of which are known to hydrolyze dipeptide drug derivatives resulting in the release of active drug inside target cells. For example, a peptidyl linker that is cleavable by the thiol-dependent protease cathepsin-B, which is highly expressed in cancerous tissue, can be used (e.g., a linker comprising or being Phe-Leu or Gly-Phe-Leu-Gly (SEQ ID NO: 53)). In specific embodiments, the peptidyl linker cleavable by an intracellular protease comprises or is Val-Cit or Phe-Lys. One advantage of using intracellular proteolytic release of the drug is that the drug is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the drug via an acylhydrazone bond).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene).

In certain preferred embodiments, the linker unit may have the following general formula:

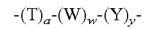

wherein:

T is a stretcher unit;

a is 0 or 1;

W is an amino acid unit;

w is an integer ranging from 0 to 12;

Y is a spacer unit;

y is 0, 1 or 2.

The stretcher unit (T), when present, links the antibody to an amino acid unit (W) when present, or to the spacer unit when present, or directly to the drug. Useful functional groups that can be present on the antibody, either naturally or via chemical manipulation, include sulfhydryl, amino, hydroxyl, the anomeric hydroxyl group of a carbohydrate, and carboxyl. Suitable functional groups are sulfhydryl and amino. Sulfhydryl groups can be generated by reduction of the intramolecular disulfide bonds of the antibody, if present. Alternatively, sulfhydryl groups can be generated by reaction of an amino group of a lysine moiety of the antibody with 2-iminothiolane or other sulfhydryl generating reagents. In specific embodiments, the antibody is engineered to carry one or more lysines. More preferably, the antibody can be engineered to carry one or more Cysteines (cf. THIOMAB™).

In certain specific embodiments, the stretcher unit forms a bond with a sulfur atom of the antibody. The sulfur atom can be derived from a sulfhydryl (—SH) group of a reduced antibody.

In certain other specific embodiments, the stretcher unit is linked to the antibody via a disulfide bond between a sulfur atom of the antibody and a sulfur atom of the stretcher unit.

In other specific embodiments, the reactive group of the stretcher contains a reactive site that can be reactive to an amino group of the antibody. The amino group can be that of an arginine or a lysine. Suitable amine reactive sites include, but are not limited to, activated esters (such as succinimide esters, 4-nitrophenyl esters, pentafluorophenyl esters), anhydrides, acid chlorides, sulfonyl chlorides, isocyanates and isothiocyanates.

In yet another aspect, the reactive function of the stretcher contains a reactive site that is reactive to a modified carbohydrate group that can be present on the antibody. In a specific embodiment, the antibody is glycosylated enzymatically to provide a carbohydrate moiety or is naturally glycosylated. The carbohydrate may be mildly oxidized with a reagent such as sodium periodate and the resulting carbonyl unit of the oxidized carbohydrate can be condensed with a stretcher that contains a functionality such as a hydrazide, an oxime, a reactive amine, a hydrazine, a thiosemicarbazide, a hydrazine carboxylate, or an arylhydrazide.

According to a particular embodiment, the stretcher unit has the following formula:

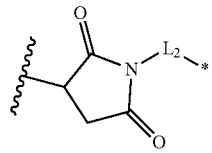

wherein
$L_2$ is $(C_4-C_{10})$cycloalkyl-carbonyl, $(C_2-C_6)$alkyl or $(C_2-C_6)$alkyl-carbonyl (the cycloalkyl or alkyl moieties being linked to the nitrogen atom of the maleimide moiety),
the asterisk indicates the point of attachment to the amino acid unit, if present, to the spacer unit, if present, or to the drug D, and
the wavy line indicates the point of attachment to the antibody Ab.

By "$(C_4-C_{10})$cycloalkyl" in the present invention is meant a hydrocarbon cycle having 4 to 10 carbon atoms including, but not limited to, cyclopentyl, cyclohexyl and the like.

$L_2$ can be advantageously $(C_2-C_6)$alkyl-carbonyl such as a pentyl-carbonyl of the following formula:

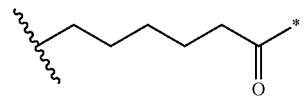 [SMILES: *CCCCCC(*)=O]

wherein
the asterisk indicates the point of attachment to the amino acid unit, if present, to the spacer unit, if present, or to the drug D; and
the wavy line indicates the point of attachment to the nitrogen atom of the maleimide moiety.

The amino acid unit (W), when present, links the stretcher unit (T) if present, or otherwise the antibody to the spacer unit (Y) if the spacer unit is present, or to the drug if the spacer unit is absent.

As above mentioned, $(W)_w$ is absent (w=0) or may be a dipeptide, tripeptide, tetrapeptide, pentapeptide, hexapeptide, heptapeptide, octapeptide, nonapeptide, decapeptide, undecapeptide or dodecapeptide unit, wherein the amino acids forming the peptides can be different from one another.

Thus $(W)_w$ can be represented by the following formula: $(W1)_{w1}(W2)_{w2}(W3)_{w3}(W4)_{w4}(W5)_{w5}$, wherein each W1 to W5 represents, independently from one another, an amino acid unit and each w1 to w5 is 0 or 1.

In some embodiments, the amino acid unit $(W)_w$ may comprise amino acid residues such as those occurring naturally, as well as minor amino acids and non-naturally occurring amino acid analogs, such as citrulline.

The amino acid residues of the amino acid unit $(W)_w$ include, without limitation, alanine, valine, leucine, isoleucine, methionine, phenylalanine, tryptophan, proline, lysine protected or not with acetyl or formyl, arginine, arginine protected or not with tosyl or nitro groups, histidine, ornithine, ornithine protected with acetyl or formyl, and citrulline. Exemplary amino acid linker components include preferably a dipeptide, a tripeptide, a tetrapeptide or a pentapeptide, notably a dipeptide or a tripeptide.

Exemplary dipeptides include: Val-Cit, Ala-Val, Ala-Ala, Val-Ala, Lys-Lys, Cit-Cit, Val-Lys, Ala-Phe, Phe-Lys, Ala-Lys, Phe-Cit, Leu-Cit, Ile-Cit, Trp-Cit, Phe-Ala, Phe-N$^9$-tosyl-Arg, Phe-N$^9$-Nitro-Arg.

Exemplary tripeptides include: Val-Ala-Val, Ala-Asn-Val, Val-Leu-Lys, Ala-Ala-Asn, Phe-Phe-Lys, Gly-Gly-Gly, D-Phe-Phe-Lys, Gly-Phe-Lys.

Exemplary tetrapeptide include: Gly-Phe-Leu-Gly (SEQ ID NO: 53), Ala-Leu-Ala-Leu (SEQ ID NO: 54).

Exemplary pentapeptide include: Pro-Val-Gly-Val-Val (SEQ ID NO: 55).

According to a particular embodiment, $(W)_w$ can be a dipeptide (i.e. w=2) such as Val-Cit, or the linker lacks an amino acid unit (w=0). When the linker lacks an amino acid unit, preferably it lacks also a spacer unit.

According to a preferred embodiment, w=0 (i.e. $(W)_w$ is a single bond) or w=2 (i.e. $(W)_w$ is a dipeptide) and $(W)_w$ can thus be selected from:

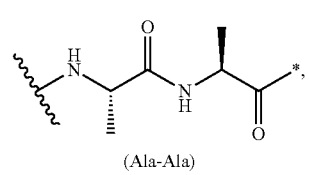

(Ala-Ala)

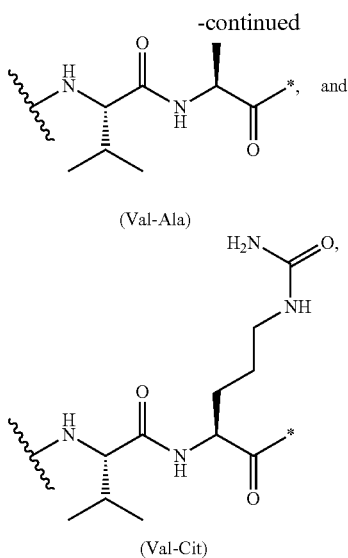

(Val-Ala)

(Val-Cit)

and in particular is Val-Cit,
wherein
the asterisk indicates the point of attachment to the spacer unit if present, or to the drug D; and
the wavy line indicates the point of attachment to $L_2$.

Amino acid linker components can be designed and optimized in their selectivity for enzymatic cleavage by a particular enzyme, for example, a tumor-associated protease, cathepsin B, C and D, or a plasmin protease.

The amino acid unit of the linker can be enzymatically cleaved by an enzyme including, but not limited to, a tumor-associated protease to liberate the drug.

The amino acid unit can be designed and optimized in its selectivity for enzymatic cleavage by a particular tumor-associated protease. The suitable units are those whose cleavage is catalyzed by the proteases, cathepsin B, C and D, and plasmin.

The spacer unit (Y), when present, links an amino acid unit if present, or the stretcher unit if present, or otherwise the antibody to the drug. Spacer units are of two general types: self-immolative and non self-immolative. A non self-immolative spacer unit is one in which part or all of the spacer unit remains bound to the drug after enzymatic cleavage of an amino acid unit from the antibody-drug conjugate. Examples of a non self-immolative spacer unit include, but are not limited to a (glycine-glycine) spacer unit and a glycine spacer unit. To liberate the drug, an independent hydrolysis reaction should take place within the target cell to cleave the glycine-drug unit bond.

In a particular embodiment, a non self-immolative the spacer unit (Y) is Gly.

Alternatively, an antibody-drug conjugate containing a self-immolative spacer unit can release the drug without the need for a separate hydrolysis step. In these embodiments, (Y) is a residue of p-aminobenzyl alcohol (PAB) unit that is linked to $(W)_w$ via the nitrogen atom of the PAB group, and connected directly to the drug via a ester, carbonate, carbamate or ether group.

Other examples of self-immolative spacers include, but are not limited to, aromatic compounds that are electronically equivalent to the PAB group such as residues of 2-aminoimidazol-5-methanol derivatives and ortho or para-aminobenzylacetals. Spacers can be used that undergo facile cyclization upon amide bond hydrolysis, such as substituted and unsubstituted 4-aminobutyric acid amides, appropriately substituted bicyclo[2.2.1] and bicyclo[2.2.2] ring systems and 2-aminophenylpropionic acid amides.

In an alternate embodiment, the spacer unit is a branched bis(hydroxymethyl)styrene (BHMS) unit, which can be used to incorporate additional drugs.

In a particular embodiment, the spacer unit (Y) is PAB-carbonyl with PAB being

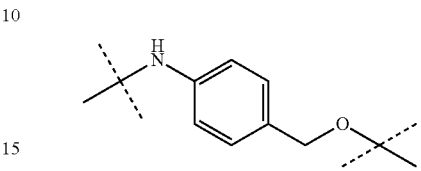

(the oxygen of the PAB unit being linked to the carbonyl), and y=1 or the linker lacks a spacer unit (y=0).

In a particular embodiment, the linker has the following formula (III):

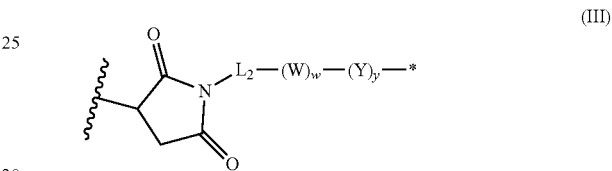

(III)

wherein
$L_2$ is $(C_4-C_{10})$cycloalkyl-carbonyl, $(C_2-C_6)$alkyl or $(C_2-C_6)$alkyl-carbonyl (the carbonyl of these moieties, when present, being linked to $(W)_w$), W represents an amino acid unit, with w representing an integer comprised between 0 and 5, Y is PAB-carbonyl, with PAB being

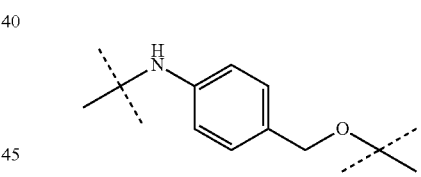

(the oxygen of the PAB unit being linked to the carbonyl), and y is 0 or 1 (preferably y is 0 when w is 0 and y is 0 or 1 when w is comprised between 1 and 5), the asterisk indicates the point of attachment to the drug D, and the wavy line indicates the point of attachment to the antibody Ab.

Advantageously, $L_2$ is $(C_2-C_6)$alkyl-carbonyl such as a pentyl-carbonyl of the following formula:

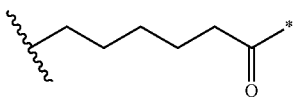 [SMILES: *CCCCCC(*)=O]

wherein
the asterisk indicates the point of attachment to $(W)_w$; and
the wavy line indicates the point of attachment to the nitrogen atom of the maleimide moiety.

According to a preferred embodiment, the linker L is selected from:

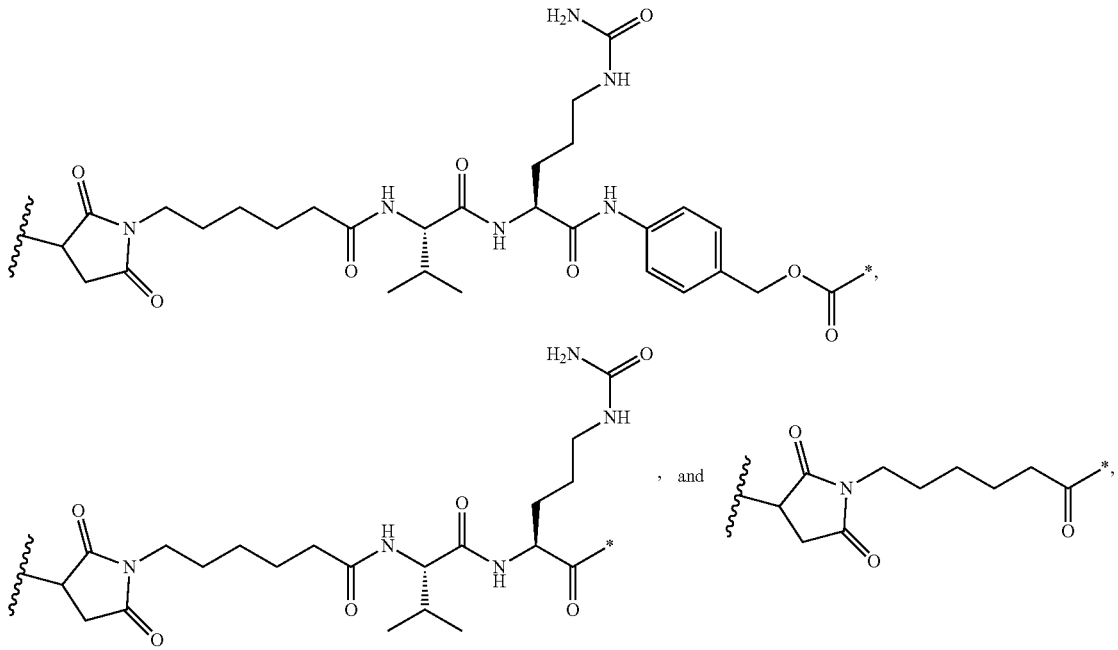

wherein the asterisk indicates the point of attachment to the drug D, and the wavy line indicates the point of attachment to the antibody Ab.

IV—The Antibody-Drug-Conjugate (ADC)

In a preferred embodiment, the antibody-drug conjugate of the invention may be prepared by any method known by the person skilled in the art such as, without limitation, i) reaction of a nucleophilic group of the antibody with a bivalent linker reagent followed by reaction with a nucleophilic group of the drug or ii) reaction of a nucleophilic group of the drug with a bivalent linker reagent followed by reaction with a nucleophilic group of the antibody.

Nucleophilic groups on antibody include, without limitation, N-terminal amine groups, side chain amine groups (e.g. lysine), side chain thiol groups, and sugar hydroxyl or amino groups when the antibody is glycosylated.

Nucleophilic groups on the drug include, without limitation, amine, thiol, and hydroxyl groups, and preferably amine groups.

Amine, thiol, and hydroxyl groups are nucleophilic and capable of reacting to form covalent bonds with electrophilic groups on linker moieties and linker reagents including, without limitation, active esters such as NETS esters, HOBt esters, haloformates, and acid halides; alkyl and benzyl halides such as haloacetamides; aldehydes; ketones; carboxyl; and maleimide groups. The antibody may have reducible interchain disulfides, i.e. cysteine bridges. The antibody may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into the antibody through any reaction known by the person skilled in the art. As non limitative example, reactive thiol groups may be introduced into the antibody by introducing one or more cysteine residues.

Antibody-drug conjugates may also be produced by modification of the antibody to introduce electrophilic moieties, which can react with nucleophilic substituents on the linker reagent. The sugars of glycosylated antibody may be oxidized to form aldehyde or ketone groups which may react with the amine group of linker reagents or drug. The resulting imine Schiff base groups may form a stable linkage, or may be reduced to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug. In another embodiment, proteins containing N-terminal serine or threonine residues can react with sodium meta-periodate, resulting in production of an aldehyde in place of the first amino acid.

In a preferred embodiment, the antibody-drug conjugate of the invention is prepared by preparation of the drug-linker moiety followed by coupling between a nucleophilic group of the antibody (for ex. the SH group of a cysteine moiety) and an electrophilic group of the drug-linker moiety (for ex. a maleimide).

1. Drug-Linker

The Drug-Linker moiety can be prepared by coupling:
the linker with the drug,
a part of the linker with the drug before completing the synthesis of the linker,
the linker with a part or a precursor of the drug before completing the synthesis of the drug, or
a part of the linker with a part or a precursor of the drug before completing the synthesis of the linker and the drug.

The coupling reactions are well known reactions for the one skilled in the art between a nucleopilic group and an electrophilic group.

The nucleophilic group can be in particular an amine, thiol or hydroxyl group, and notably an amine or hydroxyl group. In a preferred embodiment it is a primary or secondary amine group.

The electrophilic group can be a carboxylic acid group (COOH) optionally in an activated form or an activated carbonate ester moiety.

By "activated form" of a carboxylic acid is meant a carboxylic acid in which the OH moiety of the COOH function has been replaced with an activated leaving group (LG) enabling coupling of the activated carboxylic acid group with an amino group in order to form an amide bond and release the compound LG-H. Activated forms may be activated esters, activated amides, anhydrides or acyl halides such as acyl chlorides. Activated esters include derivatives formed by reaction of the carboxylic acid group with N-hydroxybenzotriazole or N-hydroxysuccinimide.

By "activated carbonate ester" is meant a carbonate ester comprising a —OC(O)OR moiety in which OR represents a good leaving group enabling coupling of the activated carbonate ester with an amino group in order to form a carbamate moiety and release the compound ROH. The R group of the activated carbonate ester includes, without limitation, the p-nitro-phenyl, pentafluorophenyl, 2,5-dioxo-2,5-dihydro-1H-pyrrol-1-yl and benzyl groups, preferably the p-nitro-phenyl and pentafluorophenyl groups.

When the linker has the following formula (III):

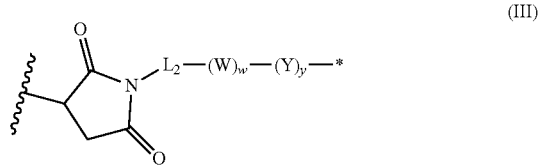

(III)

the Drug-Linker moiety has the following formula (IV):

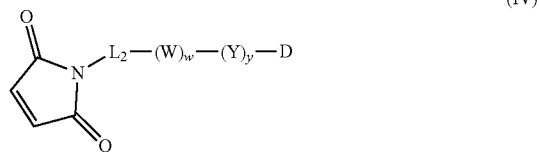

(IV)

and the last step of the synthesis of the Drug-Linker moiety is generally the coupling between a compound of the following formula (V):

(V)

where $L_2$ is as defined previously and LG represents a leaving group notably a halide such as a chloride or a group derived from N-hydroxysuccinimide, and a compound of the following formula (VI):

(VI).

When y=1 and Y=PAB-carbonyl, the compound of formula (VI) can be prepared by the coupling between the drug (DH) and a compound of the following formula (VII) or a protected form thereof:

(VII)

where W and w are as defined previously and R is as defined in the definition of the "activated carbonate ester".

When the compound of formula (VII) is in a protected form, final step of deprotection is necessary.

When y=0, the compound (VI) has the formula H-(W)$_w$-D, wherein (W)$_w$ and D are composed of amino acid units. Consequently, the compound (VI) can be prepared in this case by a conventional peptide synthesis method well known to the one skilled in the art.

2. Ab-Linker-Drug

A preferred embodiment according to the invention consists of a coupling between a cysteine present on the antibody and an electrophilic group of the Drug-Linker moiety, preferably with a maleimide moiety present on the Drug-Linker moiety.

The maleimide-cysteine coupling can be performed by methods well known to the person skilled in the art.

Generally, antibodies do not contain many, if any, free and reactive cysteine thiol groups which can be linked to a drug moiety. Most cysteine thiol residues in antibodies exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limited reducing conditions for cysteine thiol modification.

The disulfide bond structure of human IgGs is now well established (reviewed in Liu and May, mAbs 4 (2012): 17-23). There are in fact many similarities and some differences with regard to the disulfide bond structures of the 4 human IgG subclasses, namely IgG1, IgG2, IgG3 and IgG4. All IgG subclasses contain invariably 12 intra-chain disulfide bridges and the differences reside in their inter-chain disulfide bonds formed between heavy and light chains. Each intra-chain disulfide bond is associated with an individual IgG domain, i.e. variable (VL and VH) and constant (CL, CH1, CH2 and CH3) domains. The 2 heavy chains are linked in their hinge region by a variable number of disulfide bridges: 2 for IgG1 and IgG4, 4 for IgG2 and 11 for IgG3. The heavy and light chains of the IgG1 are connected by a disulfide bond between the last cysteine residue of the light chain and the fifth residue of the heavy chain, whereas for the other subclasses, IgG2, IgG3 and IgG4, the light chain is linked to the heavy chain by a disulfide bond between the last cysteine residue of the light chain and the third cysteine residue of the heavy chain, which is located at the interface of VH and CH1 domains. Disulfide bond structures other than these classical structures have been described for IgG2 and IgG4 (reviewed in Liu and May, mAbs 4 (2012): 17-23). Inter-chain disulfide bonds are highly solvent exposed and are consequently much more reactive than the intra-chain disulfide bonds, which are buried in anti-parallel beta-sheet structures within each domain and are not solvent exposed. For these reasons, whatever the antibody isotype, coupling will take place on inter-chain exposed cysteine residues after mild reduction. Each inter-chain disulfide bridge can thus form, theoretically, two sites of conjugation.

Additional nucleophilic groups can be introduced into antibodies through the reaction of lysines with 2-iminothiolane (Traut's reagent) resulting in the conversion of an amine into a thiol. Reactive thiol groups may also be introduced into the antibody (or fragment thereof) by engineering one, two, three, four, or more cysteine residues (e.g., preparing mutant antibodies comprising one or more non-native cysteine amino acid residues). U.S. Pat. No. 7,521, 541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

For some antibody-drug conjugates, drug ratio may be limited by the number of attachment sites on the antibody. High drug loading, e.g. drug ratio >5, may cause aggregation, insolubility, toxicity, or loss of cellular permeability of certain antibody-drug conjugates. Typically, less drug moieties than the theoretical maximum are conjugated to an antibody during a conjugation reaction.

The drug loading also referred as the Drug-Antibody ratio (DAR) is the average number of drugs per cell binding agent.

In the case of antibody IgG1 and IgG4 isotypes, where the drugs are bound to cysteines after partial antibody reduction, drug loading may range from 1 to 8 drugs (D) per antibody, i.e. where 1, 2, 3, 4, 5, 6, 7, and 8 drug moieties are covalently attached to the antibody.

In the case of an antibody IgG2 isotype, where the drugs are bound to cysteines after partial antibody reduction, drug loading may range from 1 to 12 drugs (D) per antibody, i.e. where 1, 2, 3, 4, 5, 6, 7, 8, 9, 10, 11 and 12 drug moieties are covalently attached to the antibody.

Compositions of ADC include collections of cell binding agents, e.g. antibodies, conjugated with a range of drugs, from 1 to 8 or 1 to 12.

The average number of drugs per antibody in preparations of ADC from conjugation reactions may be characterized by conventional means such as UV, reverse phase HPLC, HIC, mass spectrometry, ELISA assay, and electrophoresis.

As non limitative embodiment, it is presented herein the conjugation with the IGF-1R antibody c208F2. In this case, the drug is coupled to at least one cysteine selected from i) for the light chain of sequence SEQ ID NO: 28, the residue Cys. in position 214 and ii) for the heavy chain of sequence SEQ ID NO: 23, the residues Cys. in position 223, 229 and 232.

As non limitative embodiment, it is presented herein the conjugation with the IGF-1R antibody c208F2. In this case, the drug is coupled to two, three or four, cysteines selected from i) for the light chain of sequence SEQ ID NO: 28, the residue Cys. in position 214 and ii) for the heavy chain of sequence SEQ ID NO: 23, the residues Cys. in position 223, 229 and 232

As non limitative embodiment, it is presented herein the conjugation with the IGF-1R antibody hz208F2 (var. 1). In this case, the drug is coupled to at least one cysteine selected from i) for the light chain of sequence SEQ ID NO: 39, the residue Cys. in position 214 and ii) for the heavy chain of sequence SEQ ID NO: 37, the residues Cys. in position 223, 229 and 232.

As non limitative embodiment, it is presented herein the conjugation with the IGF-1R antibody hz208F2 (var. 3). In this case, the drug is coupled to two, three or four, cysteines selected from i) for the light chain of sequence SEQ ID NO: 40, the residue Cys. in position 214 and ii) for the heavy chain of sequence SEQ ID NO: 38, the residues Cys. in position 223, 229 and 232.

The same approach could be easily adapted to other antibodies such as, for example, the Axl antibodies.

An alternative consists of lysine coupling. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent.

Where the compounds of the invention are bound to lysines, drug loading may range from 1 to 80 drugs (D) per cell antibody, although an upper limit of 40, 20, 10 or 8 may be preferred. Compositions of ADC include collections of cell binding agents, e.g. antibodies, conjugated with a range of drugs, from 1 to 80, 1 to 40, 1 to 20, 1 to 10 or 1 to 8.

The ADC of formula (I) according to the invention can be in the form of a pharmaceutically acceptable salt.

In the present invention by "pharmaceutically acceptable" is meant that which can be used in the preparation of a pharmaceutical composition which is generally, safe non-toxic and neither biologically nor otherwise undesirable, and which is acceptable for veterinary use as well as for human pharmaceutical use.

By "pharmaceutically acceptable salt" of a compound is meant a salt which is pharmaceutically acceptable as defined herein and which has the desired pharmacological activity of the parent compound.

Pharmaceutically acceptable salts notably comprise:

(1) the addition salts of a pharmaceutically acceptable acid formed with pharmaceutically acceptable inorganic acids such as hydrochloric, hydrobromic, phosphoric, sulfuric and similar acids; or formed with pharmaceutically acceptable organic acids such as acetic, trifluoroacetic, propionic, succinic, fumaric, malic, tartaric, citric, ascorbic, maleic, glutamic, benzoic, salicylic, toluenesulfonic, methanesulfonic, stearic, lactic and similar acids; and (2) the addition salts of a pharmaceutically acceptable base formed when an acid proton present in the parent compound is either replaced by a metallic ion e.g. an alkaline metal ion, an alkaline-earth metal ion or an aluminium ion; or coordinated with a pharmaceutically acceptable organic base such as lysine, arginine and similar; or with a pharmaceutically acceptable inorganic base such as sodium hydroxide, potash, calcium hydroxide and similar.

These salts can be prepared from the compounds of the invention containing a base or acid function, and the corresponding acids or bases using conventional chemical methods.

V—Treatment

Finally, the invention relates to an ADC as above described for use as a medicament, in particular in the treatment of cancer.

A further subject of the present invention is a formal (I) compound such as defined above for use as medicinal product, in particular for the treatment of cancer.

The present invention also concerns the use of a formula (I) compound such as defined above for producing a medicinal product, particularly intended for the treatment of cancer.

The present invention also concerns a method for treating cancer comprising the administration to a person in need thereof of an effective mount of a formula (I) compound such as defined above.

Cancers can be preferably selected through Target-related cancers including tumoral cells expressing or over-expressing whole or part of the Target at their surface.

More particularly, said cancers are breast cancer, colon cancer, esophageal carcinoma, hepatocellular cancer, gastric cancer, glioma, lung cancer, melanoma, osteosarcoma, ovarian cancer, prostate cancer, rhabdomyosarcoma, renal cancer, thyroid cancer, uterine endometrial cancer, schwannoma, neuroblastoma, oral squamous cancer, mesothelioma, leiomyosarcoma, Kaposi sarcoma, acute leukemia, colorectal carcinoma, melanoma, pancreatic ductal adenocarcinoma and any drug resistance phenomena or cancers.

For the avoidance of doubt, by drug resistance Target-expressing cancers, it must be understood not only resistant cancers which initially express the Target but also cancers which initially do not express or overexpress the Target but which express the Target once they have become resistant to a previous treatment.

Another object of the invention is a pharmaceutical composition comprising the ADC as described in the specification.

More particularly, the invention relates to a pharmaceutical composition comprising the ADC of the invention with at least an excipient and/or a pharmaceutical acceptable vehicle.

In the present description, the expression "pharmaceutically acceptable vehicle" or "excipient" is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles and excipients are well known and will be adapted by the person skilled in the art as a function of the nature and of the mode of administration of the active compound(s) chosen.

The active ingredient can be administered in unit forms of administration, in a mixture with conventional pharmaceutical carriers, to animals or to human beings. Suitable unit forms of administration comprise forms via oral route and forms for administration via parenteral route (subcutaneous, intradermal, intramuscular or intravenous).

As solid compositions, for oral administration, use can be made of tablets, pills, powders (hard or soft gelatine capsules) or granules. In these compositions, the active ingredient of the invention is mixed with one or more inert diluents such as starch, cellulose, sucrose, lactose or silica, in a stream of argon. These compositions may also comprise substances other than diluents, for example one or more lubricants such as magnesium stearate or talc, a colouring agent, a coating (coated tablets) or a varnish.

The sterile compositions for parenteral administration may preferably be aqueous or nonaqueous solutions, suspensions or emulsions. As solvent or vehicle, use can be made of water, propylene glycol, a polyethylene glycol, vegetable oils, in particular olive oil, injectable organic esters e.g. ethyl oleate or other suitable organic solvents. These compositions may also contain adjuvants, in particular wetting, isotonic, emulsifying, dispersing and stabilising agents. Sterilisation can be performed in several manners, for example by sanitising filtration, by incorporating sterilising agents into the composition, by radiation or by heating. They can also be prepared in the form of solid sterile compositions which can be dissolved at the time of use in sterile water or any other injectable sterile medium.

Preferably, these ADCs will be administered by the systemic route, in particular by the intravenous route, by the intramuscular, intradermal, intraperitoneal or subcutaneous route, or by the oral route. In a more preferred manner, the composition comprising the ADCs according to the invention will be administered several times, in a sequential manner.

The invention concerns thus also a kit comprising at least i) an antibody-drug-conjugate according to the invention and/or a pharmaceutical composition according to the invention and ii) a syringe or vial or ampoule in which the said antibody-drug-conjugate and/or pharmaceutical composition is disposed.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

Other characteristics and advantages of the invention appear in the continuation of the description with the examples and the figures whose legends are represented below.

FIGURE LEGENDS

FIGS. 1A-1C: Antibody binding to the human native IGF-1R by FACS analyses. FIG. 1A represents the titration curve, on MCF-7 cell line. MFI represents the mean of fluorescent intensity. FIG. 1B represents the $EC_{50}$ of both murine and chimeric anti-IGF-1R antibodies on the MCF-7 cell line. FIG. 1C represents the B. of chimeric anti-IGF-1R antibodies on MCF-7 cell line.

Figure 2A:
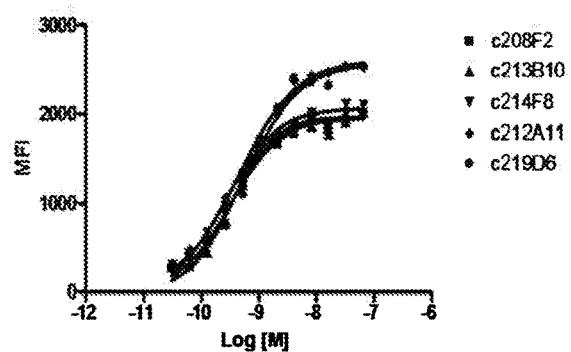
Figure 2B:
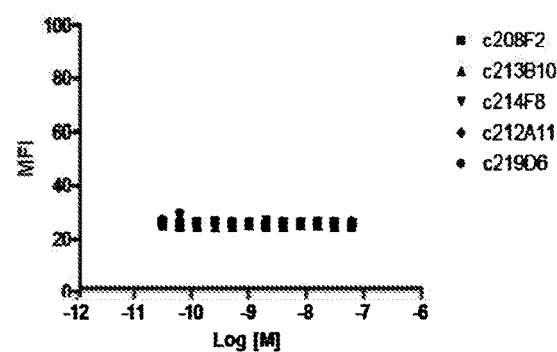

FIGS. 2A-2B: Evaluation of hIGF-1R recognition using transfected vs non transfected cells. FIG. 2A represents titration curves of one chimeric anti-IGF-1R Ab on IGF-1R$^+$ cell line. MFI represents the mean of fluorescent intensity. FIG. 2B represents the binding of chimeric anti-IGF-1R Abs on the human IGF-1R$^-$ cell line.

Figure 3A:
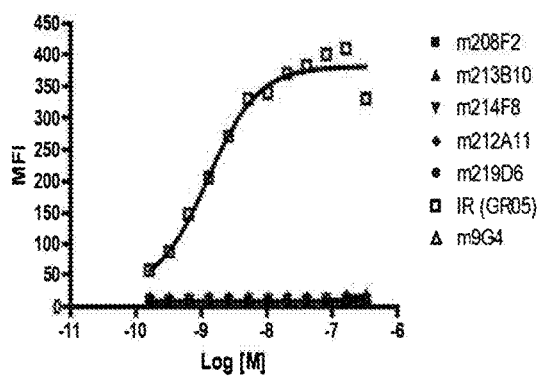
Figure 3B:
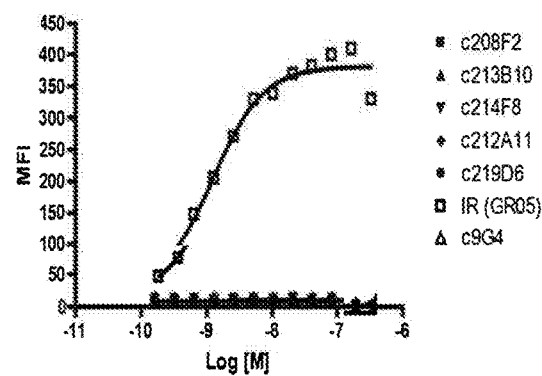

FIGS. 3A-3B: Evaluation of the specificity of Abs to IGF-1R vs hIR using transfected cells. FIG. 3A represents the binding of murine anti-IGF-1R Ab on the hIR+ transfected cell line. FIG. 3B represents the binding of chimeric anti-IGF-1R Ab on the IR+ cell line. MFI represents the mean of fluorescent intensity. GRO5 anti-hIR Mab (CAL-BIOCHEM) was introduced as a positive control.

Figure 4:
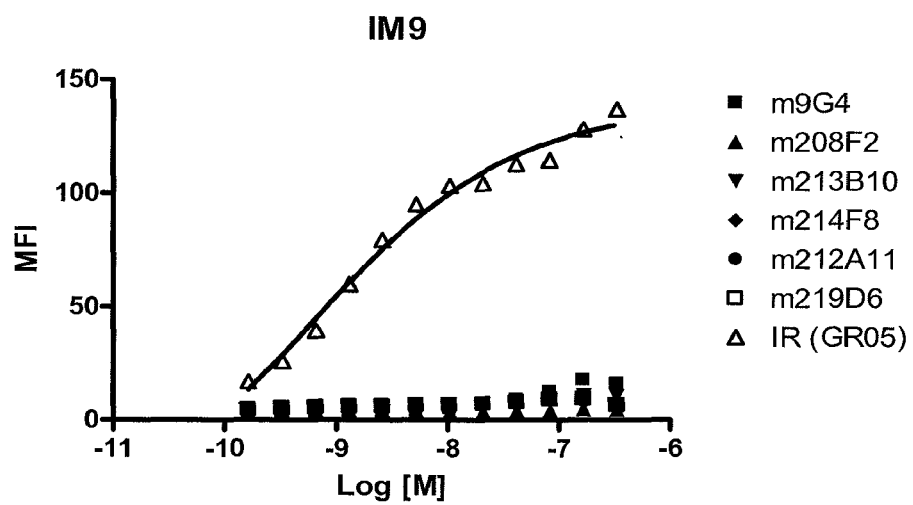

FIG. 4: Binding of murine anti-IGF-1R Ab on the IM-9 cell line. MFI represents the mean of fluorescent intensity. GRO5 anti-hIR Mab was introduced as a positive control.

Figures 5A, 5B, 5C:
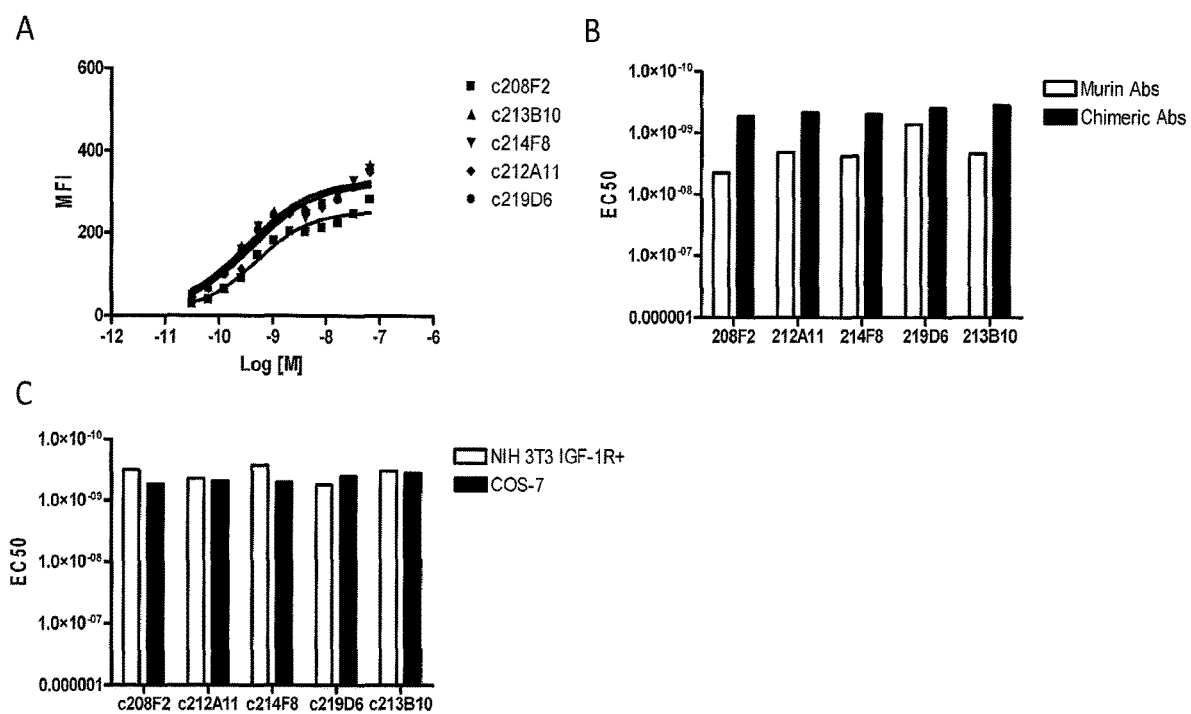

FIGS. 5A-5C: Evaluation of recognition of the monkey IGF-1R. FIG. 5A represents the titration curves of chimeric anti-IGF-1R Ab on the COS-7 cell line. MFI represents the mean of fluorescent intensity. FIG. 5B represents the $EC_{50}$ of both murine and chimeric anti-IGF-1R antibodies on COS-7 cell line. FIG. 5C represents the $EC_{50}$ of chimeric anti-IGF-1R antibodies on both NIH 3T3 transfected cells hIGF1R+ and COS-7 cell lines.

Figure 6:
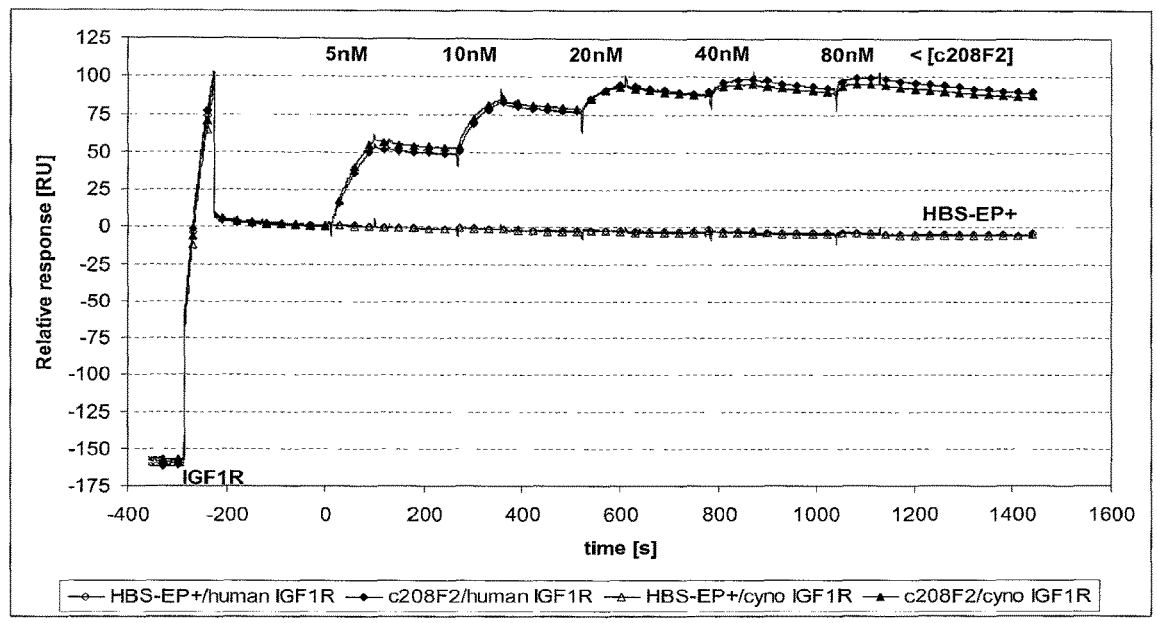

FIG. 6: Sensorgrams obtained on a SPR technology based BIACORE® X100 using a CM5 sensor chip activated with more the 11000 RU of mouse anti-Tag His antibody chemically grafted to the carboxymethyl dextran matrix. The experiment was run at a flow rate of 30 μl/min at 25° C. using the HBS-EP+ as the running and samples diluting buffer. The figure showed the superposition of 4 independent sensorgrams aligned on the x-axis at the beginning of the first injection of the analytes and on the y-axis by the baseline defined just before this first injection. The sensorgrams obtained with the capture of the human based sequence of the recombinant soluble IGF1R are marked by diamonds. The sensorgrams obtained with the capture of the cynomolgus based sequence of the recombinant soluble IGF1R are marked by triangles. White symbols correspond to the blank cycles (5 injections of the running buffer) and black symbols correspond to the injections of the growing range of concentrations of c208F2 (5, 10, 20, 40 and 80 nM).

Figure 7:
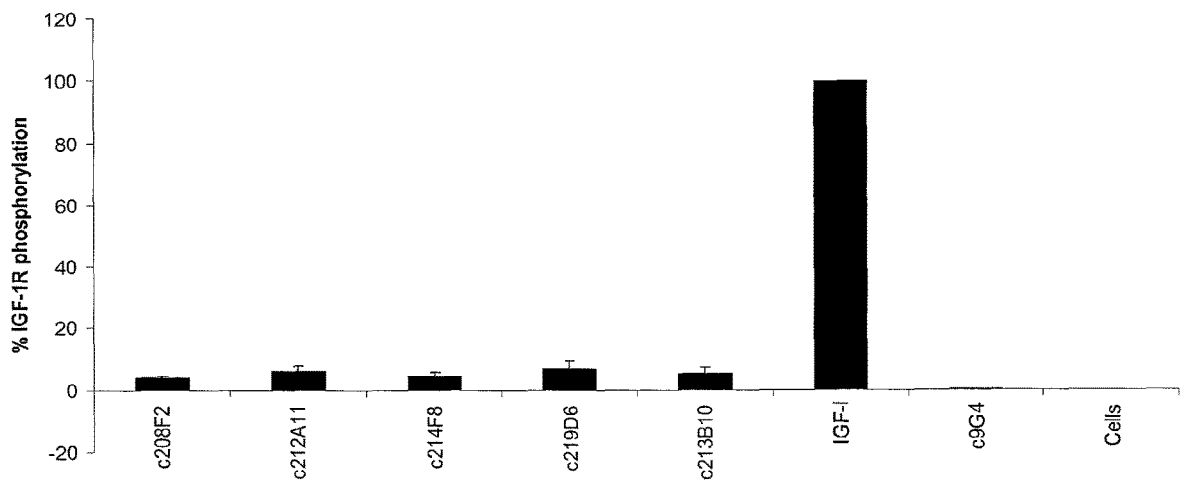

FIG. 7: Evaluation of the intrinsic effect of anti-hIGF-1R antibodies on the receptor phosphorylation compared to IGF1.

Figure 8:
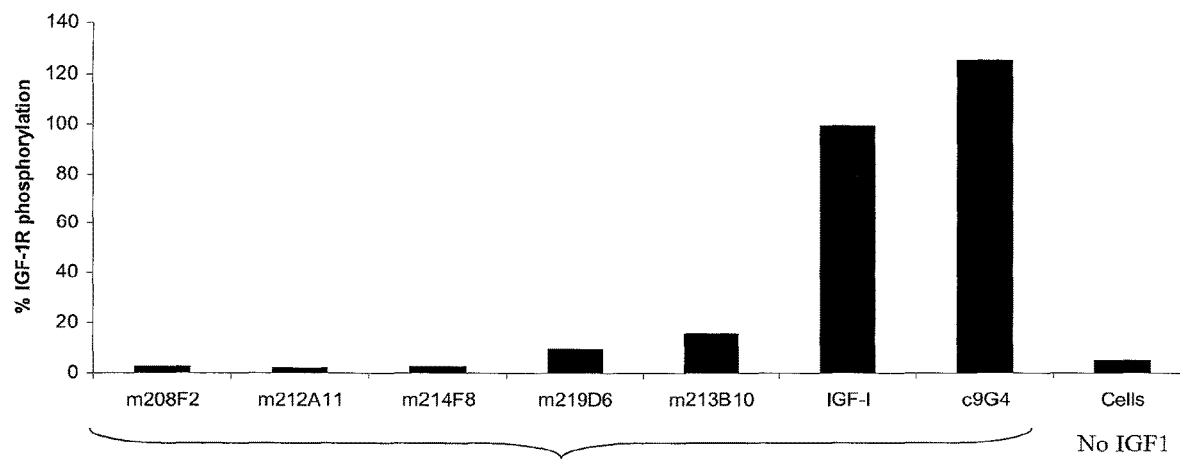
Figure 9:
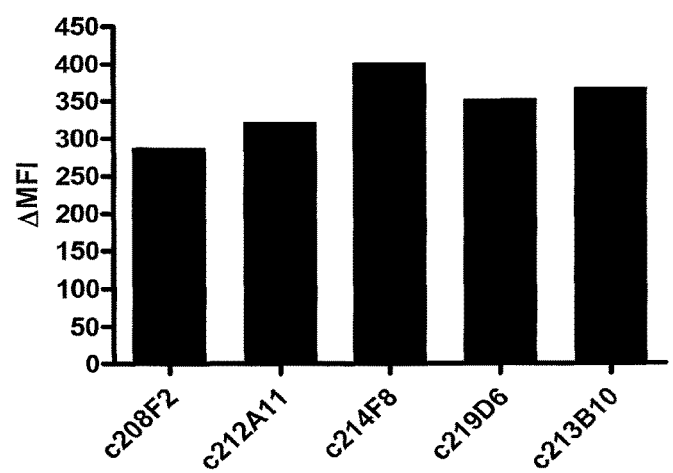

FIG. 8: Inhibition of IGF-1R phosphorylation in response to IGF-1 by murine anti-hIGF-1R FIG. 9: Cell surface signal intensity of anti-IGF-1R antibodies is down-regulated after cell incubation at 37° C. MCF-7 cells were incubated at 4° C. or 37° C. for 4 h with 10 μg/ml of Abs. The figure represents the ΔMFI.

Figures 10A, 10B:
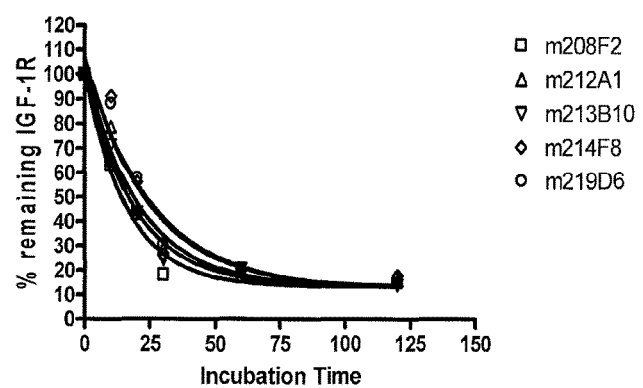

FIGS. 10A-10B: Antibody surface decay. Cell surface bound antibody was assessed after 10, 20, 30, 60 and 120 min at 37° C. FIG. 10A represents the % of remaining IGF-1R in comparison to the signal intensity measured at 4° C. FIG. 10B represents Half Life calculation using PRISM® Software and using exponential decay fitting.

Figure 11:
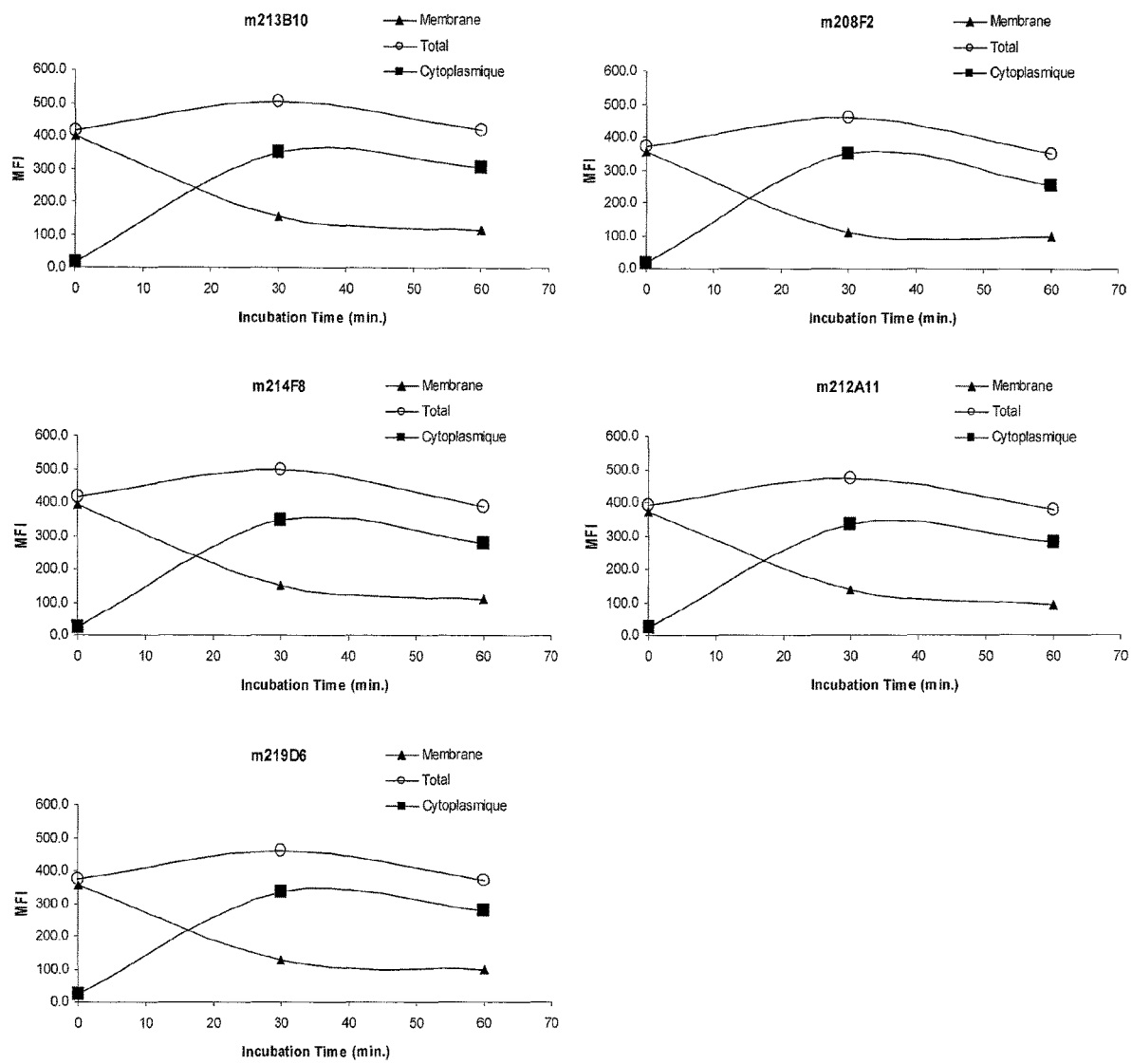

FIG. 11: Anti-hIGF-1R Abs are internalized. Cells were incubated with 10 μg/ml of murine Abs for 0, 30 or 60 min at 37° C. cells were permeabilized or not and incubated with a secondary anti-mouse IgG-Alexa FLUOR® 488. Membrane corresponds to the signal intensity w/o permeabilization. Total correspond to the signal intensity after cell permeabilization and cytoplasmic corresponds to internalized Ab. The name of each evaluated antibody is depicted on the top of each graph.

Figure 12A:
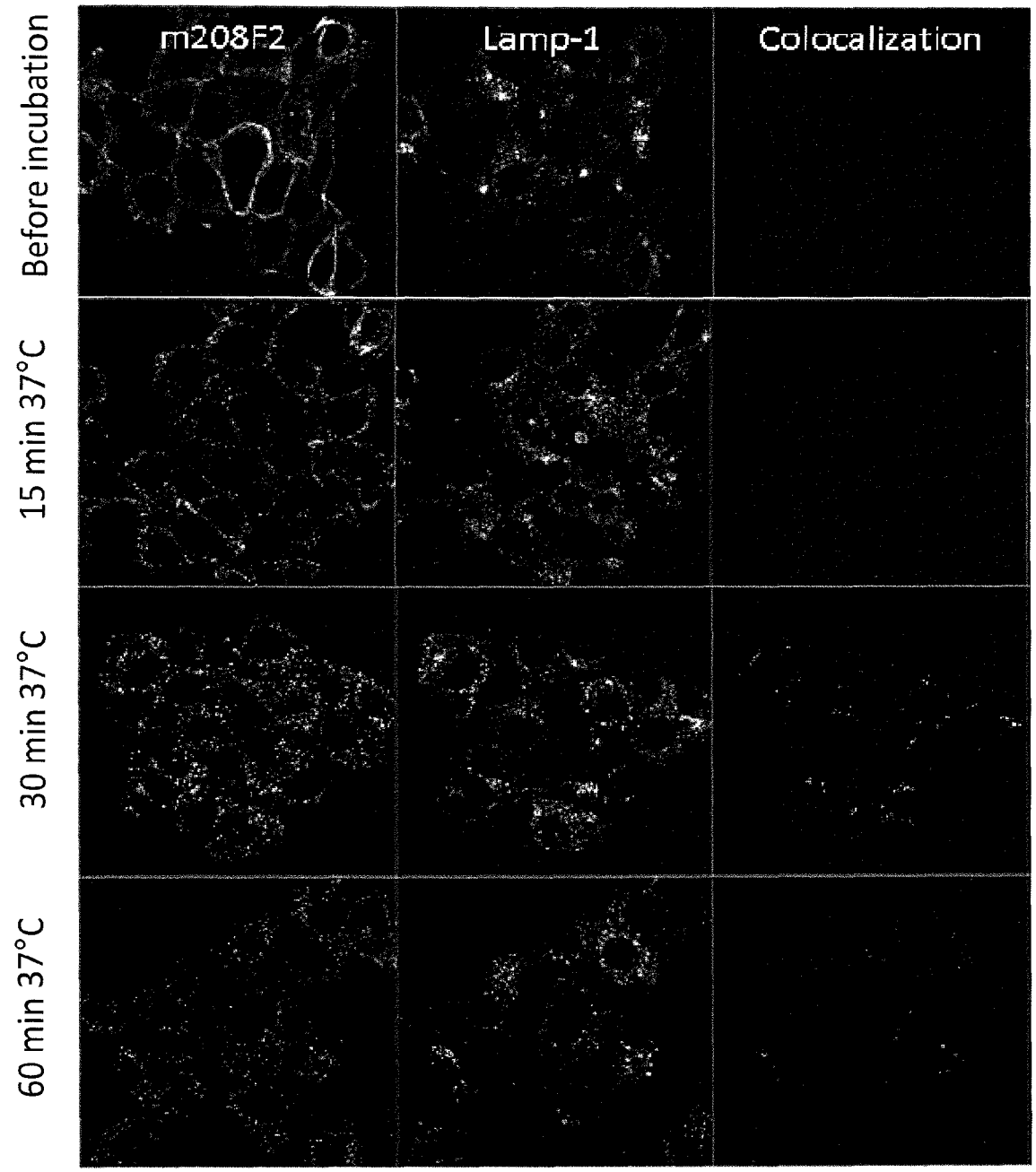
Figure 12B:
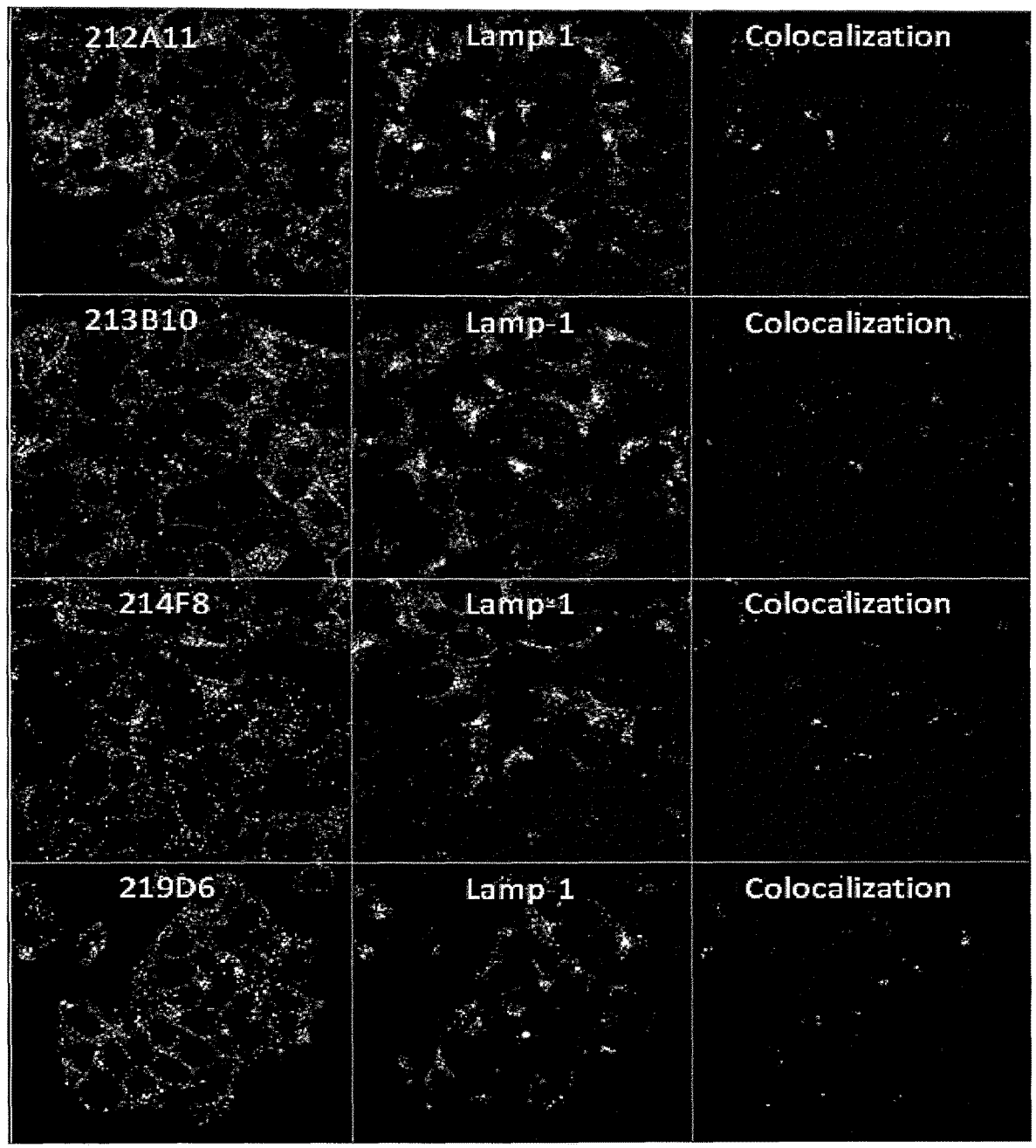

FIGS. 12A-12B: Imaging Ab internalization. FIG. 12A: MCF-7 cells incubated with m208F2 for 20 min. at 4° C. and washed before incubation (W) at 37° C. for 15 (X), 30 (Y) and 60 (Z) min. Cells were fixed and permeabilized. The m208F2 Ab was revealed using an anti-mouse IgG ALEXA FLUOR® 488 and Lamp-1 using a rabbit anti-Lamp-1 antibody and with a secondary anti-rabbit IgG Alexa FLUOR® 555. FIG. 12B: MCF-7 cells were incubated for 30 minutes at 37° C. with anti-hIGF-1R murine antibodies and stained as described above. Colocalization was identified using the colocalization high liter plug-in of the ImageJ software.

Figure 13:
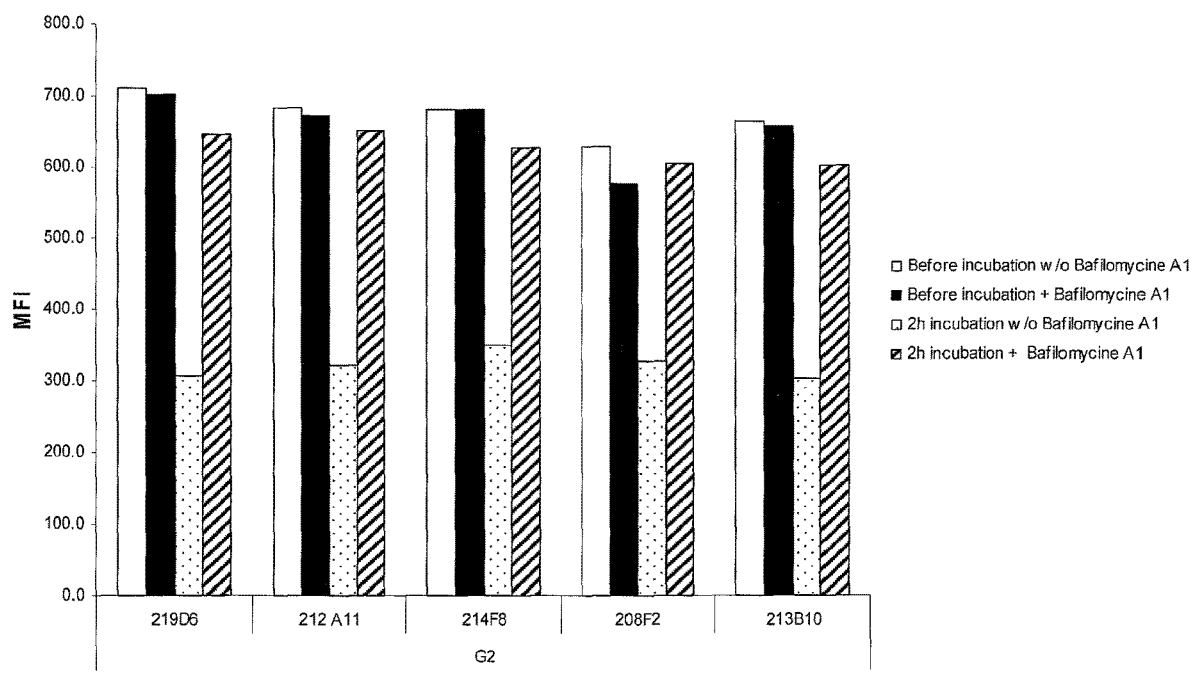

FIG. 13: Involvement of the lysosome pathway in antibody degradation

Figure 14:
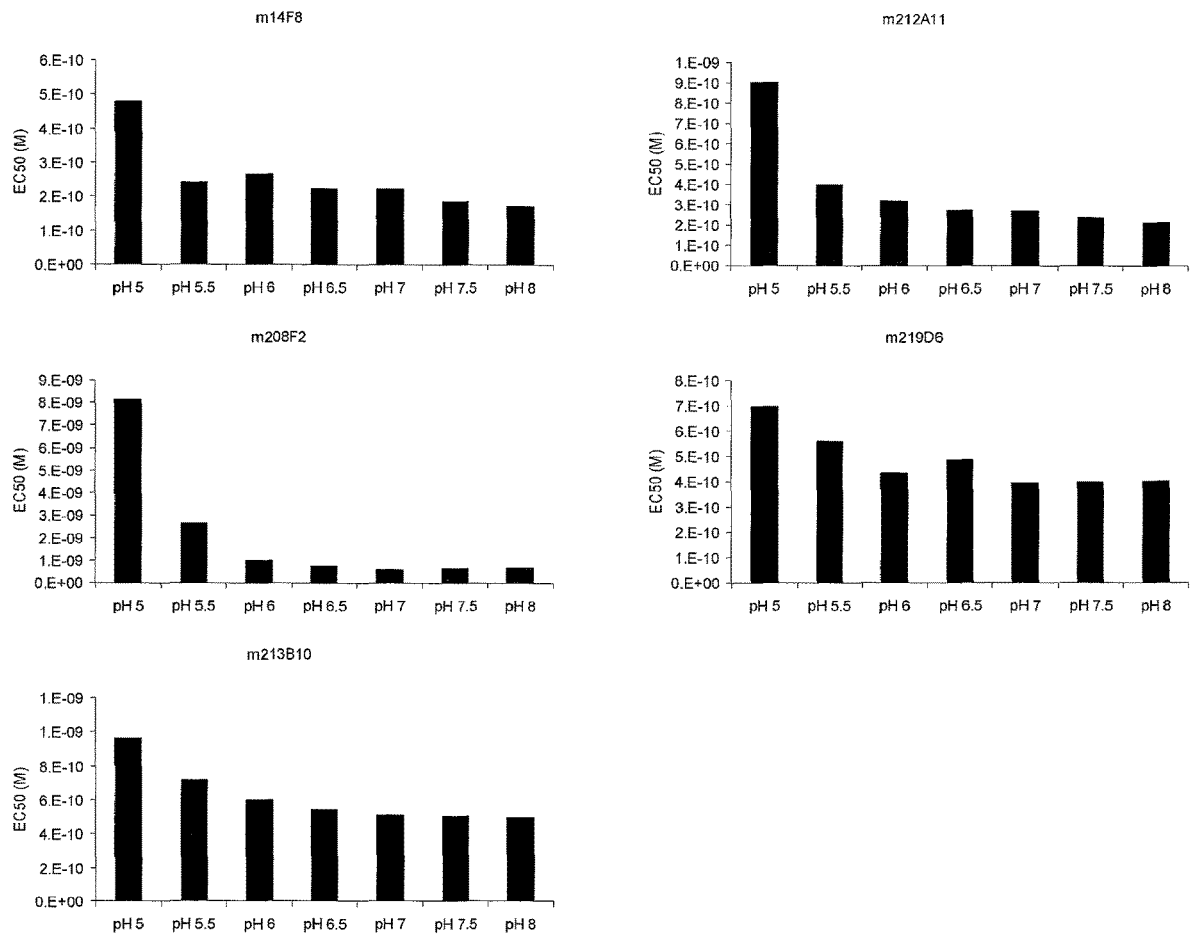

FIG. 14: Acidic pH decreases binding capacity of the five murine anti-IGF-1R antibodies.

FIGS. 15A-15D: Binding characteristic of the first humanized form of the c208F2 Mab. Binding properties of the hz208F2 VH3/VL3 mAb was evaluated on the human cell line MCF-7 (A), on the monkey cell line COS-7 (B) and on the transfected murine cell line expressing the human insulin receptor (C). The binding of both the murine and the chimeric 208F2 mAbs was evaluated in parallel. The anti-hIR antibody clone GRO5 was used to verify the expression of the hIR on the transfected cell line (D).

Figure 16:
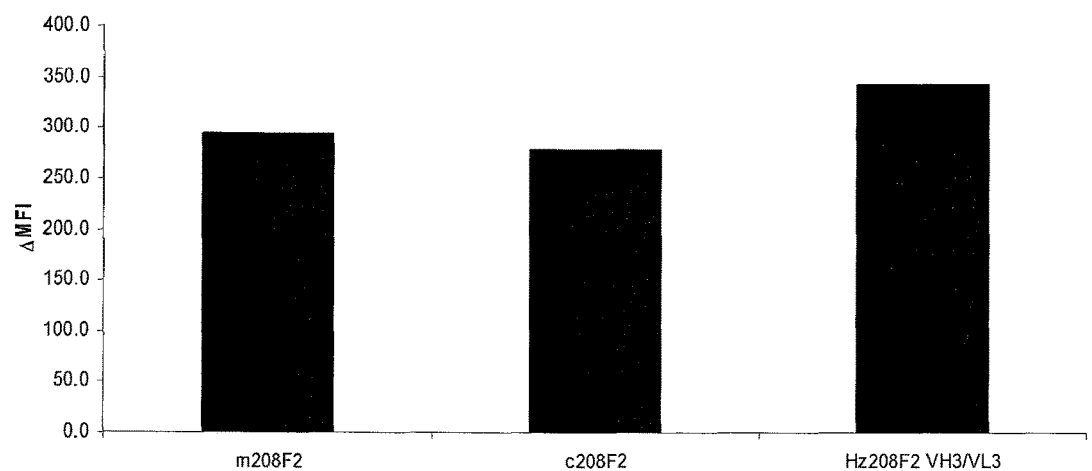

FIG. 16: hz208F2 VH3/VL3 antibody surface decay

Figure 17:
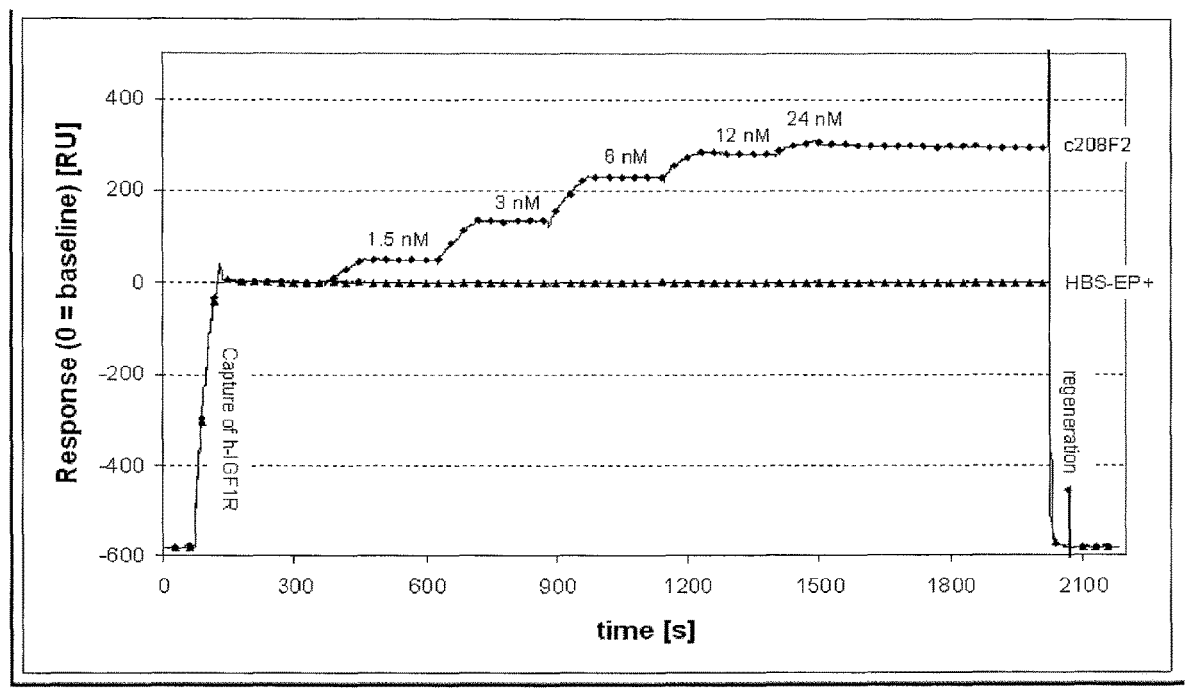

FIG. 17: Superposition of to sensor grammes obtained with a SPR based BIACORE® X100 device at a temperature of 25° C. with a CM5 sensor chip activated on both flow cells with around 12.000 RU of a mouse anti-TagHis monoclonal antibodies chemically grafted to the carboxymethyl-dextran matrix using a HBS-EP+ as the running buffer at a flow rate of 30 μl/min. Each sensorgrammes (the first one marked by triangles and the second one marked by diamonds) correspond to a complete cycle:

1—Injection during one minute of a solution of recombinant h-IGF1R (10 μg/ml) on the second flowcell.

2—For the first sensorgramme: 5 injections of running buffer during 90s each

For the second sensorgramme: five injections in the growing range of concentrations of the anti-IGF1R c208F2 antibody solutions during 90 s each.

3—A delay of 300 s for the determination of the dissociation kinetic rates.

4—A regeneration of the surface by an injection during 45 s of a 10 mM Glycine, HCl pH 1.5 buffer.

Figure 18:
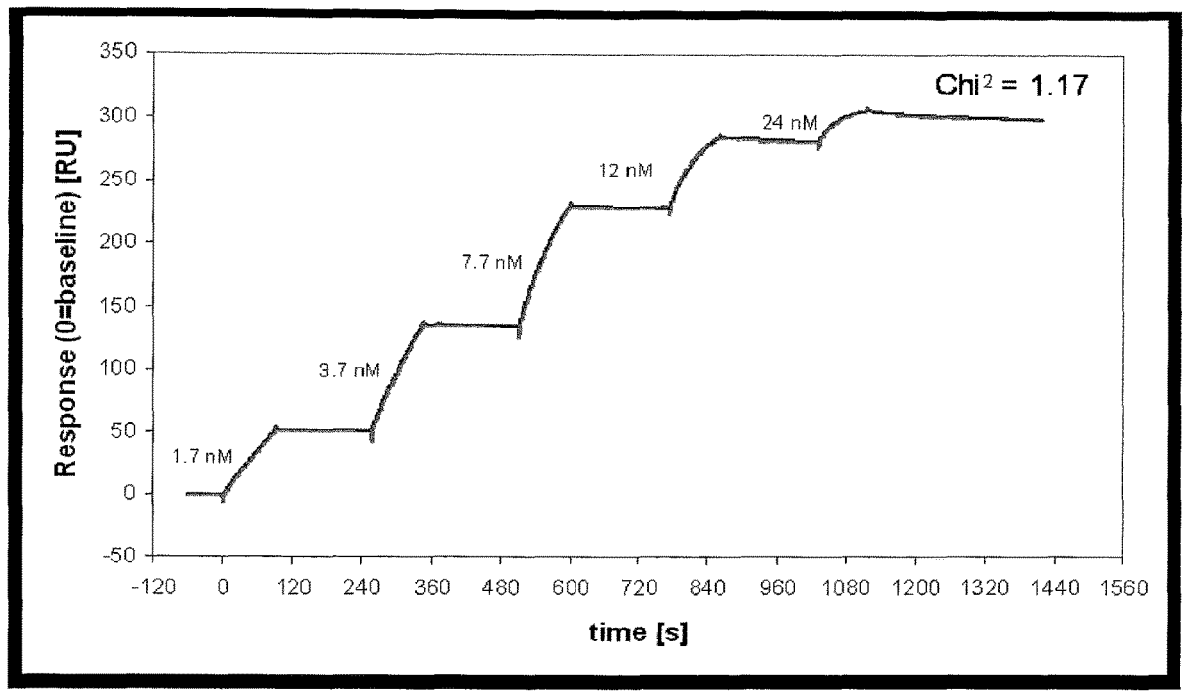

FIG. 18: The sensorgramme corresponding to the subtraction of the blank sensorgramme (5 injections of HBS-EP+) to the sensorgramme obtained with the growing range of concentrations of the anti-IGF1R c208F2 solutions is presented in grey. The theoretical sensorgramme corresponding to the 1:1 model with the following parameters: $k_{on}=(1.206\pm0.036)\times10^6$ $M^{-1} \cdot s^{-1}$, $k_{off}=(7.81\pm0.18)\times10^{-5}$ $s^{-1}$, Rmax=307.6±0.3 RU is presented by a thin black line. The calculated concentrations of c208F2 are reported on the graph: only the highest concentration (24 nM) is considered as a constant).

Figure 19:
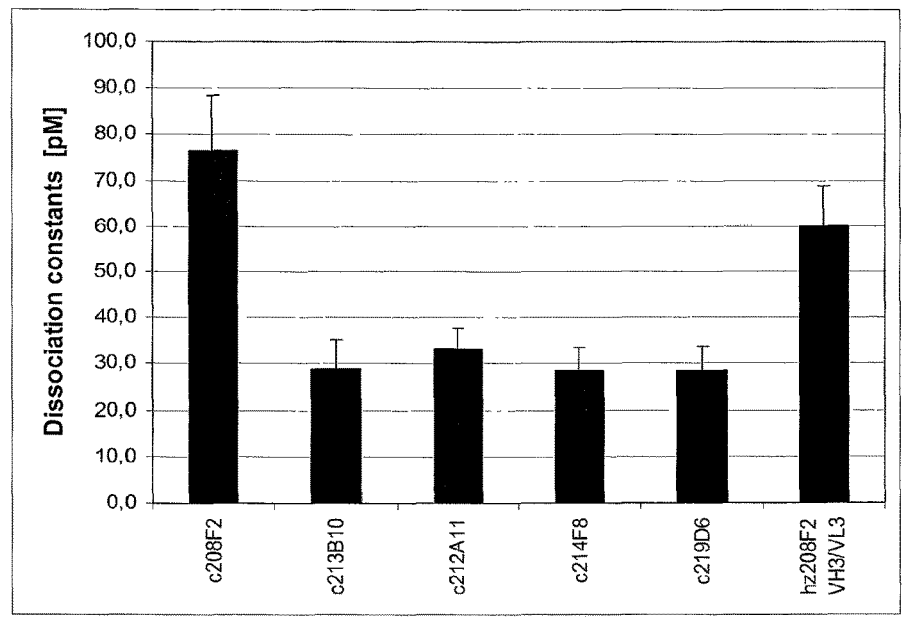

FIG. 19: The dissociation constants correspond to the mean of the four experiments run for each antibody and correspond to the ratio: $k_{off}/k_{on}\times10^{12}$ to be express in the pM unit. The error bars correspond to the standard error (n=4).

Figure 20:
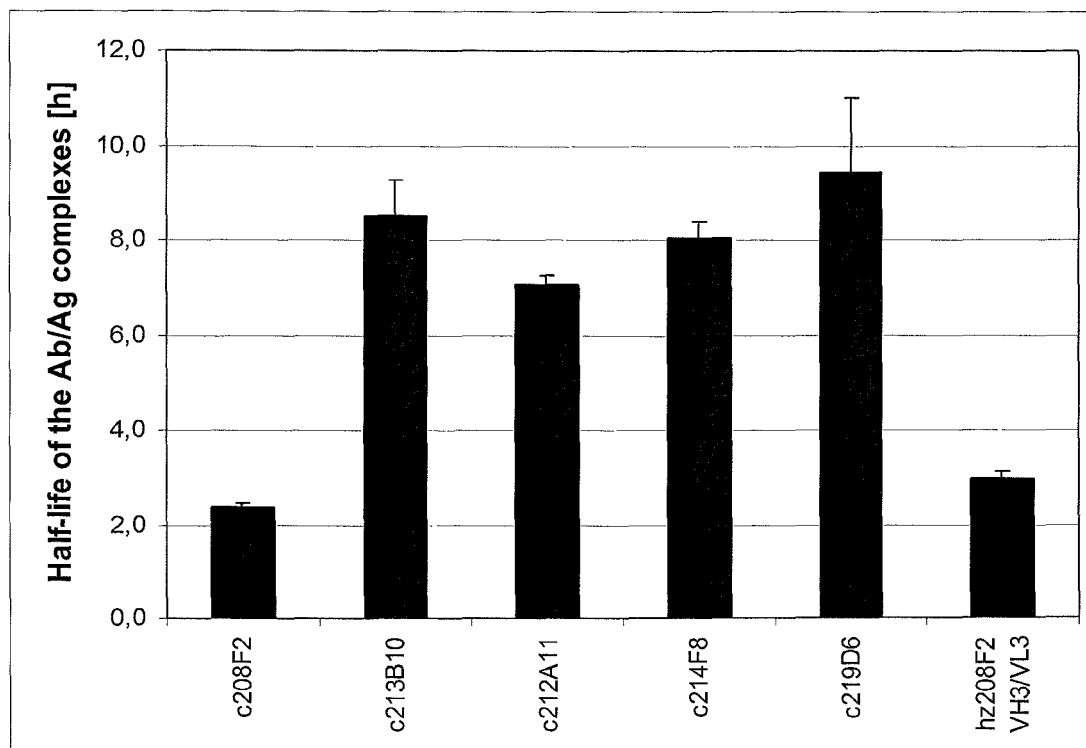

FIG. 20: the half-lives correspond to the mean of the four experiments run for each antibody and correspond to the ratio: $Ln(2)/k_{off}/3600$ to be express in the h unit. The error bars correspond to the standard error (n=4).

Figure 21:
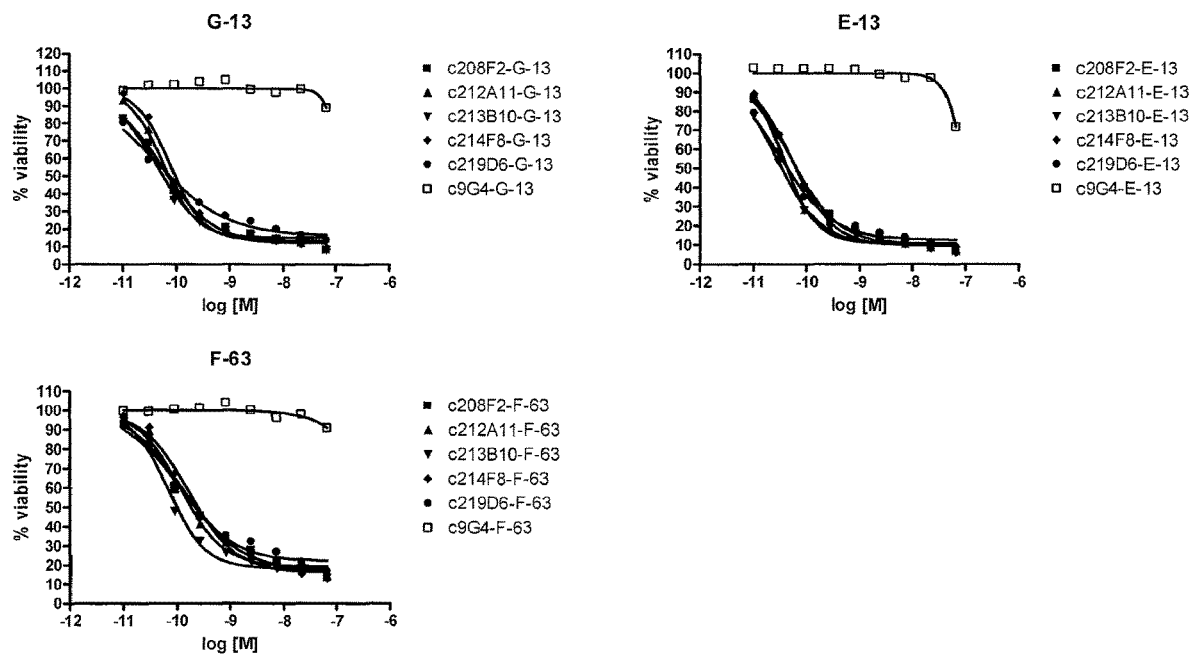

FIG. 21: Cell cytotoxicity of anti-IGF-1R coupled with three different compounds. Five chimeric antibodies anti-IGF-1R were coupled with either E-13, G-13 or F-63. An irrelevant antibody c9G4 was also coupled with the same compounds.

Figure 22A:
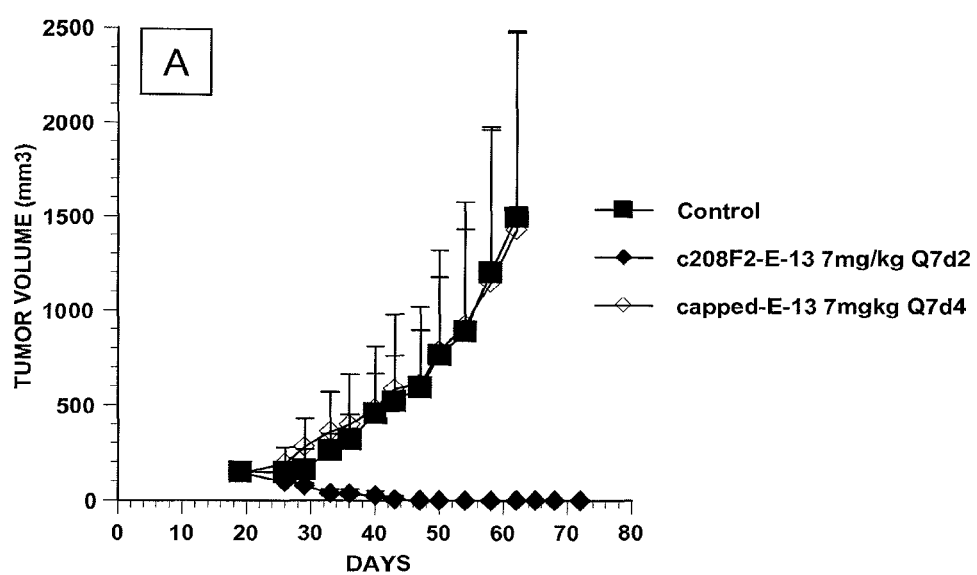
Figure 22B:
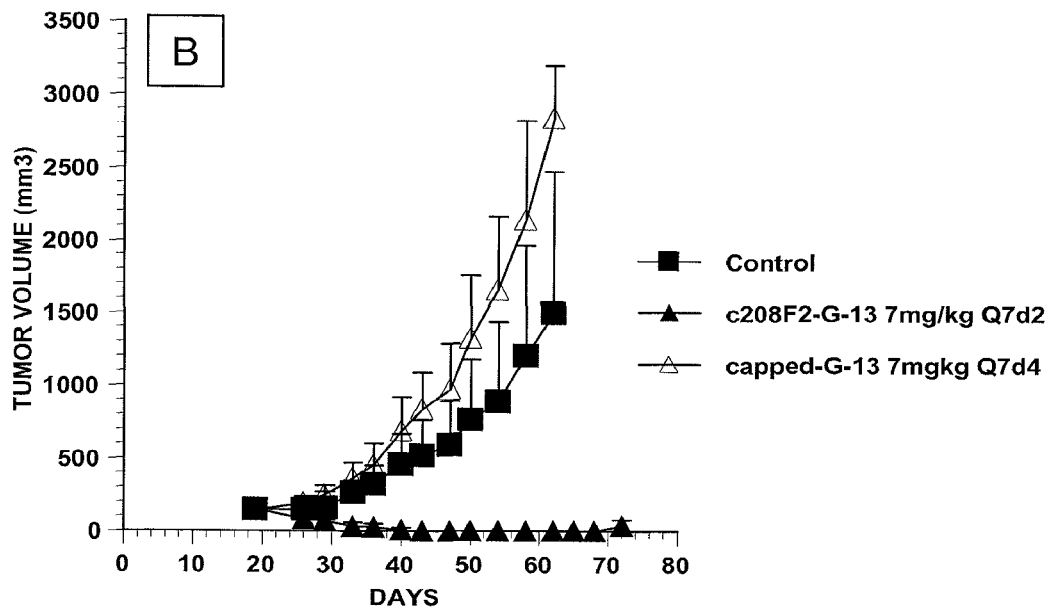
Figure 22C:
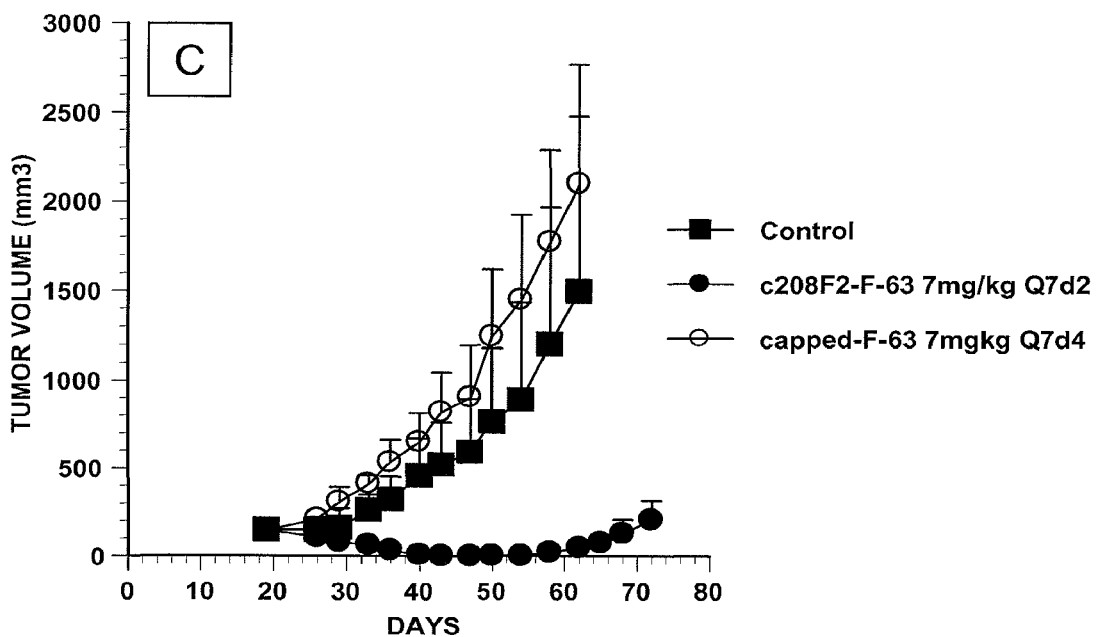

FIGS. 22A-22C: in vivo evaluation of c208F2-E-13 (FIG. 22A), c208F2-G-13 (FIG. 22B) and c208F2-F-63 (FIG. 22C) in the MCF-7 xenograft model.

Figure 23A:
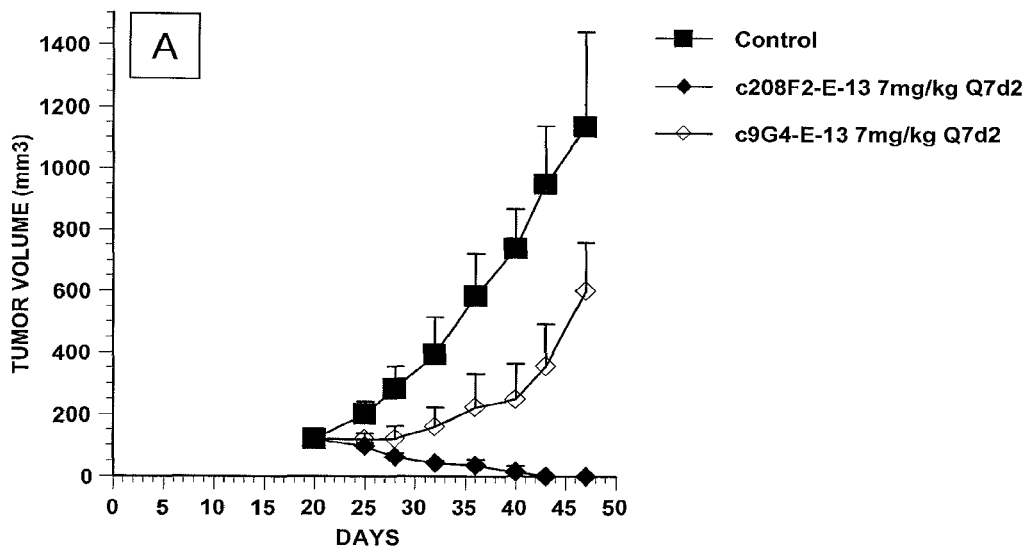
Figure 23B:
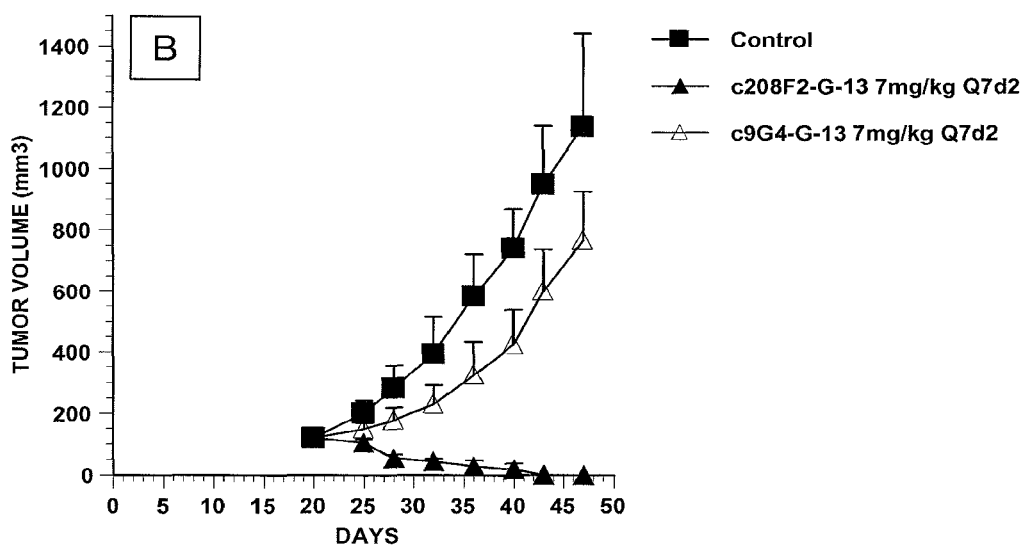

FIGS. 23A-23B: in vivo evaluation of both c208F2-E-13 (FIG. 23A) and c208F2-G-13 (FIG. 23B) compared to ADCs control (c9G4-E13 and c9G4-G-13) in the MCF-7 xenograft model.

Figure 24A:
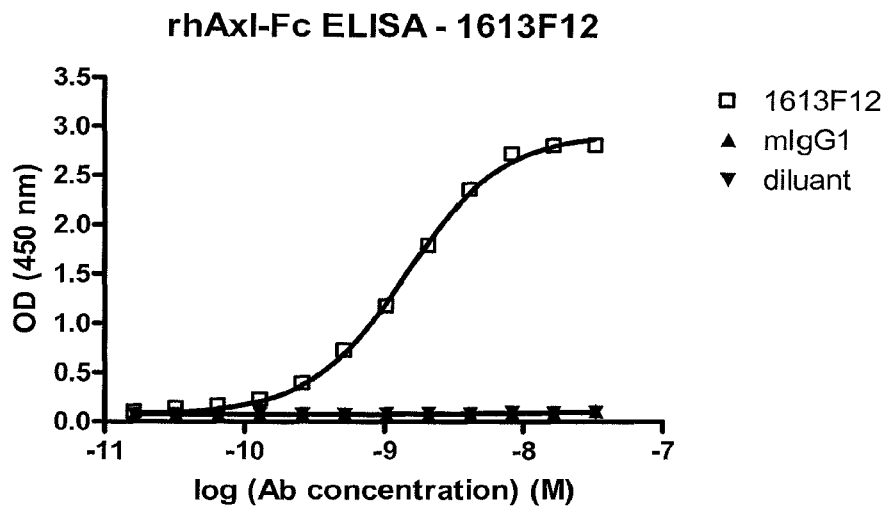
Figure 24B:
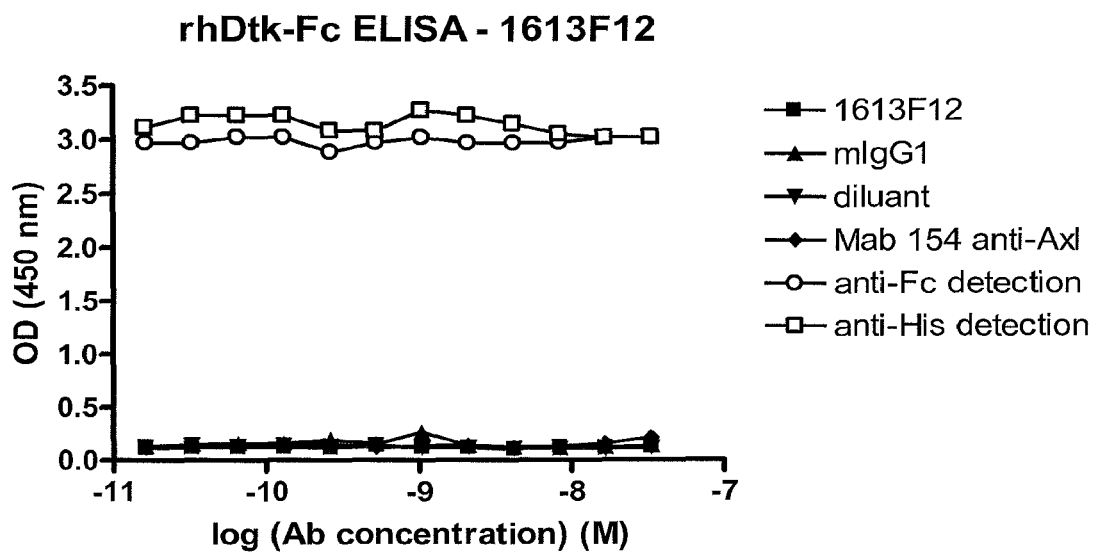
Figure 24C:
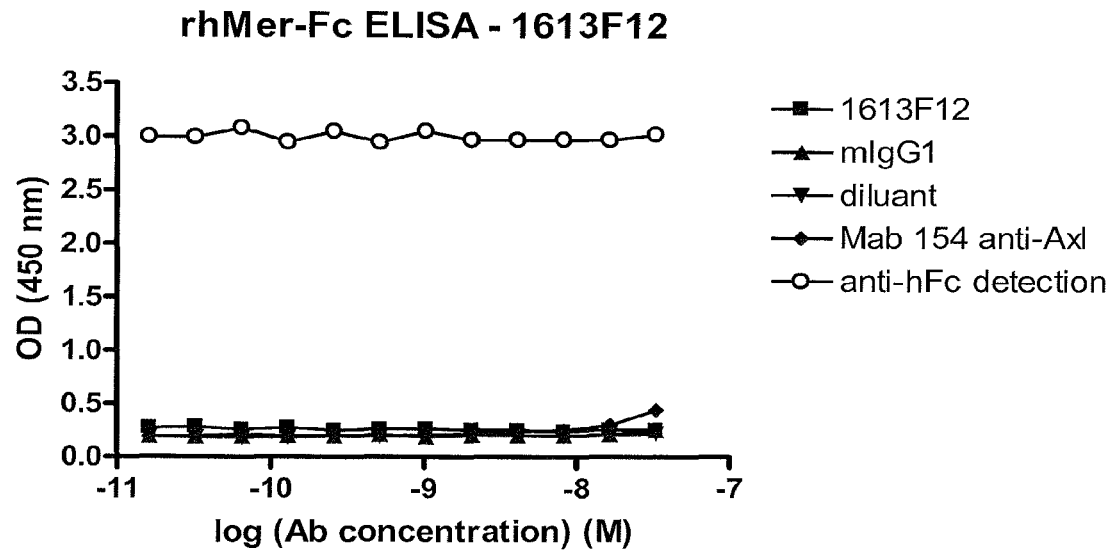

FIGS. 24A, 24B and 24C: Binding specificity of 1613F12 on the immobilized rhAxl-Fc protein (24A), rhDtk-Fc (24B) or rhMer-Fc (24C) proteins by ELISA.

Figure 25:
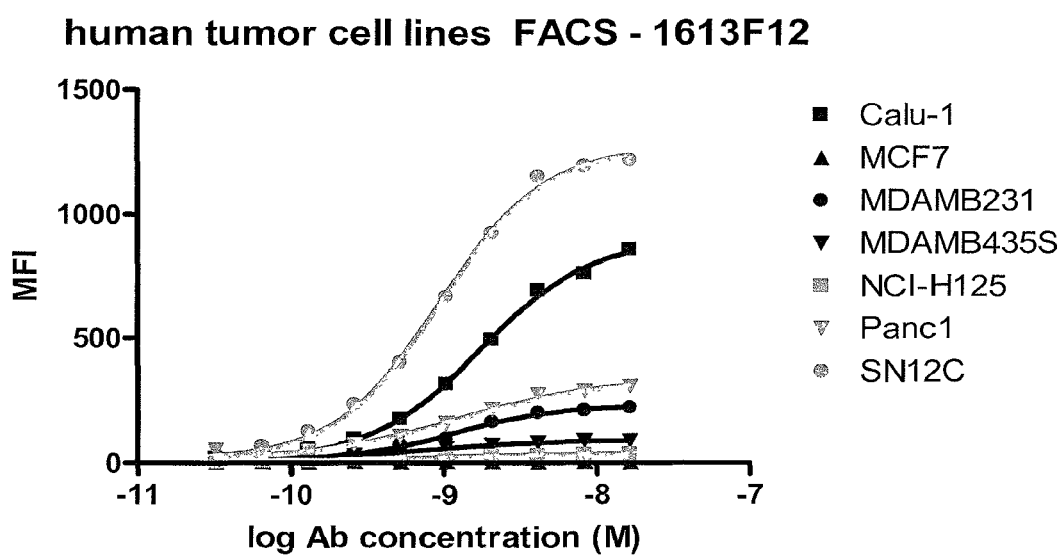

FIG. 25: FACS analysis of the 1613F12 binding on human tumor cells

Figure 26:
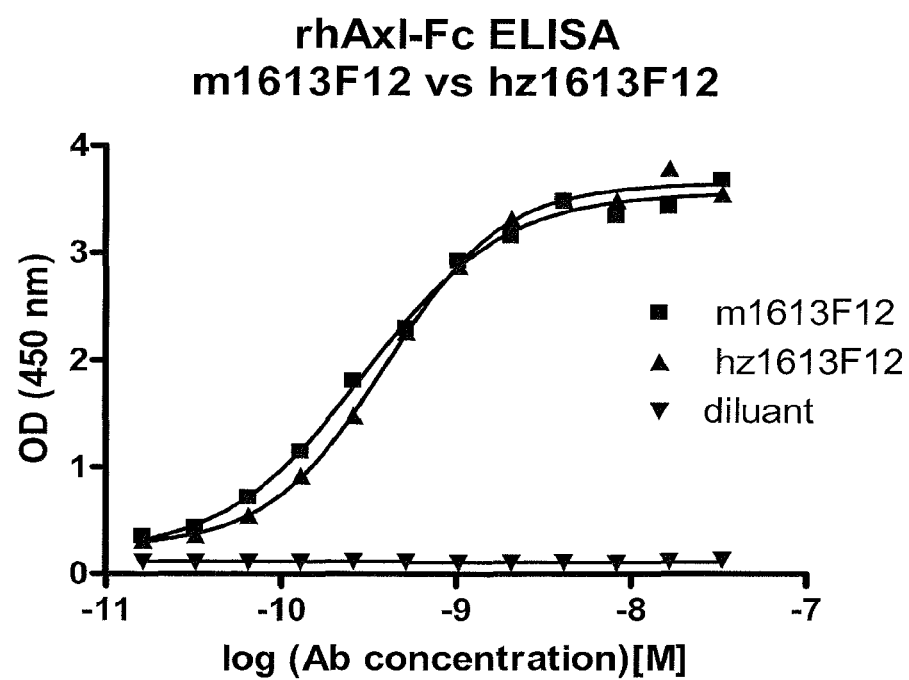

FIG. 26: ELISA experiments studying binding on rhAxl-Fc protein of both m1613F12 and hz1613F12.

Figure 27A:
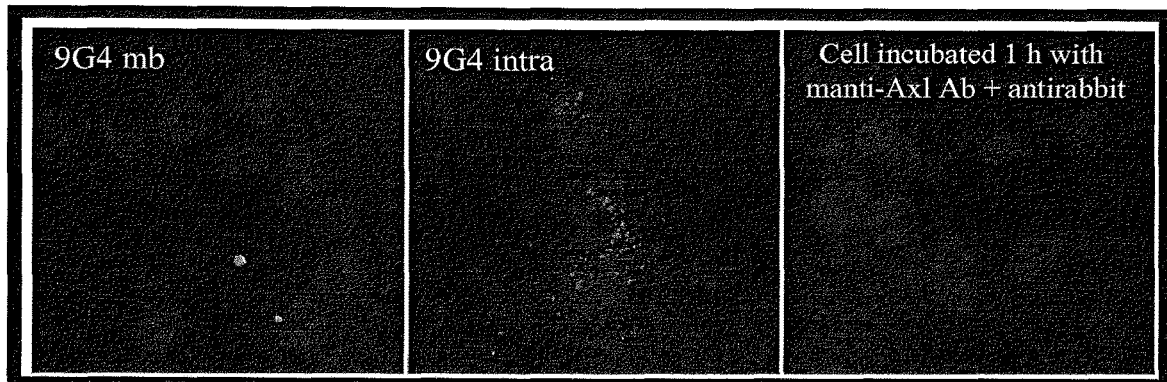
Figure 27B:
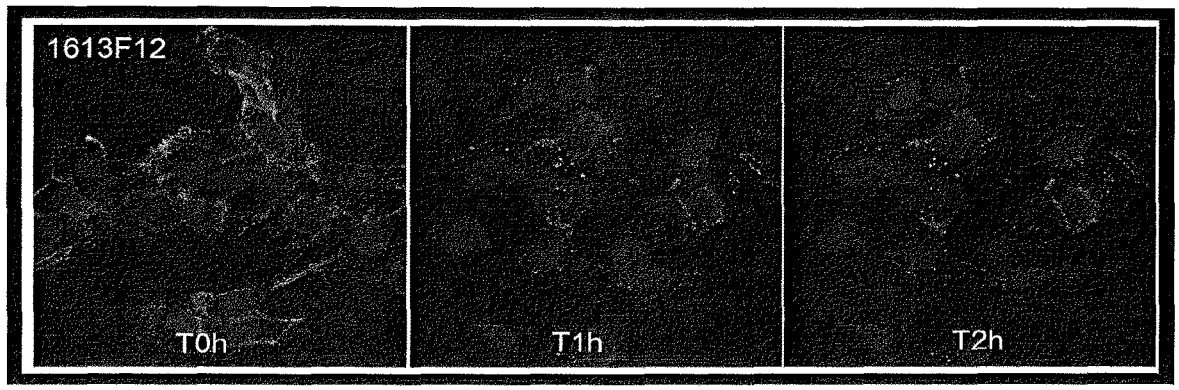
Figure 27C:
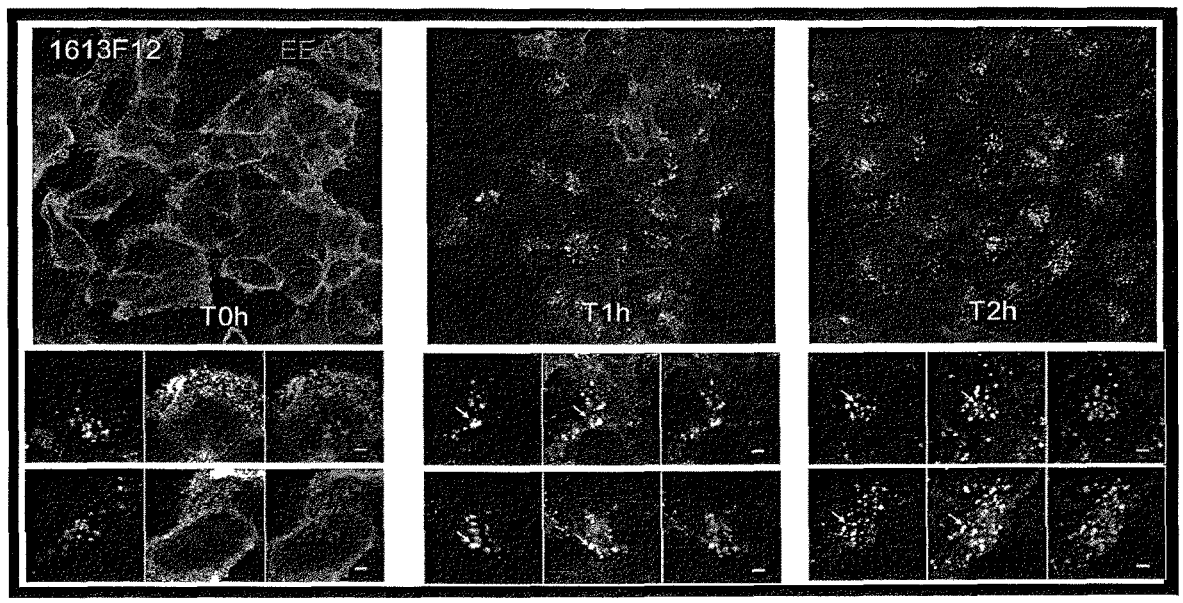

FIGS. 27A, 27B and 27C: Immunofluorescence microscopy of SN12C cells after incubation with 1613F12 FIG. 27A—Photographs of the mIgG1 isotype control conditions both for the membrane and the intracellular staining. FIG. 27B—Membrane staining. FIG. 27C—Intracellular staining of both Axl receptor using 1613F12 and of the early endosome marker EEA1. Image overlays are presented bellow and co-localizations visualized are indicated by the arrows.

Figures 28A, 28B:
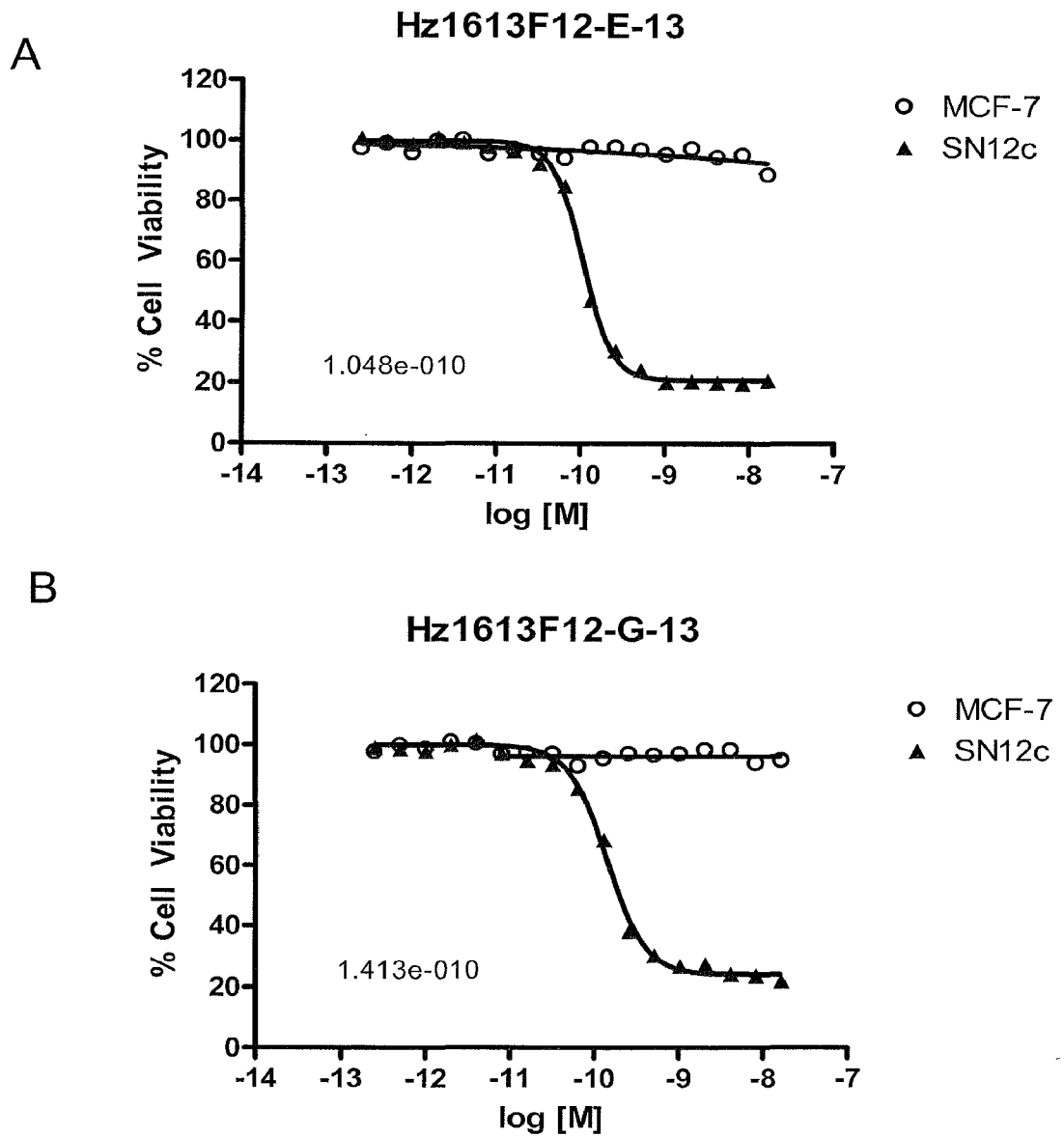

FIGS. 28A and 28B: FIG. 28A represents the cytotoxic activity of the hz1613F12-E-13 on both SN12c (Axl$^+$) and MCF-7 (Axl$^-$) cell lines. FIG. 28B represents the cytotoxic activity of the hz1613F12-G-13 on both SN12c (Axl$^+$) and MCF-7 (Axl$^-$) cell lines.

Figure 29A:
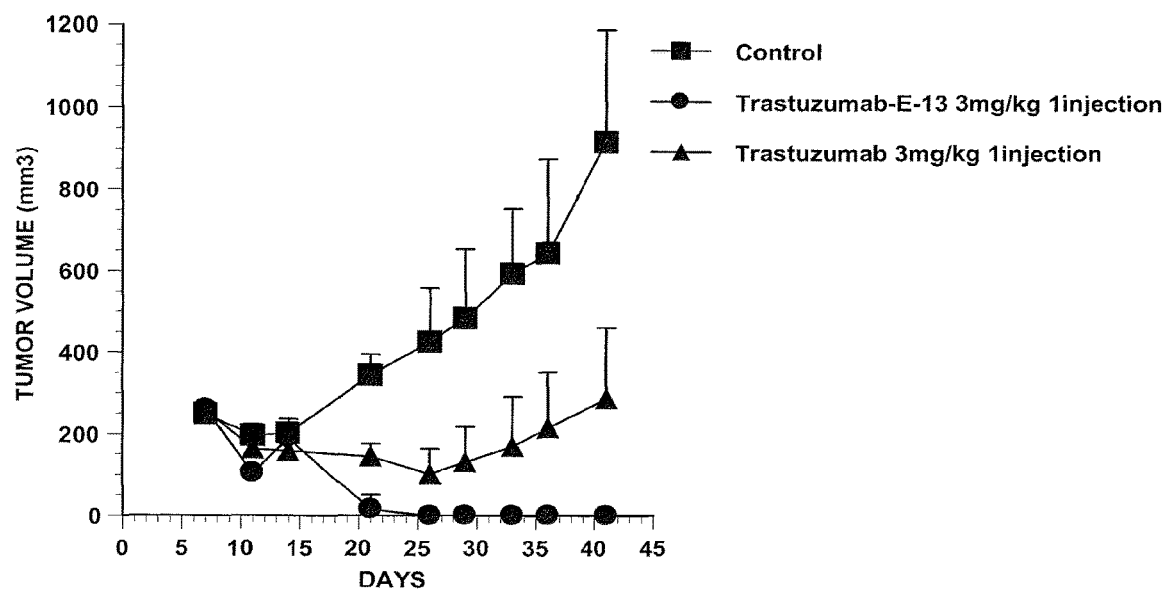

FIGS. 29A and B: In vivo activity of the trastuzumab antibody conjugated to either E-13 (29A) or G-13 (29B) compounds in the Calu-3 xenograft model.

Figure 30A:
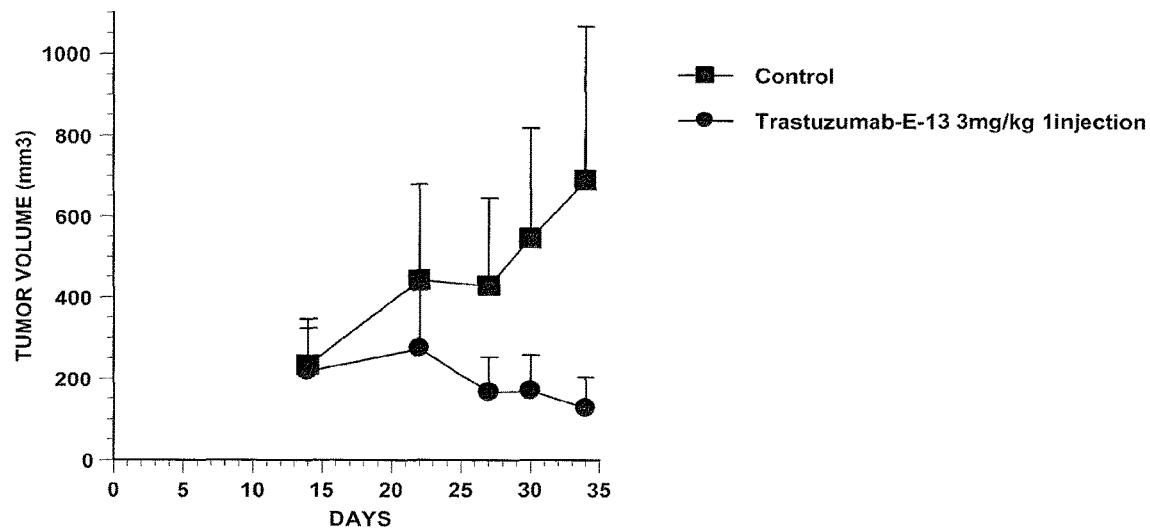
Figure 30B:
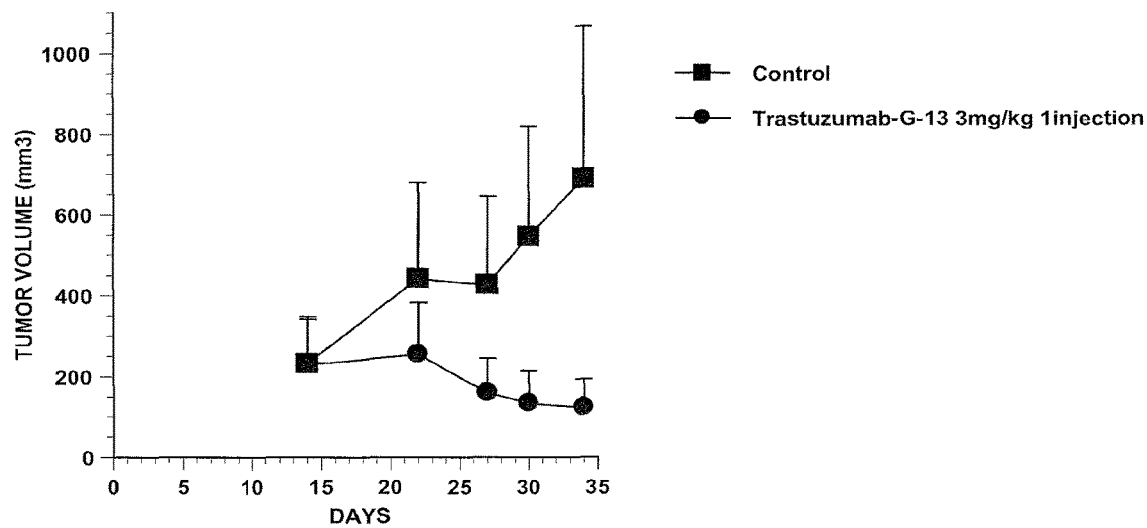
Figure 30C:
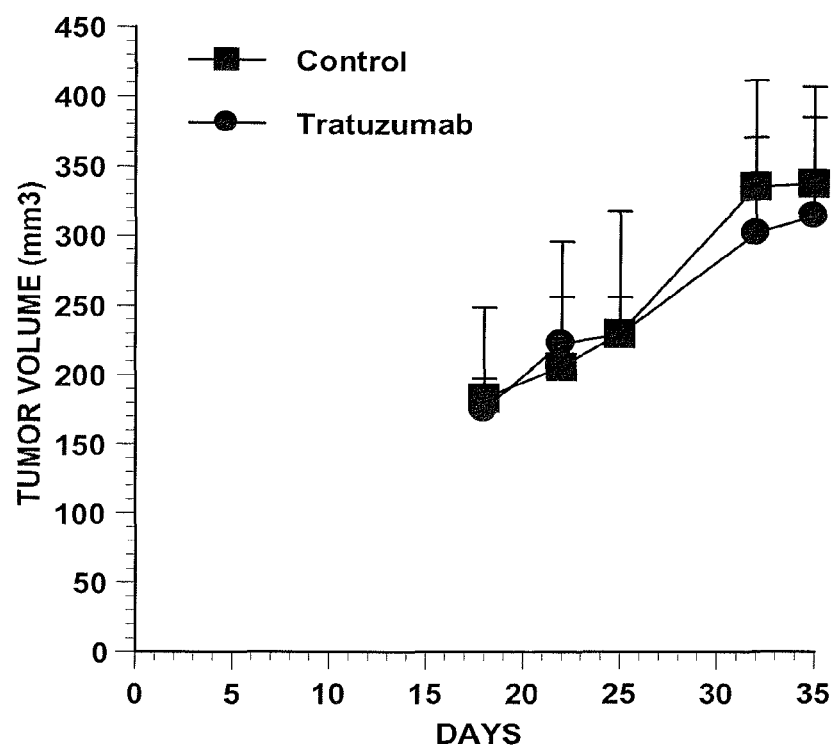

FIGS. 30A to 30C: In vivo activity of the trastuzumab antibody conjugated to either E-13 (FIG. 30A) or G-13 (FIG. 30B) compounds or alone (FIG. 30C) in the JIMT-1 xenograft model.

EXAMPLES

Example 1: Generation of Murine Antibodies Raised Against IGF-1R ECD

To generate murine monoclonal antibodies (Mabs) against human extracellular domain (ECD) of the human IGF-1 receptor (hIGF1R), 5 BALB/c mice were immunized 3-times s.c. with 10 µg of the rhIGF-1R protein (R&D SYSTEMS®, Cat No. 391-GR). As an alternative, three additional immunizations with 10 µg of the murine extracellular domain (ECD) of IGF-1R (R&D SYSTEMS®, Cat No. 6630-GR/Fc) were performed on some animals. The first immunization was done in presence of Complete Freund Adjuvant (SIGMA®, St Louis, Md., USA). Incomplete Freund adjuvant (SIGMA®) was added for following immunizations. Three days prior to the fusion, immunized mice were boosted with 10 µg of the rhIGF-1R protein. Then splenocytes and lymphocytes were prepared by perfusion of the spleen and by mincing of the proximal lymph nodes, respectively, harvested from 1 out of the 5 immunized mice (selected after sera titration of all mice) and fused to SP2/0-Ag14 myeloma cells (ATCC® (American Type Culture Collection), Rockville, Md., USA). The fusion protocol is described by Kohler and Milstein (Nature, 256:495-497, 1975). Fused cells are then subjected to HAT selection. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988). Approximately 10 days after the fusion, colonies of hybrid cells were screened. For the primary screen, supernatants of hybridomas were evaluated for the secretion of Mabs raised against the IGF-1R ECD protein by FACS analysis using human breast MCF7 tumor cells (ATCC®) and/or monkey COS7 cells (African green monkey kidney-SV40 transformed) which express monkey IGF-1R on their cell surface. More precisely, for the selection by flow cytometry, $10^5$ cells (either MCF7 or COS7) were plated in each well of a 96 well-plate in PBS containing 1% BSA and 0.01% sodium azide (FACS buffer) at 4° C. After a 2 min centrifugation at 2000 rpm, the buffer was removed and hybridoma supernatants to be tested were added. After 20 min of incubation at 4° C., cells were washed twice and an Alexa FLUOR®488-conjugated goat anti-mouse antibody 1/500° diluted in FACS buffer (# A11017, Molecular Probes Inc., Eugene, USA) was added and incubated for 20 min at 4° C. After a final wash with FACS buffer, cells were analyzed by FACS (FACSCALIBUR™, Becton-Dickinson) after addition of propidium iodide to each tube at a final concentration of 40 µg/ml. Wells containing cells alone and cells incubated with the secondary ALEXA FLUOR® 488-conjugated antibody were included as negative controls. Isotype controls were used in each experiment (SIGMA®, ref M90351MG). At least 5000 cells were assessed to calculate the mean value of fluorescence intensity (MFI).

Additionally an internalization assay was performed in order to select only internalizing antibodies. For this assay, MCF7 tumor cell line was cultured in RMPI 1640 without phenol red with 1% L-glutamine and 10% of FACS for 3 days before experiment. Cells were then detached using trypsin and 100 µl of a cell suspension at $4.10^5$ cell/ml are plated in 96-multiwell plates in RPMI1640 without phenol red with 1% L-glutamine and 5% FBS. After a 2 min centrifugation at 2000 rpm, cells were resuspended in 50 µl of either hybridoma supernatants or control antibody solutions (positive and isotype controls at 1 µg/ml). After a 20 min incubation time at 4° C., cells were centrifuged 2 min at 2000 rpm and resuspended in either cold (4° C.) or warm (37° C.) complete culture medium. Cells were then incubated for 2 hours either at 37° C. or at 4° C. Then cells were washed three times with FACS buffer. An ALEXA FLUOR® 488-labeled goat anti-mouse IgG antibody was incubated for 20 minutes and cells were washed three times before FACS analysis on propidium iodide negative cell population.

Following the FACS analysis, two parameters were determined: (i) the difference of the fluorescent signal detected on the surface of cells incubated at 4° C. with those obtained with the cells incubated at 37° C. with one hybridoma supernatant and (ii) the percentage of remaining IGF1R on the cell surface.

The percentage of remaining hIGF 1R is calculated as follows: % remaining IGF-1R=($MFI_{Ab\ 37°\ C.}/MFI_{Ab\ 4°\ C.}$)×100.

In addition three ELISAs were performed (either before or after cloning) to study the binding of antibodies on the recombinant human (hIGF-1R) and murine (mIGF-1R) proteins, and on the recombinant human Insulin Receptor (hIR) protein. Hybridoma secreting antibody showing binding on rh- and/or rm-IGF-1R and no binding on rhIR were retained. Briefly, 96-well ELISA plates (COSTAR® 3690, CORNING®, NY, USA) were coated 100 µl/well of either the rhIGF-1R protein (R&D SYSTEMS®, cat No. 391-GR) at 0.6 µg/ml or rmIGF-1R protein (R&D SYSTEMS®, cat No. 6630-GR/Fc) at 1 µg/ml or rhIR protein (R&D SYSTEMS®, cat No. 1544-IR/CF) at 1 µg/ml in PBS overnight at 4° C. The plates were then blocked with PBS containing 0.5% gelatin (#22151, Serva Electrophoresis GmbH, Heidelberg, Germany) for 2 h at 37° C. Once the saturation buffer discarded by flicking plates, 100 µl of each supernatant dilution were added to each well (either undiluted hybridoma supernatant either supernatant serial dilutions) and incubated for 1 h at 37° C. After three washes, 100 µl horseradish peroxidase-conjugated polyclonal goat anti-mouse IgG (#115-035-164, Jackson Immuno-Research Laboratories, Inc., West Grove, Pa., USA) was added at a 1/5000 dilution in PBS containing 0.1% gelatin and 0.05% TWEEN® 20 (Polyethylene glycol sorbitan monolaurate) (w:w) for 1 h at 37° C. Then, ELISA plates were washed 3-times and the TMB (# UP664782, Uptima, Interchim, France) substrate is added. After a 10 min incubation time at room temperature, the reaction was stopped using 1 M sulfuric acid and the optical density at 450 nm is measured.

Hybridoma secreting antibody of interest were expanded and cloned by limit dilution. Once isotyped, one clone of each code was expanded and frozen. Each antibody of interest was produced in in vitro production systems named CELLINE™ (Integra Biosciences) for further characterization.

Additional assays to address binding specificity FACS analyses were performed on IM9 cells (human IR expressing B lymphoblasts) as well as on hIGF-1R transfected cells versus non transfected cells.

All the data corresponding to the selected antibodies were summarized in Table 9 and demonstrated that the five selected antibodies strongly recognize the native human IGF-1R expressed either on MCF-7 breast cancer cells or on transfected cells. They also recognize monkey IGF-1R on COS-7 cells. These antibodies do not cross react with the human insulin receptor highly expressed on IM9 cells. It has to be noticed that these antibodies poorly recognize the rhIGF-1R ECD protein when directly coated to ELISA plates.

B. and expressed in mean of fluorescence intensity (MFI). The $EC_{50}$ of binding expressed in molarity (M) was calculated using a nonlinear regression analysis (GraphPad PRISM® 4.0).

The titration curve of each murine or chimeric Ab demonstrated that all generated antibodies are capable to recognize the native IGF-1R form with a typical saturation profile (FIG. 1A). In order to rank antibodies and to compare the binding properties of both murine and chimeric Abs, the binding $EC_{50}$ of each compound was determined using a non linear regression analysis. The comparison of the $EC_{50}$ of each murine Ab with its corresponding chimeric form showed that the 2 forms displayed the same binding properties demonstrating that the Ab chimerization did not affect IGF-1R recognition (FIGS. 1B-C). $EC_{50}$ and $B_{max}$ values of chimeric antibodies were summarized in Table 10.

TABLE 10

| AC | $B_{max}$ | $EC_{50}$ |
|---|---|---|
| c208F2 | 981 | 6.7E−10 |
| c212A11 | 991 | 6.7E−10 |
| c214F8 | 1069 | 5.0E−10 |
| c219D6 | 993 | 4.7E−10 |
| c213B10 | 1103 | 4.4E−10 |

Example 3: Confirmation of Antibody Specificity by Using Either IGF-1R or IR Transfected Cells or IM9 Cells that Express Significant Levels of IR In order to confirm the specificity of the generated antibodies for IGF-1R versus IR, stable transfectants expressing either hIGF-1R or hIR were evaluated by FACS analyses.

TABLE 9

| | | | ELISA (SNT at 5 µg/ml) D.O 450 nm | | | MCF7 Internalisation Assay (SNT at 5 µg/ml) | | | | FACS (SNT at 5 µg/ml) MFI | | | |
|---|---|---|---|---|---|---|---|---|---|---|---|---|---|
| | | | rh | rm | rh | MFI | | % remain- | Δ (MFI) | | Cos-7 | | non Tf |
| hybridoma name | Isotype | CNCM | IGF-1R | IGF-1R | Insulin R | 4° C. | 37° C. | ing rh IGF1R | 4° C.-MFI 37° C.) | IM9 (h IR+) | (monkey IGF1R+) | Tf hIGF1R+ | cells (h IGF1R−) |
| 208F2 | IgG1 K | I-4757 | 0.163 | 0.099 | 0.140 | 355 | 94 | 27 | 261 | 4 | 106 | 2197 | 22 |
| 212A11 | IgG1 K | I-4773 | 0.232 | 0.102 | 0.141 | 390 | 106 | 27 | 284 | 7 | 125 | 2187 | 23 |
| 213B10 | IgG1 K | I-4774 | 0.399 | 0.127 | 0.110 | 386 | 115 | 30 | 271 | 7 | 122 | 2055 | 23 |
| 214F8 | IgG1 K | I-4775 | 0.349 | 0.102 | 0.115 | 386 | 111 | 29 | 275 | 7 | 132 | 2137 | 20 |
| 219D6 | IgG1 K | I-4736 | 0.329 | 0.112 | 0.106 | 349 | 106 | 30 | 243 | 7 | 114 | 2110 | 21 |

Example 2: Antibody Binding to the Human Native IGF-1R by FACS Analyses

The five murine IGF-1R antibodies were chimerized. The binding properties of both the murine and the chimeric IGF-1R antibodies were evaluated by FACS analyses on the human MCF-7 breast adenocarcinoma cell line (ATCC® # HTB-22) using increasing antibody concentrations. For that purpose, cells (1×10⁶ cells/ml) were incubated with IGF-1R antibodies for 20 min. at 4° C. in FACS buffer (PBS, 0.1% BSA, 0.01% NaN₃). They were then washed 3 times and incubated with the appropriate secondary antibody coupled with ALEXA FLUOR® 488 for 20 additional minutes at 4° C. in the dark before being washed 3 times in FACS buffer. The binding of anti-IGF-1R antibodies was immediately performed on viable cells which were identified using propidium iodide (that stains dead cells). The maximum of signal intensity obtained with each antibody was designed as Briefly, increasing concentrations of chimeric mAbs were incubated with cells for 20 min at 4° C. in FACS buffer (PBS, 0.1% BSA, 0.01% NaN₃). Cells were then washed 3 times and incubated with the appropriate secondary antibody coupled with ALEXA FLUOR® 488 before being incubated for 20 additional minutes at 4° C. in the dark and then washed 3 times in FACS buffer. The binding of anti-IGF-1R antibodies was immediately performed on viable cells which were identified using propidium iodide (that stains dead cells). The binding $EC_{50}$ expressed in molarity (M) was calculated using a nonlinear regression analysis (GraphPad PRISM® 4.0).

Titration curves obtained on the hIGF-1R transfected cell line (FIG. 2A) versus untransfected cells (FIG. 2B) confirmed the binding specificity of chimeric Abs for the human IGF-1R. $EC_{50}$ and $B_{max}$ values were summarized in Table 11.

TABLE 11

| Ac | $B_{max}$ | $EC_{50}$ (M) |
|---|---|---|
| c208F2 | 2008 | 3.2E-10 |
| c212A11 | 2513 | 4.4E-10 |
| c214F8 | 2094 | 2.7E-10 |
| c219D6 | 2521 | 5.5E-10 |
| c213B10 | 2029 | 3.3E-10 |

In order to verify the absence of binding of both murine and chimeric antibodies on hIR, a stable cell line expressing the human IR (hIR) was used. The recognition of human cell surface hIR by both murine and chimeric Ab was performed by FACS analyses. Increasing concentration of either the murine or the chimeric mAbs were incubated on the hIR+ transfected cell line for 20 minutes at 4° C. in FACS buffer (PBS, 0.1% BSA, 0.01% NaN$_3$). Cells were then washed 3 times and incubated with the appropriate secondary antibody coupled with ALEXA FLUOR® 488 before being incubated for 20 additional minutes at 4° C. in the dark and then washed 3 times in FACS buffer. The binding of anti-IGF-1R antibodies was immediately performed on viable cells which were identified using propidium iodide (that stains dead cells). The binding $EC_{50}$ expressed in molarity (M) was calculated using a nonlinear regression analysis (GraphPad PRISM® 4.0). The anti-hIR antibody clone GRO5 was used as positive controls. The murine and chimeric 9G4 antibodies were introduced as irrelevant antibodies.

The high level of expression of hIR on cell surface of the transfected cells was confirmed using the commercial anti-hIR antibody GRO5 (FIGS. 3A and 3B). Even using high concentrations of either the murine (FIG. 3A) or the chimeric (FIG. 3B) hIGF-1R Abs, no binding on cell surface of hIR+ transfected cells was observed. These results demonstrated that neither murine nor chimeric anti-hIGF-1R Abs did recognized the hIR.

This specificity of recognition of hIGF-1R versus IR has also been demonstrated, by FACS analyses, using IM9 cells, a B-lymphoma cell line that expresses hIR (FIG. 4). For this FACS analyses, the protocol was the same as the one described above and murine antibodies were used in order to prevent the cross reactivity of the secondary anti-human Ab (IM9 cells express human Ig on their cell surface). Results presented in FIG. 4 demonstrated once again that the expected signal was observed using the GRO5 anti-hIR antibody while none of the murine antibody evaluated displayed any significant binding signal on this cell line.

Example 4: Antibody Binding to the Monkey Native IGF-1R by FACS and BIACORE® Analyses One of the first pre-requisite for regulatory toxicology studies is to find a relevant animal specie in order to evaluate the selected compound. As the series of antibodies described herein is not able to recognize murine IGF-1R, the most likely specie for toxicological evaluation is the non human primate (NHP).

In order to evaluate the binding of anti-IGF-1R antibodies on monkey IGF-1R, the binding of both murine and chimeric anti-hIGF-1R antibodies was first evaluated by FACS analyses on COS-7 cell line using increasing antibody concentrations. Cells (1×10$^6$ cells/ml) were incubated with anti-IGF-1R antibodies for 20 minutes at 4° C. in FACS buffer (PBS, 0.1%, BSA, 0.01% NaN$_3$). Then, cells were washed 3 times and incubated with the appropriate secondary antibody coupled with ALEXA FLUOR® 488 before being incubated for 20 additional minutes at 4° C. in the dark and finally washed 3 times in FACS buffer. The binding of anti-IGF-1R antibodies was immediately evaluated on viable cells identified using propidium iodide (that stains dead cells). The binding $EC_{50}$ expressed in molarity (M) was calculated using a nonlinear regression analysis (GraphPad PRISM® 4.0).

The titration curves obtained on the COS-7 monkey cell line showed that, all the anti-hIGF-1R Abs recognized specifically the IGF-1R expressed on the surface of the monkey cell line (FIG. 5A). Determination of the, $EC_{50}$ for each murine and chimeric Abs showed that the 2 forms compared well regarding to their binding properties on monkey IGF-1R (FIG. 5B). Those results showed that all the generated anti-hIGF-1R recognized the monkey IGF-1R.

A comparison of binding $EC_{50}$ on COS-7 cells versus transfected IGF-1R cells was performed in order to verify the magnitude of chimeric antibody recognition on human versus monkey IGF-1R. Results shown in FIG. 5C demonstrated a similar recognition of human and monkey IGF-1Rs by all antibodies.

In order to confirm the recognition on another type of monkey, cells were transfected with the IGF-1R form Cynomolgus monkey to produce soluble monkey IGF-1R ECD and BIACORE® experiments were performed with one of the chimeric antibodies (c208F2) in order to compare its binding properties either the hIGF-1R or the Cynomolgus IGF-1R.

The recognition experiments were run on a BIACORE® X100 device using a CM5 sensor chip activated by an anti-Tag His antibody (His capture kit GE Healthcare catalogue number 28-9950-56). More than 11000 RU of antibodies are chemically grafted on the carboxymethyldextan matrix using the amine kit chemistry. The experiments were carried out at 25° C. with a flow rate of 30 µl/min using the HBS-EP buffer (GE Healthcare) as the running and sample dilution buffer. The single cycle kinetic scheme was used to defined the kinetic parameters of the binding of the chimeric form of the 208F2 antibody (c208F2) on hIGF-1R compared to Macaca IGF-1R A solution of a soluble recombinant version of the IGF1R hetero-tetramere composed of 2α chains and the extracellular domains of 2β chains expressed with an additional C-terminal 10-His tag (SEQ ID NO: 107), based either on the sequence of the human (R&D SYSTEMS® catalogue number 305-GR-50) or of the one of cynomolgus (produced in house) was injected 1 minute on the second flowcell at a dilution defined to capture around 160 RU of antigen. After the capture phase, either the running buffer was injected 5 times (90 s each injection) or a growing range of 5 concentrations of c208F2 were injected (90s each injection) on both flowcells. At the end of the fifth injection the running buffer was passed in order to define the dissociation rate.

The surface was then regenerated with an injection of a 10 mM Glycine, HCl pH 1.5 buffer during 30 s.

The computed signal corresponds to the difference between the response of the flowcell 2 (with captured IGF-1R) and the response of the flowcell 1 (without any IGF-1R molecules) (FIG. 6).

For each IGF1R molecule (human or cyno), the signal due to the injections of the growing range of concentrations of c208F2 was corrected by subtraction of the signal obtained with the 5 injections of the buffer (double reference). The resulting sensorgrams were analysed using the Biaevaluation software with a 1:1 model. The kinetic rates are evaluated either independently (2 kinetics rates of the binding of c208F2 on each IGF-1R) or commonly (the same kinetic rates of the binding of c208F2 on the human and the cynomolgus IGF1R). The quality of the fitting was assessed by a Chi2/Rmax ratio lower than 0.05 RU.

The kinetics rates of the binding (see Table 12) defined separately for each IGF-1R are close and a fitting of both sensorgrams with the same kinetic rates is of good quality.

The c208F2 antibody recognizes as well the recombinant human and cynomolgus IGF-1Rs with a dissociation constant (KD) about 0.2 nM. The affinities defined in this study correspond to the functional affinities (avidities) of the antibodies for a level of captured human and cynomolgus IGF-1R around 160 RU.

TABLE 12

| IGF1R | kon [1/M · s] | koff [1/s] | Kd [nM] | Chi2/Rmax |
|---|---|---|---|---|
| human | 1.52E+06 | 3.40E−04 | 0.23 | 0.045 |
| cynomogus | 1.85E+06 | 3.10E−04 | 0.17 | 0.032 |
| Hum. & Cyno. | 1.52E+06 | 3.33E−04 | 0.22 | 0.039 |

Example 5: Intrinsic Effect of Generated Antibodies on IGF-1R Phosphorylation

It is well known that antibodies could induce an agonistic effect when they bind to tyrosine kinase receptors. As we would not like to select such agonist antibodies, the evaluation of hIGF-1R phosphorylation was studied using the chimeric antibodies.

For that purpose, MCF-7 cells were incubated in serum-free medium overnight. Then, either IGF-1 (100 nM) or Abs to be tested were added (10 µg/ml) for 10 minutes at 37° C. Medium was discarded and cells were scraped in a lysis buffer (pH 7.5) containing 10 mM Tris HCl buffer (pH 7.5), 15% NaCl (1 M), 10% detergent mix (10 mM Tris-HCl, 10% Igepal lysis buffer) (SIGMA® Chemical Co.), 5% sodium deoxycholate (SIGMA® Chemical Co.), 1 protease inhibitor cocktail complete TM tablet (Roche), 1% phosphatase inhibitor Cocktail Set II (CALBIOCHEM®), for 90 min at 4° C. The lysates were clarified by centrifugation at 4° C., heated for 5 min at 100° C. and kept at −20° C. or directly loaded on 4-12% SDS-PAGE gels. Incubation of the primary antibody was performed for 2 hr at room temperature and then incubation with HRP-linked secondary antibodies was done for 1 hr at room temperature. Membranes were washed in TBST prior to visualization of proteins with ECL™ (enhanced chemiluminescence). Blots were quantified using Image J software. Phospho-protein values were normalized with GAPDH. Phosphorylation of hIGF-1R in response to IGF-1 was considered as 100% of stimulation. The effect of anti-hIGF-1R Abs on the phosphorylation of hIGF-1R was determined as % of phosphorylation induced by IGF-1.

The results described in FIG. 7 represent the mean of the % of pIGF-1R in response to the chimeric anti-IGF-1R Abs of 3 independent experiments+/−S.D. compared to IGF-1. As illustrated no significant or minor (<10%) phosphorylation of hIGF-1R was detected when MCF-7 cells were incubated with 10 µg of anti-IGF-1R Abs.

Example 6: Inhibition of IGF-1R Phosphorylation in Response to IGF-1 by Murine IGF-1R Antibodies In order to characterize the selected antibodies, their ability to inhibit IGF1-induced phosphorylation was studied. For that purpose, MCF-7 cells were incubated in serum-free medium overnight. Then, cells were incubated for 5 minutes with murine anti-hIGF-1R Abs before addition of IGF-1 for 2 minutes at 37° C. Medium was discarded and cells were scraped in a lysis buffer (pH 7.5) containing 10 mM Tris HCl buffer (pH 7.5), 15% NaCl (1 M), 10% detergent mix (10 mM Tris-HCl, 10% Igepal lysis buffer) (SIGMA® Chemical Co.), 5% sodium deoxycholate (SIGMA® Chemical Co.), 1 protease inhibitor cocktail complete TM tablet (Roche), 1% phosphatase inhibitor Cocktail Set II (CALBIOCHEM®), for 90 min at 4° C. The lysates were clarified by centrifugation at 4° C., heated for 5 min at 100° C. and kept at −20° C. or directly loaded on 4-12% SDS-PAGE gels. Incubation of the primary antibody was performed for 2 h at room temperature and then incubation with HRP-linked secondary antibodies was performed for 1 hr at room temperature. Membranes were washed in TBST prior to visualization of proteins with ECL™. Blots were quantified using Image J software. Phospho-protein values were normalized with GAPDH. Phosphorylation of hIGF-1R in response to IGF-1 was considered as 100% of stimulation. The effect of anti-hIGF-1R Abs on the phosphorylation of hIGF-1R was determined as % of phosphorylation induced by IGF-1.

All anti-IGF-1R Abs inhibited strongly hIGF-1R phosphorylation in response to IGF-1 (decrease >80%) (FIG. 8). The best inhibitors of IGF1-induced phosphorylation of hIGF-1R are the m208F2, m212A11 and m214F8 Mabs.

Example 7: Study of IGF-1R Internalization after Binding of the Generated IGF-1R Antibodies by FACS Analyses MCF-7 cells were incubated with 10 µg/ml of chimeric antibodies at 4° C. for 20 min. Then, cells were washed and incubated at 4° C. or 37° C. for 4 h. The quantity of cell-surface bound antibody was determined using a secondary antibody. The ΔMFI defined as the difference between MFI measured at 4° C. and MFI measured at 37° C. after a 4 hour incubation time corresponded to the quantity of internalized Ab. The ΔMFI was presented in FIG. 9 and Table 11. The percentage of internalization at 10 µg/ml of Ab were calculated as followed 100*(MFI at 4° C.−MFI at 37° C.)/MFI at 4° C. and presented in Table 13.

TABLE 13

| Abs | % Internalization | ΔMFI | ΔMFI_EC$_{50}$ |
|---|---|---|---|
| c208F2 | 83 | 288 | 1.8E−10 |
| c212A11 | 80 | 322 | 2.7E−10 |
| c214F8 | 87 | 403 | 2.2E−10 |
| c219D6 | 80 | 353 | 4.4E−10 |
| c231B10 | 85 | 369 | 2.3E−10 |

In order to determine whether antibodies that also recognized the monkey IGF-1R were able to internalize this receptor, the same internalization experiment was performed. Results summarized in Table 14 demonstrated that all tested antibodies were able to mediate monkey IGF-1R internalization.

TABLE 14

| | Murine Abs | | Chimeric Abs | |
|---|---|---|---|---|
| Abs | ΔMFI | % internalisation | ΔMFI | % internalisation |
| 208F2 | 53 | 74 | 52 | 67 |
| 212A11 | 83 | 73 | 98 | 75 |
| 214F8 | 76 | 71 | 98 | 72 |

TABLE 14-continued

|  | Murine Abs | | Chimeric Abs | |
| --- | --- | --- | --- | --- |
| Abs | ΔMFI | % internalisation | ΔMFI | % internalisation |
| 219D6 | 80 | 71 | 102 | 74 |
| 213B10 | 84 | 74 | 101 | 73 |

The kinetic of cell surface bound antibody decrease was further evaluated. For that purpose, MCF-7 cells were seeded in 96-well plates and incubated with 10 µg/ml of murine for 20 min at 4° C. Cells were then washed to remove unbound antibody and in media at 37° C. for 10, 20, 30, 60 or 120 min. At each time point, cells were centrifuged and then surface labeled on ice with a secondary anti-mouse IgG-ALEXA FLUOR® 488 to determine the amount of antibody remaining on the cell surface. The fluorescence intensity for each murine Ab and for each time point was normalized by the signal at 4° C. (% remaining IGF-1R) and fitted to an exponential decay to determine the half life (t½). t½ was considered as the time needed to obtain a decrease of 50% of the signal. As illustrated in FIG. 10, the surface level of all murine Abs dropped rapidly over the first 30 min and the decrease was almost maximum after 60 min of incubation (FIG. 10A). The calculated half life was comprised between 10 to 18 min according to the murine Ab (FIG. 10B).

In order to validate that the decrease of the cell surface signal was due to Ab internalization and not due to receptor shedding, cells were incubated with murine Abs for 0, 30 and 60 min a 37° C. (FIG. 11). Cells were then fixed and permeabilized or not in order to determine cell surface bound antibody (w/o permeabilization) and total antibody signal corresponding to cell-surface bound+internalized Ab (with permeabilization). The quantity of internalized Ab (cytoplasmic) was determined as follow: MFI after permabilization–MFI w/o permeabilization. This experiment showed that the decrease of cell-surface bound Ab was due to an increase of cytoplasmic Abs demonstrating that Abs were internalized (FIG. 11). In addition, the degradation of the Abs started after 1 h of incubation as indicated by the decrease of the signal after permeabilization (Total).

Example 8: Study of IGF-1R Internalization after Binding of the Generated IGF-1R Antibodies by Confocal Analyses To further confirm antibodies internalization, confocal microscopy was done to assess the subcellular distribution of antibodies following cellular trafficking. Cells were incubated with anti-hIGF-1R Abs 37° C., fixed and permeabilized. Therefore, cells were stained using a secondary antibody ALEXA FLUOR®-488 and with rabbit anti-Lamp-1 antibody that was revealed using a secondary anti-Rabbit IgG ALEXA FLUOR® 555. Before incubation at 37° C., the murine 208F2 Ab was localized on the membrane of MCF-7 cells (FIG. 12A). No colocalization with the lysosome marker, lamp-1 was noted using the colocalization high liter plug-in of the Image J software. The cell surface bound antibody decreased dramatically after 15 min of incubation at 37° C. Concomitantly to the decrease of the cell surface bound antibody, intracellular antibody was detected into vesicles. Rare colocalization with lamp-1 could be observed. After 30 min of incubation, the cell surface bound antibody was hardly detected. However, the colocalization of the Ab into lysosome increased. After 1 h of incubation, the intracellular Ab staining decreased as well as the number of colocalization with lamp-1. This kinetic of cell surface bound antibody and its intracellular accumulation correlated with the kinetic of antibody surface decay measure by FACS. In addition, as already described with FACS studies, the degradation of murine Abs started after 1 h of incubation by confocal microscopy.

The internalization of all other hIGF-1R murine antibodies and their colocalization with Lamp-1 was also assessed (FIG. 12B). After 30 min of incubation at 37° C., intracellular antibody was detected and colocalization with lamp-1 could be observed indicating that all selected anti-IGF-1R antibodies were effectively internalized into lysosomes.

Example 9: Inhibition of Abs Degradation Using Lysosome Inhibitor, Bafilomycin A1

In order to confirm that antibodies reached the lysosome were they are degraded, cells were treated or not with bafilomycine A1, a potent inhibitor of lysosome functions. Cells were then incubated with 10 µg/ml of Ab to be tested at 4° C., washed and incubated for 2 h at 37° C. The internalized Ab was detected after cell permeabilisation using a secondary anti-mouse IgG-ALEXA FLUOR® 488 Ab. Addition of bafilomycine A1 prevented the degradation of intracellular Ab (FIG. 13) indicating that Abs were effectively internalized and degraded into lysosomes.

Example 10: Effect of pH on Antibody-IGF-1R Binding

As antibodies were selected on the bases of their internalizing potential and shown above to co-localize with early endosomes before entering into the lysosomal compartment, an interesting approach consisted in selecting antibodies for which the stability of the Ab/hIGF-1R binding was modulated regarding to pH environment and preferentially antibodies that dissociated preferentially from IGF-1R when the pH environment became acid. Indeed, the primary difference between early endosomes and lysosomes is their luminal pH: in the endosome compartment the pH is approximately 6 while in the lysosomal compartment the pH is about 4.5.

It is well known that once internalized after ligand binding (IGF1), hIGF-1R returns back to the cell surface through a recycling pathway.

Without being link by a theory, an hypothesis herein described is that antibodies more prone to be released from their target early at acidic pH will probably favour target recycling to the membrane and consequently could be considered as better candidates for ADC approaches. In order to investigate whether some of our antibodies display such a property and to correlate this property to cytotoxic activity, the binding of the murine anti-hIGF-1R Mabs on MCF-7 cell line was done in buffers at different pH. Increasing concentrations of murine mAbs were incubated on MCF-7 cell line for 20 min at 4° C. in different pH ranging from 5 to 8. Cells were then washed 3 times and incubated with the appropriate secondary antibody coupled with ALEXA FLUOR® 488 in FACS buffer. Cells were incubated for 20 additional minutes at 4° C. in the dark and then washed 3 times in FACS buffer. The binding of anti-hIGF-1R antibodies was immediately performed on viable cells which were identified using propidium iodide that stained dead cells. The binding $EC_{50}$ expressed in molarity (M) was calculated using a nonlinear regression analysis (GraphPad PRISM® 4.0). All murine anti-IGF-1R antibodies selected showed a lower binding capacity at acidic pH as illustrated in FIG. 14.

Example 11: Evaluation of a Humanized Form of the 208F2 Mab

Figures 15A, 15B, 15C, 15D:
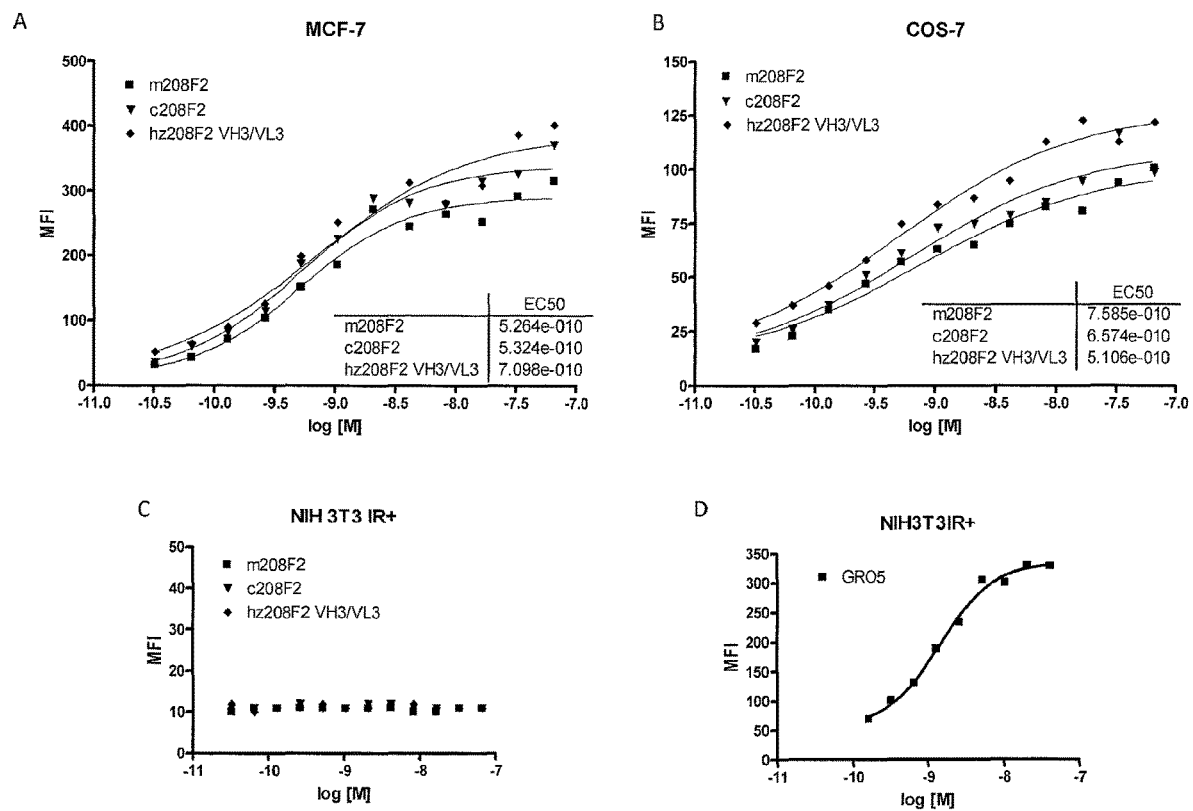

The binding of the first humanized form of the c208F2 mAb was evaluated on MCF-7, COS-7 and NIH 3T3 IR+ cell lines. Increasing concentrations of m208F2, c208F2 or hz208F2 VH3VL3 were added on each cell line for 20 min. at 4° C. Cells were then washed and the binding of the tested mAb was revealed using the corresponding secondary antibody. In order to validate the expression of the human IR on the transfected cell line, the commercial anti-hIR antibody clone GRO5 was used and its recognition profile exemplified on (FIG. 15D).

Comparison of the humanized form with either murine or chimeric ones on MCF-7 (FIG. 15A) or monkey COS-7 (FIG. 15B) cells showed close profiles for the 3 tested forms. The humanisation process did not modify the specificity of recognition of the antibody that is perfectly comparable to the murine and chimeric forms regarding to the absence of cross reactivity on the human insulin receptor (FIG. 15C).

The calculated $EC_{50}$, of the first humanized form of 208F2 on the human cell line MCF-7 and the monkey cell line COS-7 were similar to the one determined with either the murine or the chimeric form of the mAb 208F2.

The capacity of the mAb hz208F2 VH3/VL3 to be internalized was assessed by flow cytometry. MCF-7 cells were incubated with 10 μg/ml of antibodies at 4° C. for 20 min. Then, cells were washed and incubated at 4° C. or 37° C. for 4 h. The quantity of cell-surface bound antibody was determined using a secondary antibody. The ΔMFI defined as the difference between MFI measured at 4° C. and MFI measured at 37° C. after a 4 hour incubation time corresponded to the quantity of internalized Ab. The ΔMFI was presented in FIG. 16 and Table 13. The percentage of internalization at 10 μg/ml of Ab were calculated as followed 100*(MFI at 4° C.–MFI at 37° C.)/MFI at 4° C. and presented in Table 15. Therefore, the humanized hz208F2 VH3/VL3 had similar binding and internalization properties as the one measured with the corresponding murine and chimeric 208F2 antibodies.

TABLE 15

|  | ΔMFI | % internalization |
| --- | --- | --- |
| m208F2 | 294 | 88 |
| c208F2 | 278 | 82 |
| Hz208F2 VH3/VL3 | 344 | 87 |

Example 12: Definition of the Dissociation Constant (K) of the Binding of Five Chimeric Anti-IGF1R Antibodies (c208F2, c213B10, c212A11, c214F8 and c219D6) and a Humanized Version (VH3/VL3) of the 208F2 Antibody on a Soluble Recombinant Human IGF1R The dissociation constants ($K_D$) of the binding of the antibodies on a recombinant soluble human-IGF1R were defined by the ratio between the dissociation rate ($k_{off}$) and the association rate ($k_{on}$). The kinetic experiments were run on a BIACORE® X100 device using a CM5 sensor chip activated by a mouse anti-Tag His monoclobnal antibody. Around 12000 RU of antibodies are chemically grafted on the carboxymethyldextan matrix using the amine kit chemistry.

The experiments were carried out at 25° C. with a flow rate of 30 μl/min using the HBS-EP+ buffer (GE Healthcare) as the running and sample dilution buffer.

The single cycle kinetic scheme was used to define the kinetic parameters of the binding of the anti-IGF1R antibodies on a soluble recombinant human IGF1R captured by its two C-terminal 10 Histidine-tag (SEQ ID NO: 107).

1—A solution of a soluble recombinant version of the human IGF1R hetero-tetramere: 2α chains and the extracellular domains of 2β chains expressed with an additional C-terminal 10-His tag (SEQ ID NO: 107) (R&D SYSTEMS® catalogue number 305-GR-50) was injected during one minute on the second flowcell at a concentration of 10 μg/ml. A mean of 587 RU (with a standard deviation 24 RU) of the soluble receptor were captured at each of the 24 cycles realised for this study.

2—After the capture phase, either the running buffer was injected 5 times (90 s each injection) or a growing range of 5 concentrations of one of the six antibodies was injected (90s each injection) on both flowcells. At the end of the fifth injection the running buffer was passed during 5 minutes in order to define the dissociation rate.

3—The surface was then generated with an injection of a 10 mM Glycine, HCl pH 1.5 buffer during 45 s.

The computed signal corresponds to the difference between the response of the flowcell 2 (with captured IGF1R) and the response of the flowcell 1 (without any IGF1R molecules).

For each IGF1R the signal due to the injections the growing range of concentrations of one antibody was corrected by subtraction of the signal obtained with the 5 injections of the buffer (double reference) see FIG. 17.

The resulting sensorgrams were analysed by the Biaevaluation software with a 1:1 model.

Four experiences were run for each antibody using two different ranges of concentrations: 40, 20, 10, 5 and 2.5 nM for the two first experiments and: 24, 12, 6, 3 and 1.5 nM for the two last experiments run for each antibody.

For the 6 antibodies tested in this experiment the experimental data fitted well with an 1:1 model with significant $k_{off}$ values when the higher concentration was defined as a constant and the other four concentrations are calculated (see FIG. 18).

The dissociation constants ($K_D$) calculated as the ratio: $k_{off}/k_{on}$ and the half-live of the complexes calculated as the ratio: $Ln(2)/k_{off}$ are represented in the FIGS. 19 and 20. They correspond to the mean of the four independent experiments run for each antibodies. The error bars correspond to the standard errors (n=4) of the values.

The dissociation constants are in the range of 10 to 100 pM. The c208F2 antibody presents the weaker affinity (higher dissociation constant value) for the h-IGF1R (with a $K_D$ around 75 pM) and its humanized version is at least as good as the chimeric version (with a $K_D$ around 60 pM). The four other anti-IGF1R chimeric antibodies present a quite similar affinity for the hIGF1-R (with a $K_D$ around 30 pM). The difference of the affinities is principally linked to the dissociation rate or the resultant half life of the complexes. With 208F2 the half-life of the complex is between 2 and 3 hour with the chimeric and the humanized (VH3/VL3) versions. For the four other chimeric antibodies the means half lives are between 7.0 and 9.4 h.

These very slow dissociation kinetics are clearly linked to the bivalent structure of the antibodies which are able to bind simultaneously by both of their Fab arms to two adjacent h-IGF1R molecules. In this case the level of captured IGF1R molecules may have an impact on the dissociation rate. The affinities defined in this study correspond to the functional affinities (or avidities) of the antibodies for a level of captured h-IGF1R around 600 RU. The 3 fold difference of $K_D$ observed between data shown above (table 10) and values presented in example 13 is linked to a change of the level of capture of hIGF-1R (600RU versus 160 RU in example 4).

Example 13: Generation of 1613F12

To generate murine monoclonal antibodies (Mabs) against human extracellular domain (ECD) of the Axl receptor, 5 BALB/c mice were immunized 5-times s.c. with 15-20.10$^6$ CHO-Axl cells and twice with 20 µg of the rh Axl ECD. The first immunization was performed in presence of Complete Freund Adjuvant (SIGMA®, St Louis, Md., USA). Incomplete Freund adjuvant (SIGMA®) was added for following immunizations.

Three days prior to the fusion, immunized mice were boosted with both 20.10$^6$ CHO-Axl cells and 20 µg of the rhAxl ECD with IFA.

To generate hybridomas, splenocytes and lymphocytes were prepared by perfusion of the spleen and by mincing of the proximal lymph nodes, respectively, harvested from 1 out of the 5 immunized mice (selected after sera titration) and fused to SP2/0-Ag14 myeloma cells (ATCC®, Rockville, Md., USA). The fusion protocol is described by Kohler and Milstein (Nature, 256:495-497, 1975). Fused cells are then subjected to HAT selection. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988).

Approximately 10 days after the fusion, colonies of hybrid cells were screened. For the primary screen, supernatants of hybridomas were evaluated for the secretion of Mabs raised against the Axl ECD protein using an ELISA. In parallel, a FACS analysis was performed to select Mabs able to bind to the cellular form of Axl present on the cell surface using both wt CHO and Axl expressing CHO cells.

As soon as possible, selected hybridomas were cloned by limit dilution and subsequently screened for their reactivity against the Axl ECD protein. Cloned Mabs were then isotyped using an Isotyping kit (cat #5300.05, Southern Biotech, Birmingham, Ala., USA). One clone obtained from each hybridoma was selected and expanded.

ELISA assays are performed as followed either using pure hybridoma supernatant or, when IgG content in supernatants was determined, titration was realized starting at 5 µg/ml. Then a ½ serial dilution was performed in the following 11 rows. Briefly, 96-well ELISA plates (COSTAR® 3690, CORNING®, NY, USA) were coated 50 µl/well of the rh Axl-Fc protein (R&D SYSTEMS®, cat No. 154-AL) or rhAxl ECD at 2 µg/ml in PBS overnight at 4° C. The plates were then blocked with PBS containing 0.5% gelatin (#22151, Serva Electrophoresis GmbH, Heidelberg, Germany) for 2 h at 37° C. Once the saturation buffer discarded by flicking plates, 50 µl of pure hybridoma cell supernatants or 50 µl of a 5 µg/ml solution were added to the ELISA plates and incubated for 1 h at 37° C. After three washes, 50 µl horseradish peroxidase-conjugated polyclonal goat anti-mouse IgG (#115-035-164, Jackson Immuno-Research Laboratories, Inc., West Grove, Pa., USA) was added at a 1/5000 dilution in PBS containing 0.1% gelatin and 0.05% TWEEN 20® (Polyethylene glycol sorbitan monolaurate) (w:w) for 1 h at 37° C. Then, ELISA plates were washed 3-times and the TMB (# UP664782, Uptima, Interchim, France) substrate was added. After a 10 min incubation time at room temperature, the reaction was stopped using 1 M sulfuric acid and the optical density at 450 nm was measured.

For the selection by flow cytometry, 10$^5$ cells (CHO wt or CHO-Axl) were plated in each well of a 96 well-plate in PBS containing 1% BSA and 0.01% sodium azide (FACS buffer) at 4° C. After a 2 min centrifugation at 2000 rpm, the buffer was removed and hybridoma supernatants or purified Mabs (1 µg/ml) to be tested were added. After 20 min of incubation at 4° C., cells were washed twice and an ALEXA FLUOR® 488-conjugated goat anti-mouse antibody 1/500° diluted in FACS buffer (# A11017, Molecular Probes Inc., Eugene, USA) was added and incubated for 20 min at 4° C. After a final wash with FACS buffer, cells were analyzed by FACS (FACSCALIBUR™, Becton-Dickinson) after addition of propidium iodide to each tube at a final concentration of 40 µg/ml. Wells containing cells alone and cells incubated with the secondary ALEXA FLUOR® 488-conjugated antibody were included as negative controls. Isotype controls were used in each experiment (SIGMA®, ref M90351MG). At least 5000 cells were assessed to calculate the mean value of fluorescence intensity (MFI).

The hybridoma producing the 1613F12 was selected as a candidate.

Example 14: Humanization of 1613F12

The use of mouse antibodies (Mabs) for therapeutic applications in humans generally results in a major adverse effect, patients raise a human anti-mouse antibody (HAMA) response, thereby reducing the efficacy of the treatment and preventing continued administration. One approach to overcome this problem is to humanize mouse Mabs by replacing mouse sequences by their human counterpart but without modifying the antigen binding activity. This can be achieved in two major ways: (i) by construction of mouse/human chimeric antibodies where the mouse variable regions are joined to human constant regions (Boulianne et al., 1984) and (ii) by grafting the complementarity determining regions (CDRs) from the mouse variable regions into carefully selected human variable regions and then joining these "re-shaped human" variable regions to human constant regions (Riechmann et al., 1988).

14.1 Humanization of the Light Chain Variable Domain VL

As a preliminary step, the nucleotide sequence of 1613F12 VL was compared to the murine germline gene sequences part of the IMGT® database (<http://www.IMGT.org>). Murine IGKV16-104*01 and IGKJ5*01 germline genes were identified. In order to identify the best human candidate for the CDR grafting, the human germline gene displaying the best identity with 1613F12 VL murine sequence has been searched. With the help of the IMGT® database analyses tools, a possible acceptor human V regions for the murine 1613F12 VL CDRs was identified: IGKV1-27*01 and IGKJ4*02. In order to perform the humanization to the light chain variable domain each residue which is different between the human and mouse sequences was given a priority rank order. These priorities (1-4) were used to create 11 different humanized variants of the light chain variable region with up to 14 backmutations.

|  | FR1-IMGT® | CDR1-IMGT® | FR2-IMGT® | CD |
|---|---|---|---|---|
| 1613F12VL | DVQITQSPSYLATSPGETITINCRAS | KSI......SKY | LAWYQEKPGKTNKLLIY | SG |
| Homsap IGKV1-27*01 | DIQMTQSPSSLSASVGDRVTITCRAS | PSI......SNY | LAWYQQKPGKVPKLLIY | AA |
|  | V I      Y AT P ETI   N |  | E     TN |  |
| Priority | 1 1      3 34 4 433  2 |  | 3    33 |  |
|  |  |  |  |  |
| hz1613F12 (VL1) | DIQMTQSPSSLSASVGDRVTITCRAS | KSI......SKY | LAWYQQKPGKVPKLLIY | SG |
| hz1613F12 (VL1I2V) | DVQMTQSPSSLSASVGDRVTITCRAS | KSI......SKY | LAWYQQKPGKVPKLLIY | SG |
| hz1613F12 (VL1M4I) | DIQITQSPSSLSASVGDRVTITCRAS | KSI......SKY | LAWYQQKPGKVPKLLIY | SG |
| hz1613F12 (VL2.1) | DVQITUDSSLSASVGDRVTITCRAS | KSI......SKY | LAWYQQKDGKVDKLLIY | SG |
| hz1613F12 (VL2.1V49T) | DVQITQSPSSLSASVCDRVTITCRAS | KSI......SKY | LAWYQQKPCKTPKLLIY | SC |
| hz1613F12 (VL2.1P50N) | DVQITQSPSSLSASVCDRVTITCRAS | KSI......SKY | LAWYQQKPCKVNKLLIY | SC |
| hz1613F12 (VL2.2) | DVQITQSPSSLSASVCDRVTINCRAS | KSI......SKY | LAWYQQKPCKVPKLLIY | SC |
| hz1613F12 (VL2.2V49T) | DVQITQSPSSLSASVCDRVTINCRAS | KSI......SKY | LAWYQQKPCKTPKLLIY | SC |
| hz1613F12 (VL2.2P50S) | DVQITQSPSSLSASVCDRVTINCRAS | KSI......SKY | LAWYQQKPCKVNKLLIY | SC |
| hz1613F12 (VL2.3) | DVQITQSPSSLSASVCDRVTINCRAS | KSI......SKY | LAWYQEKPCKTNKLLIY | SC |
| hz1613F12 (VL3) | DVQITQSPSYLAASVCDTITINCRAS | KSI......SKY | LAWYQEKPCKTNKLLIY | SC |

|  | R2-IMGT® | FR3-IMGT® |
|---|---|---|
| 1613E12VL | .......S | TLQSGVP.SRFDGSG..SGTDFTLTISSLEPEDFAMYFC |
| Homsap IGKV1-27*01 | .......S | TLQSGVP.SRFSGSG..SGTDFTLTISSLQPEDVATYYC |
|  |  | E     F M F |
| Priority |  | 4     4 4 2 |
|  |  |  |
| hz1613F12 (VL1) | .......S | TLQSGVP.SRFSGSG..SGTDFTLTISSLQPEDVATYYC |
| hz1613F12 (VL1I2V) | .......S | TLQSGVP.SRFSGSG..SGTDFTLTISSLQPEDVATYYC |
| hz1613F12 (VL1M4I) | .......S | TLQSGVP.SRFSGSG..SGTDFTLTISSLQPEDVATYYC |
| hz1613F12 (VL2.1) | .......S | TLQSGVP.SRFSGSG..SGTDFTLTISSLQPEDVATYYC |
| hz1613F12 (VL2.1V49T) | .......S | TLQSGVP.SRFSGSG..SGTDFTLTISSLQPEDVATYYC |
| hz1613F12 (VL2.1D50S) | .......S | TLQSGVD.SRFSGSG..SGTDFTLTISSLQPEDVATYYC |
| hz1613F12 (VL2.2) | .......S | TLQSCVP.SRFSCSC..SCTDFTLTISSLQPEDVATYFC |
| hz1613F12 (VL2.2V49T) | .......S | TLQSCVP.SRFSCSC..SCTDFTLTISSLQPEDVATYFC |
| hz1613F12 (VL2.2P50S) | .......S | TLQSCVP.SRFSCSC..SCTDFTLTISSLQPEDVATYFC |
| hz1613F12 (VL2.3) | .......S | TLQSCVP.SRFSCSC..SCTDFTLTISSLQPEDVATYFC |
| hz1613F12 (VL3) | .......S | TLQSCVP.SRFSCSC..SCTDFTLTISSLQPEDVATYFC |

|  | CDR3-IMGT® | FP4-IMGT® |
|---|---|---|
| 1613F12VL | QQHHEYPLT | FGAGTELELK (SEQ ID NO: 62) |
| Homsap IGKJ4*02 | LT | FGGGTKVEIK (SEQ ID NO: 108) |
|  |  | A   EL L |
| Priority |  | 3   33 4 |
|  |  |  |
| hz1613F12 (VL1) | QQHHEYPLT | FGGGTKVEIK (SEQ ID NO: 70) |
| hz1613F12 (VL1I2V) | QQHHEYPLT | FGGGTKVEIK (SEQ ID NO: 72) |
| hz1613F12 (VL1M4I) | QQHHEYPLT | FGGGTKVEIK (SEQ ID NO: 73) |
| hz1613F12 (VL2.1) | QQHHEYPLT | FGGGTKVEIK (SEQ ID NO: 74) |
| hz1613F12 (VL2.1V49I) | QQHHEYPLT | FGGGTKVEIK (SEQ ID NO: 75) |
| hz1613F12 (VL2.1D50N) | QQHHEYPLT | FGGGTKVEIK (SEQ ID NO: 76) |
| hz1613F12 (VL2.2) | QQHHEYPLT | FCCCTKVEIK (SEQ ID NO: 77) |
| hz1613F12 (VL2.2V49I) | QQHHEYPLT | FGGGTKVEIK (SEQ ID NO: 78) |
| hz1613F12 (VL2.2P50S) | QQHHEYPLT | FGGGTKVEIK (SEQ ID NO: 79) |
| hz1613F12 (VL2.3) | QQHHEYPLT | FGGGTKVEIK (SEQ ID NO: 80) |
| hz1613F12 (VL3) | QQHHEYPLT | FGAGTELEIK (SEQ ID NO: 81) |

14.2 Humanization of the Heavy Chain Variable Domain VII

In order to identify the best human candidate for the CDR grafting, the mouse and human germline genes displaying the best identity with 1613F12 VH were searched. The nucleotide sequence of 1613F12 VH was aligned with both mouse and human germline gene sequences by using the sequence alignment software "IMGT®/V-QUEST" which is part of the IMGT® database. Alignments of amino acid sequences were also performed to verify the results of the nucleotide sequence alignment using the "ALIGNX®" software of the VECTORNTI® package. The alignment with mouse germline genes showed that the mouse germline V-gene IGHV14-3*02 and J-gene IGHJ2*01 are the most homologue mouse germline genes. Using the IMGT® database the mouse D-gene germline IGHD1-1*01 was identified as homologous sequence. In order to select an appropriate human germline for the CDR grafting, the human germline gene with the highest homology to 1613F12 VH murine sequence was identified. With the help of IMGT® databases and tools, the human IGHV1-2*02 germline gene and human IGHJ5*01 J germline gene were selected as human acceptor sequences for the murine 1613F12 VH CDRs. In order to perform the humanization to the heavy chain variable domain each residue which is different between the human and mouse sequences was given a priority rank order (1-4). These priorities were used to create 20 different humanized variants of the heavy chain variable region with up to 18 backmutations,

|  | FR1-IMGT® (1-26) | CDR1-IMGT® (27-38) | FR2-IMGT® (39-55) |
|---|---|---|---|
| 1613F12 | EVHLQQSGA.ELVEIPGASVKLSCIAS | GFNI....RDTY | IHWVKQRPEQGLEWIGR |
| Homsap IGHV1-2*02 | QVQLVQSGA.EVEIKPGASVKVSCKAS | GYTF....TGYY | MHWVRQAPGQGLEWMGW |
|  |   E H Q      LV      L    T |    I |  I   KRE     IR |
| Priority |   3 2 3      33      3    3 |    3 |  1   344     3 2 |
| hz1613F12 (VH1) | QVQLVQSGA.EVKKPGASVKVSCKAS | GFNI....RDTY | MHWVRQAPGQGLEWMGW |
| hz1613F12 (VH1M39I) | QVQLVQSGA.EVKKPGASVKVSCKAS | GFNI....RDTY | IHWVRQAPGQGLEWMGW |
| hz1613F12 (VH1W55RN66K) | QVQLVQSGA.EVKKPGASVKVSCKAS | GFNI....RDTY | MHWVRQADGQGLEWMGR |
| hz1613F12 (VH1I84S) | QVQLVQSGA.EVKKPGASVKVSCKAS | GFNI....RDTY | MHWVRQADGQGLEWMGW |
| hz1613F12 (VH1S85N) | QVQLVQSCA.EVKKPCASVKVSCKAS | CFNI....RDTY | MHWVRQAPCQCLEWMCW |
| hz1613F12 (VH1I84NS85N) | QVQLVQSCA.EVKKPCASVKVSCKAS | CFNI....RDTY | MHWVRQAPCQGLEWMCW |
| hz1613F12 (VH2.1) | QVQLVQSCA.EVKKPCASVKVSCKAS | CFNI....RDTY | IHWVRQAPCQGLEWMCW |
| hz1613F12 (VH2.1Q3H) | QVHLVQSCA.EVKKPCASVKVSCKAS | CFNI....RDTY | IHWVRQAPCQGLEWMCW |
| hz1613F12 (VH2.1W55R) | QVQLVQSCA.EVKKPCASVKVSCKAS | CFNI....RDTY | IHWVRQAPCQGLEWMCR |
| hz1613F12 (VH2.1N66K) | QVQLVQSCA.EVKKPCASVKVSCKAS | CFNI....RDTY | IHWVRQAPCQGLEWMCW |
| hz1613F12 (Vh2.1W55RN66K) | QVQLVQC4A.EVKKPCASVKVSCKAS | CFNI....RDTY | IHWVRQAPCQGLEWMCR |
| hz1613F12 (VH2.1R80S) | QVQLVQSGA.EVKKPGASVKVSCKAS | GFNI....RDWY | IHWVRQAPGQGLEWMGW |
| hz1613F12 (VH2.1N66KR80S) | QVQLVQSGA.EVKKPGASVKVSCKAS | GFNI....RDTY | IHWVRQAPGQGLEWMGW |
| hz1613F12 (VH2.2) | QVHLVQSGA.EVKKPGASVKVSCKAS | GFNI....RDTY | IHWVRQAPGQGLEWMGW |
| hz1613F12 (VH2.2M89L) | QVHLVQSGA.EVKKPGASVKVSCKAS | GFNI....RDTY | IHWVRQAPGQGLEWMGW |
| hz1613F12 (VH2.3) | QVQLQQSGA.EVKKPGASVKLSCTAS | GFNI....RDTY | IHWVRQAPGQGLEWMGW |
| hz1613F12 (VH2.3W55R) | QVQLQQSGA.EVKKPGASVKLSCTAS | GFNI....RDTY | IHWVRQAPGQGLEWMGR |
| hz1613F12 (VH2.3Q3HW55R) | QVHLQQSGA.EVKKPGASVKLSCTAS | GFNI....RDTY | IHWVRQAPGQGLEWMGR |
| hz1613F12 (VH2.4) | QVQLQQSGA.EVKKPGASVKLSCTAS | GFNI....RDTY | IHWVRQAPGQGLEWIGR |
| hz1613F12 (VH3) | EVHLQQSGA.ELVKPGASVKLSCTAS | GFNI....RDTY | IHWVKQAPGQGLEWIGR |

|  | R2-IMGT® 56-65) | FR3-IMGT® (66-104) |
|---|---|---|
| 1613F12 | LDPA..NCHT | KYCPNFQ.CRATMTSDTSSNTAYLQLSSLTSEDTAVYYC |
| Homsap ICHV1-2*02 | LDPN..SGGT | NYAQKFQ.CRVTMTRDTSISTAYMELSRLRSDDTAVYYC |
|  |  | K GPN    A    S   SN LQ    STE |
| Prority |  | 2 344    4    2   11 33    444 |
| hz1613F12 (VH1) | LDPA..NGHT | NYAQKFQ.CRVTMTRDTSISTAYMELSRLRSDDTAVYYC |
| hz1613F12 (VH1M39I) | LDPA..NGHT | NYAQKFQ.CRVTMTRDTSISTAYMELSRLRSDDTAVYYC |
| hz1613E12 (VH1W55RN66K) | LDPA..NGHT | KYAQEFQ.GRVTMTRDTSISTAYMELSRLRSDDTAVYYC |
| hz1613F12 (VH1I84S) | LDPA..NGHT | NYAQKFQ.GRVTMTRDTSSSTAYMELSRLRSDDTAVYYC |
| hz1613F12 (VH1S85N) | LDPA..NGHT | NYAQKFQ.GRVTMTRDTSINTAYMELSRLRSDDTAVYYC |
| hz1613F12 (VH1I84NS85N) | LDPA..NGHT | NYADKFQ.GRVTMTRDTSSNTAYMELSRLRSDDTAVYYC |
| hz1613F12 (VH2.1) | LDPA..NGHT | NYAQKFQ.GRVTMTRDTSSNTAYMELSRLRSDDTAVYYC |
| hz1613F12 (VH2.1Q3H) | LDPA..NGHT | NYAQKFQ.GRVTMTRDTSSNTAYMELSRLRSDDTAVYYC |
| hz1613F12 (VH2.1W55R) | LDPA..NGHT | NYAQKFQ.GRVTMTRDTSSNTAYMELSRLRSDDTAVYYC |
| hz1613F12 (VH2.1N66K) | LDPA..NGHT | KYAQKFQ.GRVTMTRDTSSNTAYMELSRLRSDDTAVYYC |
| hz1613F12 (VH2.1W55RN66K) | LDPA..NGHT | KYAQKFQ.GRVTMTRDTSSNTAYMELSRLRSDDTAVYYC |
| hz1613F12 (VH2.1R80.2) | LDPA..NGHT | NYAQKEQ.GRVTMTSDTSSNTAYMELSRLRSDDTAVYYC |
| hz1613F12 (VH2.1N66KR80S) | LDPA..NGHT | KYAQKFQ.GRVTMTSDTSSNTAYMELSRLREDDTAVYYC |
| hz1613F12 (VH2.2) | LDPA..NCHT | KYAQKFQ.CRVTMTSDTSSNTAYMELSRLREDDTAVYYC |
| hz1613F12 (VH2.2M89L) | LDPA..NCHT | KYAQKFQ.CRVTMTSDTSSNTAYLELSRLREDDTAVYYC |
| hz1613F12 (VH2.3) | LDPA..NCHT | KYAQKFQ.CRVTMTSDTSSNTAYMELSRLRSDDTAVYYC |
| hz1613F12 (VH2.3W55R) | LDPA..NGHT | KYAQKFQ.CRVTMTSDTSSNTAYMELSRLREDDTAVYYC |
| hz1613F12 (VH2.3Q3HW55R) | LDPA..NGHT | KYAQKFQ.CRVTMTSDTSSNTAYMELSRLREDDTAVYYC |
| hz1613F12 (VH2.4) | LDPA..NGHT | KYAQKFQ.CRVTMTSDTSSNTAYLELSRLREDDTAVYYC |
| hz1613F12 (VH3) | LDPA..NGHT | KYGQKFQ.CRVTMTSDTSSNTAYLQLSRLRSDDTAVYYC |

|  | CDR3-IMGT® | FR4-IMGT® |
|---|---|---|
| 1613F12VH | ARGAYYYGSSGLFYFDY | WGQGTTLSVSS (SEQ ID NO: 63) |
| Homsap IGHJ5*01 |  | WGQGTLVTVSS (SEQ ID NO: 109) |
|  |  | TLS |
| Prority |  | 444 |
| hz1613F12 (VH1) | ARGAYYYGSSGLFYFDY | WGQGTLVIVSS (SEQ ID NO: 82) |
| hz1613F12 (VH1M39I) | ARGAYYYGSSGLFYFDY | WGQGTLVTVSS (SEQ ID NO: 84) |

| | | |
|---|---|---|
| hz1613F12 (VH1W55RN66K) | ARGAYYYGSSGLFYFDY | WGQGTLVTVSS (SEQ ID NO: 85) |
| hz1613F12 (VH1I84S) | ARGAYYYGSSGLFYFDY | WGQGTLVTVSS (SEQ ID NO: 86) |
| hz1613F12 (VH1.285N) | ARGAYYYGSSGLFYFDY | WGQGTLVTVSS (SEQ ID NO: 87) |
| hz1613F12 (VH1I84NS85N) | ARGAYYYGSSGLFYFDY | WGQGTLVTVSS (SEQ ID NO: 88) |
| hz1613F12 (VH2.1) | ARGAYYYGSSGLFYFDY | WGQGTLVTVSS (SEQ ID NO: 89) |
| hz1613F12 (VH2.1Q3H) | ARCAYYYCSSGLFYFDY | WGQGTLVTVSS (SEQ ID NO: 90) |
| hz1613F12 (VH2.1W55R) | ARGAYYYGSSGLFYFDY | WGQGTLVTVSS (SEQ ID NO: 91) |
| hz1613F12 (VH2.1N66K) | ARGAYYYGSSGLFYFDY | WGQGTLVTVSS (SEQ ID NO: 92) |
| hz1613F12 (VH2.1W55RN66K) | ARGAYYYGSSGLFYFDY | WGQGTLVTVSS (SEQ ID NO: 93) |
| hz1613F12 (VH2.1R80S) | ARGAYYYGSSGLFYFDY | WGQGTLVTVSS (SEQ ID NO: 94) |
| hz1613F12 (VH2.1N66KR80S) | ARGAYYYGSSGLFYFDY | WGQGTLVTVSS (SEQ ID NO: 95) |
| hz1613F12 (VH2.2) | ARGAYYYGSSGLFYFDY | WGQGTLVTVSS (SEQ ID NO: 96) |
| hz1613F12 (VH2.2M89L) | ARGAYYYGSSGLFYFDY | WGQGTLVTVSS (SEQ ID NO: 97) |
| hz1613F12 (VH2.3) | ARGAYYYGSSGLFYFDY | WGQGTLVTVSS (SEQ ID NO: 98) |
| hz1613F12 (VH2.3W55R) | ARGAYYYGSSGLFYFDY | WGQGTLVTVSS (SEQ ID NO: 99) |
| hz1613F12 (VH2.3Q3HW55R) | ARGAYYYGSSGLFYFDY | WGQGTLVTVSS (SEQ ID NO: 101) |
| hz1613F12 (VH2.4) | ARGAYYYGSSGLFYFDY | WGQGTLVTVSS (SEQ ID NO: 101) |
| hz1613F12 (VH3) | ARGAYYYGSSGLFYFDY | WGQGTLVTVSS (SEQ ID NO: 102) |

Example 15: Axl Binding Specificity

In this example, the binding of 1613F12 was first studied on the rhAxl-Fc protein. Then, its binding on the two other members of the TAM family, rhDtk-Fc and rhMer-Fc, was studied.

Briefly, the recombinant human Axl-Fc (R&D SYSTEMS®, cat No. 154AL/CF), rhDtk (R&D SYSTEMS °, cat No. 859-DK) or rhMer-Fc (R&D SYSTEMS®, cat No. 891-MR) proteins were coated overnight at 4° C. to Immulon II 96-well plates and, after a 1 h blocking step with a 0.5% gelatine solution, 1613F12 was added for an additional 1 h at 37° C. at starting concentration of 5 µg/ml ($3.33 \cdot 10^{-8}$M). Then ½ serial dilutions were done over 12 columns. Plates were washed and a goat anti-mouse (Jackson) specific IgG-HRP was added for 1 h at 37° C. Reaction development was performed using the TMB substrate solution. The isotype control antibody mIgG1 and the commercial anti-Axl Mab 154 antibody were also used in parallel. Coating controls were performed in presence of a goat anti-human IgG Fc polyclonal serum labelled with HRP (Jackson, ref 109-035-098) and/or in presence of a HRP-coupled anti-Histidine antibody (R&D SYSTEMS®, ref: MAB050H).

Results are represented in FIGS. 24A, 24B and 24C, respectively.

This example shows that 1613F12 only binds to the rhAxl-Fc protein and does not bind on the two other members of the TAM family, rhDtk or rhMer. No cross-specificity of binding of 1613F12 is observed between TAM members. No non specific binding was observed in absence of primary antibody (diluant). No binding was observed in presence of the isotype control antibody.

Example 16: 1613F12 Recognized the Cellular Form of Axl Expressed on Human Tumor Cells Cell surface Axl expression level on human tumor cells was first established using a commercial Axl antibody (R&D SYSTEMS®, ref: MAB154) in parallel of calibration beads to allow the quantification of Axl expression level. Secondly, binding of the cell-surface Axl was studied using 1613F12.

For cell surface binding studies, two fold serial dilutions of a 10 µg/ml ($6.66 \cdot 10^{-8}$ M) primary antibody solution (1613F12, MAB154 or mIgG1 isotype control 9G4 Mab) are prepared and are applied on $2 \cdot 10^5$ cells for 20 min at 4° C. After 3 washes in phosphate-buffered saline (PBS) supplemented with 1% BSA and 0.01% NaN$_3$, cells were incubated with secondary antibody Goat anti-mouse ALEXA FLUOR® 488 (1/500° dilution) for 20 minutes at 4° C. After 3 additional washes in PBS supplemented with 1% BSA and 0.1% NaN$_3$, cells were analyzed by FACS (FACSCALIBUR™, Becton-Dickinson). At least 5000 cells were assessed to calculate the mean value of fluorescence intensity.

For quantitative ABC determination using MAB154, QIFIKIT® calibration beads are used. Then, the cells are incubated, in parallel with the QIFIKIT® beads, with Polyclonal Goat Anti-Mouse Immunoglobulins/FITC, Goat F(ab')$_2$, at saturating concentration. The number of antigenic sites on the specimen cells is then determined by interpolation of the calibration curve (the fluorescence intensity of the individual bead populations against the number of Mab molecules on the beads.

16.1. Quantification of Cell-Surface Axl Expression Level

Axl expression level on the surface of human tumor cells was determined by flow cytometry using indirect immunofluorescence assay (QIFIKIT® method (Dako, Denmark), a quantitative flow cytometry kit for assessing cell surface antigens. A comparison of the mean fluorescence intensity (MFI) of the known antigen levels of the beads via a calibration graph permits determination of the antibody binding capacity (ABC) of the cell lines.

Table 16 presents Axl expression level detected on the surface of various human tumor cell lines (SN12C, Calu-1, MDA-MB435S, MDA-MB231, NCI-H125, MCF7, Panc1) as determined using QIFIKIT® using the MAB154 (R&D) SYSTEMS®. Values are given as Antigen binding complex (ABC).

TABLE 16

| | MCF7 | NCI-H125 | MDA-MB-435S | Panc1 | MDA-MB-231 | Calu-1 | SN12C |
|---|---|---|---|---|---|---|---|
| | | | | Tumor type/organ | | | |
| | Breast | NSCLC | Breast | Pancreas | Breast | Lung | Renal |
| ABC (Qifikit) | 71 | 5 540 | 17 814 | 36 809 | 61 186 | >100 000 | >100 000 |

Results obtained with MAB154 showed that Axl receptor is expressed at various levels depending of the considered human tumor cell.

16.2. Axl Detection by 1613F12 on Human Tumor Cells

More specifically, Axl binding was studied using 1613F12.

1613F12 dose response curves were prepared. MFIs obtained using the various human tumor cells were then analysed with PRISM® software. Data are presented in FIG. 25.

Data indicate that 1613F12 binds specifically to the membrane Axl receptor as attested by the saturation curve profiles. However different intensities of labelling were observed, revealing variable levels of cell-surface Axl receptor on human tumor cells. No binding of Axl receptor was observed using MCF7 human breast tumor cell line.

Example 17: Validation of hz1613F12 vs. m1613F12

In order to establish whether hz1613F12 was comparable to its murine form, binding experiments were performed by ELISA using rhAxl-Fc protein assays.

In this assay, 96 well plates (Immulon II, THERMO FISHER®) were coated with a 5 µg/ml of 1613F12 solution in 1×PBS, overnight at 4° C. After a saturation step, a range of rh Axl-Fc protein (R&D SYSTEMS®, ref: 154-AL) is incubated for 1 hour at 37° C. on the coated plates. For the revelation step, a biotinylated-Axl antibody (in house product) was added at 0.85 µg/ml for 1 hour at 37° C. This Axl antibody belongs to a distinct epitopic group. Then an avidin-horseradish peroxidase solution at 1/2000° in diluent buffer is added to the wells. Then the TMB substrate solution is added for 5 min. After addition of the peroxydase stop solution, the absorbance at 405 nm was measured with a microplate reader.

FIG. 26 shows that both murine and humanized versions of 1613F12 bind similarly the rhAxl-Fc protein.

Example 18: 1613F12 Internalization Study Using Fluorescent Immunocytochemistry Labelling Complementary internalization results are obtained by confocal microscopy using indirect fluorescent labelling method.

Briefly, SN12C tumor cell line was cultured in RMPI1640 with 1% L-glutamine and 10% of FCS for 3 days before experiment. Cells were then detached using trypsin and plated in 6-multiwell plate containing coverslide in RPMI1640 with 1% L-glutamine and 5% FCS. The next day, 1613F12 was added at 10 µg/ml. Cells treated with an irrelevant antibody were also included. The cells were then incubated for 1 h and 2 h at 37° C., 5% $CO_2$. For T 0 h, cells were incubated for 30 minutes at 4° C. to determine antibody binding on cell surface. Cells were washed with PBS and fixed with paraformaldehyde for 15 minutes. Cells were rinsed and incubated with a goat anti-mouse IgG ALEXA FLUOR® 488 antibody for 60 minutes at 4° C. to identify remaining antibody on the cell surface. To follow antibody penetration into the cells, cells were fixed and permeabilized with saponin. A goat anti-mouse IgG ALEXA FLUOR® 488 (INVITROGEN™) was used to stained both the membrane and the intracellular antibody. Early endosomes were identified using a rabbit polyclonal antibody against EEA1 revealed with a goat anti-rabbit IgG-ALEXA FLUOR® 555 antibody (INVITROGEN™). Cells were washed three times and nuclei were stained using DRAQ5™ (Deep Red Anthraquinone 5). After staining, cells were mounted in PROLONG® Gold mounting medium (INVITROGEN™) and analyzed by using a Zeiss LSM 510 confocal microscope.

Photographs are presented in FIGS. 27A, 27B, and 27C.

Images were obtained by confocal microscopy. In presence of the mIgG1 isotype control (9G4), neither membrane staining nor intracellular labelling is observed (FIG. 27A). A progressive loss of the membrane anti-Axl labelling is observed as soon as after 1 h incubation of the SN12C cells with 1613F12 (FIG. 27B). Intracellular accumulation of 1613F12 antibody is clearly observed at 1 h and 2 h (FIG. 27C). Intracellular antibody co-localizes with EEA1, an early endosome marker. These photographs confirm the internalization of 1613F12 into SN12C cells.

Example 19: Synthesis of the Drugs of the Invention

The following abbreviations are used in the following examples:

aq. aqueous ee enantiomeric excess equiv equivalent

ESI Electrospray ionisation

LC/MS Liquid Chromatography coupled with Mass Spectrometry

HPLC High Performance Liquid Chromatography

NMR Nuclear Magnetic Resonance sat. saturated

UV ultraviolet

Compound 1

(S)-2-((S)-2-((3-aminopropyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, bis trifluoroacetic acid

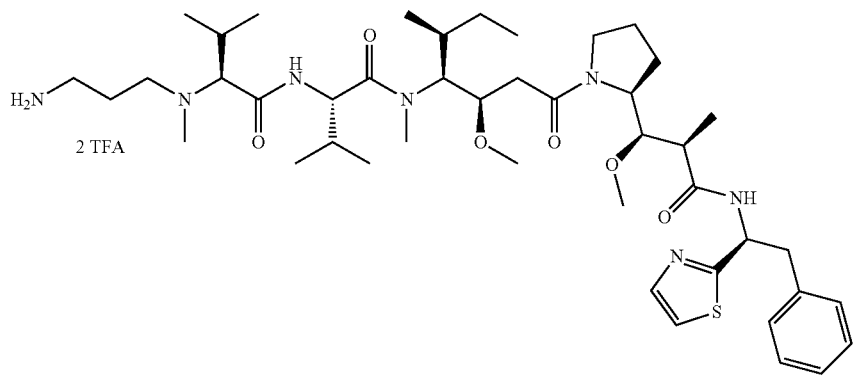 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCCN)C(C)C]

Compound 1A (4R, 5S)-4-methyl-5-phenyl-3-propanoyl-1,3-oxazolidin-2-one

Compound 1B tert-butyl (2S)-2-[(1R,2R)-1-hydroxy-2-methyl-3-[(4R,5S)-4-methyl-2-oxo-5-phenyl-1,3-oxazolidin-3-yl]-3-oxopropyl]pyrrolidine-1-carboxylate

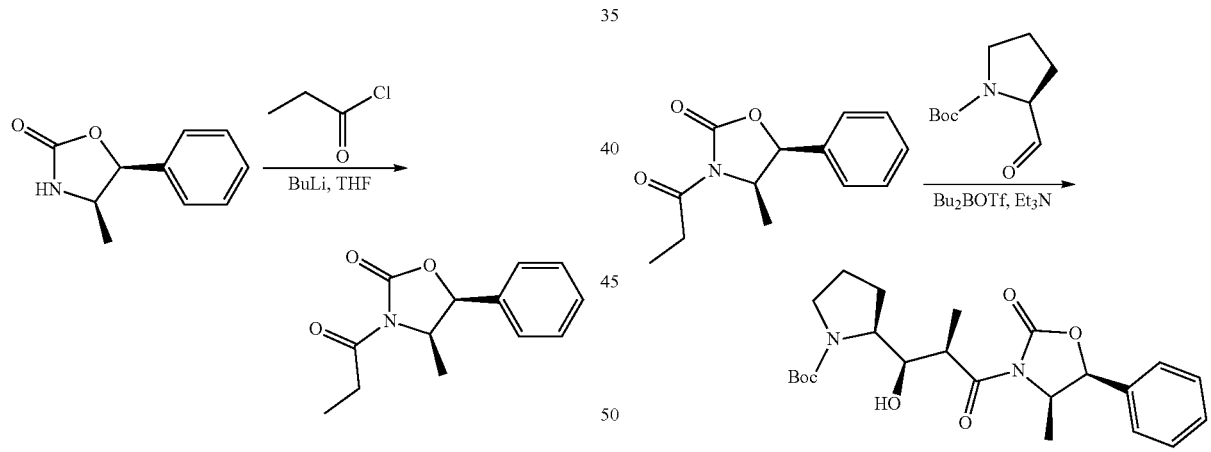

(4R, 5S)-4-methyl-5-phenyl-1,3-oxazolidin-2-one (5.8 g, 32.7 mmol, 1.00 equiv) was dissolved in tetrahydrofuran (THF, 120 mL) in an inert atmosphere. The mixture was cooled to −78° C. and n-butyllithium (14.4 mL) was added drop-wise. After agitation for 30 minutes at −78° C., propanoyl chloride (5.7 mL) was added. Agitation was continued for 30 minutes at −78° C. then overnight at ambient temperature. The reaction mixture was concentrated then re-dissolved in 200 mL of water. The pH of the solution was adjusted to 7 with sodium bicarbonate saturated aqueous solution. This aqueous phase was extracted 3 times with 100 mL of ethyl acetate (EtOAc). The organic phases were combined, dried over sodium sulfate, filtered and concentrated to yield 6.8 g (89%) of compound 1A in the form of a yellow oil.

Compound 1A (17.6 g, 75.45 mmol, 1.00 equiv) was dissolved in dichloromethane (DCM, 286 mL) in an inert atmosphere. This solution was cooled with an ice bath. Triethylamine (TEA, 12.1 mL, 1.15 equiv) and Bu$_2$BOTf (78.3 mL, 1.04 equiv) were added drop-wise whilst holding the temperature of the reaction mixture below 2° C. Agitation was continued at 0° C. for 45 minutes, after which the reaction was cooled to −78° C. A solution of tert-butyl (2S)-2-formylpyrrolidine-1-carboxylate (8.5 g, 42.66 mmol, 0.57 equiv) in DCM (42 mL) was added drop-wise. Agitation was continued for 2 hours at −78° C., then for 1 hour at 0° C. and finally 1 hour at ambient temperature. The reaction was neutralised with 72 mL of phosphate buffer (pH=7.2-7.4) and 214 mL methanol, and cooled to 0° C. A solution of 30% hydrogen peroxide in methanol (257 mL) was added drop-wise whilst maintaining the temperature below 10° C. Agitation was continued for 1 hour at 0° C. The reaction was neutralised with 142 mL of water, then concentrated under reduced pressure. The resulting aqueous solution was extracted 3 times with 200 mL EtOAc. The organic phases were combined, dried over sodium sulfate, filtered and concentrated. The residue was purified on a silica column with a mixture of EtOAc and petroleum ether (EtOAc:PE=1:8) to yield 13.16 g (40%) of compound 1B in the form of a colourless oil.

Compound 1C (2R,3R)-3-[(2S)-1-[(tert-butoxy)carbonyl]pyrrolidin-2-yl]-3-hydroxy-2-methylpropanoic acid

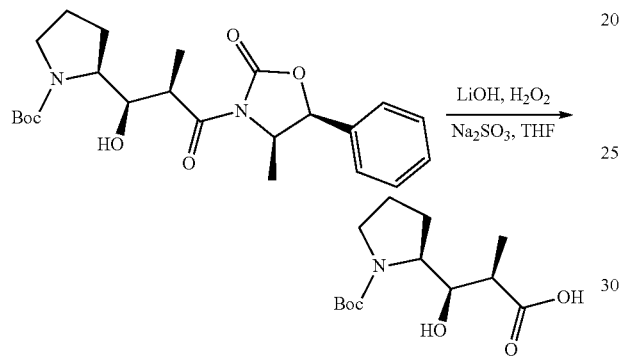

Compound 1B (13.16 g, 30.43 mmol, 1.00 equiv) was dissolved in THE (460 mL) in the presence of hydrogen peroxide (30% in water, 15.7 mL), then cooled with an ice bath. An aqueous solution of lithium hydroxide (0.4 mol/L, 152.1 mL) was added drop-wise whilst holding the reaction temperature below 4° C. The reaction mixture was agitated 2.5 hours at 0° C. An aqueous solution of Na$_2$SO$_3$ (1 mol/L, 167.3 mL) was added drop-wise whist holding the temperature at 0° C. The reaction mixture was agitated 14 hours at ambient temperature, then neutralised with 150 mL of cold sodium bicarbonate saturated solution and washed 3 times with 50 mL of DCM. The pH of the aqueous solution was adjusted to 2-3 with a 1M aqueous solution of KHSO$_4$. This aqueous solution was extracted 3 times with 100 mL of EtOAc. The organic phases were combined, washed once with saturated NaCl solution, dried over sodium sulfate, filtered and concentrated to yield 7.31 g (88%) of compound 1C in the form of a colourless oil.

Compound 1D (2R,3R)-3-[(2S)-1-[(tert-butoxy)carbonyl]pyrrolidin-2-yl]-3-methoxy-2-methylpropanoic acid

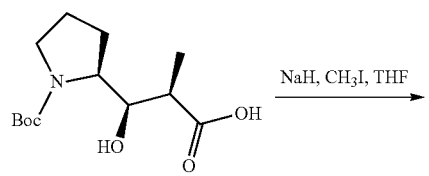

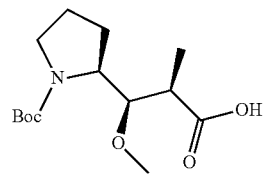

Compound 1C (7.31 g, 26.74 mmol, 1.00 equiv) was dissolved in an inert atmosphere in THE (135 mL) in the presence of iodomethane (25.3 mL). The reaction medium was cooled with an ice bath after which NaH (60% in oil, 4.28 g) was added in portions. The reaction was left under agitation 3 days at 0° C. and then neutralised with 100 mL of sodium bicarbonate saturated aqueous solution and washed 3 times with 50 mL ether. The pH of the aqueous solution was adjusted to 3 with 1M aqueous KHSO$_4$ solution. This aqueous solution was extracted 3 times with 100 mL of EtOAc. The organic phases were combined, washed once with 100 mL of Na$_2$S$_2$O$_3$ (5% in water), once with NaCl-saturated solution, then dried over sodium sulfate, filtered and concentrated to yield 5.5 g (72%) of compound 1D in the form of a colourless oil.

Compound 1E

N-methoxy-N-methyl-2-phenylacetamide

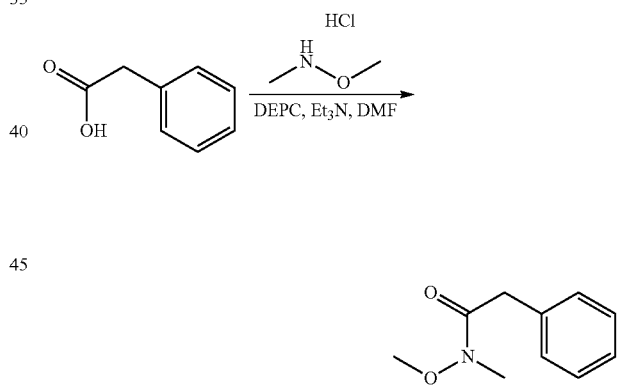

2-phenylacetic acid (16.2 g, 118.99 mmol, 1.00 equiv) was dissolved in dimethylformamide (DMF, 130 mL) then cooled to −10° C. Diethyl phosphorocyanidate (DEPC, 19.2 mL), methoxy(methyl)amine hydrochloride (12.92 g, 133.20 mmol, 1.12 equiv) and triethylamine (33.6 mL) were added. The reaction mixture was agitated 30 minutes at −10° C. then 2.5 hours at ambient temperature. It was then extracted twice with 1 litre of EtOAc. The organic phases were combined, washed twice with 500 mL of NaHCO$_3$ (sat.), once with 400 mL of water, then dried over sodium sulfate, filtered and concentrated. The residue was purified on a silica column with an EtOAc and PE mixture (1:100 to 1:3) to yield 20.2 g (95%) of compound 1E in the form of a yellow oil.

Compound 1F

2-phenyl-1-(1,3-thiazol-2-yl)ethan-1-one

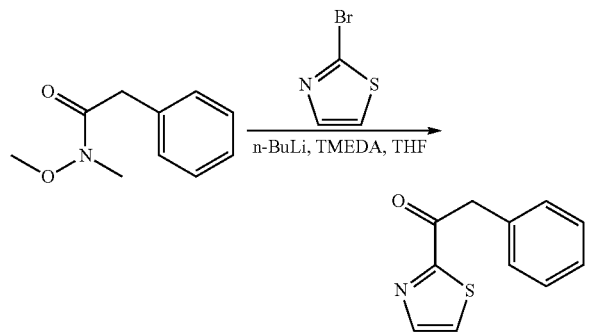

Tetramethylethylenediamine (TMEDA, 27.2 mL) was dissolved in THF 300 mL) in an inert atmosphere, then cooled to −78° C. before the drop-wise addition of n-BuLi (67.6 mL, 2.5 M). 2-bromo-1,3-thiazole (15.2 mL) was added drop-wise and agitation was continued 30 minutes at −78° C. Compound 1E (25 g, 139.50 mmol, 1.00 equiv) dissolved in THE (100 mL) was added drop-wise. Agitation was continued for 30 minutes at −78° C. then 2 hours at −10° C. The reaction was neutralised with 500 mL of KHSO$_4$ (sat.), then extracted 3 times with 1 litre of EtOAc. The organic phases were combined, washed twice with 400 mL water and twice with 700 mL of NaCl (sat.), then dried over sodium sulfate, filtered and concentrated. The residue was purified on a silica column with a mixture of EtOAc and PE (1:100 to 1:10) to yield 25 g (88%) of compound 1F in the form of a yellow oil.

Compound 1G

(1R)-2-phenyl-1-(1,3-thiazol-2-yl)ethan-1-ol

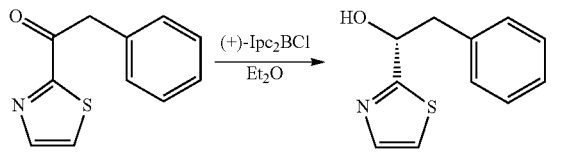 [SMILES: "Et2O" ; O=C(Cc1ccccc1)c1nccs1 ; O[C@H](Cc1ccccc1)c1nccs1]

In an inert atmosphere, a solution of compound 1F (15 g, 73.8 mmol, 1.00 equiv.) in ether (300 mL) was added drop-wise to (+)-B-chlorodiisopinocampheylborane ((+)-Ipc$_2$BCl, 110.8 mL). The reaction mixture was agitated 24 hours at 0° C., then neutralised with 300 mL of a (1:1) mixture of NaOH (10% in water) and H$_2$O$_2$ (30% in water), and finally extracted three times with 500 mL of EtOAc. The organic phases were combined, washed twice with 300 mL of K$_2$CO$_3$ (sat.) and once with 500 mL of NaCl (sat.), then dried over sodium sulfate, filtered and concentrated. The residue was purified on a silica column with a mixture of EtOAc and PE (1:20 to 1:2) to yield 6.3 g (42%) of compound 1G in the form of a white solid.

Compound 1H

2-[(1S)-1-azido-2-phenylethyl]-1,3-thiazole

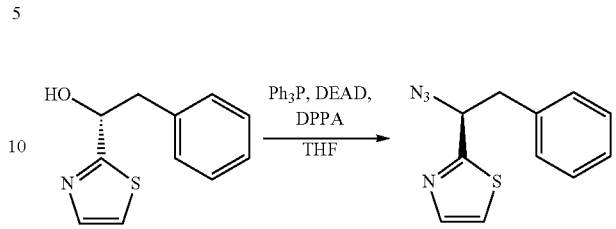

Compound 1G (6 g, 29.23 mmol, 1.00 equiv.) was dissolved in an inert atmosphere in THE (150 mL) in the presence of triphenylphosphine (13 g, 49.56 mmol, 1.70 equiv.), then cooled to 0° C. Diethylazodicarboxylate (DEAD, 7.6 mL) was added drop-wise, followed by diphenylphosphorylazide (DPPA, 11 mL), the cold bath was then removed and the solution was left under agitation 48 hours at ambient temperature. The medium was concentrated under reduced pressure. The residue was purified on a silica column with a mixture of EtOAc and PE (1:100 to 1:30) to yield 8 g of partly purified compound 1H in the form of a yellow oil. Compound 1H was used as such in the following step.

Compound 1I tert-butyl N-[(1S)-2-phenyl-1-(1,3-thiazol-2-yl)ethyl]carbamate

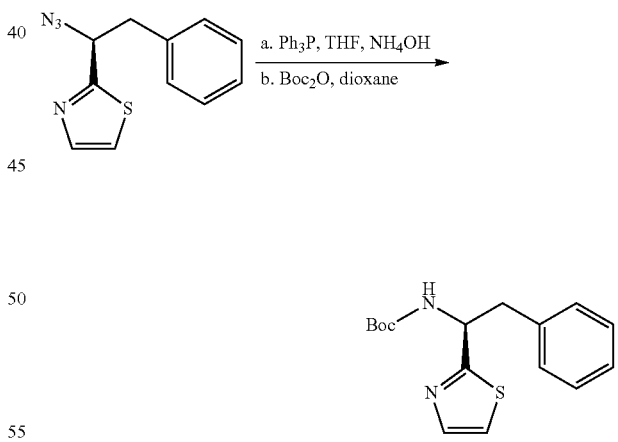

Compound 1H (6.5 g, 28.2 mmol, 1.00 equiv) was dissolved in an inert atmosphere in THE (100 mL) in the presence of triphenylphosphine (6.5 g, 33.9 mmol, 1.20 equiv.), and heated to 50° C. for 2 hours. Ammonia (70 mL) was then added and heating was continued for 3 hours. The reaction was cooled, neutralised with 500 mL water, then extracted 3 times with 500 mL of EtOAc. The organic phases were combined and extracted twice with 500 mL of 1N HCl. The aqueous phases were combined, brought to pH 8-9 by adding a sodium hydroxide solution (10% in water), then extracted 3 times with 500 mL of DCM. The organic phases were combined, dried over sodium sulfate, filtered and concentrated to yield 4.8 g (83%) of (1S)-2-phenyl-1-(1,3-thiazol-2-yl)ethan-1-amine in the form of a yellow oil. This compound was then protected with a Boc group ((tert-butoxy)carbonyl) so that it could be purified. It was dissolved in an inert atmosphere in 1,4-dioxane (40 mL), then cooled to 0° C. (Boc)$_2$O (10.26 g, 47.01 mmol, 2.00 equiv) diluted in 20 mL of 1,4-dioxane was added drop-wise. The cold bath was removed and the solution left under agitation overnight at ambient temperature before being neutralised with 300 mL of water and extracted twice with 500 mL of EtOAc. The organic phases were combined, dried over sodium sulfate, filtered and concentrated. The residue was purified on a silica column with a mixture of EtOAc and PE (1:100 to 1:20, ee=93%). It was then recrystallized in a hexane/acetone mixture (~5-10/1, 1 g/10 mL) to yield 6 g (84%) of compound 1I in the form of a white solid (ee >99%).

Compound 1J tert-butyl (2S)-2-[(1R,2R)-1-methoxy-2-methyl-2-[[(1S)-2-phenyl-1-(1,3-thiazol-2-yl)ethyl]carbamoyl]ethyl]pyrrolidine-1-carboxylate

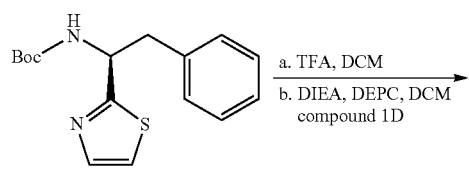

Compound 1I (3 g, 9.86 mmol, 1.00 equiv) was dissolved in an inert atmosphere in 10 mL DCM. Trifluoroacetic acid (TFA, 10 mL) was added and the solution left under agitation overnight at ambient temperature, then concentrated under reduced pressure to yield 2.0 g (64%) of (1S)-2-phenyl-1-(1,3-thiazol-2-yl)ethan-1-amine; trifluoroacetic acid in the form of a yellow oil. This intermediate was re-dissolved in 20 mL of DCM after which compound 1D (1.8 g, 6.26 mmol, 1.05 equiv), DEPC (1.1 g, 6.75 mmol, 1.13 equiv) and diisopropylethylamine (DIEA, 1.64 g, 12.71 mmol, 2.13 equiv) were added. The reaction mixture was left under agitation overnight at ambient temperature, then concentrated under reduced pressure. The residue was purified on a silica column with a mixture of EtOAc and PE (1:100 to 1:3) to yield 2.3 g (81%) of compound 1J in the form of a pale yellow solid.

Compound 1K (2R,3R)-3-methoxy-2-methyl-N-[(1S)-2-phenyl-1-(1,3-thiazol-2-yl)ethyl]-3-[(2S)-pyrrolidin-2-yl]propanamide; trifluoroacetic acid

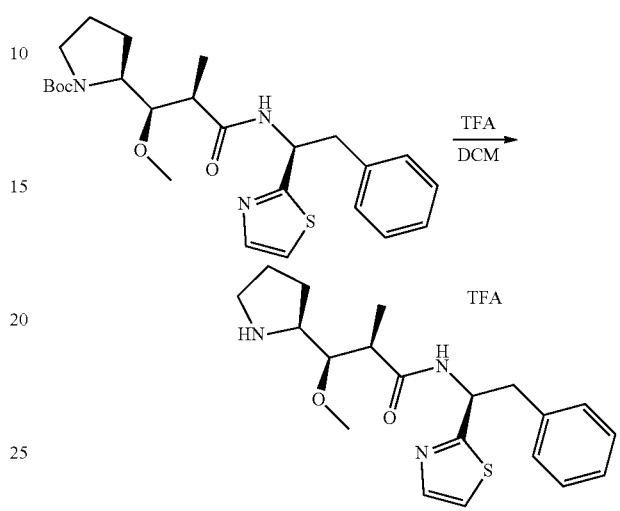

Compound 1J (2.25 g, 4.75 mmol, 1.00 equiv) was dissolved in an inert atmosphere in 10 mL of DCM. TFA (10 mL) was added and the solution left under agitation overnight at ambient temperature, then concentrated under reduced pressure to yield 2.18 g (94%) of compound 1K in the form of a yellow oil.

Compound 1L (2S,3S)-2-(benzylamino)-3-methylpentanoic acid

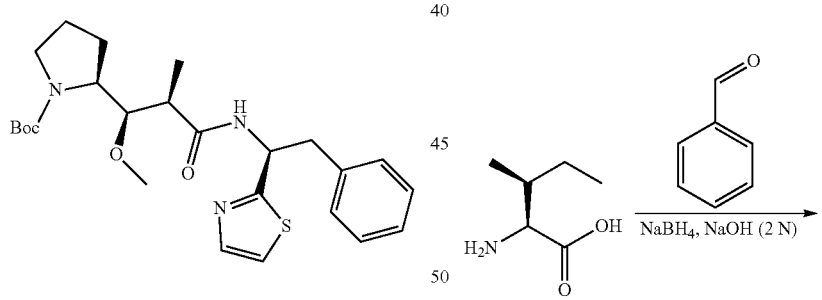

(2S,3S)-2-amino-3-methylpentanoic acid (98.4 g, 750 mmol, 1.00 equiv) was added at ambient temperature and in portions to a 2N sodium hydroxide solution (375 mL). Benzaldehyde (79.7 g, 751.02 mmol, 1.00 equiv) was quickly added and the resulting solution was agitated 30 minutes. Sodium borohydride (10.9 g, 288.17 mmol, 0.38 equiv) was added in small portions, whilst holding the temperature at between 5 and 15° C. Agitation was continued for 4 hours at ambient temperature. The reaction mixture was diluted with 200 mL of water, then washed twice with 200 mL of EtOAc. The pH of the aqueous solution was adjusted to 7 with a 2N hydrochloric acid solution. The formed precipitate was collected by filtering and gave 149.2 g (90%) of compound 1L in the form of a white solid.

Compound 1M (2S,3S)-2-[benzyl(methyl)amino]-3-methylpentanoic acid

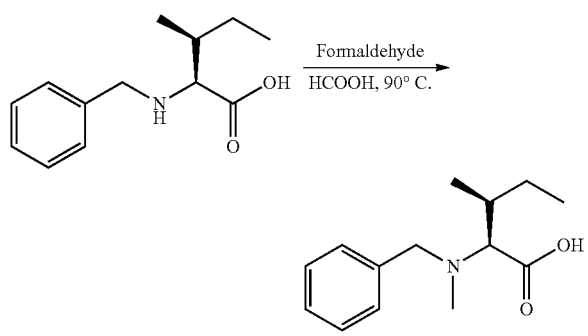

Compound 1L (25 g, 112.97 mmol, 1.00 equiv) was dissolved in an inert atmosphere in formic acid (31.2 g) in the presence of formaldehyde (36.5% in water, 22.3 g). The solution was agitated 3 hours at 90° C. then concentrated under reduced pressure. The residue was triturated in 250 mL of acetone, then concentrated. This trituration/evaporation operation was repeated twice with 500 mL of acetone to yield 21.6 g (81%) of compound 1M in the form of a white solid.

Compound 1N (2S,3S)-2-[benzyl(methyl)amino]-3-methylpentan-1-ol

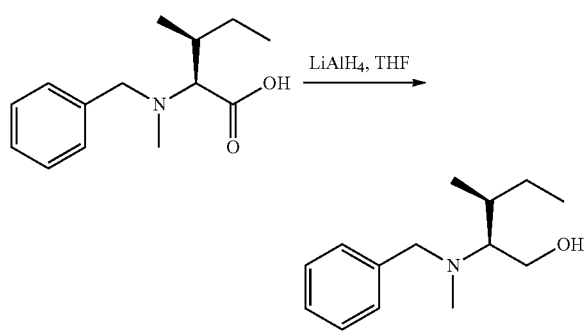

LiAlH$_4$ (0.36 g) was suspended in 10 mL of THF in an inert atmosphere at 0° C. Compound 1M (1.5 g, 6.37 mmol, 1.00 equiv) was added in small portions whilst holding the temperature at between 0 and 10° C. The reaction mixture was agitated 2 hours at 65° C., then again cooled to 0° C. before being neutralised with successive additions of 360 μL of water, 1 mL of 15% sodium hydroxide and 360 μL of water. The aluminium salts which precipitated were removed by filtering. The filtrate was dried over sodium sulfate, filtered and concentrated. The residue was purified on a silica column with a mixture of EtOAc and PE (1:50) to yield 820 mg (58%) of compound 1N in the form of a pale yellow oil.

Compound 1O (2S,3S)-2-[benzyl(methyl)amino]-3-methylpentanal

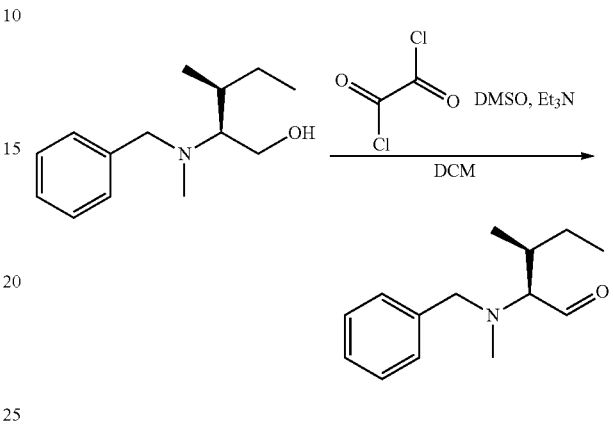

Oxalyl chloride (0.4 mL) was dissolved in DCM (15 mL) in an inert atmosphere. The solution was cooled to −70° C. and a solution of dimethylsulfoxide (DMSO (0.5 mL) in DCM (10 mL) was added drop-wise for 15 minutes. The reaction mixture was agitated 30 minutes after which a solution of compound 1N (820 mg, 3.70 mmol, 1.00 equiv) in DCM (10 mL) was added drop-wise for 15 minutes. The reaction mixture was agitated a further 30 minutes at low temperature, then triethylamine (2.5 mL) was slowly added. The reaction mixture was agitated 1 hour at −50° C., the cold bath was then removed and the reaction neutralised with 25 mL of water whilst allowing the temperature to return to normal. The solution was washed once with 30 mL of NaCl-saturated aqueous solution, then dried over sodium sulfate, filtered and concentrated. The residue was purified on a silica column with a mixture of EtOAc and PE (1:200) to yield 0.42 g (52%) of compound 1O in the form of a yellow oil.

Compound 1P (2S,3S)—N-benzyl-1,1-dimethoxy-N,3-dimethyl-pentan-2-amine

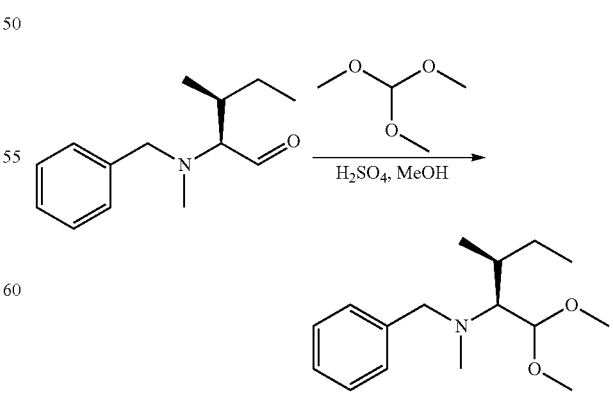

Compound 1O (4.7 g, 21.43 mmol, 1.00 equiv) was dissolved in 20 mL of methanol at 0° C. Concentrated sulfuric acid (4.3 mL) was added drop-wise and agitation was continued for 30 minutes at 0° C. Trimethyl orthoformate (21.4 mL) was added, the cold bath removed and the reaction medium left under agitation for 3 hours at ambient temperature. The reaction medium was diluted with 200 mL of EtOAc, successively washed with 100 mL of 10% Na₂CO₃ and 200 mL of saturated NaCl, then dried over sodium sulfate, filtered and concentrated under reduced pressure to yield 3.4 g (60%) of compound 1P in the form of a pale yellow oil.

Compound 1Q

[[1-(tert-butoxy)ethenyl]oxy](tert-butyl)dimethylsilane

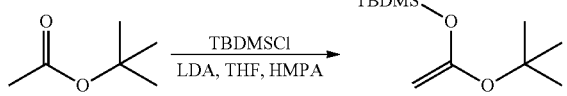

Diisopropylamine (20 g, 186.71 m mol, 1.08 equiv) was dissolved in 170 mL of THF in an inert atmosphere and cooled to −78° C. nBuLi (2.4 M, 78.8 mL) was added drop-wise and the solution agitated 30 minutes at low temperature (to give LDA-lithium diisopropylamide) before adding tert-butyl acetate (20 g, 172.18 mmol, 1.00 equiv). The reaction mixture was agitated 20 minutes at −78° C. before adding hexamethylphosphoramide (HMPA, 25.8 mL) and a solution of tertbutyldimethylchlorosilane (TBDMSCl, 28 g, 185.80 mmol, 1.08 equiv) in 35 mL of THF. Agitation was continued for 20 additional minutes at low temperature, and the cold bath was then removed. The solution was concentrated under reduced pressure. The residue was re-dissolved in 100 mL of water and extracted 3 times with 100 mL of PE. The organic phases were combined, washed once with 500 mL of NaCl-saturated aqueous solution, dried over sodium sulfate, filtered and concentrated. The residue was purified by distillation to yield 16.6 g (83%) of compound 1Q in the form of a colourless oil.

Compound 1R: tert-butyl (3R,4S,5S)-4-[benzyl (methyl)amino]-3-methoxy-5-methyl heptanoate

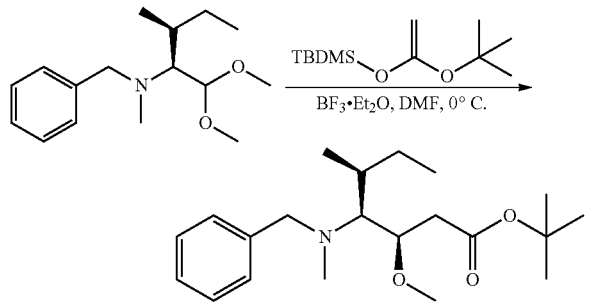

Compound 1P (2.0 g, 7.54 mmol, 1.00 equiv) and compound 1Q (2.6 g, 11.28 mmol, 1.50 equiv) were dissolved in 33 mL of DCM in an inert atmosphere. The solution was cooled to 0° C. DMF (1.2 g) was added drop-wise together with a solution of BF₃.Et₂O (2.1 g) in 7.5 mL of DCM. Agitation was continued for 24 hours at 0° C. The reaction medium was washed once with 30 mL of sodium carbonate (10%) and twice with 50 mL of NaCl-saturated aqueous solution, then dried over sodium sulfate, filtered and concentrated. The residue was purified on a silica column with a mixture of EtOAc and PE (1:100) to yield 1.82 g (91%) of compound 1R in the form of a yellow oil.

Compound 1S (3R,4S,5S)-3-methoxy-5-methyl-4-(methylamino) heptanoate hydrochloride

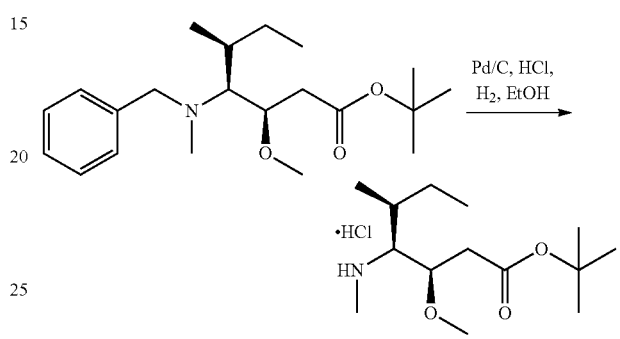

Compound 1R (2.4 g, 6.87 mmol, 1.00 equiv) was dissolved in an inert atmosphere in 35 mL of ethanol in the presence of Pd/C (0.12 g) and concentrated hydrochloric acid (0.63 mL). The nitrogen atmosphere was replaced by a hydrogen atmosphere and the reaction medium was left under agitation 18 hours at ambient temperature. The reaction medium was filtered and concentrated under reduced pressure. The residue was triturated in 50 mL of hexane and the supernatant removed which, after drying under reduced pressure, gave 1.66 g (82%) of compound 1S in the form of a white solid.

Compound 1T tert-butyl (3R,4S,5S)-4-[(2S)-2-[[(benzyloxy)carbonyl]amino]-N,3-dimethylbutanamido]-3-mthoxy-5-methylheptanoate

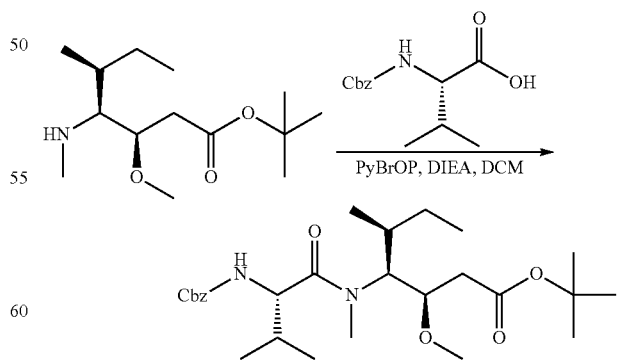

(2S)-2-[[(benzyloxy)carbonyl]amino]-3-methylbutanoic acid (15 g, 0.40 mmol, 1.00 equiv) was dissolved in 300 mL of DCM in the presence of DIEA (38.3 mL) and bromotripyrrolidinophosphonium hexafluorophosphate (Py- BrOP, 32.3 g). The solution was agitated 30 minutes at ambient temperature before adding compound 1S (15.99 g, 0.42 mmol, 1.07 equiv). The reaction medium was agitated 2 hours and then concentrated. The residue was purified in reverse phase (C18) with a mixture of acetonitrile (ACN) and water (30:70 to 100:0 in 40 minutes) to yield 17 g (58%) of compound 1T in the form of a colourless oil.

Compound 1U tert-butyl (3R,4S,5S)-4-[(2S)-2-amino-N,3-dimethylbutanamido]-3-methoxy-5-methylheptanoate

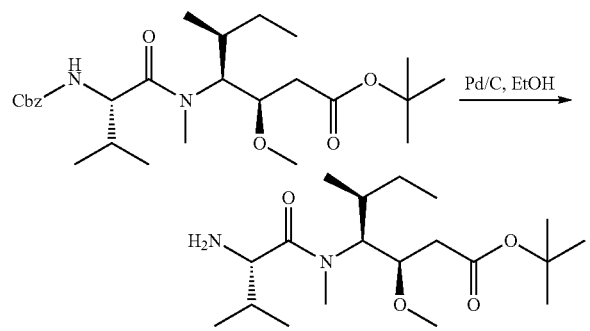

Compound 1T (76 mg, 0.15 mmol, 1.00 equiv) was dissolved in an inert atmosphere in 10 mL of ethanol in the presence of Pd/C (0.05 g). The nitrogen atmosphere was replaced by a hydrogen atmosphere and the reaction agitated 2 hours at ambient temperature. The reaction medium was filtered and concentrated under reduced pressure to yield 64 mg of compound 1U in the form of a colourless oil.

Compound 1V (3R,4S,5S)-4-[(2S)-2-[[(9H-fluoren-9-ylmethoxy)carbonyl]amino]-N,3-dimethylbutanamido]-3-methoxy-5-methylheptanoate

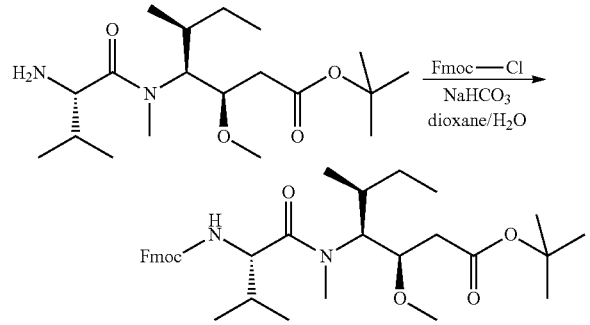

Compound 1U (18.19 g, 50.74 mmol, 1.00 equiv) was dissolved in 400 mL of a 1,4-dioxane/water mixture (1:1) in the presence of sodium bicarbonate (12.78 g, 152 mmol, 3.00 equiv) and 9H-fluoren-9-ylmethyl chloroformate (Fmoc-Cl, 19.69 g, 76 mmol, 1.50 equiv), then agitated 2 hours at ambient temperature. The reaction medium was then diluted with 500 mL of water and extracted 3 times with 200 mL of EtOAc. The organic phases were combined, washed once with 200 mL of NaCl-saturated aqueous solution, dried over sodium sulfate, filtered and concentrated to yield 40 g of partly purified compound 1V in the form of a pale yellow oil.

Compound 1W (3R,4S,5S)-4-[(2S)-2-[[(9H-fluoren-9-ylmethoxy)carbonyl]amino]-N,3-dimethylbutanamido]-3-methoxy-5-methylheptanoic acid

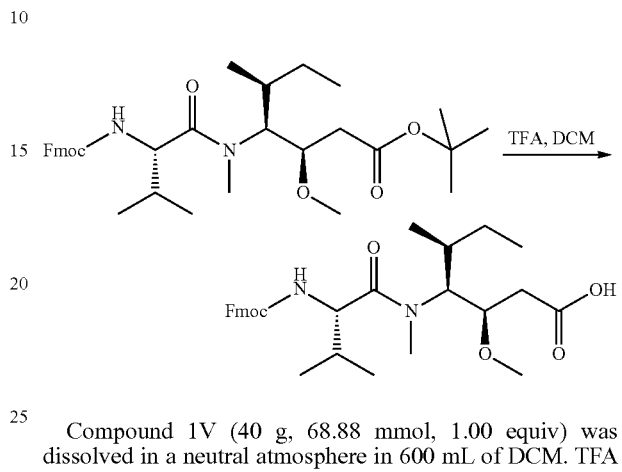

Compound 1V (40 g, 68.88 mmol, 1.00 equiv) was dissolved in a neutral atmosphere in 600 mL of DCM. TFA (300 mL) was added. The solution was agitated 2 hours at ambient temperature, then concentrated under reduced pressure. The residue was purified on a silica column with a mixture of methanol and DCM (1:10) to yield 23.6 g (65%) of compound 1W in colourless oil form.

Compound 1X 9H-fluoren-9-ylmethyl N-[(1S)-1-[[(3R,4S,5S)-3-methoxy-1-[(2S)-2-[(1R,2R)-1-methoxy-2-methyl-2-[[(1S)-2-phenyl-1-(1,3-thiazol-2-yl)ethyl]carbamoyl]ethyl]pyrrolidin-1-yl]-5-methyl-1-oxoheptan-4-yl](methyl)carbamoyl]-2-methylpropyl]carbamate

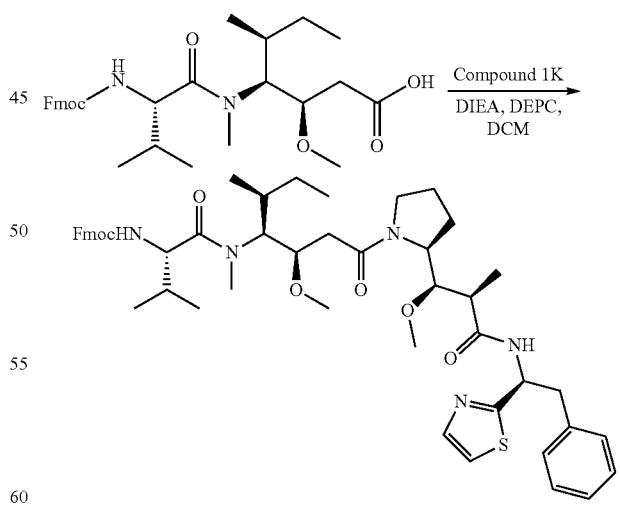

Compound 1W (2.53 g, 4.82 mmol, 1.08 equiv) was dissolved in 20 mL of DCM in the presence of compound 1K (2.18 g, 4.47 mmol, 1.00 equiv), DEPC (875 mg, 5.37 mmol, 1.20 equiv) and DIEA (1.25 g, 9.67 mmol, 2.16 equiv). The reaction mixture was left under agitation overnight at ambient temperature, then successively washed with 50 mL of saturated KHSO₄ and 100 mL of water, dried over sodium sulfate, filtered and concentrated. The residue was purified on a silica column with a mixture of methanol and DCM (1:200 to 1:40) to yield 2.8 g (71%) of compound 1X in the form of a pale yellow solid.

Compound 1Y (2S)-2-amino-N-[(3R,5S)-3-methoxy-1-[(2S)-2-[(1R,2R)-1-methoxy-2-methyl-2-[[(1S)-2-phenyl-1-(1,3-thiazol-2-yl)ethyl]carbamoyl]ethyl]pyrrolidin-1-yl]-5-methyl-1-oxoheptan-4-yl]-N,3-dimethylbutanamide

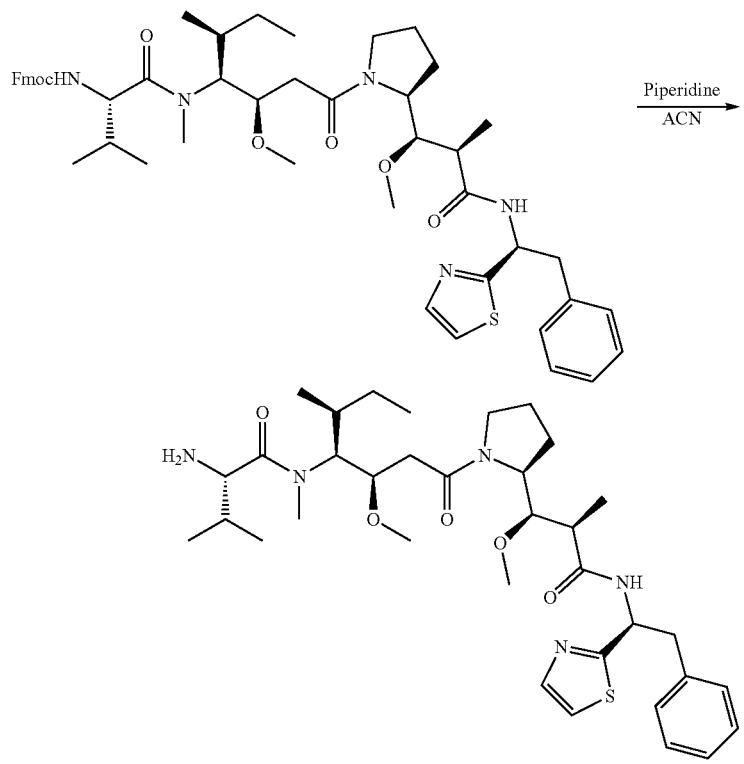

Compound 1X (2.8 g, 3.18 mmol, 1.00 equiv) was dissolved in acetonitrile (ACN, 12 mL) in the presence of piperidine (3 mL) and left under agitation 18 hours at ambient temperature. The reaction was neutralised with 50 mL of water, then extracted twice with 100 mL of DCM. The organic phases were combined, dried over sodium sulfate, filtered and concentrated. The residue was purified on a silica column with a mixture of methanol and DCM (1:100 to 1:40) to yield 1.2 g (57%) of compound 1Y in the form of a yellow solid.

Compound 1ZA (2S)-2-[[(tert-butoxy)carbonyl](methyl)amino]-3-methyl butanoic acid

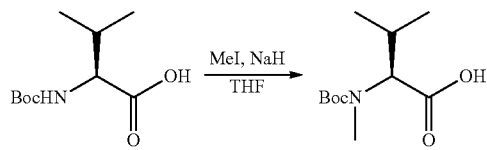 [SMILES: CC(C)[C@H](NC(=O)OC(C)(C)C)C(=O)O ; CC(C)[C@@H](C(=O)O)N(C)C(=O)OC(C)(C)C ; "THF"]

(2S)-2-[[(tert-butoxy)carbonyl]amino]-3-methylbutanoic acid (63 g, 289.97 mmol, 1.00 equiv) was dissolved in an inert atmosphere in THF (1000 mL) in the presence of iodomethane (181 mL). The solution was cooled to 0° C. before adding sodium hydride (116 g, 4.83 mol, 16.67 equiv) in small portions. The reaction mixture was agitated for 1.5 hours at 0° C., the cold bath was then removed and agitation continued for 18 hours. The reaction was neutralised with 200 mL of water and then concentrated under reduced pressure. The residual aqueous phase was diluted with 4 litres of water, washed once with 200 mL of EtOAc and its pH adjusted to between 3 and 4 with a 1N solution of hydrochloric acid. The mixture obtained was extracted 3 times with 1.2 L of EtOAc. The organic phases were combined, dried over sodium sulfate, filtered and concentrated to yield 60 g (89%) of compound 1ZA in the form of a yellow oil.

Compound 1ZB benzyl (2S)-2-[[(tert-butoxy)carbonyl](methyl)amino]-3-methylbutanoate

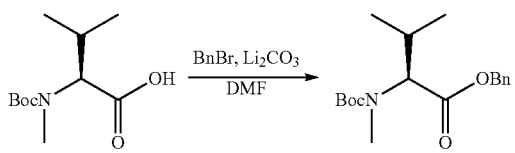

Compound 1ZA (47 g, 203.21 mmol, 1.00 equiv) was dissolved in DMF (600 mL) in the presence of Li$_2$CO$_3$ (15.8 g, 213.83 mmol, 1.05 equiv). The solution was cooled to 0° C. then benzyl bromide (BnBr 57.9 g, 338.53 mmol, 1.67 equiv) was added drop-wise. The reaction mixture was left under agitation overnight before being neutralised with 400 mL of water and filtered. The solution obtained was extracted twice with 500 mL of EtOAc. The organic phases were combined, dried over sodium sulfate, filtered and concentrated. The residue was purified on a silica column with a mixture of EtOAc and PE (1:100 to 1:20) to yield 22.5 g (34%) of compound 1ZB in the form of a yellow oil.

Compound 1ZC benzyl (2S)-3-methyl-2-(methylamino)butanoate hydrochloride

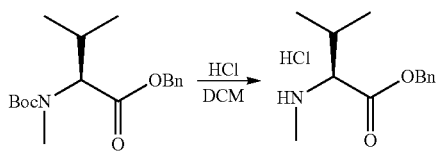 [SMILES: CC(C)[C@@H](C(=O)OCc1ccccc1)N(C)C(=O)OC(C)(C)C ; Cl ; Cl ; CN[C@H](C(=O)OCc1ccccc1)C(C)C]

Compound 1ZB (22.5 g, 70.00 mmol, 1.00 equiv) was dissolved in 150 mL of DCM. Gaseous hydrochloric acid was bubbled. The reaction was agitated 1 hour at ambient temperature and then concentrated under reduced pressure to yield 17 g (94%) of compound 1ZC in the form of a yellow solid.

Compound 1ZD tert-butyl N-(3,3-diethoxypropyl)carbamate

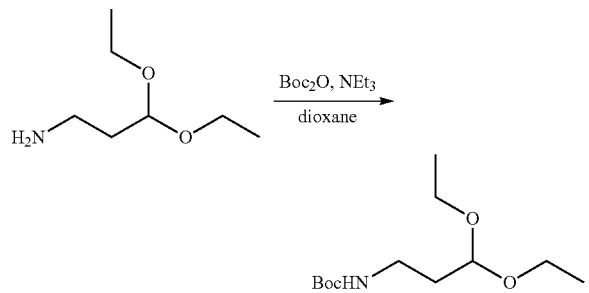

3,3-diethoxypropan-1-amine (6 g, 40.76 mmol, 1.00 equiv) was dissolved in 1,4-dioxane (30 mL) in the presence of TEA (4.45 g, 43.98 mmol, 1.08 equiv), then cooled to 0° C. (Boc)$_2$O (9.6 g, 43.99 mmol, 1.08 equiv) diluted in 20 mL of 1,4-dioxane was added drop-wise. The solution was agitated 2 hours at 0° C. then overnight at ambient temperature before being neutralised with 10 mL of water. The pH was adjusted to 5 with HCl (1%). The solution was extracted 3 times with 50 mL of EtOAc. The organic phases were combined, dried over sodium sulfate, filtered and concentrated to yield 8.21 g (81%) of compound 1ZD in the form of a pale yellow oil.

Compound 1ZE tert-butyl N-(3-oxopropyl) carbamate

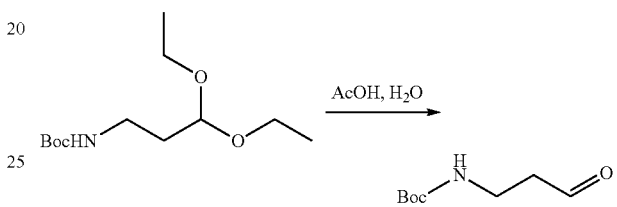

Compound 1ZD (8.20 g, 33.15 mmol, 1.00 equiv) was dissolved in 18.75 mL of acetic acid and left under agitation overnight at ambient temperature. The reaction medium was then extracted 3 times with 30 mL of EtOAc. The organic phases were combined, washed 3 times with 30 mL of saturated NaCl solution, dried over sodium sulfate, filtered and concentrated to yield 5 g (87%) of compound 1ZE in the form of a dark red oil.

Compound 1ZF (2S)-2-[(3-[[(tert-butoxy)carbonyl]amino]propyl)(methyl)amino]-3-methylbutanoicacid

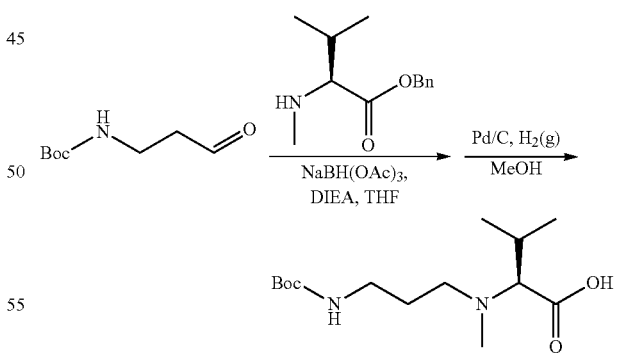

Compound 1ZE (2.4 g, 13.86 mmol, 1.00 equiv) was dissolved in 50 mL of THF in the presence of compound 1ZC (3.56 g, 13.81 mmol, 1.00 equiv) and DIEA (9.16 mL, 4.00 equiv). The reaction mixture was agitated 30 minutes at ambient temperature before adding sodium triacetoxyborohydride (5.87 g, 27.70 mmol, 2.00 equiv). Agitation was continued overnight, then the reaction was neutralised with 100 mL of water and extracted 3 times with 50 mL of EtOAc. The organic phases were combined, dried over sodium sulfate, filtered and concentrated. The residue was partly purified on a silica column with a mixture of EtOAc and PE (1:4). The crude product obtained was re-dissolved in 20 mL of methanol in the presence of Pd/C (1.2 g) and hydrogenated for 20 minutes at normal temperature and pressure. The reaction medium was filtered and concentrated under reduced pressure to yield 200 mg (5%) of compound 1ZF in the form of a white solid.

Compound 1ZG tert-butyl N-(3-[[(1S)-1-[[(1S)-1-[[(3R,4S,5S)-3-methoxy-1-[(2S)-2-[(1R,2R)-1-methoxy-2-methyl-2-[[(1S)-2-phnyl-1-(1,3-thiazol-2-yl)ethyl]carbamoyl]thyl]pyrrolidin-1-yl]-5-methyl-1-oxoheptan-4yl](methyl) carbamoyl]-2-methylpropyl]carbamoyl]-2-methylpropyl](methyl)amino]propyl) carbamate

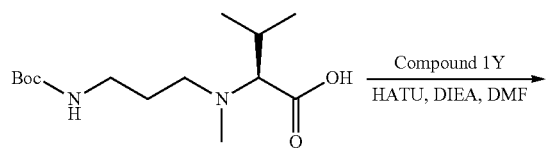

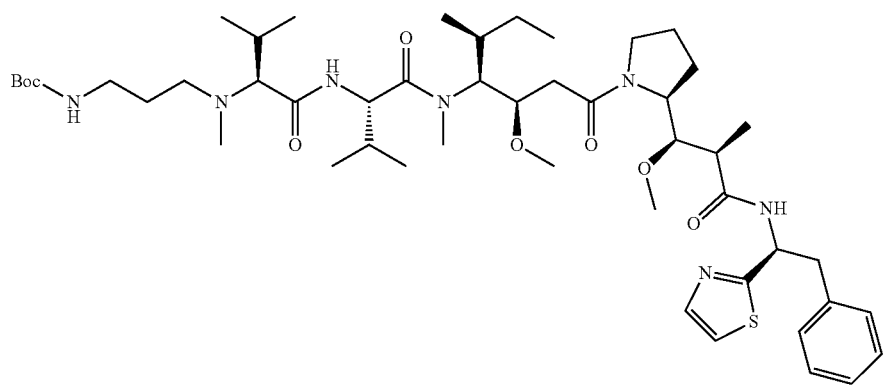

Compound 1Y (50 mg, 0.08 mmol, 1.00 equiv) was dissolved in 2 mL of DMF in the presence of compound 1ZF (26.2 mg, 0.09 mmol, 1.20 equiv), DIEA (37.7 mL) and O-(7-azabenzotriazol-1-yl)-N,N,N',N'-tetramethyluronium hexafluorophosphate (HATU, 43.3 mg, 0.11 mmol, 1.50 equiv). The reaction was left under agitation overnight at ambient temperature, then diluted with 10 mL of water and extracted 3 times with 5 mL of EtOAc. The organic phases were combined, dried over sodium sulfate, filtered and concentrated to yield 100 mg of compound 1ZG in the form of a partly purified colourless oil.

Compound 1ZG (90 mg, 0.10 mmol, 1.00 equiv) was dissolved in a neutral atmosphere in 2 mL of DCM and the solution was cooled with an ice bath. TFA (1 mL) was added and the reaction agitated for 2 hours at ambient temperature, then concentrated under reduced pressure. The residue was purified by preparative HPLC (Pre-HPLC-001 SHIMADZU, SUNFIRE™ Prep C18 OBD column, 5 μm, 19×150 mm; Eluting phase: water/ACN buffered with 0.05% of TFA; Gradient of 18% to 31% ACN in 7 minutes then 31% to 100% ACN in 2 minutes; Waters 2489 UV Detector at 254 nm and 220 nm). Compound 1 was obtained with a yield of 25% (23 mg) in the form of a white solid.

LC/MS/UV (Atlantis T3 column, 3 μm, 4.6×100 mm; 35° C.; 1 mL/min, 30% to 60% ACN in water (20 mM ammonium acetate in 6 minutes); ESI ($C_{44}H_{73}N_7O_6S$, exact masse 827.53) m/z: 829 (MH$^+$), 5.84 min (93.7%, 254 nm).

$^1$H NMR (300 MHz, CD$_3$OD, ppm): δ (Presence of rotamers) 7.85-7.80 (m, 1H); 7.69-7.66 (m, 1H); 7.40-7.10 (m, 5H), 5.80-5.63 (m, 1H), 4.80-4.65 (m, 2H), 4.22-4.00 (m, 1H), 3.89-0.74 (m, 58H).

Compound 2

(S)-2-((S)-2-(((2-aminopyridin-4-yl)methyl)(methyl)amino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-y)-N,3-dimethylbutanamide, trifluoroacetic acid

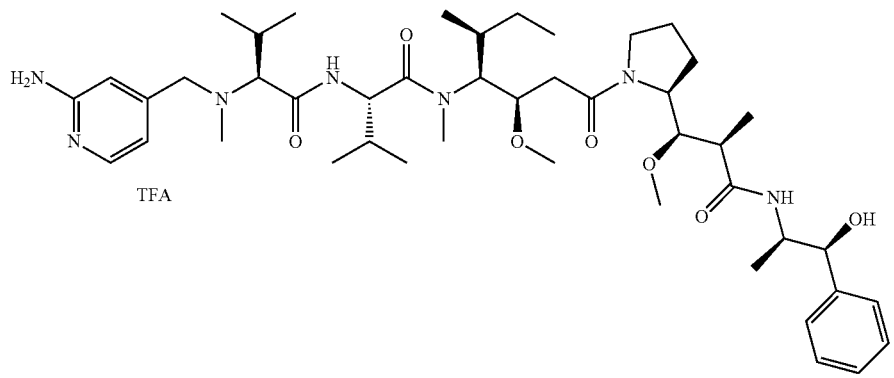 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)Cc1ccnc(N)c1)C(C)C]

Compound 2A tert-butyl (S)-2-((1R,2R)-3-(((1S,2R)-1-hydroxy-1-phenylpropan-2-yl)amino)-1-methoxy-2-methyl-3-oxopropyl)pyrrolidine-1-carboxylate

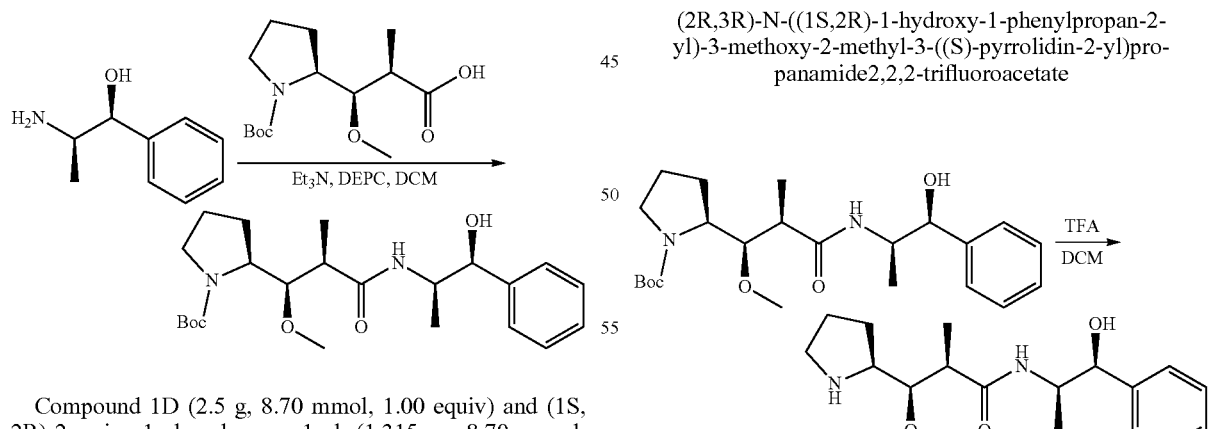

Compound 1D (2.5 g, 8.70 mmol, 1.00 equiv) and (1S,2R)-2-amino-1-phenylpropan-1-ol (1.315 g, 8.70 mmol, 1.00 equiv) were dissolved in an inert atmosphere in DMF (35 mL). The solution was cooled to 0° C. then DEPC (1.39 mL) and TEA (1.82 mL) were added drop-wise. The reaction mixture was agitated 2 hours at 0° C. then 4 hours at ambient temperature. The reaction mixture was diluted with 200 mL of water and extracted three times with 50 mL of EtOAc. The organic phases were combined, washed once with 50 mL of $KHSO_4$ (1 mol/L), once with 50 mL of $NaHCO_3$ (sat.), once with 50 mL of NaCl (sat.), then dried over sodium sulfate, filtered and concentrated under reduced pressure to yield 3.6 g (98%) of compound 2A in the form of a yellow solid.

Compound 2B (2R,3R)-N-((1S,2R)-1-hydroxy-1-phenylpropan-2-yl)-3-methoxy-2-methyl-3-((S)-pyrrolidin-2-yl)propanamide 2,2,2-trifluoroacetate Compound 2A (2.7 g, 6.42 mmol, 1.00 equiv) was dissolved in an inert atmosphere in DCM (40 mL) then cooled to 0° C. TFA (25 mL) was added and the solution agitated for 2 hours at 0° C. The reaction mixture was concentrated under reduced pressure to yield 4.4 g of compound 2B in the form of a yellow oil.

Compound 2C (9H-fluoren-9-yl)methyl ((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate

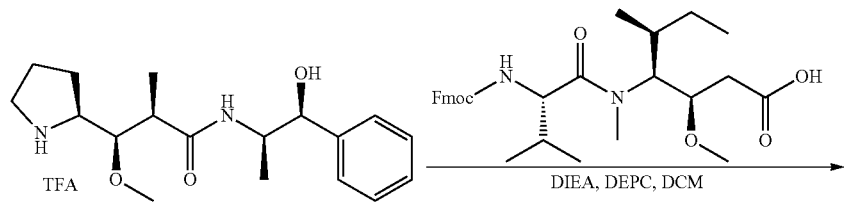

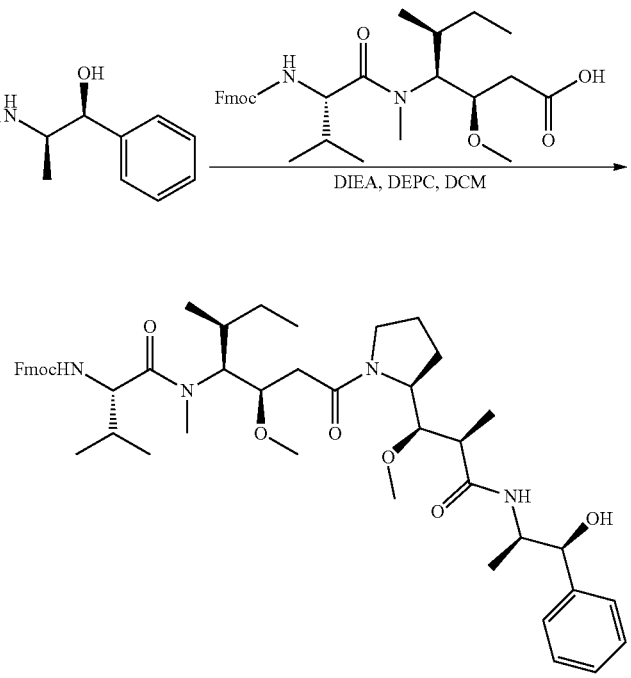

Compounds 2B (4.4 g, 10.13 mmol, 1.00 equiv) and 1W (5.31 g, 10.12 mmol, 1.00 equiv) were dissolved in an inert atmosphere in DCM (45 mL). The solution was cooled to 0° C. then DEPC (1.62 mL) and DIEA (8.4 mL) were added drop-wise. The reaction mixture was agitated for 2 hours at 0° C. then at ambient temperature overnight. The reaction mixture was diluted with 100 mL of water and extracted three times with 50 mL of DCM. The organic phases were combined, washed once with 50 mL of KHSO$_4$ (1 mol/L), once with 50 mL of NaHCO$_3$ (sat.), once with 50 mL of NaCl (sat.), then dried over sodium sulfate, filtered and concentrated under pressure to yield 3.3 g (39%) of compound 2C in the form of a yellow solid.

Compound 2D (S)-2-amino-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide

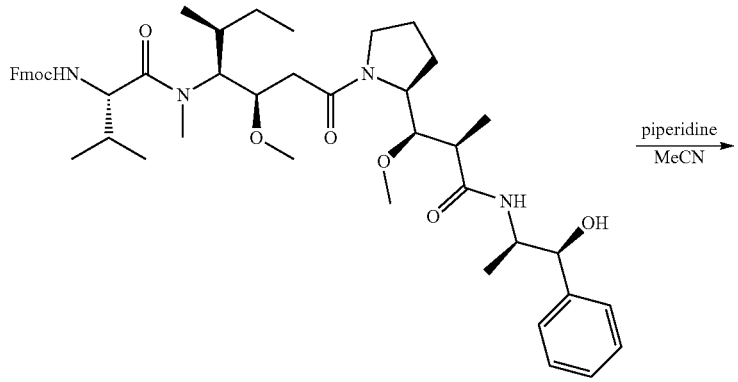

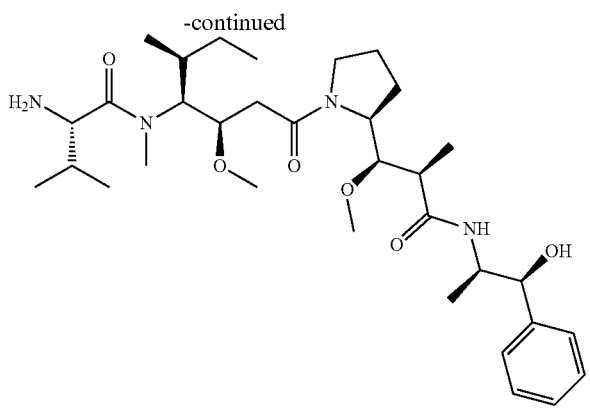

Compound 2C (300 mg, 0.36 mmol, 1.00 eq.) was dissolved in an inert atmosphere in ACN (2 mL) and piperidine (0.5 mL). The solution was left under agitation at ambient temperature overnight then evaporated to dryness under reduced pressure. The residue was purified on a silica column with a mixture of DCM and MeOH (1:100) to yield 150 mg (68%) of compound 2D in the form of a white solid.

Compound 2E methyl 2-((tert-butoxycarbonyl)amino)isonicotinate

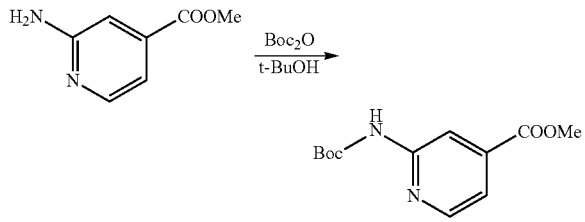

Methyl 2-aminopyridine-4-carboxylate (2 g, 13.14 mmol, 1.00 equiv) was dissolved in tert-butanol (20 mL) after which di-tert-butyl dicarbonate (4.02 g, 18.42 mmol, 1.40 equiv) was added. The reaction mixture was agitated at 60° C. overnight then the reaction was halted through the addition of an aqueous 1M NaHCO$_3$ solution (50 mL). The solid was recovered by filtration, washed with 50 mL of EtOH then dried in vacuo to yield 2.5 g (75%) of compound 2E in the form of a white solid.

Compound 2F tert-butyl (4-(hydroxymethyl)pyridin-2-yl)carbamate

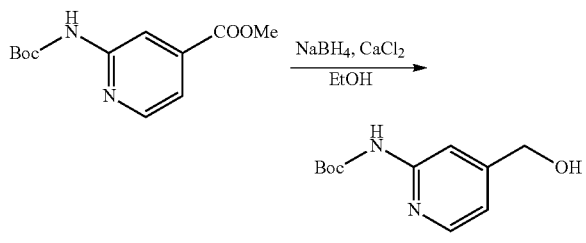

Compound 2E (2.5 g, 9.91 mmol, 1.00 equiv) and CaCl$_2$ (1.65 g) were dissolved in EtOH (30 mL). The solution was cooled to 0° C. then NaBH$_4$ (1.13 g, 29.87 mmol, 3.01 equiv) was gradually added. The solution was left under agitation overnight at ambient temperature then the reaction was halted with the addition of water (50 mL). The mixture was extracted three times with 20 mL of EtOAc. The organic phases were combined, washed twice with 20 mL of NaCl (sat.) then dried over sodium sulfate, filtered and concentrated under reduced pressure to yield 2.0 g (90%) of compound 2F in the form of a colourless solid.

Compound 2G tert-butyl (4-formylpyridin-2-yl)carbamate

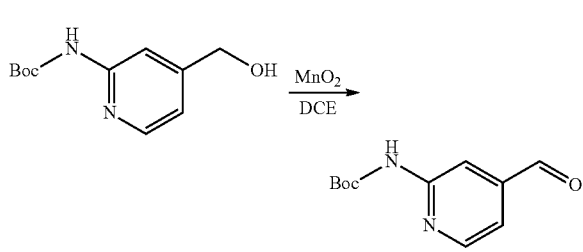

Compound 2F (2.5 g, 11.15 mmol, 1.00 equiv) was dissolved in DCE (25 mL) then 19.4 g (223.14 mmol, 20.02 equiv) of MnO$_2$ were added. The mixture was left under agitation overnight at 70° C. then the solids were removed by filtering. The filtrate was evaporated to dryness to yield 1.4 g (57%) of compound 2G in the form of a white solid.

Compound 2H benzyl (S)-2-(((2-((tert-butoxycarbonyl)amino)pyridin-4-yl)methyl) (methyl)amino)-3-methylbutanoate

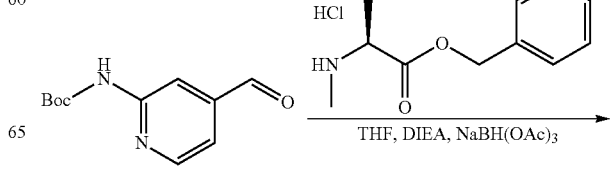

141

-continued

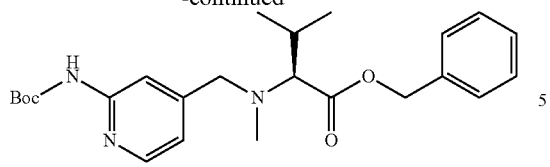

5

Compound 2G (2.3 g, 10.35 mmol, 1.00 equiv) was dissolved in 25 mL of THF in the presence of compound 1ZC (2.93 g, 11.37 mmol, 1.10 equiv), DIEA (5.39 g, 41.71 mmol, 4.03 equiv) and NaBH(OAc)₃ (4.39 g, 20.71 mmol, 2.00 equiv). The reaction mixture was agitated for 6 hours at ambient temperature then neutralised with 60 mL of NaHCO₃ (sat.) and extracted 3 times with 20 mL of AcOEt. The organic phases were combined, washed twice with 20 mL of NaCl (sat.), dried over sodium sulfate, filtered and concentrated. The residue was purified on a silica column with a mixture of EtOAc and PE (1:15) to yield 2.7 g (61%) of compound 2H in the form of a white solid.

Compound 2I (S)-2-(((2-((tert-butoxycarbonyl)amino)pyridin-4-yl)methyl)(methyl)amino)-3-methylbutanoic acid

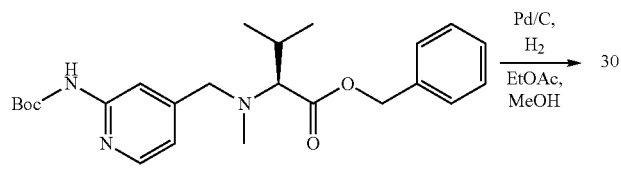

142

-continued

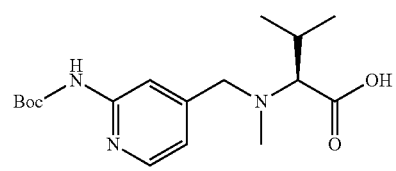

Compound 2H (500 mg, 1.17 mmol, 1.00 equiv) was dissolved in 10 mL of AcOEt and 2 mL of methanol in the presence of Pd/C (250 mg), and hydrogenated for 3 hours at ambient temperature and atmospheric pressure. The reaction medium was filtered and concentrated under reduced pressure to yield 254 mg (64%) of compound 2I in the form of a colourless solid Compound 2J tert-butyl (4-((3S,6S,9S,10R)-9-((S)-sec-butyl)-10-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-3,6-diisopropyl-2,8-dimethyl-4,7-dioxo-11-oxa-2,5,8-triazadodecyl)pyridin-2-yl) carbamate

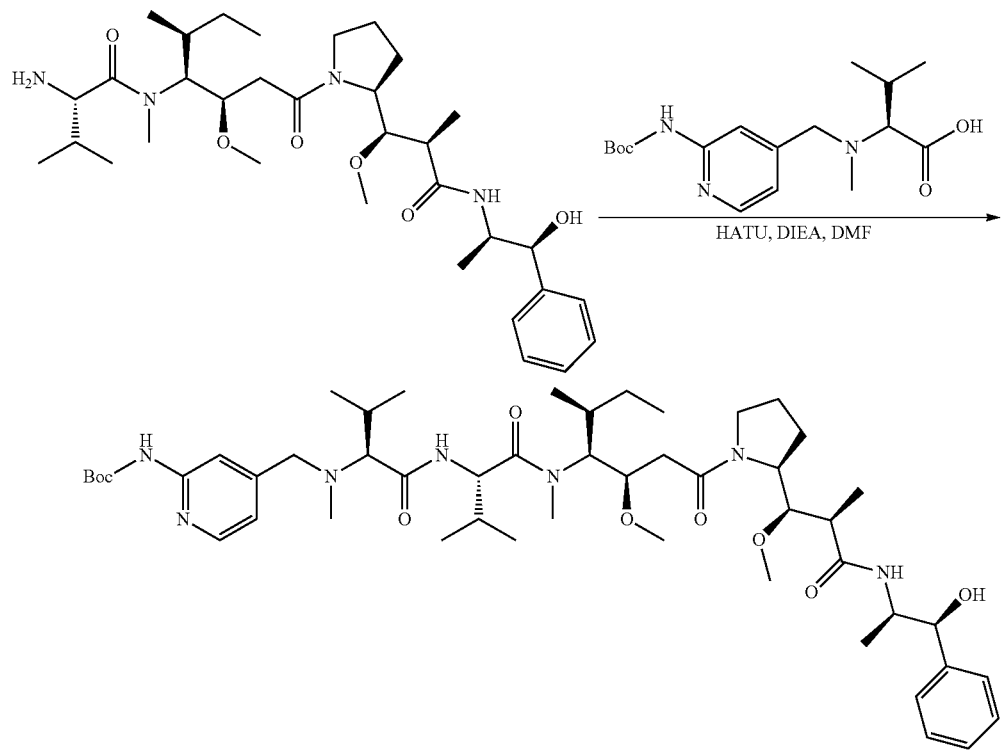

Compound 2J was prepared in similar manner to compound 1ZG from the amine 2D (85.2 mg, 0.14 mmol, 1.50 equiv), the acid 2I (31.7 mg, 0.09 mmol, 1.00 equiv), HATU (42.9 mg, 0.11 mmol, 1.20 equiv) and DIEA (36.7 mg, 0.28 mmol, 3.02 equiv) in DMF (3 mL). After evaporation to dryness, 100 mg of crude product were obtained in the form of a white solid.

Compound 2J (100 mg, 0.11 mmol, 1.00 equiv) was dissolved in 2 mL of DCM and 1 mL of TFA. The reaction was agitated for 1 hour at ambient temperature, then concentrated under reduced pressure. The residue (80 mg) was purified by preparative HPLC (Pre-HPLC-001 SHIMADZU, SUNFIRE™ Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm). Compound 2 was obtained with a yield of 6% (6.3 mg) in the form of a white solid.

LC/MS/UV (Ascentis Express C18 column, 2.7 μm, 4.6× 100 mm; 40° C.; 1.8 mL/min, from 10% to 95% ACN in water (0.05% TFA) in 6 minutes); ESI ($C_{45}H_{73}N_7O_7$, exact mass 823.56) m/z: 824.5 (MH$^+$) and 412.9 (M.2H$^+$/2, 1000) 3.21 min (99.2%, 210 nm)

$^1$H NMR (400 MHz, CD$_3$OD, ppm): δ (Presence of rotamers) 7.81-7.79 (m, 1H); 7.39-7.29 (m, 5H); 6.61-6.59 (m, 2H); 4.84-4.52 (m, 1H); 4.32-4.02 (m, 1H); 3.90-2.98 (m, 10H); 2.90-2.78 (m, 1H); 2.55-0.81 (m, 39H).

Reference Compound 3 methyl ((S)-2-((2R,3R)-3-((S)-1-((3R,4S,5S)-4-((S)—N,3-dimethyl-2-((S)-3-methyl-2-(methyl(pyridin-4-ylmethyl)amino)butanamido)butanamido)-3-methoxy-5-methylheptanoyl)pyrrolidin-2-yl)-3-methoxy-2-methylpropanamido)-3-phenylpropanoate, trifluoroacetic acid

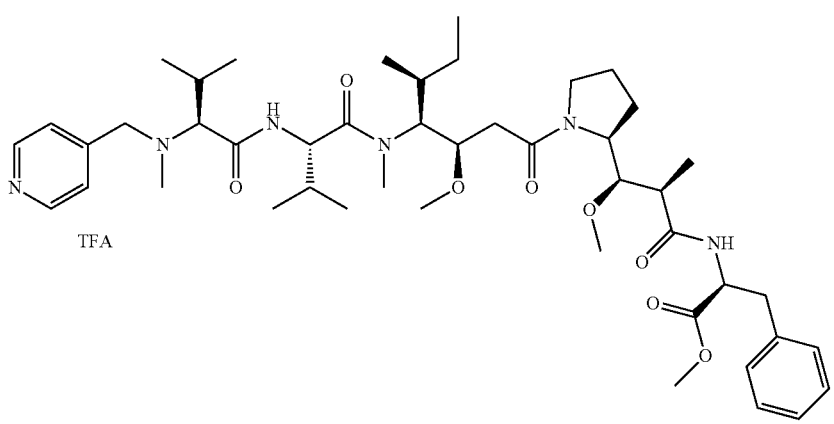 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)Cc1ccncc1)C(C)C]

145

Compound 3A tert-butyl(S)-2-((1R,2R)-1-methoxy-3-(((S)-1-methoxy-1-oxo-3-phenylpropan-2-yl)amino)-2-methyl-3-oxopropyl)pyrrolidine-1-carboxylate

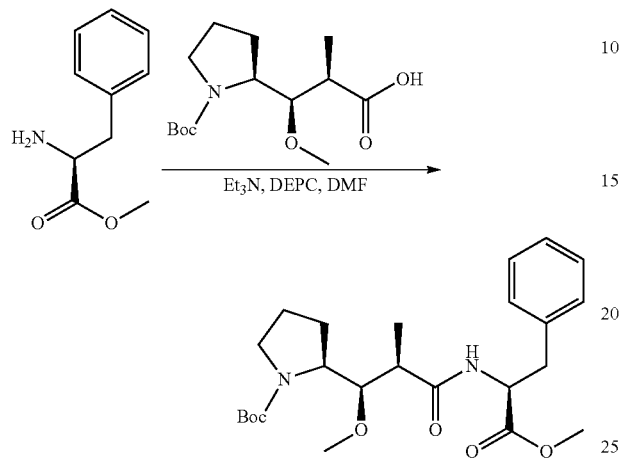

Compound 1D (3 g, 10.44 mmol, 1.00 equiv) and methyl (S)-2-amino-3-phenylpropanoate (2.25 g, 12.55 mmol, 1.20 equiv) were dissolved in an inert atmosphere in DMF (40 mL). The solution was cooled to 0° C. then DEPC (1.67 mL, 1.05 equiv) and TEA (3.64 mL, 2.50 equiv) were added drop-wise. The reaction mixture was agitated 2 hours at 0° C. then at ambient temperature overnight. The reaction mixture was diluted with 100 mL of water and extracted three times with 50 mL EtOAc. The organic phases were combined, washed once with 100 mL of $KHSO_4$ (1 mol/L), once with 100 mL of $NaHCO_3$ (sat.), once with 100 mL of NaCl (sat.), then dried over sodium sulfate, filtered and concentrated under pressure to yield 4 g (85%) of compound 3A in the form of a colourless oil.

146

Compound 3B 2,2,2-trifluoroacetate of methyl (S)-2-((2R,3R)-3-methoxy-2-methyl-3-((S)-pyrrolidin-2-yl)propanamido)-3-phenylpropanoate Compound 3A (5 g, 11.15 mmol, 1.00 equiv) was dissolved in an inert atmosphere in DCM (40 mL). TFA (25 mL) was added and the solution agitated for 2 hours. The reaction mixture was concentrated under reduced pressure to yield 8 g of compound 3B in the form of a yellow oil.

Compound 3C methyl (S)-2-((2R,3R)-3-((S)-1-((3R,4S,5S)-4-((S)-2-((((9H-fluoren-9-yl)methoxy)carbonyl)amino)-N,3-dimethylbutanamido)-3-methoxy-5-methylheptanoyl)pyrrolidin-2-yl)-3-methoxy-2-methylpropanamido)-3-phenylpropanoate

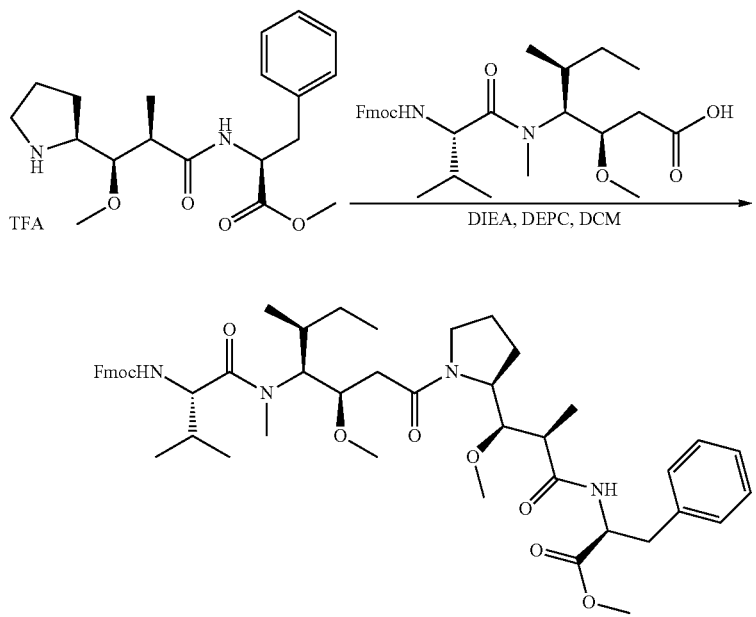

Compounds 3B (8.03 g, 17.36 mmol, 1.00 equiv) and 1W (9.1 g, 17.34 mmol, 1.00 equiv) were dissolved in an inert atmosphere in DCM (80 mL). The solution was cooled to 0° C. then DEPC (2.8 mL) and DIEA (12 mL) were added drop-wise. The reaction mixture was agitated for 2 hours at 0° C. then at ambient temperature overnight. The reaction mixture was diluted with 200 mL of water and extracted three times with 50 mL of DCM. The organic phases were combined, washed once with 50 mL of KHSO₄ (1 mol/L), once with 50 mL of NaHCO₃ (sat.), once with 50 mL of NaCl (sat.), then dried over sodium sulfate, filtered and concentrated under reduced pressure to yield 5 g (34%) of compound 3C in the form of a yellow solid.

Compound 3D methyl (S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanoate

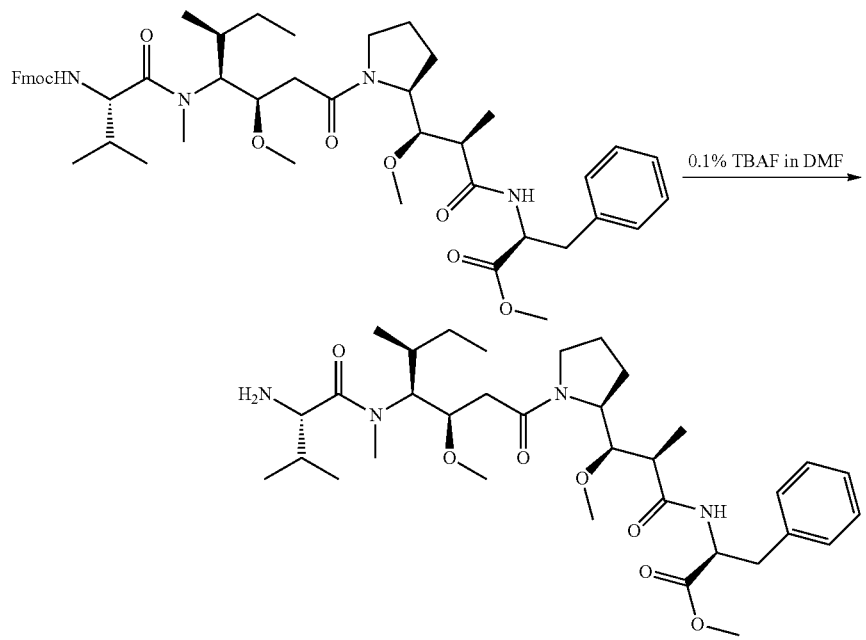

Compound 3C (5.5 g, 6.43 mmol, 1.00 equiv) was dissolved in an inert atmosphere in a solution of tetrabutylammonium fluoride (TBAF, 2.61 g, 9.98 mmol, 1.55 quiv) in DMF (100 mL). The solution was agitated at ambient temperature for 2 hours then diluted with 100 mL of water and extracted three times with 50 mL of EtOAc. The organic phases were combined then dried over sodium sulfate, filtered and concentrated under reduced pressure to yield 3.3 g (81%) of compound 3D in the form of a yellow solid.

Compound 3E benzyl (S)-3-methyl-2-(methyl(pyridin-4-ylmethyl) amino) butanoate

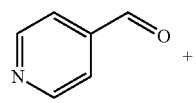

-continued

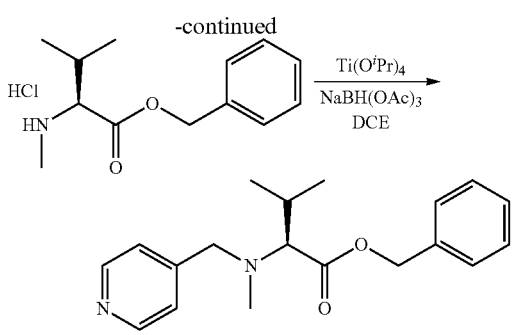

Pyridine-4-carbaldehyde (1 g, 9.34 mmol, 1.00 equiv) was dissolved in 10 mL of 1,2-dichloroethane (DCE) in the presence of compound 1ZC (2.9 g, 11.25 mmol, 1.21 equiv) and titanium isopropoxide (IV) (4.19 mL, 1.40 equiv). The mixture was agitated at ambient temperature for 30 minutes then 2.77 g of NaBH(OAc)₃ (13.07 mmol, 1.40 equiv) were added. The reaction medium was left under agitation overnight then neutralised with 100 mL of water and the mixture extracted 3 times with 50 mL of AcOEt. The organic phases were combined and evaporated to dryness. The residue was purified on a silica column with a mixture of EtOAc and PE (1:20) to yield 1.3 g (45%) of compound 3E in the form of a colourless oil.

Compound 3F (S)-3-methyl-2-(methyl(pyridin-4-ylmethyl)amino)butanoic acid

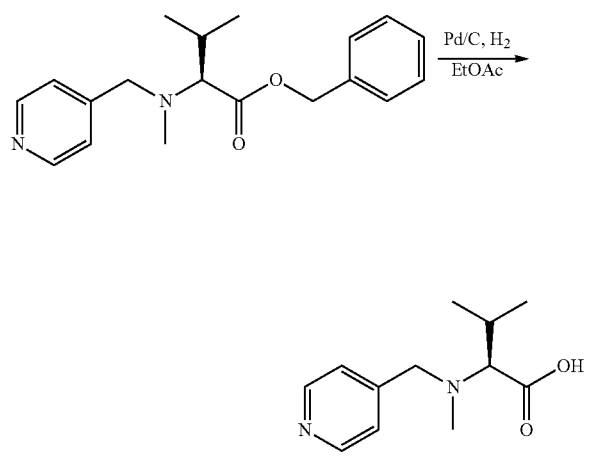

Compound 3E (800 mg, 2.56 mmol, 1.00 equiv) was dissolved in 30 mL of AcOEt in the presence of Pd/C (300 mg) and hydrogenated for 3 hours at ambient temperature and atmospheric pressure. The reaction medium was filtered and concentrated under reduced pressure. The residue was purified on a silica column with a mixture of DCM and MeOH (100:1 to 5:1) to yield 100 mg (18%) of compound 3F in the form of a white solid.

Compounds 3D (50 mg, 0.08 mmol, 1.00 equiv) and 3F (26.34 mg, 0.12 mmol, 1.50 equiv) were dissolved in 3 mL of DCM. The solution was cooled to 0° C. then 0.018 mL of DEPC and 0.0392 mL of DIEA were added. The reaction was agitated at 0° C. for 2 hours then at ambient temperature overnight. The reaction medium was concentrated under reduced pressure and the residue (70 mg) was purified by preparative HPLC (Pre-HPLC-001 SHIMADZU, SUN-FIRE™ Prep C18 OBD column, 5 µm, 19×150 mm; Eluting phase: water/ACN buffered with 0.05% of TFA; Gradient of 20% to 40% ACN in 10 minutes then 40% to 100% ACN in 2 minutes; Waters 2545 UV Detector at 254 nm and 220 nm). Compound 3 was obtained with a yield of 27% (20 mg) in the form of a white solid.

LC/MS/UV (Ascentis Express C18 column, 2.7 µm, 4.6× 100 mm; 40° C.; 1.5 mL/min, 10% to 95% ACN in water (0.05% TFA) in 8 minutes); ESI ($C_{46}H_{72}N_6O_8$, exact mass 836.5) m/z: 837.5 (MH$^+$) and 419.4 (M.2H$^+$/2 (100%)), 7.04 min (90.0%, 210 nm)

$^1$H NMR (400 MHz, CD$_3$OD, ppm): δ (Presence of rotamers) 8.76-8.74 (m, 2H); 8.53-8.48 (m, 0.4H, NHCO incomplete exchange); 8.29-8.15 (m, 0.8H, NHCO incomplete exchange); 8.01 (s, 2H), 7.31-7.22 (m, 5H), 4.88-4.68 (m, 3H); 4.31-4.07 (m, 2H); 3.94-2.90 (m, 18H); 2.55-0.86 (m, 38H).

Reference Compound 4

(S)-2-((2R,3R)-3-((S)-1-((3R,4S,5S)-4-((S)—N,3-dimethyl-2-((S)-3-methyl-2-(methyl(pyridin-4-ylmethyl)amino)butanamido)butanamido)-3-methoxy-5-methylheptanoyl)pyrrolidin-2-yl)-3-methoxy-2-methylpropanamido)-3-phenylpropanoic acid, trifluoroacetic acid

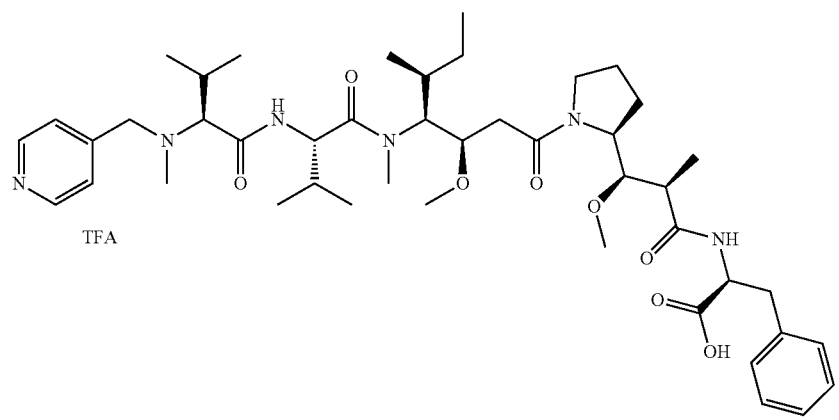 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)Cc1ccncc1)C(C)C]

Compound 3 (100 mg, 0.11 mmol, 1.00 equiv) was dissolved in a mixture of water (5 mL), ACN (5 mL) and piperidine (2.5 mL). The reaction mixture was left under agitation overnight then concentrated under reduced pressure. The residue was purified by preparative HPLC (Pre-HPLC-001 SHIMADZU, SUNFIRE™ Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 20 mg (20%) of compound 4 in the form of a white solid.

LC/MS/UV (Ascentis Express C18 column, 2.7 μm, 4.6× 100 mm; 40° C.; 1.5 mL/min, 10% to 95% ACN in water (0.05% TFA) in 8 minutes); ESI ($C_{45}H_{70}N_6O_8$, exact mass 822.5) m/z: 823.5 (MH$^+$) and 412.4 (M.2H$^+$/2, 100%) 6.84 min (89.1%, 210 nm).

$^1$H NMR (400 MHz, CD$_3$OD, ppm): δ (Presence of rotamers) 8.79-8.78 (m, 2H); 8.09 (m, 2H); 7.30-7.21 (m, 5H); 4.80-4.80 (m, 1H), 4.36-0.87 (m, 58H).

Compound 6 methyl (S)-2-((2R,3R)-3-((S)-1-((3R,4S,5S)-4-((S)-2-((S)-2-((3-aminopropyl) (methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate, bis trifluoroacetic acid

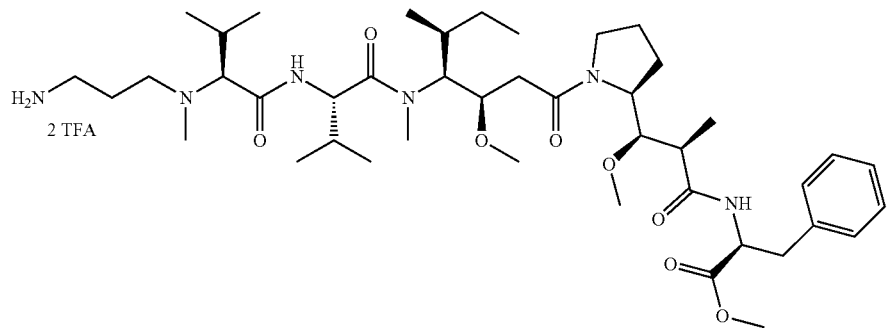 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCCN)C(C)C]

Compound 6A methyl (2S)-2-[(2R)-2-[(R)-[(2S)-1-[(3R,4S,5S)-4-[(2S)-2-[(2S)-2-[(3-[[(tert-butoxy)carbonyl]amino] propyl)(methyl)amino]-3-methyl butanamido]-N,3-dimethylbutanamido]-3-methoxy-5-methylheptanoyl]pyrrolidin-2-yl](methoxy)methyl] propanamido]-3-phenylpropanoate

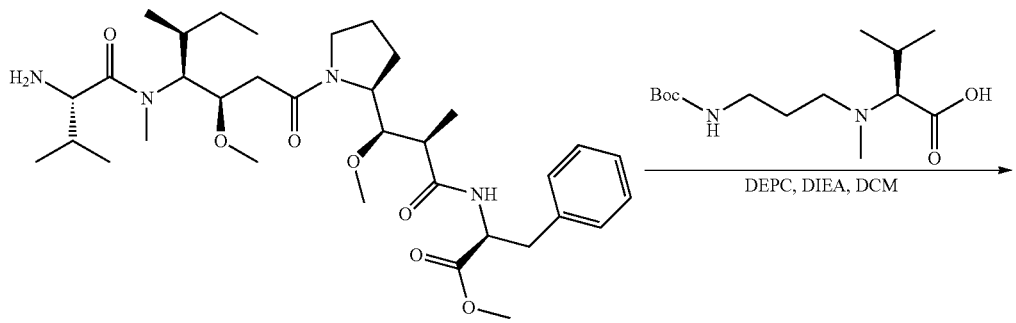

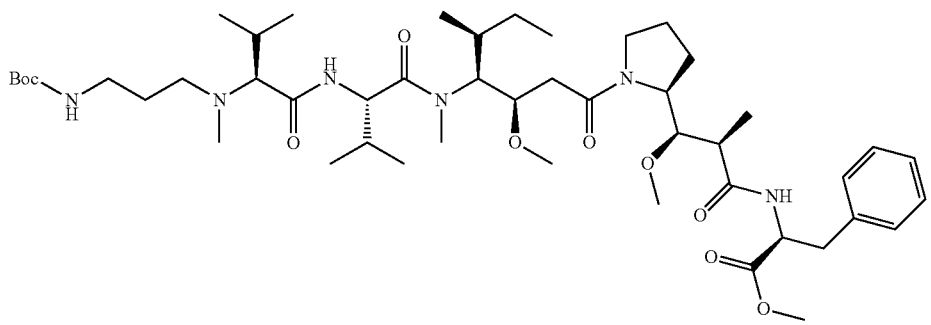

Compound 3D 157.5 mg, 0.25 mmol, 1.00 equiv was dissolved at 0° in an inert atmosphere in 3 mL of DCM in the presence of carboxylic acid 1ZF (78.7 mg, 0.27 mmol, 1.10 equiv), DEPC (46 µl) and DIEA (124 µl). The reaction mixture was agitated 2 hours at low temperature and the cold bath was then removed and agitation continued for 4 hours. It was then concentrated under reduced pressure to yield 200 mg of compound 6A in the form of a crude yellow oil. It was used as such in the following step.

Compound 6A (200 mg, 0.22 mmol, 1.00 equiv) was dissolved in an inert atmosphere at 0° C. in 2 mL of DCM. TFA (1 mL) was added drop-wise and the cold bath removed. The reaction mixture was agitated 1 hour at ambient temperature then concentrated under reduced pressure. The residue was purified by preparative HPLC (Pre-HPLC-001 SHIMADZU, SunFire Prep C18 OBD column, 5 µm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm), to yield 60 mg (26%, yield in 2 steps) of compound 6 in the form of a white solid.

LC/MS/UV (ZORBAX® Eclipse Plus C8, 3.5 µm, 4.6×150 mm; 1 mL/min, 40° C., 30 to 80% methanol in water (0.1% $H_3PO_4$) in 18 minutes); ESI ($C_{43}H_{74}N_6O_8$, exact mass 802.56) m/z: 804 (MH$^+$); 11.50 min (91.5%, 210 nm).

$^1$H NMR (300 MHz, $CD_3OD$, ppm): δ (Presence of rotamers) 8.52 (d, 0.3H, NHCO incomplete exchange); 8.25 (d, 0.5H, NHCO incomplete exchange); 7.30-7.22 (m, 5H); 4.9-4.6 (m, 3H); 4.2-4.0 (m, 1H); 4.0-0.86 (m, 61H).

Compound 7

(S)-2-((2R,3R)-3-((S)-1-((3R,4S,5S)-4-((S)-2-((S)-2-((3-aminopropyl) (methyl)amino)-3-methylbutanamido)-N,3-dimethylbutanamido)-3-methoxy-5-methylheptanoyl) pyrrolidin-2-yl)-3-methoxy-2-methylpropanamido)-3-phenylpropanoic acid, bis trifluoroacetic acid

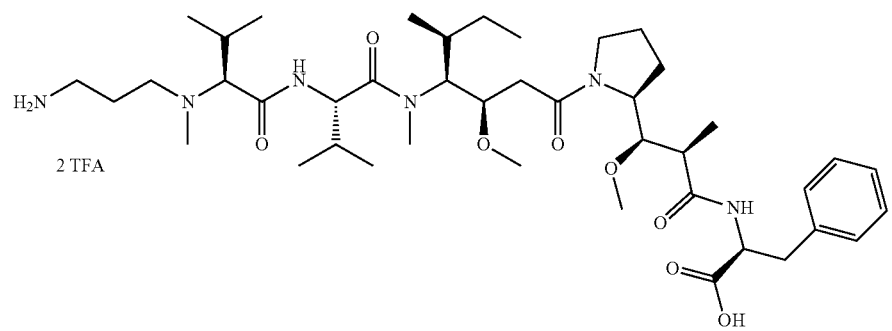 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCCN)C(C)C]

Compound 6 (70 mg, 0.08 mmol, 1.00 equiv) was dissolved in a mixture of water (5 mL), ACN (2.5 mL) and piperidine (5 mL). The reaction mixture was left under agitation overnight at ambient temperature, then concentrated under reduced pressure. The residue was purified by preparative HPLC (Pre-HPLC-001 SHIMADZU, SUN-FIRE™ Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; UV Waters 2489 UV Detector at 254 nm and 220 nm), to yield 14.6 mg (21%) of compound 7 in the form of a white solid.

LC/MS/UV (Ascentis Express C18, 2.7 μm, 4.6×100 mm; 1.5 mL/min, 40° C., 0 to 80% methanol in water (0.05% TFA) in 8 minutes); ESI ($C_{42}H_{72}N_6O_8$, exact mass 788.54) m/z: 790 (MH$^+$), 5.71 min (96.83%, 210 nm).

$^1$H NMR (300 MHz, CD$_3$OD, ppm): δ (Presence of rotamers) 8.42 (d, 0.3H, NHCO incomplete exchange); 8.15 (d, 0.2H, NHCO incomplete exchange); 7.31-7.21 (m, 5H); 4.9-4.6 (m, 3H); 4.25-4.0 (m, 1H); 4.0-0.86 (m, 59H).

Compound 8

(S)-2-((S)-2-(((2-aminopyridin-4-yl)methyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, trifluoroacetic acid

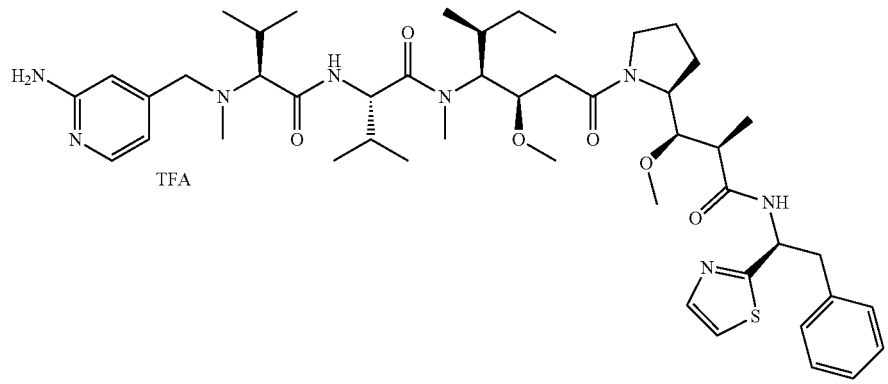 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)Cc1ccnc(N)c1)C(C)C]

Compound 8A tert-butyl (4-((3S,6S,9S,10R)-9-((S)-sec-butyl)-3,6-diisopropyl-10-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-2,8-dimethyl-4,7-dioxo-11-oxa-2,5,8-triazadodecyl)pyridin-2-yl) carbamate

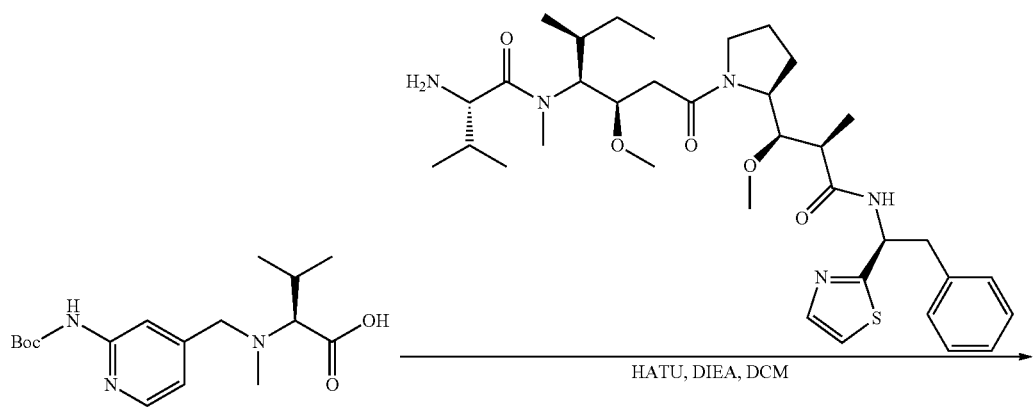

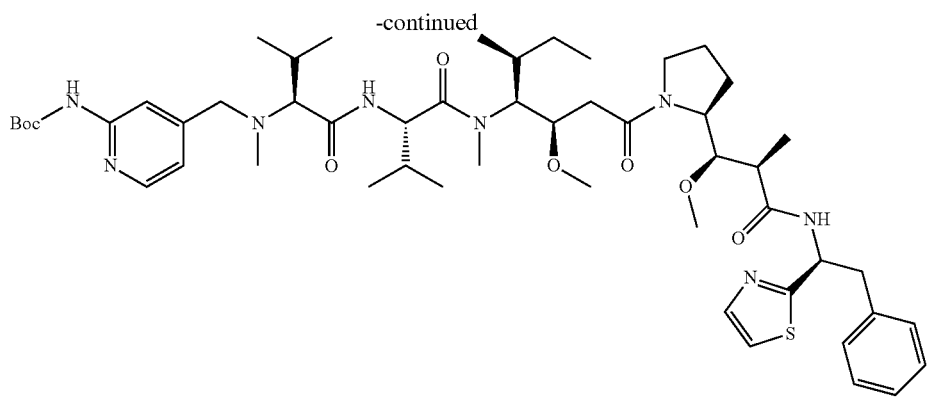

Compound 8A was synthesised in the same manner as for compound 2J from the amine 1Y (39 mg, 0.06 mmol, 1.00 equiv), the acid 2I (20 mg, 0.06 mmol, 1.00 equiv), HATU (27 mg, 0.07 mmol, 1.20 equiv) and DIEA (23.2 mg, 0.18 mmol, 3.01 equiv) in DCM (3 mL). The crude product was not purified.

Compound 8

Compound 8 was synthesised in similar manner to compound 2 from the intermediate 8A (100 mg, 0.10 mmol, 1.00 equiv). The crude product (100 mg) was purified by preparative HPLC (Pre-HPLC-001 SHIMADZU, SunFire Prep C18 OBD column, 5 μm, 19×150 mm; Eluting phase: water/ACN buffered with 0.05% TFA; Gradient of 18% to 31% ACN in 7 minutes then 31% to 100% ACN in 2 minutes; Waters 2489 UV Detector at 254 nm and 220 nm). Compound 8 was obtained with a yield of 8% (8 mg) in the form of a white solid.

LC/MS/UV (Atlantis T3 column, 3 μm, 4.6×100 mm; 35° C.; 1.8 mL/min, 25% to 80% ACN in water (0.05% TFA) in 7 minutes); ESI ($C_{47}H_{72}N_8O_6S$, exact mass 876.5) m/z: 877.5 (MH$^+$) and 439.5 (M.2H$^+$/2, 100%), 4.87 min (95.1%, 254 nm).

$^1$H NMR (400 MHz, CD$_3$OD, ppm): δ (Presence of rotamers) 7.83-7.78 (m, 2H); 7.56-7.52 (m, 1H); 7.34-7.17 (m, 5H); 6.64-6.62 (m, 2H); 5.77-5.61 (m, 1H); 4.86-4.68 (m, 2H); 4.25-4.05 (m, 1H); 3.87-2.83 (m, 17H); 2.56-0.84 (m, 37H).

Compound 9 methyl (S)-2-((2R,3R)-3-((S)-1-((3R,4S,5S)-4-((S)-2-((S)-2-(((2-aminopyridin-4-yl)methyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate, trifluoroacetic acid

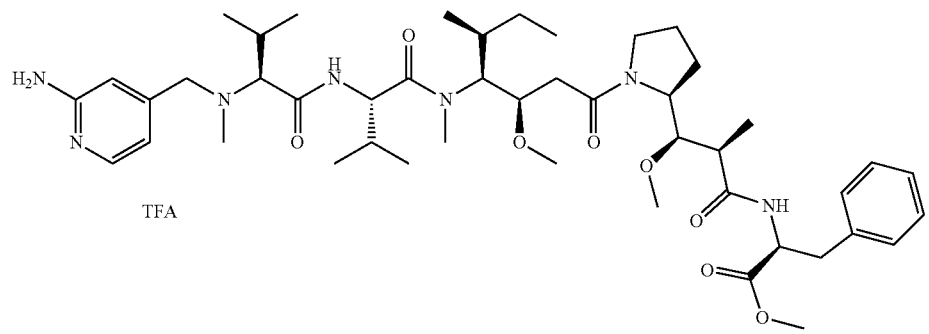 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)Cc1ccnc(N)c1)C(C)C]

Compound 9A methyl (S)-2-((2R,3R)-3-((S)-1-((3R,4S,5S)-4-((S)-2-((S)-2-(((2-((tert-butoxycarbonyl)amino)pyridin-4-yl)methyl)(methyl)amino)-3-methyl butanamido)-N,3-dimethylbutanamido)-3-methoxy-5-methylheptanoyl)pyrrolidin-2-yl)-3-methoxy-2-methylpropanamido)-3-phenylpropanoate

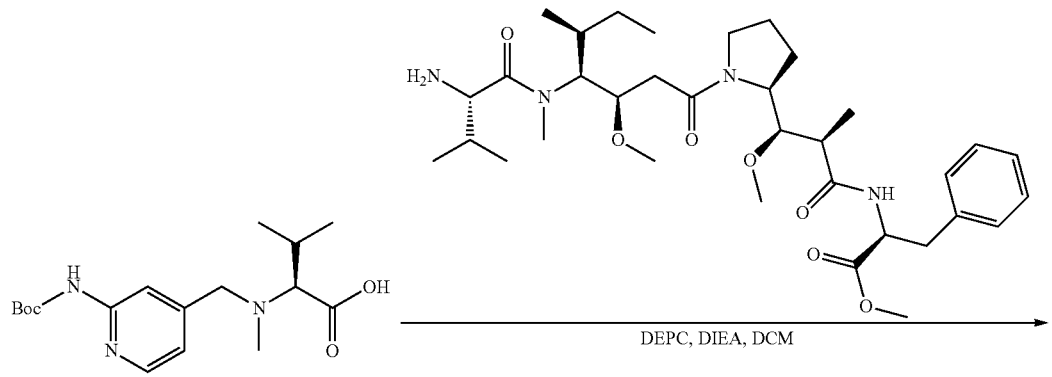

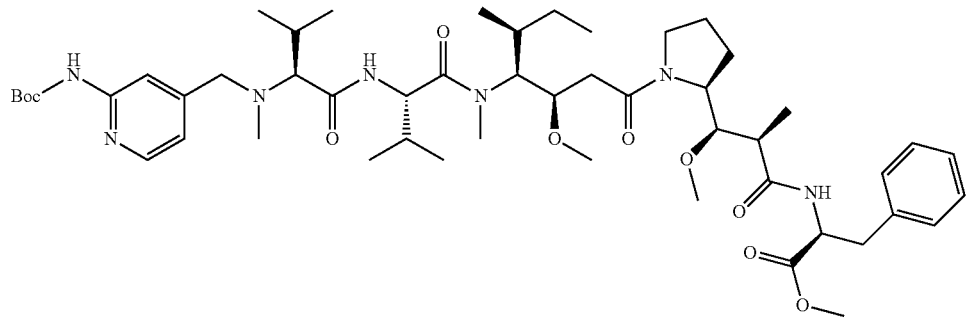

Compound 9A was synthesised in the same manner as for compound 3 from the amine 3D (170 mg, 0.27 mmol, 1.00 equiv), the acid 2I (99.7 mg, 0.30 mmol, 1.10 equiv), DEPC (0.049 mL, 1.05 equiv) and DIEA (0.133 mL, 3.00 equiv) in DCM (5 mL). The crude product was purified on a silica column with a mixture of EtOAc and PE (1:1) to yield 200 mg (78%) of compound 9A in the form of a pale yellow solid.

Compound 9

Compound 9 was synthesised in the same manner as for compound 2 from the intermediate 9A (200 mg, 0.21 mmol, 1.00 equiv) in DCM (4 mL) and TFA (2 mL). The crude product was purified by preparative HPLC (Pre-HPLC-001 SHIMADZU, SUNFIRE™ Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm). Compound 9 was obtained with a yield of 10% (20 mg) in the form of a white solid.

LC/MS/UV (Ascentis Express C18 column, 2.7 μm, 4.6× 100 mm; 40° C.; 1.5 mL/min, 10% to 95% MeOH in water (0.05% TFA) in 8 minutes); ESI ($C_{46}H_{73}N_7O_8$, exact mass 851.6) m/z: 852.5 ($MH^+$) and 426.9 ($M.2H^+/2$, 100) 6.92 min (92.7%, 254 nm).

$^1$H NMR (400 MHz, $CD_3OD$, ppm): δ (Presence of rotamers) 8.51-8.45 (m, 0.5H, NH incomplete exchange); 8.30-8.24 (m, 0.3H, NH incomplete exchange); 8.17-8.07 (m, 0.8H, NH incomplete exchange); 7.79-7.77 (m, 1H); 7.36-7.18 (m, 5H); 7.21-7.16 (m, 1H); 6.94-6.89 (m, 1H); 4.85-4.65 (m, 3H); 4.20-3.10 (m, 20H); 3.00-2.85 (m, 2H); 2.55-0.80 (m, 36H).

Compound 10

(S)-2-((2R,3R)-3-((S)-1-((3R,4S,5S)-4-((S)-2-((S)-2-(((2-aminopyridin-4-yl)methyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid, trifluoroacetic acid

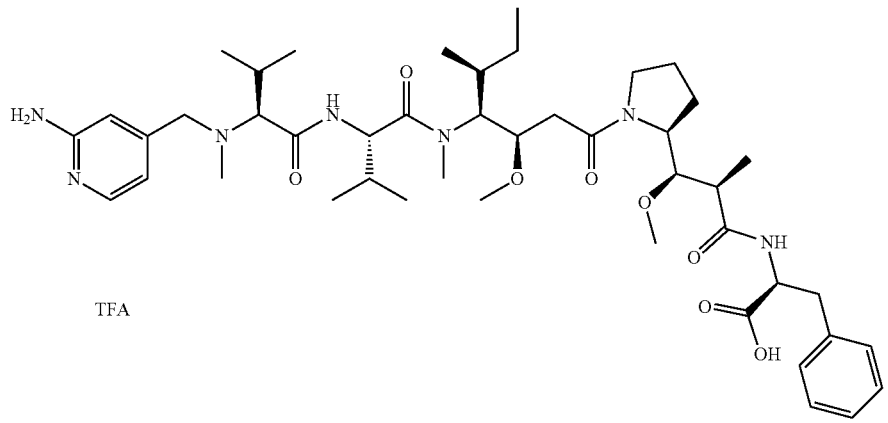 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)Cc1ccnc(N)c1)C(C)C]

Compound 10: Compound 9 (100 mg, 0.11 mmol, 1.00 equiv) was dissolved in a mixture of water (5 mL), ACN (5 mL) and piperidine (2.5 mL). The reaction mixture was left under agitation overnight at ambient temperature and then concentrated under reduced pressure. The residue was purified by preparative HPLC (Pre-HPLC-001 SHIMADZU, SUNFIRE™ Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 32.2 mg (33%) of compound 10 in the form of a white solid.

LC/MS/UV (Ascentis Express C18 column, 2.7 μm, 4.6×100 mm; 40° C.; 1.5 mL/min, 10% to 95% MeOH in water (0.05% TFA) in 8 minutes); ESI ($C_{45}H_{71}N_7O_6$, exact mass 837.5) m/z: 838.5 (MH$^+$) and 419.9 (M.2H$^+$/2, 100) 6.81 min (97.7%, 220 nm).

$^1$H NMR (400 MHz, CD$_3$OD, ppm): δ (Presence of rotamers) 8.41-8.32 (m, 0.3H, NH incomplete exchange); 8.20-8.07 (m, 0.8H, NH incomplete exchange); 7.82-7.75 (m, 1H); 7.36-7.158 (m, 5H); 7.12-7.03 (m, 1H); 6.94-6.88 (m, 1H); 4.85-4.66 (m, 3H); 4.20-3.10 (m, 16H); 3.00-2.85 (m, 2H); 2.57-0.80 (m, 37H).

Compound 11

(S)—N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethyl-2-((S)-3-methyl-2-(methyl(4-(methylamino)phenethyl)amino)butanamido)butanamide, trifluoroacetic acid

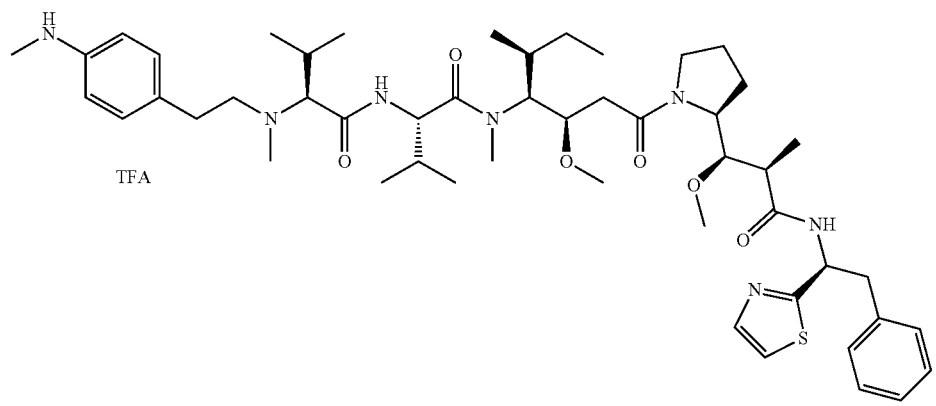 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCc1ccc(NC)cc1)C(C)C]

Compound 11A tert-butyl N-[4-(2-hydroxyethyl)phenyl]carbamate

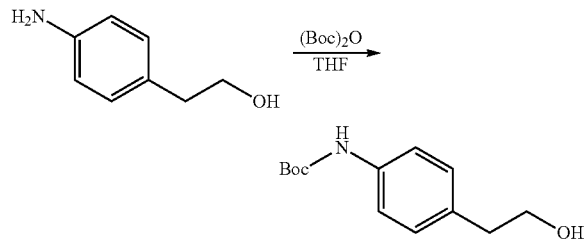

Di-tert-butyl dicarbonate (16.7 g, 77 mmol, 1.05 eq.) was added to a solution of 2-(4-aminophenyl)ethanol (10 g, 72.9 mmol, 1 eq.) in THF (200 mL), and the reaction stirred overnight at ambient temperature. The mixture was diluted with EtOAc (200 mL), washed with water (200 mL), then HCl 1M (100 mL), then saturated aqueous NaHCO$_3$ solution (100 mL) then brine (100 mL). The organic phase was dried over MgSO$_4$ then evaporated to dryness under reduced pressure. The crude product was triturated twice with heptane (150 mL) and dried under vacuum to furnish compound 11A as a white solid (14.7 g, 84%).

Compound 11B tert-butyl N-[4-(2-oxoethyl)phenyl]carbamate

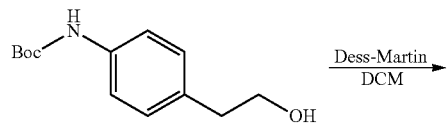

Compound 11A (2.5 g, 10.5 mmol, 1.00 equiv) was dissolved in 25 mL of DCM then cooled to −78° C. A Dess-Martin Periodinane solution (DMP, 6.71 g, 15.8 mmol, 1.5 equiv) in DCM (10 mL) was added drop-wise. The cold bath was removed and agitation continued for 1 hour at ambient temperature. The reaction was neutralised with 60 mL of a 50/50 mixture of sodium bicarbonate-saturated aqueous solution and Na$_2$S$_2$O$_3$-saturated aqueous solution. The resulting solution was extracted 3 times with 30 mL of EtOAc. The organic phases were combined, washed twice with NaCl-saturated aqueous solution, dried over anhydrous sodium sulfate, filtered and concentrated under reduced pressure. The residue was purified on silica gel (EtOAc/PE 1/15) to yield 1.0 g (40%) of compound 11B in the form of a pale yellow solid.

Compound 11C benzyl (2S)-2-[[2-(4-[[(tert-butoxy)carbonyl]amino]phenyl) ethyl](methyl)amino]-3-methylbutanoate

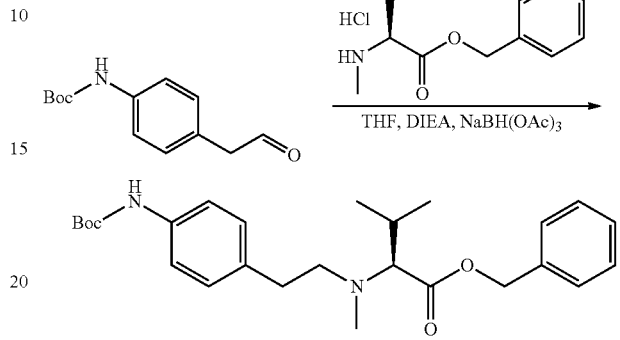

Compound 1ZC (3.5 g, 13.6 mmol, 1.1 equiv) was dissolved in THF (30 mL) in the presence of DIEA (6.4 g, 49.7 mmol, 4.0 equiv), aldehyde 11B (2.9 g, 12.3 mmol, 1.0 equiv) and sodium triacetoxyborohydride (5.23 g, 49.7 mmol, 2.0 equiv). The reaction mixture was left under agitation overnight at ambient temperature, then neutralised with 60 mL of sodium bicarbonate-saturated solution. The resulting solution was extracted 3 times with 30 mL EtOAc. The organic phases were combined, washed twice with NaCl-saturated aqueous solution, dried over anhydrous sodium sulfate, filtered and concentrated under reduced pressure. The residue was purified on silica gel (EtOAc/PE 1:20) to yield 3.7 g (68%) of compound 11C in the form of a yellow oil.

Compound 11D (2S)-2-[[2-(4-[[(tert-butoxy)carbonyl]amino]phenyl) ethyl](methyl)amino]-3-methylbutanoicacid

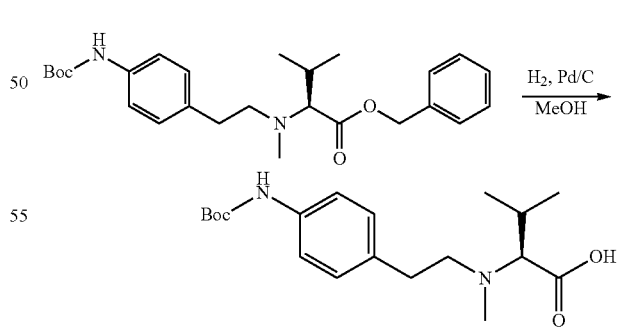

Compound 11C (2 g, 4.5 mmol, 1 equiv) was dissolved in 10 mL of methanol in the presence of Pd/C (2 g) and hydrogenated for 2 hours at normal temperature and pressure. The reaction medium was filtered and concentrated under reduced pressure to yield 1.2 g (75%) of compound 11D in the form of a yellow oil.

Compound 11E (2S)-2-[[2-(4-[[(tert-butoxy)carbonyl](methyl)amino]phenyl) ethyl](methyl) amino]-3-methylbutanoic acid

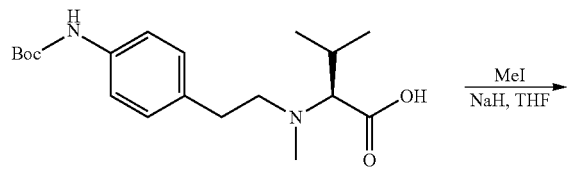

Compound 11D (1.2 g, 3.4 mmol, 1.00 equiv) was dissolved in an inert atmosphere in THF (20 mL). The reaction medium was cooled with an ice bath after which NaH (60% in oil, 549 mg, 13.7 mmol, 4.0 equiv) was added in portions, followed by iodomethane (4.9 g, 34 mmol, 10 equiv). The reaction was left under agitation overnight at ambient temperature, then neutralised with water and washed with 100 mL of EtOAc. The pH of the aqueous solution was adjusted to 6-7 with 1N HCl. This aqueous solution was extracted 3 times with 100 mL of EtOAc. The organic phases were combined, dried over sodium sulfate, filtered and concentrated to yield 800 mg (64%) of compound 11E in the form of a yellow solid.

Compound 11F tert-butyl N-[4-(2-[[(1S)-1-[[(1S)-1-[[(3R,4S,5S)-3-methoxy-1-[(2S)-2-[(1R,2R)-1-methoxy-2-methyl-2-[[(1S)-2-phenyl-1-(1,3-thiazol-2-yl)ethyl]carbamoyl]ethyl]pyrrolidin-1-yl]-5-methyl-1-oxoheptan-4yl](methyl)carbamoyl]-2-methylpropyl]carbamoyl]-2-methylpropyl](methyl)amino]ethyl)phenyl]-N-methylcarbamate

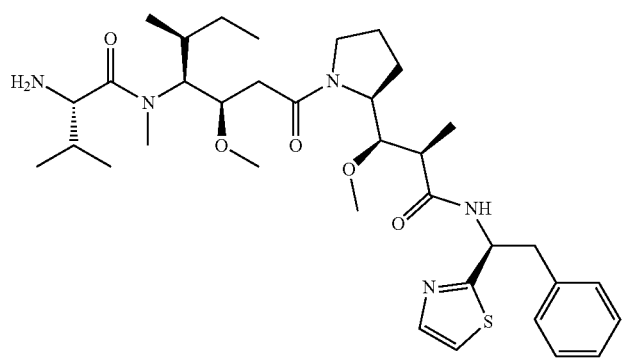

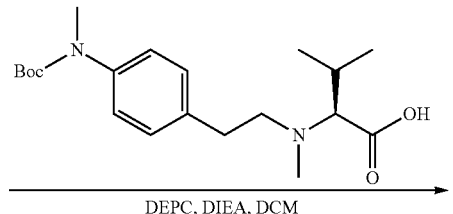

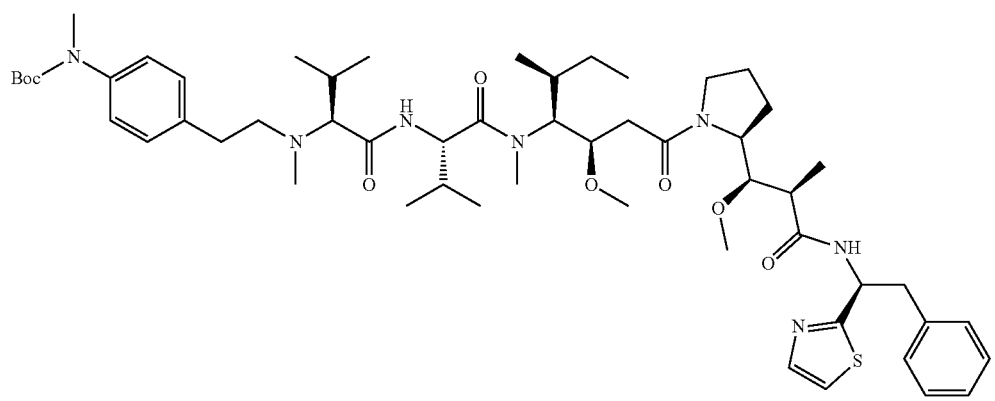

Compound 11F was prepared in similar manner to compound 6A from the amine 1Y (150 mg, 0.22 mmol, 1.2 equiv) and the acid 11E (70 mg, 0.19 mmol, 1.0 equiv). After purification on silica gel (EtOAc/PE 1:1) 100 mg (52%) of desired product were obtained in the form of a pale yellow solid.

Compound 11 was prepared in the same manner as for compound 1 from the intermediate 11F (100 mg, 0.1 mmol). The residue was purified by preparative HPLC (Pre-HPLC-001 SHIMADZU, SUNFIRE™ Prep C18 OBD column, 5 µm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm). Compound 11 was obtained with a yield of 39% (39.7 mg) in the form of a white solid.

LC/MS/UV (Eclipse Plus C8, 3.5 µm, 4.6×150 mm; 1 mL/min, 40° C., 50 to 95% methanol in water (0.05% TFA) in 18 minutes); ESI ($C_{50}H_{77}N_7O_6S$, exact mass 903.57) m/z: 904.5 (MH$^+$), 7.53 min (93.68%, 254 nm).

$^1$H NMR (300 MHz, CD$_3$OD, ppm): δ (Presence of rotamers) 8.84 (d, 0.5H, NHCO incomplete exchange); 8.7-8.5 (m, 0.9H, NHCO incomplete exchange); 7.76-7.73 (m, 1H); 7.55-7.4 (m, 1H); 7.28-7.22 (m, 7H); 7.08-7.05 (m, 2H); 5.51-5.72 (m, 1H); 4.9-4.80 (m, 2H); 4.3-0.7 (m, 60H).

Compound 12 methyl (S)-2-((2R,3R)-3-((S)-1-((3R,4S,5S)-4-((S)—N,3-dimethyl-2-((S)-3-methyl-2-(methyl(4-(methylamino)phenethyl)amino)butanamido)butanamido)-3-methoxy-5-methylheptanoyl)pyrrolidin-2-yl)-3-methoxy-2-methylpropanamido)-3-phenylpropanoate, trifluoroacetic acid

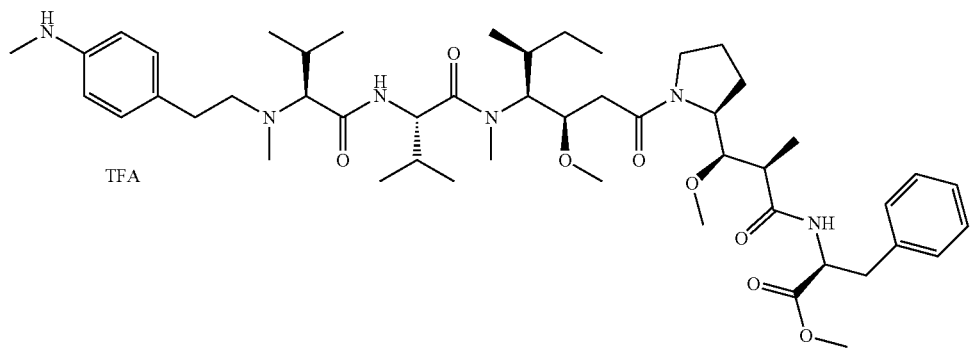 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(NC)cc1)C(C)C]

In the same manner as for the final phases in the synthesis of compound 1, compound 12 was prepared in two steps from the amine 3D (118 mg, 0.19 mmol) and the acid 11E (82 mg, 0.22 mmol). The final residue was purified by preparative HPLC (Pre-HPLC-001 SHIMADZU, SUNFIRE™ Prep C18 OBD column, 5 µm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm). Compound 12 was obtained with a yield of 7% (13.7 mg) in the form of a white solid.

LC/MS/UV (Eclipse Plus C8, 3.5 µm, 4.6×150 mm; 1 mL/min, 40° C., 40 to 95% methanol in water (0.05% TFA) in 18 minutes); ESI ($C_{49}H_{78}N_6O_8$, exact mass 878.59) m/z: 879.7 (MH$^+$), 10.07 min (90.6%, 254 nm).

$^1$H:NMR (300 MHz, CD$_3$OD, ppm): δ (Presence of rotamers) 7.40 (se, 2H); 7.38-7.22 (m, 7H); 4.95-4.7 (m, 3H); 4.2-4.0 (m, 1H); 3.9-0.86 (m, 62H).

Compound 13

(S)-2-((2R,3R)-3-((S)-1-((3R,4S,5S)-4-((S)—N,3-dimethyl-2-((S)-3-methyl-2-(methyl(4-(methylamino)phenethyl)amino)butanamido)butanamido)-3-methoxy-5-methyl heptanoyl)pyrrolidin-2-yl)-3-methoxy-2-methylpropanamido)-3-phenylpropanoic acid, trifluoroacetic acid

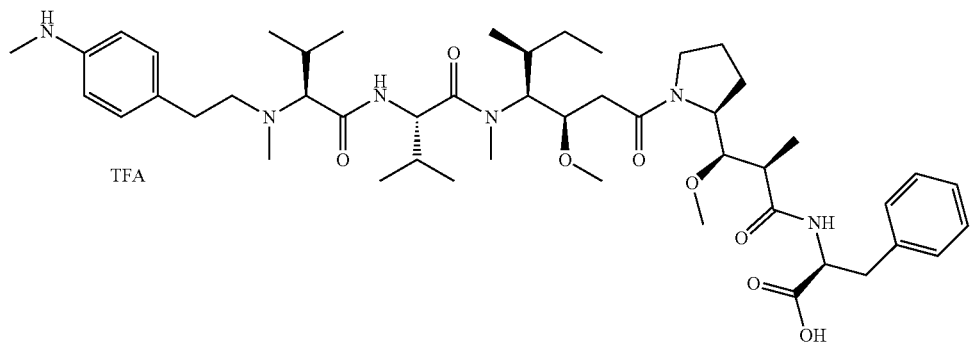 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(NC)cc1)C(C)C]

Compound 13 was prepared in the same manner as for compound 7 from compound 12 (100 mg, 0.10 mmol). The residue was purified by preparative HPLC (Pre-HPLC-001 SHIMADZU, SUNFIRE™ Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm). Compound 13 was obtained with a yield of 20% (20 mg) in the form of a white solid.

LC/MS/UV (Ascentis Express C18, 2.7 μm, 4.6×100 mm; 1.5 mL/min, 40° C., 10 to 95% methanol in water (0.05% TFA) in 8 minutes); ESI ($C_{48}H_{76}N_6O_8$, exact mass 864.57) m/z: 865.6 (MH$^+$), 6.05 min (90.9%, 210 nm).

$^1$H NMR: (300 MHz, CD$_3$OD, ppm): δ (Presence of rotamers) 7.32-7.19 (m, 9H); 4.9-4.65 (m, 3H); 4.2-4.0 (m, 1H); 3.9-0.86 (m, 59H).

Compound 14

(S)-2-((S)-2-((3-aminobenzyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, trifluoroacetic acid

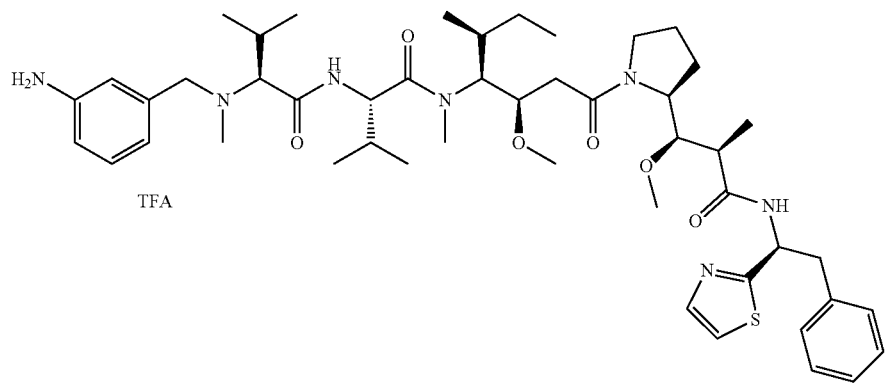 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)Cc1cccc(N)c1)C(C)C]

171
Compound 14A tert-butyl (3-(hydroxymethyl)phenyl) carbamate

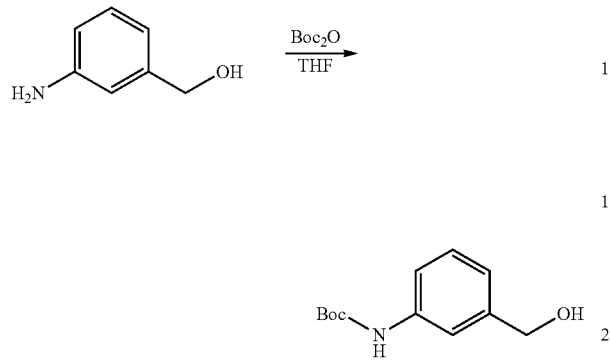

(3-aminophenyl)methanol (3 g, 24.36 mmol, 1.00 equiv) was dissolved in THF (60 mL) after which di-tert-butyl dicarbonate (6.38 g, 29.23 mmol, 1.20 equiv) was then added. The reaction mixture was left under agitation overnight at ambient temperature and the reaction was then diluted by adding 200 mL of water. The product was extracted 3 times with 100 mL of AcOEt and the organic phases were then recombined, dried over sodium sulfate, filtered and concentrated under reduced pressure to yield the crude product (13.85 g of compound 14A) in the form of a yellow oil.

Compound 14B tert-butyl (3-formylphenyl)carbamate

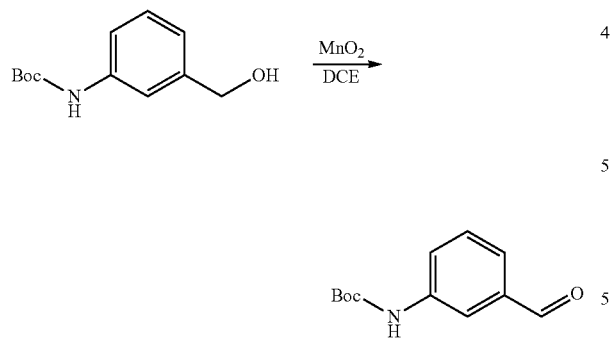

Compound 14A (13.8 g, 61.81 mmol, 1.00 equiv) was dissolved in DCE (400 mL) and $MnO_2$ (54 g, 621.14 mmol, 10.05 equiv) was then added. The mixture was left under agitation at ambient temperature for 3 days after which the solids were removed by filtering. The filtrate was evaporated to dryness and the residue was purified on a silica column with a mixture of EtOAc and PE (1:30) to yield 3 g (22%) of compound 14B in the form of a white solid.

172
Compound 14C benzyl (S)-2-((3-((tert-butoxycarbonyl)amino)benzyl)(methyl)amino)-3-methylbutanoate

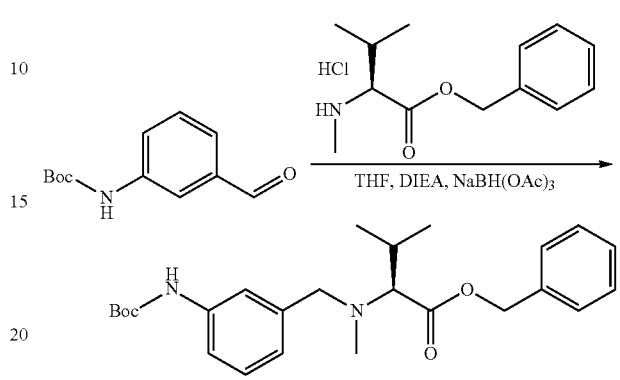

Compound 14B (1 g, 4.52 mmol, 1.00 equiv) was dissolved in 20 mL of THF in the presence of compound 1ZC (1.16 g, 4.50 mmol, 1.00 equiv), DIEA (3 mL) and $NaBH(OAc)_3$ (1.92 g, 9.06 mmol, 2.01 equiv). The reaction mixture was left under agitation overnight at ambient temperature and then neutralised with 100 mL of water and extracted 3 times with 50 mL of AcOEt. The organic phases were combined, dried over sodium sulfate, filtered and concentrated. The residue was purified on a silica column with a mixture of EtOAc and PE (1:50) to yield 1.9 g (99%) of compound 14C in the form of a white solid.

Compound 14D (S)-2-((3-((tert-butoxycarbonyl)amino)benzyl)(methyl)amino)-3-methylbutanoicacid

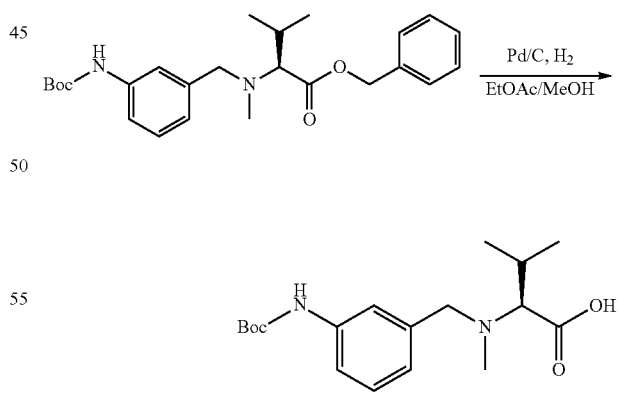

Compound 14C (1 g, 2.34 mmol, 1.00 equiv) was dissolved in 30 mL of AcOEt and 4 mL of methanol in the presence of Pd/C (400 mg) and hydrogenated for 1 hour at ambient temperature and atmospheric pressure. The reaction medium was filtered and concentrated under reduced pressure to yield 680 mg (86%) of compound 14D in the form of a white solid.

Compound 14E tert-butyl (3-((3S,6S,9S,10R)-9-((S)-sec-butyl)-3,6-diisopropyl-10-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-2,8-dimethyl-4,7-dioxo-11-oxa-2,5,8-triazadodecyl)phenyl)carbamate

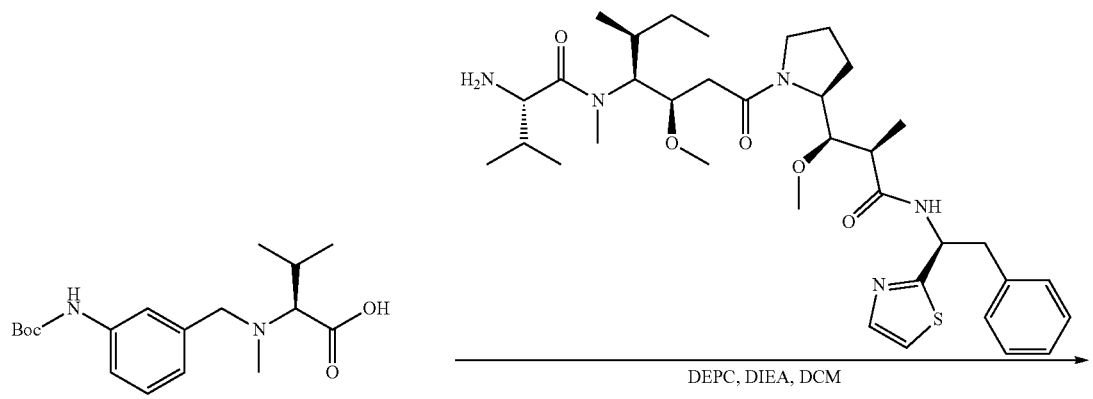

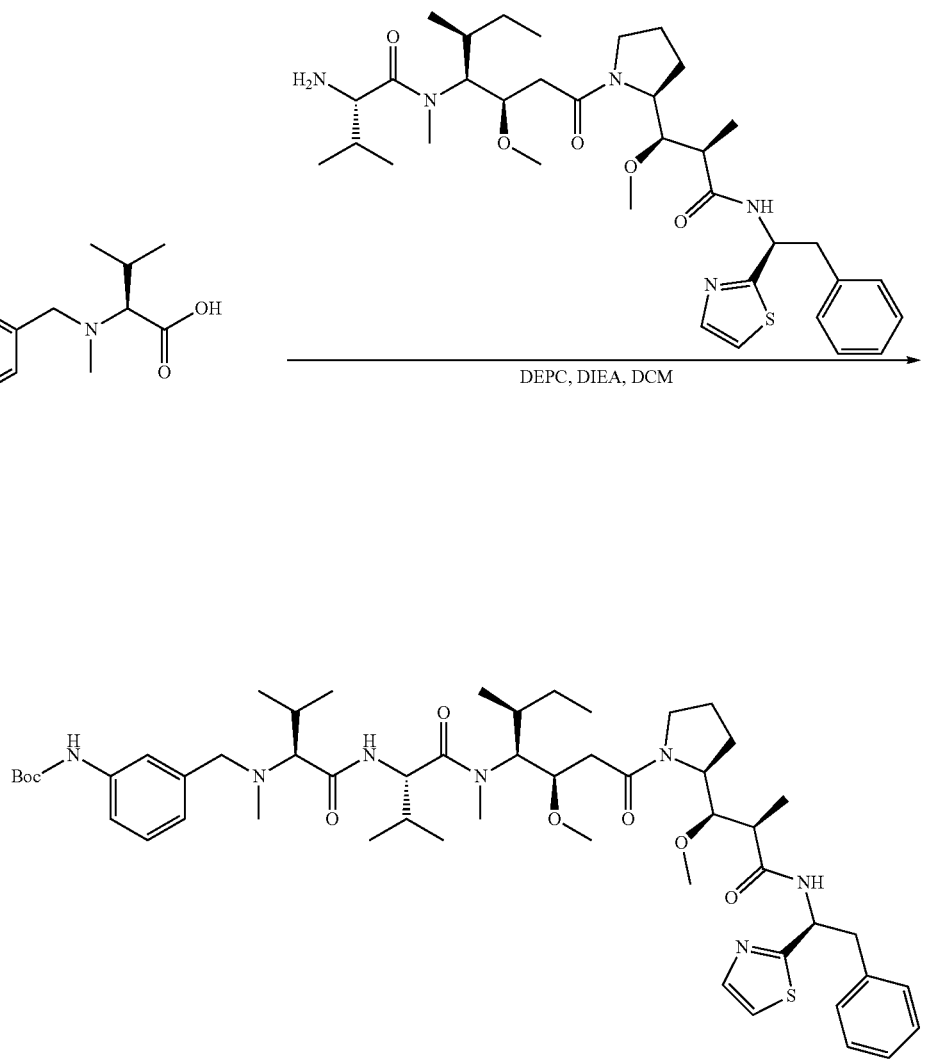

Compound 14E was synthesised in the same manner as for compound 3 from the amine 1Y (100 mg, 0.15 mmol, 1.00 equiv), the acid 14D (102.27 mg, 0.30 mmol, 2.00 equiv), DEPC (0.053 mL) and DIEA (0.046 mL) in DCM (3 mL). The crude product (80 mg) was purified on a silica column with a mixture of EtOAc and PE (1:1) to yield 100 mg (67%) of compound 14E in the form of a pale yellow solid.

Compound 14 was synthesised in the same manner as for compound 2 from the intermediate 14E (100 mg, 0.10 mmol, 1.00 equiv). The crude product (80 mg) was purified by preparative HPLC (Pre-HPLC-001 SHIMADZU, SUN-FIRE™ Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm). Compound 14 was obtained with a yield of 10% (10 mg) in the form of a white solid.

LC/MS/UV (Eclipse plus C8 column, 3.5 μm, 4.6×150 mm; 40° C.; 1.0 mL/min, 40% to 95% MeOH in water (0.05% TFA) in 18 minutes); ESI ($C_{48}H_{73}N_7O_6S$, exact mass 875.5) m/z: 876.5 ($MH^+$) and 438.9 ($M.2H^+/2$, 100%), 11.35 min (95.60% 210 nm).

$^1$H NMR (400 MHz, $CD_3OD$, ppm): δ (Presence of rotamers) 8.92-8.86 (m, 0.4H, NH incomplete exchange); 8.70-8.54 (m, 0.6H, NH incomplete exchange); 7.88-7.78 (m, 1H); 7.60-7.50 (m, 1H); 7.45-6.97 (m, 9H); 5.80-5.65 (m, 1H); 4.85-4.70 (m, 1H); 4.40-0.80 (m, 56H).

Compound 15 methyl (S)-2-((2R,3R)-3-((S)-1-((3R,4S,5S)-4-((S)-2-((S)-2-((3-aminobenzyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate, trifluoroacetic acid

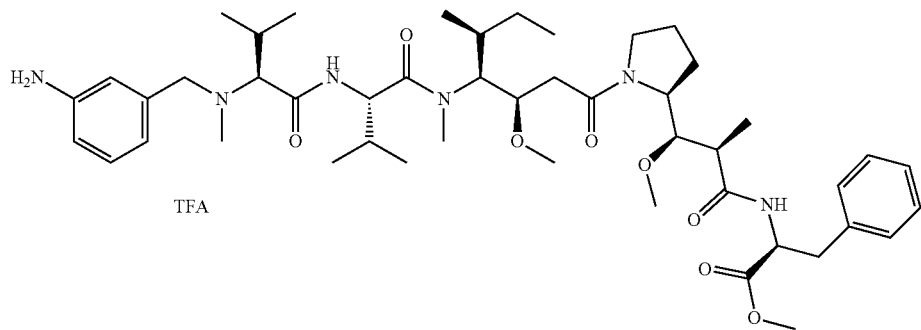 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)Cc1cccc(N)c1)C(C)C]

TFA

Compound 15A methyl (S)-2-((2R,3R)-3-((S)-1-((3R,4S,5S)-4-((S)-2-((S)-2-((3-((tert-butoxycarbonyl)amino)benzyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate

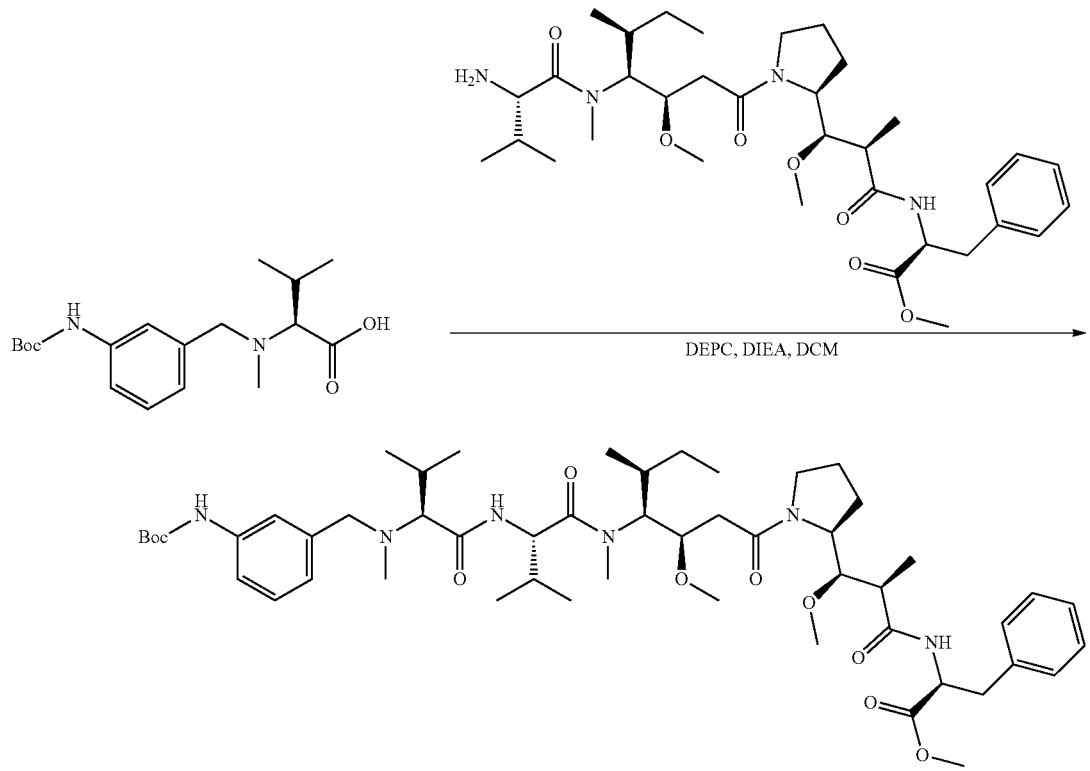

Compound 15A was synthesised in the same manner as for compound 3 from the amine 3D (200 mg, 0.32 mmol, 1.00 equiv), the acid 14D (212.6 mg, 0.63 mmol, 2.00 equiv), DEPC (0.1103 mL) and DIEA (0.157 mL, 3.00 equiv) in DCM (5 mL). The crude product was purified on a silica column with a mixture of EtOAc and PE (1:1) to yield 200 mg (67%) of compound 15A in the form of a yellow solid.

Compound 15 was synthesised in the same manner as for compound 2 from the intermediate 15A (200 mg, 0.21 mmol, 1.00 equiv). The crude product was purified by preparative HPLC (Pre-HPLC-001 SHIMADZU, SUNFIRE™ Prep C18 OBD column, 5 µm, 19×150 mm; Eluting phase: water/ACN buffered with 0.05% TFA; Gradient of 20% to 40% ACN in 10 minutes then 40% to 100% ACN in 2 minutes; Waters UV Detector 2545 at 254 nm and 220 nm). Compound 15 was obtained with a yield of 19% (38.6 mg) in the form of a white solid.

LC/MS/UV (Ascentis Express C18 column, 2.7 µm, 4.6× 100 mm; 40° C.; 1.5 mL/min, 10% to 95% MeOH in water (0.05% TFA) in 8 minutes); ESI ($C_{47}H_{74}N_6O_8$, exact mass 850.5) m/z: 851.5 (MH$^+$) and 426.4 (M.2H$^+$/2, 100%) 6.61 min (91.1%, 210 nm).

$^1$H NMR (400 MHz, CD$_3$OD, ppm): δ (Presence of rotamers) 7.53-7.42 (m, 1H); 7.35-7.18 (m, 8H); 4.88-4.79 (m, 2H); 4.42-4.00 (m, 3H); 3.93-2.71 (m, 22H); 2.61-0.81 (m, 33H).

Compounds 16 to 20

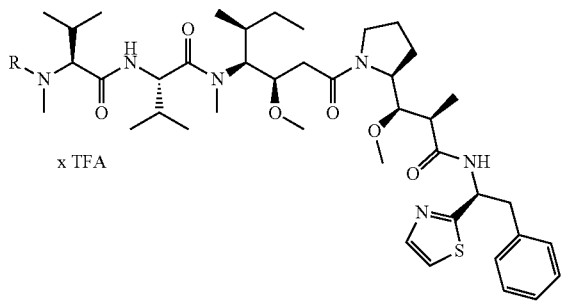

x TFA

Compounds 16 to 20 were prepared in the same manner as for compound 1, from the amines 1Y and 1ZC and corresponding aldehydes.

The tert-butyl (4-oxobutyl)carbamate, involved in the preparation of compound 16, was prepared as for compound ZE in 2 steps from 4,4-diethoxybutan-1-amine.

The tert-butyl-N-methyl-N-(2-oxoethyl)carbamate involved in the preparation of compound 17 was commercial.

The 2-(2-((tert-butyldimethylsilyl)oxy)ethoxy)acetaldehyde, involved in the preparation of compound 18, was prepared in 2 steps as follows:

2-(2-Hydroxyethoxy)ethan-1-ol (7 g, 66 mmol, 9.9 equiv) was dissolved in an inert atmosphere in pyridine (10 mL) in the presence of 4-dimethylaminopyridine (DMAP, 80 mg, 0.65 mmol, 0.1 equiv). The solution was cooled to 0° C. then TBDMSCl (1 g, 6.6 mmol, 1.0 equiv) was added in portions. The reaction mixture was left under agitation overnight at ambient temperature, diluted with 100 mL of EtOAc and successively washed twice with 100 mL of 1N HCl and twice with NaCl-saturated aqueous solution. The organic phase was dried over anhydrous sodium sulphate, filtered and concentrated under reduced pressure to yield 1.3 g (88%) of 2-[2-[(tert-butyldimethylsilyl)oxy]ethoxy]ethan-1-ol in the form of a colourless oil.

The oxalyl chloride (760 mg, 6 mmol, 1.3 equiv) was dissolved in an inert atmosphere in DCM (40 mL) and cooled to −78° C. Dimethylsulfoxide (DMSO, 1.07 g, 13.7 mmol, 3 equiv) diluted in DCM (5 mL) was added dropwise. After an agitation time of 30 minutes at low temperature, 2-[2-[(tert-butyldimethyl silyl)oxy]ethoxy]ethan-1-ol (1 g, 4.5 mmol, 1.0 equiv) dissolved in 5 mL of DCM was added. Agitation was continued for 1 hour at low temperature before adding TEA (2.78 g, 27 mmol, 6 equiv). The reaction mixture was agitated 15 minutes at −78° C. and overnight at ambient temperature before being neutralised with 100 mL of water. It was then extracted 3 times with 100 mL of DCM. The organic phases were combined, dried over anhydrous sodium sulfate, filtered and concentrated under reduced pressure. The residue was purified on silica gel (EtOAc/PE 1:20) and yielded 0.8 g (80%) of 2-[2-[(tert-butyldimethylsilyl)oxy]ethoxy]acetaldehyde in the form of a colourless oil.

The tert-butyl 4-formylphenyl carbonate involved in the preparation of compound 19 was prepared in a single step as follows: 4-hydroxybenzaldehyde (2.5 g, 20.5 mmol, 1.0 equiv) was dissolved in an inert atmosphere in THF (20 mL) in the presence of 18-crown-6 (0.25 g) and potassium carbonate (5 g). The reaction mixture was cooled to 0° C. and the di-tert-butyl dicarbonate (5.8 g, 26.58 mmol, 1.30 equiv) was then added. Agitation was continued for 1 hour at low temperature after which the reaction was neutralised with 30 mL of water. The resulting solution was extracted three times with 200 mL of EtOAc. The organic phases were combined, dried over anhydrous sodium sulfate filtered and concentrated under reduced pressure. The residue was purified on silica gel (EtOAc/PE 1:10) and yielded 4.2 g (92%) of tert-butyl 4-formylphenyl carbonate in the form of a pale yellow solid.

The 4-nitrobenzaldehyde involved in the preparation of compound 20 was commercial.

The synthesis of compound 18 was completed by deprotection of the silylated alcohol. This was performed as follows: (S)—N—((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-11-isopropyl-2,2,3,3,10-pentamethyl-4,7-dioxa-10-aza-3-siladodecan-12-amide (40 mg, 0.04 mmol, 1.0 equiv) was dissolved in an inert atmosphere in THF (10 mL) in the presence of TBAF (2 mg, 0.09 mmol, 2 equiv) and agitated 4 hours at ambient temperature. The reaction was neutralised with 50 mL of water then extracted three times with 50 mL of EtOAc. The organic phases were combined, dried over anhydrous sodium sulfate, filtered and concentrated under reduced pressure to yield compound 18 in the crude state.

The synthesis of compound 20 was completed by reducing the nitro group. This was performed as follows: (2S)—N-[(3R,4S,5S)-1-[(2S)-2-[(1R,2R)-2-[[(1S,2R)-1-hydroxy-1-phenylpropan-2-yl]carbamoyl]-1-methoxy-2-methylethyl]pyrrolidin-1-yl]-3-methoxy-5-methyl-1-oxoheptan-4-yl]-N,3-dimethyl-2-[(2S)-3-methyl-2-[methyl[(4-nitrophenyl)methyl]amino]butanamido]butanamide (40 mg, 0.05 mmol, 1.0 equiv) was dissolved in 15 mL of ethanol. Dihydrated tin chloride (II) (317 mg, 1.4 mmol, 30 equiv) was added and the solution left under agitation for 3 days at ambient temperature. The reaction was neutralised with 50 mL of water, then extracted three times with 50 mL of EtOAc. The organic phases were combined, dried over anhydrous sodium sulfate, filtered and concentrated under reduced pressure to yield compound 20 in the crude state.

| No | Name | x | R | Purity* | Quantity |
|---|---|---|---|---|---|
| 16 | (S)-2-((S)-2-((4-aminobutyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, bis trifluoroacetic acid | 2 |  | 94.9% | 11.5 mg |
| 17 | (S)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethyl-2-((S)-3-methyl-2-(methyl(2-(methylamino)ethyl)amino)butanamido)butanamide, bis trifluoroacetic acid | 2 | 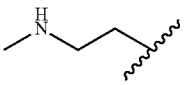 [SMILES: *CCNC] | 99.6% | 65.5 mg |
| 18 | (S)-2-((S)-2-((2-(2-hydroxyethoxy)ethyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, trifluoroacetic acid | 1 | 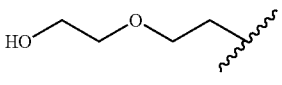 | 94.5% | 46.4 mg |
| 19 | (S)-2-((S)-2-((4-hydroxybenzyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, trifluoroacetic acid | 1 | 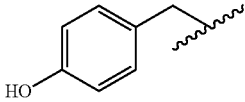 | 93.2% | 21.6 mg |
| 20 | (S)-2-((S)-2-((4-aminobenzyl)(methyl)amino)-3-methyl butanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, trifluoroacetic acid | 1 | 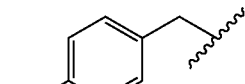 | 96.7% | 21.1 mg |

*The compounds were purified by preparative HPLC (Pre-HPLC-001 SHIMADZU, SUNFIRE ™ Prep C18 OBD column, 5 µm, 19 × 150 mm;

Eluting phase: water/ACN buffered with 0.05% TFA;

Gradient of 20% to 40% ACN in 10 minutes then 40% to 100% ACN in 2 minutes;

Waters 2489 UV Detector at 254 nm and 220 nm), to give the corresponding TFA salts in the form of white solids.

Characterization of the end products: Compound 16 LC/MS/UV (Eclipse Plus C8, 3.5 μm, 4.6×150 mm; 1 mL/min, 40° C., 5 to 95% methanol in water (0.05% TFA) in 18 minutes); ESI: ($C_{45}H_{75}N_7O_6S$, exact mass 841.55) m/z 842.5 (MH$^+$), 421.9 (100%, (M.2H$^+$)/2); UV: 14.02 min (94.9%, 210 nm). $^1$H NMR (300 MHz, CD$_3$OD, ppm): δ (Presence of rotamers) 8.55-8.2 (m, 0.8H, NHCO incomplete exchange); 8.0 (0.55H, NHCO incomplete exchange); 7.70 (d, 1H); 7.44 (d, 1H); 7.21-7.15 (m, 5H); 5.65-5.45 (m, 1H); 4.8-4.5 (m, 2H); 4.15-3.9 (m, 2H); 3.8-0.6 (m, 59H). Compound 17 LC/MS/UV ESI: ($C_{44}H_{73}N_7O_6S$, exact mass 827.53) m/z 828 (MH$^+$), 415 [100%, (M.2H$^+$)/2]; UV: RT=6.72 min (99.6%,254 nm)$^1$H NMR (400 MHz, CD$_3$OD, ppm): δ (Presence of rotamers) 7.82-7.80 (m, 1H); 7.56-7.54 (m, 1H); 7.35-7.20 (m, 5H); 5.8-5.55 (m, 1H); 4.85-4.6 (m, 1H); 4.25-4.05 (m, 1H); 3.95-0.8 (m, 60H). Compound 18 LC/MS/UV (Atlantis T3, 3 μm, 4.6×100 mm; 1.2 mL/min, 40° C., 5 to 95% methanol in water (0.05% TFA) in 7 minutes) i; ESI ($C_{45}H_{74}N_6O_8S$, exact mass 858.53) m/z 859 (MH$^+$), 881 (MNa$^+$), 430 (100%, (M.2H$^+$)/2); UV: 4.85 min (96.8%, 220 nm). $^1$H NMR (400 MHz, CD$_3$OD, ppm): δ (Presence of rotamers) 8.75-8.55 (m, 0.5H, NHCO incomplete exchange); 7.85-7.80 (m, 1H); 7.6-7.5 (m, 1H); 7.40-7.15 (m, 5H); 5.8-5.6 (m, 1H); 4.8-4.55 (m, 2H); 4.15-4.0 (m, 1H); 4.0-0.8 (m, 60H). Compound 19 LC/MS/UV ESI ($C_{48}H_{72}N_6O_7S$, exact mass 876.52) m/z 877 (MH$^+$), 439 [100%, (M.2H$^+$)/2]; UV: RT=1.76 min (93.2%, 220 nm). Compound 20 $^1$H NMR: (400 MHz, CD$_3$OD, ppm): δ (Presence of rotamers) 7.85-7.80 (m, 1H); 7.6-7.5 (m, 1H); 7.4-7.15 (m, 5H); 7.1-7.05 (m, 2H); 6.73-6.70 (m, 2H); 5.8-5.55 (m, 1H); 5.0-4.7 (m, 2H); 4.25-4.05 (m, 1H); 4.0-0.8 (m, 54H). LC/MS/UV ESI ($C_{48}H_{73}N_7O_7S$, exact mass 875.53) m/z 876 (MH$^+$), 439 [75%, (M.2H$^+$)/2]; UV: RT=4.83 min (96.8%, 254 nm). $^1$H NMR (400 MHz, CD$_3$OD, ppm): δ (Presence of rotamers) 7.85-7.80 (m, 1H); 7.6-7.5 (m, 1H); 7.4-7.1 (m, 7H); 6.76-6.72 (m, 2H); 5.8-5.55 (m, 1H); 4.9-4.65 (m, 2H); 4.25-4.05 (m, 1H); 4.0-0.8 (m, 54H).

Compounds 21 to 24

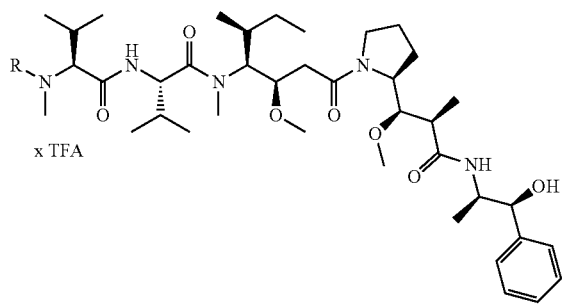

x TFA

Compounds 21 to 24 were prepared in the same manner as for compounds 17 to 20, replacing the amine 1Y by the amine 2D.

| No | Name | x | R | Purity* | Quantity |
|---|---|---|---|---|---|
| 21 | (S)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methyl(2-(methylamino)ethyl)amino)butanamido)butanamide, bis trifluoroacetic acid | 2 | (methylaminoethyl-methylamino group) | 97.5% | 24.4 mg |
| 22 | (S)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-2-((S)-2-((2-(2-hydroxyethoxy)ethyl)(methyl)amino)-3-methylbutanamido)-N,3-dimethylbutanamide, trifluoroacetic acid | 1 | HO-CH$_2$CH$_2$-O-CH$_2$CH$_2$- | 95.5% | 26.1 mg |
| 23 | (S)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-2-((S)-2-((4-hydroxybenzyl)(methyl)amino)-3-methylbutanamido)-N,3-dimethylbutanamide, trifluoroacetic acid | 1 | 4-hydroxybenzyl | 98.5% | 5.8 mg |

-continued

| No | Name | x | R | Purity* | Quantity |
|---|---|---|---|---|---|
| 24 | (S)-2-((S)-2-((4-aminobenzyl)(methyl)amino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide, trifluoroacetic acid | 1 | ![structure] | 99.1% | 6.9 mg |

*The compounds were purified by preparative HPLC (Pre-HPLC-001 SHIMADZU, SUNFIRE™ Prep C18 OBD column, 5 µm, 19 × 150 mm;
Eluting phase: water/ACN buffered with 0.05 % TFA;
Gradient of 20% to 40% ACN in 10 minutes then 40% to 100% ACN in 2 minutes;
Waters 2489 UV Detector at 254 nm and 220 nm), to give the corresponding TFA salts in the form of white solids.

Characterization of the end products: Compound 21 LC/MS/UV (ESI) ($C_{42}H_{74}N_6O_7$, exact mass 774.56) m/z 775 (MH$^+$), 797 (MNa$^+$), 388 (100%, (M.2H$^+$)/2); UV: 3.14 min (97.600, 215 nm). $^1$H NMR (400 MHz, CD$_3$OD, ppm): δ (Presence of rotamers) 8.05-7.7 (m, 0.8H, NHCO incomplete exchange); 7.45-7.15 (m, 5H); 4.9-4.45 (m, 2H); 4.35-4.00 (m, 2H); 3.95-0.8 (m, 61H). Compound 22 LC/MS/UV (ESI) ($C_{43}H_{75}N_5O_9$, exact mass 805.56) m/z 806 (MH$^+$), 828 (MNa$^+$), 404 (100%, (M.2H$^+$)/2); UV: 4.47 min (95.6%, 215 nm). $^1$H NMR: (400 MHz, CD$_3$OD, ppm): δ (Presence of rotamers) 8.1-7.7 (m, 0.4H, NHCO incomplete exchange); 7.45-7.15 (m, 5H); 4.9-4.5 (m, 3H); 4.4-4.05 (m, 2H); 4.05-0.8 (m, 61H). Compound 23 LC/MS/UV (ESI) ($C_{46}H_{73}N_5O_8$, exact mass 823.55) m/z 824 (MH$^+$), 846 (MNa$^+$), 413 (100%, (M.2H$^+$)/2); UV: 4.76 min (98.5%, 215 nm). $^1$H NMR (400 MHz, CDCl$_3$, ppm): δ (Presence of rotamers) 7.5-7.2 (m, 5H); 7.9-7.75 (m, 2H); 5.5-5.3 (m, 1H); 4.9-4.6 (m, 2H); 4.55-4.15 (m, 4H); 4.0-0.8 (m, 55H). Compound 24 LC/MS/UV (ESI) ($C_{46}H_{74}N_6O_7$, exact mass 822.56) m/z 823 (MH$^+$), 845 (MNa$^+$), 861 (MK$^+$); UV: 3.68 min (99.15%, 254 nm). $^1$H NMR (400 MHz, CD$_3$OD, ppm): δ (Presence of rotamers) 8.0-7.7 (m, 0.5H, NHCO incomplete exchange); 7.5-7.0 (m, 7H); 6.75-6.65 (m, 2H); 4.85-4.5 (m, 2H); 4.4-4.05 (m, 2H); 4.0-0.8 (m, 56H).

Compound 26

(S)-2-((S)-2-((2-aminoethyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, bis trifluoroacetic acid

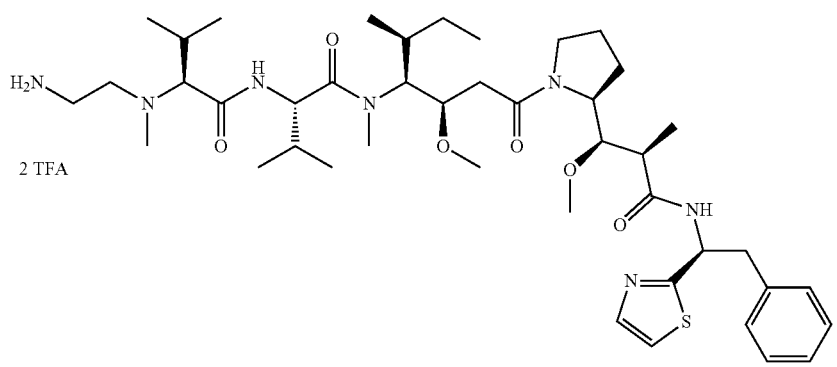 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCN)C(C)C]

2 TFA

Compound 26A benzyl (S)-2-((2-((tert-butoxycarbonyl)amino)ethyl)(methyl) amino)-3-methylbutanoate

Compound 26B (S)-2-((2-((tert-butoxycarbonyl)amino)ethyl)(methyl)amino)-3-methylbutanoicacid

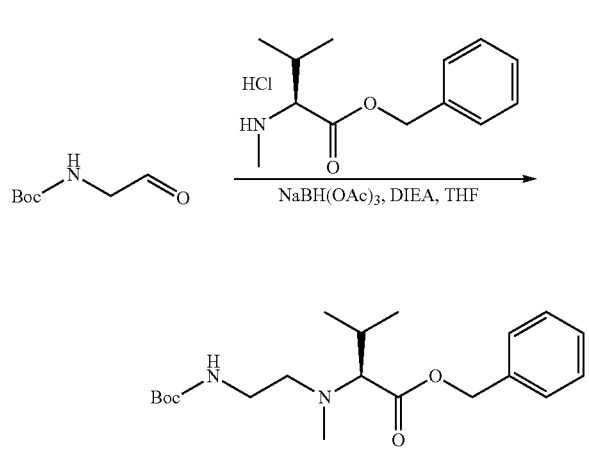

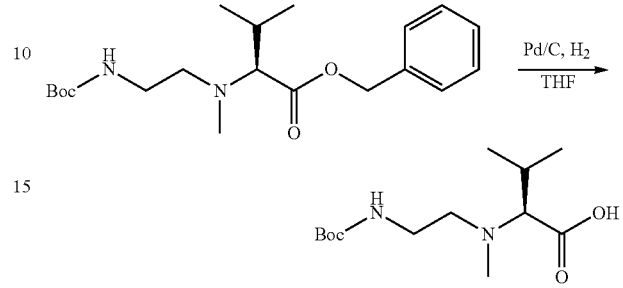

Compound 26A was prepared in the same manner as for compound 2H from the amine 1ZC (1.3 g, 5.04 mmol, 1.00 equiv), tert-butyl (2-oxoethyl)carbamate (800 mg, 5.03 mmol, 1.00 equiv), DIEA (3.52 g, 27.24 mmol, 5.42 equiv) and NaBH(OAc)₃ (2.25 g, 10.62 mmol, 2.11 equiv) in THF (25 mL). The mixture was left under agitation overnight and neutralised with 50 mL of water. The residue was purified on a silica column with a mixture of EtOAc and PE (10:1) to yield 0.6 g (33%) of compound 26A in the form of a colourless oil.

Compound 26A (600 mg, 1.65 mmol, 1.00 equiv) was dissolved in 40 mL of THF in the presence of Pd/C (300 mg) and hydrogenated for 1 hour at ambient temperature and atmospheric pressure. The reaction medium was filtered and concentrated under reduced pressure. The residue was purified on a silica column with a mixture of EtOAc and MeOH to yield 0.4 g (89%) of compound 26B in the form of a colourless oil.

Compound 26C tert-butyl ((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl) carbamate

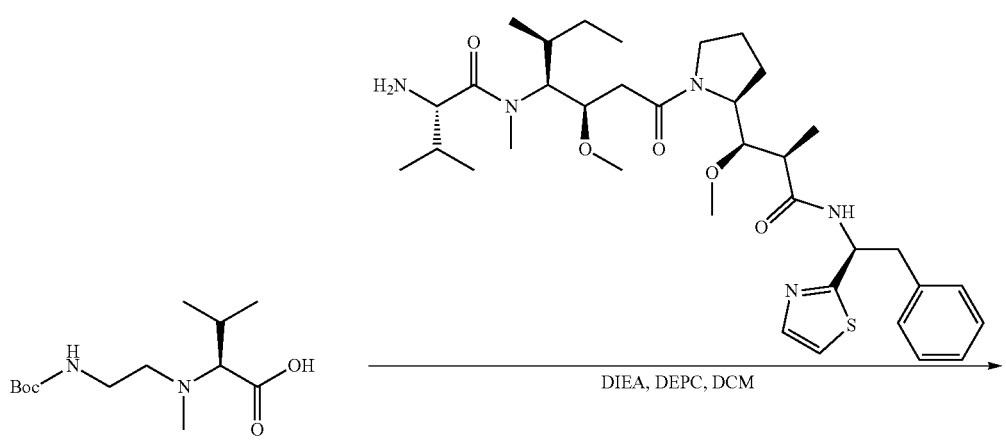

-continued

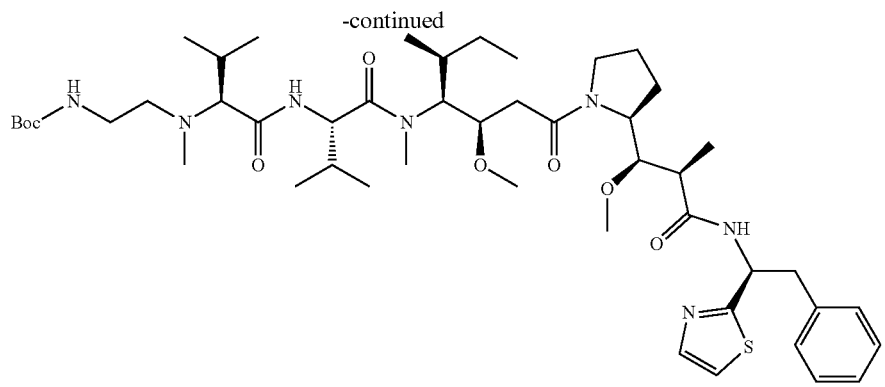

Compound 26C was prepared in the same manner as for compound 3 from the amine 1Y (70 mg, 0.11 mmol, 1.00 equiv), the acid 26B (58.4 mg, 0.21 mmol, 2.00 equiv), DEPC (0.032 mL) and DIEA (0.053 mL) in DCM (3 mL). After evaporation to dryness, compound 26C was obtained in the form of a yellow oil (100 mg).

Compound 26

Compound 26 was synthesised in the same manner as for compound 2 from the intermediate 26C (100 mg, 0.11 mmol, 1.00 equiv) in DCM (3 mL) and TFA (1.5 mL). The crude product was purified by preparative HPLC (Pre-HPLC-001 SHIMADZU, SUNFIRE™ Prep C18 OBD column, 5 μm, 19×150 mm; Eluting phase: water/ACN buffered with 0.05% TFA; Gradient of 20% to 45% ACN in 10 minutes then 40% to 100% ACN in 2 minutes; Waters 2545 UV Detector at 254 nm and 220 nm). Compound 26 was obtained with a yield of 38% (38.1 mg) in the form of a white solid.

LC/MS/UV (Ascentis Express C18 column, 2.7 μm, 4.6× 100 mm; 40° C.; 1.0 mL/min, 5% to 95% MeOH in water (0.05% TFA) on 18 minutes); ESI ($C_{43}H_{71}N_7O_6S$, exact mass 813.52) m/z: 814.5 (MH$^+$) and 407.9 (M.2H$^+$/2, 100%) 15.78 min (91.2%, 210 nm).

$^1$H NMR: (400 MHz, CD$_3$OD, ppm): δ (Presence of rotamers) 8.90-8.82 (m, 0.5H, NH incomplete exchange); 8.71-8.65 (m, 0.3H, NH incomplete exchange); (7.85-7.77 (m, 1H); 7.60-7.49 (m, 1H); 7.37-7.15 (m, 5H); 5.78-5.55 (m, 1H); 4.82-4.62 (m, 1.6H); 4.32-3.83 (m, 3.6H); 3.75-3.35 (m, 7.4H); 3.30-2.60 (m, 13H); 2.58-0.80 (m, 42H).

Compound 27 methyl (S)-2-((2R,3R)-3-((S)-1-((3R,4S,5S)-4-((S)-2-((S)-2-((4-hydroxyphenethyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate, trifluoroacetic acid

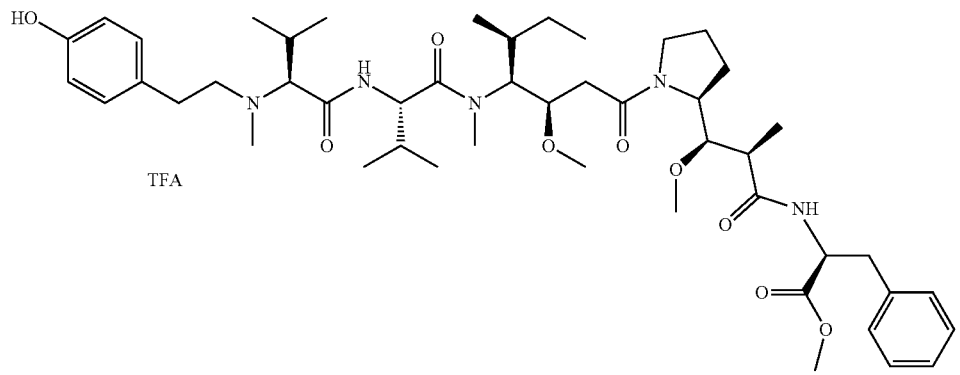 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(O)cc1)C(C)C]

Compound 27

Compound 27 was prepared in the same manner as for compound 3 from the amine 3D (70 mg, 0.11 mmol, 1.00 equiv), the acid 49C (55.5 mg, 0.22 mmol, 2.00 equiv), DEPC (0.034 mL, 2.00 equiv) and DIEA (0.055 mL, 3.00 equiv) in DCM (3 mL). The crude product was purified by preparative HPLC (Pre-HPLC-001 SHIMADZU, SUNFIRE™ Prep C18 OBD column, 5 μm, 19×150 mm; Eluting phase: water/ACN buffered with 0.05% TFA; Gradient of 20% to 45% ACN in 10 minutes then 40% to 100% ACN in 2 minutes; Waters 2545 UV Detector at 254 nm and 220 nm). Compound 27 was obtained with a yield of 3% (2.9 mg) in the form of a white solid.

LC/MS/UV (Eclipse Plus C8 column, 3.5 μm, 4.6×150 mm; 40° C.; 1.5 mL/min, 10% to 95% MeOH in water (0.05% TFA) in 8 minutes); ESI ($C_{48}H_{75}N_5O_9$, exact mass 866.56) m/z: 866.5 (MH$^+$) and 433.9 (M.2H$^+$/2, 100%), 6.61 min (89.1%, 210 nm).

$^1$H NMR (400 MHz, CD$_3$OD, ppm): δ (Presence of rotamers) 8.70-8.49 (m, 0.9H, NH/OH incomplete exchange); 8.30-8.22 (m, 0.3H, NH incomplete exchange); 7.36-7.02 (m, 7H); 6.86-6.62 (m, 2H); 4.82-4.69 (m, 2H); 4.20-4.03 (m, 1H); 3.91-3.33 (m, 12H); 3.30-2.90 (m, 17H); 2.55-0.80 (m, 35H).

Compound 28

(S)-2-((S)-2-((3-aminobenzyl)(methyl)amino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide, trifluoroacetic acid

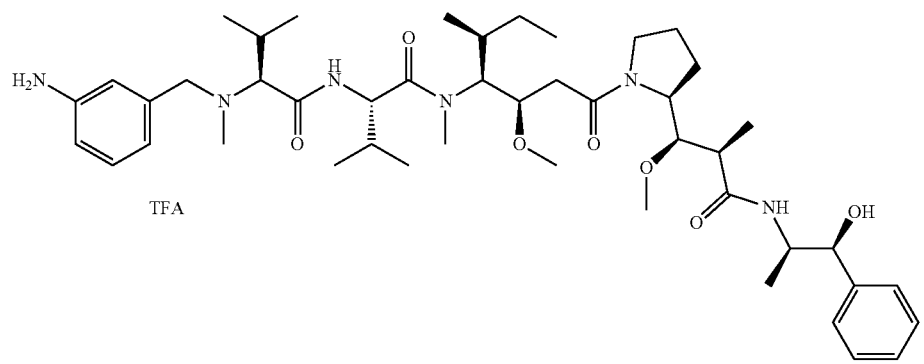 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)Cc1cccc(N)c1)C(C)C]

TFA

Compound 28A tert-butyl (3-((3S,6S,9S,10R)-9-((S)-sec-butyl)-10-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-3,6-diisopropyl-2,8-dimethyl-4,7-dioxo-11-oxa-25,8-triazadodecyl)phenyl)carbamate

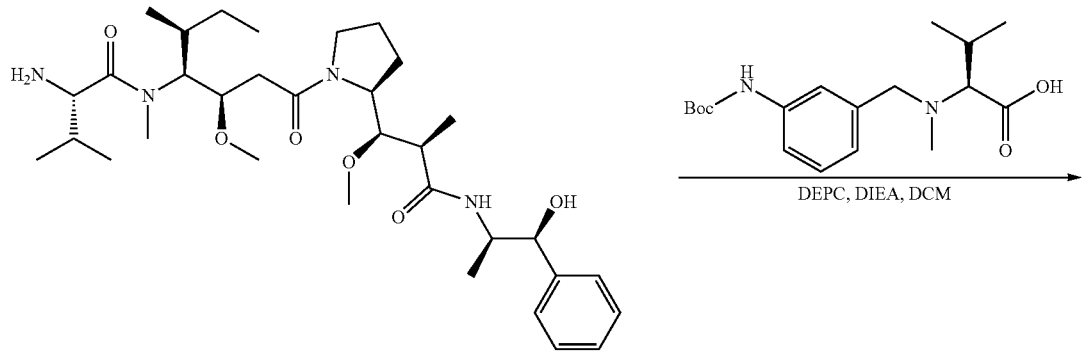

DEPC, DIEA, DCM

-continued

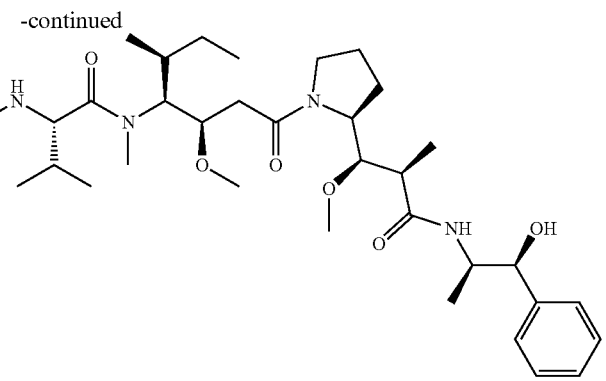

Compound 28A was prepared in the same manner as for compound 3 from the amine 2D (100 mg, 0.17 mmol, 1.00 equiv), the acid 14D (111.25 mg, 0.33 mmol, 2.00 equiv), DEPC (0.058 mL) and DIEA (0.05 mL) in DCM (3 mL). The residue was purified on a silica column with a mixture of EtOAc and hexane (1:1) to yield 100 mg (66%) of compound 28A in the form of a white solid.

Compound 28

Compound 28 was synthesised in the same manner as for compound 2 from the intermediate 28A (100 mg, 0.11 mmol, 1.00 equiv). The crude product (80 mg) was purified by preparative HPLC (Pre-HPLC-001 SHIMADZU, SUN-FIRE™ Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm). Compound 28 was obtained with a yield of 20% (20 mg) in the form of a white solid.

LC/MS/UV (Ascentis Express C18 column, 2.7 μm, 4.6× 100 mm; 40° C.; 1.5 mL/min, 10% to 95% MeOH in water (0.05% TFA) in 8 minutes); ESI ($C_{46}H_{74}N_6O_7$, exact mass 822.56) m/z: 823.5 (MH$^+$) and 412.4 (M.2H$^+$/2, 100%) 12.45 min (87.2%, 210 nm).

$^1$H NMR: (400 MHz, CD$_3$OD, ppm): δ (Presence of rotamers) 7.47-7.20 (m, 5H); 7.10-7.01 (m, 1H); 6.80-6.56 (m, 3H); 4.82-4.52 (m, 3H); 4.33-4.03 (m, 2H); 3.91-3.82 (m, 0.5H); 3.75-3.35 (m, 9.5H); 3.28-3.10 (m, 2H); 2.79-2.90 (m, 1H); 2.60-2.40 (m, 2H); 2.30-0.80 (m, 40H).

Compound 29

(S)-2-((2R,3R)-3-((S)-1-((3R,4S,5S)-4-((S)-2-((S)-2-((3-aminobenzyl) (methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid, trifluoroacetic acid

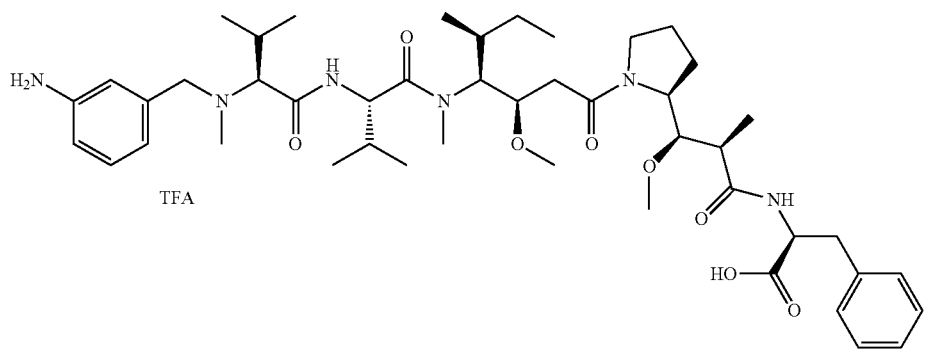 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)Cc1cccc(N)c1)C(C)C]

Compound 15 (100 mg, 0.10 mmol, 1.00 equiv) was dissolved in a mixture of water (5 mL), ACN (5 mL) and piperidine (2.5 mL). The reaction mixture was left under agitation overnight at ambient temperature and then concentrated under reduced pressure. The residue was purified by preparative HPLC (Pre-HPLC-001 SHIMADZU, SUNFIRE™ Prep C18 OBD column, 5 µm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 20 mg (20%) of compound 29 in the form of a white solid.

LC/MS/UV (Eclipse Plus C8 column, 3.5 µm, 4.6×150 mm; 40° C.; 1.0 mL/min, 40% to 95% MeOH in water (0.05% TFA) in 18 minutes); ESI ($C_{46}H_{72}N_6O_8$, exact mass 836.54) m/z: 837.5 (MH$^+$) and 419.4 (M.2H$^+$/2, 100%), 10.61 min (92.5%, 210 nm).

$^1$H NMR: (400 MHz, CD$_3$OD, ppm): δ (Presence of rotamers) 7.38-7.15 (m, 6H); 7.00-6.99 (m, 3H); 4.85-4.68 (m, 2H); 4.37-3.38 (m, 11H); 3.31-2.70 (m, 8H); 2.60-0.82 (m, 35H).

Compound 30 methyl (S)-2-((2R,3R)-3-((S)-1-((3R,4S,5S)-4-((S)-2-((S)-2-((4-aminobutyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate, bis trifluoroacetic acid

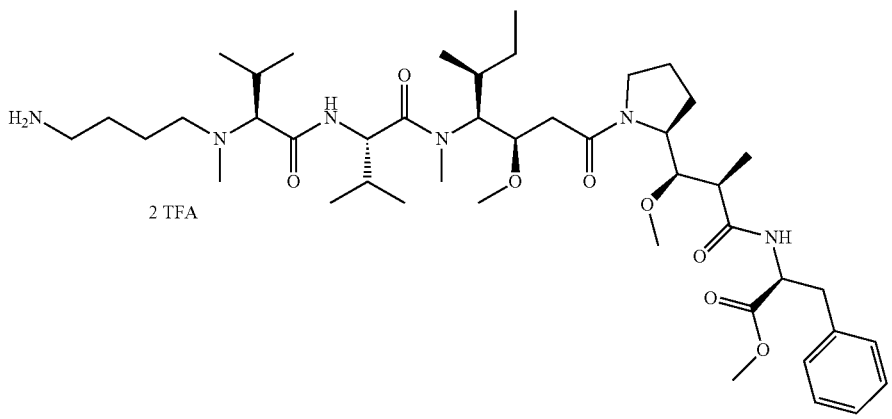 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCCCN)C(C)C]

Compound 30 was prepared in the same manner as for compound 16, from the amine 3D and the corresponding carboxylic acid.

LC/MS/UV (Ascentis Express C18, 2.7 µm, 4.6×100 mm; 1.5 mL/min, 40° C., 10 to 95% methanol in water (0.05% TFA) in 15 minutes); ESI ($C_{44}H_{76}N_6O_8$, exact mass 816.57) m/z: 817.6 (MH$^+$), 409.4 (M.2H$^+$/2); 12.0 min (90%, 210 nm).

$^1$H NMR (300 MHz, CD$_3$OD, ppm): δ (Presence of rotamers) 8.7-8.2 (m, 1H, NHCOs, incomplete exchange); 7.4-7.1 (m, 5H); 4.95-4.7 (m, 3H); 4.2-4.0 (m, 1H); 3.9-0.8 (m, 63H).

Compound 31

(S)-2-((2R,3R)-3-((S)-1-((3R,4S,5S)-4-((S)-2-((S)-2-((4-aminobutyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid, bis trifluoroacetic acid

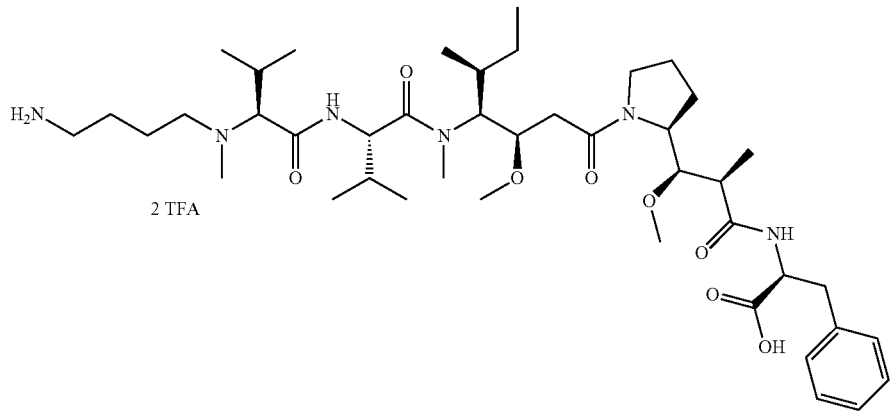 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCCCN)C(C)C]

Compound 31 was prepared in the same manner as for compound 4, from the methyl ester 30.

LC/MS/UV (Ascentis Express C18, 2.7 µm, 4.6×100 mm; 1.5 mL/min, 40° C., 10 to 95% methanol in water (0.05% TFA) in 18 minutes); ESI ($C_{43}H_{74}N_6O_8$, exact mass 802.56) m/z: 803.6 (MH$^+$), 402.4 (M.2H$^+$/2); 13.68 min (98.9%.210 nm).

$^1$H NMR (300 MHz, CD$_3$OD, ppm): δ (Presence of rotamers) 7.4-7.1 (m, 5H); 4.95-4.7 (m, 3H); 4.2-4.0 (m, 1H); 3.9-0.8 (m, 61H).

Compound 32

(S)—N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethyl-2-((S)-3-methyl-2-(methyl(3-(methylamino)propyl)amino)butanamido)butanamide, bis trifluoroacetic acid

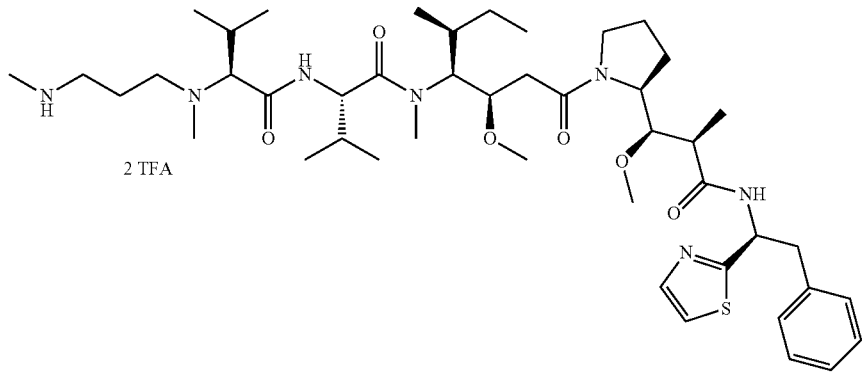 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCCNC)C(C)C]

Compound 32A tert-butyl (3,3-diethoxypropyl)(methyl)carbamate

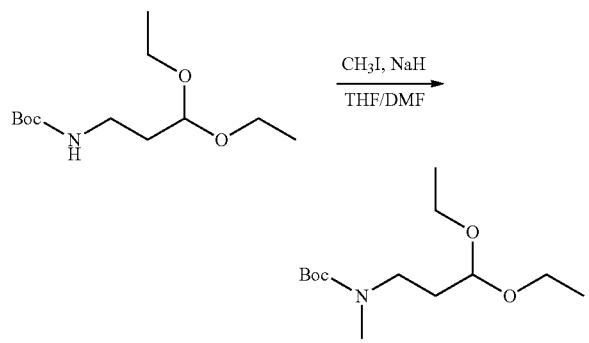

Compound 1ZD (247 mg, 1 mmol, 1.00 equiv) was dissolved in an inert atmosphere in 30 mL of a 1:1 mixture of TH and DMF. The reaction medium was cooled over an ice bath after which the NaH (60% in oil, 60 mg, 1.5 equiv) was added in portions, followed by the MeI (0.28 mL) drop-wise. The reaction was left under agitation for 2 days at ambient temperature, then neutralised with 5 mL of NH$_4$Cl-saturated aqueous solution and extracted twice with 15 mL of EtOAc. The organic phases were combined, dried over sodium sulfate, filtered and concentrated under reduced pressure to yield 200 mg (77%) of compound 32A in the form of a yellow solid.

Compound 32B (S)-2-((3-((tert-butoxycarbonyl)(methyl)amino)propyl)(methyl)amino)-3-methylbutanoicacid

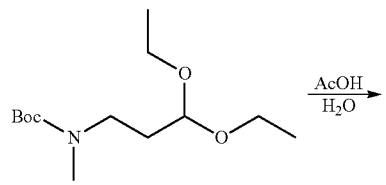

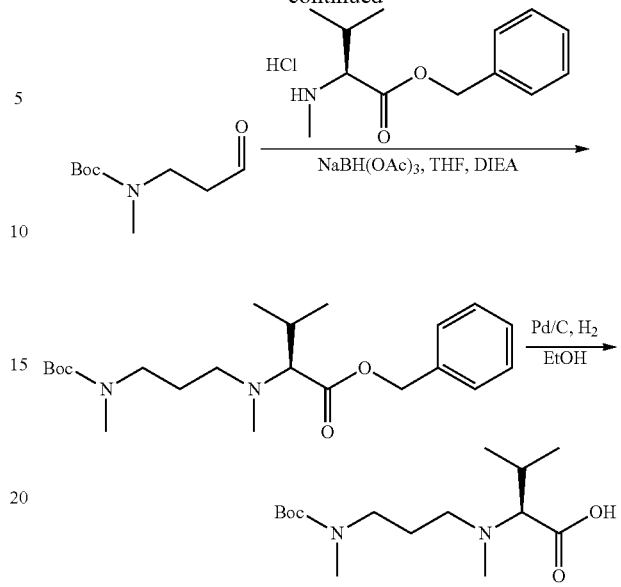

Compound 32B was prepared following the same protocol described for the preparation of compound 1ZF, replacing compound 1ZD by compound 32A.

Compound 32

Compound 32 was prepared in two steps, following the same protocol described for the preparation of compound 1, from the amine 1Y and the carboxylic acid 32B.

LC/MS/UV (ZORBAX® SB-Aq, 1.8 μm, 4.6×100 mm, 40° C., 10 to 95% methanol in water (0.05% TFA) in 13 minutes); ESI (C$_{45}$H$_{75}$N$_7$O$_6$S, exact mass 842.19) m/z: 843 (MH$^+$), 421.9 (M.2H$^+$/2); 11.91 min (88%,210 nm).

$^1$H NMR: (300 MHz, CD$_3$OD, ppm): δ (Presence of rotamers) 8.5-9.0 (m, 0.5H, incomplete exchange NHCOs), 7.85-7.80 (m, 1H); 7.60-7.50 (m, 1H), 7.35-7.15 (m, 5H), 5.80-5.63 (m, 1H), 4.80-4.65 (m, 2H), 4.30-4.00 (m, 1H), 3.95-0.80 (m, 61H).

Compounds 33 and 34

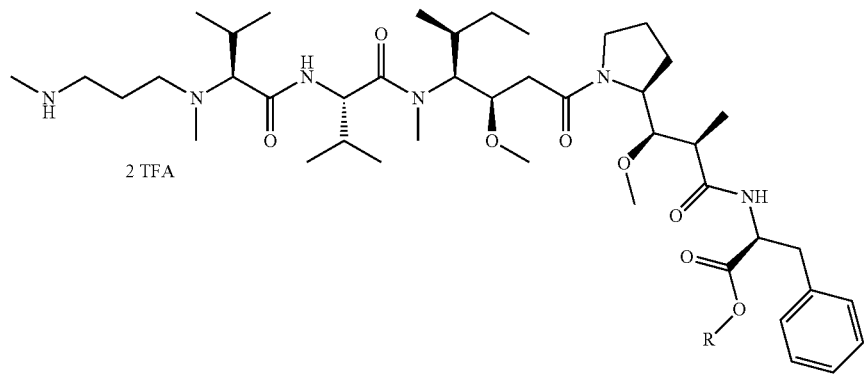

Compounds 33 and 34 were prepared in the same manner as for compounds 6 and 7, replacing the carboxylic acid 1ZF by compound 32B.

| No. | Name | R | Purity* | Quantity |
|---|---|---|---|---|
| 33 | methyl (S)-2-((2R,3R)-3-((S)-1-((7S,10S,13S,14R)-13-((S)-sec-butyl)-7,10-diisopropyl-14-methoxy-6,12-dimethyl-8,11-dioxo-2,6,9,12-tetraazahexadecan-16-oyl)pyrrolidin-2-yl)-3-methoxy-2-methylpropanamido)-3-phenylpropanoate, bis trifluoroacetic acid | Me | 95% | 32 mg |
| 34 | (S)-2-((2R,3R)-3-((S)-1-((7S,10S,13S,14R)-13-((S)-sec-butyl)-7,10-diisopropyl-14-methoxy-6,12-dimethyl-8,11-dioxo-2,6,9,12-tetraazahexadecan-16-oyl)pyrrolidin-2-yl)-3-methoxy-2-methylpropanamido)-3-phenylpropanoic acid, bis trifluoroacetic acid | H | 98% | 18 mg |

*The compounds were purified by preparative HPLC (Pre-HPLC-001 SHIMADZU, SUNFIRE ™ Prep C18 OBD column, 5 μm, 19 × 150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm), to yield the corresponding TFA salts in the form of white solids.

Characterization of the end products: Compound 33 LC/MS/UV (ESI) ($C_{44}H_{76}N_6O_8$, exact mass 816.57) m/z 817.6 (MH$^+$), 409.4 (M.2H$^+$/2); UV: 5.94 min (95%, 210 nm). $^1$H NMR: (400 MHz, CD$_3$OD, ppm): δ (Presence of rotamers) δ 8.6-8.2 (m, 0.8H, NHCO incomplete exchange) 7.30-7.22 (m, 5H), 4.80 (m, 2H), 4.23-0.86 (m, 66H). Compound 34 LC/MS/UV (ESI) ($C_{43}H_{74}N_6O_8$, exact mass 802.56) m/z 803.6 (MH$^+$), 402.4 (M.2H$^+$/2); UV: 5.94 min (97.5%, 210 nm). $^1$H NMR: (400 MHz, CD$_3$OD, ppm): δ (Presence of rotamers) δ 7.30-7.20 (m, 5H), 4.80 (m, 2H), 4.25-0.86 (m, 63H).

Compound 35

(S)-2-((S)-2-((2-(2-aminoethoxy)ethyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, bis trifluoroacetic acid

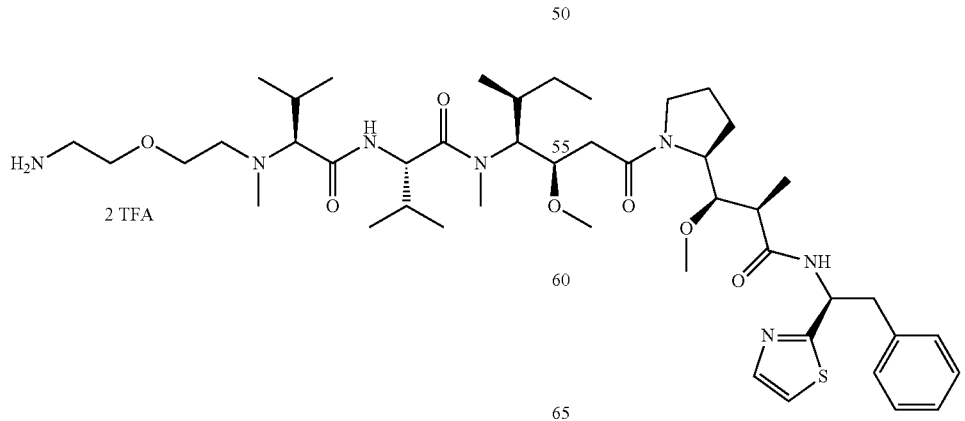

201

Compound 35A tert-butyl (2-(2-hydroxyethoxy)ethyl)carbamate

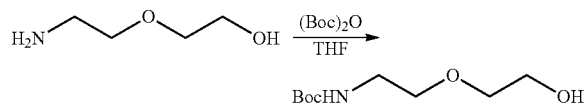

2-(2-aminoethoxy)ethanol (5 g, 47.56 mmol, 1.00 equiv) was dissolved in THF (100 mL) at 0° C. and sodium hydroxide (2 g, 50.00 mmol, 1.05 equiv) was then added (solution in 25 mL of water). A solution of di-tert-butyl dicarbonate (10.38 g, 47.56 mmol, 1.00 equiv) in THF (20 mL) was added drop-wise and the reaction was then left under agitation overnight at ambient temperature. The reaction was diluted by adding 50 mL of water and the product was extracted with 3 times 75 mL of AcOEt. The organic phases were combined, washed once with 100 mL of NaCl (sat.), then dried over sodium sulfate, filtered and concentrated under reduced pressure to yield 9 g (92%) of compound 35A in the form of a yellow oil.

Compound 35B tert-butyl (2-(2-oxoethoxy)ethyl)carbamate

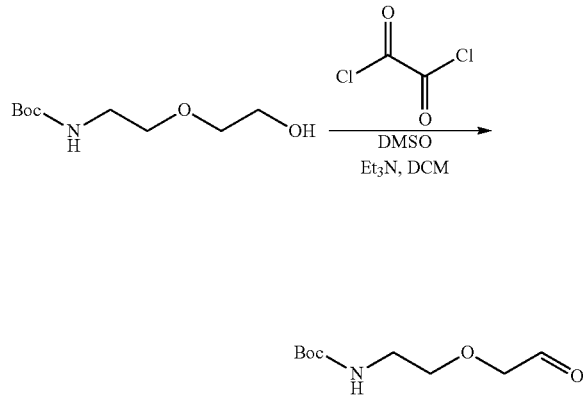

A solution of DMSO (3.46 mL, 5.00 equiv) in DCM (20 mL) was added drop-wise to a solution of oxalyl chloride (1.9 mL, 2.30 equiv) in DCM (20 mL) at −78° C. under nitrogen. After the addition (30 min), the solution was agitated for 30 minutes and a solution of compound 35A (2 g, 9.74 mmol, 1.00 equiv) in 20 mL DCM was then added. After the addition of TEA (12.2 mL), the reaction was agitated at −78° C. for 30 minutes and then at ambient temperature overnight. The reaction was diluted by adding 100 mL of water and the product was extracted 3 times with 50 mL of AcOEt. The organic phases were combined, dried over sodium sulfate, filtered and concentrated under reduced pressure to yield 1.9 g of compound 35B in the form of a yellow oil.

202

Compound 35C benzyl (S)-12-isopropyl-2,2,11-trimethyl-4-oxo-3,8-dioxa-5,11-diazatridecan-13-oate

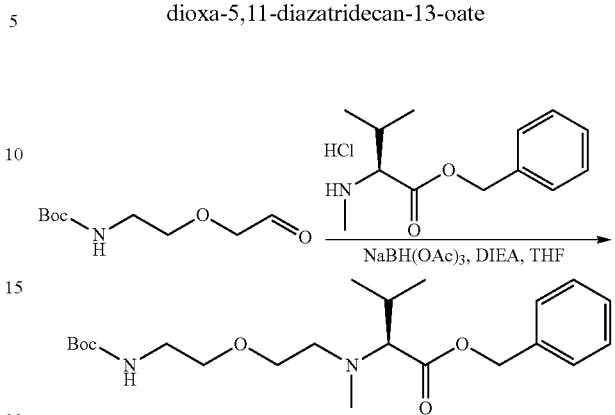

Compound 35C was synthesised in the same manner as for compound 14C from the amine 1ZC (2.4 g, 9.31 mmol, 1.00 equiv), the aldehyde 35B (1.9 g, 9.35 mmol, 1.00 equiv), NaBH(OAc)$_3$ (3.96 g, 18.68 mmol, 2.00 equiv) and DIEA (6.2 mL) in THF (40 mL). The reaction mixture was neutralised with 200 mL of water and extracted 3 times with 100 mL of AcOEt. The organic phases were combined, dried over sodium sulfate, filtered and concentrated to yield 2.3 g of compound 35C in the form of a yellow oil.

Compound 35D (S)-12-isopropyl-2,2,11-trimethyl-4-oxo-3,8-dioxa-5,11-diazatridecan-13-oic acid

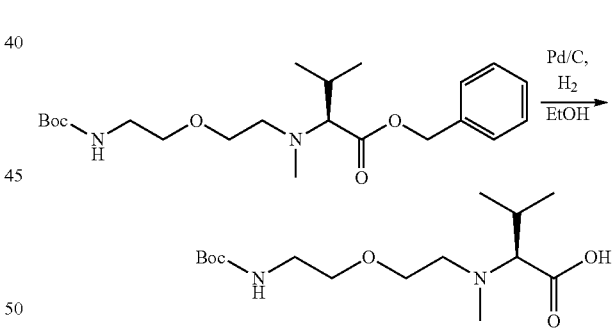

Compound 35C (200 mg, 0.49 mmol, 1.00 equiv) was dissolved in 10 mL of EtOH in the presence of Pd/C (200 mg) and hydrogenated overnight. The reaction medium was filtered and concentrated under reduced pressure to yield 150 mg (96%) of compound 35D in the form of a white solid.

Compound 35E tert-butyl ((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2,14-dioxa-5,8,11-triazahexadecan-16-yl) carbamate

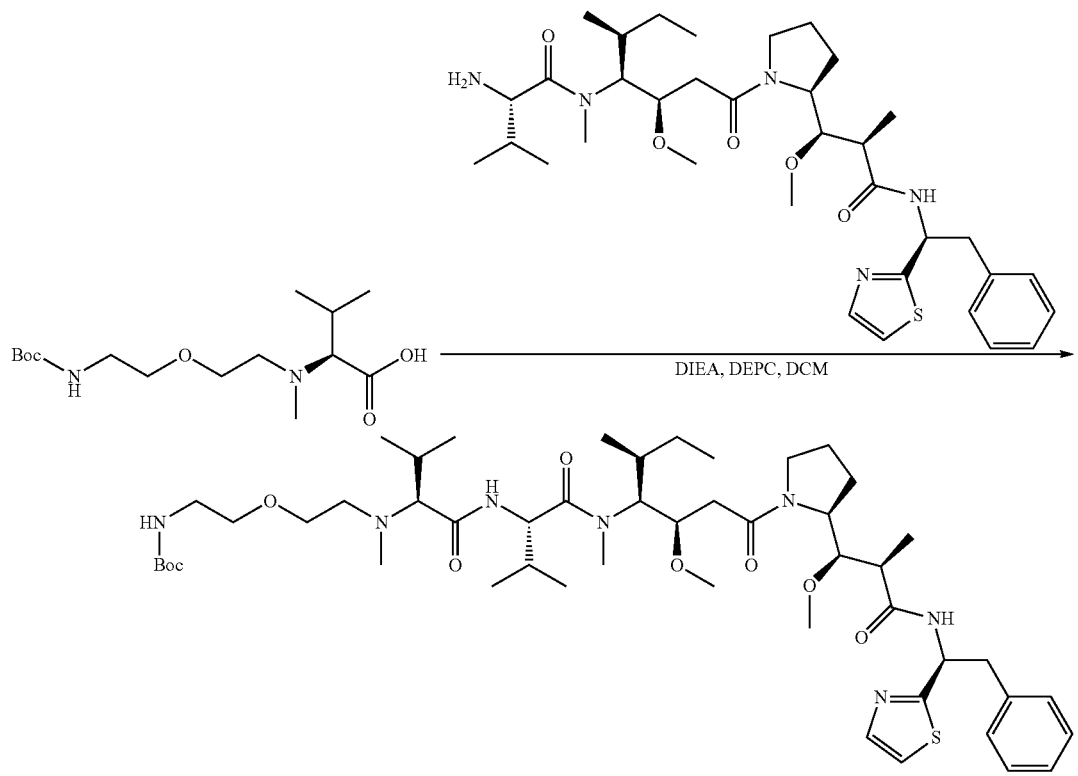

Compound 35E was synthesised in the same manner as for compound 3 from the amine 1Y (70 mg, 0.11 mmol, 1.00 equiv), the acid 35D (40.6 mg, 0.13 mmol, 1.20 equiv), DEPC (0.0324 mL) and DIEA (0.0527 mL) in DCM (3 mL). The crude product (100 mg, 98%) was isolated in the form of a yellow oil and subsequently used as such.

Compound 35

Compound 35 was synthesised in the same manner as for compound 2 from the intermediate 35E (100 mg, 0.10 mmol, 1.00 equiv). The crude product was purified by preparative HPLC (Pre-HPLC-010), SUNFIRE™ Prep C18 OBD column, 5 μm, 19×100 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm). Compound 35 was obtained with a yield of 23% (22.9 mg) in the form of a white solid.

LC/MS/UV (Ascentis Express C18 column, 2.7 μm, 4.6× 100 mm; 40° C.; 1.5 mL/min, 10% to 95% MeOH in water (0.05% TFA) in 8 minutes); ESI ($C_{45}H_{75}N_7O_7S$, exact mass 857.54) m/z: 858.5 (MH$^+$) and 429.9 (M.2H$^+$/2, 100%) 5.89 min (89.7%, 210 nm).

$^1$H NMR: (400 MHz, CD$_3$OD, ppm): δ (Presence of rotamers) δ 8.9-8.5 (m, 0.5H, NHCO incomplete exchange), 7.8-7.7 (m, 1H), 7.55-7.45 (m, 1H), 7.35-7.1 (m, 5H), 5.45-5.5 (m, 1H), 4.9-4.6 (m, 1H), 4.3-0.75 (m, 62H).

Compound 36 methyl (S)-2-((2R,3R)-3-((S)-1-((7S,10S,13S,14R)-1-amino-13-((S)-sec-butyl)-7,10-diisopropyl-14-methoxy-6,12-dimethyl-8,11-dioxo-3-oxa-6,9,12-triazahexadecan-16-oyl)pyrrolidin-2-yl)-3-methoxy-2-methylpropanamido)-3-phenylpropanoate, bis trifluoroacetic acid

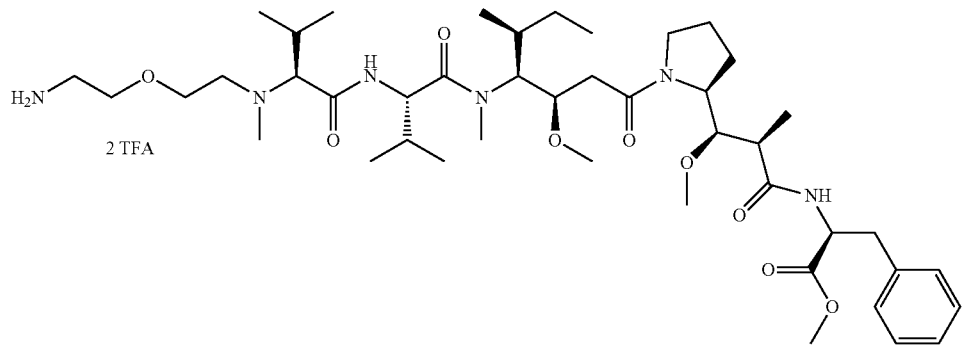 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCOCCN)C(C)C]

Compound 36A methyl (S)-2-((2R,3R)-3-((S)-1-((12S,15S,18S,19R)-18-((S)-sec-butyl)-12,15-diisopropyl-19-methoxy-2,2,11,17-tetramethyl-4,13,16-trioxo-3,8-dioxa-5,11,14,17-tetraazahenicosan-21-oyl)pyrrolidin-2-yl)-3-methoxy-2-methylpropanamido)-3-phenylpropanoate

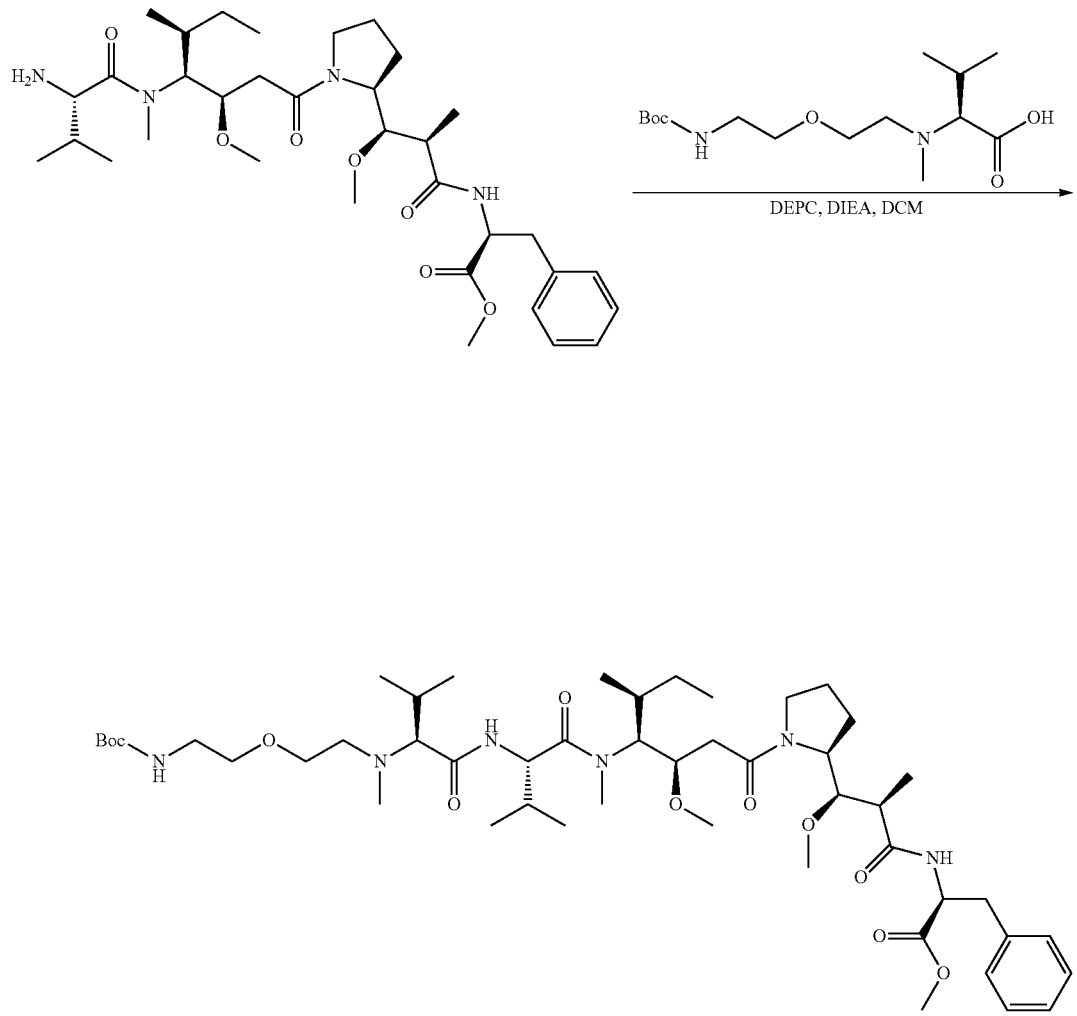

Compound 36A was synthesised in the same manner as for compound 3 from the amine 3D (50 mg, 0.08 mmol, 1.00 equiv), the acid 35D (25 mg, 0.11 mmol, 1.48 equiv), DEPC (0.0337 mL) and DIEA (0.0548 mL) in DCM (3 mL). The crude product (100 mg) was isolated in the form of a yellow oil and subsequently used as such.

Compound 36

Compound 36 was synthesised in the same manner as for compound 2 from the intermediate 36A (100 mg, 0.11 mmol, 1.00 equiv). The crude product was purified by preparative HPLC (Pre-HPLC-001 SHIMADZU, SUN-FIRE™ Prep C18 OBD column, 5 μm, 19×100 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm). Compound 36 was obtained with a yield of 13% (12.7 mg) in the form of a white solid.

LC/MS/UV (AGILENT® ZORBAX® SB-Aq column, 1.8 μm, 4.6×100 mm; 40° C.; 1.5 mL/min, 2% MeOH in water (0.05% TFA) for 1 minute then 2% to 95% MeOH in water in 13 minutes, then 95% MeOH in water for 2 minutes); ESI ($C_{44}H_{76}N_6O_9$, exact mass 832.57) m/z: 833.5 (MH$^+$) and 417.4 (M.2H$^+$/2, 100%) 11.58 min (98.5%, 210 nm).

$^1$H NMR: (400 MHz, CD$_3$OD, ppm): δ (Presence of rotamers) 8.1-8.5 (m, 0.8H, NHCO incomplete exchange), 7.30-7.1 (m, 5H), 4.9-4.6 (m, 3H), 4.2-0.8 (m, 64H).

Compound 37

(S)-2-((2R,3R)-3-((S)-1-((7S,10S,13S,14R)-1-amino-13-((S)-sec-butyl)-7,10-diisopropyl-14-methoxy-6,12-dimethyl-8,11-dioxo-3-oxa-6,9,12-triazahexadecan-16-oyl)pyrrolidin-2-yl)-3-methoxy-2-methylpropanamido)-3-phenylpropanoic acid, bis trifluoroacetic acid

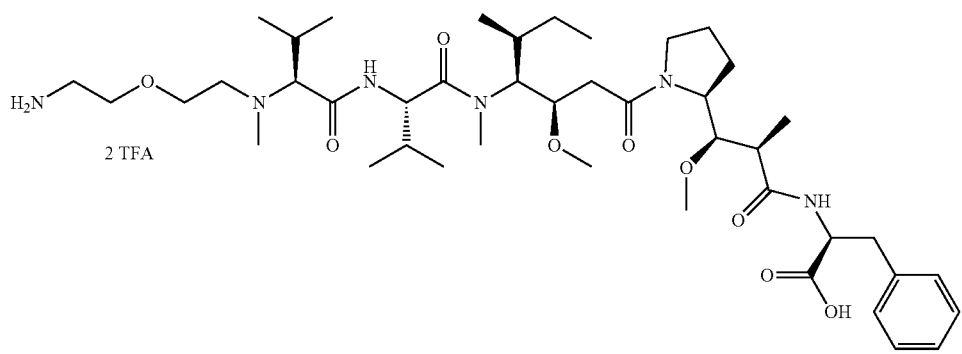 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCOCCN)C(C)C]

Compound 37 was prepared in the same manner as for compound 4, from compound 36 (100 mg, 0.11 mmol, 1.00 equiv). The residue was purified by preparative HPLC (Pre-HPLC-001 SHIMADZU, Atlantis Prep OBD T3 column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 18.4 mg (19%) of compound 37 in the form of a white solid.

LC/MS/UV (Ascentis Express C18 column, 2.7 μm, 4.6×100 mm; 40° C.; 1.5 mL/min, 10% to 95% MeOH in water (0.05% TFA) in 8 minutes); ESI ($C_{43}H_{74}N_6O_9$, exact mass 818.6) m/z: 819.6 (MH$^+$) and 410.4 (M.2H$^+$/2, 100%) 5.48 min (96.7%, 210 nm).

$^1$H NMR: (400 MHz, CD$_3$OD, ppm): δ (Presence of rotamers) 7.35-7.2 (m, 5H), 5.0-4.65 (m, 3H), 4.3-0.8 (m, 61H).

Compound 38 methyl (S)-2-((2R,3R)-3-((S)-1-((3R,4S,5S)-4-((S)-2-((S)-2-((2-aminoethyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate, bis trifluoroacetic acid

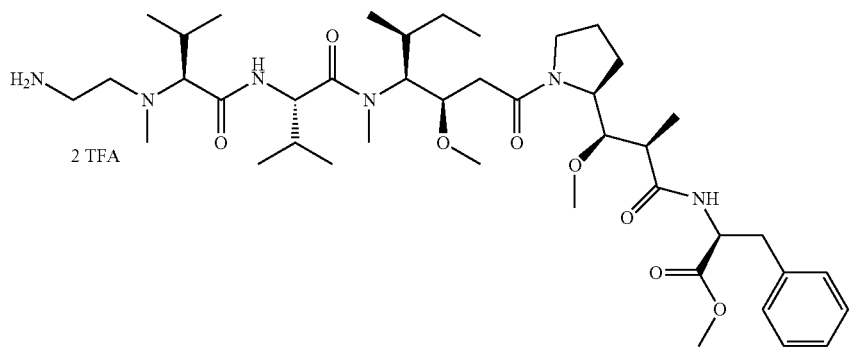 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCN)C(C)C]

Compound 38A methyl (S)-2-((2R,3R)-3-((S)-1-((9S,12S,15S,16R)-15-((S)-sec-butyl)-9,12-diisopropyl-16-methoxy-2,2,8,14-tetramethyl-4,10,13-trioxo-3-oxa-5,8,11,14-tetraazaoctadecan-18-oyl)pyrrolidin-2-yl)-3-methoxy-2-methylpropanamido)-3-phenylpropanoate

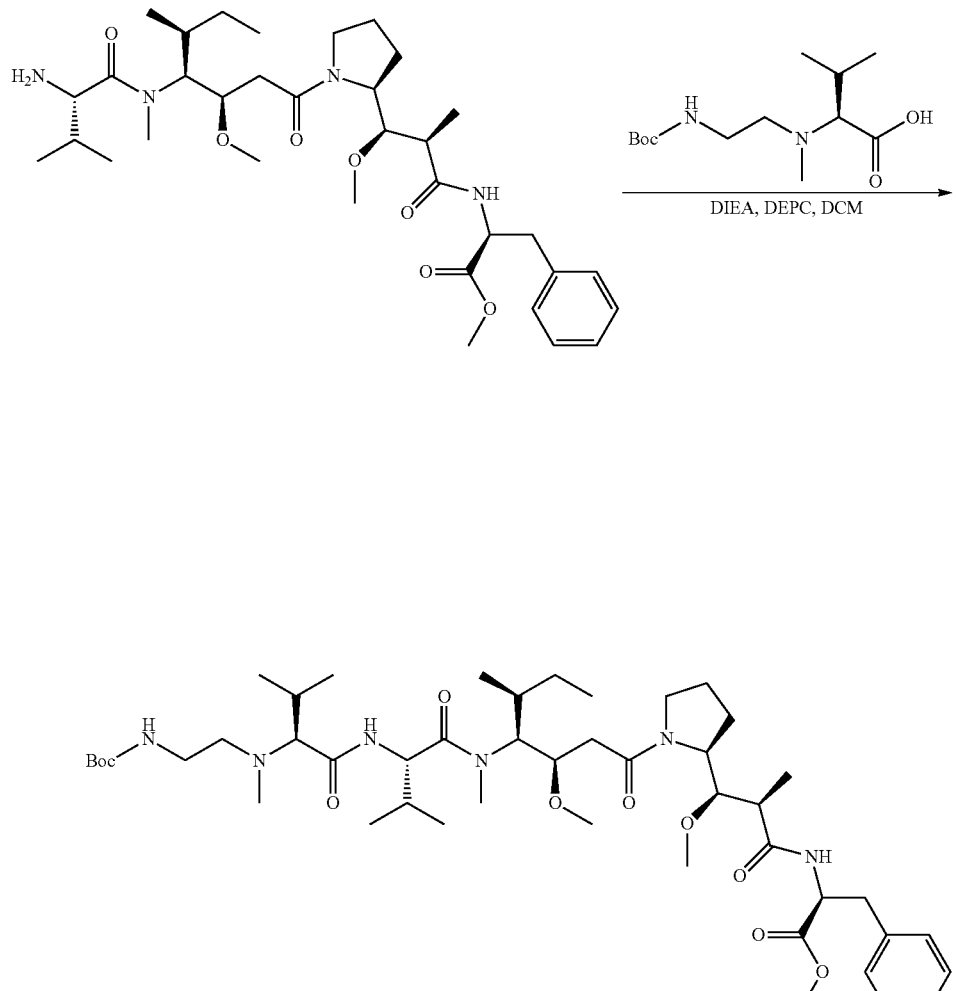

Compound 38A was synthesised in the same manner as for compound 3 from the amine 3D (70 mg, 0.11 mmol, 1.00 equiv), the acid 26B (60.7 mg, 0.22 mmol, 2.00 equiv), DEPC (0.0337 mL) and DIEA (0.0548 mL) in DCM (3 mL). The crude product (100 mg) was isolated in the form of a yellow oil.

Compound 38

Compound 38 was synthesised in the same manner as for compound 2 from the intermediate 38A (100 mg, 0.11 mmol, 1.00 equiv). The crude product was purified by preparative HPLCPre-HPLC-001 SHIMADZU, SUN-FIRE™ Prep C18 OBD column, 5 µm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm). Compound 38 was obtained with a yield of 10% (10.3 mg) in the form of a white solid.

LC/MS/UV (AGILENT® ZORBAX® SB-Aq column, 1.8 µm, 4.6×100 mm; 40° C.; 1.5 mL/min, 2% MeOH in water (0.05% TFA) for 1 minute then 2% to 95% MeOH in water in 13 minutes then 95% MeOH in water for 2 minutes); ESI ($C_{42}H_{72}N_6O_8$, exact mass 788.5) m/z: 789.5 (MH$^+$) and 395.4 (M.2H$^+$/2, 100%) 12.97 min (91.0%,210 nm).

$^1$H NMR: (400 MHz, CD$_3$OD, ppm): δ (Presence of rotamers) 7.30-7.1 (m, 5H), 4.9-4.6 (m, 3H), 4.2-0.8 (m, 60H).

Compound 39

(S)-2-((2R,3R)-3-((S)-1-((3R,4S,5S)-4-((S)-2-((S)-2-((2-aminoethyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid, bis trifluoroacetic acid

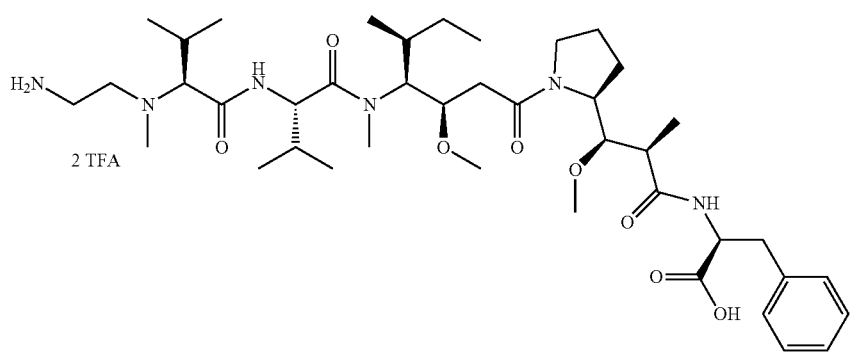 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCN)C(C)C]

Compound 39 was prepared in the same manner as for compound 4, from compound 38 (100 mg, 0.11 mmol, 1.00 equiv). The residue was purified by preparative HPLC (Pre-HPLC-001 SHIMADZU, SUNFIRE™ Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 8.2 mg (8%) of compound 39 in the form of a white solid.

LC/MS/UV (Eclipse Plus C18 column, 3.5 μm, 4.6×150 mm; 40° C.; 1.5 mL/min, 10% to 95% MeOH in water (0.05% TFA) in 8 minutes); ESI ($C_{41}H_{70}N_6O_8$, exact mass 774.5) m/z: 775.5 (MH$^+$) and 388.4 (M.2H$^+$/2, 100%) 6.47 min (93.6%, 210 nm).

$^1$H NMR: (400 MHz, CD$_3$OD, ppm): δ (Presence of rotamers) 7.35-7.15 (m, 5H), 4.9-4.6 (m, 3H), 4.2-0.8 (m, 57H).

Compound 40

(S)—N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethyl-2-((S)-3-methyl-2-(methyl(4-(methylamino)butyl)amino)butanamido)butanamide, bis trifluoroacetic acid

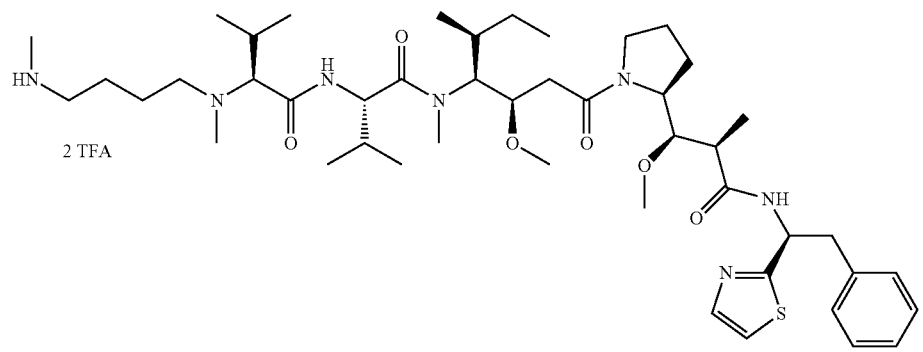 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCCCNC)C(C)C]

Compound 40A tert-butyl (4,4-diethoxybutyl)(methyl)carbamate

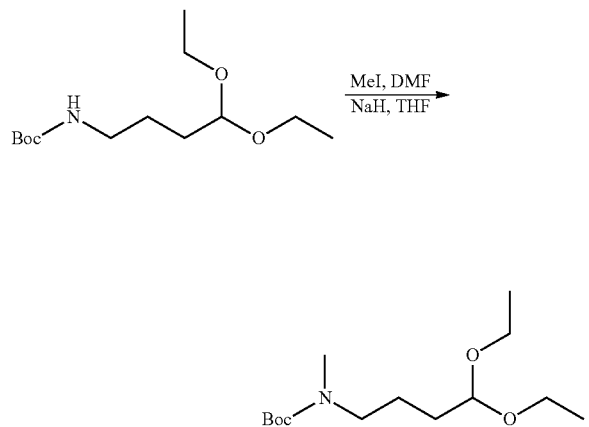

Compound 40A was prepared in the same manner as for compound 11E, from tert-butyl(4,4-diethoxybutyl)(methyl) carbamate (5.5 g, 19.97 mmol, 1.00 equiv), NaH (60% in oil, 3.2 g, 80.00 mmol, 4.01 equiv) and iodomethane (14 mL) in THF/DMF (40/20 mL). The reaction was neutralised with 50 mL of NH$_4$Cl (aq). Compound 40A was isolated in the form of a yellow oil, 5.5 g (95%).

Compound 40B tert-butyl methyl(4-oxobutyl)carbamate

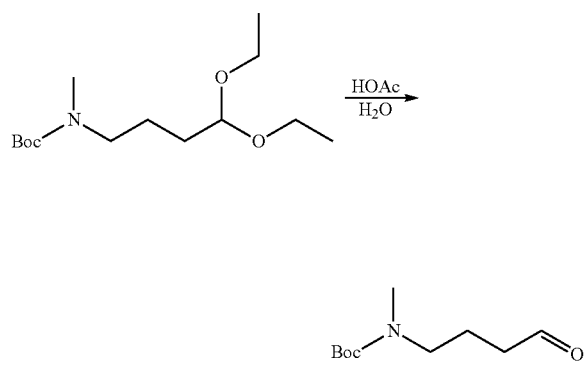

Compound 40A (3 g, 10.89 mmol, 1.00 equiv) was dissolved in a mixture of AcOH and water (15/4 mL) and the solution was left under agitation overnight. The pH was brought to 7-8 with NaHCO$_3$-saturated aqueous solution and then extracted twice with 50 mL of EtOAc. The organic phases were combined, washed twice with 50 mL of NaCl-saturated aqueous solution, dried over anhydrous sodium sulfate, filtered and concentrated under reduced pressure. Compound 40B was isolated in the form of yellow oil, 2.1 g (96%).

Compound 40C benzyl(S)-2-((4-((tert-butoxycarbonyl)(methyl) amino)butyl) (methyl)amino)-3-methylbutanoate

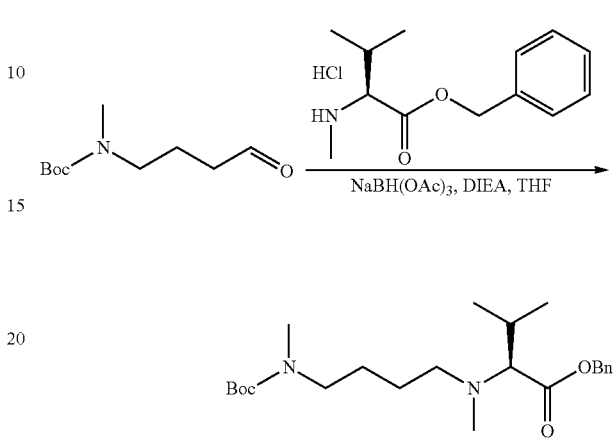

Compound 40C was synthesised in the same manner as for compound 14C from the amine 1ZC (2.45 g, 9.53 mmol, 0.80 equiv), the aldehyde 40B (2.4 g, 11.92 mmol, 1.00 equiv), NaBH(OAc)$_3$ (5.06 g, 23.87 mmol, 2.00 equiv) and DIEA (6.16 g, 47.66 mmol, 4.00 equiv) in THF (15 mL). The reaction mixture was neutralised with 100 mL of water and extracted twice with 100 mL of AcOEt. The organic phases were combined, dried over sodium sulfate, filtered and concentrated. The residue was purified on silica gel (EtOAc/PE (1:100-1:20)) to yield 1.2 g (25%) of compound 40C in the form of a yellow oil.

Compound 40D (S)-2-((4-((tert-butoxycarbonyl)(methyl)amino) butyl) (methyl) amino)-3-methylbutanoic acid

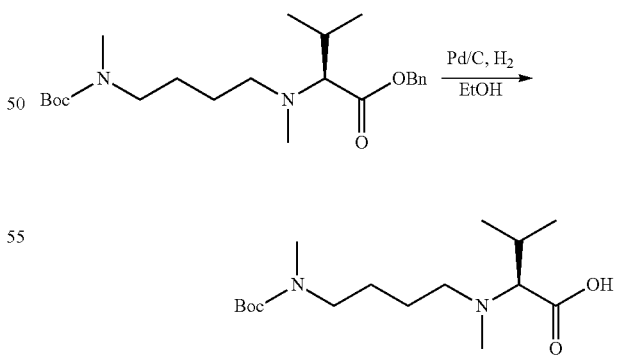

Compound 40C (500 mg, 1.23 mmol, 1.00 equiv) was dissolved in 20 mL of EtOH in the presence of Pd/C (550 mg) and hydrogenated for 1 hour at ambient temperature and atmospheric pressure. The reaction medium was filtered and concentrated under reduced pressure to yield 350 mg (90%) of compound 40D in the form of a colourless oil.

Compound 40E tert-butyl ((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazapentadecan-15-yl)(methyl)carbamate

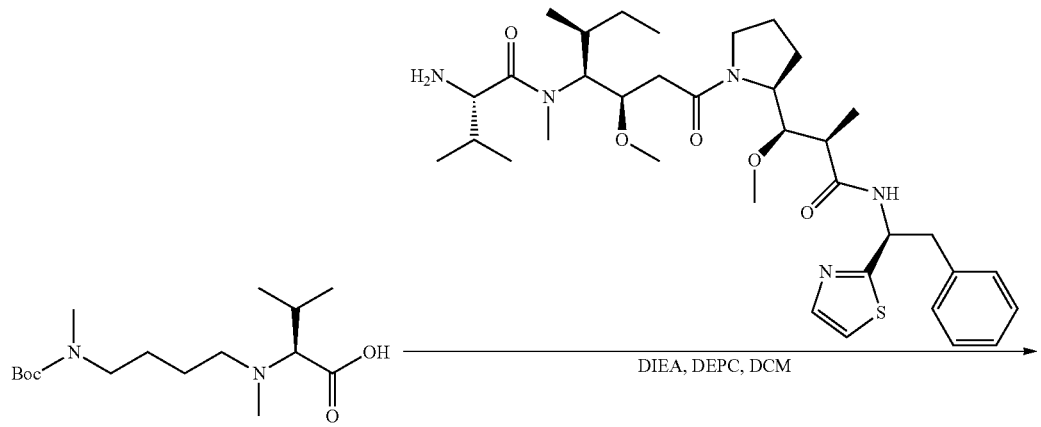

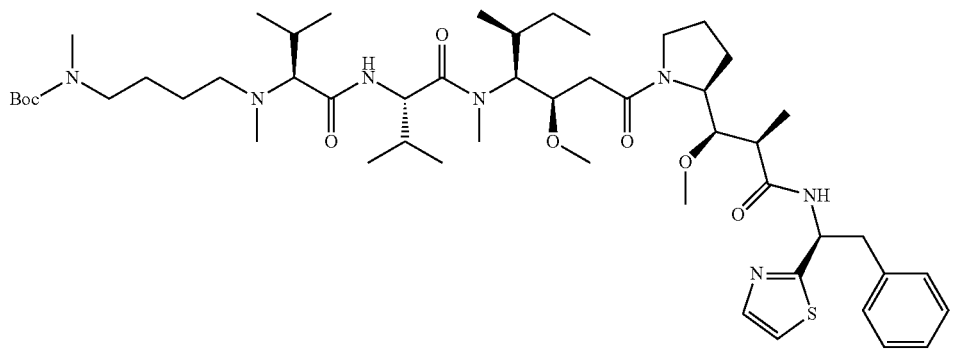

Compound 40E was synthesised in the same manner as for compound 3 from the amine 1Y (60 mg, 0.09 mmol, 1.00 equiv), the acid 40D (57.8 mg, 0.18 mmol, 2.00 equiv), DEPC (0.0278 mL) and DIEA (0.0452 mL) in DCM (3 mL). The crude product (100 mg) was subsequently used as such.

Compound 40

Compound 40 was synthesised in the same manner as for compound 2 from the intermediate 40E (100 mg, 0.10 mmol, 1.00 equiv). The crude product was purified by preparative HPLC (Pre-HPLC-001 SHIMADZU, SUNFIRE™ Prep C18 OBD column, 5 μm, 19×100 mm Eluting phase: water/ACN buffered with 0.05% TFA; Gradient of 20% to 40% ACN in 10 minutes then 40% to 95% ACN in 2 minutes; Waters 2545 UV Detector at 254 nm and 220 nm). Compound 40 was obtained with a yield of 24% (24.6 mg) in the form of a white solid.

LC/MS/UV (Ascentis Express C18 column, 2.7 μm, 4.6× 100 mm; 40° C.; 1.5 mL/min, 10% to 95% MeOH in water (0.05% TFA) in 8 minutes); ESI ($C_{46}H_{77}N_7O_6S$, exact mass 855.6) m/z: 856.6 (MH$^+$) and 428.8 (M.2H$^+$/2, 100%) 5.89 min (97.0%,210 nm).

$^1$H NMR: (400 MHz, CD$_3$OD, ppm): δ (Presence of rotamers) 8.9-8.5 (0.7H, NHCO incomplete exchange), 7.8-7.7 (m, 1H), 7.55-4.45 (m, 1H), 7.35-7.1 (m, 5H), 5.5-5.75 (m, 1H), 4.9-4.6 (m, 2H), 4.2-0.8 (m, 64H).

Compound 41
methyl (S)-2-((2R,3R)-3-((S)-1-((8S,11S,14S,15R)-14-((S)-sec-butyl)-8,11-diisopropyl-15-methoxy-7,13-dimethyl-9,12-dioxo-2,7,10,13-tetraazaheptadecan-17-oyl)pyrrolidin-2-yl)-3-methoxy-2-methylpropanamido)-3-phenylpropanoate, bis trifluoroacetic acid
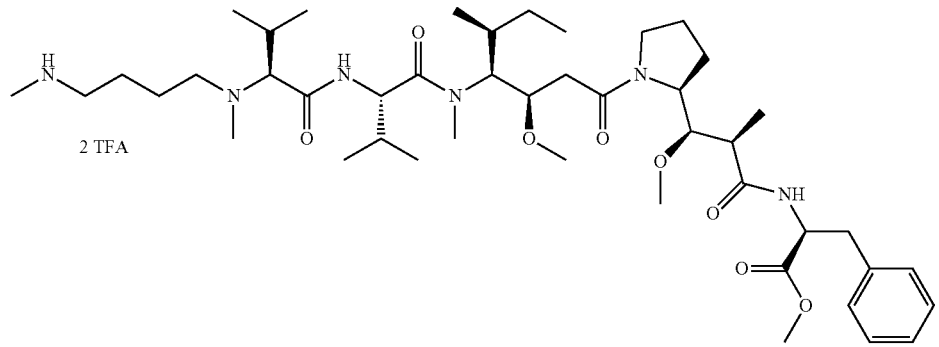 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCCCNC)C(C)C]
Compound 41A
methyl (S)-2-((2R,3R)-3-((S)-1-((11S,14S,17S,18R)-17-((S)-sec-butyl)-11,14-diisopropyl-18-methoxy-2,2,5,10,16-pentamethyl-4,12,15-trioxo-3-oxa-5,10,13,16-tetraazaicosan-20-oyl)pyrrolidin-2-yl)-3-methoxy-2-methylpropanamido)-3-phenylpropanoate
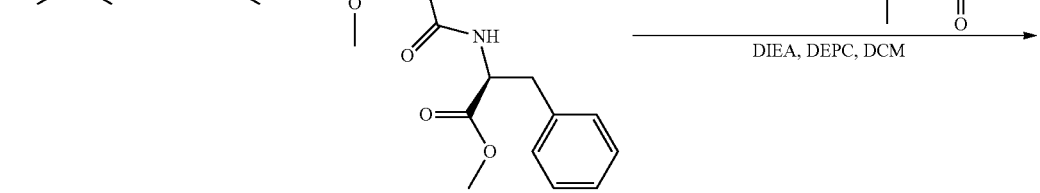
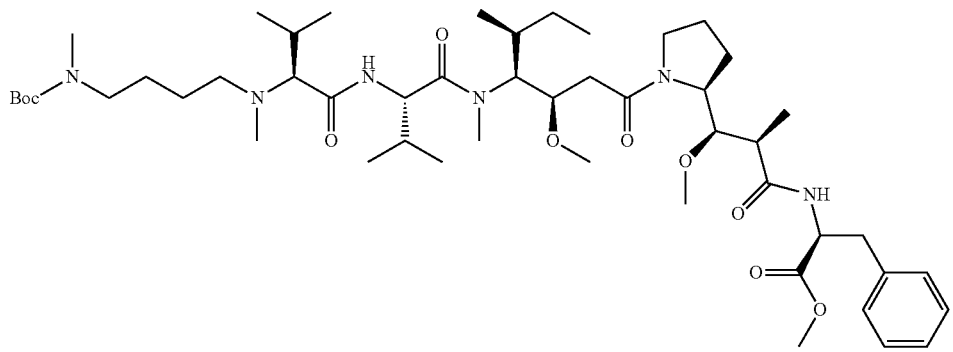

Compound 41A was synthesised in the same manner as for compound 3 from the amine 3D (170 mg, 0.27 mmol, 1.00 equiv), the acid 40D (170 mg, 0.54 mmol, 2.09 equiv), DEPC (0.0819 mL) and DIEA (0.133 mL) in DCM (5 mL). The crude product (200 mg) was subsequently used as such.

Compound 41

Compound 41 was synthesised in the same manner as for compound 2 from the intermediate 41A (100 mg, 0.11 mmol, 1.00 equiv). The crude product was purified by preparative HPLC (Pre-HPLC-001 SHIMADZU, SUN-FIRE™ Prep C18 OBD column, 5 μm, 19×100 mm; Eluting phase: water/ACN buffered with 0.05% TFA; Gradient of 20% to 40% ACN in 10 minutes then 40% to 95% ACN in 2 minutes; Waters 2545 UV Detector at 254 nm and 220 nm). Compound 41 was obtained with a yield of 25% (25 mg) in the form of a white solid.

LC/MS/UV (AGILENT® ZORBAX® SB-Aq column, 1.8 μm, 4.6×100 mm; 40° C.; 1.5 mL/min, 2% MeOH in water (0.05% TFA) for 1 minute then 2% to 95% MeOH in water in 13 minutes, then 95% MeOH in water for 2 minutes); ESI ($C_{45}H_{78}N_6O_8$, exact mass 830.6) m/z: 831.6 (MH$^+$) and 416.4 (M.2H$^+$/2, 100) 11.58 min (97.2%,210 nm).

$^1$H NMR: (400 MHz, CD$_3$OD, ppm): δ (Presence of rotamers) 8.55-8.15 (0.75H, NHCO incomplete exchange), 7.30-7.1 (m, 5H), 4.9-4.6 (m, 3H), 4.2-0.8 (m, 67H).

Compound 42

(S)-2-((2R,3R)-3-((S)-1-((8S,11S,14S,15R)-14-((S)-sec-butyl)-8,11-diisopropyl-15-methoxy-7,13-dimethyl-9,12-dioxo-2,7,10,13-tetraazaheptadecan-17-oyl)pyrrolidin-2-yl)-3-methoxy-2-methylpropanamido)-3-phenylpropanoic acid, bis trifluoroacetic acid

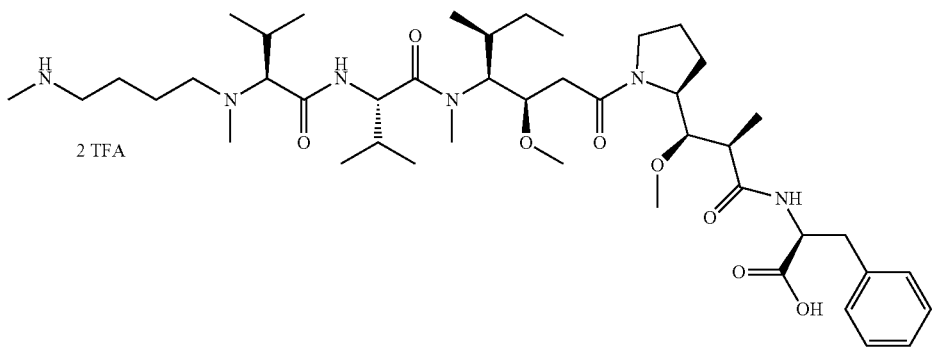 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCCCNC)C(C)C]

Compound 42 was prepared in the same manner as for compound 4, from compound 41 (100 mg, 0.11 mmol, 1.00 equiv). The residue was purified by preparative HPLC (Pre-HPLC-001 SHIMADZU, Atlantis Prep OBD T3 column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 30.6 mg (31%) of compound 42 in the form of a white solid.

LC/MS/UV (Ascentis Express C18 column, 2.7 μm, 4.6×100 mm; 40° C.; 1.5 mL/min, 0% to 95% MeOH in water (0.05% TFA) in 8 minutes); ESI ($C_{44}H_{76}N_6O_8$, exact mass 816.6) m/z: 817.6 (MH$^+$) and 409.4 (M.2H$^+$/2, 100) 5.75 min (100%, 210 nm).

$^1$H NMR: (400 MHz, CD$_3$OD, ppm): δ (Presence of rotamers) 8.5-8.1 (0.3H, NHCO incomplete exchange), 7.30-7.1 (m, 5H), 4.9-4.6 (m, 3H), 4.2-0.8 (m, 64H).

Compound 43

(S)—N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethyl-2-((R)-3-methyl-2-(methyl(2-(2-(methylamino) ethoxy)ethyl) amino)butanamido)butanamide, bis trifluoroacetic acid

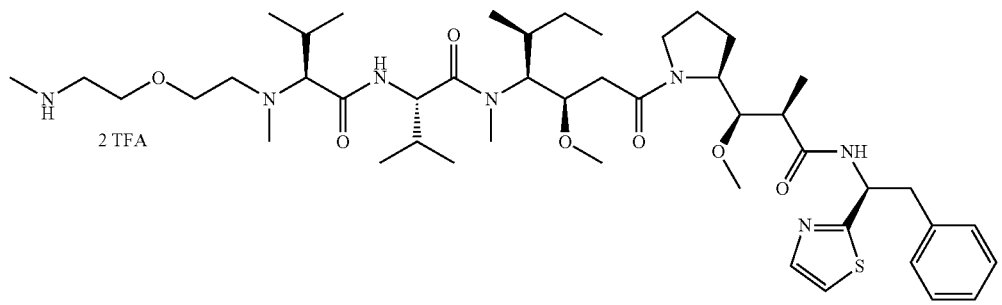 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCOCCNC)C(C)C]

Compound 43A tert-butyl(2-(2-((tertbutyldimethylsilyl)oxy)ethoxy) ethyl) carbamate

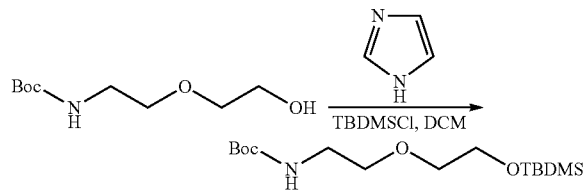

Compound 35A (tert-butyl ((2-(2-hydroxyethoxy)ethyl) carbamate) (8.21 g, 40.00 mmol, 1.00 equiv) and imidazole (6 g, 88.14 mmol, 2.20 equiv) were dissolved in an inert atmosphere in DCM (200 mL). Tertbutyldimethylsilane chloride (TBDMSCl, 6.62 g, 43.92 mmol, 1.10 equiv) was added drop-wise and the reaction medium was left under agitation overnight at ambient temperature. The reaction mixture was diluted with 100 mL of DCM then washed twice with 200 mL of 0.5 M HCl, twice with 200 mL of NaHCO₃ (sat.), then 300 mL of NaCl (sat.). The organic phase was dried over sodium sulfate, filtered and concentrated under reduced pressure. The residue was purified on silica gel (EtOAc/PE (1:3) to yield 10 g (78%) of compound 43A in the form of a white solid.

Compound 43B tert-butyl (2-(2-((tert-butyldimethylsilyl)oxy)ethoxy) ethyl)(methyl)carbamate

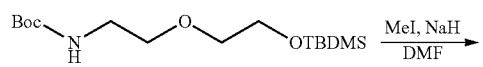

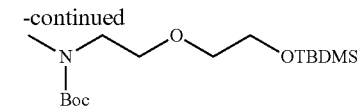

Compound 43B was prepared in the same manner as for compound 11E, from compound 43A (10 g, 31.30 mmol, 1.00 equiv), NaH (60% in oil, 5 g, 208.33 mmol, 4.00 equiv) and iodomethane (22 g, 5.00 equiv) in DMF (200 mL). The reaction medium was neutralised with 200 mL of water and washed 3 times with 100 mL of AcOEt then 300 mL of NaCl (sat.). The organic phase was dried over sodium sulfate, filtered and concentrated under reduced pressure to yield 10 g (96%) of compound 43B in the form of a white solid.

Compound 43C tert-butyl (2-(2-hydroxyethoxy)ethyl)(methyl)carbamate

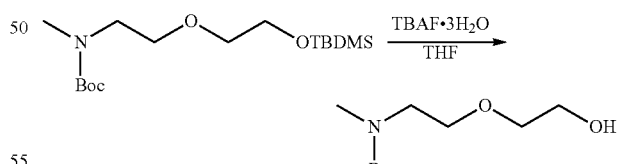

Compound 43B (10 g, 29.89 mmol, 1.00 equiv) and TBAF.3H₂O (20.8 g, 65.93 mmol, 2.20 equiv) were dissolved in THF (200 mL). The mixture was agitated at ambient temperature for 2 hours then extracted 3 times with 100 mL of AcOEt. The organic phases were recombined, washed twice with 300 mL of water, then twice with 300 mL of NaCl (sat.), dried over sodium sulfate, filtered and concentrated under reduced pressure. The residue was purified on silica gel (EtOAc/PE (1:3-1:1) to yield 6.6 g of compound 43C in the form of colourless oil.

223

Compound 43D tert-butylmethyl(2-(2-oxoethoxy)ethyl)carbamate

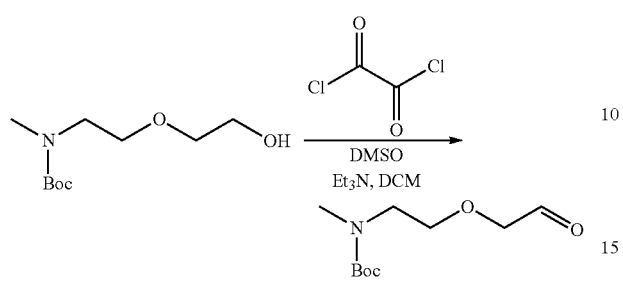

Compound 43D was prepared in the same manner as for compound 35B, from compound 43C (2 g, 9.12 mmol, 1.00 equiv), oxalyl chloride (1.9 mL), TEA (11.3 mL) and DMSO (3.3 mL). Compound 43D (2 g) was isolated in the form of yellow oil.

Compound 43E benzyl (S)-12-isopropyl-2,2,5,11-tetramethyl-4-oxo-3,8-dioxa-5,11-diazatridecan-13-oate

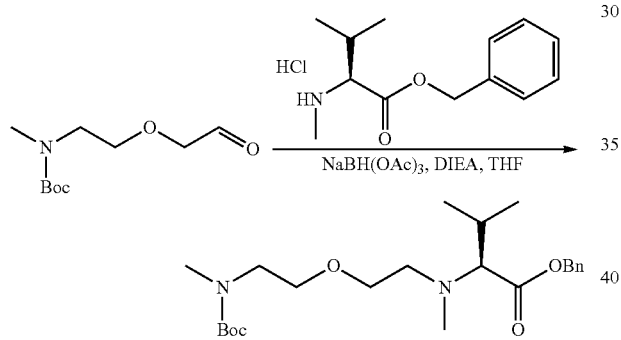

Compound 43E was synthesised in the same manner as for compound 14C from the amine 1ZC (2.4 g, 9.31 mmol,

224

1.00 equiv), the aldehyde 43D (2 g, 9.16 mmol, 1.00 equiv), NaBH(OAc)$_3$ (4 g, 18.87 mmol, 2.06 equiv) and DIEA (6 mL) in THF (100 mL). The reaction mixture was neutralised with 100 mL of water and extracted 3 times with 100 mL of AcOEt. The organic phases were combined, dried over sodium sulfate, filtered and concentrated. The residue was purified on silica gel (EtOAc/PE (4:1) to yield 1 g (37%) of compound 43E in the form of a white solid.

Compound 43F (S)-12-isopropyl-2,2,5,11-tetramethyl-4-oxo-3,8-dioxa-5,11-diazatridecan-13-oic acid

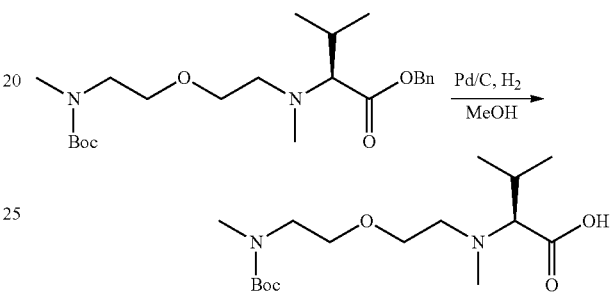

Compound 43E (1 g, 2.37 mmol, 1.00 equiv) was dissolved in 40 mL of MeOH in the presence of Pd/C (1 g) and hydrogenated for 1 hour at ambient temperature and atmospheric pressure. The reaction medium was filtered and concentrated under reduced pressure to yield 600 mg (76%) of compound 43F in the form of a white solid.

Compound 43G tert-butyl ((3R,4S,7S,10R)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2,14-dioxa-5,8,11-triazahexadecan-16-yl)(methyl)carbamate

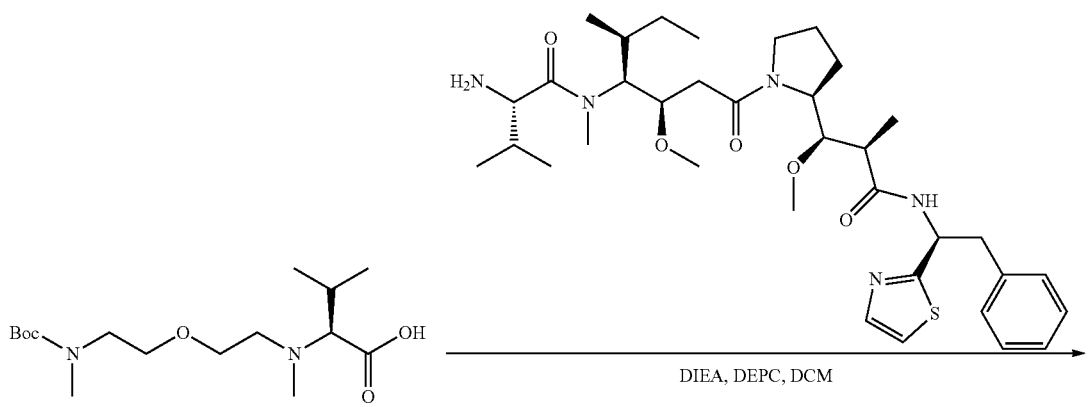

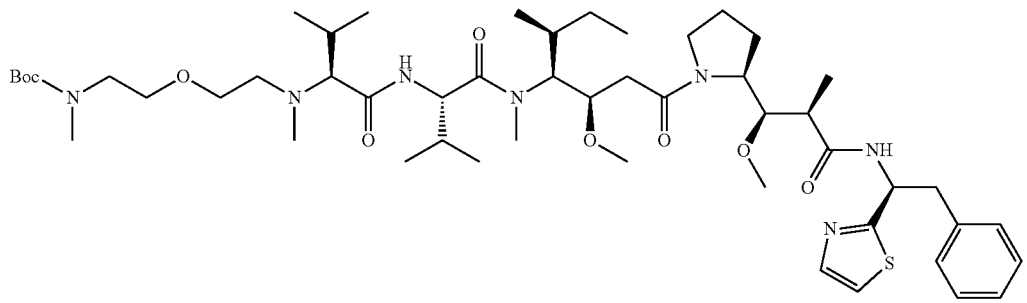

Compound 43G was synthesised in the same manner as for compound 3 from the amine 1Y (50 mg, 0.08 mmol, 1.00 equiv), the acid 43F (50 mg, 0.08 mmol, 1.00 equiv), DEPC (24.79 mg, 0.15 mmol, 2.00 equiv) and DIEA (29.46 mg, 0.23 mmol, 3.00 equiv) in DCM (1 mL). The crude product (59 mg) was subsequently used as such.

Compound 43

Compound 43 was synthesised in the same manner as for compound 2 from the intermediate 43G (81 mg, 0.08 mmol, 1.00 equiv). The crude product was purified by preparative HPLC (Pre-HPLC-001 SHIMADZU, SUNFIRE™ Prep C18 OBD column, 5 μm, 19×100 mm; Eluting phase: water/ACN buffered with 0.05% TFA; Gradient of 20% to 40% ACN in 10 minutes then 40% to 95% ACN in 2 minutes; Waters 2545 UV Detector at 254 nm and 220 nm). Compound 43 was obtained with a yield of 64% (52.6 mg) in the form of a white solid.

LC/MS/UV (Ascentis Express C18 column, 2.7 μm, 4.6× 100 mm; 40° C.; 1.5 mL/min, 10% to 95% MeCN in water (0.05% TFA) for 8 minutes then 95% MeCN in water for 2 minutes); ESI ($C_{48}H_{77}N_7O_7S$, exact mass 871.6) m/z: 872.5 (MH$^+$) and 436.9 (M.2H$^+$/2, 100%), 3.90 min (100%, 210 nm).

$^1$H NMR: (400 MHz, CD$_3$OD, ppm): δ (Presence of rotamers) 7.8-7.7 (m, 1H), 7.55-4.45 (m, 1H), 7.35-7.1 (m, 5H), 5.5-5.75 (m, 1H), 4.9-4.6 (m, 2H), 4.2-0.8 (m, 64H).

Compound 44 methyl (S)-2-((2R,3R)-3-((S)-1-((9S,12S,15S,16R)-15-((S)-sec-butyl)-9,12-diisopropyl-16-methoxy-8,14-dimethyl-10,13-dioxo-5-oxa-2,8,11,14-tetraazaoctadecan-18-oyl)pyrrolidin-2-yl)-3-methoxy-2-methylpropanamido)-3-phenylpropanoate, bis trifluoroacetic acid

Compound 44A methyl (S)-2-((2R,3R)-3-((S)-1-((12S,15S,18S,19R)-18-((S)-sec-butyl)-12,15-diisopropyl-19-methoxy-2,2,5,11,17-pentamethyl-4,13,16-trioxo-3,8-dioxa-5,11,14,17-tetraazahenicosan-21-oyl)pyrrolidin-2-yl)-3-methoxy-2-methylpropanamido)-3-phenylpropanoate

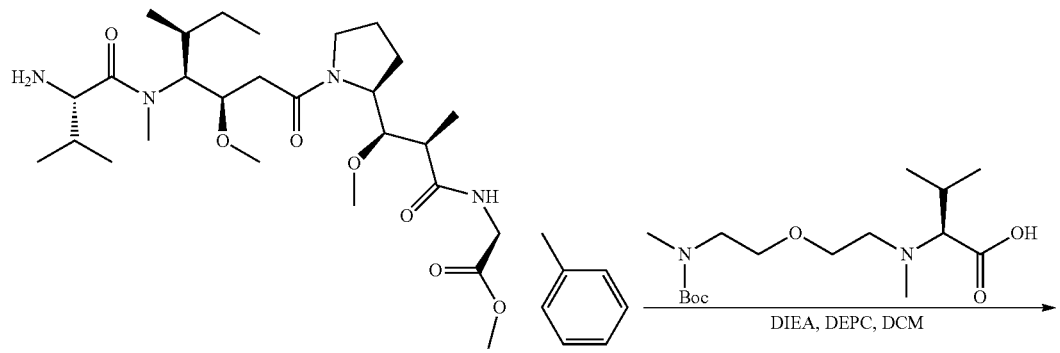

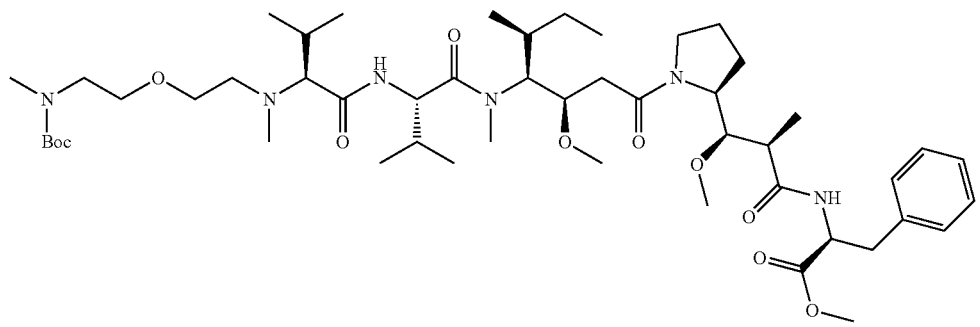 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCOCCNC)C(C)C]

Compound 44A was synthesised in the same manner as for compound 3 from the amine 3D (60 mg, 0.09 mmol, 1.00 equiv), the acid 43F (47 mg, 0.14 mmol, 1.50 equiv), DEPC (31 mg, 0.19 mmol, 2.00 equiv) and DIEA (37 mg, 0.28 mmol, 3.00 equiv) in DCM (1.5 mL). The crude product (58 mg) was subsequently used as such.

Compound 44

Compound 44 was synthesised in the same manner as for compound 2 from the intermediate 44A (58 mg, 0.06 mmol, 1.00 equiv). The crude product was purified by preparative HPLC (Pre-HPLC-001 SHIMADZU, SUNFIRE™ Prep C18 OBD column, 5 μm, 19×100 mm; Eluting phase: water/ACN buffered with 0.05% TFA; Gradient of 20% to 40% ACN in 10 minutes then 40% to 95% ACN in 2 minutes; Waters 2545 UV Detector at 254 nm and 220 nm). Compound 44 was obtained with a yield of 40% (23.7 mg) in the form of a white solid.

LC/MS/UV (Ascentis Express C18 column, 2.7 μm, 4.6× 100 mm; 40° C.; 1.5 mL/min, 10% to 95% MeCN in water (0.05% TFA) for 8 minutes then 95% MeCN in water for 2 minutes); ESI ($C_{45}H_{78}N_6O_9$, exact mass 846.6) m/z: 847.6 (MH$^+$) and 424.4 (M.2H$^+$/2, 100%), 3.20 min (100%, 210 nm).

$^1$H NMR: (400 MHz, CD$_3$OD, ppm): δ (Presence of rotamers) 7.3-7.1 (m, 5H), 4.9-4.6 (m, 3H), 4.2-0.8 (m, 67H).

Compound 45

(S)—N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethyl-2-((S)-3-methyl-2-(methyl(2-(piperazin-1-yl)ethyl)amino)butanamido)butanamide, tris trifluoroacetic acid

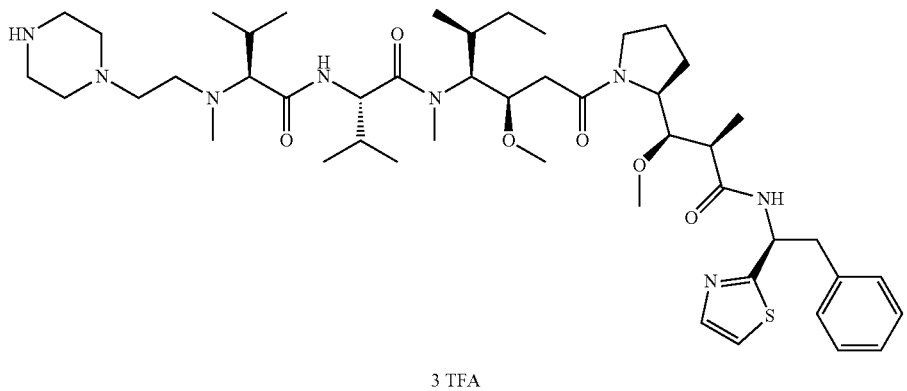 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCN1CCNCC1)C(C)C]

3 TFA

Compound 45A: tert-butyl 4-(2-hydroxyethyl)piperazine-1-carboxylate

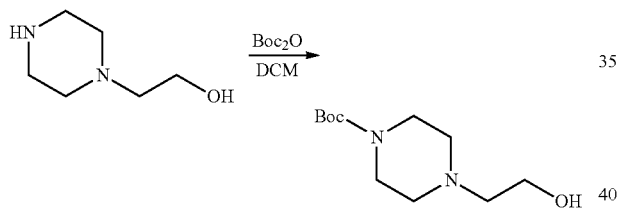

2-(piperazin-1-yl)ethan-1-ol (5 g, 38.41 mmol, 1.00 equiv) was dissolved in DCM (100 mL), and a solution of di-tert-butyl dicarbonate (8.38 g, 38.40 mmol, 1.00 equiv) in DCM (20 mL) was added drop-wise. The reaction was left under agitation overnight at ambient temperature. The reaction was evaporated to dryness and the residue dissolved in 200 mL of AcOEt, washed 5 times with NaCl (sat.), dried over sodium sulfate, filtered and concentrated under reduced pressure to yield 8.5 g (96%) of compound 45A in the form of a white solid.

Compound 45B tert-butyl 4-(2-oxoethyl)piperazine-1-carboxylate

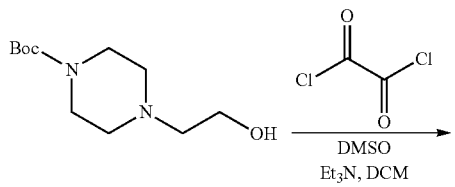

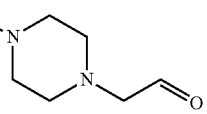

Compound 45B was prepared in the same manner as for compound 35B, from compound 45A (1 g, 4.34 mmol, 1.00 equiv), oxalyl chloride (610 mg, 4.80 mmol, 1.12 equiv), TEA (2.13 g, 21.09 mmol, 4.90 equiv) and DMSO (0.82 g, 2.40 equiv). Compound 45B (0.8 g, 81%) was isolated in the form of a colourless oil.

Compound 45C tert-butyl (S)-4-(2-((1-(benzyloxy)-3-methyl-1-oxobutan-2-yl)(methyl)amino)ethyl)piperazine-1-carboxylate

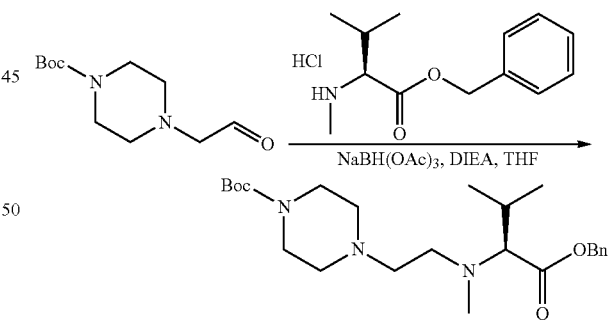

Compound 45C was synthesised in the same manner as for compound 14C from the amine 1ZC (720 mg, 2.79 mmol, 0.80 equiv), the aldehyde 45B (800 mg, 3.50 mmol, 1.00 equiv), NaBH(OAc)$_3$ (1.6 g, 7.55 mmol, 2.15 equiv) and DIEA (2.5 mL) in THF (50 mL). The reaction mixture was neutralised with 5 mL of water and extracted 3 times with 5 mL of AcOEt. The organic phases were combined, dried over sodium sulfate, filtered and concentrated. The residue was purified on silica gel (EtOAc/PE (3:1) to yield 400 mg (33%) of compound 45C in the form of a colourless oil.

Compound 45D (S)-2-((2-(4-(tert-butoxycarbonyl)piperazin-1-yl)
ethyl) (methyl)amino)-3-methylbutanoic acid

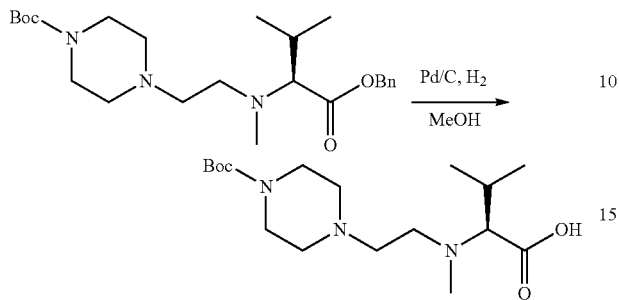

Compound 45C (400 mg, 0.92 mmol, 1.00 equiv) was dissolved in 30 mL of MeOH in the presence of Pd/C (400 mg) and hydrogenated for 1 hour at ambient temperature and atmospheric pressure. The reaction medium was filtered and concentrated under reduced pressure to yield 300 mg (95%) of compound 45D in the form of a white solid.

Compound 45E tert-butyl 4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)piperazine-1-carboxylate

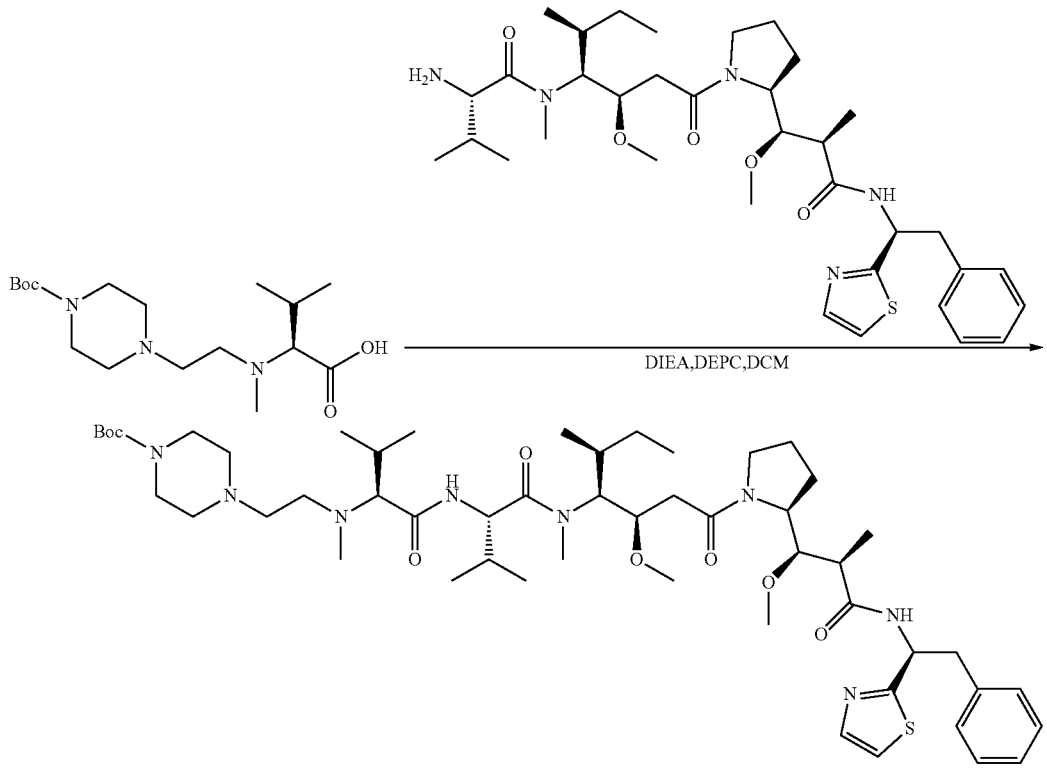

Compound 45E was synthesised in the same manner as for compound 3 from the amine 1Y (60 mg, 0.09 mmol, 1.00 equiv), the acid 45D (62.7 mg, 0.18 mmol, 2.00 equiv), DEPC (0.0278 mL) and DIEA (0.0452 mL) in DCM (3 mL). The crude product (100 mg) was subsequently used as such.

Compound 45

Compound 45 was synthesised in the same manner as for compound 2 from the intermediate 45E (100 mg, 0.10 mmol, 1.00 equiv). The crude product was purified by preparative HPLC (Pre-HPLC-001 SHIMADZU, SUNFIRE™ Prep C18 OBD column, 5 μm, 19×100 mm; Eluting phase: water/ACN buffered with 0.05% TFA; Gradient of 20% to 40% ACN in 10 minutes then 40% to 95% ACN in 2 minutes; Waters 2545 UV Detector at 254 nm and 220 nm). Compound 45 was obtained with a yield of 19% (19.4 mg) in the form of a white solid.

LC/MS/UV (AGILENT® ZORBAX® SB-Aq column, 1.8 μm, 4.6×100 mm; 40° C.; 1.0 mL/min, 2% MeOH in water (0.05% TFA) for 1 minute then 2% to 95% MeOH in water in 13 minutes then 95% MeOH in water for 2 minutes); ESI ($C_{47}H_{78}N_8O_6S$, exact mass 882.6) m/z: 883.5 ($MH^+$) and 442.4 ($M.2H^+/2$, 100%), 10.95 min (98.8%,210 nm).

$^1$H NMR: (400 MHz, $CD_3OD$, ppm): δ (Presence of rotamers), 7.80-7.70 (m, 1H), 7.52-7.43 (m, 1H), 7.31-7.09 (m, 5H), 5.70-5.51 (m, 1H), 4.80-4.60 (m, 1H), 4.20-0.75 (m, 66H).

Compound 46 methyl (S)-2-((2R,3R)-3-((S)-1-((3R,4S,5S)-4-((S)—N,3-dimethyl-2-((S)-3-methyl-2-(methyl(2-(piperazin-1-yl)ethyl)amino)butanamido)butanamido)-3-methoxy-5-methylheptanoyl)pyrrolidin-2-yl)-3-methoxy-2-methylpropanamido)-3-phenylpropanoate, tris trifluoroacetic acid

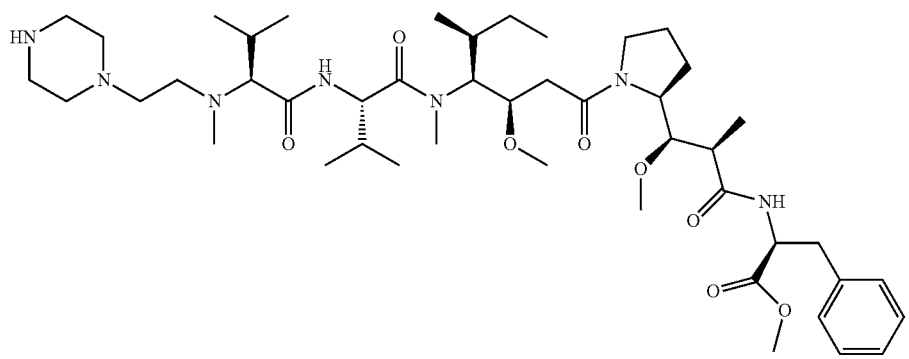

3 TFA

Compound 46A tert-butyl 4-((3R,4S,7S,10S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11-dimethyl-6,9-dioxo-2-oxa-5,8,11-triazatridecan-13-yl)piperazine-1-carboxylate

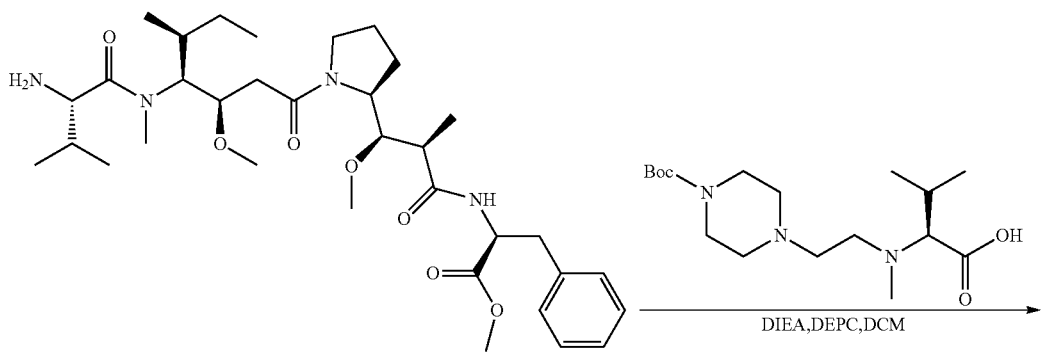

235

-continued

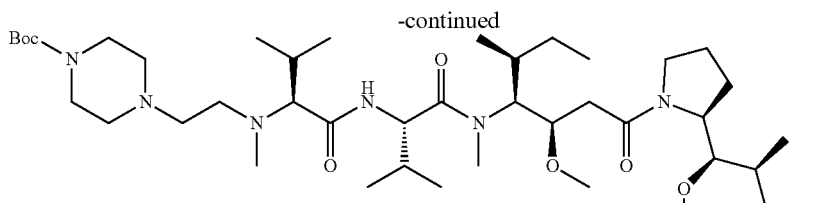

Compound 46A was synthesised in the same manner as for compound 3 from the amine 3D (170 mg, 0.27 mmol, 1.00 equiv) the acid 45D (184.6 mg, 0.54 mmol, 2.00 equiv), DEPC (0.0819 mL) and DIEA (0.133 mL) in DCM (5 mL). The crude product (200 mg) was subsequently used as such.

Compound 46

Compound 46 was synthesised in the same manner as for compound 2 from the intermediate 46A (100 mg, 0.10 mmol, 1.00 equiv). The crude product was purified by preparative HPLC (Pre-HPLC-001 SHIMADZU, SUN-FIRE™ Prep C18 OBD column, 5 μm, 19×100 mm; Eluting phase: water/ACN buffered with 0.05% TFA; Gradient of 20% to 40% ACN in 10 minutes then 40% to 95% ACN in 2 minutes; Waters 2545 UV Detector at 254 nm and 220 nm). Compound 46 was obtained with a yield of 19% (19.1 mg) in the form of a white solid.

236

LC/MS/UV (Ascentis Express C18 column, 2.7 μm, 4.6× 100 mm; 40° C.; 1.5 mL/min, 10% to 95% MeCN in water (0.05% TFA) for 8 minutes then 95% MeCN in water for 2 minutes); ESI ($C_{46}H_{79}N_7O_8$, exact mass 857.6) m/z: 858.6 (MH$^+$) an 429.9 (M.2H$^+$/2, 100%), 5.93 min (100%, 210 nm).

$^1$H NMR: (400 MHz, CD$_3$OD, ppm): δ (Presence of rotamers) 8.58-8.50 (m, 0.5H, NHCO, incomplete exchange), 8.29-8.22 (m, 0.4H, NHCO, incomplete exchange), 7.35-7.15 (m, 5H), 4.87-4.69 (m, 3H), 4.22-0.82 (m, 68H).

Compound 47

(S)-2-((2R,3R)-3-((S)-1-((3R,4S,5S)-4-((S)—N,3-dimethyl-2-((S)-3-methyl-2-(methyl(2-(piperazin-1-yl)ethyl)amino)butanamido)butanamido)-3-methoxy-5-methylheptanoyl)pyrrolidin-2-yl)-3-methoxy-2-methylpropanamido)-3-phenylpropanoic acid, tris trifluoroacetic acid

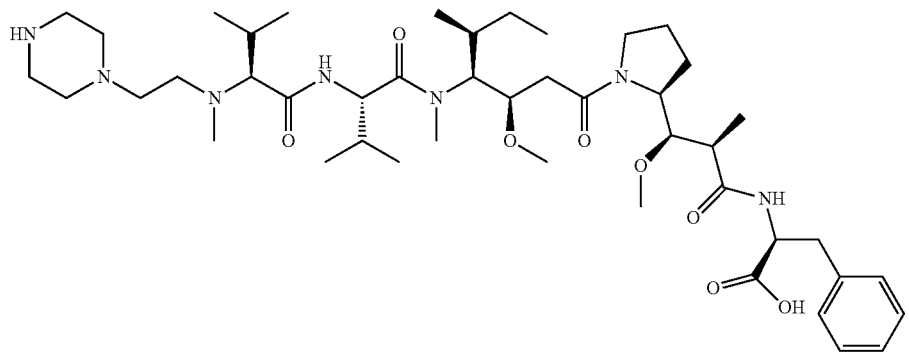

3 TFA

Compound 47 was prepared in the same manner as for compound 4, from compound 46 (100 mg, 0.10 mmol, 1.00 equiv). The residue was purified by preparative HPLC (Pre-HPLC-001 SHIMADZU, Atlantis Prep OBD T3 column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 32.6 mg (33%) of compound 47 in the form of a white solid.

LC/MS/UV (Ascentis Express C18 column, 2.7 μm, 4.6× 100 mm; 40° C.; 1.5 mL/min, 10% to 95% MeOH in water (0.05% TFA) in 8 minutes); ESI ($C_{46}H_{77}N_7O_8$, exact mass 843.6) m/z: 844.6 (MH$^+$) and 422.9 (M.2H$^+$/2, 100%), 5.73 min (100%, 210 nm).

$^1$H NMR: (400 MHz, CD$_3$OD, ppm): δ (Presence of rotamers) 8.66-8.57 (m, 0.3H, NHCO, incomplete exchange), 8.41-8.32 (m, 0.3H, NHCO, incomplete exchange), 8.13-8.06 (m, 0.2H, NHCO, incomplete exchange), 7.30-7.10 (m, 5H), 4.80-4.61 (m, 3H), 4.19-0.78 (m, 65H).

Compound 48

(S)-2-((S)-2-(((1H-imidazol-2-yl)methyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, trifluoroacetic acid

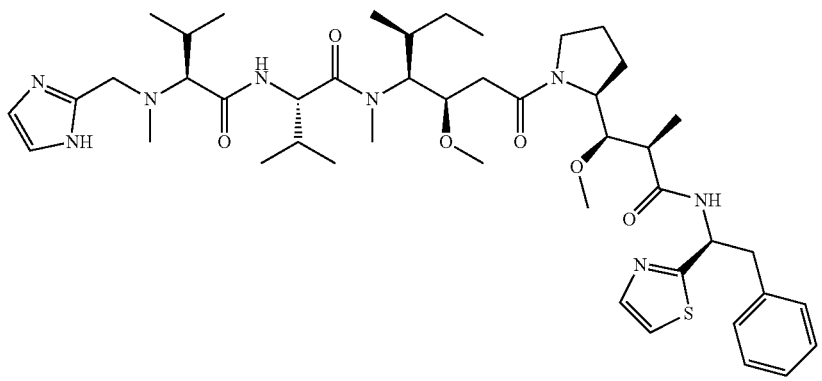

TFA

Compound 48 was prepared in the same manner as for compound 1, from the amines 1Y and 1ZC and 1H-imidazole-2-carbaldehyde. The end product was purified by preparative HPLC under the following conditions: SUNFIRE™ Prep C18 OBD column, 5 μm, 19×150 mm, mobile phases buffered with 0.05% TFA, gradient of 15.0 to 30% ACN in water in 10 minutes then up to 95.0% ACN in 2 minutes, UV Detection UV 220 nm.

LC/MS/UV (ZORBAX® Eclipse Plus C8, 1.8 μm, 4.6× 100 mm; 1 mL/min, 40° C., 2% methanol in water (eluting phases buffered with 0.05% TFA) for 1 minute, then 2% to 95% methanol for 12 minutes; ESI ($C_{45}H_{70}N_8O_6S$, exact mass 850.51) m/z: 851.2 (MH$^+$), 873.5 (MNa$^+$), 426.3 (M.2H$^+$/2); 12.75 min (90.5%,210 nm).

$^1$H NMR: (400 MHz, CD$_3$OD, ppm): δ (Presence of rotamers) 7.83-7.81 (m, 1H), 7.80-7.53 (m, 3H), 7.53-7.22 (m, 5H), 5.6-5.8 (m, 1H), 5.0-4.6 (m, 2H); 4.6-0.85 (m, 55H).

Compound 49

(S)-2-((S)-2-((4-hydroxyphenethyl)(mthyl)amino)-3-methylbutanamido)-N-((3R,4S,5S)-3-mthoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, trifluoroacetic acid

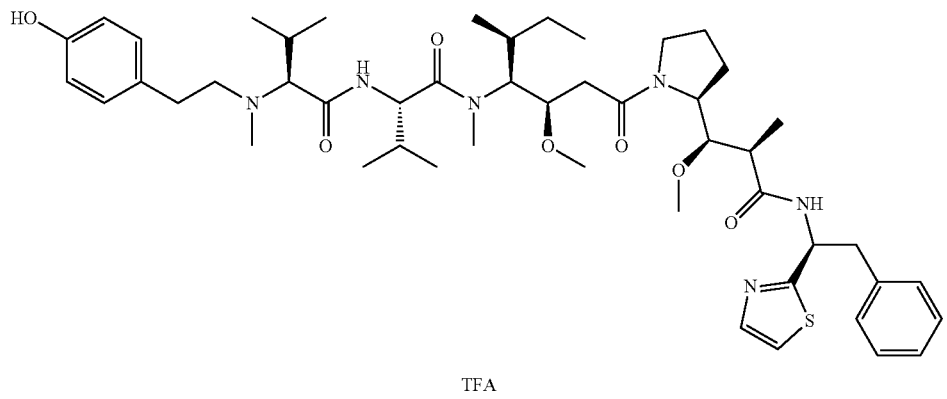 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCc1ccc(O)cc1)C(C)C]

TFA

Compound 49A: 2-(4-hydroxyphenyl)acetaldehyde

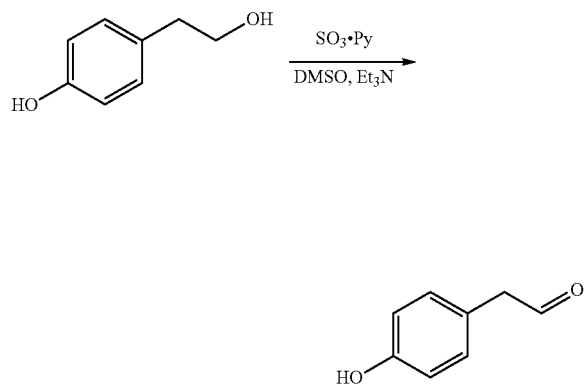

Compound 49B benzyl (S)-2-((4-hydroxyphenethyl)(methyl)amino)-3-methylbutanoate

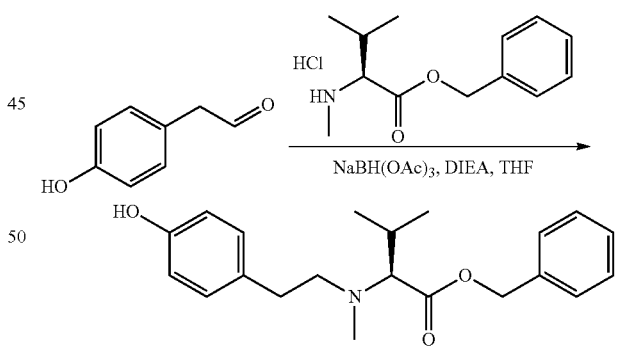

4-(2-hydroxyethyl)phenol (4 g, 28.95 mmol, 1.00 quiv) was dissolved in DMSO (32 mL) and TEA (8.8 mL, 2.20 equiv) was then added dropwise. A solution of $SO_3 \cdot Py$ (10 g, 2.20 equiv) in DMSO (36 mL) was added and the mixture was left under agitation overnight at ambient temperature. The reaction mixture was neutralised with 250 mL of water and extracted 3 times with 100 mL of AcOEt. The organic phases were combined, washed 5 times with water (100 mL) then twice with 150 mL of NaCl (sat.), dried over sodium sulfate, filtered and concentrated. The residue was purified on silica gel (EtOAc/PE (1:10)) to yield 1 g (25%) of compound 49A in the form of a colourless oil.

Compound 49B was synthesised in the same manner as for compound 14C from the amine 1ZC (1.5 g, 5.82 mmol, 0.99 equiv), the aldehyde 49A (800 mg, 5.88 mmol, 1.00 equiv), $NaBH(OAc)_3$ (2.7 g, 12.74 mmol, 2.17 equiv) and DIEA (4.23 mL) in THF (25 mL). The reaction mixture was neutralised with 50 mL of water and extracted 3 times with 50 mL of AcOEt. The organic phases were combined, dried over sodium sulfate, filtered and concentrated. The residue was purified on silica gel (EtOAc/PE (1:10)) to yield 600 mg (37%) of compound 49B in the form of a white solid.

Compound 49C (S)-2-((4-hydroxyphenethyl)(methyl)amino)-3-methylbutanoic acid

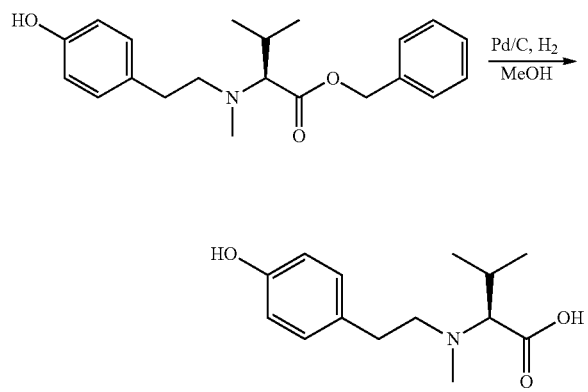

Compound 49B (0.5 g, 1.46 mmol, 1.00 equiv) was dissolved in 40 mL of MeOH in the presence of Pd/C (250 mg) and hydrogenated for 3 hours at ambient temperature and atmospheric pressure. The reaction medium was filtered and concentrated under reduced pressure to yield 0.4 g of compound 49C in the form of a white solid.

Compound 49

Compound 49 was synthesised in the same manner as for compound 3 from the amine 1Y (53.4 mg, 0.08 mmol, 2.00 equiv), the acid 49C (70 mg, 0.28 mmol, 1.00 equiv), DEPC (0.032 mL, 2.00 equiv) and DIEA (0.053 mL, 3.00 equiv) in DCM (3 mL). The residue was purified by preparative HPLC (Pre-HPLC-001 SHIMADZU, Atlantis Prep OBD T3 column, 5 μm, 19×150 mm; Eluting phase: water/ACN buffered with 0.05% TFA; Gradient of 20% to 45% ACN in 10 minutes then 45% to 100% ACN in 2 minutes; Waters 2545 UV Detector at 254 nm and 220 nm), to yield 3 mg (1%) of compound 49 in the form of a white solid.

LC/MS/UV (Ascentis Express C18 column, 2.7 μm, 4.6× 100 mm; 40° C.; 1.5 mL/min, 10% to 95% MeOH in water (0.05% TFA) in 8 minutes); ESI ($C_{49}H_{74}N_6O_7S$, exact mass 890.5) m/z: 891.5 (MH$^+$) and 446.4 (M.2H$^+$/2, 100%), 6.69 min (100%, 210 nm).

$^1$H NMR: (400 MHz, CD$_3$OD, ppm): δ (Presence of rotamers) 8.92-8.87 (m, 0.5H, NHCO, incomplete exchange), 8.70-8.63 (m, 0.4H, NHCO, incomplete exchange), 8.85-8.77 (m, 1H), 7.59-7.51 (m, 1H), 7.35-7.03 (m, 7H), 6.82-6.71 (m, 2H), 5.77-5.58 (m, 1H), 5.81-5.70 (m, 1H), 4.21-0.80 (m, 58H).

Compound 50

(S)-2-((2R,3R)-3-((S)-1-((3R,4S,5S)-4-((S)-2-((S)-2-((4-hydroxyphenethyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid, trifluoroacetic acid

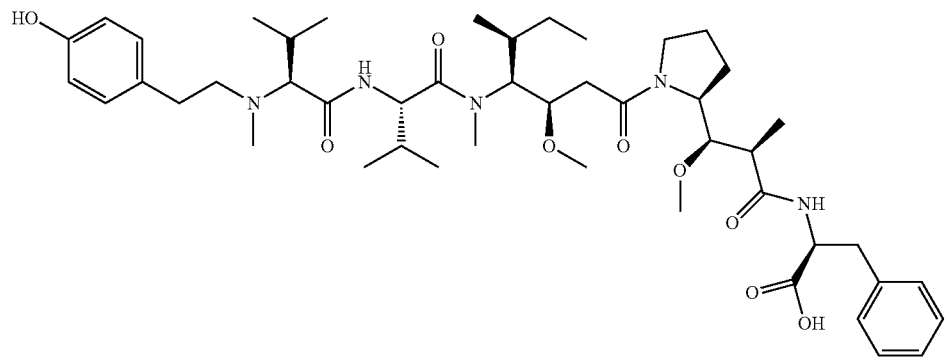

TFA

Compound 50 was prepared in the same manner as for compound 4, from compound 27 (100 mg, 0.10 mmol, 1.00 equiv). The residue was purified by preparative HPLC (Pre-HPLC-001 SHIMADZU, Atlantis Prep OBD T3 column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 10.7 mg (11%) of compound 50 in the form of a white solid.

LC/MS/UV (Ascentis Express C18 column, 2.7 μm, 4.6× 100 mm; 40° C.; 1.5 mL/min, 10% to 95% MeOH in water (0.05% TFA) in 8 minutes); ESI ($C_{47}H_{73}N_5O_9$, exact mass 851.5) m/z: 852.5 ($MH^+$) and 426.8 ($M.2H^+/2$, 100%), 6.46 min (91.70% 210 nm).

$^1$H NMR: (400 MHz, $CD_3OD$, ppm): δ (Presence of rotamers) 7.34-7.15 (m, 5H); 7.15-7.04 (se, 2H), 6.82-6.83 (m, 2H), 4.83-4.70 (m, 1H), 4.21-4.00 (m, 1H), 3.90-3.80 (m, 1H), 3.74-3.62 (m, 1H), 3.57-2.86 (m, 20H), 2.56-0.80 (m, 36H).

Compound 51 methyl (S)-2-((2R,3R)-3-((S)-1-((3R,4S,5S)-4-((S)-2-((S)-2-((4-hydroxybenzyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate, trifluoroacetic acid

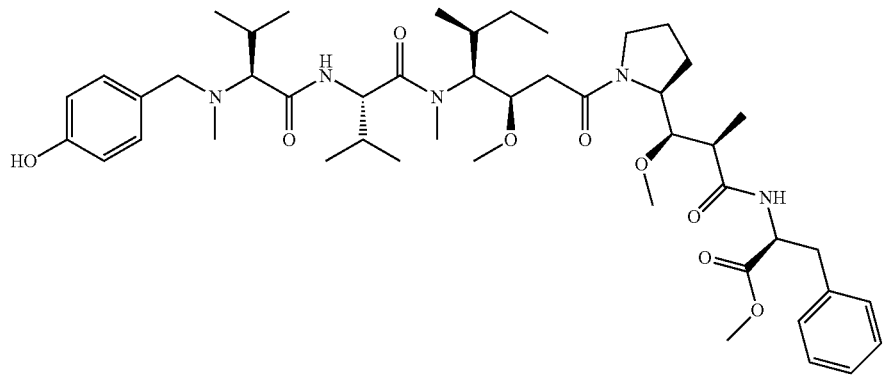

TFA

Compound 51A tert-butyl (4-formylphenyl)carbonate

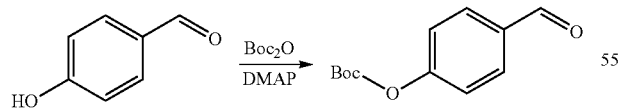

4-hydroxybenzaldehyde (3.0 g, 24 mmol) was dissolved in 30 mL of DCM in the presence of 4-DMAP (300 mg, 2.46 mmol, 0.1 equiv.) and di-tert-butyl dicarbonate (5.35 g, 24 mmol, 1.0 equiv.) and agitated 1 hour at ambient temperature. The solution was then diluted with 200 mL of water and extracted 3 times with 100 mL of DCM. The organic phases were combined, dried over sodium sulfate, filtered and concentrated under reduced pressure to yield 5 g (92%) of compound 51A in the form of a white solid.

Compound 51B benzyl(S)-2-((4-((tert-butoxycarbonyl)oxy)benzyl)(methyl) amino)-3-methylbutanoate

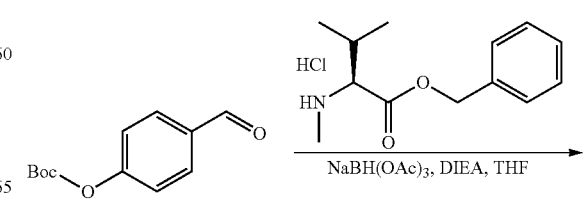

245

-continued

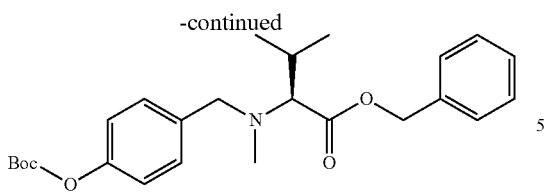

Compound 51A (220 mg, 0.99 mmol) was dissolved in 5 mL of THF in the presence of compound 1ZC (255 mg, 0.99 mmol, 1.0 equiv.), NaBH(OAc)₃ (420 mg, 2 mmol, 2.0 equiv.) and DIEA (654 µl) and agitated overnight at ambient temperature. The solution was then diluted with 100 mL of water and extracted 3 times with 50 mL of EtOAc. The organic phases were combined, dried over sodium sulfate, filtered and concentrated under reduced pressure. The residue was purified on a silica column with a mixture of EtOAc and PE (1:100) to yield 200 mg (47%) of compound 51B in the form of a white solid.

Compound 51C (S)-2-((4-(((tert-butoxycarbonyl)oxy)benzyl)(methyl)amino)-3-methyl butanoic acid

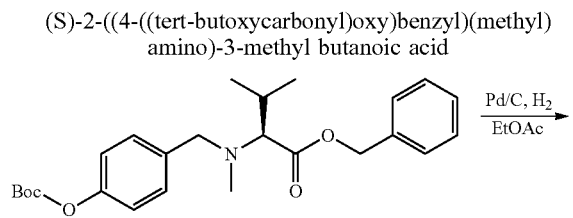

246

-continued

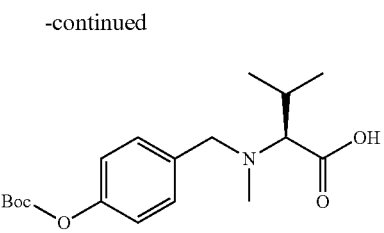

Compound 51C was prepared by hydrogenation of compound 51B (200 mg), following the protocol used for the preparation of compound 3F.

Compound 51D methyl (S)-2-((2R,3R)-3-((S)-1-((3R,4S,5S)-4-((S)-2-((S)-2-((4-(((tert-butoxycarbonyl)oxy)benzyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate

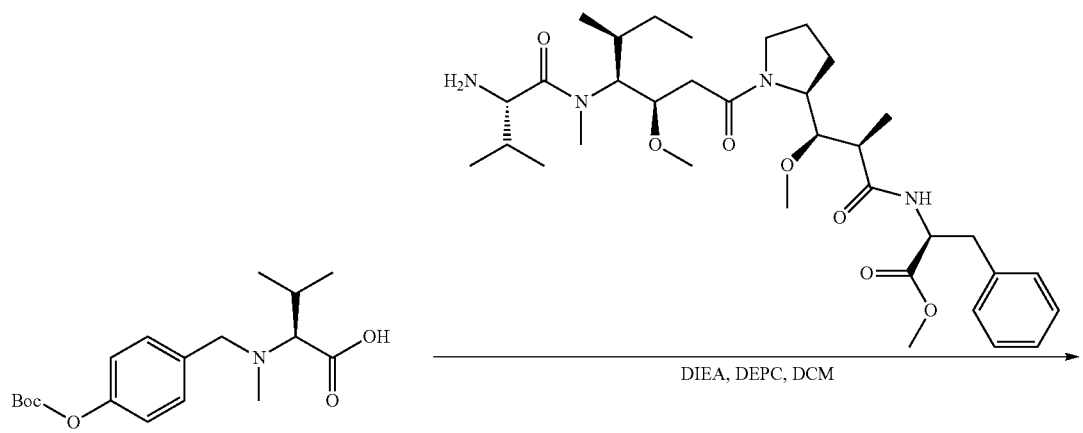

Compound 51D was prepared by coupling compound 51C with amine 3D, following the protocol used for the preparation of compound 3 to obtain the desired product in the form of yellow oil with a yield of 60%.

Compound 51

Compound 51D (80 mg, 0.08 mmol) was dissolved in 1 mL of DCM in the presence of 0.5 mL TFA, agitated 2 hours at ambient temperature and then concentrated under reduced pressure. The residue was purified by preparative HPLC (Pre-HPLC-010, SUNFIRE™ Prep C18 OBD column, 5 μm, 19×150 mm; Eluting phase: water/ACN buffered with 0.05% TFA; Gradient of 23% to 40% ACN in 10 minutes then 40% to 95% ACN in 2 minutes; Waters 2489 UV Detector at 254 nm and 220 nm). Compound 51 was obtained with a yield of 24% (20 mg) in the form of a white solid.

LC/MS/UV (ZORBAX® SB-Aq, 1.8 μm, 4.6×100 mm; 2% MeOH in water (0.05% TFA) for 1 minute then 2% to 95% MeOH in 13 minutes); ESI ($C_{47}H_{73}N_5O_9$, exact mass 851.54) m/z: 874.5 (MNa$^+$), 426.9 (M.2H$^+$/2); 12.48 min (96%. 210 nm).

$^1$H NMR: (300 MHz, CD$_3$OD, ppm): δ (Presence of rotamers) 8.1-8.6 (m, 0.9H, NHCO incomplete exchange); 7.29-7.27 (m, 2H), 7.25-6.86 (m, 5H), 6.84-6.83 (m, 2H), 4.83-4.72 (m, 3H), 4.26-0.82 (m, 58H).

Compound 61

(S)-2-((S)-2-((4-aminophenethyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide

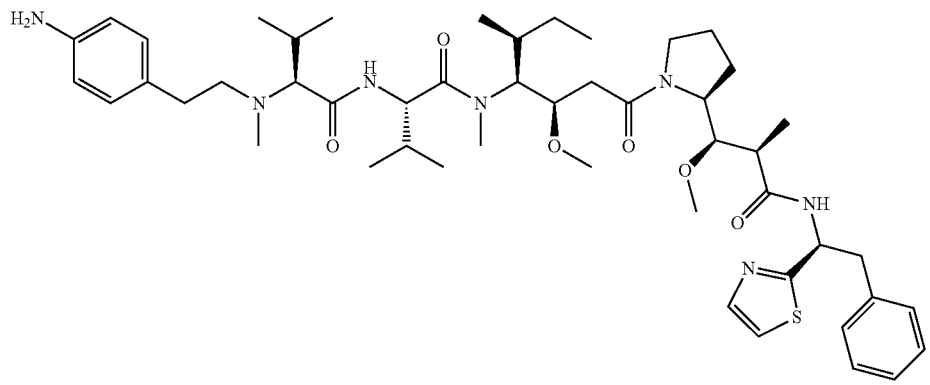 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCc1ccc(N)cc1)C(C)C]

Compound 61A

N-(4-aminophenethyl)-N-methyl-L-valine dihydrochloride

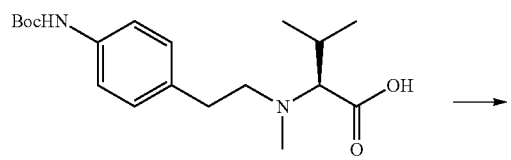

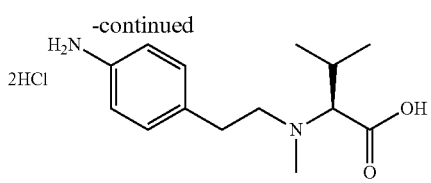

Compound 11D (962 mg, 2.75 mmol) was dissolved in 10 ml of a commercially available solution of HCl in propan-2-ol (5-6 M), and stirred at room temperature for 2 hours. TLC analysis indicated complete consumption of starting material. The solvent was evaporated under reduced pressure, and the resulting yellow solid triturated with Et$_2$O (2×10 ml). The product was dried under vacuum to furnish compound 61A as a yellow solid (322 mg, 47%).

Compound 61

Carboxylic acid 61A (73 mg, 0.23 mmol, 1 eq.) and amine 1Y (150 mg, 0.23 mmol, 1 eq.) were dissolved in dry DMF (2 ml). DIEA (158 μl, 0.90 mmol, 4 eq.) and DECP (51 μl, 0.34 mmol, 1.5 eq.) were added and the reaction stirred for 4 hours at room temperature. Analysis by LC-MS showed complete consumption of the starting material. The solvent was evaporated under reduced pressure, and the residue purified by flash chromatography on silica gel (DCM/MeOH) to furnish compound 61 as a light yellow solid (83 mg, 40%).

$^1$H NMR: (500 MHz, DMSO-$d_6$, ppm): δ (Presence of rotamers), 8.86 (d, 0.5H, NHCO); 8.65 (d, 0.5H, NHCO), 8.11-8.05 (m, 1H, NHCO), 7.80 (d, 0.5H, thiazole), 7.78 (d, 0.5H, thiazole), 7.65 (d, 0.5H, thiazole), 7.63 (d, 0.5H, thiazole), 7.32-7.12 (m, 5H), 6.83 (d, J=8.3 Hz, 2H), 6.45 (d, J=8.3 Hz, 2H), 5.56-5.49 (m, 0.5H), 5.42-5.35 (m, 0.5H), 4.78 (s, 2H, NH$_2$), 4.74-4.46 (m, 2H), 4.01-0.66 (m, 57H).

HPLC (XBRIDGE™ Shield C18, 3.5 μm, 4.6×50 mm; 3.5 ml/min, 40° C., 0 to 95% MeCN in water (0.1% TFA) in 2.25 minutes then 95% MeCN for 0.5 minutes, Tr=1.31 min (96.5%, 220 nm).

m/z (Q-TOF ESI$^+$) 890.5558 (2%, MH$^+$, $C_{49}H_{76}N_7O_6S$ requires 890.5572), 445.7834 (100%, (MH$_2$)$^{2+}$, $C_{49}H_{77}N_7O_6S$ requires 445.7823).

Compound 62

Methyl ((2R,3R)-3-((S)-1-((3R,4S,5S)-4-((S)-2-((S)-2-((4-aminophenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate

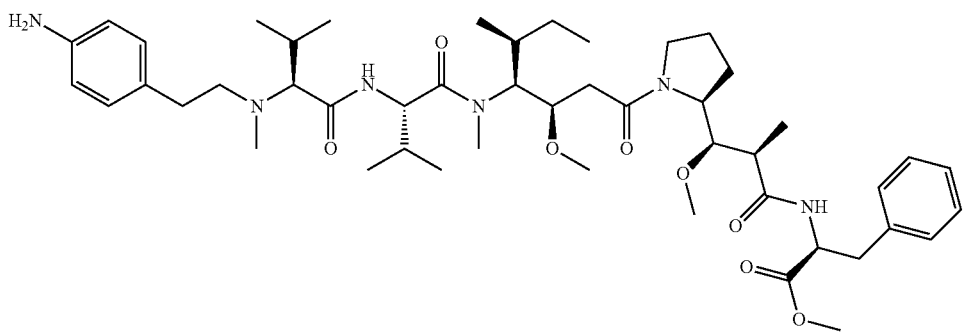 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(N)cc1)C(C)C]

Compound 62 was prepared in the same manner as for compound 61, using carboxylic acid 61A (69 mg, 0.21 mmol, 1 eq.), amine 3D (135 mg, 0.21 mmol, 1 eq.), DIEA (75 μl, 0.43 mmol, 2 eq.) and DECP (49 μl, 0.32 mmol, 1.5 eq.). The crude product was purified by flash chromatography on silica gel (DCM/MeOH) to furnish compound 62 as a yellowish solid (82 mg, 45%).

$^1$H NMR: (500 MHz, DMSO-$d_6$, ppm): δ (Presence of rotamers), 8.50 (d, J=8.3, 0.5H, NHCO); 8.27 (d, J=8.0, 0.5H, NHCO), 8.15-8.04 (m, 1H, NHCO), 7.27-7.13 (m, 5H), 6.86-6.79 (m, 2H), 6.48-6.42 (m, 2H), 4.78 (s, 2H, NH$_2$), 4.74-4.44 (m, 3H), 4.01-3.72 (m, 1.5H), 3.66 (s, 1.5H, CO$_2$Me), 3.63 (s, 1.5H, CO$_2$Me), 3.57-0.65 (m, 55.5H).

HPLC (Xbridge Shield C18, 3.5 μm, 4.6×50 mm; 3.5 ml/min, 40° C., 0 to 95% MeCN in water (0.1% TFA) in 2.25 minutes then 95% MeCN for 0.5 minutes, Tr=1.29 min (95.3%, 220 nm).

m/z (Q-TOF ESI$^+$) 865.5800 (2%, MH$^+$, $C_{48}H_{77}N_6O_8$ requires 865.5797), 433.2937 (100%, (MH$_2$)$^{2+}$, $C_{48}H_{78}N_6O_8$ requires 433.2935).

Compound 63

((2R,3R)-3-((S)-1-((3R,4S,5S)-4-((S)-2-((S)-2-((4-aminophenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate

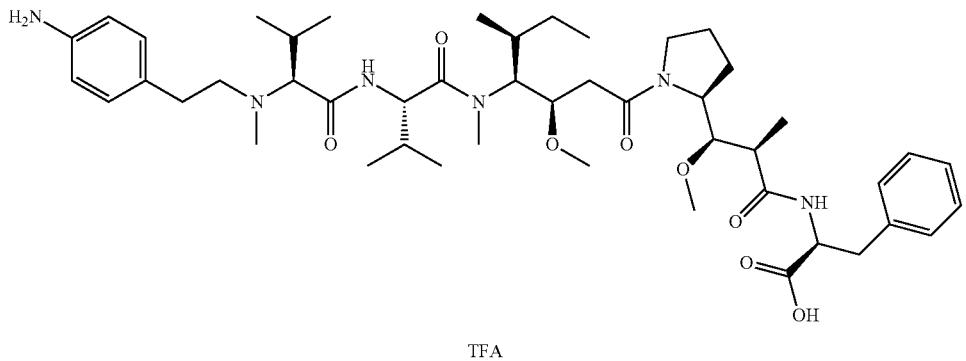 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N)cc1)C(C)C]

TFA

Compound 62 (23 mg, 0.03 mmol) was dissolved in a mixture of water (1 ml) and acetonitrile (1 ml). Piperidine (0.75 ml) was added and the mixture stirred at room temperature for 5 hours. TLC analysis indicated complete consumption of the starting material. The solvent was evaporated under reduced pressure, and the residue purified by preparative HPLC (SUNFIRE™ Prep column C18 OBD, 5 µm, 19×150 mm; Mobile phase: water/MeCN buffered with 0.1% TFA; Gradient of 20% to 40% MeCN in 10 minutes, then from 40% to 100% MeCN in 2 minutes; Detector UV Waters 2545 at 254 nm et 220 nm). Compound 63 was obtained as a white solid (14 mg, 66%).

$^1$H NMR: (500 MHz, DMSO-$d_6$, ppm): δ (Presence of rotamers), 12.7 (s(br), 1H, CO$_2$H), 9.58 (m(br), 1H); 9.04-8.89 (m, 1H), 8.41 (d, 0.6H, NHCO), 8.15 (d, 0.4H, NHCO), 7.27-7.13 (m, 5H), 7.13-6.99 (m(br), 2H), 6.90-6.64 (s(br), 2H), 4.77-3.40 (m, 10H), 3.34-2.75 (m, 20H), 2.34-1.94 (m, 4H), 1.90-0.7 (m, 25H).

HPLC (Xbridge Shield C18, 3.5 µm, 4.6×50 mm; 3.5 ml/min, 40° C., 0 to 95% MeCN in water (0.1% TFA) in 2.25 minutes then 95% MeCN for 0.5 minutes, Tr=1.24 min (100%, 220 nm).

m/z (Q-TOF ESI$^+$) 851.5641 (6%, MH$^+$, C$_{47}$H$_{75}$N$_6$O$_8$ requires 851.5641), 426.2854 (100%, (MH$_2$)$^{2+}$, C$_{47}$H$_{76}$N$_6$O$_8$ requires 426.2857).

Example 20: Antiproliferative activity of the Drugs

Method:
Cell Culture.
A549 (Non Small Cell Lung Cancer—ATCC® CCL-185™) and MDA-MB-231 (breast adenocarcinoma—ATCC® HTB-26m) cells were cultured in Minimum Essential Medium Eagle (MEM) with 5% fetal calf serum (FCS) and Dulbecco's modified Eagle Medium (DMEM) with 10% FCS respectively. MCF7 (breast ductal carcinoma—ATCC® HTB-22m) and SN-12C (kidney carcinoma—ATCC) cells were maintained in RPMI1640 medium (without phenol red for MCF7 cells) containing 10% FCS. All the media were supplemented with fungizone (1.25 µg/mL) and penicillin-streptomycin (100 U/100 µg/mL). Cells were cultured under standard conditions in an incubator at 37° C., 5% CO$_2$ and 95% atmospheric humidity.

Antiproliferative Activity on 4 Tumor Cell Lines.
Selected drugs were investigated for their antiproliferative activity using an ATPLITE® proliferation assay (Perkin Elmer, Villebon sur Yvette, France) on a comprehensive panel of 4 cell lines. Cells were seeded in 96 well plates (10$^3$ cells/well for A549, 2.103 for MCF7, MDA-MB-231 and SN12C) at day 0 at a concentration to ensure cells remained in logarithmic cell growth phase throughout the 72 h drug treatment period. After a 24h incubation period, all the cells were treated with serial dilutions of the tested compounds (11 µL of a 10× solution in 1% DMSO—6 wells/condition). To avoid adherence of the compounds onto the tips, tips were changed between two consecutive dilutions. Cells were then placed in 37° C., 5% CO$_2$ incubator. On day 4, cell viability was evaluated by dosing the ATP released by viable cells. The number of viable cells was analyzed in comparison with the number of solvent treated cells. The EC$_{50}$ values were determined with curve fitting analysis (non linear regression model with a sigmoidal dose response, variable hill slope coefficient), performed with the algorithm provided by the GRAPHPAD® Software (GRAPHPAD® Software Inc., CA, USA).

Results:
Various Drugs:
Various drugs were tested to determine their antiproliferative activity on the MDA-MB-231 cell line following the above-described method. The measured activities gave values of EC$_{50}$<0.1 µM.

The few following examples chosen from among the above exemplified drugs illustrate their fully remarkable antiproliferative properties:
Example 12: EC$_{50}$=5.80×10$^{-10}$ M; Example 13: EC$_{50}$=7.95×10$^{-8}$ M; Example 15: EC$_{50}$=1.70×10$^{-10}$ M; Example 27: EC$_{50}$=1.20×10$^{-10}$ M.

Various Cell Lines:
Compound 15 was tested on different cell lines (A549, MDA-MB-231, MCF-7, SN12C) following the above-described method. The measured activities gave values of EC$_{50}$<0.1 µM on all the tested cell lines.

| EC$_{50}$ (M) | A549 | MDA-MB-231 | MCF-7 | SN12C |
|---|---|---|---|---|
| Compound 15 | 1.45 × 10$^{-10}$ | 1.70 × 10$^{-10}$ | 7.15 × 10$^{-10}$ | 2.18 × 10$^{-10}$ |

COMPARATIVE EXAMPLES

The substitution on the phenyl ring (amino/hydroxyl v. carboxyl) was studied in the comparative examples below showing the improved antiproliferative activity of the drugs according to the invention comprising an amino or hydroxyl substituent.

| No | Structure | EC$_{50}$ (M) A549 | EC$_{50}$ (M) MDA-MB-231 |
|---|---|---|---|
| 12 | 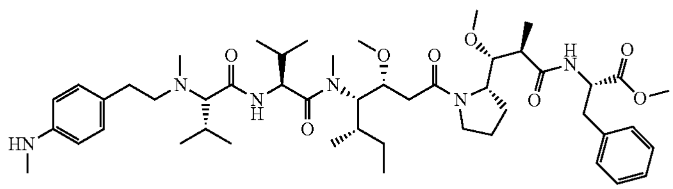 | $1.48 \times 10^{-10}$ | $5.80 \times 10^{-10}$ |
| 15 | 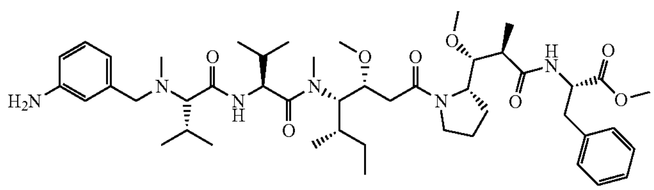 | $1.45 \times 10^{-10}$ | $1.70 \times 10^{-10}$ |
| 27 | 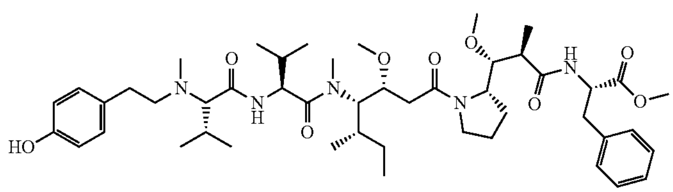 | $8.60 \times 10^{-11}$ | $1.20 \times 10^{-10}$ |
| Comparative example | | $3.76 \times 10^{-9}$ | $2.29 \times 10^{-9}$ |
| 13 | 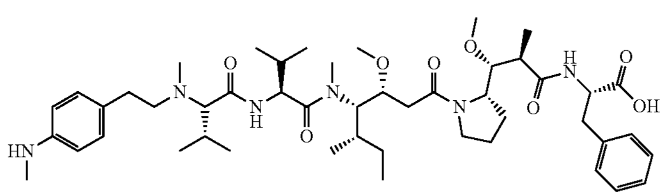 | $2.71 \times 10^{-8}$ | $7.95 \times 10^{-8}$ |
| Comparative example | | $4.03 \times 10^{-7}$ | $9.75 \times 10^{-7}$ |

Example 21: Synthesis of the Drug-Linker Moiety

Compound E-11

4-((S)-2-((S)-2-(6-(2,5-dioxo-2,5-dihydro-1H-pyrrol-1-yl)hexanamido)-3-methylbutanamido)-5-ureidopentanamido)benzyl(4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)phenyl)(methyl)carbamate 2,2,2-trifluoroacetate

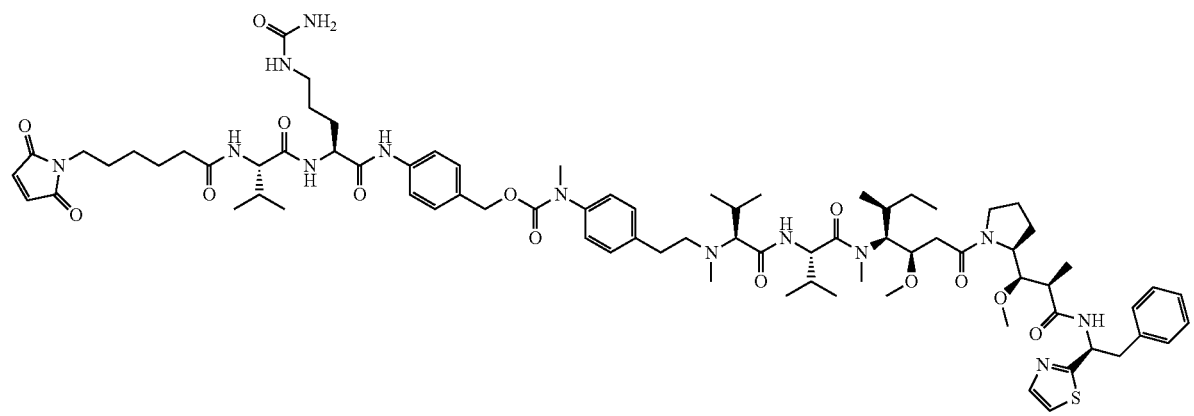

TFA

Compound E-11-1 methyl (S)-2-amino-5-ureidopentanoate hydrochloride

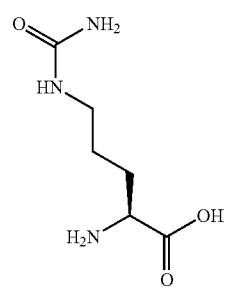

Acetyl chloride (10 mL) was added dropwise to MeOH (120 mL) at 0° C. with stirring. After 20 minutes, L-Citrulline (10 g, 57 mmol, 1.00 eq.) was added and the mixture heated at reflux overnight. The solvent was evaporated under reduced pressure to yield 15 g (116%) of compound E-11-1 as a white solid. The product was used in the next step without further drying.

Compound E-11-2 methyl (S)-2-((S)-2-((tert-butoxycarbonyl)amino)-3-methylbutanamido)-5-ureidopentanoate

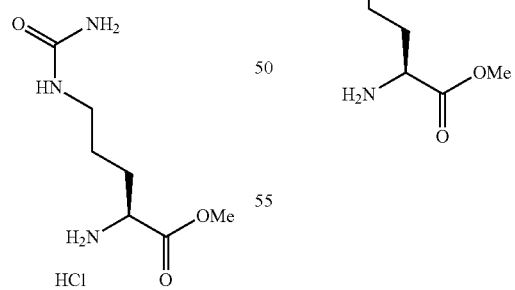

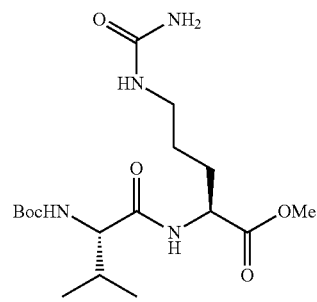

Compound E-11-1 (13 g, 57.6 mmol, 1.1 eq.) was dissolved in DMF (140 mL) at 0° C. under an inert atmosphere.

DIEA (30 mL, 173 mmol, 3.0 eq.), hydroxybenzotriazole (HOBt—10.59 g, 69.1 mmol, 1.2 eq.) and Boc-L-valine hydroxysuccinimide ester (Boc-Val-OSu—18.1 g, 57.6 mmol, 1.0 eq.) were added. The reaction mixture was agitated overnight at ambient temperature, then the solvent was evaporated under reduced pressure. The residue was dissolved in water (100 mL) and extracted twice with DCM (150 mL). The organic phases were combined, dried over $Na_2SO_4$ and concentrated under reduced pressure. The residue was purified on silica gel (DCM/MeOH) to yield 18.8 g (84%) of compound E-11-2 as a white solid.

Compound E-11-3

(S)-2-((S)-2-((tert-butoxycarbonyl)amino)-3-methyl butanamido)-5-ureidopentanoic acid

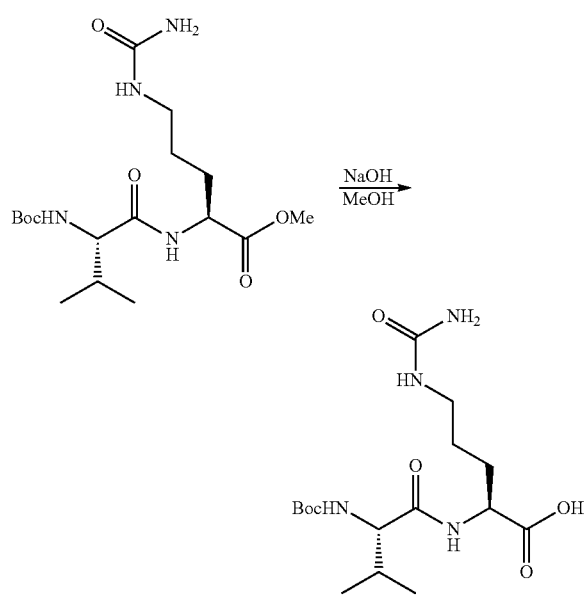

Compound E-11-2 (18.8 g, 48.4 mmol, 1 eq.) was dissolved in MeOH (200 mL) at 0° C. A solution of NaOH 1M (72 mL, 72 mmol, 1.5 eq.) was added and the mixture stirred for 2 hours at room temperature. The MeOH was removed under reduced pressure and the remaining aqueous solution acidified with HCl 1M. The aqueous phase was evaporated to dryness and the residue purified on silica gel (DCM/MeOH) to yield 18 g (99%) of compound E-11-3 as a white solid.

Compound E-11-4 tert-butyl ((S)-1-(((S)-1-((4-(hydroxymethyl)phenyl)amino)-1-oxo-5-ureidopentan-2-yl)amino)-3-methyl-1-oxobutan-2-yl)carbamate

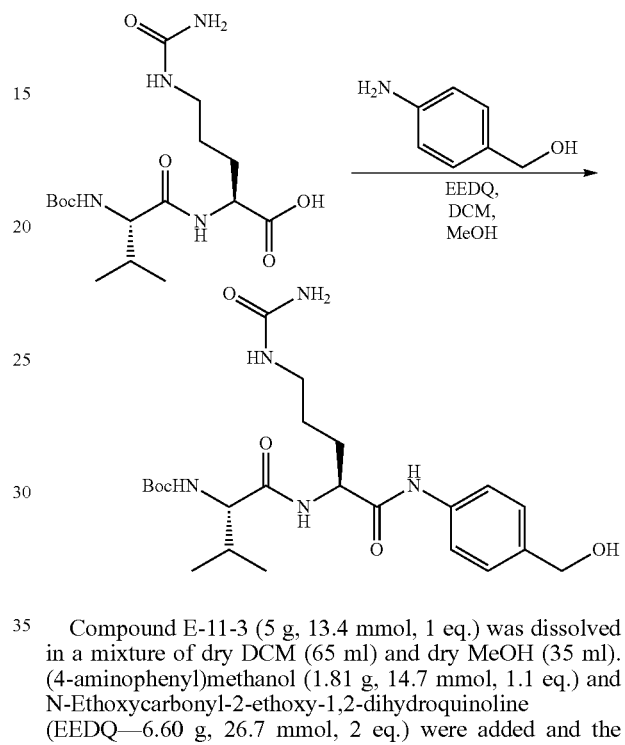

Compound E-11-3 (5 g, 13.4 mmol, 1 eq.) was dissolved in a mixture of dry DCM (65 ml) and dry MeOH (35 ml). (4-aminophenyl)methanol (1.81 g, 14.7 mmol, 1.1 eq.) and N-Ethoxycarbonyl-2-ethoxy-1,2-dihydroquinoline (EEDQ—6.60 g, 26.7 mmol, 2 eq.) were added and the mixture stirred in the dark overnight. The solvents were evaporated under reduced pressure, and the residue purified on silica gel (DCM/MeOH) to yield 5.2 g (73%) of compound E-11-4 as an off-white solid.

Compound E-11-5 tert-butyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate

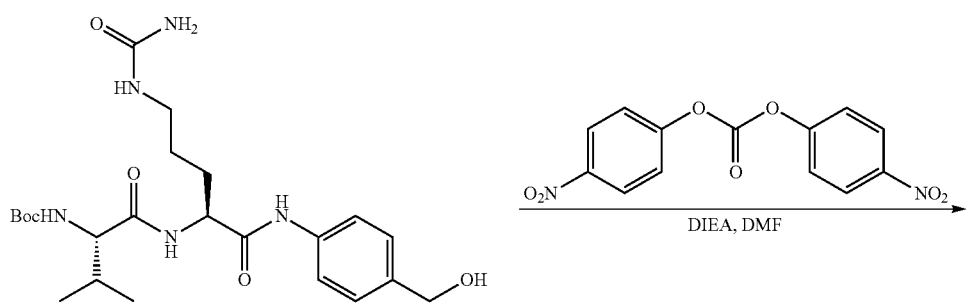

-continued

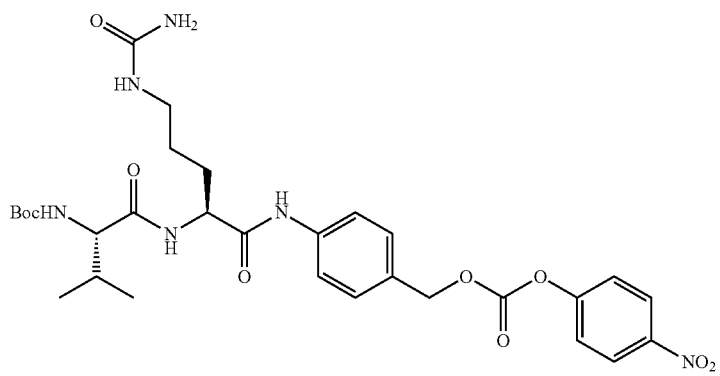

Compound E-11-4 (1.1 g, 2.29 mmol, 1 eq.) was dissolved in dry DMF (5 ml) at ambient temperature under an inert atmosphere. Bis(4-nitrophenyl) carbonate (1.40 g, 4.59 mmol, 2 eq.) was added, followed by DIEA (600 μl, 3.44 mmol, 1.5 eq.), and the resulting yellow solution stirred overnight. The DMF was evaporated under reduced pressure, and the residue purified on silica gel (DCM/MeOH) to yield 1.27 g (84%) of compound E-11-5 as an off-white solid.

Compound E-11-6

4-((S)-2-((S)-2-((tert-butoxycarbonyl)amino)-3-methylbutanamido)-5-ureidopentanamido)benzyl (4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)phenyl)(methyl)carbamate 2,2,2-trifluoroacetate

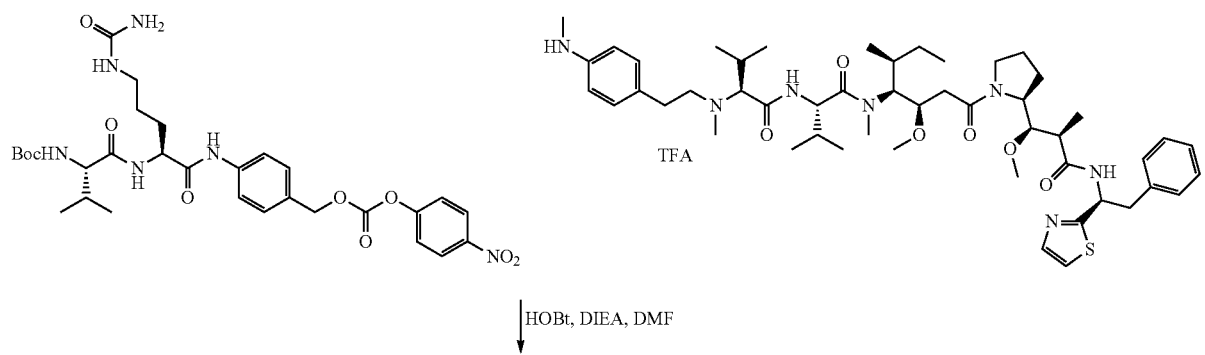

HOBt, DIEA, DMF

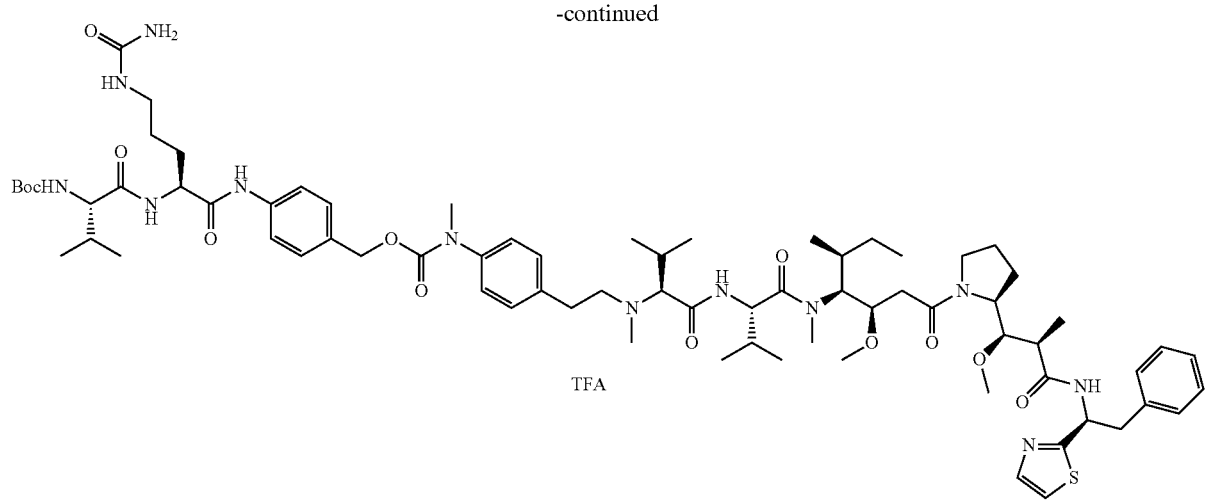

TFA

Carbonate E-11-5 (114 mg, 0.177 mmol, 1.2 eq.) and aniline 11F (150 mg, 0.147 mmol, 1 eq.) were dissolved in dry DMF (4 mL). HOBt (38 mg, 0.295 mmol, 2 eq.) and DIEA (54 µL, 0.295 mmol, 2 eq.) were added and the mixture stirred for the weekend at room temperature. The DMF was evaporated under reduced pressure and the residue purified by flash chromatography on silica, eluting with DCM. The product was repurified by preparative HPLC (Waters 600E, SUNFIRE™ Prep C18 OBD column, 5 µm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound E-11-6 as a white solid (89 mg, 39%).

Compound E-11

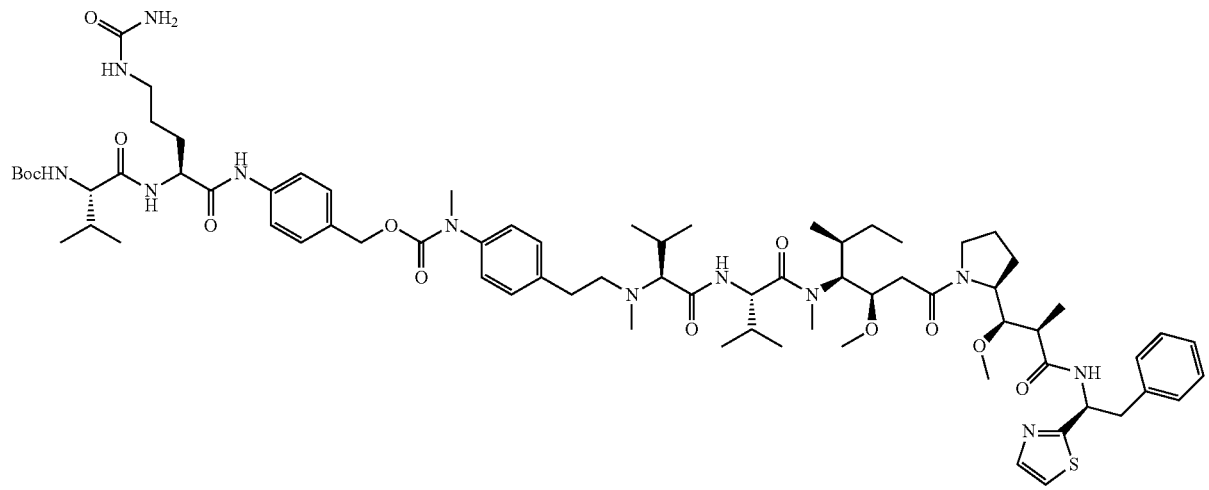

1) TFA, DCM
2) DIEA, DMF

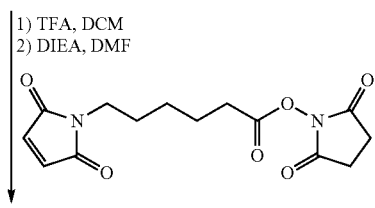

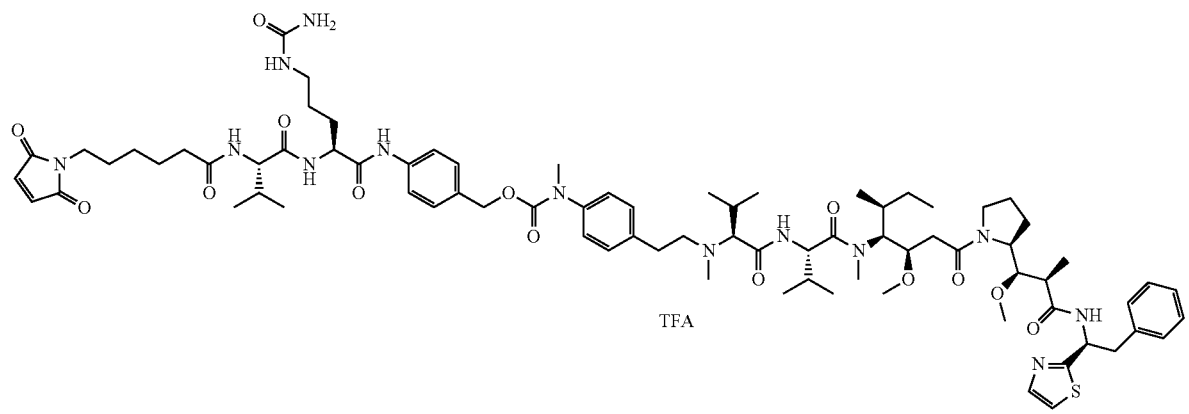

TFA

Compound E-11-6 (21 mg, 0.014 mmol, 1.0 eq.) was dissolved in DCM (0.25 mL) and TFA (40 μL) was added. The solution was stirred for 2 hours at room temperature, after which, LC-MS analysis indicated complete consumption of starting material. The mixture was briefly cooled (bath of liquid nitrogen) whilst simultaneously adding DMF (0.5 mL) then DIEA (100 μL) in order to neutralise the TFA. The cooling bath was then removed and 2,5-dioxopyrrolidin-1-yl 6-(2,5-dioxo-2,5-dihydro-1H-pyrrol-1-yl)hexanoate (4 mg, 0.012 mmol, 1 eq.) was added. The mixture was stirred at room temperature for 48 hours and the product purified by preparative HPLC (Waters 600E, SUNFIRE™ Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound E-11 as a white solid (11 mg, 54%).

m/z (Q-TOF MS ESI+) 1524.8282 (2%, MNa+, $C_{79}H_{115}N_{13}NaO_{14}S$ requires 1524.8299), 751.9283 (100%, $(MH_2)^{2+}$, $C_{79}H_{117}N_{13}O_{14}S$ requires 751.9276).

Compound E-12 methyl ((2R,3R)-3-((S)-1-((3R,4S,5S)-4-((S)-2-((S)-2-((4-(((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)phenethyl)(methyl) amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

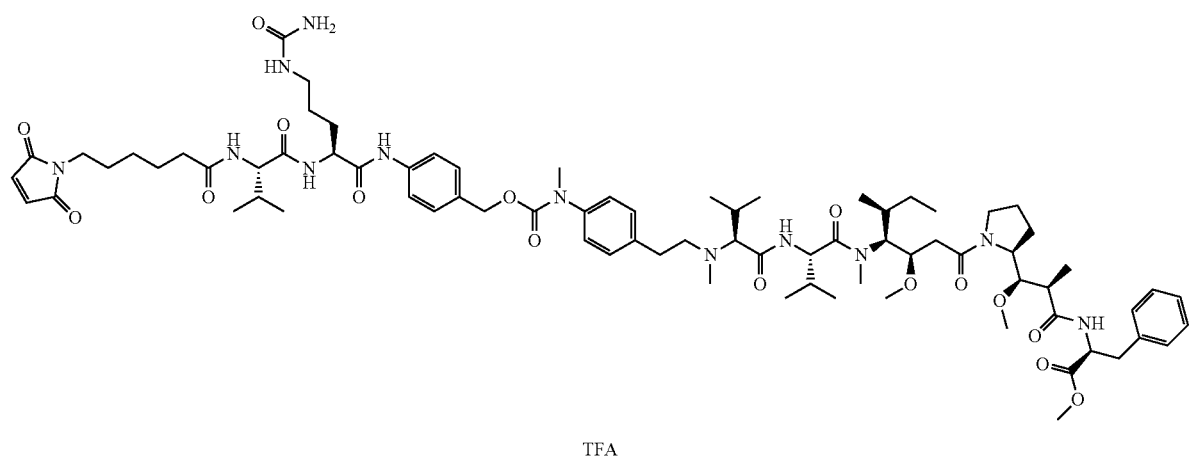 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(N(C)C(=O)OCc2ccc(NC(=O)[C@H](CCCNC(N)=O)NC(=O)[C@@H](NC(=O)CCCCCN3C(=O)C=CC3=O)C(C)C)cc2)cc1)C(C)C]

TFA

Compound E-12-1
tert-butyl ((S)-3-methyl-1-oxo-1-(((S)-1-oxo-1-((4-(((((perfluorophenoxy)carbonyl)oxy)methyl)phenyl)amino)-5-ureidopentan-2-yl)amino)butan-2-yl)carbamate
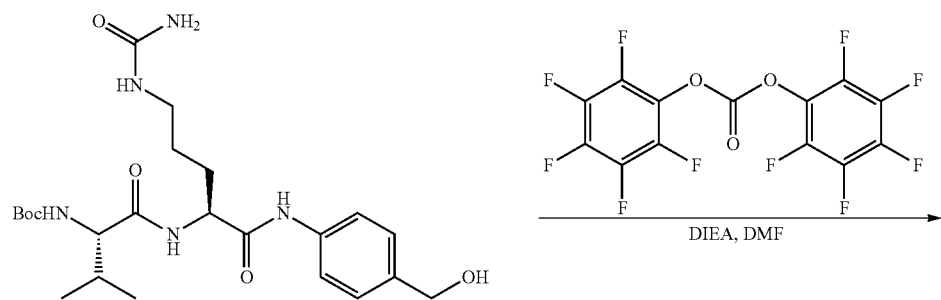
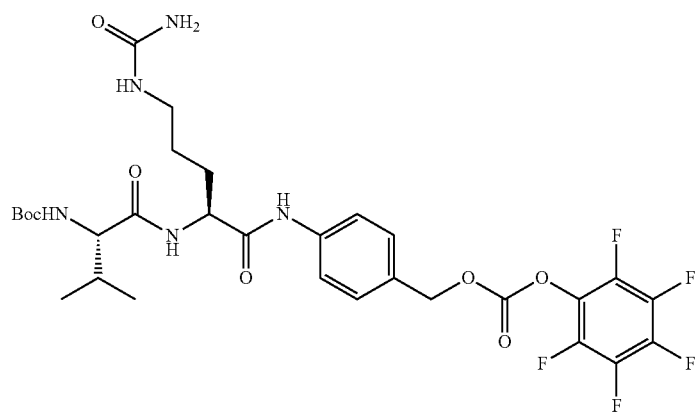

Compound E-11-4 (670 mg, 1.26 mmol, 1 eq.) was dissolved in dry DMF (6 ml) at 0° C. under an inert atmosphere. Bis(perfluorophenyl) carbonate (991 mg, 2.51 mmol, 2 eq.) was added, followed by DIEA (329 µl, 1.89 mmol, 1.5 eq.), and the resulting colourless solution stirred for 30 minutes at room temperature. The DMF was evaporated under reduced pressure, and the residue purified on silica gel (DCM/MeOH) to yield 836 mg (96%) of compound E-12-1 as an off-white solid.

Compound E-12-2 methyl ((2R,3R)-3-((S)-1-((3R,4S,5S)-4-((S)-2-((S)-2-((4-((((4-((S)-2-((S)-2-((tert-butoxycarbonyl)amino)-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

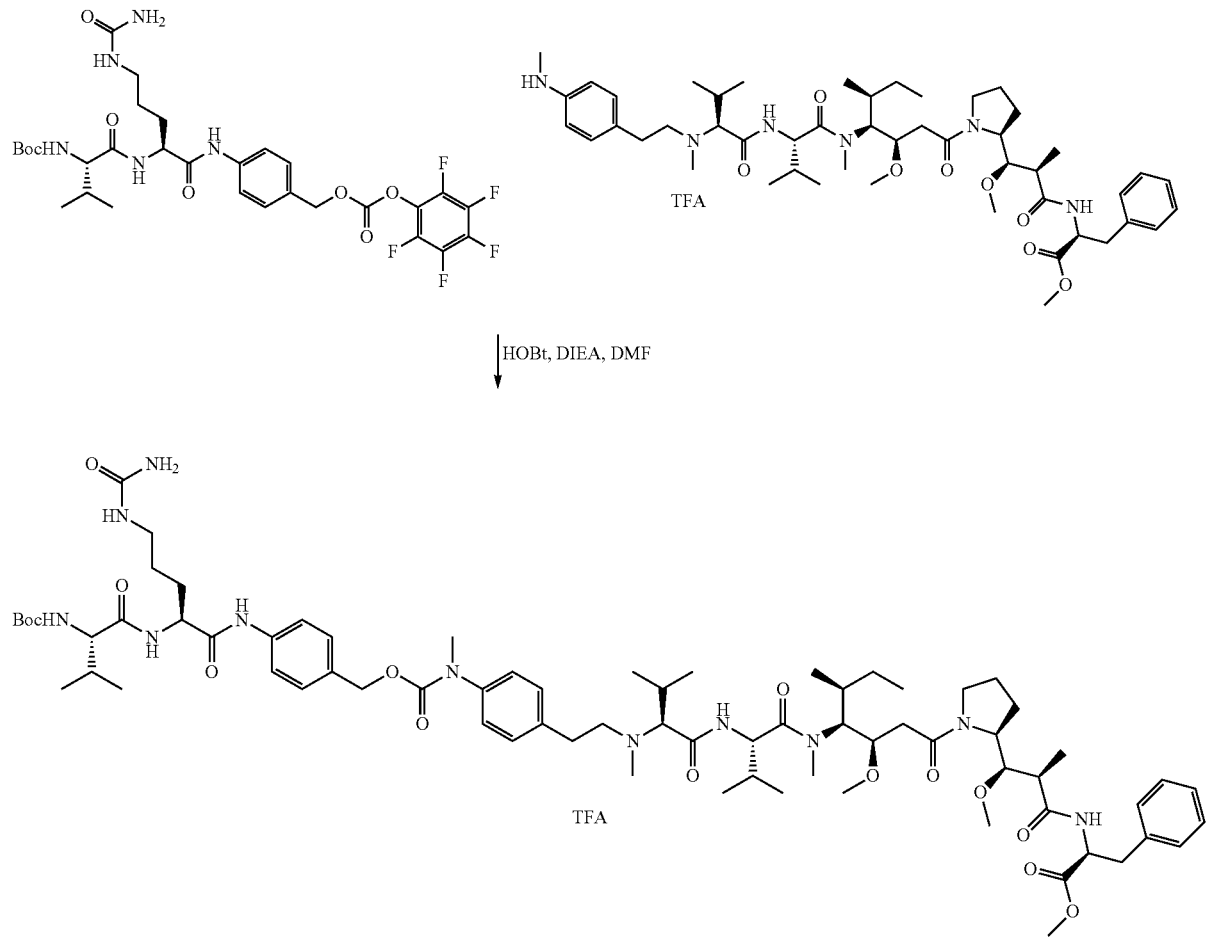 [SMILES: CC(C)[C@H](NC(=O)OC(C)(C)C)C(=O)N[C@@H](CCCNC(N)=O)C(=O)Nc1ccc(COC(=O)Oc2c(F)c(F)c(F)c(F)c2F)cc1 ; CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(NC)cc1)C(C)C ; CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(N(C)C(=O)OCc2ccc(NC(=O)[C@H](CCCNC(N)=O)NC(=O)[C@@H](NC(=O)OC(C)(C)C)C(C)C)cc2)cc1)C(C)C]

Aniline 12 (165 mg, 0.189 mmol, 1.0 eq.) was dissolved in DMF (5 mL) at 0° C. under an inert atmosphere. Carbonate E-12-1 (194 mg, 0.282 mmol, 1.5 eq.), HOBt (51 mg, 0.375 mmol, 2 eq.) and DIEA (66 µL, 0.375 mmol, 2 eq.) were added and the mixture stirred at room temperature for 8 hours. The solvent was evaporated under reduced pressure and the residue purified by preparative HPLC (Waters 600E, SUNFIRE™ Prep C18 OBD column, 5 µm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound E12-7 as a white solid (247 mg, 77%).

Compound E-12-3
methyl ((2R,3R)-3-((S)-1-((3R,4S,5S)-4-((S)-2-((S)-2-((4-((((4-((S)-2-((S)-2-amino-3-methylbutanamido)-5-ureidopentanamido)benzyl)oxy) carbonyl) (methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate bis(2,2,2-trifluoroacetate)
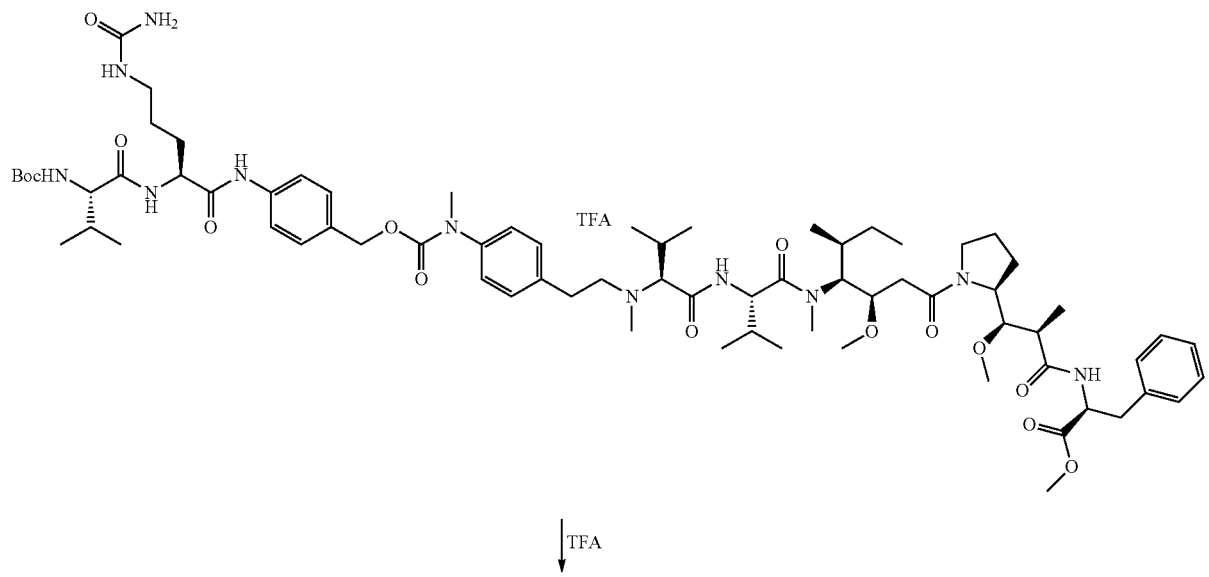

Compound E-12-2 (5.6 mg, 4.04 µmol, 1.0 eq.) was dissolved TFA (100 µL). After 5 minutes, 2 ml of water was added and the mixture lyophilised overnight to yield compound E-12-3 as an off-white solid (5.6 mg, 98%).

Compound E-12

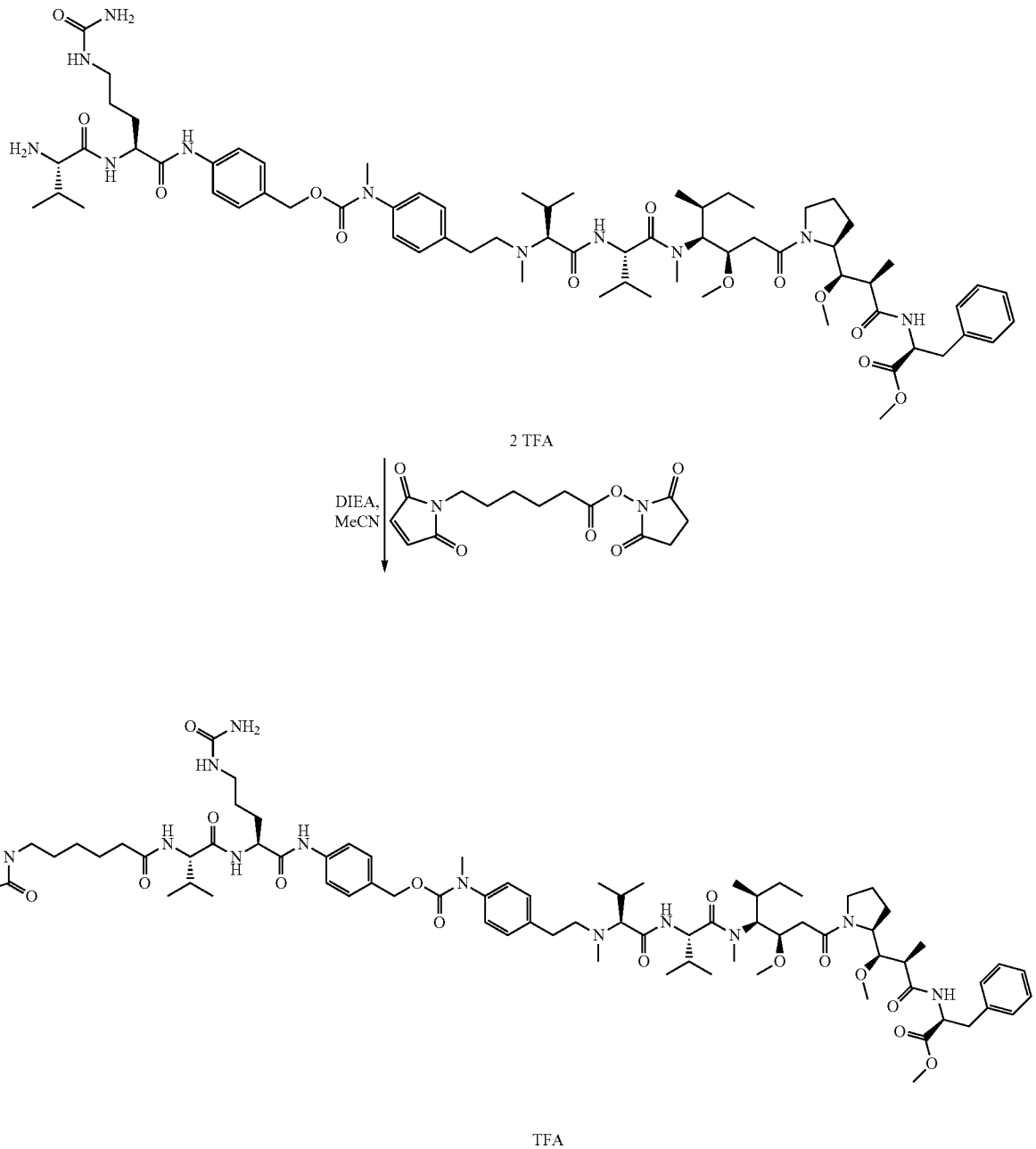

Compound E-12-3 (5.6 mg, 4 µmol, 1.0 eq.) was dissolved in acetonitrile (0.5 mL), and DIEA (5 µL, 7 eq.) was added, followed by 2,5-dioxopyrrolidin-1-yl 6-(2,5-dioxo-2,5-dihydro-1H-pyrrol-1-yl)hexanoate (2.5 mg, 8 µmol, 2 eq.). The mixture was stirred for 6 hours at room temperature. After controlling the reaction by LC-MS, 200 µL of water was added, and the resulting solution purified by preparative HPLC (Waters 600E, SUNFIRE™ Prep C18 OBD column, 5 µm, 19×100 mm; Eluting phase:water/MeCN buffered with 0.10% TFA; Gradient of 50% to 100% MeCN in 15 minutes; Waters 2487 UV Detector at 220 nm). The selected fractions were combined and lyophilised to furnish compound E-12 as a white solid (4.6 mg, 70%).

m/z (Q-TOF MS ESI+1739.4389 (100%, $MH_2^{2+}$, $C_{78}H_{118}N_{12}O_{16}$ requires 739.4389).

Compound E-13

((2R,3R)-3-((S)-1-((3R,4S,5S)-4-((S)-2-((S)-2-((4-
((((4-((S)-2-((S)-2-(6-(2,5-dioxo-2,5-dihydro-1H-
pyrrol-1-yl)hexanamido)-3-methylbutanamido)-5-
ureidopentanamido)benzyl)oxy)carbonyl)(methyl)
amino)phenethyl)(methyl)amino)-3-
methylbutanamido)-N,3-dimethylbutanamido)-3-
methoxy-5-methylheptanoyl)pyrrolidin-2-yl)-3-
methoxy-2-methylpropanoyl)-L-phenylalanine 2,2,
2-trifluoroacetate

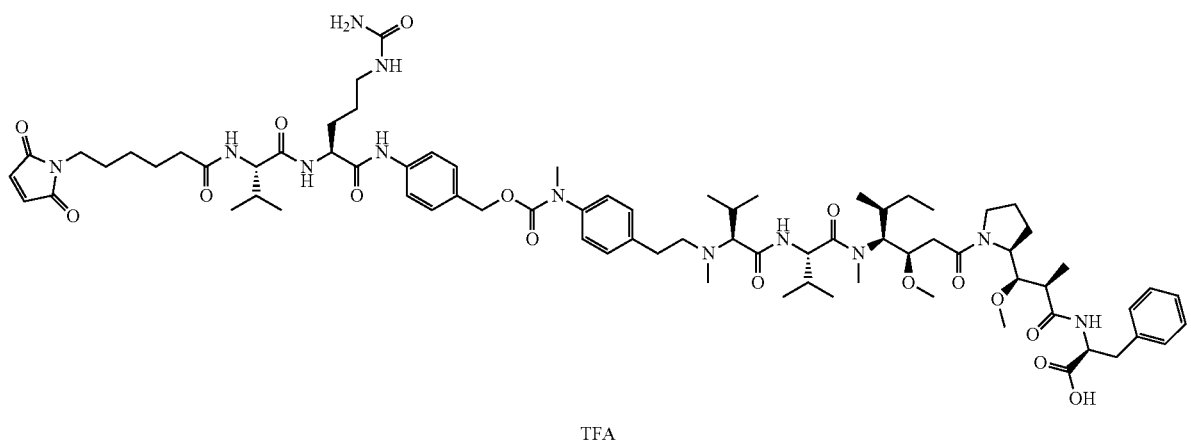 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)OCc2ccc(NC(=O)[C@H](CCCNC(N)=O)NC(=O)[C@@H](NC(=O)CCCCCN3C(=O)C=CC3=O)C(C)C)cc2)cc1)C(C)C]

TFA

Compound E-13-1

((2R,3R)-3-((S)-1-((3R,4S,5S)-4-((S)-2-((S)-2-((4-
((((4-((S)-2-((S)-2-((tert-butoxycarbonyl)amino)-3-
methylbutanamido)-5-ureidopentanamido)benzyl)
oxy)carbonyl)(methyl)amino)phenethyl)(methyl)
amino)-3-methylbutanamido)-N,3-
dimethylbutanamido)-3-methoxy-5-
methylheptanoyl)pyrrolidin-2-yl)-3-methoxy-2-
methylpropanoyl)-L-phenylalanine

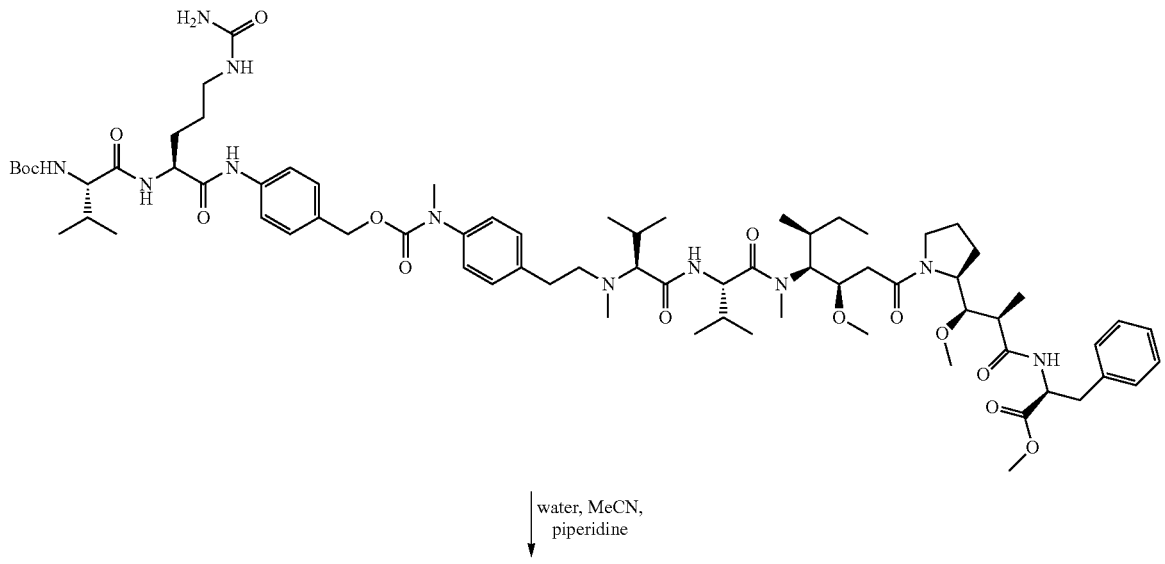

water, MeCN,
piperidine

-continued

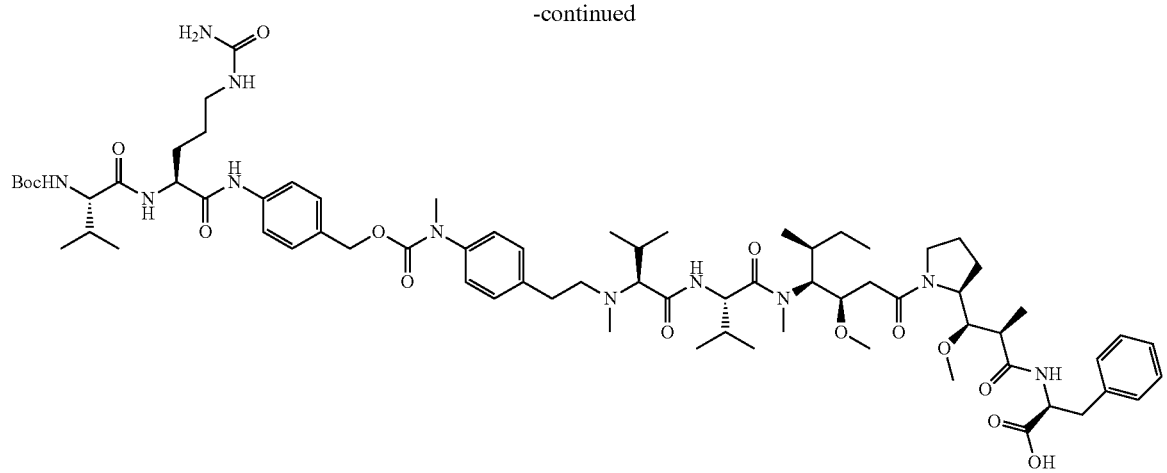

Compound E-12-2 (185 mg, 0.123 mmol, 1.0 eq.) was dissolved in a mixture of water (5 mL) and acetonitrile (5 mL) at room temperature. Piperidine (3.67 mL, 300 eq.) was added and the mixture stirred for 6 hours at room temperature. The solvents were evaporated to dryness under reduced pressure, and the residue triturated with Et$_2$O (60 mL). The solid was rinsed with twice Et$_2$O (20 ml) and dried under vacuum to yield compound E-13-1 as an off-white solid (175 mg, 95%).

Compound E-13-2

((2R,3R)-3-((S)-1-((3R,4S,5S)-4-((S)-2-((S)-2-((4-(((((4-((S)-2-((S)-2-amino-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine bis (2,2,2-trifluoroacetate)

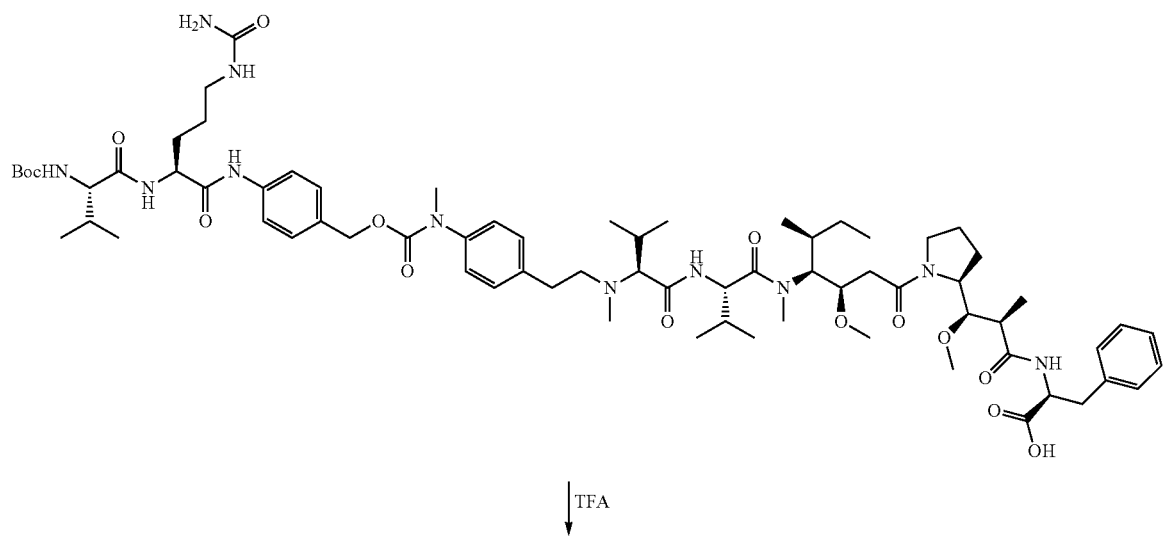

↓ TFA

-continued

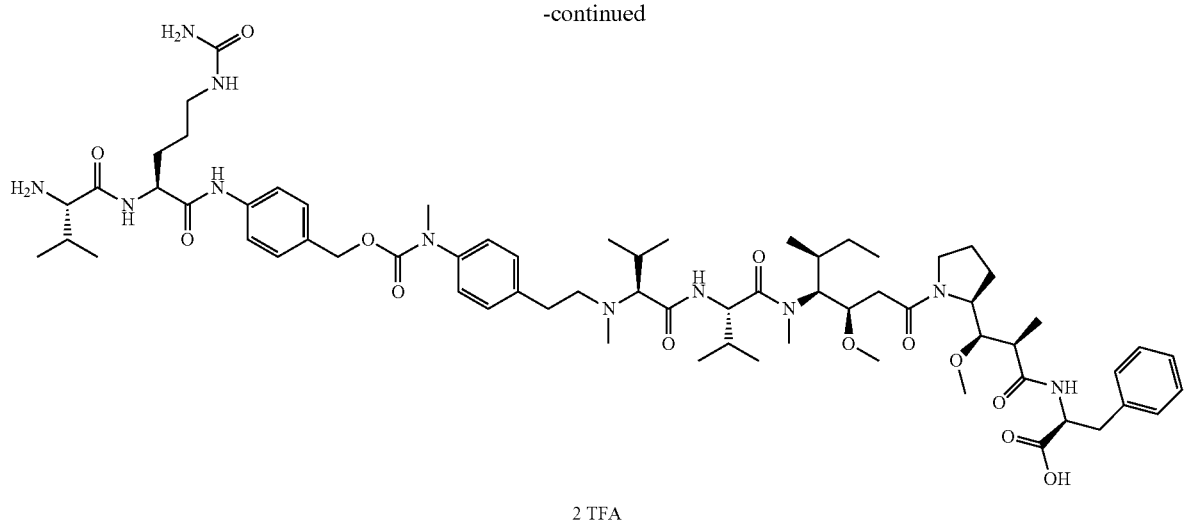

2 TFA

Compound E-13-1 (175 mg, 0.128 mmol, 1.0 eq.) was dissolved TFA (200 μL). After 5 minutes, water (1 mL) and acetonitrile (1 mL) were added and the solution lyophilised overnight to yield compound E-13-2 as an off-white solid (180 mg, 87%).

Compound E-13

((2R,3R)-3-((S)-1-((3R,4S,5S)-4-((S)-2-((S)-2-((4-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl) pyrrolidin-2-yl)-3-methoxy-2-methylpropanoyl)-L-phenylalanine, 2,2,2-trifluoroacetate

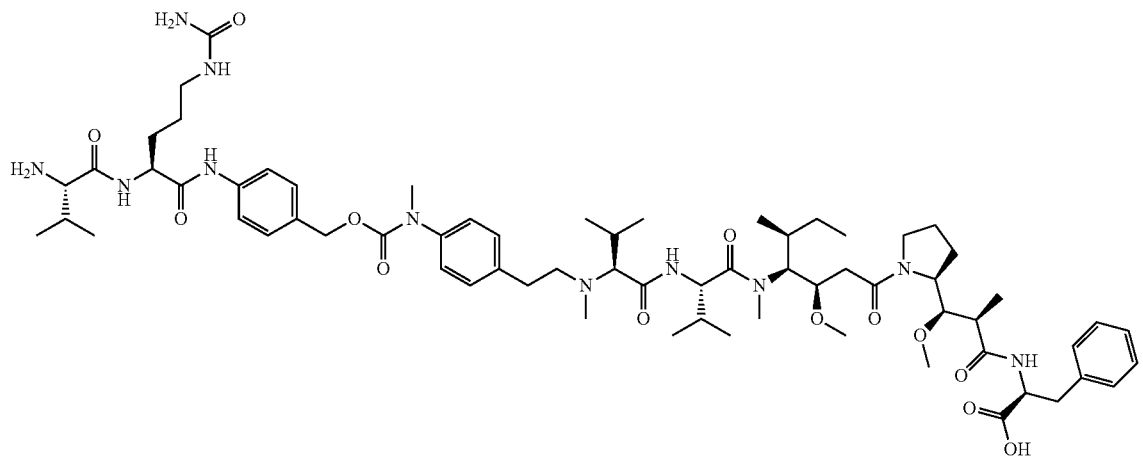

2 TFA

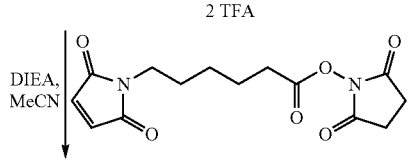

DIEA, MeCN

-continued

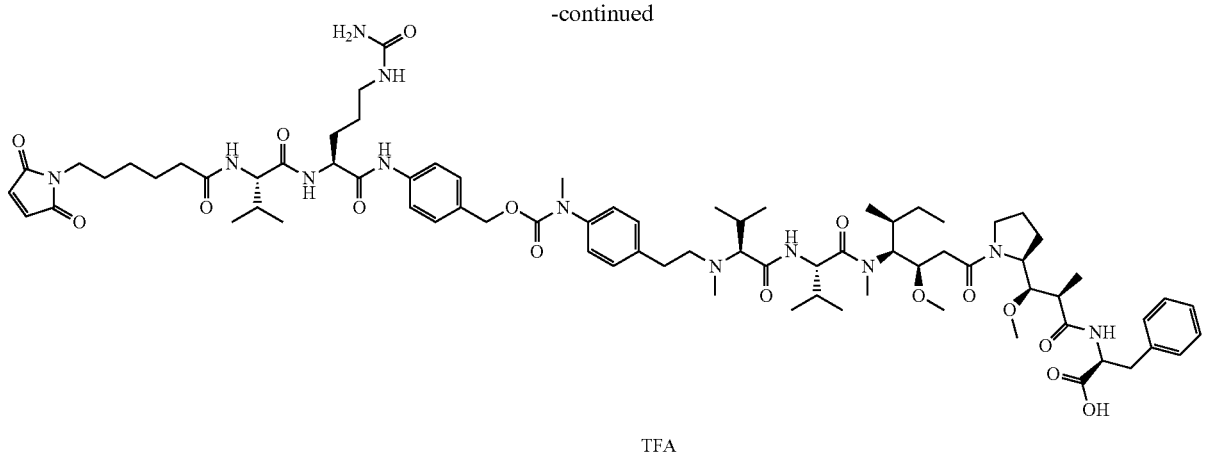

TFA

Compound E-13-2 (80 mg, 0.058 mmol, 1.0 eq.) was dissolved in a mixture of acetonitrile (1.5 mL) and DMF (0.4 mL). DIEA (50 μL, 0.289 mmol, 5 eq.) was added, followed by 2,5-dioxopyrrolidin-1-yl 6-(2,5-dioxo-2,5-dihydro-1H-pyrrol-1-yl)hexanoate (36 mg, 0.116 mmol, 2 eq.). The mixture was stirred for 3 hours at room temperature. After controlling the reaction by LC-MS, the solvent was evaporated under reduced pressure and the residue purified by preparative HPLC (Waters 600E, SUNFIRE™ Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound E-13 as a white solid (32 mg, 35%).

m/z (Q-TOF MS ESI−) 1461.8336 (100% (M−H)−, $C_{77}H_{113}N_{12}O_{16}$ requires 1461.8403).

m/z (Q-TOF MS ESI+) 1463.8565 (2% MH+, $C_{77}H_{115}N_{12}O_{16}$ requires 1463.8549), 732.4317 (100%, $(MH_2)^{2+}$, $C_{77}H_{116}N_{12}O_{16}$ requires 732.4311).

Compound E-15 methyl ((2R,3R)-3-((S)-1-((3R,4S,5S)-4-((S)-2-((S)-2-((3-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)benzyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

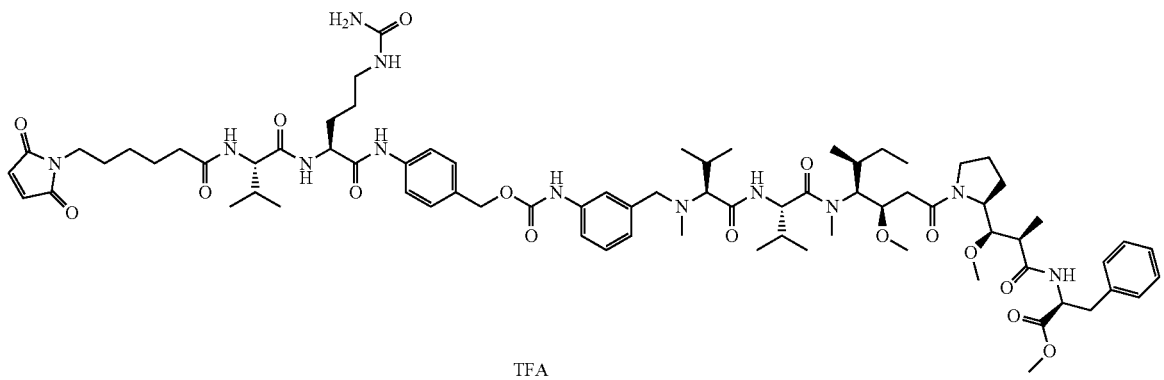 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)Cc1cccc(NC(=O)OCc2ccc(NC(=O)[C@H](CCCNC(N)=O)NC(=O)[C@@H](NC(=O)CCCCCN3C(=O)C=CC3=O)C(C)C)cc2)c1)C(C)C]

TFA

Compound E-15-1
methyl ((2R,3R)-3-((S)-1-((3R,4S,5S)-4-((S)-2-((S)-2-((3-((((4-((S)-2-((S)-2-((tert-butoxycarbonyl)amino)-3-methylbutanamido)-5-ureidopentanamido)benzyl)oxy)carbonyl)amino)benzyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate
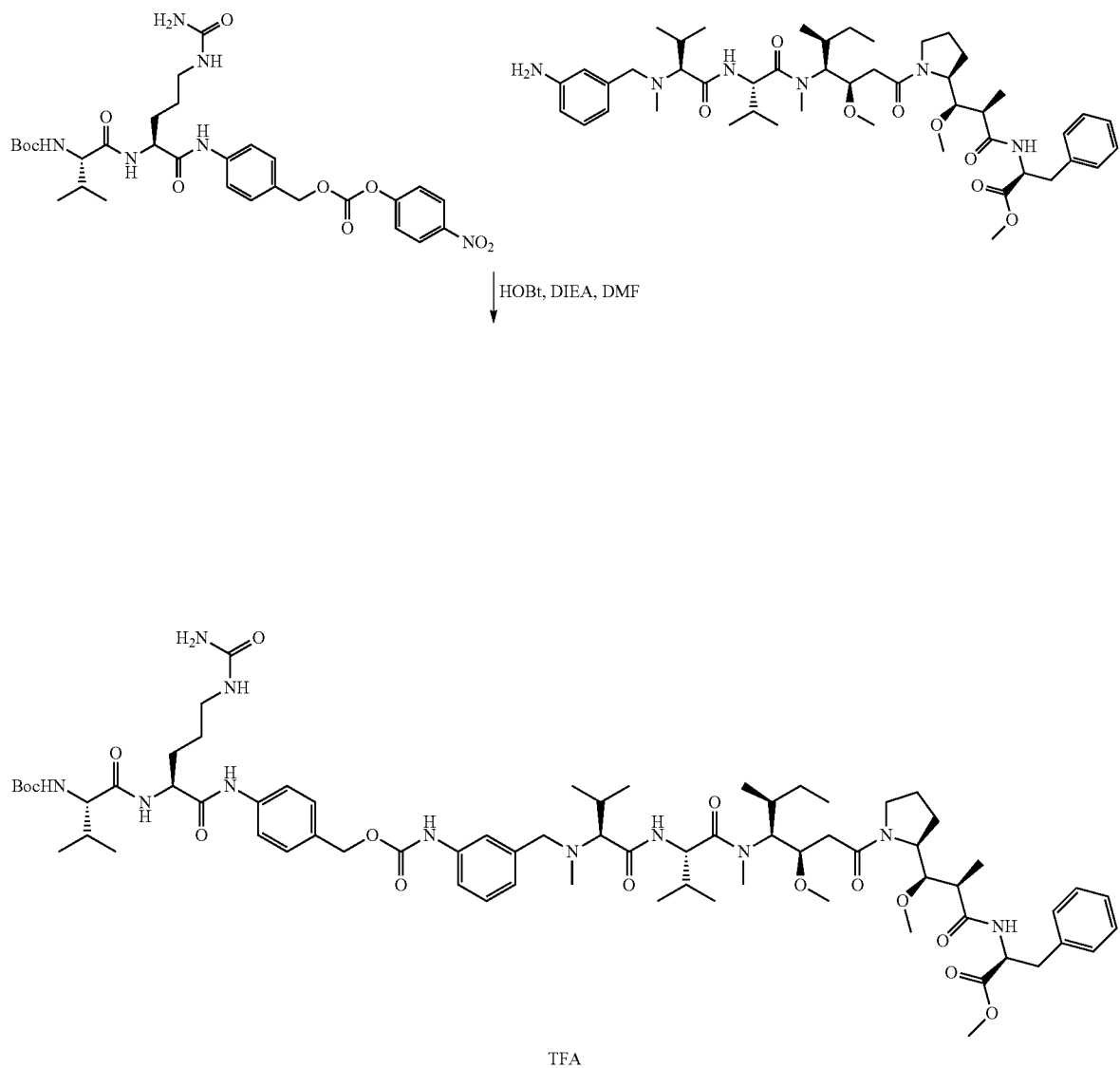

Compound E-15-1 was prepared according to the same method as for compound E-11-6, using carbonate E-11-5 (28 mg, 0.044 mmol, 1 eq.), aniline 15 (42 mg, 0.044 mmol, 1 eq.), HOBt (3 mg, 0.022 mmol, 0.5 eq.), and DIEA (15 µL, 0.087 mmol, 2 eq.) in DMF (2 mL). Compound E-15-1 was isolated as a white solid (8.2 mg, 13%).

Compound E-15-2 methyl ((2R,3R)-3-((S)-1-((3R,4S,5S)-4-((S)-2-((S)-2-((3-(((((4-((S)-2-((S)-2-amino-3-methylbutanamido)-5-ureidopentanamido)benzyl)oxy) carbonyl) amino)benzyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate bis(2,2,2-trifluoroacetate)

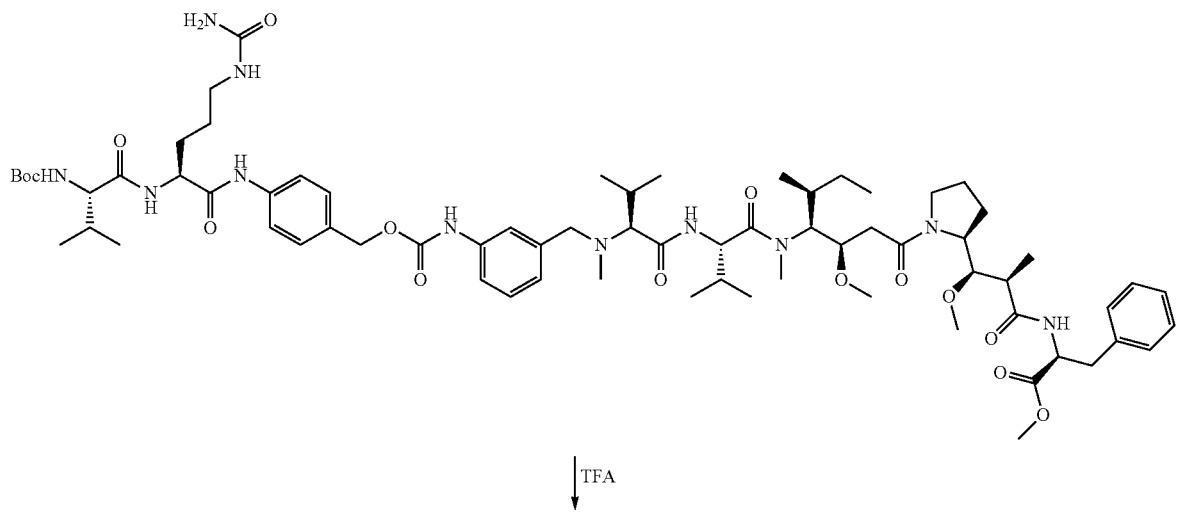

↓ TFA

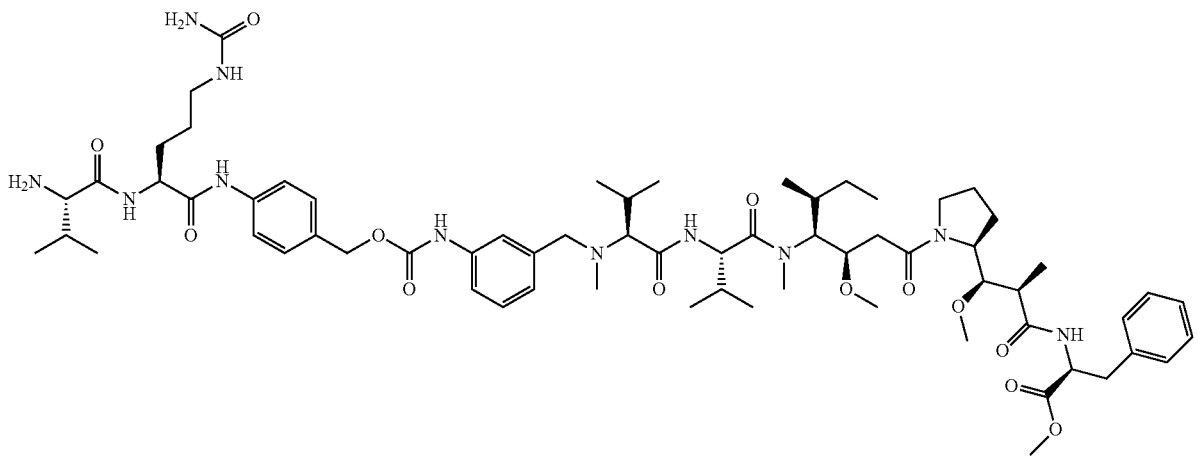

2 TFA

Compound E-15-1 (8.2 mg, 5.58 μmol, 1.0 eq.) was dissolved in TFA (200 μL). After 5 minutes, water (1 mL) was added and the solution lyophilised overnight to yield compound E-15-8 as a white solid (7.6 mg, 99%).
Compound E-15
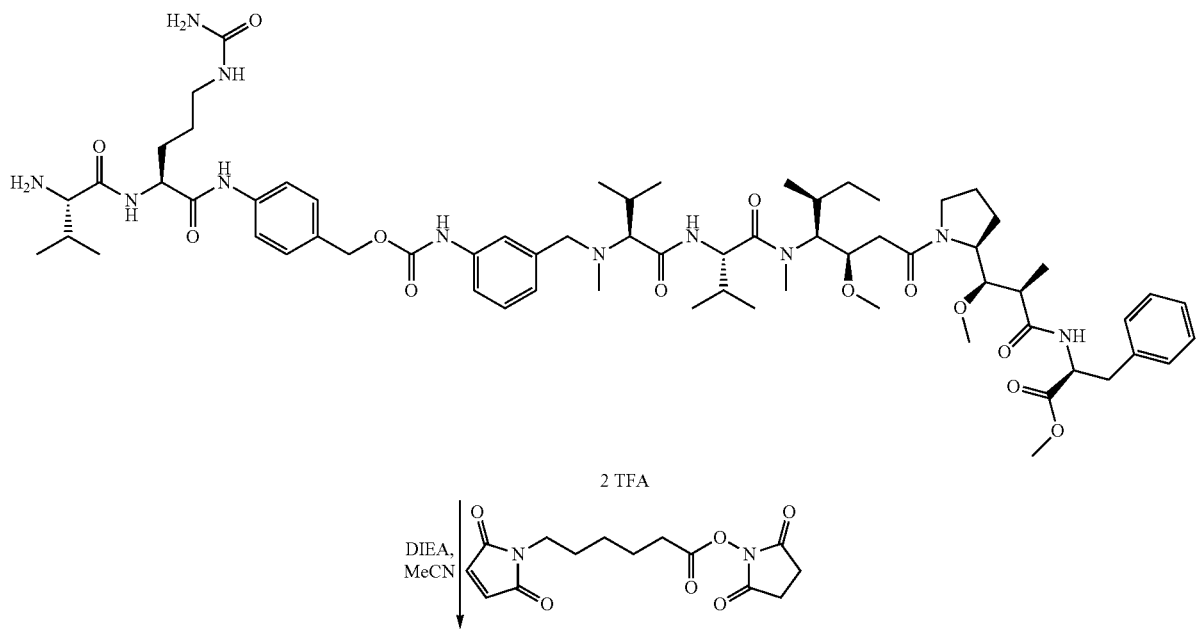
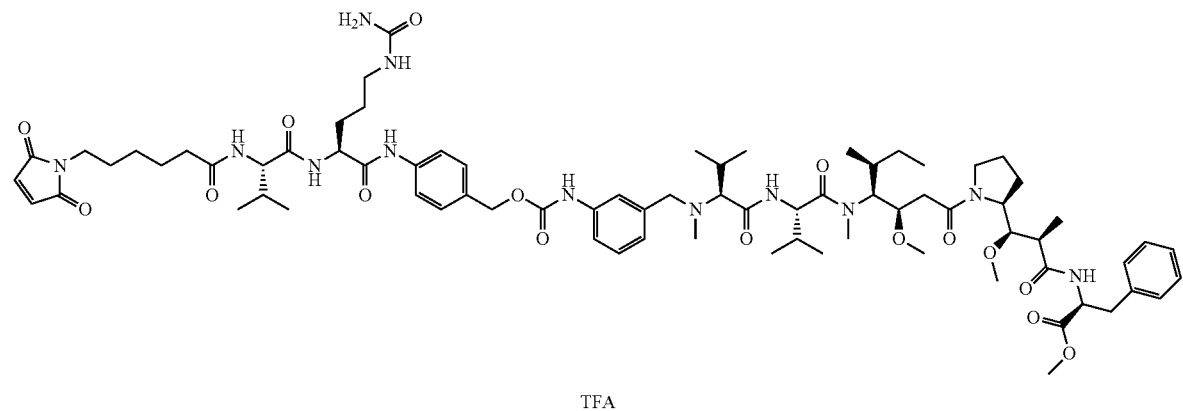

Compound E-15 was prepared according to the same method as for compound E-12, using amine E-15-2 (7.6 mg, 5.55 μmol, 1 eq.), 2,5-dioxopyrrolidin-1-yl 6-(2,5-dioxo-2,5-dihydro-1H-pyrrol-1-yl)hexanoate (2 mg, 6.65 μmol, 1.2 eq.) and DIEA (5 μL, 0.028 mmol, 5 eq.) in acetonitrile (0.5 mL). Compound E-15 was isolated as a white solid (4.2 mg, 480%).

m/z (Q-TOF MS ES+) 1471.8169 (2%, MNa$^+$, $C_{76}H_{112}N_{12}NaO_{16}$ requires 1471.8211), 725.4223 (100% $(MH_2)^{2+}$, $C_{76}H_{114}N_{12}O_{16}$ requires 725.4232), 483.9482 (10% $(MH_3)^{3+}$, $C_{76}H_{115}N_{12}O_{16}$ requires 483.9513).

Compound F-13

((2R,3R)-3-((S)-1-((3R,4S,5S)-4-((S)-2-((S)-2-((4-((S)-2-((S)-2-(6-(2,5-dioxo-2,5-dihydro-1H-pyrrol-1-yl)hexanamido)-3-methylbutanamido)-N-methyl-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl-L-phenylalanine 2,2,2-trifluoroacetate

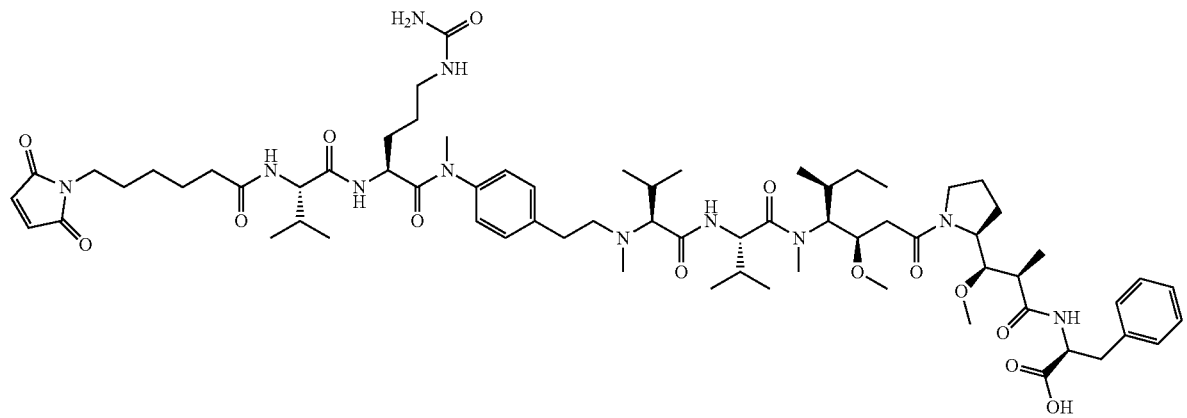

TFA

Compound F-13-1 benzyl N-(4-((tert-butoxycarbonyl)(methyl)amino)phenethyl)-N-methyl-L-valinate

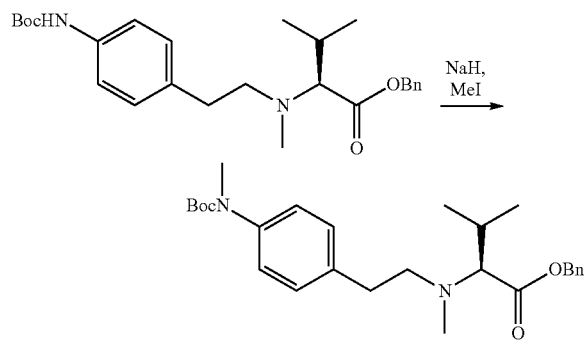

Compound 11C (250 mg, 0.567 mmol, 1 eq.) was dissolved in THF (10 ml) followed by the addition of NaH (60% suspension in mineral oil, 68 mg, 1.702 mmol, 3 eq.). The mixture was stirred for 5 minutes before adding iodomethane (106 μL, 1.702 mmol, 3 eq.). The reaction was stirred for 2 hours at room temperature before quenching with water and separating between EtOAc (100 mL) and water (50 mL). The organic phase was dried over MgSO$_4$ and evaporated to dryness to yield compound F-13-1 as a yellow oil (250 mg, 97%), which was used without further purification.

Compound F-13-2 benzyl N-methyl-N-(4-(methylamino)phenethyl)-L-valinate

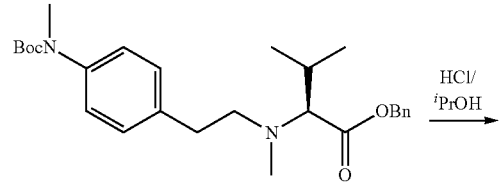

-continued

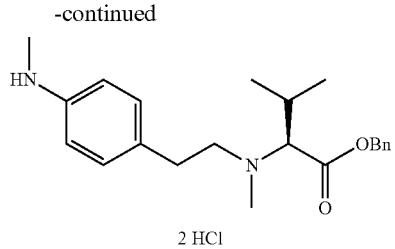

2 HCl

Boc-protected aniline F-13-1 (250 mg, 0.550 mmol, 1 eq) was dissolved in MeOH (5 mL) followed by the addition of 1 mL of a commercially-available solution of HCl in $^i$PrOH (5-6 M). The solution was stirred at room temperature for 2 hours before evaporating to dryness under reduced pressure. The resulting yellow oil was triturated with Et$_2$O to yield compound F-13-2 as a yellow solid (202 mg, 94%).

Compound F-13-3 benzyl N-(4-((S)-2-((S)-2-((tert-butoxycarbonyl)amino)-3-methylbutanamido)-N-methyl-5-ureidopentanamido)phenethyl)-N-methyl-L-valinate

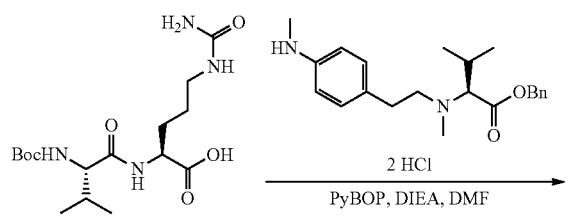

2 HCl
→
PyBOP, DIEA, DMF

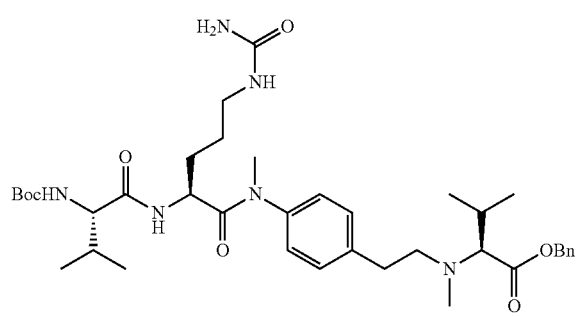

Acid E-11-3 (190 mg, 0.508 mmol, 1.5 eq.) was dissolved in dry DMF (1 ml), followed by the addition of DIEA (118 μL, 0.677 mmol, 2 eq.), benzotriazol-1-yl-oxytripyrrolidinophosphonium hexafluorophosphate (PyBOP—264 mg, 0.508 mmol, 1.5 eq.) and aniline F-13-2 (120 mg, 0.339 mmol, 1 eq.). The mixture was stirred at room temperature overnight and the solvents evaporated under reduced pressure. The residue was purified by preparative HPLC (Waters 600E, SUNFIRE™ Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F-13-3 as a white solid (140 mg, 45%).

Compound F-13-4

N-(4-((S)-2-((S)-2-((tert-butoxycarbonyl)amino)-3-methylbutanamido)-N-methyl-5-ureidopentanamido)phenethyl)-N-methyl-L-valine

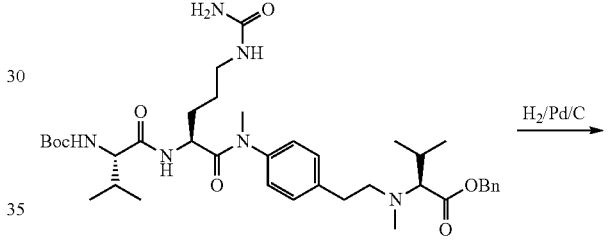

H$_2$/Pd/C
→

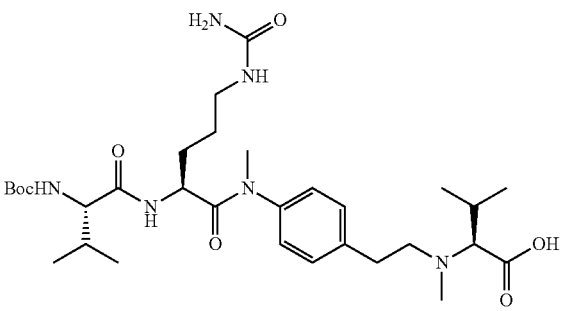

Compound F-13-3 (116 mg, 0.163 mmol, 1 eq.) was dissolved in MeOH (5 ml) in the presence of Pd/C 10% (30 mg) and hydrogenated for 2 hours at ambient temperature and atmospheric pressure. The reaction medium was filtered and concentrated under reduced pressure to yield 110 mg (99%) of compound F-13-4 as a beige solid.

291 292
Compound F-13-5
methyl ((2R,3R)-3-((S)-1-((3R,4S,5S)-4-((S)-2-((S)-2-((4-((S)-2-((S)-2-((tert-butoxycarbonyl)amino)-3-methylbutanamido)-N-methyl-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate
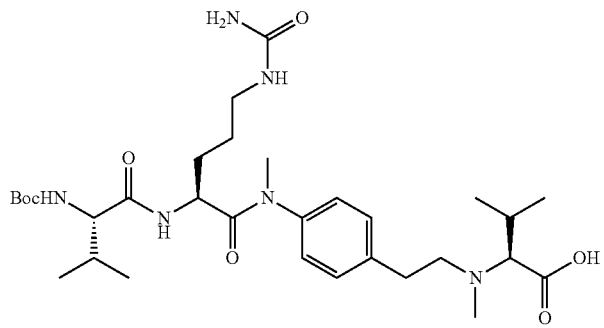 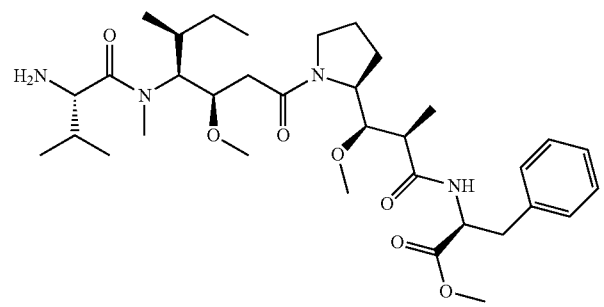
PyBOP, DIEA, DMF
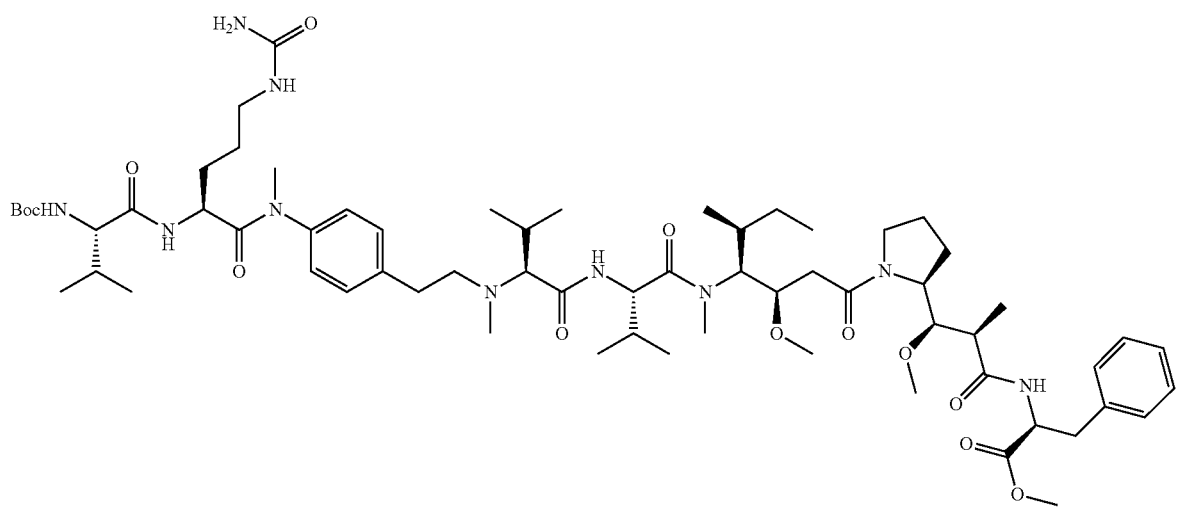
TFA Amine 3D (89 mg, 0.140 mmol, 1 eq.) and acid F-13-4 (145 mg, 0.210 mmol, 1.5 eq.) were dissolved in dry DMF (4 mL), and PyBOP (109 mg, 0.210 mmol, 1.5 eq.) and DIEA (73 µL, 0.420 mmol, 3 eq.) were added. The mixture was stirred for 1 hour at room temperature and the solvent evaporated. The residue was separated between EtOAc and water, and the organic phase dried over MgSO$_4$, filtered and evaporated under reduced pressure. The crude product was purified by preparative HPLC (Waters 600E, SUNFIRE™ Prep C18 OBD column, 5 µm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F-13-5 as a white solid (140 mg, 73%).

Compound F-13-6

((2R,3R)-3-((S)-1-((3R,4S,5S)-4-((S)-2-((S)-2-((4-((S)-2-((S)-2-((tert-butoxycarbonyl)amino)-3-methylbutanamido)-N-methyl-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate

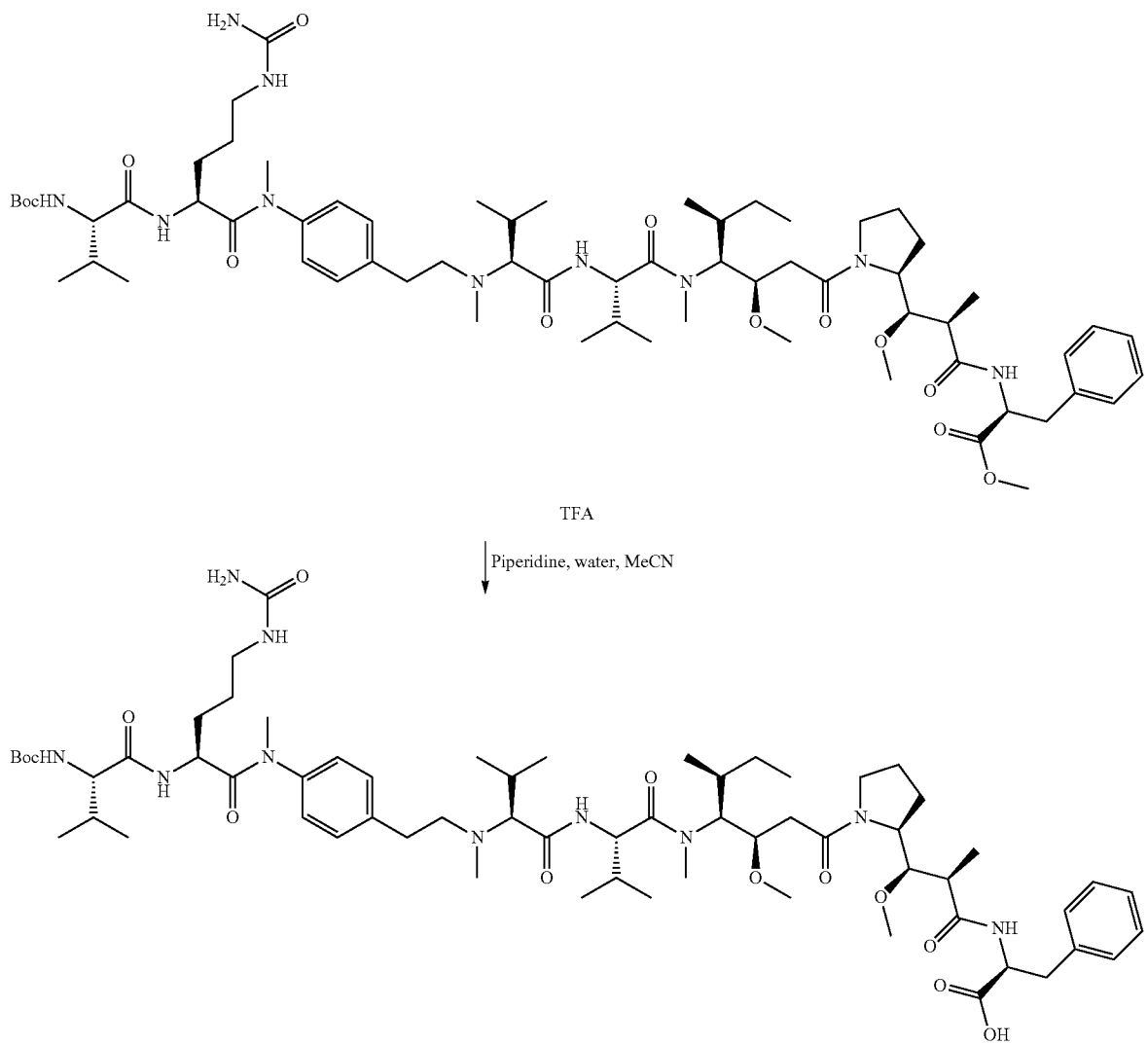

Compound F-13-5 (140 mg, 0.104 mmol, 1 eq.) was dissolved in a mixture of water (4 mL), acetonitrile (4 mL) and piperidine (2 mL) and stirred at room temperature for 4 hours. The solvent was evaporated under reduced pressure and the residue purified by preparative HPLC (Waters 600E, SUNFIRE™ Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F-13-6 as a white solid (115 mg, 83%).

Compound F-13

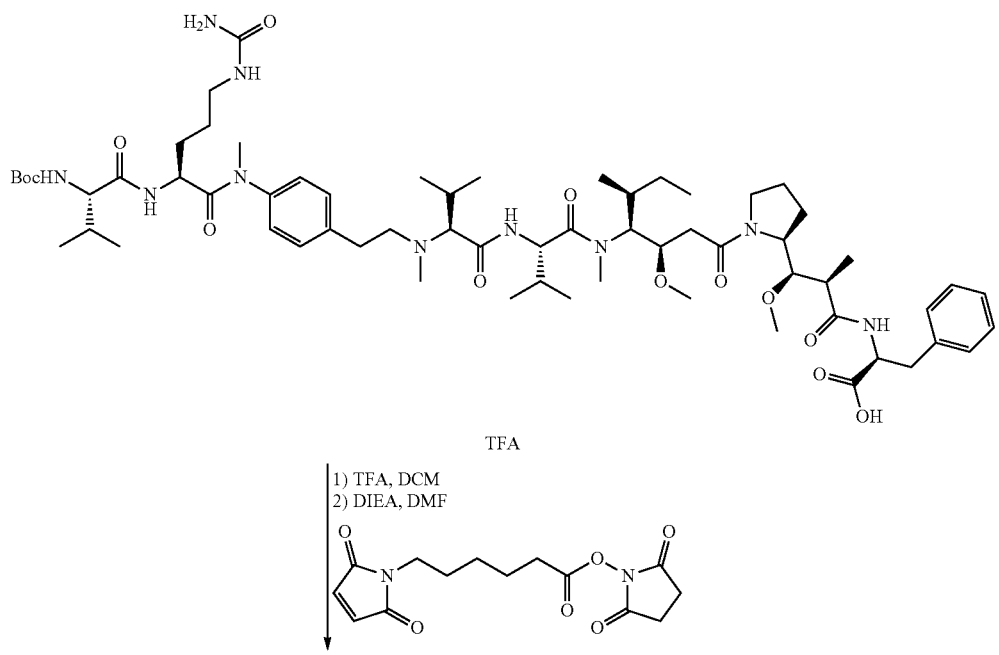

TFA

1) TFA, DCM
2) DIEA, DMF

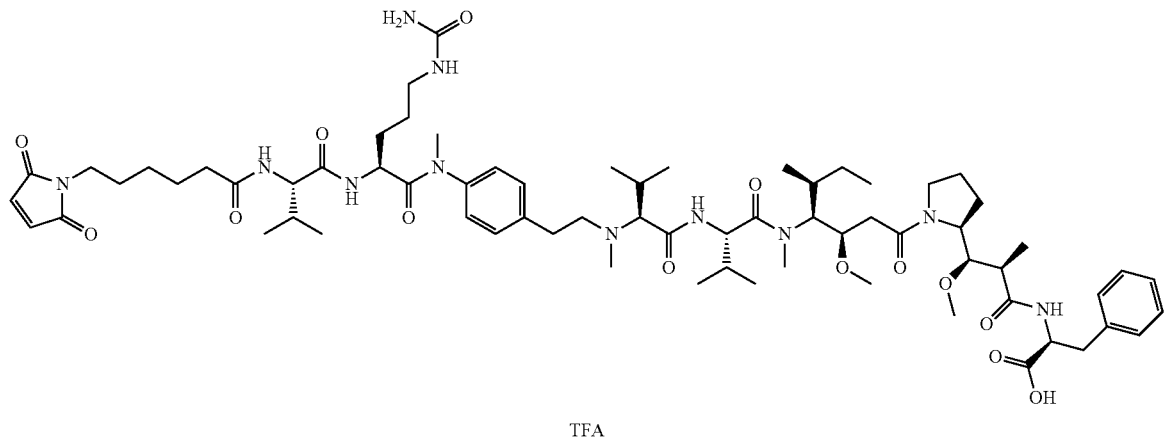 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)[C@H](CCCNC(N)=O)NC(=O)[C@@H](NC(=O)CCCCCN2C(=O)C=CC2=O)C(C)C)cc1)C(C)C]

TFA

Compound F-13 was prepared according to the same method as for compound E-11, using Boc-protected amine F-13-6 (55 mg, 0.041 mmol, 1.0 eq.) in DCM (0.5 mL) and TFA (100 L, 30 eq.), followed by dilution with DMF (1 mL), quenching with (DIEA (320 μL, 45 eq) then reaction with 2,5-dioxopyrrolidin-1-yl 6-(2,5-dioxo-2,5-dihydro-1H-pyrrol-1-yl)hexanoate (15 mg, 0.049 mmol, 1.2 eq.). After purification by preparative HPLC and lyophilisation, compound F-13 was obtained as a white solid (14 mg, 24%).

m/z (Q-TOF MS ESI+) 1314.8067 (2%, MH$^+$, $C_{69}H_{108}N_{11}O_{14}$ requires 1314.8072), 657.9067 (100%, (MH$_2$)$^{2+}$, $C_{69}H_{109}N_{11}O_{14}$ requires 657.9072).

Compound F-61

N—((S)-1-(((S)-1-((4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)phenyl)amino)-1-oxo-5-ureidopentan-2-yl)amino)-3-methyl-1-oxobutan-2-yl)-6-(2,5-dioxo-2,5-dihydro-1H-pyrrol-1-yl)hexanamide 2,2,2-trifluoroacetate

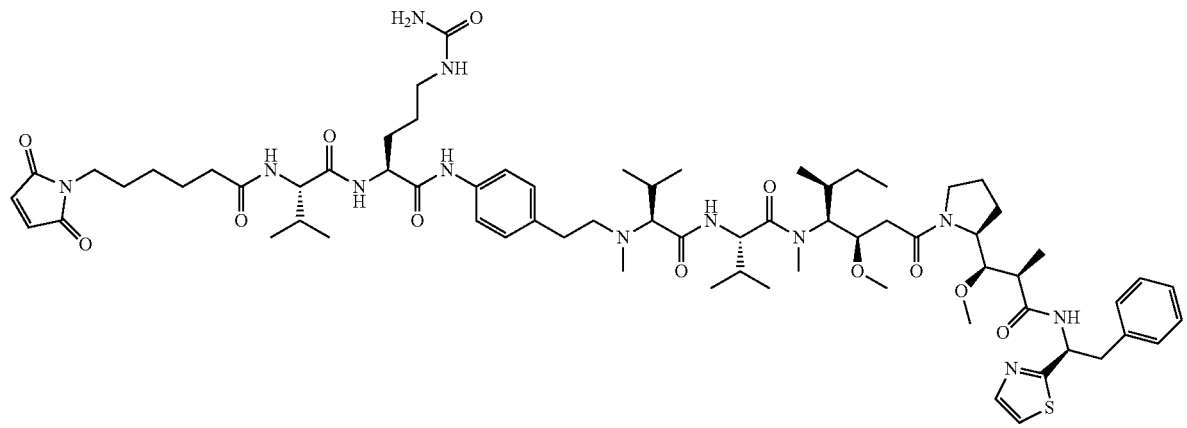

Compound F-61-1 benzyl N-(4-aminophenethyl)-N-methyl-L-valinate dihydrochloride

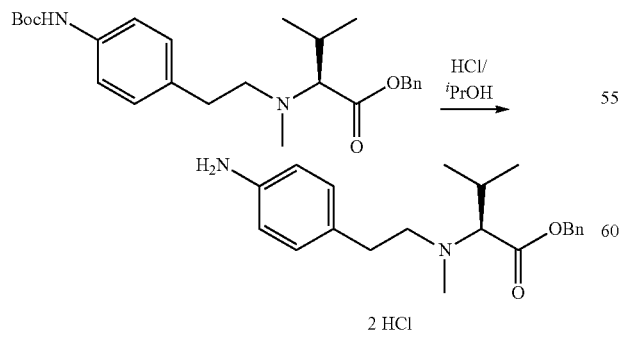

Compound 11C (1.0 g, 2.27 mmol, 1 eq.) was dissolved in 8 mL of a commercially-available solution of HCl in $^i$PrOH (5-6 M). The mixture was stirred for 2 hours at room temperature before evaporating to dryness under reduced pressure. The residue was triturated twice with Et$_2$O (30 mL) and dried under vacuum to yield compound F-61-1 as a white solid (916 mg, 98%).

Compound F-61-2 benzyl N-(4-((S)-2-((S)-2-((tert-butoxycarbonyl)amino)-3-methylbutanamido)-5-ureidopentanamido)phenethyl)-N-methyl-L-valinate

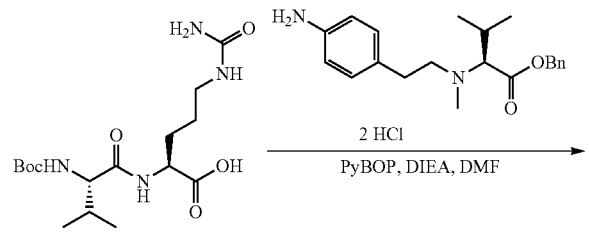

299

-continued

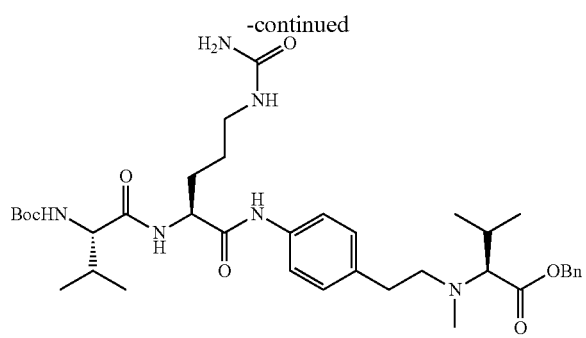

Acid E-11-3 (769 mg, 2.05 mmol, 1.5 eq.) was dissolved in dry DMF (2.5 ml) followed by the addition of DIEA (957 µL, 5.48 mmol, 4 eq.) and PyBOP (1.07 g, 2.05 mmol, 1.5 eq.). Aniline F-61-1 (566 mg, 1.369 mmol, 1 eq.) was added and the mixture stirred at room temperature overnight. The solvents were evaporated under reduced pressure, and the residue purified on silica gel (DCM/MeOH) to yield 969 mg (102%) of compound F-61-2 as a white solid.

Compound F-61-3

N-(4-((S)-2-((S)-2-((tert-butoxycarbonyl)amino)-3-methylbutanamido)-5-ureidopentanamido)phenethyl)-N-methyl-L-valine

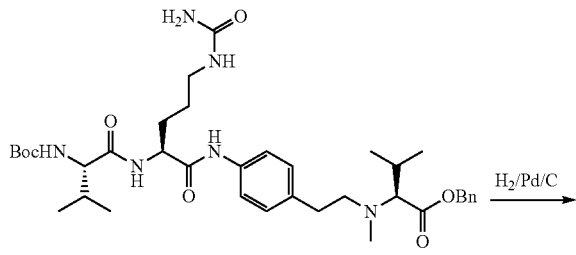

300

-continued

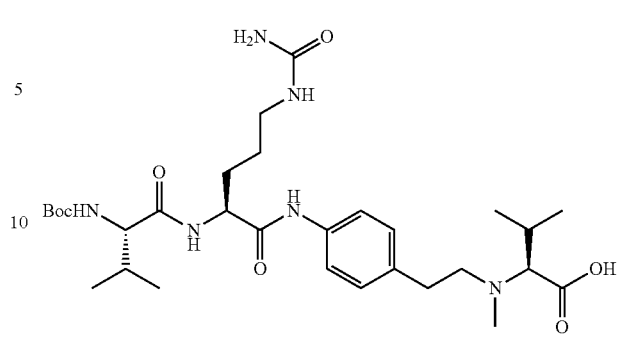

Compound F-61-2 (969 mg, 1.28 mmol, 1 eq.) was dissolved in MeOH (20 ml) in the presence of Pd/C 10% (270 mg) and hydrogenated for 3 hours at ambient temperature and atmospheric pressure. The reaction medium was filtered and concentrated under reduced pressure, and the residue purified on silica gel (DCM/MeOH/AcOH) to yield 520 mg (67%) of compound F-61-3 as a white solid.

Compound F-61-4 tert-butyl ((S)-1-(((S)-1-((4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)phenyl)amino)-1-oxo-5-ureidopentan-2-yl)amino)-3-methyl-1-oxobutan-2-yl)carbamate 2,2,2-trifluoroacetate

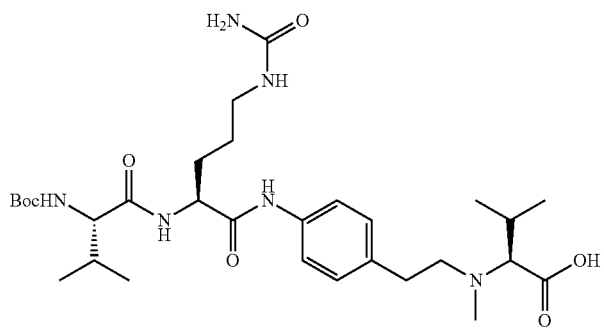

DECP, DIEA, DMF

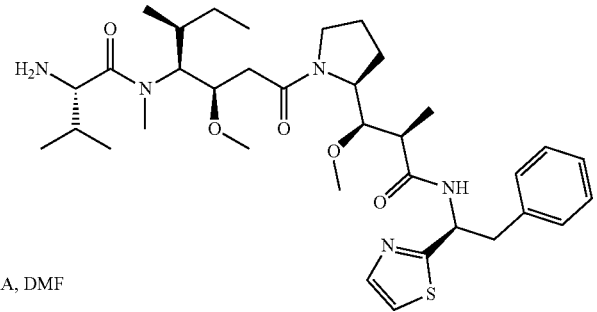

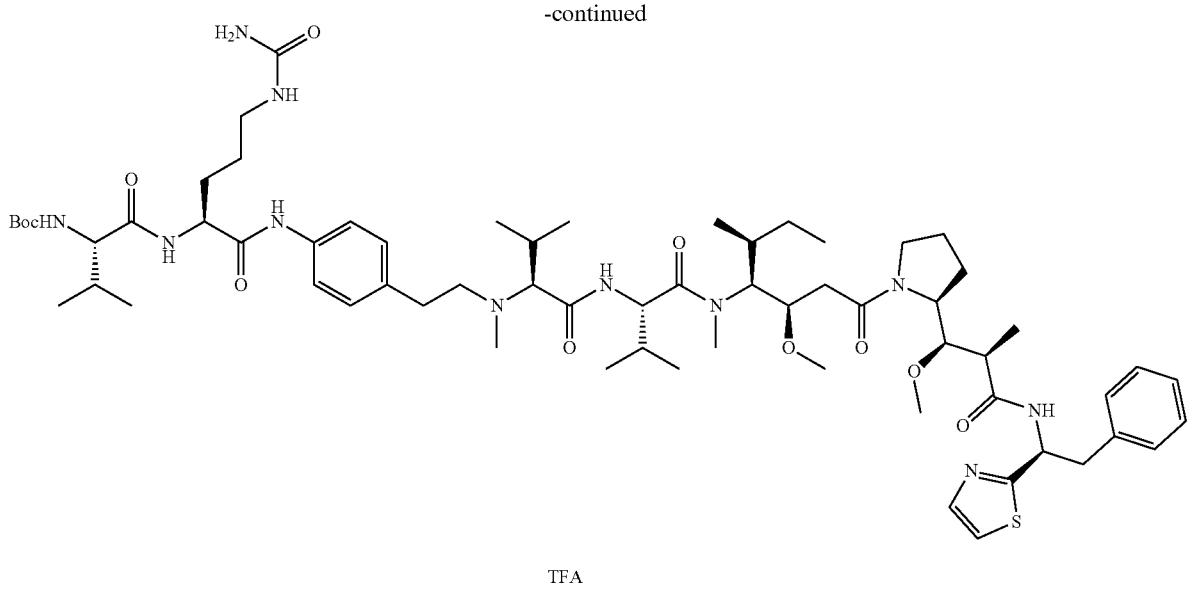

TFA

Acid F-61-3 (67.5 mg, 0.111 mmol, 1.5 eq.) was dissolved in dry DMF (2 mL) and DECP (17 μL, 0.111 mmol, 1.5 eq.) and DIEA (39 μL, 0.223 mmol, 3 eq.) were added. After stirring for 15 minutes at room temperature, amine 1Y (50 mg, 0.074 mmol, 1 eq.) was added and the solution stirred overnight. The solvent was evaporated under reduced pressure, and the residue purified by preparative HPLC (Waters 600E, SUNFIRE™ Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F61-4 as a white solid (28 mg, 28%).

Compound F-61-5

(S)-2-((S)-2-amino-3-methylbutanamido)-N-(4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)phenyl)-5-ureidopentanamide bis(2,2,2-trifluoroacetate)

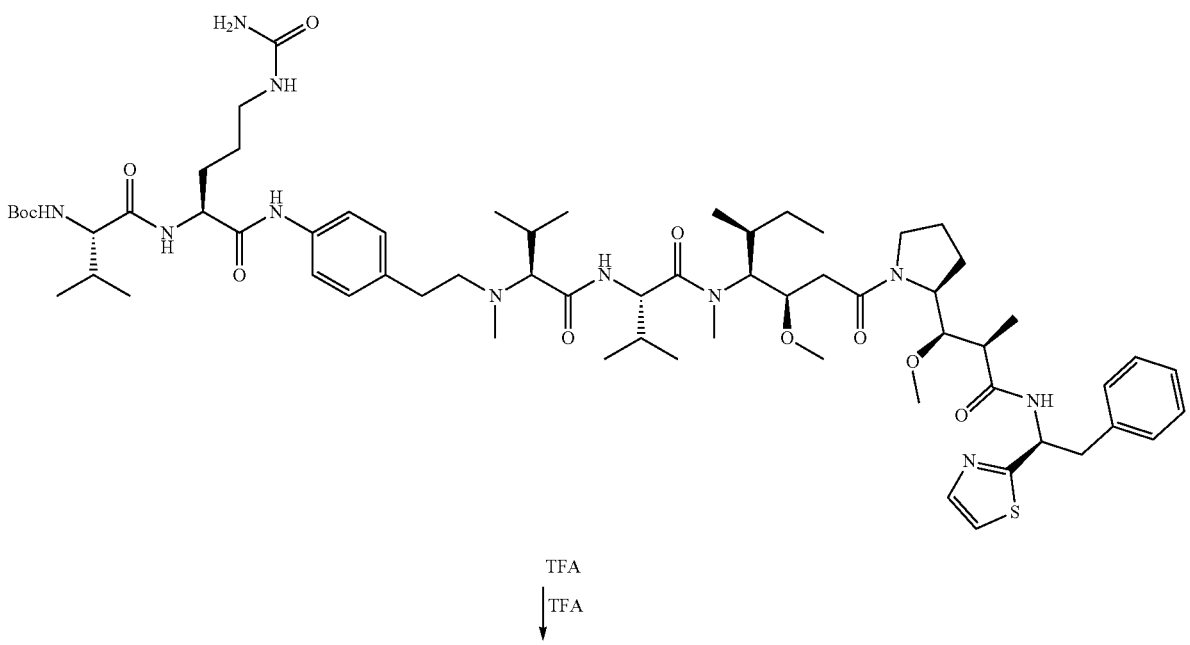

TFA

↓ TFA

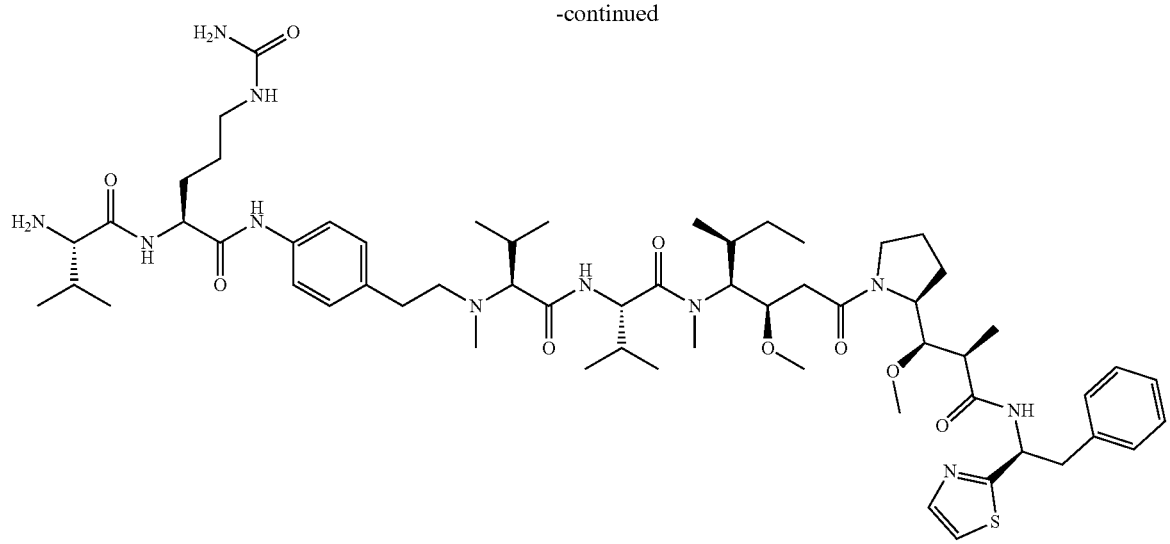
2 TFA
Compound F-61-4 (28 mg, 0.021 mmol, 1.0 eq.) was dissolved in TFA (200 μL). After 5 minutes, water (2 mL) and acetonitrile (0.5 mL) were added and the solution lyophilised overnight to yield compound F-61-5 as a colourless oil (38 mg, 134%).
Compound F-61
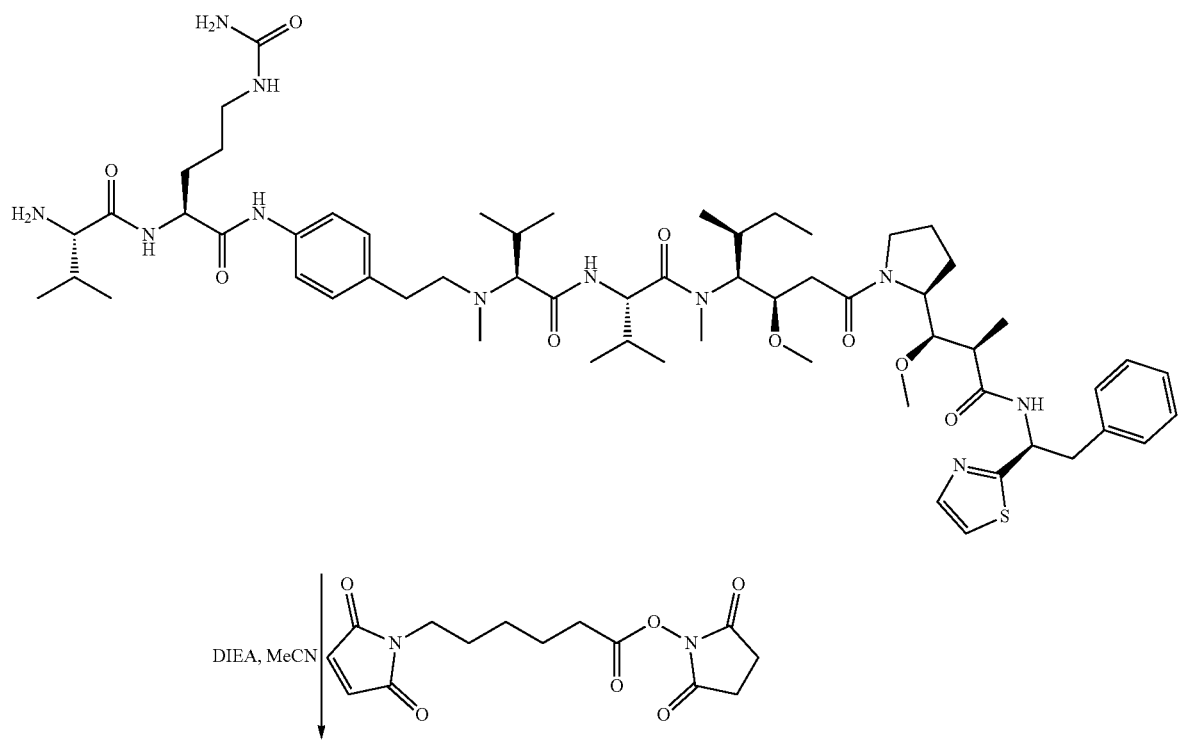

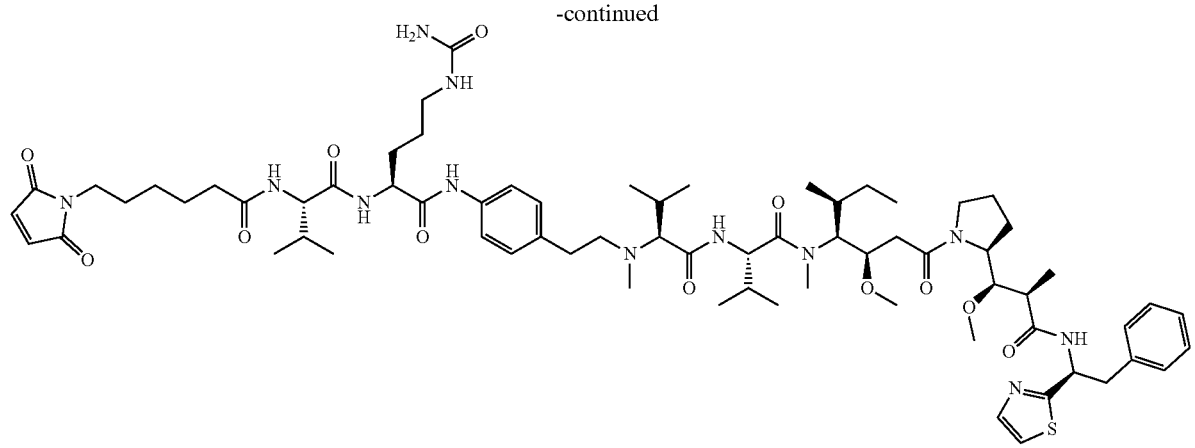

Compound F-61-5 (28.3 mg, 0.020 mmol, 1 eq.) was dissolved in acetonitrile (0.5 mL), followed by 2,5-dioxopyrrolidin-1-yl 6-(2,5-dioxo-2,5-dihydro-1H-pyrrol-1-yl)hexanoate (9 mg, 0.029 µmol, 1.4 eq.) and DIEA (25 µL, 0.143 mmol, 7 eq.). The mixture was stirred for 4.5 hours, after which time HPLC analysis showed the presence of starting material but complete consumption of the succinimide. Supplementary 2,5-dioxopyrrolidin-1-yl 6-(2,5-dioxo-2,5-dihydro-1H-pyrrol-1-yl)hexanoate was therefore added (3 mg, 0.01 µmol, 0.5 eq.) and the reaction stirred for 1.5 hours. HPLC analysis showed complete consumption of the starting material. The solvent was evaporated to dryness and the residue triturated twice with a mixture of EtOAc/Et$_2$O (80/20) to yield compound F-61 as an off-white solid (19.4 mg, 70%).

m/z (Q-TOF MS ESI+) 1361.7725 (2%, MNa$^+$, C$_{70}$H$_{106}$N$_{12}$NaO$_{12}$S requires 1361.7666), 670.3961 (1000%, (MH$_2$)$^{2+}$, C$_{70}$H$_{108}$N$_{12}$O$_{12}$S requires 670.3960).

Compound F-62 methyl((2R,3R)-3-((S)-1-((3R,4S,5S)-4-((S)-2-((S)-2-((4-((S)-2-((S)-2-(6-(2,5-dioxo-2,5-dihydro-1H-pyrrol-1-yl)hexanamido)-3-methylbutanamido)-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

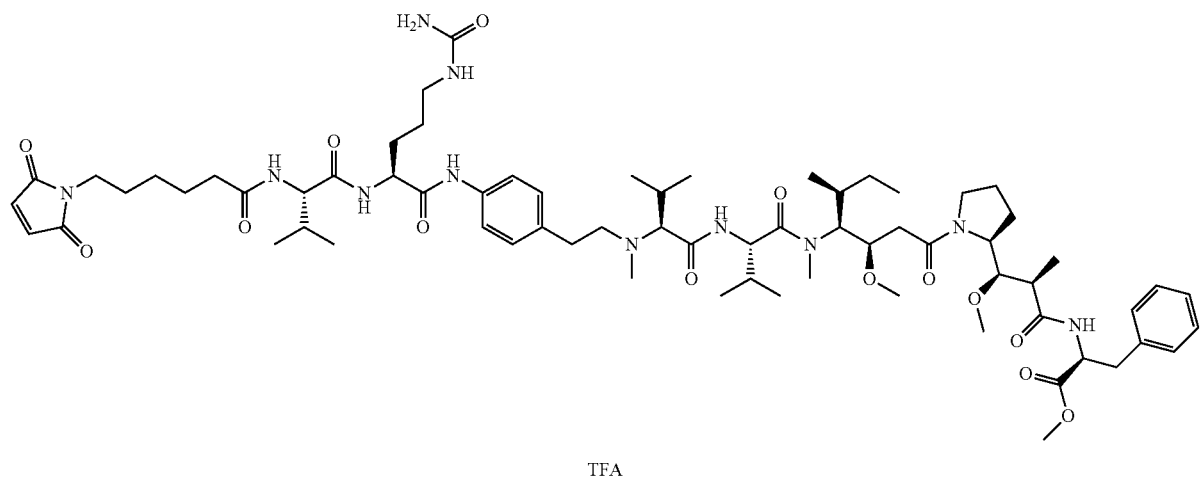 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(NC(=O)[C@H](CCCNC(N)=O)NC(=O)[C@@H](NC(=O)CCCCCN2C(=O)C=CC2=O)C(C)C)cc1)C(C)C]

TFA

Compound F-62-1
methyl ((2R,3R)-3-((S)-1-((3R,4S,5S)-4-((S)-2-((S)-2-((4-((S)-2-((S)-2-((tert-butoxycarbonyl)amino)-3-methylbutanamido)-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate
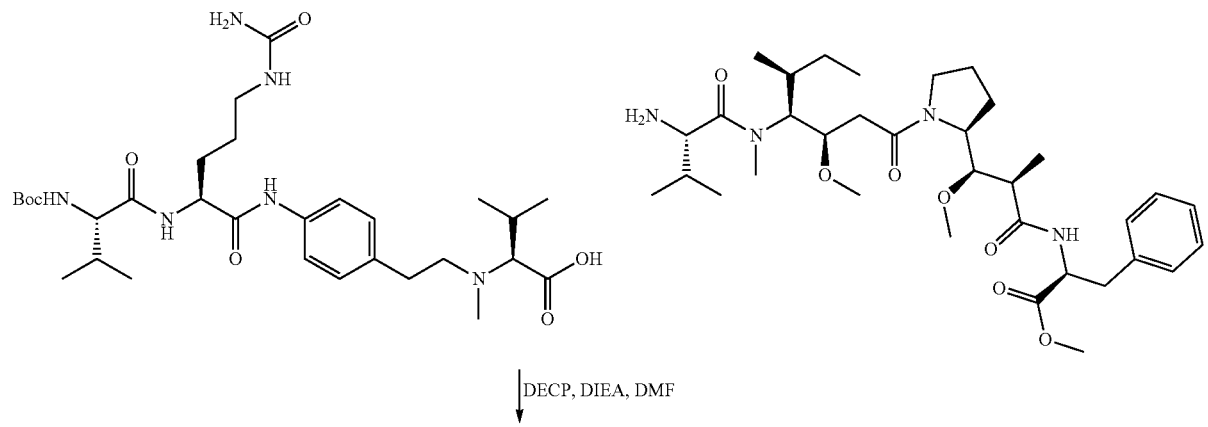
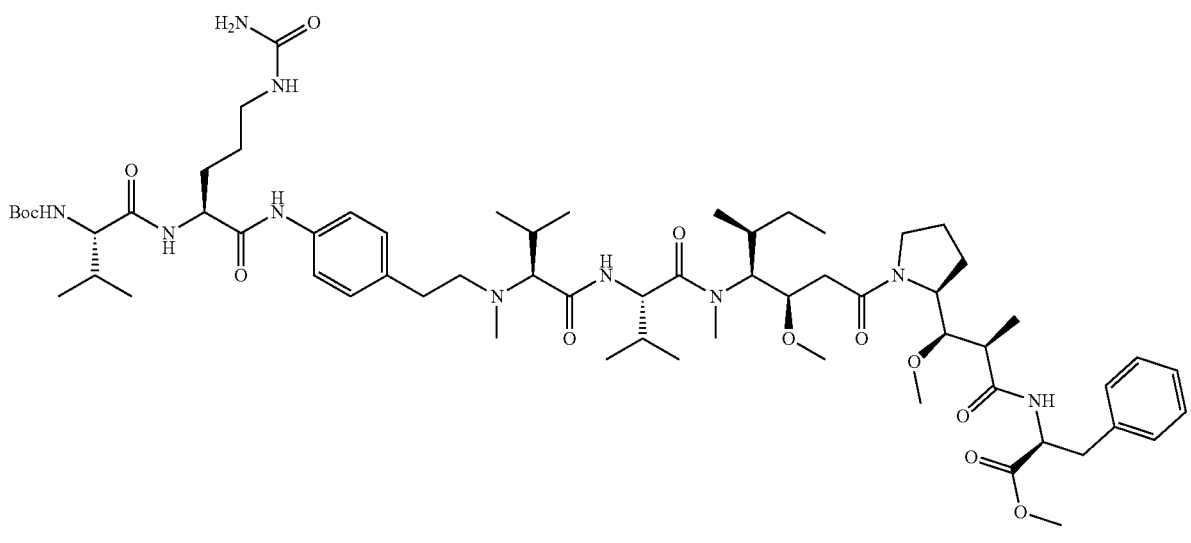

Compound F-62-1 was prepared in similar manner to compound F-61-4 from amine 3D (100 mg, 0.158 mmol, 0.9 eq.), acid F-61-3 (108 mg, 0.178 mmol, 1 eq.), DECP (41 µL, 0.267 mmol, 1.5 eq.) and DIEA (93 µL, 0.534 mmol, 3 eq.) in DMF (2 mL). After purification by preparative HPLC, compound F-62-1 was obtained as a white solid (93 mg, 39%).

Compound F-62-2 methyl ((2R,3R)-3-((S)-1-((3R,4S,5S)-4-((S)-2-((S)-2-((4-((S)-2-((S)-2-amino-3-methylbutanamido)-5-ureidopentanamido)phenethyl)(methyl) amino)-3-methylbutanamido)-N,3-dimethylbutanamido)-3-methoxy-5-methylheptanoyl) pyrrolidin-2-yl)-3-methoxy-2-methylpropanoyl)-L-phenylalaninate bis(2,2,2-trifluoroacetate)

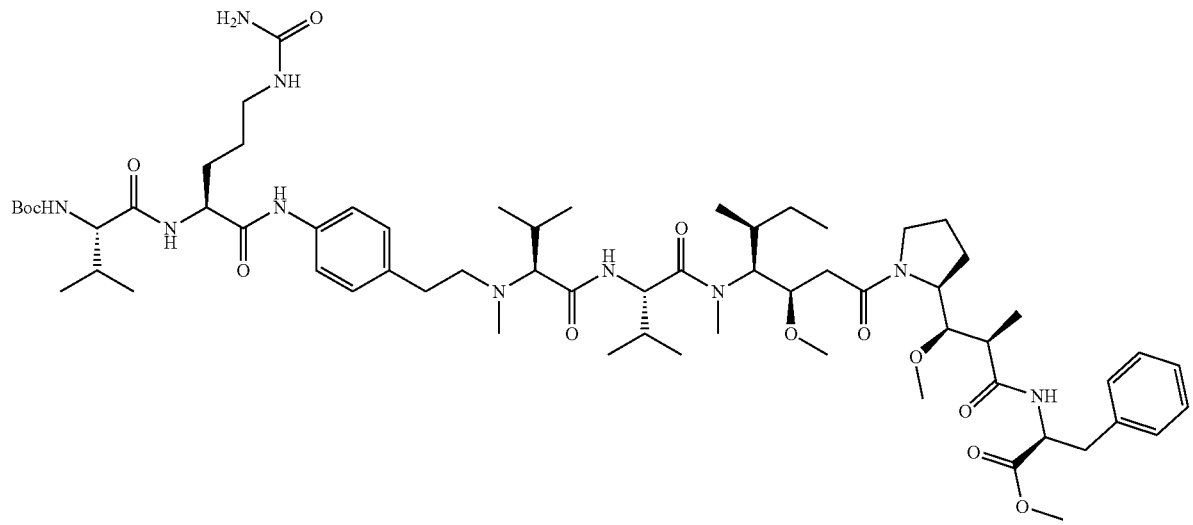

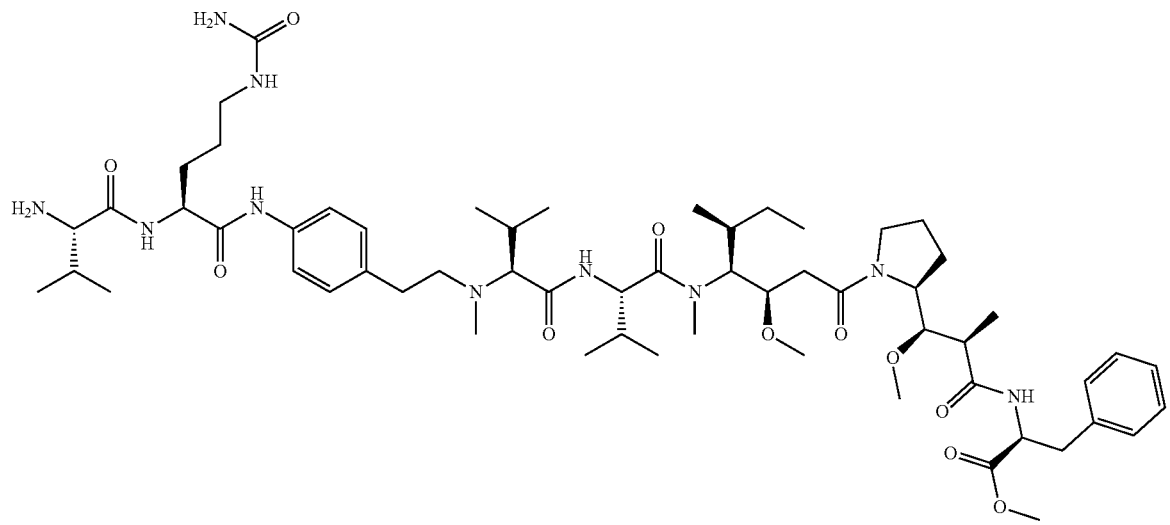

Compound F-62-1 (35 mg, 0.026 mmol, 1.0 eq.) was dissolved in TFA (200 μL). After 10 minutes, water (2 mL) and acetonitrile (0.5 mL) were added and the solution lyophilised overnight to yield compound F-62-2 as a white solid (34 mg, 105%).

Compound F-62

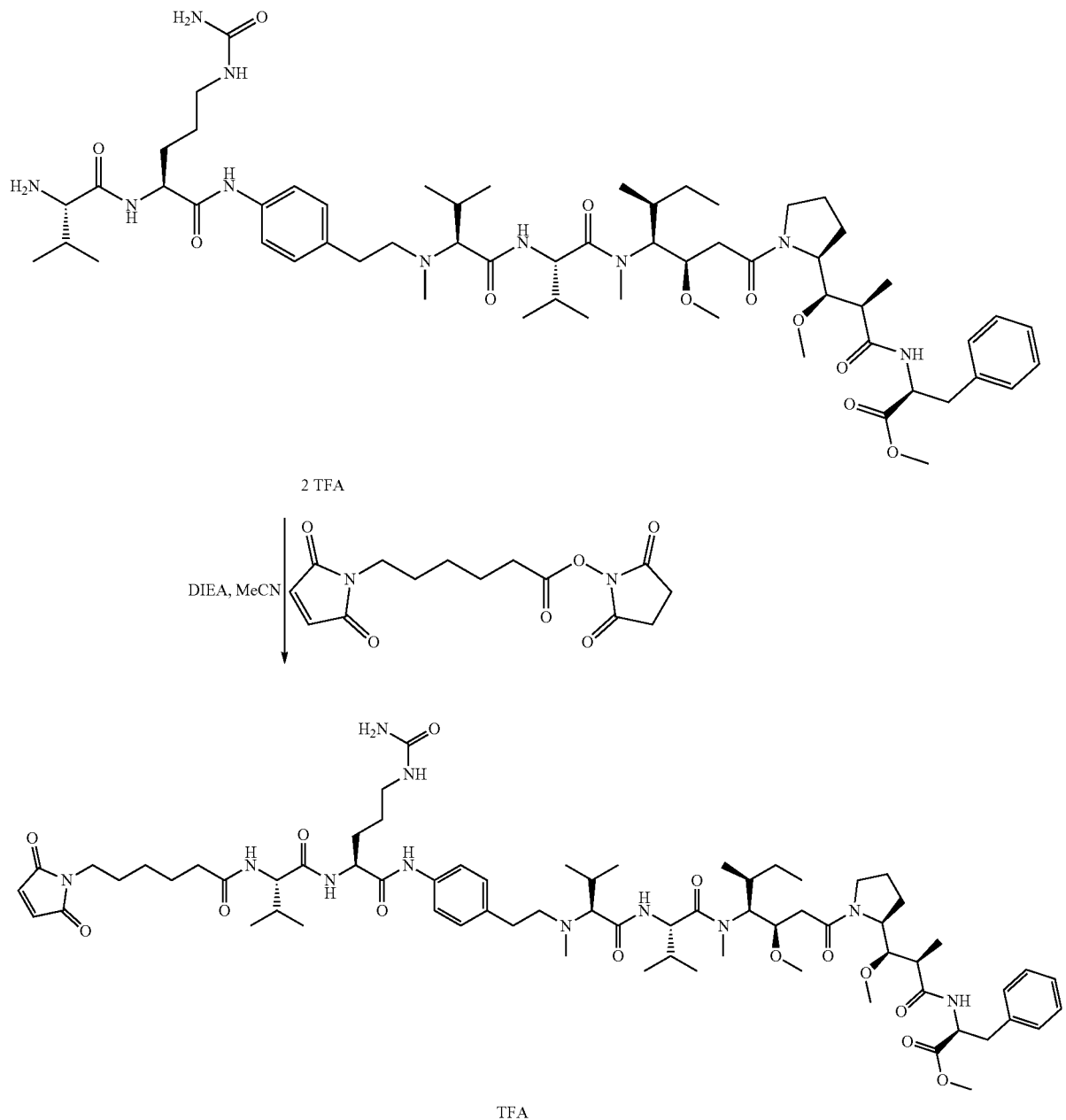

Amine F-62-2 (34 mg, 5.55 μmol, 1 eq.) was dissolved in acetonitrile (3 mL). DIEA (5 μL, 0.028 mmol, 5 eq.) and 2,5-dioxopyrrolidin-1-yl 6-(2,5-dioxo-2,5-dihydro-1H-pyrrol-1-yl)hexanoate (2 mg, 6.65 μmol, 1.2 eq.) were added. HPLC analysis showed complete consumption of the starting material. The solvent was evaporated to dryness and the residue triturated with a mixture of EtOAc/Et$_2$O (80/20). The crude product was purified by preparative HPLC (Waters 600E, SUNFIRE™ Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F-62 as a white solid (5.5 mg, 13%).

m/z (Q-TOF MS ESI+) 1336.7859 (2%, MNa$^+$, C$_{69}$H$_{107}$N$_{11}$NaO$_{14}$ requires 1336.7891), 657.9073 (100%, (MH$_2$)$^{2+}$, C$_{69}$H$_{109}$N$_{11}$O$_{14}$ requires 657.9072).

Compound F-63

((2R,3R)-3-((S)-1-((3R,4S,5S)-4-((S)-2-((S)-2-((4-((S)-2-((S)-2-(6-(2,5-dioxo-2,5-dihydro-1H-pyrrol-1-yl)hexanamido)-3-methylbutanamido)-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate

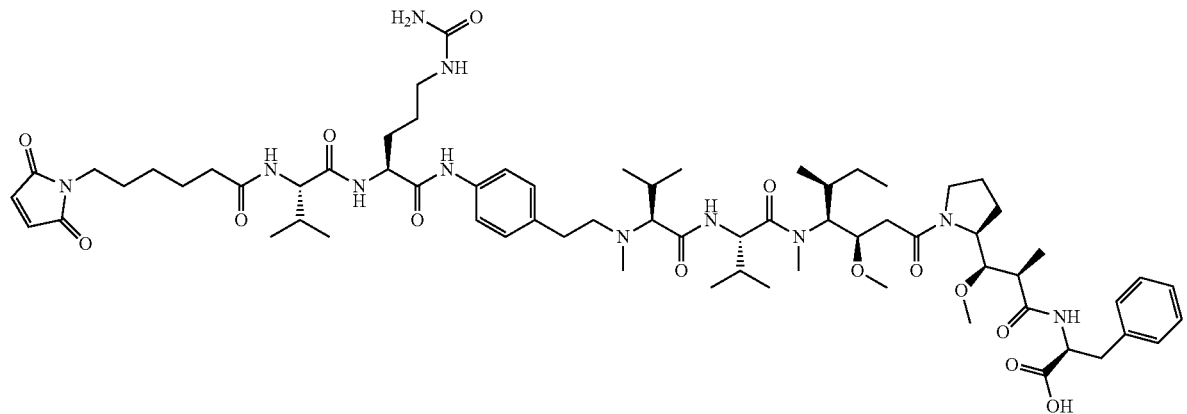

TFA

Compound F-63-1

((2R,3R)-3-((S)-1-((3R,4S,5S)-4-((S)-2-((S)-2-((4-((S)-2-((S)-2-((tert-butoxycarbonyl)amino)-3-methylbutanamido)-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine

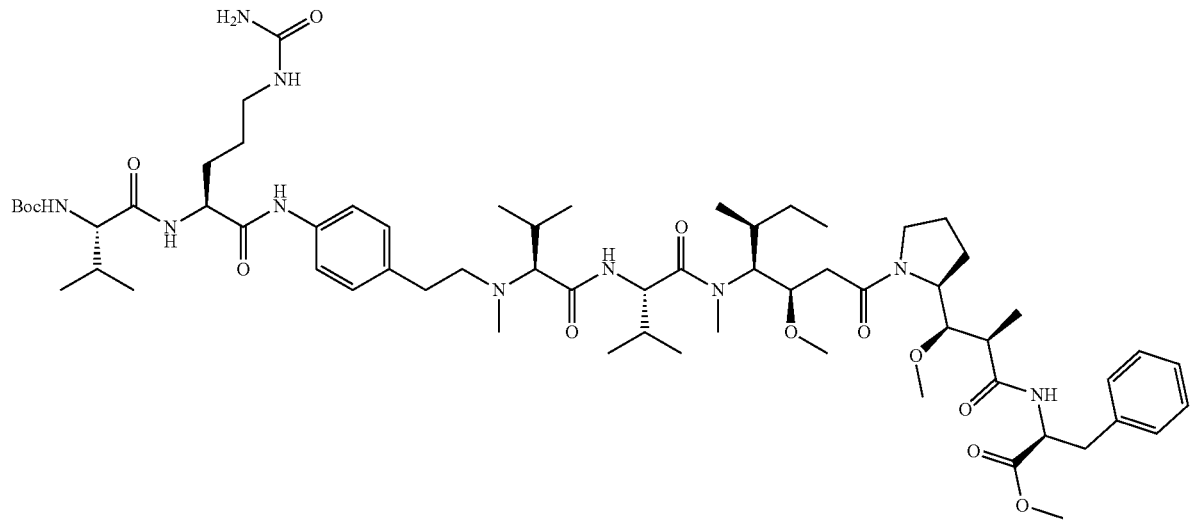

TFA

Piperidine, water, MeCN

-continued

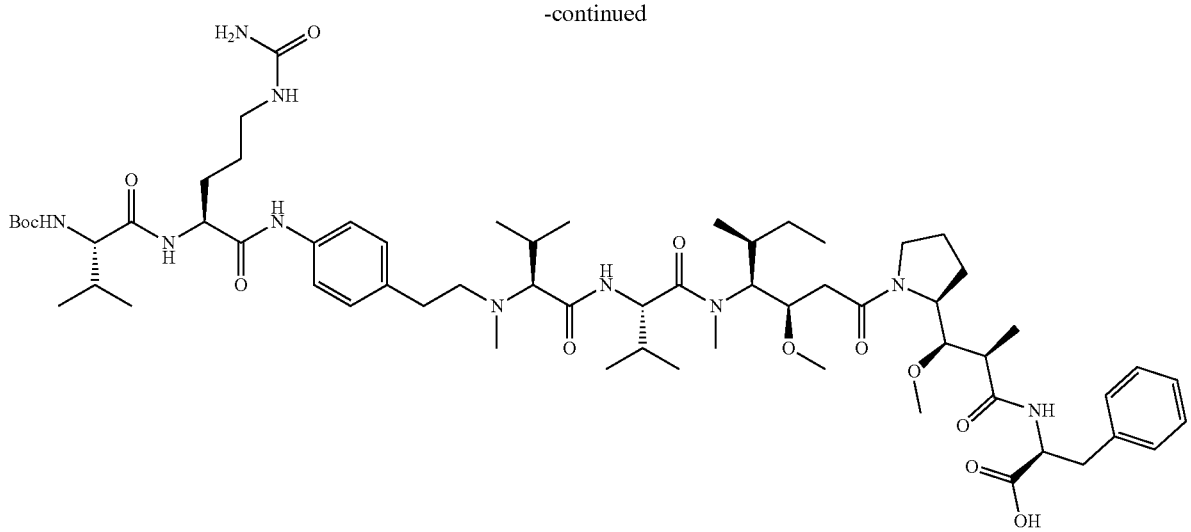

Compound F-62-1 (157 mg, 0.118 mmol, 1 eq.) was dissolved in a mixture of water (4.5 mL), acetonitrile (4.5 mL) and piperidine (3.5 mL) and stirred at room temperature for 5 hours. The solvent was evaporated under reduced pressure and the residue triturated Et₂O (60 mL). The solid was collected by filtration and rinsed twice with Et₂O (10 mL) to yield compound F-63-1 as an off-white solid (153 mg, 100%).

Compound F-63-2

((2R,3R)-3-((S)-1-((3R,4S,5S)-4-((S)-2-((S)-2-((4-((S)-2-((S)-2-amino-3-methylbutanamido)-5-ureidopentanamido)phenethyl)(methyl)amino)-3-methylbutanamido)-N,3-dimethylbutanamido)-3-methoxy-5-methylheptanoyl) pyrrolidin-2-yl)-3-methoxy-2-methylpropanoyl)-L-phenylalanine bis 2,2,2-trifluoroacetate

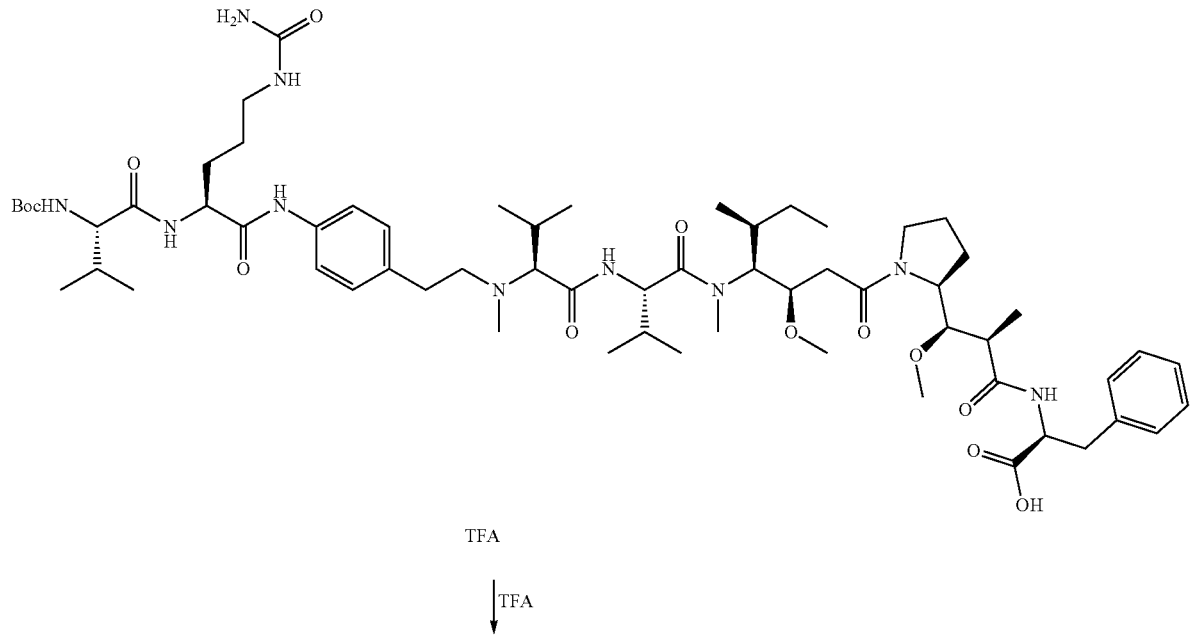

TFA

↓ TFA

-continued
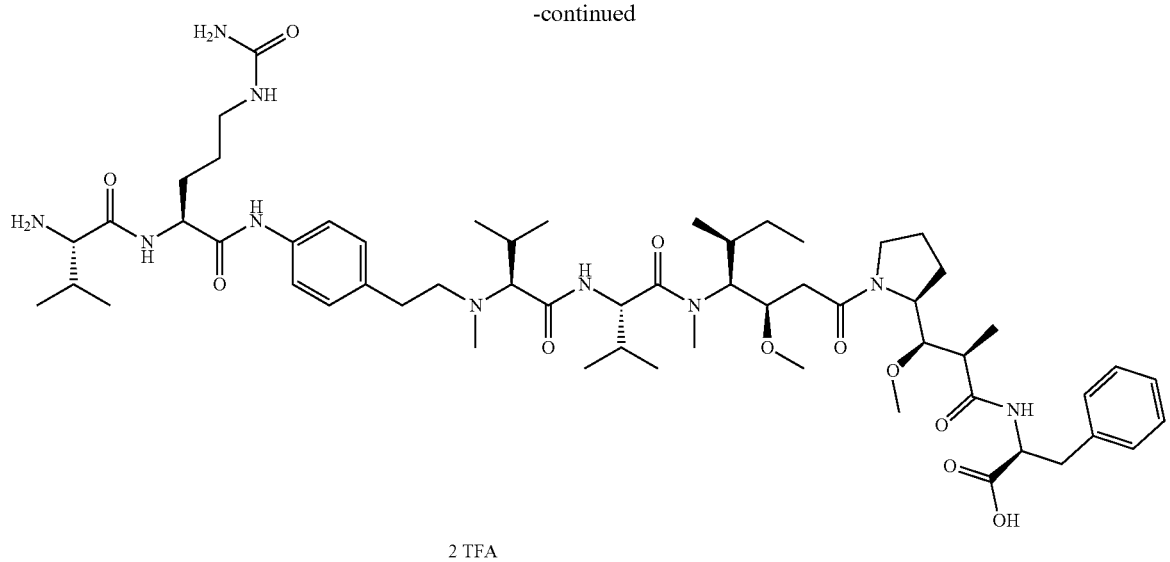
2 TFA
Compound F-63-1 (153 mg, 0.127 mmol, 1.0 eq.) was dissolved in TFA (200 μL). After 10 minutes, water (2 mL) and acetonitrile (0.5 mL) were added and the solution lyophilised overnight to yield compound F-63-2 as a white solid (34 mg, 105%).
Compound F-63
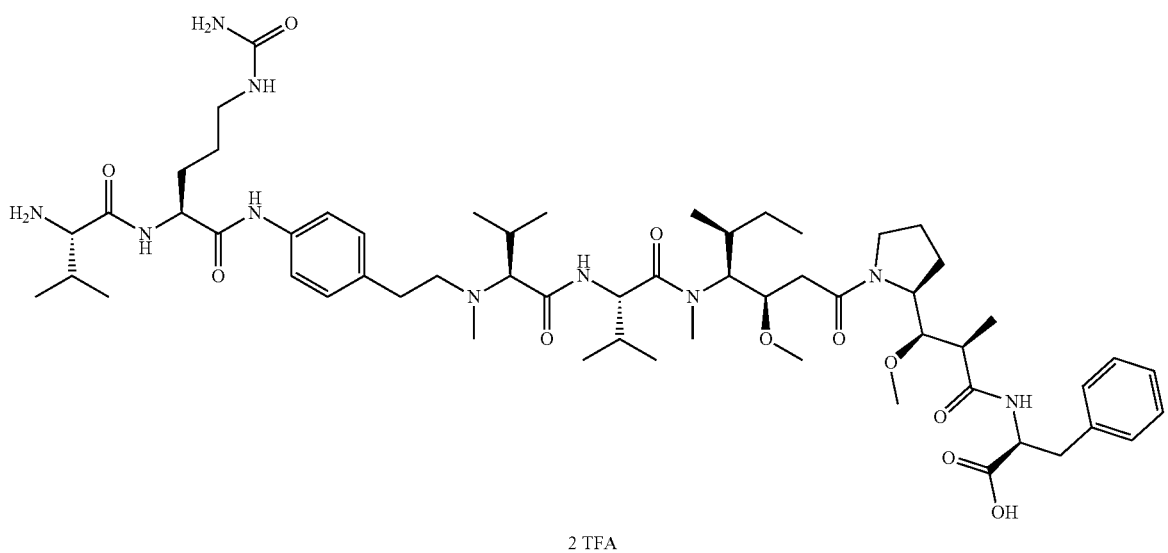
2 TFA
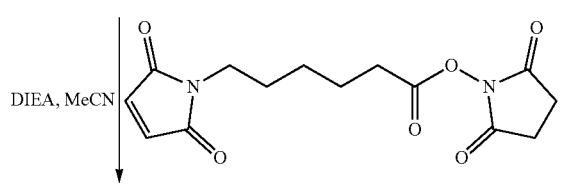
DIEA, MeCN

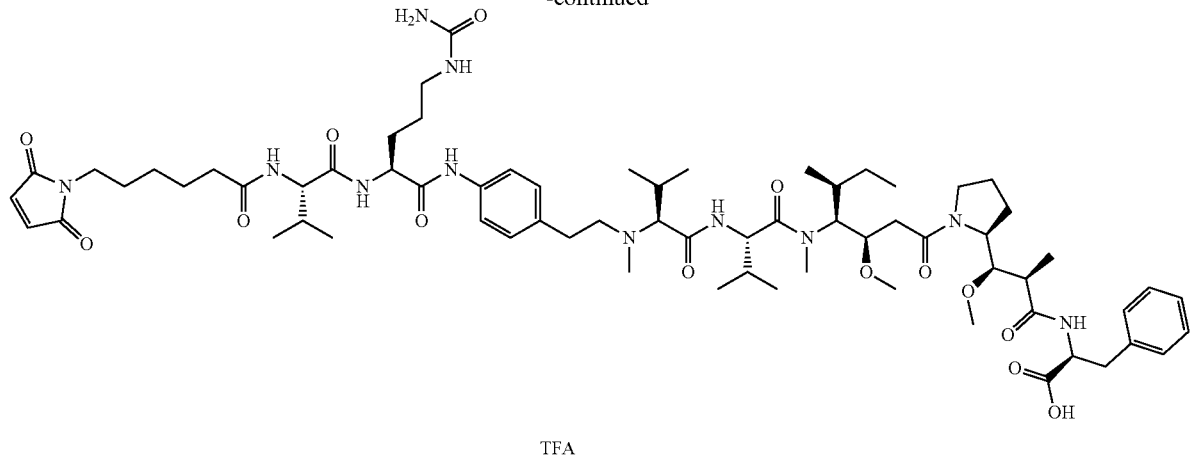

TFA

Amine F-63-2 (100 mg, 0.082 mmol, 1 eq.) was dissolved in a mixture of acetonitrile (2 mL) and DMF (0.5 mL), and 2,5-dioxopyrrolidin-1-yl 6-(2,5-dioxo-2,5-dihydro-1H-pyrrol-1-yl)hexanoate (45 mg, 0.147 mmol, 1.8 eq.) and DIEA (71 µL, 0.409 mmol, 5 eq.) were added. After stirring at room temperature for 4.5 hours, the solvent was evaporated under reduced pressure. The crude product was purified by preparative HPLC (Waters 600E, SUNFIRE™ Prep C18 OBD column, 5 µm, 19×100 mm; Eluting phase: water/MeCN buffered with 0.100 TFA; Gradient of 500 to 10000 MeCN in 15 minutes; Waters 2487 UV Detector at 220 nm). The selected fractions were combined and lyophilised to furnish compound F-63 as a white solid after (42 mg, 36%).

m/z (Q-TOF MS ESI+) 1300.7901 (2%, MH$^+$, $C_{68}H_{106}N_{11}O_{14}$ requires 1300.7915), 650.8990 (100%, (MH$_2$)$^{2+}$, $C_{68}H_{107}N_{11}O_{14}$ requires 650.8994).

Compound G-12 methyl ((2R,3R)-3-((S)-1-((3R,4S,5S)-4-((S)-2-((S)-2-((4-(6-(2,5-dioxo-2,5-dihydro-1H-pyrrol-1-yl)-N-methylhexanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

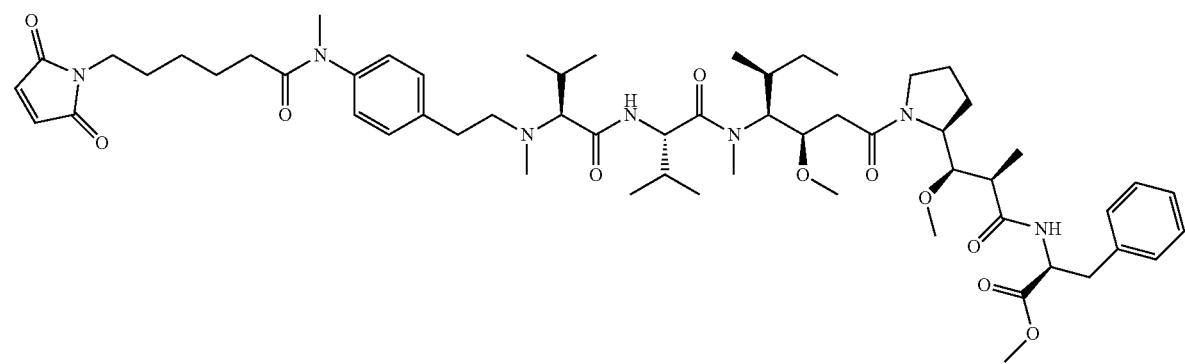

TFA

321
Compound G-12-1 benzyl N-(4-aminophenethyl)-N-methyl-L-valinate dihydrochloride

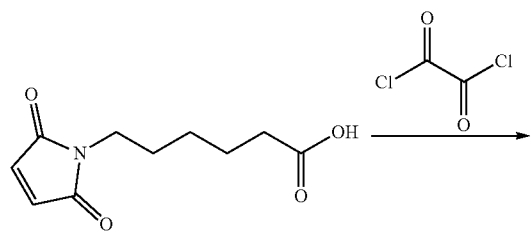

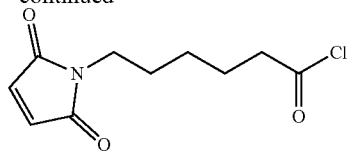

Into oxalyl chloride (3 mL) was dissolved 6-(2,5-dioxo-2,5-dihydro-H-pyrrol-1-yl)hexanoic acid (200 mg, 0.947 mmol, 1 eq.). The solution was stirred at room temperature for 5 hours before evaporating to dryness under reduced pressure. Compound G-12-1 was obtained as a beige solid (217 mg, 100%) and used in the next step without purification.

Compound G-12

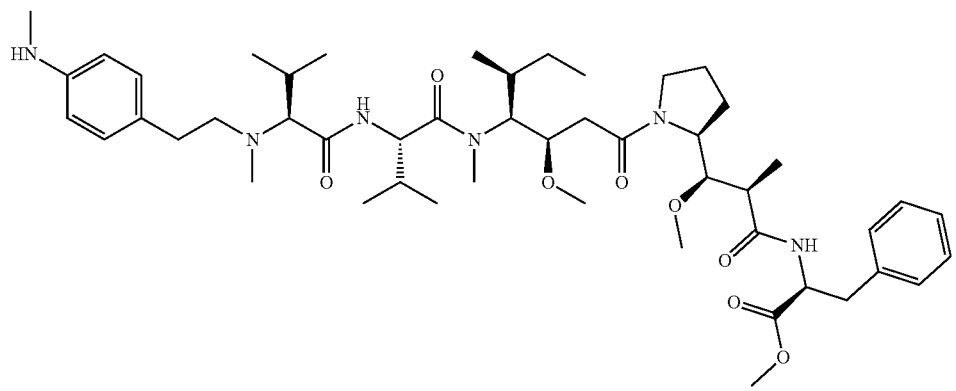

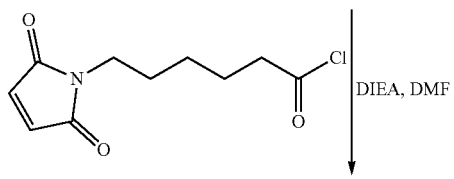

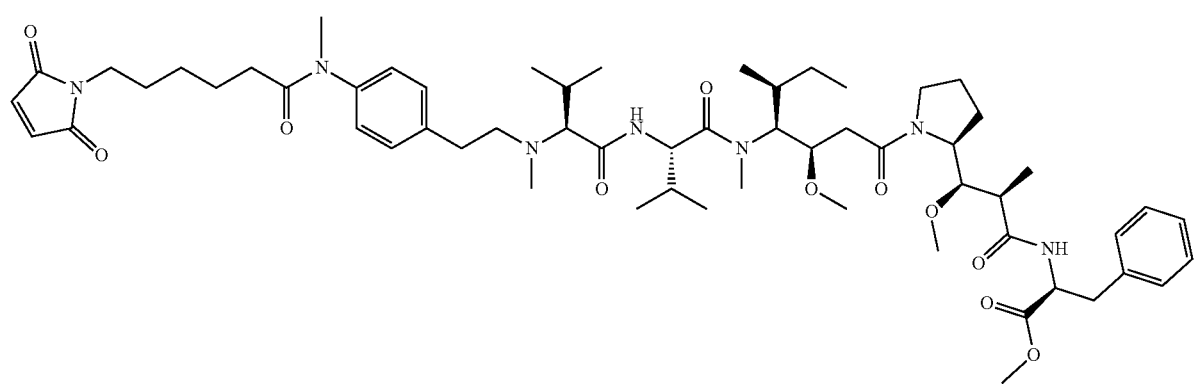

TFA

Aniline 12 (40 mg, 0.045 mmol, 1 eq.) was dissolved in dry DCM (1 mL) at 0° C. and DIEA (8 µL, 0.045 mmol, 1 eq.) was added. After stirring for 30 minutes, a solution of compound G-12-1 (10 mg, 0.45 mmol, 1 eq.) in dry DCM (1 mL) was introduced and the reaction stirred for 1 hour at 0° C. The mixture was diluted with DCM (25 ml) and washed twice with water (20 mL), once with brine (10 mL). The organic phase was dried over $Na_2SO_4$, filtered and evaporated under reduced pressure to yield the crude product as a light brown solid (54 mg). This was purified by flash chromatography on silica gel (DCM/MeOH) followed by preparative HPLC (Waters 600E, SUNFIRE™ Prep C18 OBD column, 5 µm, 19×100 mm; Eluting phase: water/MeCN buffered with 0.1% TFA; Gradient of 5% to 100% MeCN in 15 minutes; Waters 2487 UV Detector at 220 nm). The isolated product was lyophilised to yield a white solid (23 mg), which was repurified by preparative HPLC and the selected fractions combined and lyophilised to furnish compound G-12 as a white solid (9 mg, 16%).

m/z (Q-TOF MS ESI+) 1094.6543 (20%, MNa+, $C_{59}H_{89}N_7NaO_{11}$ requires 1094.6512), 1072.6722 (160%, MH+, $C_{59}H_{90}N_7O_{11}$ requires 1072.6693), 536.8358 (1000%, $(MH_2)^{2+}$, $C_{59}H_{91}N_7O_{11}$ requires 536.8383).

Compound G-13

((2R,3R)-3-((S)-1-((3R,4S,5S)-4-((S)-2-((S)-2-((4-(6-(2,5-dioxo-2,5-dihydro-1H-pyrrol-1-yl)-N-methylhexanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate

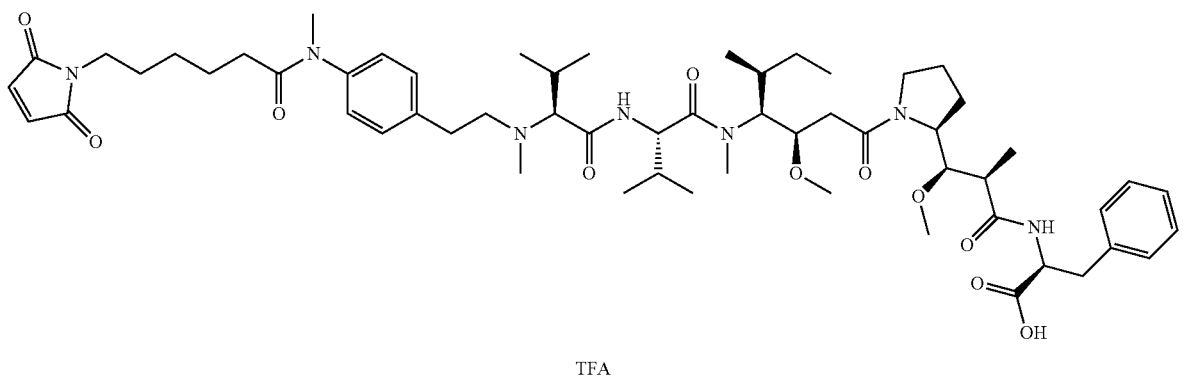 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)CCCCCN2C(=O)C=CC2=O)cc1)C(C)C]

TFA

Compound G-13

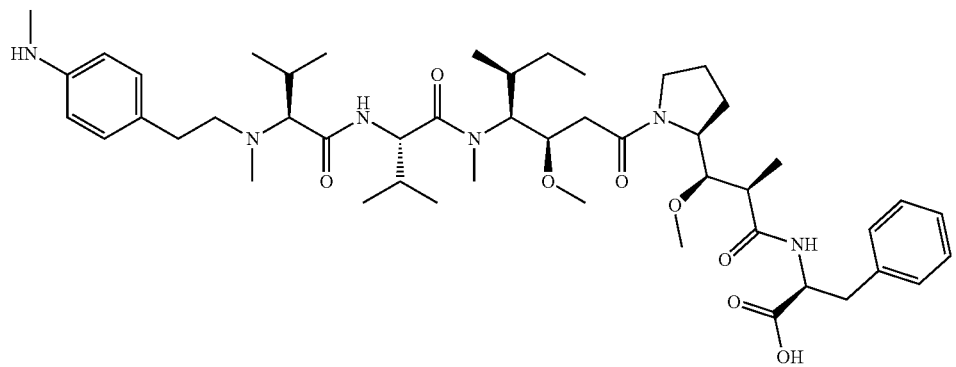

TFA

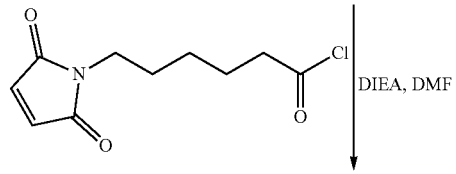

DIEA, DMF

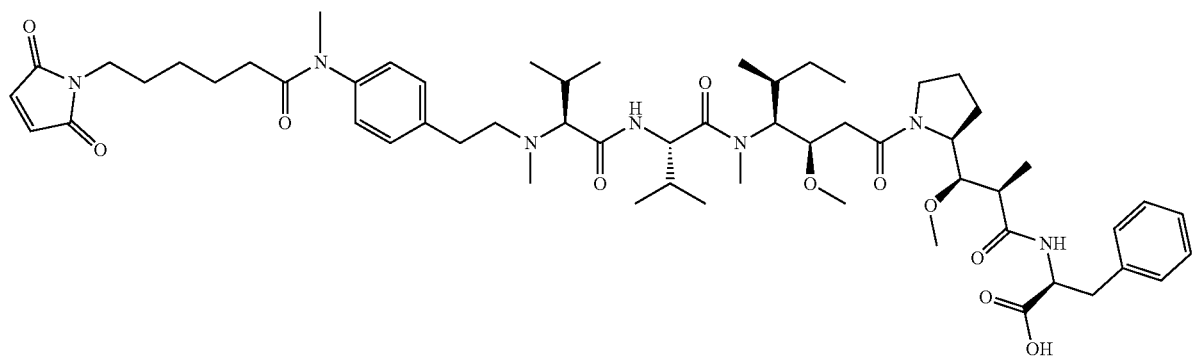

TFA

Aniline 13 (15 mg, 0.015 mmol, 1 eq.) was dissolved in dry DCM (1.5 mL) at 0° C. and DIEA (8 μL, 0.046 mmol, 3 eq.) was added. A solution of compound G-12-1 (3.5 mg, 0.046 mmol, 1 eq.) in dry DCM (0.5 mL) was introduced and the reaction stirred for 1.5 hours at 0° C. The solvent was evaporated under reduced pressure and the crude product purified by preparative HPLC (Waters 600E, SUNFIRE™ Prep C18 OBD column, 5 μm. 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound G-13 as a white solid (11.4 mg, 62%).

m/z (Q-TOF MS ESI+) 1058.6510 (30%, MH$^+$, $C_{58}H_{88}N_7O_{11}$ requires 1058.6536), 529.8285 (100%, $(MH_2)^{2+}$, $C_{58}H_{89}N_7O_{11}$ requires 529.8305).

Compound G-15 methyl ((2R,3R)-3-((S)-1-((3R,4S,5S)-4-((S)-2-((S)-2-((3-(6-(2,5-dioxo-2,5-dihydro-1H-pyrrol-1-yl)hexanamido)benzyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

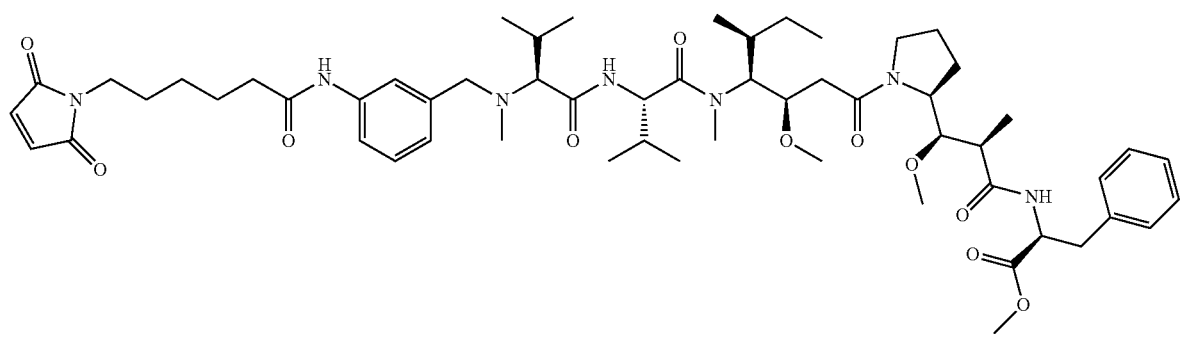

TFA

Compound G-15

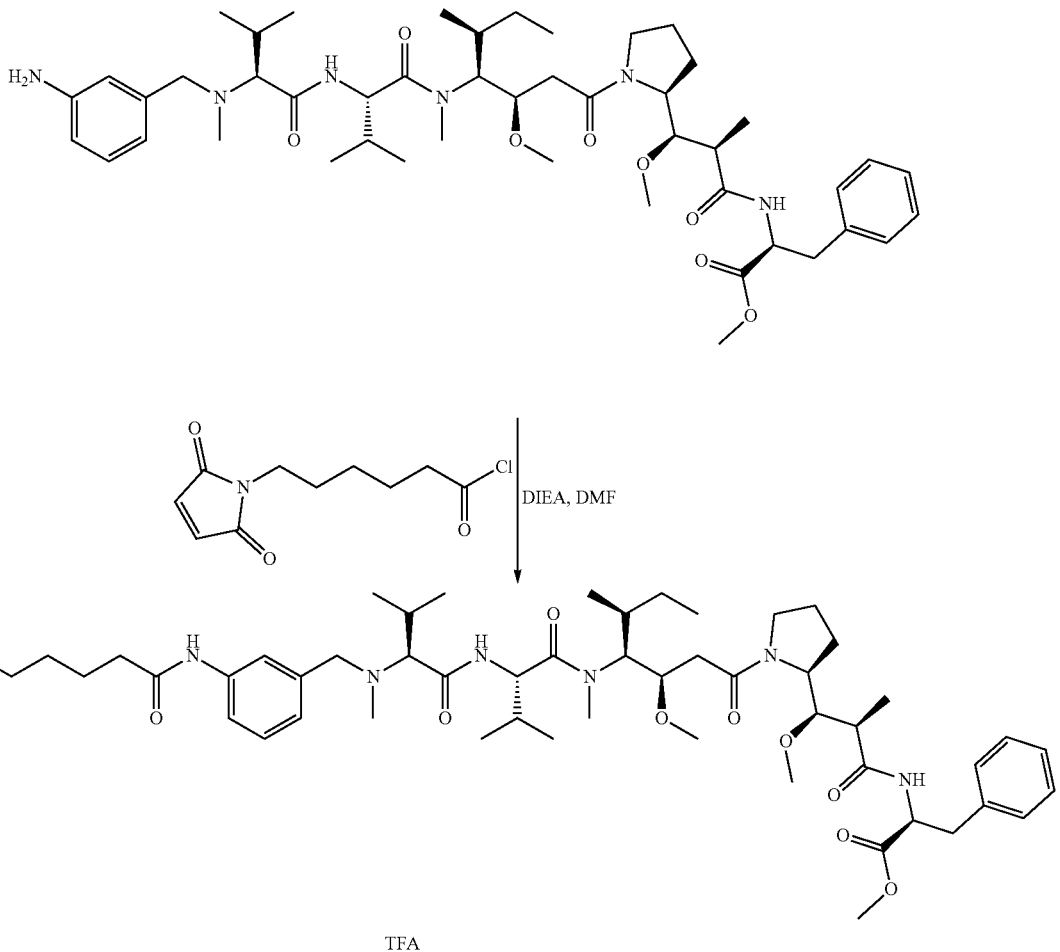

Aniline 15 (40 mg, 0.047 mmol, 1 eq.) was dissolved in dry DCM (2 mL) at 0° C. and DIEA (10 µL, 0.056 mmol, 1.2 eq.) was added. A solution of compound G-12-1 (108 mg, 0.47 mmol, 10 eq.) in dry DCM (1 mL) was introduced and the reaction stirred for 1.5 hours at 0° C. The mixture was diluted with DCM (10 ml) and washed twice with water (5 mL). The organic phase was dried over MgSO$_4$, filtered and evaporated under reduced pressure to yield the crude product as a beige solid. This was purified by preparative HPLC (Waters 600E, SUNFIRE™ Prep C18 OBD column, 5 µm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound G15 as a white solid (27 mg, 50%).

m/z (Q-TOF MS ESI+) 1066.6517 (2%, MNa$^+$, C$_{57}$H$_{85}$N$_7$NaO$_{11}$ requires 1066.6199), 522.8224 (100%, (MH$_2$)$^{2+}$, C$_{57}$H$_{87}$N$_7$O$_{11}$ requires 522.8226).

Example 22: ADC Synthesis, Purification and Characterization

The procedure described below applies to chimeric and humanized IgG1 forms. It must be understood that for any other forms, such as IgG2, IgG4, etc., the person skilled n the art would be capable of adapting this procedure using the general knowledge.

Antibodies (1-5 mg/ml) were partially reduced with Tris (2-carboxyethyl)phosphine hydrochloride (TCEP) in 10 mM borate buffer pH 8.4 containing 150 mM NaCl and 2 mM EDTA for 2 h at 37° C. Typically, 2.5-3 molar equivalents of TCEP were used to target a Drug-to-Antibody Ratios (DAR) of around 4, respectively. The partial antibody reduction was confirmed by SDS-PAGE analysis under non reducing conditions. Before Linker-Drug coupling to the released interchain cysteine residues, the reduction mixture was allowed to cool to room temperature. The antibody concentration was then adjusted to 1 mg/ml with 10 mM borate buffer pH 8.4 containing 150 mM NaCl and 2 mM EDTA, and a 5 molar excess of drug to antibody was added from a 10 mM solution in dimethyl sulfoxide (DMSO). The final DMSO concentration was adjusted to 10% to maintain the solubility of the drug in the aqueous medium during coupling. The reaction was carried out for 1 h at room temperature. The drug excess was quenched by addition of 1.5 moles of N-acetylcysteine per mole of drug and incubation for 1 h at room temperature. After dialysis against 25 mM His buffer pH 6.5 containing 150 mM NaCl overnight at 4° C., the antibody-drug-conjugates were purified by using methods known to persons skilled in the art based with commercial chromatography columns and ultrafiltration units. First, the non coupled drug and the ADC aggregates were eliminated by size exclusion chromatography (SEC) on S200 (GE Life Sciences) or TSK G3000 SW (Tosoh) column. The purified ADC monomers were then concentrated to 2-3 mg/ml by ultrafiltration on 30 or 50 kDa MWCO filtration units or by affinity chromatography on Protein A. The purified ADCs were stored at 4° C. after sterile filtration on 0.2 μm filter. They were further analyzed by SDS-PAGE under reducing and non reducing conditions to confirm drug conjugation and by SEC on analytical S200 or TSK G3000 SWXL columns to determine the content of monomers and aggregated forms. Protein concentrations were determined by using the bicinchoninic acid (BCA) assay with IgG as standard. The DAR was estimated for each purified ADC by HIC and LC-MS. Typically, the content of aggregated forms was lower than 5% and the DAR was comprised between 3.5 and 5.

Example 23: Cytotoxicity Evaluation of IGF-1R Antibodies Coupled with Different Drugs The five IGF-1R antibodies were shown to be rapidly internalized into lysosomes and to have a lower binding capacity into acidic environments. In that respect, those Abs had all properties to be used as ADCs. Thus, the five chimeric anti-IGF-1R antibodies were coupled with three different compounds (G-13; E-13 and F-63). The drug antibody ratio of those ADCs was about 4. In order to evaluate the non specific cytotoxicity, an irrelevant chimeric antibody c9G4 was also coupled with those compounds at the same DAR. MCF-7 cells were incubated with increasing concentrations of each ADCs at 37° C. for 6 days in complete culture medium. Cell viability was assessed using a luminescent cell viability assay (CELLTITER-GLO®, PROMEGA®). Luminescent signal was read using a the Mithras plate reader (Berthold Technologies). The irrelevant chimeric antibody c9G4 coupled with either E-13, G-13 or F-63 showed no or modest cytotoxic activity on MCF-7 cells (FIG. 21). On the contrary, addition of all other ADCs obtained after coupling anti-IGF-1R antibodies with either E-13, G-13 or F-63 decreased dramatically MCF-7 cell viability.

Example 24: In Vivo Activity of the c208F2 Antibody Conjugated to Either E-13, G-13 or F-63 Compounds in the MCF-7 Xenograft Model In order to confirm that the in vitro efficacy of the c208F2 coupled to G-13, E-13 or F-63 compounds could be translated in vivo, they have been tested in the MCF-7 xenograft model.

All animal procedures were performed according to the guidelines of the 2010/63/UE Directive on the protection of animals used for scientific purposes. The protocol was approved by the Animal Ethical Committee of the Pierre Fabre Institute. Five millions MCF-7 cells were injected subcutaneous into 7 weeks old Swiss/Nude mice. Prior to cell injection, oestrogen pellets (Innovative Research of America) were implanted to the left flank to mice in order to release estrogens necessary to the in vivo growth of MCF-7 tumors.

Twenty days after MCF-7 cell implantation, when tumors reached an average size of 120-150 mm³, the animals were divided into groups of 5 mice according to tumor size and aspect. The different treatments were inoculated by intraperitoneal injections. The health status of animals was monitored daily. Tumor volume was measured twice a week with an electronic calliper until study end. Tumor volume is calculated with the following formula: π/6×length×width×height. Toxicity was evaluated following the weight of animals three times per week. Statistical analyses were performed at each measure using a Mann-Whitney test. All compounds were injected intraperitoneally (i.p.). In this example, the anti-tumor activity of c208F2 mAb coupled with either E-13, F-13 or F-63 at about DAR 4 was evaluated after 2 injections of a 7 mg/kg dose at D20 and D27 (FIGS. 22A, 22B and 22C). In parallel the capped-drug moieties E-13, F-13 and F-63 were injected at the equivalent dose of the one corresponding to 7 mg/kg of c208F2-E-13, c208F2-F-13 and c208F2-F-63 DAR about 4.

Injection of either c208-E-13 (FIG. 22A), c208F2-G-13 (FIG. 22B) or c208F2-F-63 (FIG. 22C) significantly inhibited and even induced a complete tumor growth regression (p<0.05 vs corresponding capped-drug). No statistical activity difference between c208-E-13, c208F2-G-13 and c208F2-F-63 could be noted. Capped drugs had no effect on MCF-7 tumor growth (p >0.05 vs control group)

A second set of experiments was performed with c208F2 coupled with either E-13 or G-13 and with the irrelevant antibody c9G4 coupled with either E-13 or G-13 in MCF-7 xenograft models as described previously. Mice were injected i.p. with 7 mg/kg of each ADCs at D20 and D27 (FIGS. 23A and 23B).

Injection of both c9G4-E-13 and c9G4-F-13 affected moderately and transiently the growth of MCF-7 xenograft tumors. However, this second experiment confirmed that injections of either c208-E-13 or c208F2-G-13 induced complete tumor regression since D43 showing the high anti-tumor activity of those ADCs.

Example 25: Potent Cytotoxicity In Vitro of Axl ADCs Coupled with Different Drugs The cytotoxic activity of ADCs for inhibition of tumor cell growth was tested in a cell proliferation assay using SN12C (Axl⁺ human renal cell carcinoma) and MCF-7 (Axl⁻ human breast adenocarcinoma). Briefly, cells were seeded into 96 well multi-well plates the day before drug treatment at 2500 cells per well. ADCs and controls were serially diluted and then added to the mw-96 plates. Cells were then incubated for 6 days at 37° C. and 5% $CO_2$. The cell viability was quantified by measuring the level of ATP in the wells using the CELLTITER-GLO® Luminescent Cell Viability Assay (PROMEGA® catalog # G7571). The percentage of cell viability was calculated considering untreated cells as 100%. Using a nonlinear regression analysis (GraphPad PRISM® 4.0), the $IC_{50}$, the concentration of compound needed to yield a 50% reduction in viability compared with untreated cells (control=100%), was determined and expressed in molarity (FIG. 28).

Data showed in FIGS. 28A and 28B that hz1613F12 conjugated to either E-13 or G-13 give $IC_{50}$ values of 1.048 $10^{-10}$ M, 1.413 $10^{-10}$ M, respectively. Thus E-13 and G-13 can trigger a strong cytotocixity when coupled to an Axl antibody such as 1613F12. No cytotoxicity is observed on MCF7 cells (Axl.).

Example 26: In Vivo Activity of the Trastuzumab Antibody Conjugated to Either E-13 or G-13 Compounds in the Calu-3 Xenograft Model In order to confirm the in vivo efficacy of antibodies coupled to G-13 or E-13 compounds, they have been coupled to Trastuzumab and tested in the HER2 sensitive xenograft model Calu-3 known for its HER2 amplification and (3+) expression. The antibody Tratuzumab was purchased from Euromedex, 24 Rue des Tuileries 67460 SOUFFELWEYERSHEIM/France.

All animal procedures were performed according to the guidelines of the 2010/63/UE Directive on the protection of animals used for scientific purposes. The protocol was approved by the Animal Ethical Committee of the Pierre Fabre Institute. Seven millions Calu-3 cells were injected subcutaneous into 7 weeks old SCID mice.

Six days after Calu-3 cell implantation, when tumors reached an average size of 250-260 mm$^3$, the animals were divided into groups of 6 mice according to tumor size and aspect. The different treatments were inoculated by intraperitoneal injections. The health status of animals was monitored daily. Tumor volume was measured twice a week with an electronic calliper until study end. Tumor volume is calculated with the following formula: (length×width$^2$)/2. Toxicity was evaluated following the weight of animals three times per week. Statistical analyses were performed at each measure using a Mann-Whitney test. All compounds were injected intraperitoneally (i.p.). In this example, the anti-tumor activity of Tratuzumab mAb coupled with either E-13 or G-13 at about DAR 4 was evaluated after 1 injections of a 3 mg/kg dose at D6. In parallel Trastuzumab alone was injected at the equivalent dose of the one corresponding to 3 mg/kg of naked antibody.

Figure 29B:
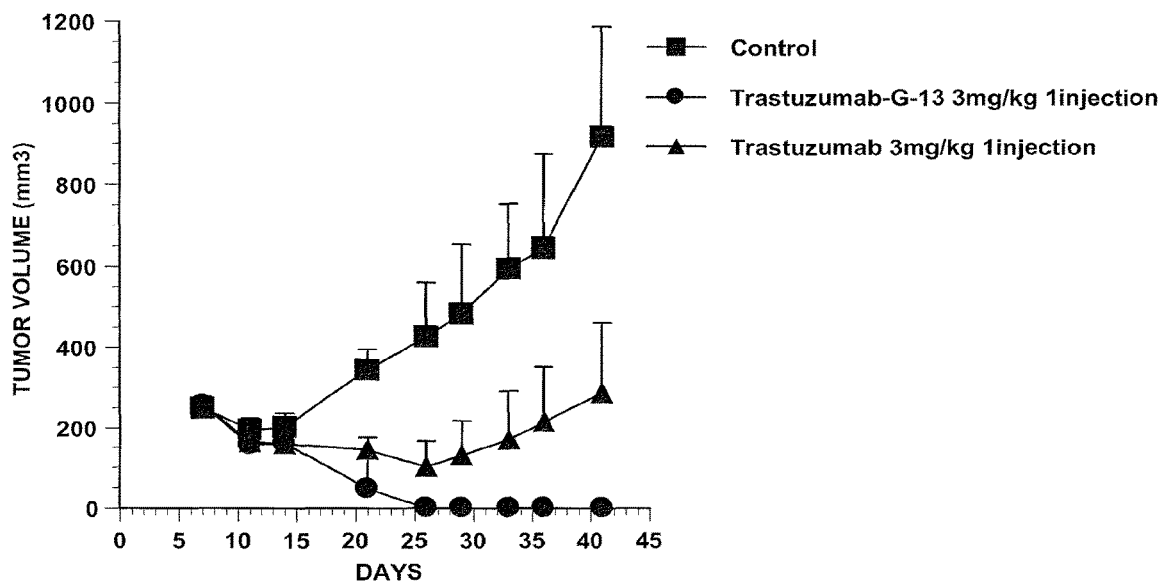

Injection of either Trastuzumab-E-13 (FIG. 29A) or Trastuzumab-G-13 (FIG. 29B) significantly inhibited the tumor growth and even induced a complete tumor growth regression in all treated mice (p<0.05 vs corresponding naked antibody). No statistical activity difference was observed between Trastuzumab-E-13, and Trastuzumab-G-13 groups. Compared to published data (Cretella et al. Molecular Cancer 2014, 13:143) on this Calu-3 model, TDM-1 did not induced complete regression even if its dosing was higher (15 mg/kg every 6 days vs 3 mg/kg, one injection respectively) than the one used for either Trastuzumab-E-13 or Trastuzumab-G-13.

Example 27: In Vivo Activity of the Trastuzumab Antibody Conjugated to Either E-13 or G-13 Compounds in the JIMT-1 Xenograft Model In order to know whether Trastuzumab antibody conjugates display also an activity on a model known to be resistant to Trastuzumab, the JIMT-1 xenograft model that highly expressed HER2 but that was resistant to Trastuzumab therapy was evaluated. All animal procedures were performed according to the guidelines of the 2010/63/UE Directive on the protection of animals used for scientific purposes. The protocol was approved by the Animal Ethical Committee of the Pierre Fabre Institute. Seven millions JIMT-1 cells were injected subcutaneous into 7 weeks old SCID mice.

Fourteen days after JIMT-1 cell implantation, when tumors reached an average size of 220-230 mm$^3$, the animals were divided into groups of 5 mice according to tumor size and aspect. The different treatments were inoculated by intraperitoneal injections. The health status of animals was monitored daily. Tumor volume was measured twice a week with an electronic calliper until study end. Tumor volume is calculated with the following formula: (length×width$^2$)/2. Toxicity was evaluated following the weight of animals three times per week. Statistical analyses were performed at each measure using a Mann-Whitney test. All compounds were injected intraperitoneally (i.p.). In this example, the anti-tumor activity of Trastuzumab mAb coupled with either E-13 or G-13 at about DAR 4 was evaluated after 1 injections of a 3 mg/kg dose at D6 (FIGS. 30A and 30B). In a first experiment, we have showed that Trastuzumab alone did not have any anti-tumoral effect (FIG. 30C). This result is in agreement with published data.

Injection of either Trastuzumab-E-13 (FIG. 30A) or Trastuzumab-G-13 (FIG. 30B) significantly inhibited the tumor growth traduced by respectively 73 and 70% of growth inhibition at day 34. No statistical activity difference could be noted between Trastuzumab-E-13, and Trastuzumab-G-13. As already observed in the Calu-3 model and compared to published data (Barok et al. Breast Cancer Research 2011, 13:R46) on this JIMT-1 model, TDM-1 seems to be less potent even if its dosing (15 mg/kg every 6 days vs 3 mg/kg, one injection respectively) was higher than the one used for either Trastuzumab-E-13 or Trastuzumab-G-13.

The invention claimed is:
1. A compound of the following formula:

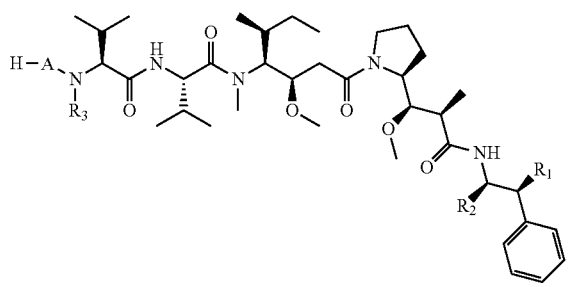

or a pharmaceutically acceptable salt thereof,
wherein:
$R_1$ is H or OH,
$R_2$ is a $(C_1-C_6)$alkyl, COOH, COO—$(C_1-C_6)$alkyl or thiazolyl group,
$R_3$ is H or a $(C_1-C_6)$alkyl group, and
A-H is:
  a group of formula Het-Alk-, wherein Alk is a $(C_1-C_8)$alkanediyl group and is linked to $NR_3$, and Het is a heterocycle optionally substituted by a $(C_1-C_6)$alkyl group and containing at least one nitrogen atom linked to a hydrogen atom, or
  a group of formula H-$A_a$-$A_b$-, wherein $A_a$ is O or $NR_9$ with $R_9$ being H or $(C_1-C_6)$alkyl, and $A_b$ is linked to $NR_3$ and is an aryl-$(C_1-C_8)$alkanediyl or heterocycle-$(C_1-C_8)$alkanediyl group, said group being optionally substituted by a $(C_1-C_6)$alkyl group, the aryl or heterocycle moiety being linked to $A_a$ and the $(C_1-C_8)$alkanediyl moiety being linked to $NR_3$.

2. The compound according to claim 1, wherein:
  $R_1$ is OH and $R_2$ represents a $(C_1-C_6)$alkyl group, or
  $R_1$ is H and $R_2$ represents a COOH, COO—$(C_1-C_6)$alkyl or thiazolyl group.

3. The compound according to claim 1, wherein $R_1$ represents H and $R_2$ represents COOH or COOMe.

4. The compound according to claim 1, wherein $R_3$ represents H or a methyl group.

5. The compound according to claim 1, wherein A-H is:
  a group of formula Het-Alk-, wherein Alk is a $(C_1-C_2)$ alkanediyl group and is linked to $NR_3$, and Het is a heterocycle optionally substituted by a $(C_1-C_6)$alkyl group and containing at least one nitrogen atom linked to a hydrogen atom, or
  a group of formula H-$A_a$-$A_b$-, wherein $A_a$ is O or $NR_9$ with $R_9$ being H or $(C_1-C_6)$alkyl, and $A_b$ is linked to $NR_3$ and is an aryl-$(C_1-C_2)$alkanediyl or heterocycle-$(C_1-C_2)$alkanediyl group, said group being optionally substituted by a $(C_1-C_6)$alkyl group, the aryl or heterocycle moiety being linked to $A_a$ and the $(C_1-C_2)$alkanediyl moiety being linked to $NR_3$.

6. The compound according to claim 1, wherein A-H is a group of formula H-$A_a$-$A_b$- in which $A_a$ is as defined in claim 1, and $A_b$ is a group:
  phenyl-$(C_1-C_2)$alkanediyl, or
  heterocycle-$(C_1-C_2)$alkanediyl optionally substituted by a $(C_1-C_6)$alkyl group, the heterocycle being chosen from among pyridine, piperidine and imidazole.

7. The compound according to claim 1, wherein the compound is selected from the group consisting of:

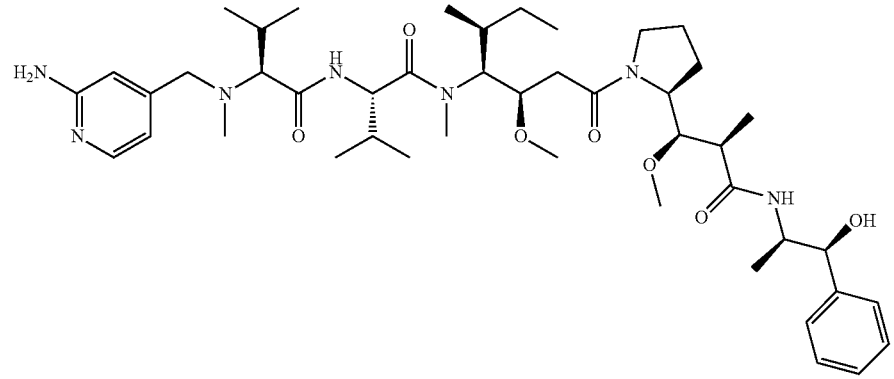 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)Cc1ccnc(N)c1)C(C)C]

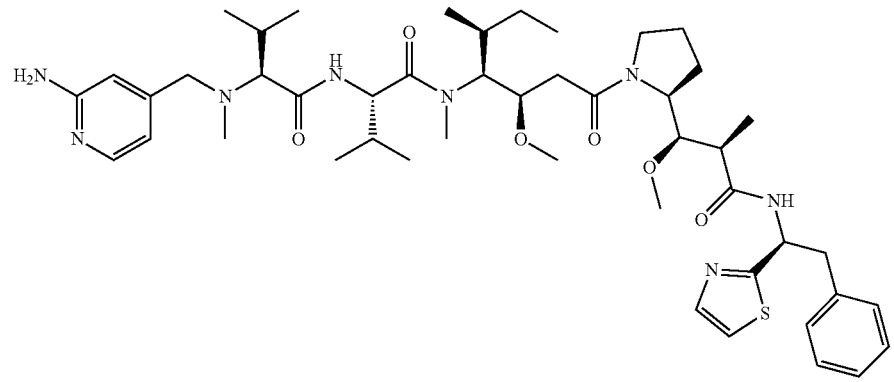

-continued
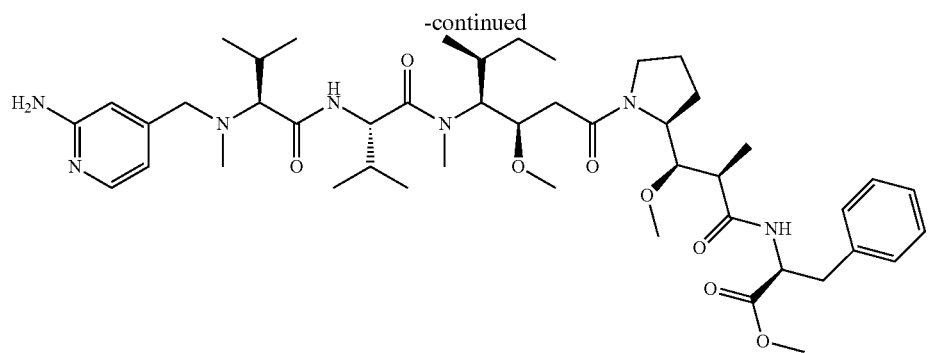
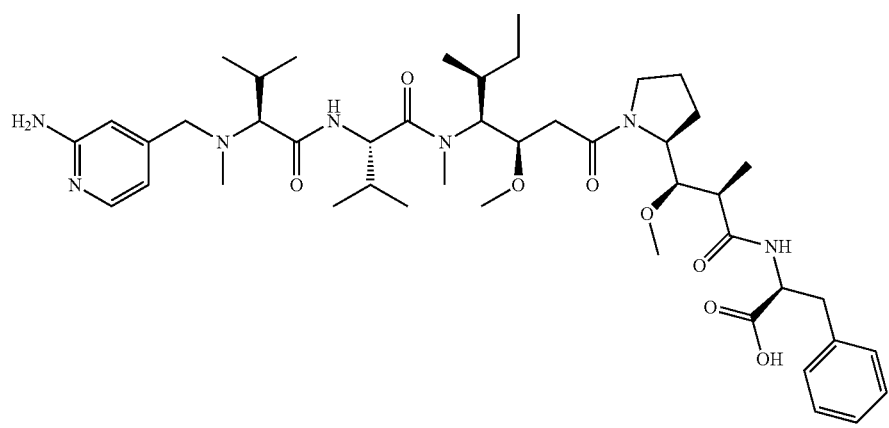
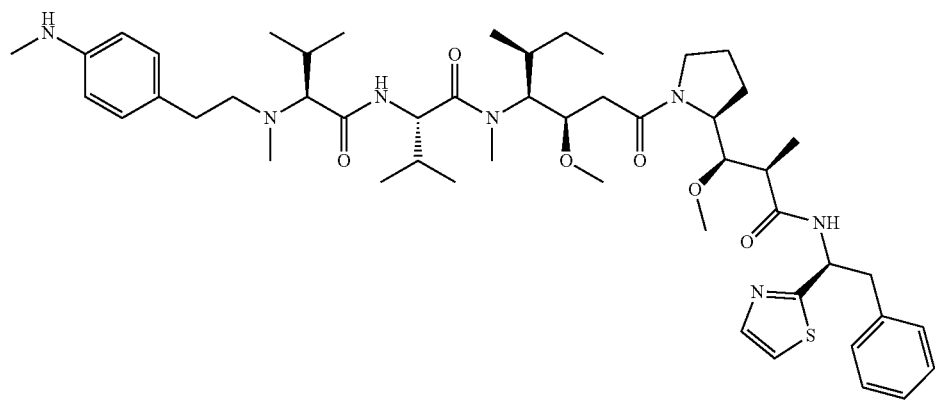
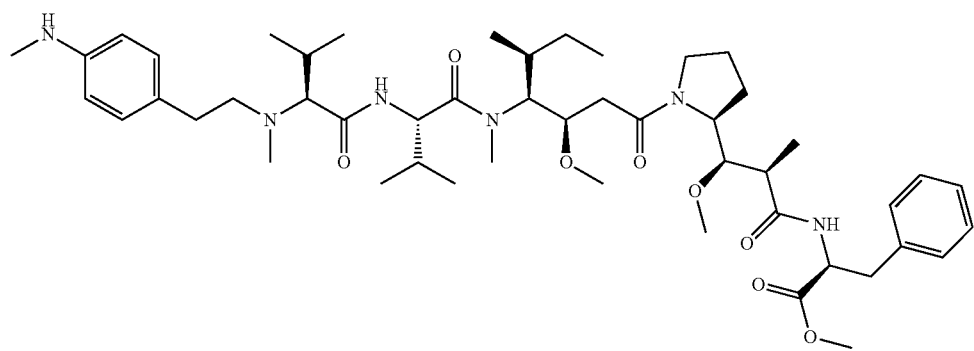

-continued
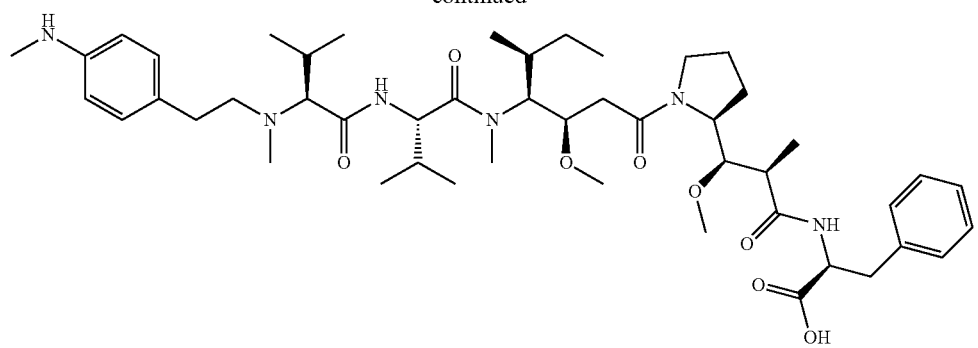
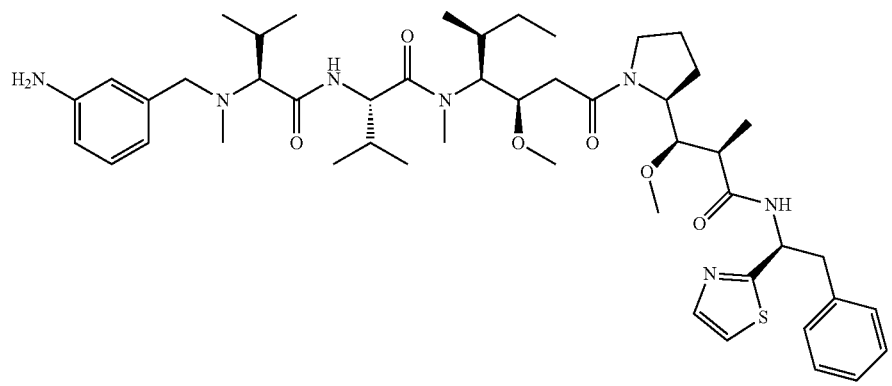
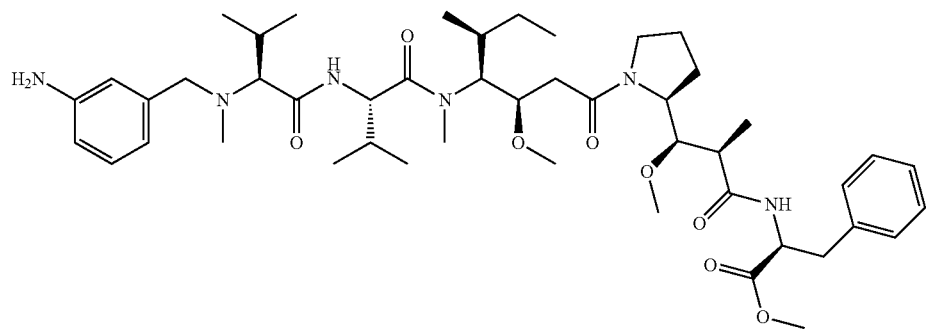
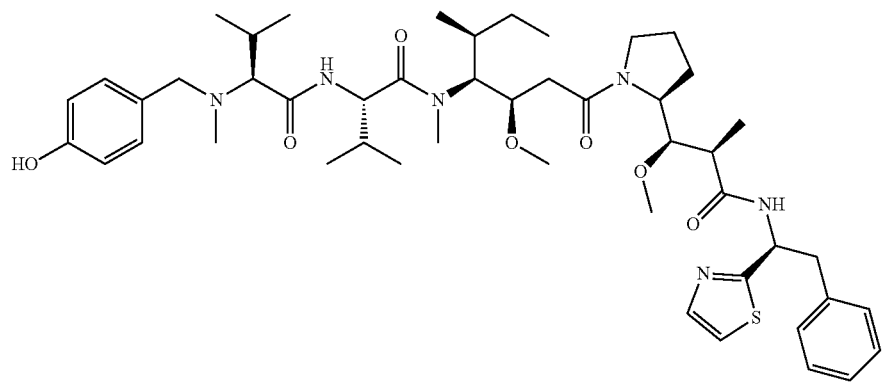 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)Cc1ccc(O)cc1)C(C)C]

-continued
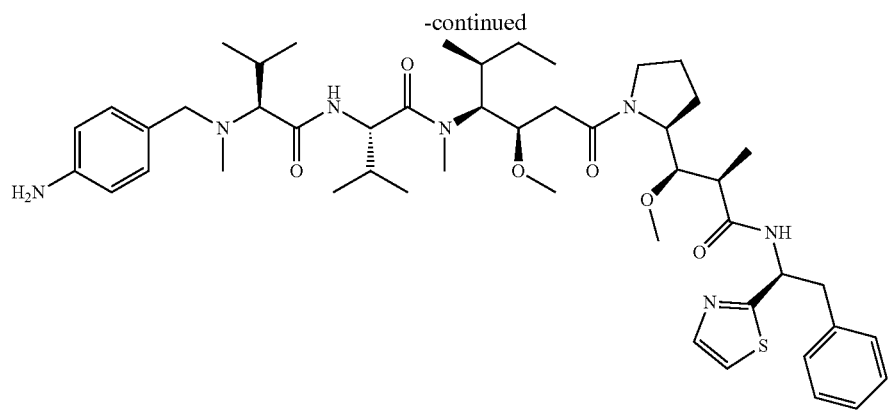
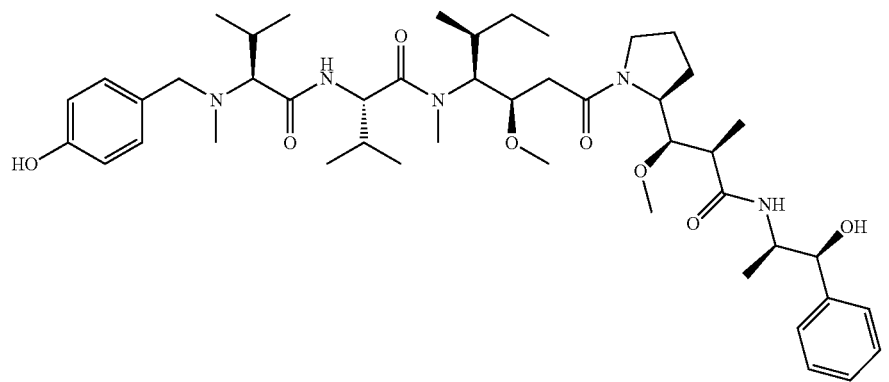
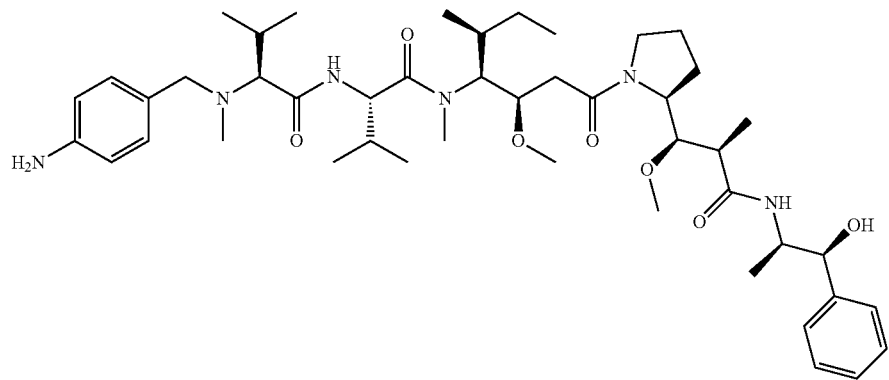
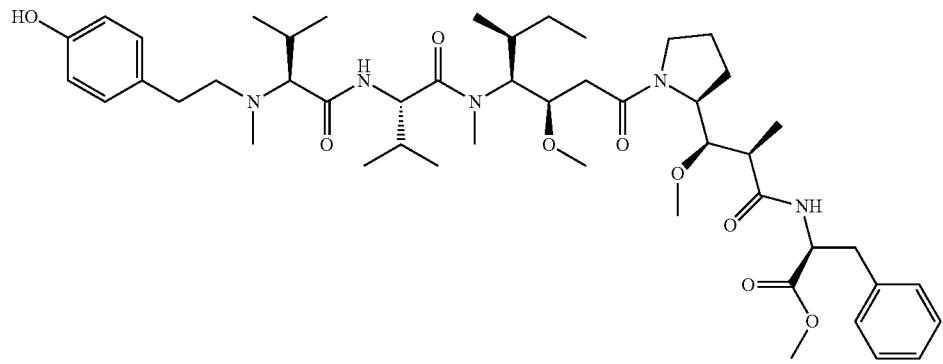

-continued
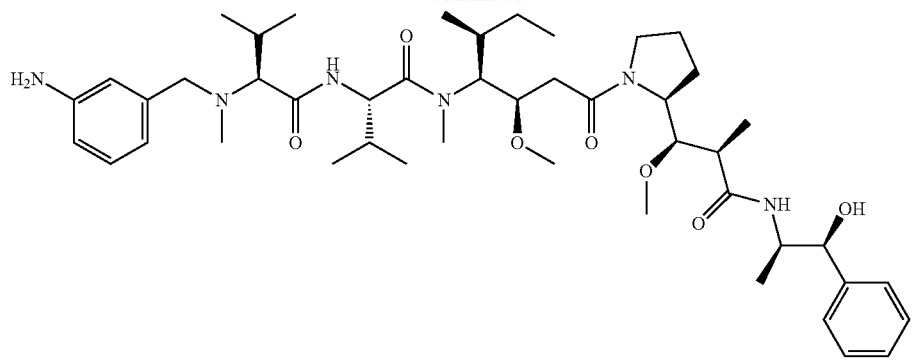
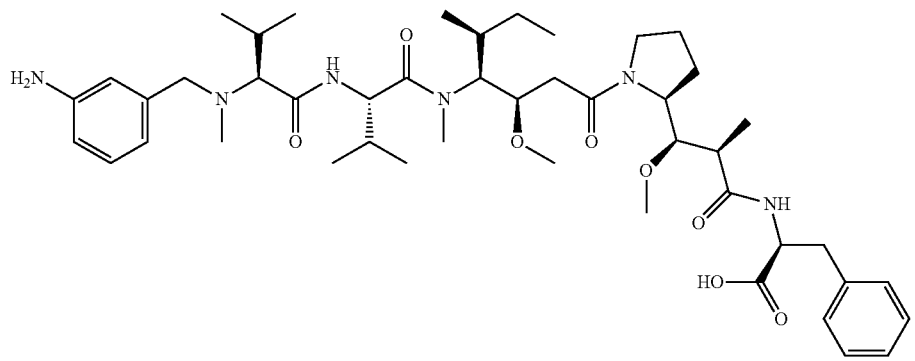 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)Cc1cccc(N)c1)C(C)C]
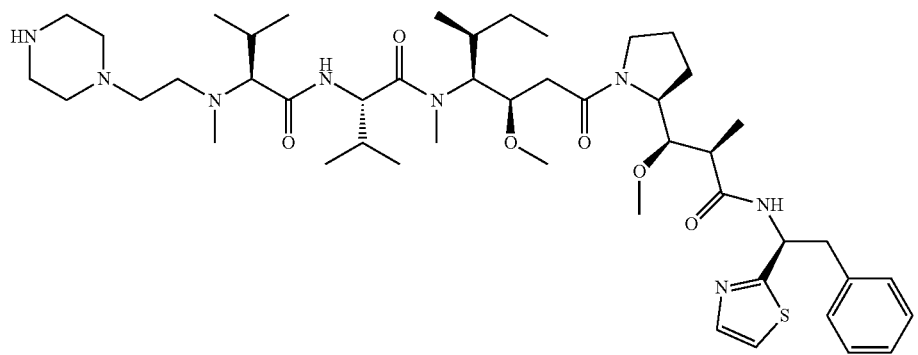
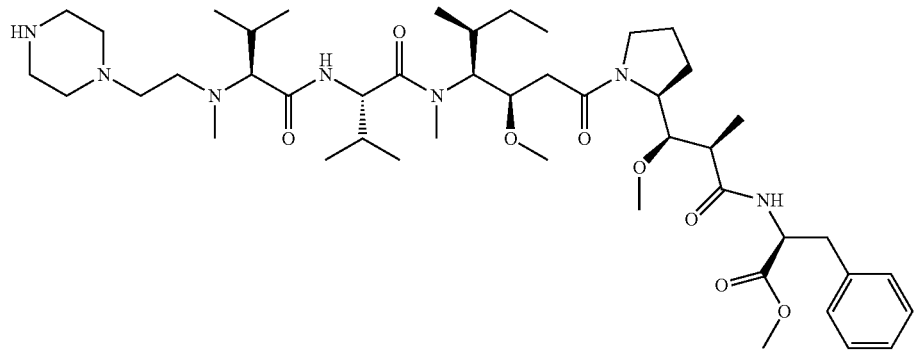

461
-continued
462
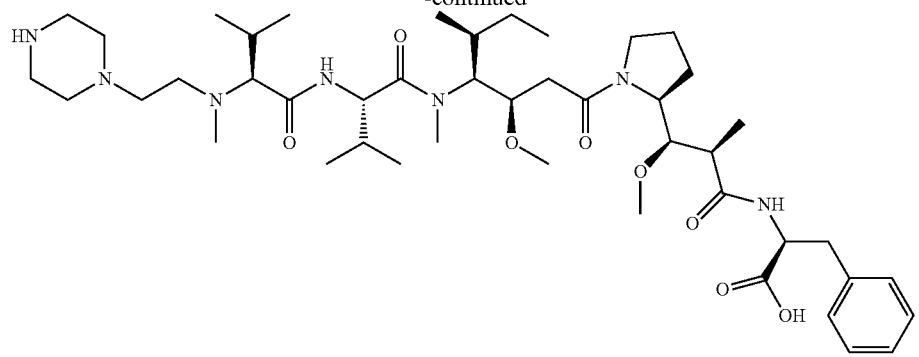
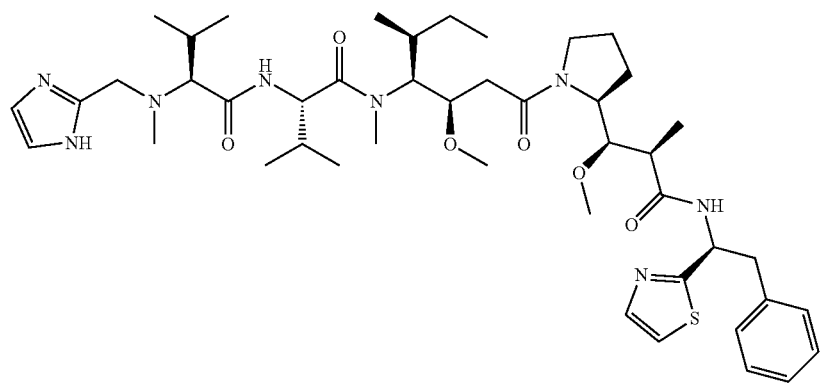
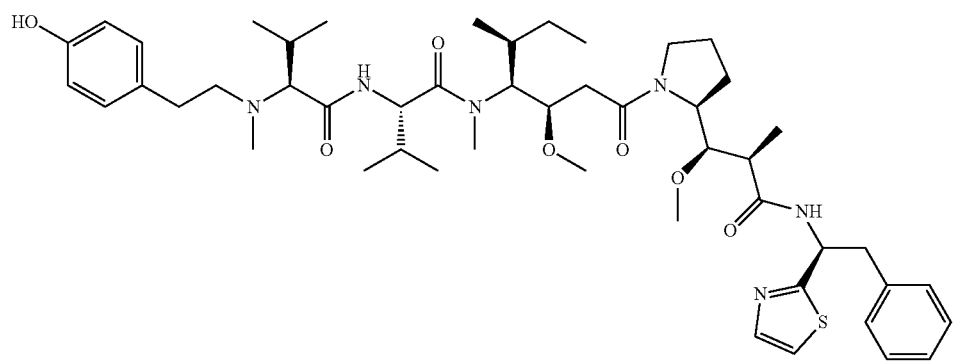
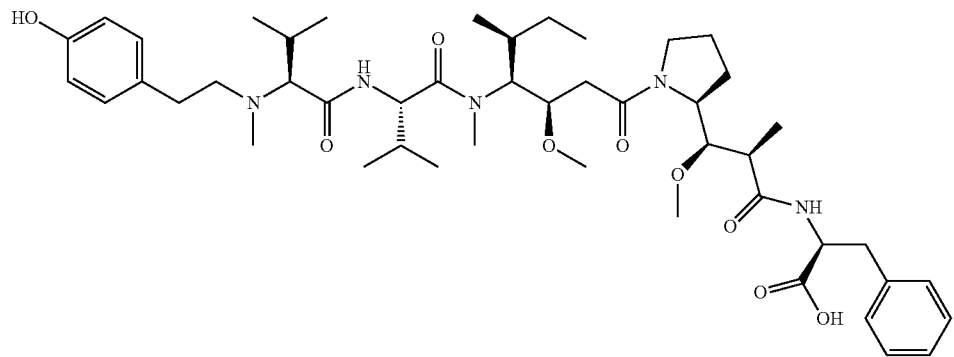

-continued
463
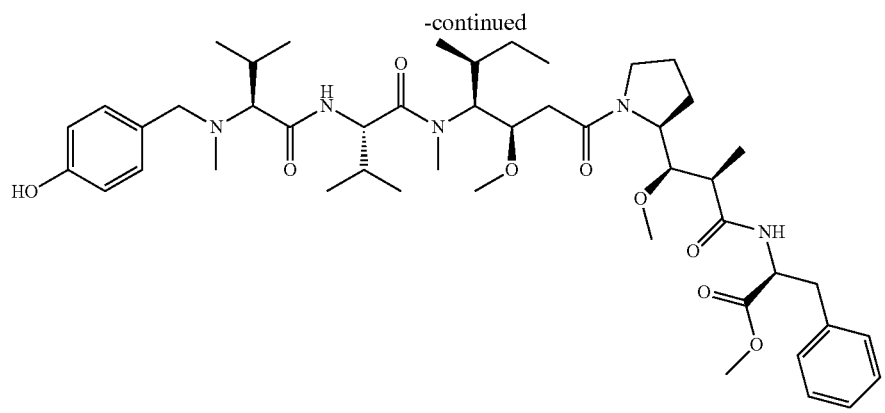
464
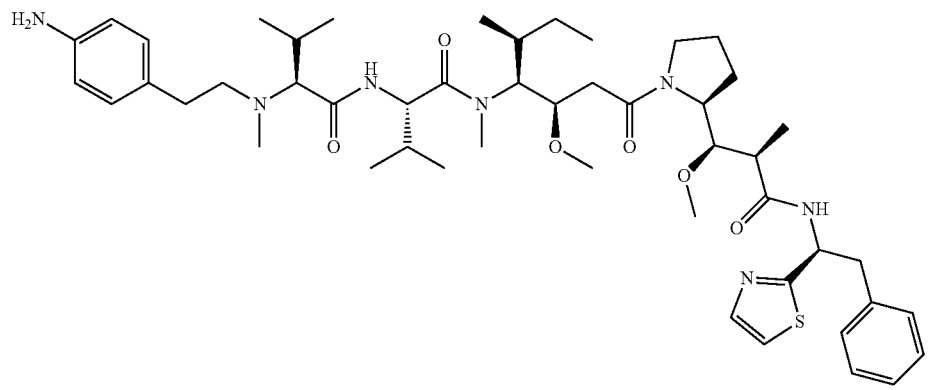
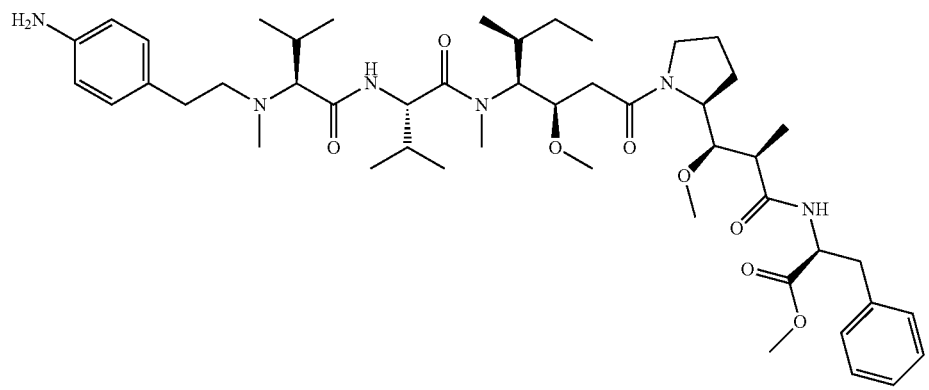
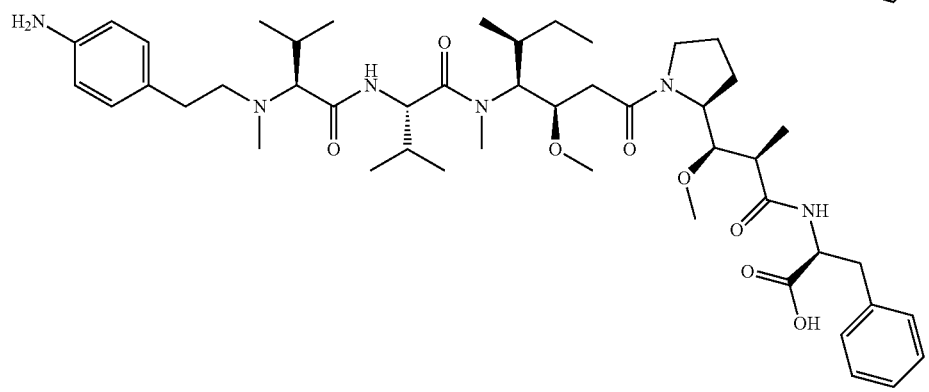

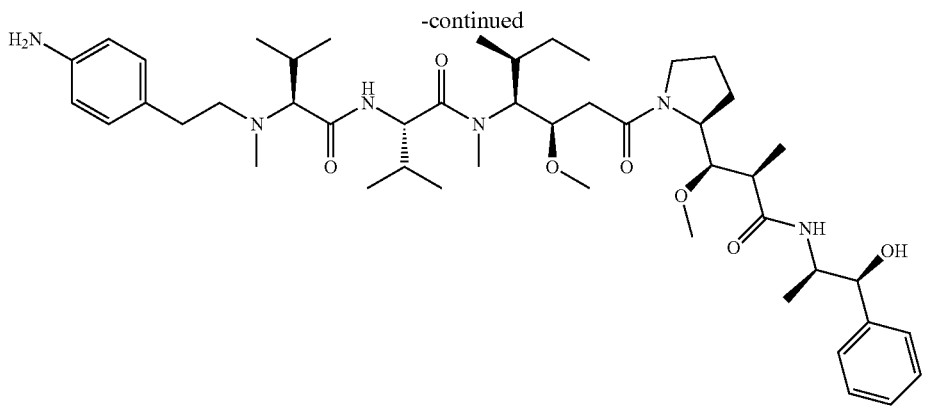

and the pharmaceutically acceptable salts thereof.

8. The compound according to claim 7, wherein the pharmaceutically acceptable salts are salts formed with trifluoroacetic acid.

9. A compound of the following formula:

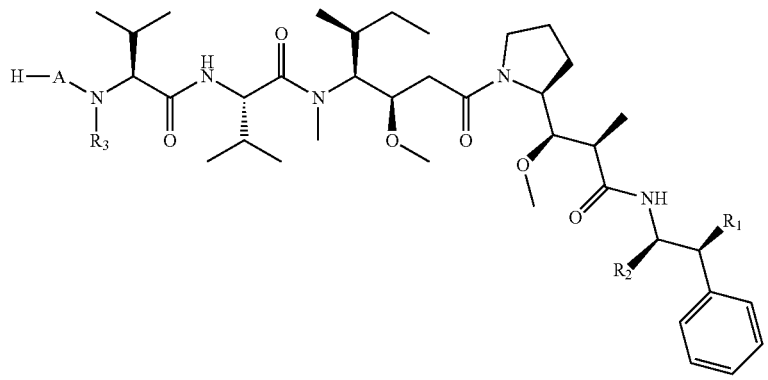

or a pharmaceutically acceptable salt thereof,
wherein:
$R_1$ is H or OH,
$R_2$ is a ($C_1$-$C_6$)alkyl, COOH, COO—($C_1$-$C_6$)alkyl or thiazolyl group,
$R_3$ is H or a ($C_1$-$C_6$)alkyl group, and
A-H is a group of formula H-$A_a$-$A_b$-, wherein $A_a$ is O or $NR_9$ with $R_9$ being H or ($C_1$-$C_6$)alkyl, and $A_b$ is linked to $NR_3$ and is an aryl-($C_1$-$C_8$)alkanediyl group optionally substituted by a ($C_1$-$C_6$)alkyl group, the aryl moiety being linked to $A_a$ and the ($C_1$-$C_8$) alkanediyl moiety being linked to $NR_3$.

10. The compound according to claim 9, wherein:
$R_1$ is OH and $R_2$ represents a ($C_1$-$C_6$)alkyl group, or
$R_1$ is H and $R_2$ represents a COOH, COO—($C_1$-$C_6$)alkyl or thiazolyl group.

11. The compound according to claim 9, wherein $R_1$ represents H and $R_2$ represents COOH or COOMe.

12. The compound according to claim 9, wherein $R_3$ represents H or a methyl group.

13. The compound according to claim 9, wherein A-H is a group of formula H-$A_a$-$A_b$- in which $A_a$ is as defined in claim 9 and $A_b$ is a phenyl-($C_1$-$C_2$)alkanediyl group.

14. The compound according to claim 9, wherein A-H is a group of the following formula:

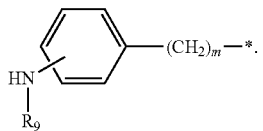

wherein:
$R_9$ is H or ($C_1$-$C_6$)alkyl,
m is an integer between 1 and 8, and
\* is the point of attachment to $NR_3$.

15. The compound according to claim 14, wherein $R_9$ is H or methyl (Me) and m is 1 or 2.

16. The compound according to claim 9, wherein the compound 1s selected from the group consisting of:

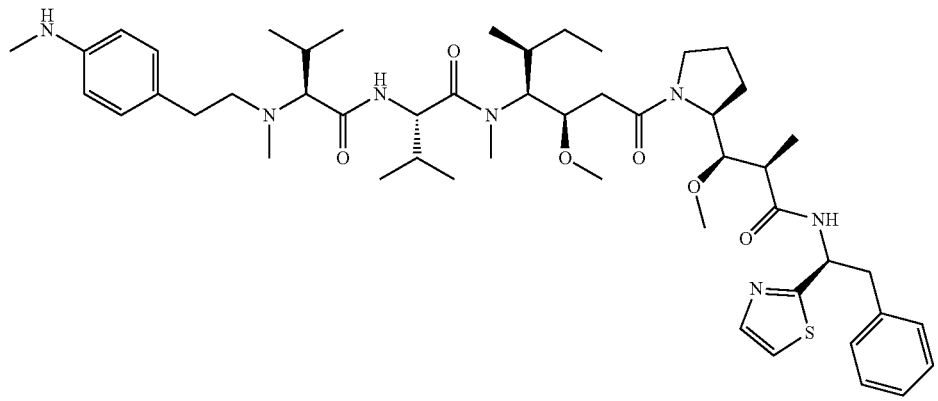 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCc1ccc(NC)cc1)C(C)C]
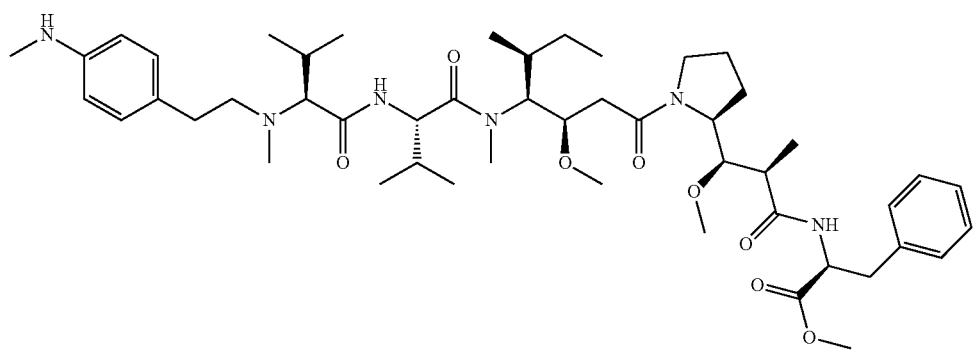
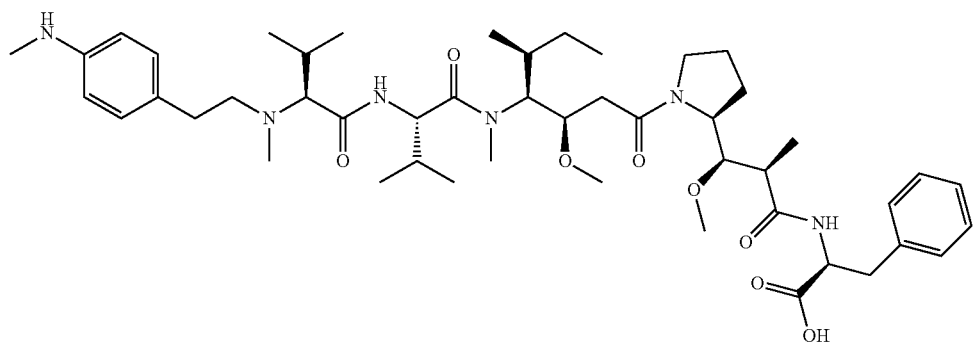
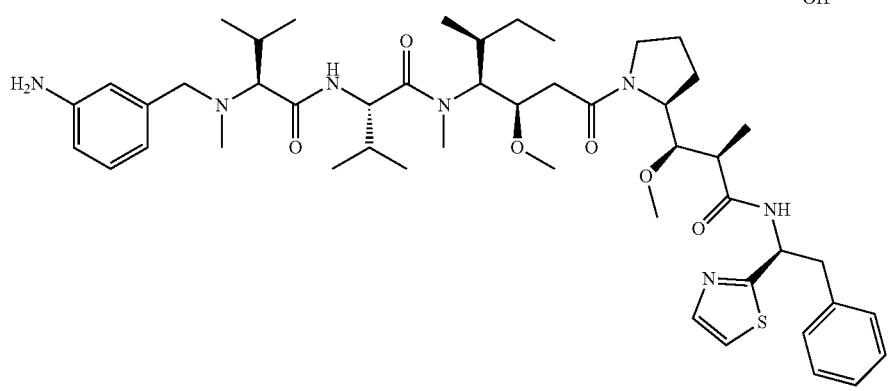

-continued
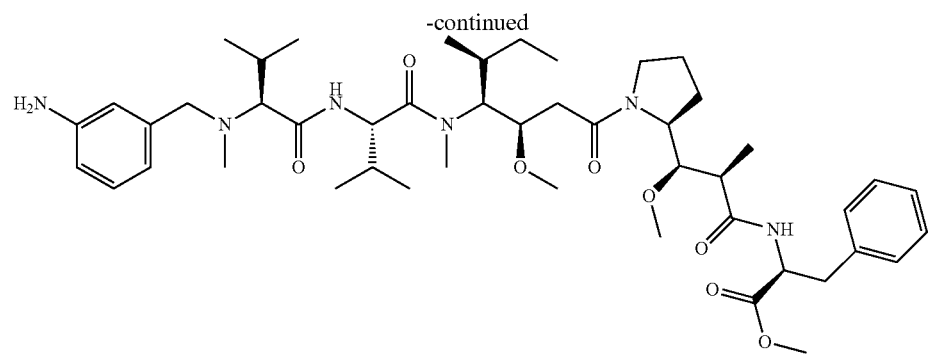
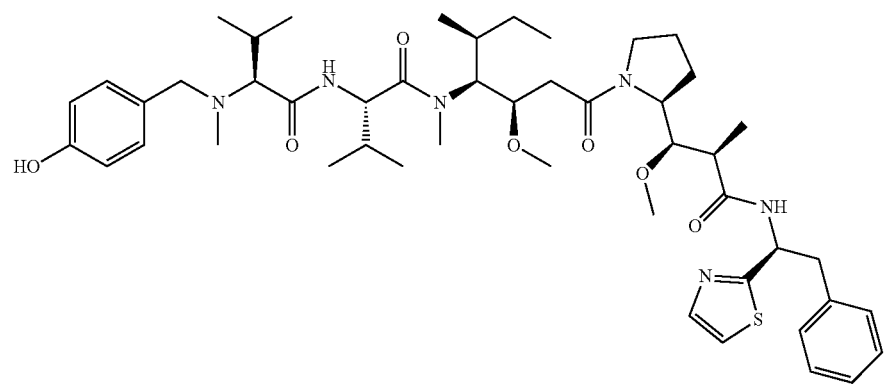
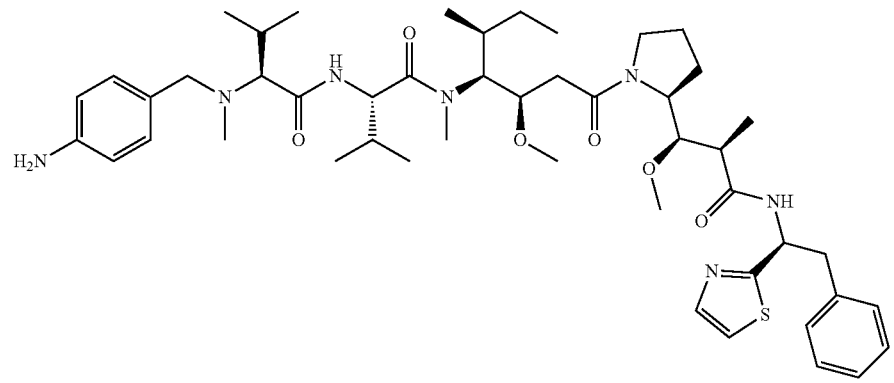
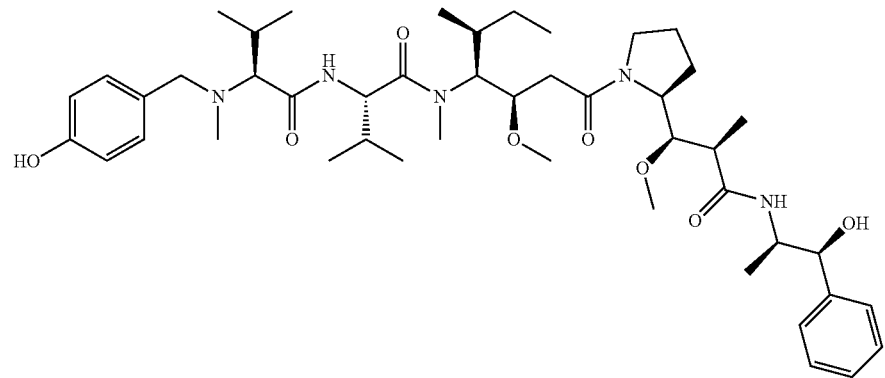

-continued
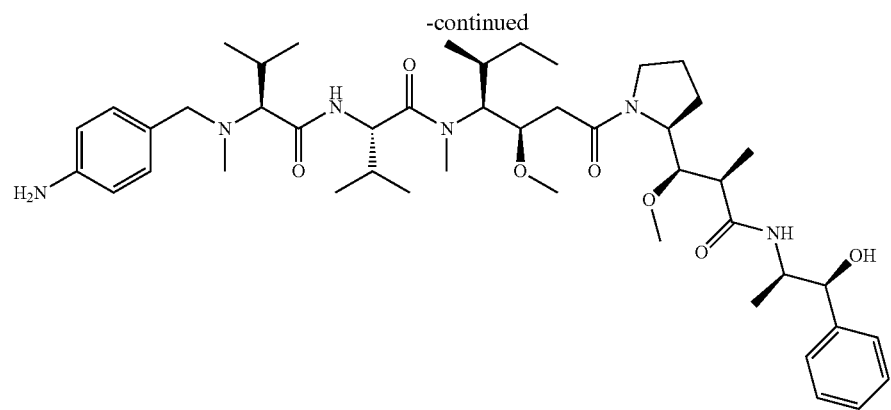
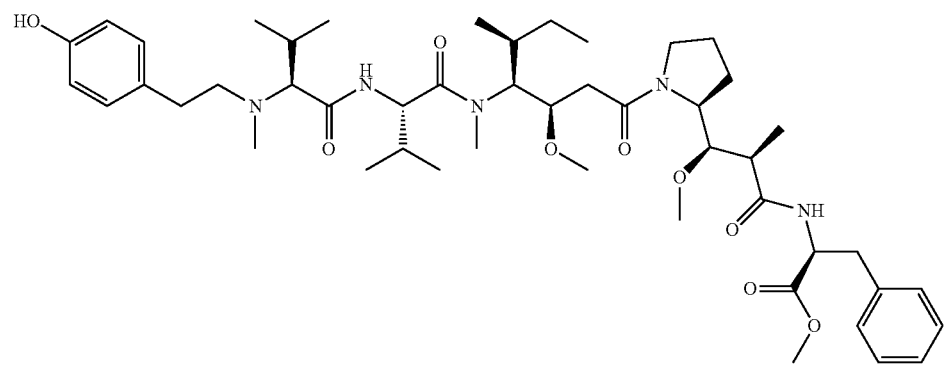
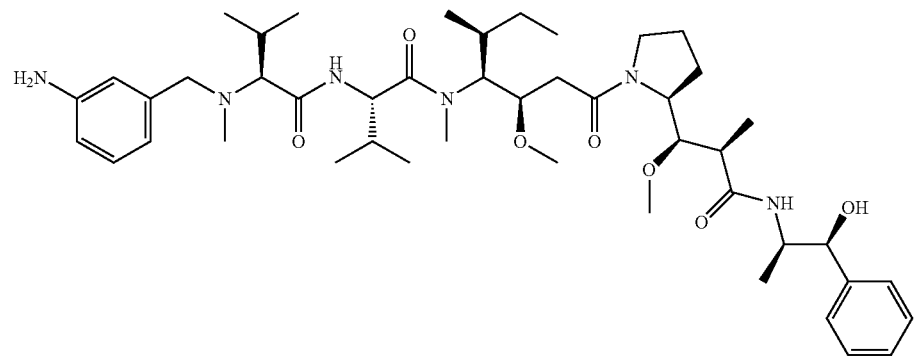
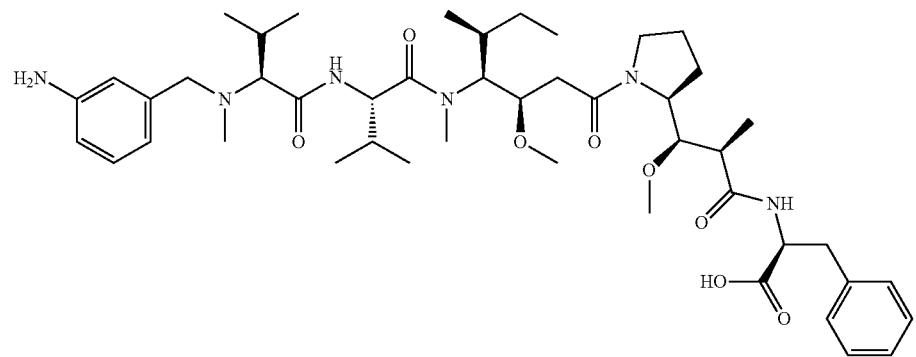

-continued
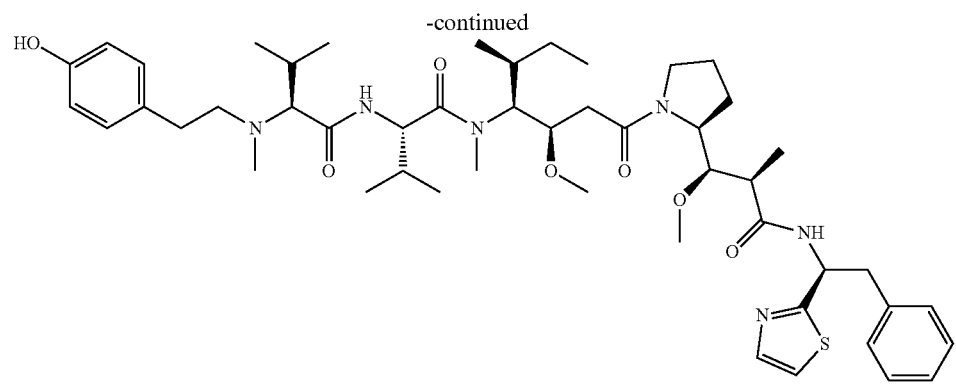
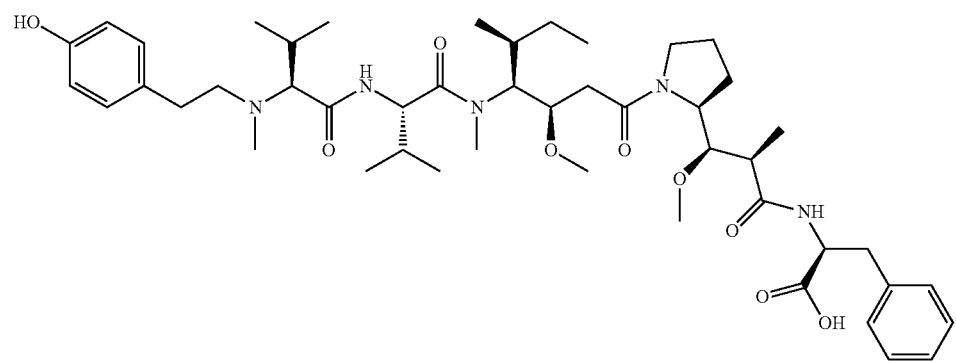
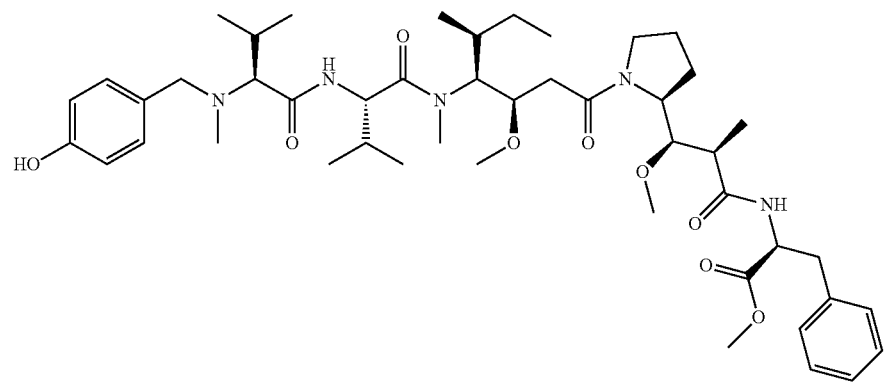
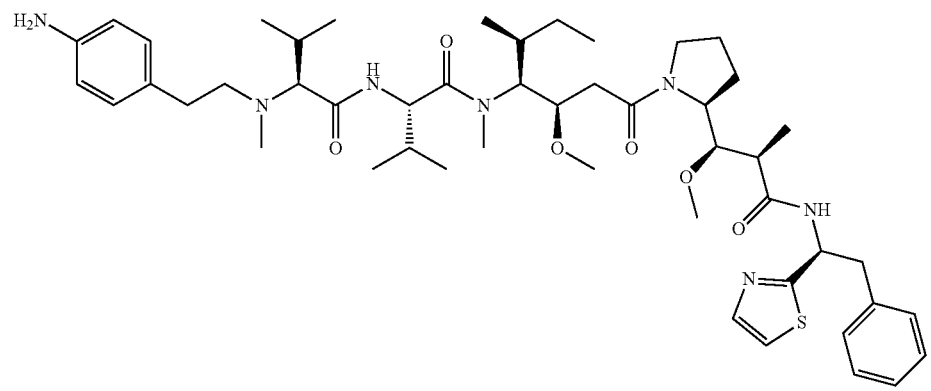

-continued
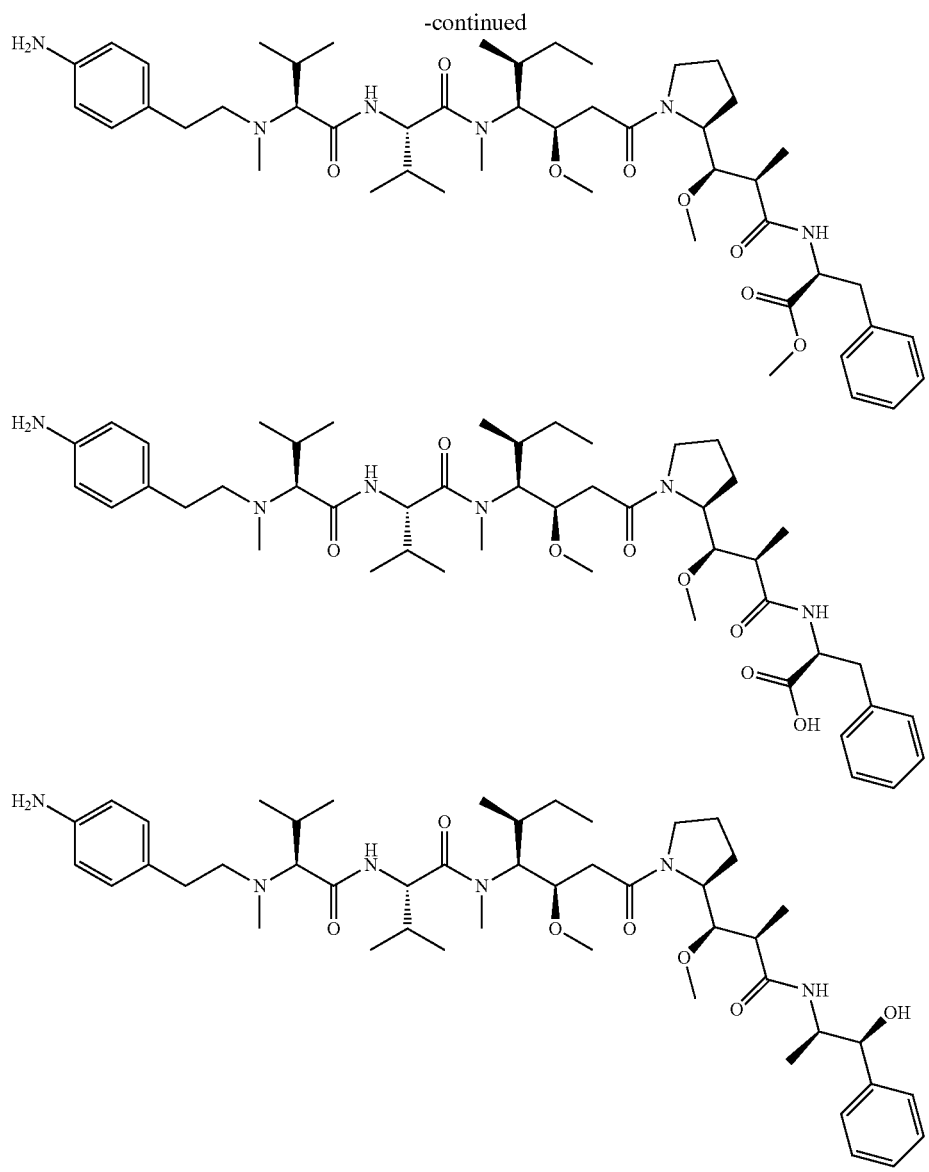
and the pharmaceutically acceptable salts thereof.
17. The compound according to claim 16, wherein the pharmaceutically acceptable salts are salts formed with trifluoroacetic acid.
* * * * *

SEQUENCE LISTING

```
<160> NUMBER OF SEQ ID NOS: 106

<210> SEQ ID NO 1
<211> LENGTH: 8
<212> TYPE: PRT
<213> ORGANISM: Artificial Sequence
<220> FEATURE:
<223> OTHER INFORMATION: Consensus CDR -H1
<220> FEATURE:
<221> NAME/KEY: MISC_FEATURE
<222> LOCATION: (3)..(3)
<223> OTHER INFORMATION: Xaa is Thr or Ser
<220> FEATURE:
<221> NAME/KEY: MISC_FEATURE
<222> LOCATION: (8)..(8)
<223> OTHER INFORMATION: Xaa is Tyr or Phe

<400> SEQUENCE: 1

Gly Tyr Xaa Phe Thr Ser Tyr Xaa
1               5
```

```
<210> SEQ ID NO 2
<211> LENGTH: 8
<212> TYPE: PRT
<213> ORGANISM: Artificial Sequence
<220> FEATURE:
<223> OTHER INFORMATION: Consensus CDR-H2

<400> SEQUENCE: 2

Ile Trp Pro Gly Asp Gly Ser Thr
1               5

<210> SEQ ID NO 3
<211> LENGTH: 13
<212> TYPE: PRT
<213> ORGANISM: Artificial Sequence
<220> FEATURE:
<223> OTHER INFORMATION: Consensus CDR-H3

<400> SEQUENCE: 3

Ala Ser Pro Met Ile Thr Pro Asn Tyr Ala Met Asp Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Consensus CDR-L1
<220> FEATURE:
<221> NAME/KEY: MISC_FEATURE
<222> LOCATION: (4)..(4)
<223> OTHER INFORMATION: Xaa is Ser or Asn

<400> SEQUENCE: 4

Gln Asp Ile Xaa Lys Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Consensus CDR-L2

<400> SEQUENCE: 5

Tyr Thr Ser
1

<210> SEQ ID NO 6
<211> LENGTH: 9
<212> TYPE: PRT
<213> ORGANISM: Artificial Sequence
<220> FEATURE:
<223> OTHER INFORMATION: Consensus CDR-L3
<220> FEATURE:
<221> NAME/KEY: MISC_FEATURE
<222> LOCATION: (5)..(5)
<223> OTHER INFORMATION: Xaa is Thr or Ala

<400> SEQUENCE: 6

Gln Gln Gly Ser Xaa Leu Pro Tyr Thr
1               5

<210> SEQ ID NO 7
<211> LENGTH: 8
<212> TYPE: PRT
<213> ORGANISM: Artificial Sequence
```

```
<220> FEATURE:
<223> OTHER INFORMATION: CDR-H1

<400> SEQUENCE: 7

Gly Tyr Thr Phe Thr Ser Tyr Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: CDR-H1

<400> SEQUENCE: 8

Gly Tyr Ser Phe Thr Ser Tyr Phe
1               5

<210> SEQ ID NO 9
<211> LENGTH: 6
<212> TYPE: PRT
<213> ORGANISM: Artificial Sequence
<220> FEATURE:
<223> OTHER INFORMATION: CDR-L1

<400> SEQUENCE: 9

Gln Asp Ile Ser Lys Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: CDR-L1

<400> SEQUENCE: 10

Gln Asp Ile Asn Lys Tyr
1               5

<210> SEQ ID NO 11
<211> LENGTH: 9
<212> TYPE: PRT
<213> ORGANISM: Artificial Sequence
<220> FEATURE:
<223> OTHER INFORMATION: CDR-L3

<400> SEQUENCE: 11

Gln Gln Gly Ser Thr Leu Pro Tyr Thr
1               5

<210> SEQ ID NO 12
<211> LENGTH: 9
<212> TYPE: PRT
<213> ORGANISM: Artificial Sequence
<220> FEATURE:
<223> OTHER INFORMATION: CDR-L3

<400> SEQUENCE: 12

Gln Gln Gly Ser Ala Leu Pro Tyr Thr
1               5

<210> SEQ ID NO 13
<211> LENGTH: 120
<212> TYPE: PRT
<213> ORGANISM: Artificial Sequence
<220> FEATURE:
```

<223> OTHER INFORMATION: c208F2, heavy chain, VH

<400> SEQUENCE: 13

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Lys Asp Lys Thr Thr Leu Thr Ala Asp Lys Ser Ser Asn Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120

<210> SEQ ID NO 14
<211> LENGTH: 120
<212> TYPE: PRT
<213> ORGANISM: Artificial Sequence
<220> FEATURE:
<223> OTHER INFORMATION: c212A11, heavy chain, VH

<400> SEQUENCE: 14

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: c214F8, heavy chain, VH

<400> SEQUENCE: 15

Gln Val Gln Leu Gln Gln Ser Gly Ser Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile

```
                35                  40                  45
Gly Trp Ile Trp Pro Gly Asp Gly Ser Thr Lys Tyr Asn Glu Arg Phe
 50                  55                  60
Lys Gly Lys Thr Thr Leu Thr Ala Asp Lys Ser Ser Ser Thr Ala Tyr
 65                  70                  75                  80
Met Phe Leu Ser Ser Leu Thr Ser Glu Asp Ser Ala Val Tyr Phe Cys
                 85                  90                  95
Ala Ser Pro Met Ile Thr Pro Asn Tyr Ala Met Asp Tyr Trp Gly Gln
            100                 105                 110
Gly Ala Ser Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: c219D6, heavy chain, VH

<400> SEQUENCE: 16

Gln Val Gln Leu Gln Gln Ser Gly Pro Glu Leu Val Lys Pro Gly Asp
 1               5                  10                  15
Ser Val Lys Met Ser Cys Lys Ala Ser Gly Tyr Ser Phe Thr Ser Tyr
             20                  25                  30
Phe Ile His Trp Val Lys Gln Arg Pro Gly Gln Gly Leu Glu Trp Ile
         35                  40                  45
Gly Trp Ile Trp Pro Gly Asp Gly Ser Thr Lys Tyr Asn Glu Lys Phe
 50                  55                  60
Lys Gly Lys Thr Thr Leu Thr Thr Asp Lys Ser Ser Ser Thr Ala Tyr
 65                  70                  75                  80
Met Phe Leu Asn Ser Leu Thr Ser Glu Asp Ser Ala Val Tyr Phe Cys
                 85                  90                  95
Ala Ser Pro Met Ile Thr Pro Asn Tyr Ala Met Asp Tyr Trp Gly Gln
            100                 105                 110
Gly Ala Ser Val Thr Val Ser Ser
        115                 120

<210> SEQ ID NO 17
<211> LENGTH: 120
<212> TYPE: PRT
<213> ORGANISM: Artificial Sequence
<220> FEATURE:
<223> OTHER INFORMATION: c213B10, heavy chain, VH

<400> SEQUENCE: 17

Gln Val Gln Leu Gln Gln Ser Gly Ser Glu Leu Val Lys Pro Gly Ala
 1               5                  10                  15
Ser Val Lys Met Ser Cys Lys Ala Ser Gly Tyr Thr Phe Thr Ser Tyr
             20                  25                  30
Tyr Ile His Trp Val Lys Gln Arg Pro Gly Gln Gly Leu Glu Trp Ile
         35                  40                  45
Gly Trp Ile Trp Pro Gly Asp Gly Ser Thr Lys Tyr Asn Glu Arg Phe
 50                  55                  60
Lys Gly Lys Thr Thr Leu Thr Ala Asp Lys Ser Ser Ser Thr Ala Tyr
 65                  70                  75                  80
Met Phe Leu Ser Ser Leu Thr Ser Glu Asp Ser Ala Val Tyr Phe Cys
                 85                  90                  95
```

```
Ala Ser Pro Met Ile Thr Pro Asn Tyr Ala Met Asp Tyr Trp Gly Gln
            100                 105                 110

Gly Ala Ser Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: c208F2, light chain, VL

<400> SEQUENCE: 18

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Val Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: c212A11, light chain, VL

<400> SEQUENCE: 19

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: c214F8, light chain, VL

<400> SEQUENCE: 20

Asp Ile Gln Met Thr Gln Thr Thr Ser Ser Leu Ser Ala Ser Leu Gly
```

```
                1               5                   10                  15
Asp Arg Val Thr Phe Ser Cys Arg Ala Ser Gln Asp Ile Ser Lys Tyr
                20                  25                  30

Leu Asn Trp Tyr Gln Gln Gln Pro Asp Gly Thr Ile Lys Leu Leu Ile
            35                  40                  45

Tyr Tyr Thr Ser Arg Leu His Ser Gly Val Pro Ser Arg Phe Ser Gly
        50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys
                100                 105

<210> SEQ ID NO 21
<211> LENGTH: 107
<212> TYPE: PRT
<213> ORGANISM: Artificial Sequence
<220> FEATURE:
<223> OTHER INFORMATION: c219D6, light chain, VL

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Gln Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
                100                 105

<210> SEQ ID NO 22
<211> LENGTH: 107
<212> TYPE: PRT
<213> ORGANISM: Artificial Sequence
<220> FEATURE:
<223> OTHER INFORMATION: c213B10, light chain, VL

<400> SEQUENCE: 22

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Gln Pro Asp Gly Thr Ile Lys Leu Leu Ile
            35                  40                  45

Tyr Tyr Thr Ser Arg Leu His Ser Gly Val Pro Ser Arg Phe Ser Gly
        50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95
```

Thr Phe Gly Gly Gly Thr Lys Leu Glu Ile Lys
            100                 105

<210> SEQ ID NO 23
<211> LENGTH: 449
<212> TYPE: PRT
<213> ORGANISM: Artificial Sequence
<220> FEATURE:
<223> OTHER INFORMATION: c208F2, heavy chain, full length

<400> SEQUENCE: 23

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Lys Asp Lys Thr Thr Leu Thr Ala Asp Lys Ser Ser Asn Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 24
<211> LENGTH: 449
<212> TYPE: PRT
<213> ORGANISM: Artificial Sequence
<220> FEATURE:
<223> OTHER INFORMATION: c212A11, heavy chain, full length

<400> SEQUENCE: 24

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Lys Phe
50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu

```
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 25
<211> LENGTH: 449
<212> TYPE: PRT
<213> ORGANISM: Artificial Sequence
<220> FEATURE:
<223> OTHER INFORMATION: c214F8, heavy chain, full length

<400> SEQUENCE: 25

Gln Val Gln Leu Gln Gln Ser Gly Ser Glu Leu Val Lys Pro Gly Ala
1               5                   10                  15
Ser Val Lys Leu Ser Cys Lys Ala Ser Gly Tyr Thr Phe Thr Ser Tyr
            20                  25                  30
Tyr Ile His Trp Val Lys Gln Arg Pro Gly Gln Gly Leu Glu Trp Ile
        35                  40                  45
Gly Trp Ile Trp Pro Gly Asp Gly Ser Thr Lys Tyr Asn Glu Arg Phe
    50                  55                  60
Lys Gly Lys Thr Thr Leu Thr Ala Asp Lys Ser Ser Ser Thr Ala Tyr
65                  70                  75                  80
Met Phe Leu Ser Ser Leu Thr Ser Glu Asp Ser Ala Val Tyr Phe Cys
                85                  90                  95
Ala Ser Pro Met Ile Thr Pro Asn Tyr Ala Met Asp Tyr Trp Gly Gln
            100                 105                 110
Gly Ala Ser Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Thr Val Pro
                180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 26
<211> LENGTH: 449
<212> TYPE: PRT
<213> ORGANISM: Artificial Sequence
<220> FEATURE:
<223> OTHER INFORMATION: c219D6, heavy chain, full length

<400> SEQUENCE: 26

Gln Val Gln Leu Gln Gln Ser Gly Pro Glu Leu Val Lys Pro Gly Asp
1               5                   10                  15

Ser Val Lys Met Ser Cys Lys Ala Ser Gly Tyr Ser Phe Thr Ser Tyr
                20                  25                  30

Phe Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Lys Phe
        50                  55                  60

Lys Gly Lys Thr Thr Leu Thr Thr Asp Lys Ser Ser Ser Thr Ala Tyr
65                  70                  75                  80
```

```
Met Phe Leu Asn Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 27
<211> LENGTH: 449
<212> TYPE: PRT
<213> ORGANISM: Artificial Sequence
<220> FEATURE:
<223> OTHER INFORMATION: c213B10, heavy chain, full length
```

-continued

```
<400> SEQUENCE: 27

Gln Val Gln Leu Gln Gln Ser Gly Ser Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Arg Phe
    50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 28
<211> LENGTH: 214
<212> TYPE: PRT
<213> ORGANISM: Artificial Sequence
<220> FEATURE:
<223> OTHER INFORMATION: c208F2, light chain, full length

<400> SEQUENCE: 28

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Val Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 214
<212> TYPE: PRT
<213> ORGANISM: Artificial Sequence
<220> FEATURE:
<223> OTHER INFORMATION: c212A11, light chain, full length

<400> SEQUENCE: 29

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Lys Tyr
            20                  25                  30

Leu Asn Trp Tyr Gln Gln Pro Asp Gly Thr Val Lys Leu Leu Ile
        35                  40                  45
```

Tyr Tyr Thr Ser Arg Leu His Ser Gly Val Pro Ser Arg Phe Ser Gly
 50                  55                  60

Arg Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Ser Thr Leu Pro Tyr
                 85                  90                  95

Thr Phe Gly Gly Gly Thr Lys Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 214
<212> TYPE: PRT
<213> ORGANISM: Artificial Sequence
<220> FEATURE:
<223> OTHER INFORMATION: c214F8, light chain, full length

<400> SEQUENCE: 30

Asp Ile Gln Met Thr Gln Thr Thr Ser Ser Leu Ser Ala Ser Leu Gly
 1               5                  10                  15

Asp Arg Val Thr Phe Ser Cys Arg Ala Ser Gln Asp Ile Ser Lys Tyr
                 20                  25                  30

Leu Asn Trp Tyr Gln Gln Pro Asp Gly Thr Ile Lys Leu Leu Ile
             35                  40                  45

Tyr Tyr Thr Ser Arg Leu His Ser Gly Val Pro Ser Arg Phe Ser Gly
 50                  55                  60

Arg Gly Ser Gly Thr Asp Tyr Ser Leu Thr Ile Thr Asn Leu Glu Gln
 65                  70                  75                  80

Glu Asp Ile Ala Thr Tyr Phe Cys Gln Gln Gly Ser Ala Leu Pro Tyr
                 85                  90                  95

Thr Phe Gly Gly Gly Thr Lys Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 31
<211> LENGTH: 214
<212> TYPE: PRT
<213> ORGANISM: Artificial Sequence
<220> FEATURE:
<223> OTHER INFORMATION: c219D6, light chain, full length

<400> SEQUENCE: 31

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 32
<211> LENGTH: 214
<212> TYPE: PRT
<213> ORGANISM: Artificial Sequence
<220> FEATURE:
<223> OTHER INFORMATION: c213B10, light chain, full length

<400> SEQUENCE: 32

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
```

```
                    50                  55                  60
Arg Gly Ser Gly Thr Asp Tyr Ser Leu Thr Ile Thr Asn Leu Glu Gln
 65                  70                  75                  80

Glu Asp Ile Ala Thr Tyr Phe Cys Gln Gln Gly Ser Ala Leu Pro Tyr
                     85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 33
<211> LENGTH: 120
<212> TYPE: PRT
<213> ORGANISM: Artificial Sequence
<220> FEATURE:
<223> OTHER INFORMATION: hz208F2 (var.1) heavy chain, VH

<400> SEQUENCE: 33

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Trp Pro Gly Asp Gly Ser Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Ser Pro Met Ile Thr Pro Asn Tyr Ala Met Asp Tyr Trp Gly Gln
                100                 105                 110

Gly Thr Leu Val Thr Val Ser Ser
            115                 120
```

<210> SEQ ID NO 34
<211> LENGTH: 120
<212> TYPE: PRT
<213> ORGANISM: Artificial Sequence
<220> FEATURE:
<223> OTHER INFORMATION: hz208F2 (var.3), VH

<400> SEQUENCE: 34

```
Gln Val Gln Leu Val Gln Ser Gly Ala Glu Val Lys Lys Pro Gly Ala
 1               5                  10                  15
```

```
Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
            35                  40                  45

Gly Trp Ile Trp Pro Gly Asp Gly Ser Thr Lys Tyr Asn Glu Lys Phe
 50                  55                  60

Gln Gly Arg Val Thr Leu Thr Ala Asp Lys Ser Ser Asn Thr Ala Tyr
 65                  70                  75                  80

Met Phe Leu Ser Ser Leu Arg Ser Glu Asp Thr Ala Val Tyr Phe Cys
                 85                  90                  95

Ala Ser Pro Met Ile Thr Pro Asn Tyr Ala Met Asp Tyr Trp Gly Gln
             100                 105                 110

Gly Thr Leu Val Thr Val Ser Ser
             115                 120

<210> SEQ ID NO 35
<211> LENGTH: 107
<212> TYPE: PRT
<213> ORGANISM: Artificial Sequence
<220> FEATURE:
<223> OTHER INFORMATION: hz208F2 (var.1), VL

<400> SEQUENCE: 35

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Lys Tyr
             20                  25                  30

Leu Asn Trp Tyr Gln Gln Lys Pro Gly Lys Ala Pro Lys Leu Leu Ile
             35                  40                  45

Tyr Tyr Thr Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ser Thr Leu Pro Tyr
                 85                  90                  95

Thr Phe Gly Gly Gly Thr Lys Val Glu Ile Lys
             100                 105

<210> SEQ ID NO 36
<211> LENGTH: 107
<212> TYPE: PRT
<213> ORGANISM: Artificial Sequence
<220> FEATURE:
<223> OTHER INFORMATION: hz208F2 (var.3), VL

<400> SEQUENCE: 36

Asp Ile Gln Met Thr Gln Ser Pro Ser Ser Leu Ser Ala Ser Val Gly
 1               5                  10                  15

Asp Arg Val Thr Ile Ser Cys Arg Ala Ser Gln Asp Ile Ser Lys Tyr
             20                  25                  30

Leu Asn Trp Tyr Gln Gln Lys Pro Gly Lys Ala Pro Lys Leu Leu Ile
             35                  40                  45

Tyr Tyr Thr Ser Arg Leu His Ser Gly Val Pro Ser Arg Phe Ser Gly
 50                  55                  60

Arg Gly Ser Gly Thr Asp Tyr Ser Leu Thr Ile Ser Asn Leu Gln Pro
 65                  70                  75                  80

Glu Asp Phe Ala Thr Tyr Phe Cys Gln Gln Gly Ser Thr Leu Pro Tyr
                 85                  90                  95
```

```
Thr Phe Gly Gly Gly Thr Lys Val Glu Ile Lys
            100                 105

<210> SEQ ID NO 37
<211> LENGTH: 449
<212> TYPE: PRT
<213> ORGANISM: Artificial Sequence
<220> FEATURE:
<223> OTHER INFORMATION: hz208F2 (var.1), heavy chain, full length

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Trp Pro Gly Asp Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 38
<211> LENGTH: 449
<212> TYPE: PRT
<213> ORGANISM: Artificial Sequence
<220> FEATURE:
<223> OTHER INFORMATION: hz208F2 (var.3), heavy chain, full length

<400> SEQUENCE: 38

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 39
<211> LENGTH: 214
<212> TYPE: PRT
<213> ORGANISM: Artificial Sequence
<220> FEATURE:
<223> OTHER INFORMATION: hz208F2 (var.1), light chain, full length

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 40
<211> LENGTH: 214
<212> TYPE: PRT
<213> ORGANISM: Artificial Sequence
<220> FEATURE:
<223> OTHER INFORMATION: hz208F2 (var.3), light chain, full length

<400> SEQUENCE: 40

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 120
<212> TYPE: PRT
<213> ORGANISM: Artificial Sequence
<220> FEATURE:
<223> OTHER INFORMATION: hz208F2 (var.2) heavy chain, VH
<220> FEATURE:
<221> NAME/KEY: MISC_FEATURE
<222> LOCATION: (20)..(20)
<223> OTHER INFORMATION: Xaa is Met or Val
<220> FEATURE:
<221> NAME/KEY: MISC_FEATURE
<222> LOCATION: (34)..(34)
<223> OTHER INFORMATION: Xaa is Ile or Met
<220> FEATURE:
```

<210> NAME/KEY: MISC_FEATURE
<222> LOCATION: (35)..(35)
<223> OTHER INFORMATION: Xaa is Tyr or His
<220> FEATURE:
<221> NAME/KEY: MISC_FEATURE
<222> LOCATION: (38)..(38)
<223> OTHER INFORMATION: Xaa is Lys or Arg
<220> FEATURE:
<221> NAME/KEY: MISC_FEATURE
<222> LOCATION: (48)..(48)
<223> OTHER INFORMATION: Xaa is Leu or Met
<220> FEATURE:
<221> NAME/KEY: MISC_FEATURE
<222> LOCATION: (50)..(50)
<223> OTHER INFORMATION: Xaa is Trp or Ile
<220> FEATURE:
<221> NAME/KEY: MISC_FEATURE
<222> LOCATION: (59)..(59)
<223> OTHER INFORMATION: Xaa is Lys or Ser
<220> FEATURE:
<221> NAME/KEY: MISC_FEATURE
<222> LOCATION: (61)..(61)
<223> OTHER INFORMATION: Xaa is Asn or Ala
<220> FEATURE:
<221> NAME/KEY: MISC_FEATURE
<222> LOCATION: (62)..(62)
<223> OTHER INFORMATION: Xaa is Glu or Gln
<220> FEATURE:
<221> NAME/KEY: MISC_FEATURE
<222> LOCATION: (70)..(70)
<223> OTHER INFORMATION: Xaa is Leu or Met
<220> FEATURE:
<221> NAME/KEY: MISC_FEATURE
<222> LOCATION: (72)..(72)
<223> OTHER INFORMATION: Xaa is Ala or Arg
<220> FEATURE:
<221> NAME/KEY: MISC_FEATURE
<222> LOCATION: (74)..(74)
<223> OTHER INFORMATION: Xaa is Lys or Thr
<220> FEATURE:
<221> NAME/KEY: MISC_FEATURE
<222> LOCATION: (76)..(76)
<223> OTHER INFORMATION: Xaa is Ser or Thr
<220> FEATURE:
<221> NAME/KEY: MISC_FEATURE
<222> LOCATION: (77)..(77)
<223> OTHER INFORMATION: Xaa is Asn or Ser
<220> FEATURE:
<221> NAME/KEY: MISC_FEATURE
<222> LOCATION: (79)..(79)
<223> OTHER INFORMATION: Xaa is Ala or Val
<220> FEATURE:
<221> NAME/KEY: MISC_FEATURE
<222> LOCATION: (82)..(82)
<223> OTHER INFORMATION: Xaa is Phe or Glu
<220> FEATURE:
<221> NAME/KEY: MISC_FEATURE
<222> LOCATION: (95)..(95)
<223> OTHER INFORMATION: Xaa is Phe or Tyr

<400> SEQUENCE: 41

Gln Val Gln Leu Val Gln Ser Gly Ala Glu Val Lys Lys Pro Gly Ala
1               5                   10                  15

Ser Val Lys Xaa Ser Cys Lys Ala Ser Gly Tyr Thr Phe Thr Ser Tyr
            20                  25                  30

Tyr Xaa Xaa Trp Val Xaa Gln Ala Pro Gly Gln Gly Leu Glu Trp Xaa
        35                  40                  45

Gly Xaa Ile Trp Pro Gly Asp Gly Ser Thr Xaa Tyr Xaa Xaa Lys Phe
    50                  55                  60

Gln Gly Arg Val Thr Xaa Thr Xaa Asp Xaa Ser Xaa Xaa Thr Xaa Tyr
65                  70                  75                  80

Met Xaa Leu Ser Ser Leu Arg Ser Glu Asp Thr Ala Val Tyr Xaa Cys
            85                  90                  95

```
Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: hz208F2 (var.2), light chain, VL
<220> FEATURE:
<221> NAME/KEY: MISC_FEATURE
<222> LOCATION: (22)..(22)
<223> OTHER INFORMATION: Xaa is Ser or Thr
<220> FEATURE:
<221> NAME/KEY: MISC_FEATURE
<222> LOCATION: (53)..(53)
<223> OTHER INFORMATION: Xaa is Arg or Ser
<220> FEATURE:
<221> NAME/KEY: MISC_FEATURE
<222> LOCATION: (55)..(55)
<223> OTHER INFORMATION: Xaa is His or Gln
<220> FEATURE:
<221> NAME/KEY: MISC_FEATURE
<222> LOCATION: (65)..(65)
<223> OTHER INFORMATION: Xaa is Arg or Ser
<220> FEATURE:
<221> NAME/KEY: MISC_FEATURE
<222> LOCATION: (71)..(71)
<223> OTHER INFORMATION: Xaa is Tyr or Phe
<220> FEATURE:
<221> NAME/KEY: MISC_FEATURE
<222> LOCATION: (72)..(72)
<223> OTHER INFORMATION: Xaa is Ser or Thr
<220> FEATURE:
<221> NAME/KEY: MISC_FEATURE
<222> LOCATION: (77)..(77)
<223> OTHER INFORMATION: Xaa is Asn or Ser
<220> FEATURE:
<221> NAME/KEY: MISC_FEATURE
<222> LOCATION: (87)..(87)
<223> OTHER INFORMATION: Xaa is Phe or Tyr

<400> SEQUENCE: 42

Asp Ile Gln Met Thr Gln Ser Pro Ser Ser Leu Ser Ala Ser Val Gly
1               5                   10                  15

Asp Arg Val Thr Ile Xaa Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Xaa Leu Xaa Ser Gly Val Pro Ser Arg Phe Ser Gly
50                  55                  60

Xaa Gly Ser Gly Thr Asp Xaa Xaa Leu Thr Ile Ser Xaa Leu Gln Pro
65                  70                  75                  80

Glu Asp Phe Ala Thr Tyr Xaa Cys Gln Gln Gly Ser Thr Leu Pro Tyr
                85                  90                  95

Thr Phe Gly Gly Gly Thr Lys Val Glu Ile Lys
            100                 105

<210> SEQ ID NO 43
<211> LENGTH: 329
<212> TYPE: PRT
<213> ORGANISM: Artificial Sequence
<220> FEATURE:
<223> OTHER INFORMATION: Constant domain (VH) IgG1

<400> SEQUENCE: 43
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 44
<211> LENGTH: 326
<212> TYPE: PRT
<213> ORGANISM: Artificial Sequence
<220> FEATURE:
<223> OTHER INFORMATION: Constant domain (VH) IgG4 (S228P)

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 45
<211> LENGTH: 107
<212> TYPE: PRT
<213> ORGANISM: Artificial Sequence
<220> FEATURE:
<223> OTHER INFORMATION: Domain kappa (VL)

<400> SEQUENCE: 45

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 46
<211> LENGTH: 98
<212> TYPE: PRT
<213> ORGANISM: Artificial Sequence
<220> FEATURE:
<223> OTHER INFORMATION: Human germline IGHV1-46*01

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 47
<211> LENGTH: 95
<212> TYPE: PRT
<213> ORGANISM: Artificial Sequence
<220> FEATURE:
<223> OTHER INFORMATION: Human germline IGKV1-39*01

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 48
<211> LENGTH: 15
<212> TYPE: PRT
<213> ORGANISM: Artificial Sequence
<220> FEATURE:
<223> OTHER INFORMATION: Human germline IGHJ4*01

<400> SEQUENCE: 48

Tyr Phe Asp Tyr Trp Gly Gln Gly Thr Leu Val Thr Val Ser Ser
```

<210> SEQ ID NO 49
<211> LENGTH: 12
<212> TYPE: PRT
<213> ORGANISM: Artificial Sequence
<220> FEATURE:
<223> OTHER INFORMATION: Human germline IGKJ4*01

<400> SEQUENCE: 49

Leu Thr Phe Gly Gly Gly Thr Lys Val Glu Ile Lys
1               5                   10

<210> SEQ ID NO 50
<211> LENGTH: 1367
<212> TYPE: PRT
<213> ORGANISM: Artificial Sequence
<220> FEATURE:
<223> OTHER INFORMATION: IGF-1R (human)

<400> SEQUENCE: 50

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

```
Glu Ser Ser Asp Ser Glu Gly Phe Val Ile His Asp Gly Glu Cys Met
290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Lys
            325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
            355                 360                 365
Asn Ile Ala Ser Glu Leu Glu Asn Phe Met Gly Leu Ile Glu Val Val
370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
            435                 440                 445
Ala Phe Asn Pro Lys Leu Cys Val Ser Glu Ile Tyr Arg Met Glu Glu
450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
            500                 505                 510
Arg Pro Pro Asp Tyr Arg Asp Leu Ile Ser Phe Thr Val Tyr Tyr Lys
            515                 520                 525
Glu Ala Pro Phe Lys Asn Val Thr Glu Tyr Asp Gly Gln Asp Ala Cys
530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
            595                 600                 605
Ser Val Pro Ser Ile Pro Leu Asp Val Leu Ser Ala Ser Asn Ser Ser
610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Glu Val Thr Glu Asn Pro Lys
            675                 680                 685
Thr Glu Val Cys Gly Gly Glu Lys Gly Pro Cys Cys Ala Cys Pro Lys
690                 695                 700
Thr Glu Ala Glu Lys Gln Ala Glu Lys Glu Glu Ala Glu Tyr Arg Lys
```

```
              705                 710                 715                 720
Val Phe Glu Asn Phe Leu His Asn Ser Ile Phe Val Pro Arg Pro Glu
                        725                 730                 735
Arg Lys Arg Arg Asp Val Met Gln Val Ala Asn Thr Thr Met Ser Ser
                        740                 745                 750
Arg Ser Arg Asn Thr Thr Ala Ala Asp Thr Tyr Asn Ile Thr Asp Pro
                        755                 760                 765
Glu Glu Leu Glu Thr Glu Tyr Pro Phe Phe Glu Ser Arg Val Asp Asn
                        770                 775                 780
Lys Glu Arg Thr Val Ile Ser Asn Leu Arg Pro Phe Thr Leu Tyr Arg
785                         790                 795                 800
Ile Asp Ile His Ser Cys Asn His Glu Ala Glu Lys Leu Gly Cys Ser
                        805                 810                 815
Ala Ser Asn Phe Val Phe Ala Arg Thr Met Pro Ala Glu Gly Ala Asp
                        820                 825                 830
Asp Ile Pro Gly Pro Val Thr Trp Glu Pro Arg Pro Glu Asn Ser Ile
                        835                 840                 845
Phe Leu Lys Trp Pro Glu Pro Glu Asn Pro Asn Gly Leu Ile Leu Met
                        850                 855                 860
Tyr Glu Ile Lys Tyr Gly Ser Gln Val Glu Asp Gln Arg Glu Cys Val
865                         870                 875                 880
Ser Arg Gln Glu Tyr Arg Lys Tyr Gly Gly Ala Lys Leu Asn Arg Leu
                        885                 890                 895
Asn Pro Gly Asn Tyr Thr Ala Arg Ile Gln Ala Thr Ser Leu Ser Gly
                        900                 905                 910
Asn Gly Ser Trp Thr Asp Pro Val Phe Phe Tyr Val Gln Ala Lys Thr
                        915                 920                 925
Gly Tyr Glu Asn Phe Ile His Leu Ile Ile Ala Leu Pro Val Ala Val
                        930                 935                 940
Leu Leu Ile Val Gly Gly Leu Val Ile Met Leu Tyr Val Phe His Arg
945                         950                 955                 960
Lys Arg Asn Asn Ser Arg Leu Gly Asn Gly Val Leu Tyr Ala Ser Val
                        965                 970                 975
Asn Pro Glu Tyr Phe Ser Ala Ala Asp Val Tyr Val Pro Asp Glu Trp
                        980                 985                 990
Glu Val Ala Arg Glu Lys Ile Thr  Met Ser Arg Glu Leu  Gly Gln Gly
                        995                 1000                1005
Ser Phe Gly Met Val Tyr Glu  Gly Val Ala Lys Gly  Val Val Lys
                        1010                1015                1020
Asp Glu Pro Glu Thr Arg Val  Ala Ile Lys Thr Val  Asn Glu Ala
                        1025                1030                1035
Ala Ser Met Arg Glu Arg Ile  Glu Phe Leu Asn Glu  Ala Ser Val
                        1040                1045                1050
Met Lys Glu Phe Asn Cys His  His Val Val Arg Leu  Leu Gly Val
                        1055                1060                1065
Val Ser Gln Gly Gln Pro Thr  Leu Val Ile Met Glu  Leu Met Thr
                        1070                1075                1080
Arg Gly Asp Leu Lys Ser Tyr  Leu Arg Ser Leu Arg  Pro Glu Met
                        1085                1090                1095
Glu Asn Asn Pro Val Leu Ala  Pro Pro Ser Leu Ser  Lys Met Ile
                        1100                1105                1110
Gln Met Ala Gly Glu Ile Ala  Asp Gly Met Ala Tyr  Leu Asn Ala
                        1115                1120                1125
```

```
Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 51
<211> LENGTH: 932
<212> TYPE: PRT
<213> ORGANISM: Artificial Sequence
<220> FEATURE:
<223> OTHER INFORMATION: IGF-1R ECD (human)

<400> SEQUENCE: 51

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                    85                  90                  95

Gly Asp Leu Phe Pro Asn Leu Thr Val Ile Arg Gly Trp Lys Leu Phe
                100                 105                 110
```

```
Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525
```

```
Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
            915                 920                 925

Gly Tyr Glu Asn
930
```

<210> SEQ ID NO 52
<211> LENGTH: 512
<212> TYPE: PRT
<213> ORGANISM: Artificial Sequence
<220> FEATURE:
<223> OTHER INFORMATION: IGF-1R ECD Nterminal (human)

<400> SEQUENCE: 52

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
```

```
                370             375                 380
Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
                435                 440                 445

Ala Phe Asn Pro Lys Leu Cys Val Ser Glu Ile Tyr Arg Met Glu Glu
                450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
                500                 505                 510
```

<210> SEQ ID NO 53
<211> LENGTH: 4
<212> TYPE: PRT
<213> ORGANISM: Artificial Sequence
<220> FEATURE:
<223> OTHER INFORMATION: tetrapeptide (linker)

<400> SEQUENCE: 53

Gly Phe Leu Gly
1

<210> SEQ ID NO 54
<211> LENGTH: 4
<212> TYPE: PRT
<213> ORGANISM: Artificial Sequence
<220> FEATURE:
<223> OTHER INFORMATION: tetrapeptide (linker)

<400> SEQUENCE: 54

Ala Leu Ala Leu
1

<210> SEQ ID NO 55
<211> LENGTH: 5
<212> TYPE: PRT
<213> ORGANISM: Artificial Sequence
<220> FEATURE:
<223> OTHER INFORMATION: tetrapeptide (linker)

<400> SEQUENCE: 55

Pro Val Gly Val Val
1               5

<210> SEQ ID NO 56
<211> LENGTH: 6
<212> TYPE: PRT
<213> ORGANISM: Artificial Sequence
<220> FEATURE:
<223> OTHER INFORMATION: 1613F12 antibody CDR-L1

<400> SEQUENCE: 56

Lys Ser Ile Ser Lys Tyr
1               5

```
<210> SEQ ID NO 57
<211> LENGTH: 3
<212> TYPE: PRT
<213> ORGANISM: Artificial Sequence
<220> FEATURE:
<223> OTHER INFORMATION: 1613F12 antibody CDR-L2

<400> SEQUENCE: 57

Ser Gly Ser
1

<210> SEQ ID NO 58
<211> LENGTH: 9
<212> TYPE: PRT
<213> ORGANISM: Artificial Sequence
<220> FEATURE:
<223> OTHER INFORMATION: 1613F12 antibody CDR-L3

<400> SEQUENCE: 58

Gln Gln His His Glu Tyr Pro Leu Thr
1               5

<210> SEQ ID NO 59
<211> LENGTH: 8
<212> TYPE: PRT
<213> ORGANISM: Artificial Sequence
<220> FEATURE:
<223> OTHER INFORMATION: 1613F12 antibody CDR-H1

<400> SEQUENCE: 59

Gly Phe Asn Ile Arg Asp Thr Tyr
1               5

<210> SEQ ID NO 60
<211> LENGTH: 8
<212> TYPE: PRT
<213> ORGANISM: Artificial Sequence
<220> FEATURE:
<223> OTHER INFORMATION: 1613F12 antibody CDR-H2

<400> SEQUENCE: 60

Leu Asp Pro Ala Asn Gly His Thr
1               5

<210> SEQ ID NO 61
<211> LENGTH: 17
<212> TYPE: PRT
<213> ORGANISM: Artificial Sequence
<220> FEATURE:
<223> OTHER INFORMATION: 1613F12 antibody CDR-H3

<400> SEQUENCE: 61

Ala Arg Gly Ala Tyr Tyr Tyr Gly Ser Ser Gly Leu Phe Tyr Phe Asp
1               5                   10                  15

Tyr

<210> SEQ ID NO 62
<211> LENGTH: 107
<212> TYPE: PRT
<213> ORGANISM: Artificial Sequence
<220> FEATURE:
<223> OTHER INFORMATION: 1613F12 antibody Mu. variable domain (light
      chain)

<400> SEQUENCE: 62

Asp Val Gln Ile Thr Gln Ser Pro Ser Tyr Leu Ala Thr Ser Pro Gly
1               5                   10                  15
```

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Val Pro Ser Arg Phe Ser Gly
50                      55                  60

Ser Gly Ser Gly Thr Asp Phe Thr Leu Thr Ile Ser Ser Leu Glu Pro
65                  70                  75                  80

Glu Asp Phe Ala Met Tyr Phe Cys Gln Gln His His Glu Tyr Pro Leu
                85                  90                  95

Thr Phe Gly Ala Gly Thr Glu Leu Glu Leu Lys
            100                 105

<210> SEQ ID NO 63
<211> LENGTH: 124
<212> TYPE: PRT
<213> ORGANISM: Artificial Sequence
<220> FEATURE:
<223> OTHER INFORMATION: 1613F12 antibody Mu. variable domain (heavy
      chain)

<400> SEQUENCE: 63

Glu Val His Leu Gln Gln Ser Gly Ala Glu Leu Val Lys Pro Gly Ala
1               5                   10                  15

Ser Val Lys Leu Ser Cys Thr Ala Ser Gly Phe Asn Ile Arg Asp Thr
            20                  25                  30

Tyr Ile His Trp Val Lys Gln Arg Pro Glu Gln Gly Leu Glu Trp Ile
            35                  40                  45

Gly Arg Leu Asp Pro Ala Asn Gly His Thr Lys Tyr Gly Pro Asn Phe
50                  55                  60

Gln Gly Arg Ala Thr Met Thr Ser Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Thr Leu Ser Val Ser Ser
            115                 120

<210> SEQ ID NO 64
<211> LENGTH: 18
<212> TYPE: DNA
<213> ORGANISM: Artificial Sequence
<220> FEATURE:
<223> OTHER INFORMATION: 1613F12 antibody CDR-L1

<400> SEQUENCE: 64
aagagcatta gcaaatat                                                18

<210> SEQ ID NO 65
<211> LENGTH: 9
<212> TYPE: DNA
<213> ORGANISM: Artificial Sequence
<220> FEATURE:
<223> OTHER INFORMATION: 1613F12 antibody CDR-L2

<400> SEQUENCE: 65 tctggatcc                                                           9

```
<210> SEQ ID NO 66
<211> LENGTH: 27
<212> TYPE: DNA
<213> ORGANISM: Artificial Sequence
<220> FEATURE:
<223> OTHER INFORMATION: 1613F12 antibody CDR-L3

<400> SEQUENCE: 66
caacagcatc atgaataccc gctcacg                                              27

<210> SEQ ID NO 67
<211> LENGTH: 24
<212> TYPE: DNA
<213> ORGANISM: Artificial Sequence
<220> FEATURE:
<223> OTHER INFORMATION: 1613F12 antibody CDR-H1

<400> SEQUENCE: 67
ggcttcaaca ttagagacac ctat                                                 24

<210> SEQ ID NO 68
<211> LENGTH: 24
<212> TYPE: DNA
<213> ORGANISM: Artificial Sequence
<220> FEATURE:
<223> OTHER INFORMATION: 1613F12 antibody CDR-H2

<400> SEQUENCE: 68
cttgatcctg cgaatggtca tact                                                 24

<210> SEQ ID NO 69
<211> LENGTH: 51
<212> TYPE: DNA
<213> ORGANISM: Artificial Sequence
<220> FEATURE:
<223> OTHER INFORMATION: 1613F12 antibody CDR-H3

<400> SEQUENCE: 69
gctagagggg cctattacta cggtagtagt ggtctcttct actttgacta c                   51

<210> SEQ ID NO 70
<211> LENGTH: 107
<212> TYPE: PRT
<213> ORGANISM: Artificial Sequence
<220> FEATURE:
<223> OTHER INFORMATION: Hz1613F12 VL consensus
<220> FEATURE:
<221> NAME/KEY: VARIANT
<222> LOCATION: (2)..(2)
<223> OTHER INFORMATION: Xaa is Ile or Val
<220> FEATURE:
<221> NAME/KEY: VARIANT
<222> LOCATION: (4)..(4)
<223> OTHER INFORMATION: Xaa is Met or Ile
<220> FEATURE:
<221> NAME/KEY: VARIANT
<222> LOCATION: (10)..(10)
<223> OTHER INFORMATION: Xaa is Ser cor Tyr
<220> FEATURE:
<221> NAME/KEY: VARIANT
<222> LOCATION: (12)..(12)
<223> OTHER INFORMATION: Xaa is Ser or Ala
<220> FEATURE:
<221> NAME/KEY: VARIANT
<222> LOCATION: (18)..(18)
<223> OTHER INFORMATION: Xaa is Arg or Thr
<220> FEATURE:
<221> NAME/KEY: VARIANT
<222> LOCATION: (19)..(19)
<223> OTHER INFORMATION: Xaa is Val or Ile
<220> FEATURE:
```

```
<221> NAME/KEY: VARIANT
<222> LOCATION: (22)..(22)
<223> OTHER INFORMATION: Xaa is Thr or Asn
<220> FEATURE:
<221> NAME/KEY: VARIANT
<222> LOCATION: (38)..(38)
<223> OTHER INFORMATION: Xaa is Gln or Glu
<220> FEATURE:
<221> NAME/KEY: VARIANT
<222> LOCATION: (43)..(43)
<223> OTHER INFORMATION: Xaa is Val or Thr
<220> FEATURE:
<221> NAME/KEY: VARIANT
<222> LOCATION: (44)..(44)
<223> OTHER INFORMATION: Xaa is Pro or Asn
<220> FEATURE:
<221> NAME/KEY: VARIANT
<222> LOCATION: (87)..(87)
<223> OTHER INFORMATION: Xaa is Tyr or Phe
<220> FEATURE:
<221> NAME/KEY: VARIANT
<222> LOCATION: (100)..(100)
<223> OTHER INFORMATION: Xaa is Gly or Ala
<220> FEATURE:
<221> NAME/KEY: VARIANT
<222> LOCATION: (103)..(103)
<223> OTHER INFORMATION: Xaa is Lys or Glu
<220> FEATURE:
<221> NAME/KEY: VARIANT
<222> LOCATION: (104)..(104)
<223> OTHER INFORMATION: Xaa is Val or Leu

<400> SEQUENCE: 70

Asp Xaa Gln Xaa Thr Gln Ser Pro Ser Xaa Leu Xaa Ala Ser Val Gly
1               5                   10                  15

Asp Xaa Xaa Thr Ile Xaa Cys Arg Ala Ser Lys Ser Ile Ser Lys Tyr
            20                  25                  30

Leu Ala Trp Tyr Gln Xaa Lys Pro Gly Lys Xaa Xaa Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Xaa Cys Gln Gln His His Glu Tyr Pro Leu
                85                  90                  95

Thr Phe Gly Xaa Gly Thr Xaa Xaa Glu Ile Lys
            100                 105

<210> SEQ ID NO 71
<211> LENGTH: 107
<212> TYPE: PRT
<213> ORGANISM: Artificial Sequence
<220> FEATURE:
<223> OTHER INFORMATION: Hz1613F12 VL1

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Val Ala Thr Tyr Tyr Cys Gln Gln His His Glu Tyr Pro Leu
                85                  90                  95

Thr Phe Gly Gly Gly Thr Lys Val Glu Ile Lys
            100                 105

<210> SEQ ID NO 72
<211> LENGTH: 107
<212> TYPE: PRT
<213> ORGANISM: Artificial Sequence
<220> FEATURE:
<223> OTHER INFORMATION: Hz1613F12 VL1 I2V

<400> SEQUENCE: 72

Asp Val Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His His Glu Tyr Pro Leu
                85                  90                  95

Thr Phe Gly Gly Gly Thr Lys Val Glu Ile Lys
            100                 105

<210> SEQ ID NO 73
<211> LENGTH: 107
<212> TYPE: PRT
<213> ORGANISM: Artificial Sequence
<220> FEATURE:
<223> OTHER INFORMATION: Hz1613F12 VL1 M4I

<400> SEQUENCE: 73

Asp Ile Gln Ile Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His His Glu Tyr Pro Leu
                85                  90                  95

Thr Phe Gly Gly Gly Thr Lys Val Glu Ile Lys
            100                 105

<210> SEQ ID NO 74
<211> LENGTH: 107
<212> TYPE: PRT
<213> ORGANISM: Artificial Sequence
<220> FEATURE:
<223> OTHER INFORMATION: Hz1613F12 VL2.1

<400> SEQUENCE: 74

-continued

Asp Val Gln Ile Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His His Glu Tyr Pro Leu
                85                  90                  95

Thr Phe Gly Gly Gly Thr Lys Val Glu Ile Lys
            100                 105

<210> SEQ ID NO 75
<211> LENGTH: 107
<212> TYPE: PRT
<213> ORGANISM: Artificial Sequence
<220> FEATURE:
<223> OTHER INFORMATION: Hz1613F12 VL2.1 V49T

<400> SEQUENCE: 75

Asp Val Gln Ile Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Thr Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His His Glu Tyr Pro Leu
                85                  90                  95

Thr Phe Gly Gly Gly Thr Lys Val Glu Ile Lys
            100                 105

<210> SEQ ID NO 76
<211> LENGTH: 107
<212> TYPE: PRT
<213> ORGANISM: Artificial Sequence
<220> FEATURE:
<223> OTHER INFORMATION: Hz1613F12 VL2.1 P50N

<400> SEQUENCE: 76

Asp Val Gln Ile Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Val Asn Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His His Glu Tyr Pro Leu
                85                  90                  95

-continued

Thr Phe Gly Gly Gly Thr Lys Val Glu Ile Lys
            100                 105

<210> SEQ ID NO 77
<211> LENGTH: 107
<212> TYPE: PRT
<213> ORGANISM: Artificial Sequence
<220> FEATURE:
<223> OTHER INFORMATION: Hz1613F12 VL2.2

<400> SEQUENCE: 77

Asp Val Gln Ile Thr Gln Ser Pro Ser Ser Leu Ser Ala Ser Val Gly
1               5                   10                  15

Asp Arg Val Thr Ile Asn Cys Arg Ala Ser Lys Ser Ile Ser Lys Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln His His Glu Tyr Pro Leu
                85                  90                  95

Thr Phe Gly Gly Gly Thr Lys Val Glu Ile Lys
            100                 105

<210> SEQ ID NO 78
<211> LENGTH: 107
<212> TYPE: PRT
<213> ORGANISM: Artificial Sequence
<220> FEATURE:
<223> OTHER INFORMATION: Hz1613F12 VL2.2 V49T

<400> SEQUENCE: 78

Asp Val Gln Ile Thr Gln Ser Pro Ser Ser Leu Ser Ala Ser Val Gly
1               5                   10                  15

Asp Arg Val Thr Ile Asn Cys Arg Ala Ser Lys Ser Ile Ser Lys Tyr
            20                  25                  30

Leu Ala Trp Tyr Gln Gln Lys Pro Gly Lys Thr Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln His His Glu Tyr Pro Leu
                85                  90                  95

Thr Phe Gly Gly Gly Thr Lys Val Glu Ile Lys
            100                 105

<210> SEQ ID NO 79
<211> LENGTH: 107
<212> TYPE: PRT
<213> ORGANISM: Artificial Sequence
<220> FEATURE:
<223> OTHER INFORMATION: Hz1613F12 VL2.2 P50N

<400> SEQUENCE: 79

Asp Val Gln Ile Thr Gln Ser Pro Ser Ser Leu Ser Ala Ser Val Gly
1               5                   10                  15

Asp Arg Val Thr Ile Asn Cys Arg Ala Ser Lys Ser Ile Ser Lys Tyr
            20                  25                  30

Leu Ala Trp Tyr Gln Gln Lys Pro Gly Lys Val Asn Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln His His Glu Tyr Pro Leu
                85                  90                  95

Thr Phe Gly Gly Gly Thr Lys Val Glu Ile Lys
            100                 105

<210> SEQ ID NO 80
<211> LENGTH: 107
<212> TYPE: PRT
<213> ORGANISM: Artificial Sequence
<220> FEATURE:
<223> OTHER INFORMATION: Hz1613F12 VL2.3

<400> SEQUENCE: 80

Asp Val Gln Ile Thr Gln Ser Pro Ser Ser Leu Ser Ala Ser Val Gly
1               5                   10                  15

Asp Arg Val Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln His His Glu Tyr Pro Leu
                85                  90                  95

Thr Phe Gly Gly Gly Thr Lys Val Glu Ile Lys
            100                 105

<210> SEQ ID NO 81
<211> LENGTH: 107
<212> TYPE: PRT
<213> ORGANISM: Artificial Sequence
<220> FEATURE:
<223> OTHER INFORMATION: Hz1613F12 VL3

<400> SEQUENCE: 81

Asp Val Gln Ile Thr Gln Ser Pro Ser Tyr Leu Ala Ala Ser Val Gly
1               5                   10                  15

Asp Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln His His Glu Tyr Pro Leu
                85                  90                  95

Thr Phe Gly Ala Gly Thr Lys Leu Glu Ile Lys
            100                 105

```
<210> SEQ ID NO 82
<211> LENGTH: 124
<212> TYPE: PRT
<213> ORGANISM: Artificial Sequence
<220> FEATURE:
<223> OTHER INFORMATION: Hz1613F12 consensus
<220> FEATURE:
<221> NAME/KEY: VARIANT
<222> LOCATION: (1)..(1)
<223> OTHER INFORMATION: Xaa is Gln or Glu
<220> FEATURE:
<221> NAME/KEY: VARIANT
<222> LOCATION: (3)..(3)
<223> OTHER INFORMATION: Xaa is Gln or His
<220> FEATURE:
<221> NAME/KEY: VARIANT
<222> LOCATION: (5)..(5)
<223> OTHER INFORMATION: Xaa is Val or Gln
<220> FEATURE:
<221> NAME/KEY: VARIANT
<222> LOCATION: (11)..(11)
<223> OTHER INFORMATION: Xaa is Val or Leu
<220> FEATURE:
<221> NAME/KEY: VARIANT
<222> LOCATION: (12)..(12)
<223> OTHER INFORMATION: Xaa is Lys or Val
<220> FEATURE:
<221> NAME/KEY: VARIANT
<222> LOCATION: (20)..(20)
<223> OTHER INFORMATION: Xaa is Val or Leu
<220> FEATURE:
<221> NAME/KEY: VARIANT
<222> LOCATION: (23)..(23)
<223> OTHER INFORMATION: Xaa is Lys or Thr
<220> FEATURE:
<221> NAME/KEY: VARIANT
<222> LOCATION: (34)..(34)
<223> OTHER INFORMATION: Xaa is Met or Ile
<220> FEATURE:
<221> NAME/KEY: VARIANT
<222> LOCATION: (38)..(38)
<223> OTHER INFORMATION: Xaa is Arg or Lys
<220> FEATURE:
<221> NAME/KEY: VARIANT
<222> LOCATION: (48)..(48)
<223> OTHER INFORMATION: Xaa is Met or Ile
<220> FEATURE:
<221> NAME/KEY: VARIANT
<222> LOCATION: (50)..(50)
<223> OTHER INFORMATION: Xaa is Trp or Arg
<220> FEATURE:
<221> NAME/KEY: VARIANT
<222> LOCATION: (59)..(59)
<223> OTHER INFORMATION: Xaa is Asn or Lys
<220> FEATURE:
<221> NAME/KEY: VARIANT
<222> LOCATION: (61)..(61)
<223> OTHER INFORMATION: Xaa is Ala or Gly
<220> FEATURE:
<221> NAME/KEY: VARIANT
<222> LOCATION: (72)..(72)
<223> OTHER INFORMATION: Xaa is Arg or Ser
<220> FEATURE:
<221> NAME/KEY: VARIANT
<222> LOCATION: (76)..(76)
<223> OTHER INFORMATION: Xaa is Ile or Ser
<220> FEATURE:
<221> NAME/KEY: VARIANT
<222> LOCATION: (77)..(77)
<223> OTHER INFORMATION: Xaa is Ser or Asn
<220> FEATURE:
<221> NAME/KEY: VARIANT
<222> LOCATION: (81)..(81)
<223> OTHER INFORMATION: Xaa is Met or Leu
<220> FEATURE:
<221> NAME/KEY: VARIANT
<222> LOCATION: (82)..(82)
```

<223> OTHER INFORMATION: Xaa is Glu or Gln

<400> SEQUENCE: 82

```
Xaa Val Xaa Leu Xaa Gln Ser Gly Ala Glu Xaa Xaa Lys Pro Gly Ala
1               5                   10                  15

Ser Val Lys Xaa Ser Cys Xaa Ala Ser Gly Phe Asn Ile Arg Asp Thr
            20                  25                  30

Tyr Xaa His Trp Val Xaa Gln Ala Pro Gly Gln Gly Leu Glu Trp Xaa
        35                  40                  45

Gly Xaa Leu Asp Pro Ala Asn Gly His Thr Xaa Tyr Xaa Gln Lys Phe
    50                  55                  60

Gln Gly Arg Val Thr Met Thr Xaa Asp Thr Ser Xaa Xaa Thr Ala Tyr
65                  70                  75                  80

Xaa Xaa Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120
```

<210> SEQ ID NO 83
<211> LENGTH: 124
<212> TYPE: PRT
<213> ORGANISM: Artificial Sequence
<220> FEATURE:
<223> OTHER INFORMATION: Hz1613F12 VH1

<400> SEQUENCE: 83

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Met His Trp Val Arg Gln Ala Pro Gly Gln Gly Leu Glu Trp Met
        35                  40                  45

Gly Trp Leu Asp Pro Ala Asn Gly His Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120
```

<210> SEQ ID NO 84
<211> LENGTH: 124
<212> TYPE: PRT
<213> ORGANISM: Artificial Sequence
<220> FEATURE:
<223> OTHER INFORMATION: Hz1613F12 VH1 M39I

<400> SEQUENCE: 84

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Ile His Trp Val Arg Gln Ala Pro Gly Gln Gly Leu Glu Trp Met
```

```
                35                  40                  45
Gly Trp Leu Asp Pro Ala Asn Gly His Thr Asn Tyr Ala Gln Lys Phe
        50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                85                  90                  95
Ala Arg Gly Ala Tyr Tyr Tyr Gly Ser Ser Gly Leu Phe Tyr Phe Asp
                100                 105                 110
Tyr Trp Gly Gln Gly Thr Leu Val Thr Val Ser Ser
        115                 120
```

<210> SEQ ID NO 85
<211> LENGTH: 124
<212> TYPE: PRT
<213> ORGANISM: Artificial Sequence
<220> FEATURE:
<223> OTHER INFORMATION: Hz1613F12 VH1 W55R N66K

<400> SEQUENCE: 85

```
Gln Val Gln Leu Val Gln Ser Gly Ala Glu Val Lys Lys Pro Gly Ala
 1               5                  10                  15
Ser Val Lys Val Ser Cys Lys Ala Ser Gly Phe Asn Ile Arg Asp Thr
                20                  25                  30
Tyr Met His Trp Val Arg Gln Ala Pro Gly Gln Gly Leu Glu Trp Met
                35                  40                  45
Gly Arg Leu Asp Pro Ala Asn Gly His Thr Lys Tyr Ala Gln Lys Phe
        50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                85                  90                  95
Ala Arg Gly Ala Tyr Tyr Tyr Gly Ser Ser Gly Leu Phe Tyr Phe Asp
                100                 105                 110
Tyr Trp Gly Gln Gly Thr Leu Val Thr Val Ser Ser
        115                 120
```

<210> SEQ ID NO 86
<211> LENGTH: 124
<212> TYPE: PRT
<213> ORGANISM: Artificial Sequence
<220> FEATURE:
<223> OTHER INFORMATION: Hz1613F12 VH1 I84S

<400> SEQUENCE: 86

```
Gln Val Gln Leu Val Gln Ser Gly Ala Glu Val Lys Lys Pro Gly Ala
 1               5                  10                  15
Ser Val Lys Val Ser Cys Lys Ala Ser Gly Phe Asn Ile Arg Asp Thr
                20                  25                  30
Tyr Met His Trp Val Arg Gln Ala Pro Gly Gln Gly Leu Glu Trp Met
                35                  40                  45
Gly Trp Leu Asp Pro Ala Asn Gly His Thr Asn Tyr Ala Gln Lys Phe
        50                  55                  60
Gln Gly Arg Val Thr Met Thr Arg Asp Thr Ser Ser Ser Thr Ala Tyr
 65                  70                  75                  80
Met Glu Leu Ser Arg Leu Arg Ser Asp Asp Thr Ala Val Tyr Tyr Cys
                85                  90                  95
```

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 87
<211> LENGTH: 124
<212> TYPE: PRT
<213> ORGANISM: Artificial Sequence
<220> FEATURE:
<223> OTHER INFORMATION: Hz1613F12 VH1 S85N

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Met His Trp Val Arg Gln Ala Pro Gly Gln Gly Leu Glu Trp Met
        35                  40                  45

Gly Trp Leu Asp Pro Ala Asn Gly His Thr Asn Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 88
<211> LENGTH: 124
<212> TYPE: PRT
<213> ORGANISM: Artificial Sequence
<220> FEATURE:
<223> OTHER INFORMATION: Hz1613F12 VH1 I84N S85N

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Met His Trp Val Arg Gln Ala Pro Gly Gln Gly Leu Glu Trp Met
        35                  40                  45

Gly Trp Leu Asp Pro Ala Asn Gly His Thr Asn Tyr Ala Gln Lys Phe
    50                  55                  60

Gln Gly Arg Val Thr Met Thr Arg Asp Thr Ser Ser Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 89
<211> LENGTH: 124
<212> TYPE: PRT
<213> ORGANISM: Artificial Sequence

```
<220> FEATURE:
<223> OTHER INFORMATION: Hz1613F12 VH2.1

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Ile His Trp Val Arg Gln Ala Pro Gly Gln Gly Leu Glu Trp Met
        35                  40                  45

Gly Trp Leu Asp Pro Ala Asn Gly His Thr Asn Tyr Ala Gln Lys Phe
    50                  55                  60

Gln Gly Arg Val Thr Met Thr Arg Asp Thr Ser Ser Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 90
<211> LENGTH: 124
<212> TYPE: PRT
<213> ORGANISM: Artificial Sequence
<220> FEATURE:
<223> OTHER INFORMATION: Hz1613F12 VH2.1 Q3H

<400> SEQUENCE: 90

Gln Val His Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Ile His Trp Val Arg Gln Ala Pro Gly Gln Gly Leu Glu Trp Met
        35                  40                  45

Gly Trp Leu Asp Pro Ala Asn Gly His Thr Asn Tyr Ala Gln Lys Phe
    50                  55                  60

Gln Gly Arg Val Thr Met Thr Arg Asp Thr Ser Ser Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 91
<211> LENGTH: 124
<212> TYPE: PRT
<213> ORGANISM: Artificial Sequence
<220> FEATURE:
<223> OTHER INFORMATION: Hz1613F12 VH2.1 W55R

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30
```

```
Tyr Ile His Trp Val Arg Gln Ala Pro Gly Gln Gly Leu Glu Trp Met
        35                  40                  45

Gly Arg Leu Asp Pro Ala Asn Gly His Thr Asn Tyr Ala Gln Lys Phe
 50                  55                  60

Gln Gly Arg Val Thr Met Thr Arg Asp Thr Ser Ser Asn Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Ala Tyr Tyr Tyr Gly Ser Ser Gly Leu Phe Tyr Phe Asp
                100                 105                 110

Tyr Trp Gly Gln Gly Thr Leu Val Thr Val Ser Ser
        115                 120
```

<210> SEQ ID NO 92
<211> LENGTH: 124
<212> TYPE: PRT
<213> ORGANISM: Artificial Sequence
<220> FEATURE:
<223> OTHER INFORMATION: Hz1613F12 VH2.1 N66K

<400> SEQUENCE: 92

```
Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Arg Asp Thr
                 20                  25                  30

Tyr Ile His Trp Val Arg Gln Ala Pro Gly Gln Gly Leu Glu Trp Met
        35                  40                  45

Gly Trp Leu Asp Pro Ala Asn Gly His Thr Lys Tyr Ala Gln Lys Phe
 50                  55                  60

Gln Gly Arg Val Thr Met Thr Arg Asp Thr Ser Ser Asn Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Ala Tyr Tyr Tyr Gly Ser Ser Gly Leu Phe Tyr Phe Asp
                100                 105                 110

Tyr Trp Gly Gln Gly Thr Leu Val Thr Val Ser Ser
        115                 120
```

<210> SEQ ID NO 93
<211> LENGTH: 124
<212> TYPE: PRT
<213> ORGANISM: Artificial Sequence
<220> FEATURE:
<223> OTHER INFORMATION: Hz1613F12 VH2.1 W55R N66K

<400> SEQUENCE: 93

```
Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Arg Asp Thr
                 20                  25                  30

Tyr Ile His Trp Val Arg Gln Ala Pro Gly Gln Gly Leu Glu Trp Met
        35                  40                  45

Gly Arg Leu Asp Pro Ala Asn Gly His Thr Lys Tyr Ala Gln Lys Phe
 50                  55                  60

Gln Gly Arg Val Thr Met Thr Arg Asp Thr Ser Ser Asn Thr Ala Tyr
 65                  70                  75                  80

Met Glu Leu Ser Arg Leu Arg Ser Asp Asp Thr Ala Val Tyr Tyr Cys
                 85                  90                  95
```

```
Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 94
<211> LENGTH: 124
<212> TYPE: PRT
<213> ORGANISM: Artificial Sequence
<220> FEATURE:
<223> OTHER INFORMATION: Hz1613F12 VH2.1 R80S

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Ile His Trp Val Arg Gln Ala Pro Gly Gln Gly Leu Glu Trp Met
        35                  40                  45

Gly Trp Leu Asp Pro Ala Asn Gly His Thr Asn Tyr Ala Gln Lys Phe
    50                  55                  60

Gln Gly Arg Val Thr Met Thr Ser Asp Thr Ser Ser Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 95
<211> LENGTH: 124
<212> TYPE: PRT
<213> ORGANISM: Artificial Sequence
<220> FEATURE:
<223> OTHER INFORMATION: Hz1613F12 VH2.1 N66K R80S

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Ile His Trp Val Arg Gln Ala Pro Gly Gln Gly Leu Glu Trp Met
        35                  40                  45

Gly Trp Leu Asp Pro Ala Asn Gly His Thr Lys Tyr Ala Gln Lys Phe
    50                  55                  60

Gln Gly Arg Val Thr Met Thr Ser Asp Thr Ser Ser Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 96
<211> LENGTH: 124
<212> TYPE: PRT
```

<213> ORGANISM: Artificial Sequence
<220> FEATURE:
<223> OTHER INFORMATION: Hz1613F12 VH2.2

<400> SEQUENCE: 96

Gln Val His Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Ile His Trp Val Arg Gln Ala Pro Gly Gln Gly Leu Glu Trp Met
        35                  40                  45

Gly Trp Leu Asp Pro Ala Asn Gly His Thr Lys Tyr Ala Gln Lys Phe
50                  55                  60

Gln Gly Arg Val Thr Met Thr Ser Asp Thr Ser Ser Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 97
<211> LENGTH: 124
<212> TYPE: PRT
<213> ORGANISM: Artificial Sequence
<220> FEATURE:
<223> OTHER INFORMATION: Hz1613F12 VH2.2 M89L

<400> SEQUENCE: 97

Gln Val His Leu Val Gln Ser Gly Ala Glu Val Lys Lys Pro Gly Ala
1               5                   10                  15

Ser Val Lys Val Ser Cys Lys Ala Ser Gly Phe Asn Ile Arg Asp Thr
            20                  25                  30

Tyr Ile His Trp Val Arg Gln Ala Pro Gly Gln Gly Leu Glu Trp Met
        35                  40                  45

Gly Trp Leu Asp Pro Ala Asn Gly His Thr Lys Tyr Ala Gln Lys Phe
50                  55                  60

Gln Gly Arg Val Thr Met Thr Ser Asp Thr Ser Ser Asn Thr Ala Tyr
65                  70                  75                  80

Leu Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
        115                 120

<210> SEQ ID NO 98
<211> LENGTH: 124
<212> TYPE: PRT
<213> ORGANISM: Artificial Sequence
<220> FEATURE:
<223> OTHER INFORMATION: Hz1613F12 VH2.3

<400> SEQUENCE: 98

Gln Val Gln Leu Gln Gln Ser Gly Ala Glu Val Lys Lys Pro Gly Ala
1               5                   10                  15

Ser Val Lys Leu Ser Cys Thr Ala Ser Gly Phe Asn Ile Arg Asp Thr
            20                  25                  30

Tyr Ile His Trp Val Arg Gln Ala Pro Gly Gln Gly Leu Glu Trp Met
            35                  40                  45

Gly Trp Leu Asp Pro Ala Asn Gly His Thr Lys Tyr Ala Gln Lys Phe
        50                  55                  60

Gln Gly Arg Val Thr Met Thr Ser Asp Thr Ser Ser Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
            115                 120

<210> SEQ ID NO 99
<211> LENGTH: 124
<212> TYPE: PRT
<213> ORGANISM: Artificial Sequence
<220> FEATURE:
<223> OTHER INFORMATION: Hz1613F12 VH2.3 W55R

<400> SEQUENCE: 99

Gln Val Gln Leu Gln Gln Ser Gly Ala Glu Val Lys Lys Pro Gly Ala
1               5                   10                  15

Ser Val Lys Leu Ser Cys Thr Ala Ser Gly Phe Asn Ile Arg Asp Thr
            20                  25                  30

Tyr Ile His Trp Val Arg Gln Ala Pro Gly Gln Gly Leu Glu Trp Met
            35                  40                  45

Gly Arg Leu Asp Pro Ala Asn Gly His Thr Lys Tyr Ala Gln Lys Phe
        50                  55                  60

Gln Gly Arg Val Thr Met Thr Ser Asp Thr Ser Ser Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Leu Val Thr Val Ser Ser
            115                 120

<210> SEQ ID NO 100
<211> LENGTH: 124
<212> TYPE: PRT
<213> ORGANISM: Artificial Sequence
<220> FEATURE:
<223> OTHER INFORMATION: Hz1613F12 VH2.3 Q3H W55R

<400> SEQUENCE: 100

Gln Val His Leu Gln Gln Ser Gly Ala Glu Val Lys Lys Pro Gly Ala
1               5                   10                  15

Ser Val Lys Leu Ser Cys Thr Ala Ser Gly Phe Asn Ile Arg Asp Thr
            20                  25                  30

Tyr Ile His Trp Val Arg Gln Ala Pro Gly Gln Gly Leu Glu Trp Met
            35                  40                  45

Gly Arg Leu Asp Pro Ala Asn Gly His Thr Lys Tyr Ala Gln Lys Phe
        50                  55                  60

Gln Gly Arg Val Thr Met Thr Ser Asp Thr Ser Ser Asn Thr Ala Tyr
65                  70                  75                  80

Met Glu Leu Ser Arg Leu Arg Ser Asp Asp Thr Ala Val Tyr Tyr Cys

```
                    85                  90                  95

Ala Arg Gly Ala Tyr Tyr Tyr Gly Ser Ser Gly Leu Phe Tyr Phe Asp
                100                 105                 110

Tyr Trp Gly Gln Gly Thr Leu Val Thr Val Ser Ser
        115                 120

<210> SEQ ID NO 101
<211> LENGTH: 124
<212> TYPE: PRT
<213> ORGANISM: Artificial Sequence
<220> FEATURE:
<223> OTHER INFORMATION: Hz1613F12 VH2.4

<400> SEQUENCE: 101

Gln Val Gln Leu Gln Gln Ser Gly Ala Glu Val Lys Lys Pro Gly Ala
1               5                   10                  15

Ser Val Lys Leu Ser Cys Thr Ala Ser Gly Phe Asn Ile Arg Asp Thr
                20                  25                  30

Tyr Ile His Trp Val Arg Gln Ala Pro Gly Gln Gly Leu Glu Trp Ile
            35                  40                  45

Gly Arg Leu Asp Pro Ala Asn Gly His Thr Lys Tyr Ala Gln Lys Phe
        50                  55                  60

Gln Gly Arg Val Thr Met Thr Ser Asp Thr Ser Ser Asn Thr Ala Tyr
65                  70                  75                  80

Leu Glu Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
                100                 105                 110

Tyr Trp Gly Gln Gly Thr Leu Val Thr Val Ser Ser
        115                 120

<210> SEQ ID NO 102
<211> LENGTH: 124
<212> TYPE: PRT
<213> ORGANISM: Artificial Sequence
<220> FEATURE:
<223> OTHER INFORMATION: Hz1613F12 VH3

<400> SEQUENCE: 102

Glu Val His Leu Gln Gln Ser Gly Ala Glu Leu Val Lys Pro Gly Ala
1               5                   10                  15

Ser Val Lys Leu Ser Cys Thr Ala Ser Gly Phe Asn Ile Arg Asp Thr
                20                  25                  30

Tyr Ile His Trp Val Lys Gln Ala Pro Gly Gln Gly Leu Glu Trp Ile
            35                  40                  45

Gly Arg Leu Asp Pro Ala Asn Gly His Thr Lys Tyr Gly Gln Lys Phe
        50                  55                  60

Gln Gly Arg Val Thr Met Thr Ser Asp Thr Ser Ser Asn Thr Ala Tyr
65                  70                  75                  80

Leu Gln Leu Ser Arg Leu Arg Ser Asp Asp Thr Ala Val Tyr Tyr Cys
                85                  90                  95

Ala Arg Gly Ala Tyr Tyr Tyr Gly Ser Ser Gly Leu Phe Tyr Phe Asp
                100                 105                 110

Tyr Trp Gly Gln Gly Thr Leu Val Thr Val Ser Ser
        115                 120

<210> SEQ ID NO 103
<211> LENGTH: 894
```

```
<212> TYPE: PRT
<213> ORGANISM: Artificial Sequence
<220> FEATURE:
<223> OTHER INFORMATION: Axl protein (with signal peptide)

<400> SEQUENCE: 103
```

| | | | | | | | | | | | | | | |
|---|---|---|---|---|---|---|---|---|---|---|---|---|---|---|
| Met | Ala | Trp | Arg | Cys | Pro | Arg | Met | Gly | Arg | Val | Pro | Leu | Ala | Trp | Cys |
| 1 | | | | 5 | | | | | 10 | | | | | 15 | |
| Leu | Ala | Leu | Cys | Gly | Trp | Ala | Cys | Met | Ala | Pro | Arg | Gly | Thr | Gln | Ala |
| | | | 20 | | | | | 25 | | | | | 30 | | |
| Glu | Glu | Ser | Pro | Phe | Val | Gly | Asn | Pro | Gly | Asn | Ile | Thr | Gly | Ala | Arg |
| | | 35 | | | | | 40 | | | | | 45 | | | |
| Gly | Leu | Thr | Gly | Thr | Leu | Arg | Cys | Gln | Leu | Gln | Val | Gln | Gly | Glu | Pro |
| | 50 | | | | | 55 | | | | | 60 | | | | |
| Pro | Glu | Val | His | Trp | Leu | Arg | Asp | Gly | Gln | Ile | Leu | Glu | Leu | Ala | Asp |
| 65 | | | | | 70 | | | | | 75 | | | | | 80 |
| Ser | Thr | Gln | Thr | Gln | Val | Pro | Leu | Gly | Glu | Asp | Glu | Gln | Asp | Asp | Trp |
| | | | | 85 | | | | | 90 | | | | | 95 | |
| Ile | Val | Val | Ser | Gln | Leu | Arg | Ile | Thr | Ser | Leu | Gln | Leu | Ser | Asp | Thr |
| | | | 100 | | | | | 105 | | | | | 110 | | |
| Gly | Gln | Tyr | Gln | Cys | Leu | Val | Phe | Leu | Gly | His | Gln | Thr | Phe | Val | Ser |
| | | 115 | | | | | 120 | | | | | 125 | | | |
| Gln | Pro | Gly | Tyr | Val | Gly | Leu | Glu | Gly | Leu | Pro | Tyr | Phe | Leu | Glu | Glu |
| | 130 | | | | | 135 | | | | | 140 | | | | |
| Pro | Glu | Asp | Arg | Thr | Val | Ala | Ala | Asn | Thr | Pro | Phe | Asn | Leu | Ser | Cys |
| 145 | | | | | 150 | | | | | 155 | | | | | 160 |
| Gln | Ala | Gln | Gly | Pro | Pro | Glu | Pro | Val | Asp | Leu | Leu | Trp | Leu | Gln | Asp |
| | | | | 165 | | | | | 170 | | | | | 175 | |
| Ala | Val | Pro | Leu | Ala | Thr | Ala | Pro | Gly | His | Gly | Pro | Gln | Arg | Ser | Leu |
| | | | 180 | | | | | 185 | | | | | 190 | | |
| His | Val | Pro | Gly | Leu | Asn | Lys | Thr | Ser | Ser | Phe | Ser | Cys | Glu | Ala | His |
| | | 195 | | | | | 200 | | | | | 205 | | | |
| Asn | Ala | Lys | Gly | Val | Thr | Thr | Ser | Arg | Thr | Ala | Thr | Ile | Thr | Val | Leu |
| | 210 | | | | | 215 | | | | | 220 | | | | |
| Pro | Gln | Gln | Pro | Arg | Asn | Leu | His | Leu | Val | Ser | Arg | Gln | Pro | Thr | Glu |
| 225 | | | | | 230 | | | | | 235 | | | | | 240 |
| Leu | Glu | Val | Ala | Trp | Thr | Pro | Gly | Leu | Ser | Gly | Ile | Tyr | Pro | Leu | Thr |
| | | | | 245 | | | | | 250 | | | | | 255 | |
| His | Cys | Thr | Leu | Gln | Ala | Val | Leu | Ser | Asn | Asp | Gly | Met | Gly | Ile | Gln |
| | | | 260 | | | | | 265 | | | | | 270 | | |
| Ala | Gly | Glu | Pro | Asp | Pro | Pro | Glu | Glu | Pro | Leu | Thr | Ser | Gln | Ala | Ser |
| | | 275 | | | | | 280 | | | | | 285 | | | |
| Val | Pro | Pro | His | Gln | Leu | Arg | Leu | Gly | Ser | Leu | His | Pro | His | Thr | Pro |
| | 290 | | | | | 295 | | | | | 300 | | | | |
| Tyr | His | Ile | Arg | Val | Ala | Cys | Thr | Ser | Ser | Gln | Gly | Pro | Ser | Ser | Trp |
| 305 | | | | | 310 | | | | | 315 | | | | | 320 |
| Thr | His | Trp | Leu | Pro | Val | Glu | Thr | Pro | Glu | Gly | Val | Pro | Leu | Gly | Pro |
| | | | | 325 | | | | | 330 | | | | | 335 | |
| Pro | Glu | Asn | Ile | Ser | Ala | Thr | Arg | Asn | Gly | Ser | Gln | Ala | Phe | Val | His |
| | | | 340 | | | | | 345 | | | | | 350 | | |
| Trp | Gln | Glu | Pro | Arg | Ala | Pro | Leu | Gln | Gly | Thr | Leu | Leu | Gly | Tyr | Arg |
| | | 355 | | | | | 360 | | | | | 365 | | | |
| Leu | Ala | Tyr | Gln | Gly | Gln | Asp | Thr | Pro | Glu | Val | Leu | Met | Asp | Ile | Gly |
| | 370 | | | | | 375 | | | | | 380 | | | | |

-continued

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
            405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
            435                 440                 445

Pro Trp Trp Tyr Val Leu Leu Gly Ala Val Val Ala Ala Ala Cys Val
    450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
            515                 520                 525

Val Met Val Asp Arg His Lys Val Ala Leu Gly Lys Thr Leu Gly Glu
    530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
            595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
            675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
            755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro

-continued

```
                805                 810                 815
Asp Glu Ile Leu Tyr Val Asn Met Asp Glu Gly Gly Tyr Pro Glu
            820                 825                 830

Pro Pro Gly Ala Ala Gly Gly Ala Asp Pro Pro Thr Gln Pro Asp Pro
            835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
            885                 890

<210> SEQ ID NO 104
<211> LENGTH: 869
<212> TYPE: PRT
<213> ORGANISM: Artificial Sequence
<220> FEATURE:
<223> OTHER INFORMATION: Axl protein (without signal peptide)

<400> SEQUENCE: 104

Ala Pro Arg Gly Thr Gln Ala Glu Glu Ser Pro Phe Val Gly Asn Pro
1               5                   10                  15

Gly Asn Ile Thr Gly Ala Arg Gly Leu Thr Gly Thr Leu Arg Cys Gln
            20                  25                  30

Leu Gln Val Gln Gly Glu Pro Pro Glu Val His Trp Leu Arg Asp Gly
        35                  40                  45

Gln Ile Leu Glu Leu Ala Asp Ser Thr Gln Thr Gln Val Pro Leu Gly
    50                  55                  60

Glu Asp Glu Gln Asp Asp Trp Ile Val Val Ser Gln Leu Arg Ile Thr
65                  70                  75                  80

Ser Leu Gln Leu Ser Asp Thr Gly Gln Tyr Gln Cys Leu Val Phe Leu
                85                  90                  95

Gly His Gln Thr Phe Val Ser Gln Pro Gly Tyr Val Gly Leu Glu Gly
            100                 105                 110

Leu Pro Tyr Phe Leu Glu Glu Pro Glu Asp Arg Thr Val Ala Ala Asn
        115                 120                 125

Thr Pro Phe Asn Leu Ser Cys Gln Ala Gln Gly Pro Pro Glu Pro Val
    130                 135                 140

Asp Leu Leu Trp Leu Gln Asp Ala Val Pro Leu Ala Thr Ala Pro Gly
145                 150                 155                 160

His Gly Pro Gln Arg Ser Leu His Val Pro Gly Leu Asn Lys Thr Ser
                165                 170                 175

Ser Phe Ser Cys Glu Ala His Asn Ala Lys Gly Val Thr Thr Ser Arg
            180                 185                 190

Thr Ala Thr Ile Thr Val Leu Pro Gln Gln Pro Arg Asn Leu His Leu
        195                 200                 205

Val Ser Arg Gln Pro Thr Glu Leu Glu Val Ala Trp Thr Pro Gly Leu
    210                 215                 220

Ser Gly Ile Tyr Pro Leu Thr His Cys Thr Leu Gln Ala Val Leu Ser
225                 230                 235                 240

Asn Asp Gly Met Gly Ile Gln Ala Gly Glu Pro Asp Pro Pro Glu Glu
                245                 250                 255

Pro Leu Thr Ser Gln Ala Ser Val Pro Pro His Gln Leu Arg Leu Gly
            260                 265                 270

Ser Leu His Pro His Thr Pro Tyr His Ile Arg Val Ala Cys Thr Ser
```

-continued

```
                275                 280                 285
Ser Gln Gly Pro Ser Ser Trp Thr His Trp Leu Pro Val Glu Thr Pro
    290                 295                 300
Glu Gly Val Pro Leu Gly Pro Pro Glu Asn Ile Ser Ala Thr Arg Asn
305                 310                 315                 320
Gly Ser Gln Ala Phe Val His Trp Gln Glu Pro Arg Ala Pro Leu Gln
                325                 330                 335
Gly Thr Leu Leu Gly Tyr Arg Leu Ala Tyr Gln Gly Gln Asp Thr Pro
            340                 345                 350
Glu Val Leu Met Asp Ile Gly Leu Arg Gln Glu Val Thr Leu Glu Leu
        355                 360                 365
Gln Gly Asp Gly Ser Val Ser Asn Leu Thr Val Cys Val Ala Ala Tyr
    370                 375                 380
Thr Ala Ala Gly Asp Gly Pro Trp Ser Leu Pro Val Pro Leu Glu Ala
385                 390                 395                 400
Trp Arg Pro Gly Gln Ala Gln Pro Val His Gln Leu Val Lys Glu Pro
                405                 410                 415
Ser Thr Pro Ala Phe Ser Trp Pro Trp Trp Tyr Val Leu Leu Gly Ala
            420                 425                 430
Val Val Ala Ala Ala Cys Val Leu Ile Leu Ala Leu Phe Leu Val His
        435                 440                 445
Arg Arg Lys Lys Glu Thr Arg Tyr Gly Glu Val Phe Glu Pro Thr Val
    450                 455                 460
Glu Arg Gly Glu Leu Val Val Arg Tyr Arg Val Arg Lys Ser Tyr Ser
465                 470                 475                 480
Arg Arg Thr Thr Glu Ala Thr Leu Asn Ser Leu Gly Ile Ser Glu Glu
                485                 490                 495
Leu Lys Glu Lys Leu Arg Asp Val Met Val Asp Arg His Lys Val Ala
            500                 505                 510
Leu Gly Lys Thr Leu Gly Glu Gly Glu Phe Gly Ala Val Met Glu Gly
        515                 520                 525
Gln Leu Asn Gln Asp Asp Ser Ile Leu Lys Val Ala Val Lys Thr Met
    530                 535                 540
Lys Ile Ala Ile Cys Thr Arg Ser Glu Leu Glu Asp Phe Leu Ser Glu
545                 550                 555                 560
Ala Val Cys Met Lys Glu Phe Asp His Pro Asn Val Met Arg Leu Ile
                565                 570                 575
Gly Val Cys Phe Gln Gly Ser Glu Arg Glu Ser Phe Pro Ala Pro Val
            580                 585                 590
Val Ile Leu Pro Phe Met Lys His Gly Asp Leu His Ser Phe Leu Leu
        595                 600                 605
Tyr Ser Arg Leu Gly Asp Gln Pro Val Tyr Leu Pro Thr Gln Met Leu
    610                 615                 620
Val Lys Phe Met Ala Asp Ile Ala Ser Gly Met Glu Tyr Leu Ser Thr
625                 630                 635                 640
Lys Arg Phe Ile His Arg Asp Leu Ala Ala Arg Asn Cys Met Leu Asn
                645                 650                 655
Glu Asn Met Ser Val Cys Val Ala Asp Phe Gly Leu Ser Lys Lys Ile
            660                 665                 670
Tyr Asn Gly Asp Tyr Tyr Arg Gln Gly Arg Ile Ala Lys Met Pro Val
        675                 680                 685
Lys Trp Ile Ala Ile Glu Ser Leu Ala Asp Arg Val Tyr Thr Ser Lys
    690                 695                 700
```

```
Ser Asp Val Trp Ser Phe Gly Val Thr Met Trp Glu Ile Ala Thr Arg
705                 710                 715                 720

Gly Gln Thr Pro Tyr Pro Gly Val Glu Asn Ser Glu Ile Tyr Asp Tyr
                725                 730                 735

Leu Arg Gln Gly Asn Arg Leu Lys Gln Pro Ala Asp Cys Leu Asp Gly
            740                 745                 750

Leu Tyr Ala Leu Met Ser Arg Cys Trp Glu Leu Asn Pro Gln Asp Arg
        755                 760                 765

Pro Ser Phe Thr Glu Leu Arg Glu Asp Leu Glu Asn Thr Leu Lys Ala
770                 775                 780

Leu Pro Pro Ala Gln Glu Pro Asp Glu Ile Leu Tyr Val Asn Met Asp
785                 790                 795                 800

Glu Gly Gly Gly Tyr Pro Glu Pro Pro Gly Ala Ala Gly Gly Ala Asp
                805                 810                 815

Pro Pro Thr Gln Pro Asp Pro Lys Asp Ser Cys Ser Cys Leu Thr Ala
                820                 825                 830

Ala Glu Val His Pro Ala Gly Arg Tyr Val Leu Cys Pro Ser Thr Thr
            835                 840                 845

Pro Ser Pro Ala Gln Pro Ala Asp Arg Gly Ser Pro Ala Ala Pro Gly
        850                 855                 860

Gln Glu Asp Gly Ala
865

<210> SEQ ID NO 105
<211> LENGTH: 451
<212> TYPE: PRT
<213> ORGANISM: Artificial Sequence
<220> FEATURE:
<223> OTHER INFORMATION: extracellular domain of the Axl protein (with
      the signal peptide)

<400> SEQUENCE: 105

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
```

-continued

```
                180                 185                 190
His Val Pro Gly Leu Asn Lys Thr Ser Ser Phe Ser Cys Glu Ala His
            195                 200                 205

Asn Ala Lys Gly Val Thr Thr Ser Arg Thr Ala Thr Ile Thr Val Leu
        210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asn Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp
    450
```

<210> SEQ ID NO 106
<211> LENGTH: 426
<212> TYPE: PRT
<213> ORGANISM: Artificial Sequence
<220> FEATURE:
<223> OTHER INFORMATION: extracellular domain of the Axl protein
      (without the signal peptide)

<400> SEQUENCE: 106

```
Ala Pro Arg Gly Thr Gln Ala Glu Glu Ser Pro Phe Val Gly Asn Pro
1               5                   10                  15

Gly Asn Ile Thr Gly Ala Arg Gly Leu Thr Gly Thr Leu Arg Cys Gln
            20                  25                  30

Leu Gln Val Gln Gly Glu Pro Pro Glu Val His Trp Leu Arg Asp Gly
        35                  40                  45

Gln Ile Leu Glu Leu Ala Asp Ser Thr Gln Thr Gln Val Pro Leu Gly
    50                  55                  60

Glu Asp Glu Gln Asp Asp Trp Ile Val Val Ser Gln Leu Arg Ile Thr
65                  70                  75                  80
```

```
Ser Leu Gln Leu Ser Asp Thr Gly Gln Tyr Gln Cys Leu Val Phe Leu
             85                  90                  95

Gly His Gln Thr Phe Val Ser Gln Pro Gly Tyr Val Gly Leu Glu Gly
            100                 105                 110

Leu Pro Tyr Phe Leu Glu Glu Pro Glu Asp Arg Thr Val Ala Ala Asn
            115                 120                 125

Thr Pro Phe Asn Leu Ser Cys Gln Ala Gln Gly Pro Pro Glu Pro Val
            130                 135                 140

Asp Leu Leu Trp Leu Gln Asp Ala Val Pro Leu Ala Thr Ala Pro Gly
145                 150                 155                 160

His Gly Pro Gln Arg Ser Leu His Val Pro Gly Leu Asn Lys Thr Ser
            165                 170                 175

Ser Phe Ser Cys Glu Ala His Asn Ala Lys Gly Val Thr Thr Ser Arg
            180                 185                 190

Thr Ala Thr Ile Thr Val Leu Pro Gln Gln Pro Arg Asn Leu His Leu
            195                 200                 205

Val Ser Arg Gln Pro Thr Glu Leu Glu Val Ala Trp Thr Pro Gly Leu
210                 215                 220

Ser Gly Ile Tyr Pro Leu Thr His Cys Thr Leu Gln Ala Val Leu Ser
225                 230                 235                 240

Asn Asp Gly Met Gly Ile Gln Ala Gly Glu Pro Asp Pro Pro Glu Glu
            245                 250                 255

Pro Leu Thr Ser Gln Ala Ser Val Pro Pro His Gln Leu Arg Leu Gly
            260                 265                 270

Ser Leu His Pro His Thr Pro Tyr His Ile Arg Val Ala Cys Thr Ser
            275                 280                 285

Ser Gln Gly Pro Ser Ser Trp Thr His Trp Leu Pro Val Glu Thr Pro
            290                 295                 300

Glu Gly Val Pro Leu Gly Pro Pro Glu Asn Ile Ser Ala Thr Arg Asn
305                 310                 315                 320

Gly Ser Gln Ala Phe Val His Trp Gln Glu Pro Arg Ala Pro Leu Gln
            325                 330                 335

Gly Thr Leu Leu Gly Tyr Arg Leu Ala Tyr Gln Gly Gln Asp Thr Pro
            340                 345                 350

Glu Val Leu Met Asp Ile Gly Leu Arg Gln Glu Val Thr Leu Glu Leu
            355                 360                 365

Gln Gly Asp Gly Ser Val Ser Asn Leu Thr Val Cys Val Ala Ala Tyr
            370                 375                 380

Thr Ala Ala Gly Asp Gly Pro Trp Ser Leu Pro Val Pro Leu Glu Ala
385                 390                 395                 400

Trp Arg Pro Gly Gln Ala Gln Pro Val His Gln Leu Val Lys Glu Pro
            405                 410                 415

Ser Thr Pro Ala Phe Ser Trp Pro Trp Trp
            420                 425
```